United States Patent
Freeman et al.

(10) Patent No.: US 12,103,972 B2
(45) Date of Patent: Oct. 1, 2024

(54) KIR3DL3 AS AN HHLA2 RECEPTOR, ANTI-HHLA2 ANTIBODIES, AND USES THEREOF

(71) Applicant: Dana-Farber Cancer Institute, Inc., Boston, MA (US)

(72) Inventors: Gordon J. Freeman, Brookline, MA (US); Antonio R. Arulanandam, Winchester, MA (US)

(73) Assignee: Dana-Farber Cancer Institute, Inc., Boston, MA (US)

( * ) Notice: Subject to any disclaimer, the term of this patent is extended or adjusted under 35 U.S.C. 154(b) by 948 days.

(21) Appl. No.: 17/044,493

(22) PCT Filed: Apr. 5, 2019

(86) PCT No.: PCT/US2019/026034
§ 371 (c)(1),
(2) Date: Oct. 1, 2020

(87) PCT Pub. No.: WO2019/204057
PCT Pub. Date: Oct. 24, 2019

(65) Prior Publication Data
US 2021/0115144 A1    Apr. 22, 2021

Related U.S. Application Data

(60) Provisional application No. 62/654,068, filed on Apr. 6, 2018.

(51) Int. Cl.
C07K 16/28     (2006.01)
A61K 39/00     (2006.01)
(Continued)

(52) U.S. Cl.
CPC .......... C07K 16/2827 (2013.01); A61K 45/06 (2013.01); A61K 47/6803 (2017.08);
(Continued)

(58) Field of Classification Search
None
See application file for complete search history.

(56) References Cited

U.S. PATENT DOCUMENTS 7,291,721 B2 * 11/2007 Giles-Komar .......... A61P 37/00
                                                                435/69.6
7,977,461 B2    7/2011 Takayama et al.
(Continued)

FOREIGN PATENT DOCUMENTS

EP        2464661 A2      6/2012
WO    WO-2008/020586 A1   2/2008
(Continued)

OTHER PUBLICATIONS

Culang et al. The structural basis of antibody-antigen recognition. Front. Immunol., Oct. 8, 2013. Sec. B Cell Biology. vol. 4—2013 (Year: 2013).*

(Continued)

Primary Examiner — Daniel E Kolker
Assistant Examiner — Hilary Ann Petrash
(74) Attorney, Agent, or Firm — Foley Hoag LLP

(57) ABSTRACT

The present invention is based, in part, on the discovery of monoclonal antibodies, and antigen-binding fragments thereof, that specifically bind to HHLA2, as well as immunoglobulins, polypeptides, nucleic acids thereof, and methods of using such antibodies for diagnostic, prognostic, and therapeutic purposes.

19 Claims, 35 Drawing Sheets

Specification includes a Sequence Listing.

|          | 1C8         | 2C4      | 2G2            | 4D1     | 6D10           | 6F10    | 8A12      | 8D2       |
|----------|-------------|----------|----------------|---------|----------------|---------|-----------|-----------|
| EC-50    | 0.63        | 0.24     | 0.21           | 0.44    | 22.49          | 0.25    |           |           |
| Function | Non blocker | Augments | Weak Blocker   | Blocker | Non Blocker    | Blocker | IHC WB    | IHC WB    |

(51) Int. Cl.
    *A61K 45/06*     (2006.01)
    *A61K 47/68*     (2017.01)
    *A61P 35/00*     (2006.01)
    *G01N 33/50*     (2006.01)
    *G01N 33/68*     (2006.01)

(52) U.S. Cl.
    CPC .......... *A61K 47/6849* (2017.08); *A61P 35/00* (2018.01); *G01N 33/5011* (2013.01); *G01N 33/6854* (2013.01); *A61K 2039/505* (2013.01)

(56) References Cited

U.S. PATENT DOCUMENTS

| | | | |
|---|---|---|---|
| 8,481,687 | B2 | 7/2013 | Vincent et al. |
| 8,802,097 | B2 | 8/2014 | Gurney et al. |
| 9,416,189 | B2 | 8/2016 | Kawada et al. |
| 9,556,281 | B2 | 1/2017 | Schneewind et al. |
| 2017/0081410 | A1 | 3/2017 | Crawley et al. |
| 2017/0129942 | A1 | 5/2017 | Plante et al. |
| 2017/0218055 | A1* | 8/2017 | Schneewind ...... C07K 16/4233 |
| 2021/0115144 | A1 | 4/2021 | Freeman et al. |

FOREIGN PATENT DOCUMENTS

| | | | | |
|---|---|---|---|---|
| WO | WO-2011/020024 | A2 | 2/2011 | |
| WO | WO-2014/133728 | A2 | 9/2014 | |
| WO | WO-2014/190356 | A2 | 11/2014 | |
| WO | WO-2018026969 | A2 * | 2/2018 | .......... A61K 47/643 |
| WO | WO-2019/204057 | A1 | 10/2019 | |

OTHER PUBLICATIONS

International Search Report and Written Opinion for International Application No. PCT/US2019/026034 dated Oct. 3, 2019.

Janakiram et al., "HHLA2 amd TMIGD2: New Immunotherapeutic Targets of the B7 and CD28 Families'," OncoImmunology, 4(8): e1026534 (3 pages)(2015).

Singapore Search Report for Application No. 10202251461W dated Nov. 14, 2023.

Chapoval et al., "New Immunological Checkpoints for Cancer Immunotherapy", Rossiyskiy Onkologicheskiy Zhurnal (Russian Journal of Oncology), 2017; 22(4): 175-179.

Extended European Search Report for EP Application No. EP 19789172 dated Mar. 29, 2022.

Janakiram et al., "Expression, Clinical Significance, and Receptor Identification of the Newest B7 Family Member HHLA2 Protein," Clinical Cancer Research, 21(10): 2359-2366 (2015).

Mariuzza et al., "The Structural Basis of Antigen-Antibody Recognition," Ann. Rev. Biophys. Biophys. Chem., 16: 139-159 (1987).

Rudikoff et al., "Single amino acid substitution altering antigen-binding specificity," PNAS, 79: 1979-1983 (1982).

Zhao et al., "HHLA2 is a member of the B7 family and inhibits human CD4 and CD8 T-cell function," PNAS, 110(24): 9879-9884 (2013).

Chun et al., "Changes in HHLA2 expression in non-small cell lung cancer tissues and its significance," Shandong Medicine (2017).

* cited by examiner

Figure 6C

| Position | Gene ID | Accession |
|---|---|---|
| 1 | KIR3DL3 | BC143802 |
| 2 | KIR2DL1 | BC069344 |
| 3 | KIR2DL2 | NM_014219 |
| 4 | KIR2DL3 | BC032422 |
| 5 | KIR2DL4 | BC041611 |
| 6 | KIR2DL5A | NM_020535 |
| 7 | KIR2DL5B | NM_001018081 |
| 8 | KIR2DS1 | NM_014512 |
| 9 | KIR2DS2 | BC108917 |
| 10 | KIR2DS3 | NM_012313 |
| 11 | KIR2DS5 | NM_014513 |
| 12 | KIR3DL1 | BC028206 |
| 13 | KIR3DS1 | NM_001083539 |
| 14 | KIR3DS1 | BC098107 |
| 15 | KIR3DL2 | NM_006737 |
| 16 | KIR2DL1 | NM_014218 |

| Position | Gene ID | Accession |
|---|---|---|
| 17 | TMIGD2 | NM_144615.1 |
| 18 | CD86 | |
| 19 | EGFR | |
| 20 | FCGR2A | |

SEQUENCE LISTING

<160> NUMBER OF SEQ ID NOS: 371

<210> SEQ ID NO 1
<211> LENGTH: 2679
<212> TYPE: DNA
<213> ORGANISM: Homo sapiens

<400> SEQUENCE: 1

| | | | | | |
|---|---|---|---|---|---|
| agttctcttc | aagtcatgta | atcgactttt | ttgaattagt | tttcagtttc | attttgtttt | 60 |
| ccctaattca | agttgggaac | acttcatttt | ccccaattca | agttgggaac | acttccttgg | 120 |
| tatttccttg | ctacatggac | tttagcaaat | gctactttac | tctccttcca | gctactcagg | 180 |
| aggctgaggc | aggagaatcg | cttgaacccg | ggaggcggag | gttacagtga | gccttttcct | 240 |
| agttttactg | ttggaagcct | aactcacagg | agagattatg | caatacagtc | ctgaagtcaa | 300 |
| gggaggagag | catgtaggag | aatactaacc | ctgcacagat | tgtgatggtg | atgtggaata | 360 |
| tactaaagcc | tagaacgcac | ctcctctgca | tgactaatat | gttctgcaca | agacatgaag | 420 |
| gcacagacag | cactgtcttt | cttcctcatt | ctcataacat | ctctgagtgg | atctcaaggc | 480 |
| atattcccctt | tggctttctt | catttatgtt | cctatgaatg | aacaaatcgt | cattggaaga | 540 |
| cttgatgaag | atataattct | cccttcttca | tttgagaggg | gatccgaagt | cgtaatacac | 600 |
| tggaagtatc | aagatagcta | taaggttcac | agttactaca | aaggcagtga | ccatttggaa | 660 |
| agccaagatc | ccagatatgc | aaacaggaca | tcccttttct | ataatgagat | tcaaaatggg | 720 |
| aatgcgtcgc | tattttttcag | aagagtaagc | cttctggacg | aaggaattta | cacctgctat | 780 |
| gtaggaacag | caattcaagt | gattacaaac | aaagtggtgc | taaaggtggg | agtttttctc | 840 |
| acacccgtga | tgaagtatga | aaagaggaac | acaaacagct | tcttaatatg | cagcgtgtta | 900 |
| agtgtttatc | ctcgtccaat | tatcacgtgg | aaaatggaca | acacacctat | ctctgaaaac | 960 |
| aacatggaag | aaacagggtc | tttggattct | ttttctatta | acagcccact | gaatattaca | 1020 |
| ggatcaaatt | catcttatga | atgtacaatt | gaaaattcac | tgctgaagca | aacatggaca | 1080 |
| gggcgctgga | cgatgaaaga | tggccttcat | aaaatgcaaa | gtgaacacgt | ttcactctca | 1140 |
| tgtcaacctg | taaatgatta | tttttcacca | aaccaagact | tcaaagttac | ttggtccaga | 1200 |
| atgaaaagtg | ggacttttctc | tgtcctggct | tactatctga | gctcctcaca | aaatacaatt | 1260 |
| atcaatgaat | cccgattctc | atggaacaaa | gagctgataa | accagagtga | cttctctatg | 1320 |
| aatttgatgg | atcttaatct | ttcagacagt | ggggaatatt | tatgcaatat | ttcttcggat | 1380 |
| gaatatactt | tacttaccat | ccacacagtg | catgtagaac | cgagccaaga | aacagcttcc | 1440 |
| cataacaaag | gcttatggat | tttggtgccc | tctgcgattt | tggcagcttt | tctgctgatt | 1500 |
| tggagcgtaa | aatgttgcag | agcccagcta | gaagccagga | ggagcagaca | ccctgctgat | 1560 |
| ggagcccaac | aagaaagatg | ttgtgtccct | cctggtgagc | gctgtcccag | tgcacccgat | 1620 |
| aatggcgaag | aaaatgtgcc | tctttcagga | aaagtatagg | aaatgagaga | agactgtgac | 1680 |
| aactcatgac | ctgcatcctt | aatatccagt | gacttcatct | cccctttctt | caccacaatt | 1740 |
| ccaggcaatg | gcctgtcgga | gcagacaatt | ctaccactgc | aaagagttgt | aaccattttc | 1800 |
| tggtatcaca | tttatttttc | aagacatact | tttcaagaca | tcattcactg | acccactacc | 1860 |
| tgcattgagt | ataaatgcct | ggatgttaag | gattccaatt | taactttgaa | agaactgtc | 1920 |
| tcattcattt | acatttctgt | tacagtcagc | ccaggaggtt | acagtgagct | ctccactaag | 1980 |
| aatctgaag | aaatgcatca | ctaggggttg | attcccaatc | tgatcaactg | ataatgggtg | 2040 |
| agagagcagg | taagagccaa | agtcaccttα | gtggaaaggt | taaaaaccag | agcctggaaa | 2100 |

```
ccaagatgat tgatttgaca aggtatttta gtctagtttt atatgaacgg ttgtatcagg    2160
gtaaccaact cgatttggga tgaatcttag ggcaccaaag actaagacag tatctttaag    2220
attgctaggg aaaagggccc tatgtgtcag gcctctgagc ccaagccaag catcgcatcc    2280
cctgtgattt gcacgtatac atccagatgg cctaaagtaa ctgaagatcc acaaaagaag    2340
taaaaatagc cttaactgat gacattccac cattgtgatt tgttcctgcc ccaccctaac    2400
tgatcaatgt actttgtaat ctcccccacc cttaagaagg tactttgtaa tcttccccac    2460
ccttaagaag gttctttgta attctcccca cccttgagaa tgtactttgt gagatccacc    2520
ctgcccacaa acattgctc ttaacttcac cgcctaaccc aaaacctata agaactaatg    2580
ataatccatc acccttcgct gactctcttt tcggactcag cccacctgca cccaggtgaa    2640
ataaacagct ttattgctca cacaaaaaaa aaaaaaaa                           2679
```

<210> SEQ ID NO 2
<211> LENGTH: 414
<212> TYPE: PRT
<213> ORGANISM: Homo sapiens

<400> SEQUENCE: 2

```
Met Lys Ala Gln Thr Ala Leu Ser Phe Phe Leu Ile Leu Ile Thr Ser
1               5                   10                  15

Leu Ser Gly Ser Gln Gly Ile Phe Pro Leu Ala Phe Phe Ile Tyr Val
            20                  25                  30

Pro Met Asn Glu Gln Ile Val Ile Gly Arg Leu Asp Glu Asp Ile Ile
        35                  40                  45

Leu Pro Ser Ser Phe Glu Arg Gly Ser Glu Val Val Ile His Trp Lys
    50                  55                  60

Tyr Gln Asp Ser Tyr Lys Val His Ser Tyr Tyr Lys Gly Ser Asp His
65                  70                  75                  80

Leu Glu Ser Gln Asp Pro Arg Tyr Ala Asn Arg Thr Ser Leu Phe Tyr
                85                  90                  95

Asn Glu Ile Gln Asn Gly Asn Ala Ser Leu Phe Phe Arg Arg Val Ser
            100                 105                 110

Leu Leu Asp Glu Gly Ile Tyr Thr Cys Tyr Val Gly Thr Ala Ile Gln
        115                 120                 125

Val Ile Thr Asn Lys Val Val Leu Lys Val Gly Val Phe Leu Thr Pro
    130                 135                 140

Val Met Lys Tyr Glu Lys Arg Asn Thr Asn Ser Phe Leu Ile Cys Ser
145                 150                 155                 160

Val Leu Ser Val Tyr Pro Arg Pro Ile Ile Thr Trp Lys Met Asp Asn
                165                 170                 175

Thr Pro Ile Ser Glu Asn Asn Met Glu Glu Thr Gly Ser Leu Asp Ser
            180                 185                 190

Phe Ser Ile Asn Ser Pro Leu Asn Ile Thr Gly Ser Asn Ser Ser Tyr
        195                 200                 205

Glu Cys Thr Ile Glu Asn Ser Leu Leu Lys Gln Thr Trp Thr Gly Arg
    210                 215                 220

Trp Thr Met Lys Asp Gly Leu His Lys Met Gln Ser Glu His Val Ser
225                 230                 235                 240

Leu Ser Cys Gln Pro Val Asn Asp Tyr Phe Ser Pro Asn Gln Asp Phe
                245                 250                 255

Lys Val Thr Trp Ser Arg Met Lys Ser Gly Thr Phe Ser Val Leu Ala
            260                 265                 270
```

```
Tyr Tyr Leu Ser Ser Ser Gln Asn Thr Ile Ile Asn Glu Ser Arg Phe
            275                 280                 285

Ser Trp Asn Lys Glu Leu Ile Asn Gln Ser Asp Phe Ser Met Asn Leu
        290                 295                 300

Met Asp Leu Asn Leu Ser Asp Ser Gly Glu Tyr Leu Cys Asn Ile Ser
305                 310                 315                 320

Ser Asp Glu Tyr Thr Leu Leu Thr Ile His Thr Val His Val Glu Pro
                325                 330                 335

Ser Gln Glu Thr Ala Ser His Asn Lys Gly Leu Trp Ile Leu Val Pro
                340                 345                 350

Ser Ala Ile Leu Ala Ala Phe Leu Leu Ile Trp Ser Val Lys Cys Cys
            355                 360                 365

Arg Ala Gln Leu Glu Ala Arg Arg Ser Arg His Pro Ala Asp Gly Ala
        370                 375                 380

Gln Gln Glu Arg Cys Cys Val Pro Pro Gly Arg Cys Pro Ser Ala
385                 390                 395                 400

Pro Asp Asn Gly Glu Glu Asn Val Pro Leu Ser Gly Lys Val
                405                 410

<210> SEQ ID NO 3
<211> LENGTH: 2488
<212> TYPE: DNA
<213> ORGANISM: Homo sapiens

<400> SEQUENCE: 3
aaatcaaacg taccttggac tttactctct gagaaactca tagctgaatt caatgtttat      60
tcttatggac tacttagcat ttgactagac ggtatgaatt ctaagtaag cacatataga     120 actggatgcc cttgtggtac atctcaaggc tgatttgaaa gcttgagaga ccatcaagaa     180
ttggatttgg ggaagagcat gactaatatg ttctgcacaa gacatgaagg cacagacagc     240
actgtctttc ttcctcattc tcataacatc tctgagtgga tctcaaggca tattcccttt     300
ggctttcttc atttatgttc ctatgaatga acaaatcgtc attggaagac ttgatgaaga     360
tataattctc ccttcttcat ttgagagggg atccgaagtc gtaatacact ggaagtatca     420
agatagctat aaggttcaca gttactacaa aggcagtgac catttggaaa gccaagatcc     480
cagatatgca acaggacat cccttttcta taatgagatt caaaatggga atgcgtcgct     540 attttttcaga gagtaagcc ttctggacga aggaatttac acctgctatg taggaacagc     600
aattcaagtg attacaaaca aagtggtgct aaaggtggga gttttctca cacccgtgat     660 gaagtatgaa agaggaaca caaacagctt cttaatatgc agcgtgttaa gtgtttatcc     720
tcgtccaatt atcacgtgga aaatggacaa cacacctatc tctgaaaaca catggaaga     780 aacagggtct ttggattctt tttctattaa cagcccactg aatattacag gatcaaattc     840
atcttatgaa tgtacaattg aaaattcact gctgaagcaa acatggacag gcgctggac     900 gatgaaagat ggccttcata aatgcaaag tgaacacgtt tcactctcat gtcaacctgt     960
aaatgattat ttttcaccaa accaagactt caaagttact tggtccagaa tgaaagtgg    1020 gactttctct gtcctggctt actatctgag ctcctcacaa aatacaatta tcaatgaatc    1080
ccgattctca tggaacaaag agctgataaa ccagagtgac ttctctatga atttgatgga    1140
tcttaatctt tcagacagtg gggaatattt atgcaatatt tcttcggatg aatatacttt    1200
acttaccatc cacacagtgc atgtagaacc gagccaagaa acagcttccc ataacaaagg    1260
cttatggatt ttggtgccct ctgcgatttt ggcagctttt ctgctgattt ggagcgtaaa    1320
```

-continued

```
atgttgcaga gcccagctag aagccaggag gagcagacac cctgctgatg gagcccaaca    1380
agaaagatgt tgtgtccctc ctggtgagcg ctgtcccagt gcacccgata atggcgaaga    1440
aaatgtgcct ctttcaggaa aagtatagga aatgagagaa gactgtgaca actcatgacc    1500
tgcatcctta atatccagtg acttcatctc ccctttcttc accacaattc caggcaatgg    1560
cctgtcggag cagacaattc taccactgca aagagttgta accattttct ggtatcacat    1620
ttattttca agacatactt ttcaagacat cattcactga cccactacct gcattgagta    1680
taaatgcctg gatgttaagg attccaattt aactttgaaa agaactgtct cattcattta    1740
catttctgtt acagtcagcc caggaggtta cagtgagctc tccactaaga atctggaaga    1800
aatgcatcac taggggttga ttcccaatct gatcaactga taatgggtga gagagcaggt    1860
aagagccaaa gtcaccttag tggaaaggtt aaaaaccaga gcctggaaac caagatgatt    1920
gatttgacaa ggtattttag tctagttttta tatgaacggt tgtatcaggg taaccaactc    1980
gatttgggat gaatcttagg gcaccaaaga ctaagacagt atctttaaga ttgctaggga    2040
aaagggccct atgtgtcagg cctctgagcc caagccaagc atcgcatccc ctgtgatttg    2100
cacgtataca tccagatggc ctaaagtaac tgaagatcca caaagaagt aaaaatagcc    2160
ttaactgatg acattccacc attgtgattt gttcctgccc cacccttaact gatcaatgta    2220
ctttgtaatc tcccccaccc ttaagaaggt actttgtaat cttccccacc cttaagaagg    2280
ttctttgtaa ttctccccac ccttgagaat gtactttgtg agatccaccc tgcccacaaa    2340
acattgctct taacttcacc gcctaaccca aaacctataa gaactaatga taatccatca    2400
cccttcgctg actctctttt cggactcagc ccacctgcac ccaggtgaaa taaacagctt    2460
tattgctcac acaaaaaaaa aaaaaaaa                                      2488
```

<210> SEQ ID NO 4
<211> LENGTH: 414
<212> TYPE: PRT
<213> ORGANISM: Homo sapiens

<400> SEQUENCE: 4

```
Met Lys Ala Gln Thr Ala Leu Ser Phe Phe Leu Ile Leu Ile Thr Ser
1               5                   10                  15

Leu Ser Gly Ser Gln Gly Ile Phe Pro Leu Ala Phe Phe Ile Tyr Val
            20                  25                  30

Pro Met Asn Glu Gln Ile Val Ile Gly Arg Leu Asp Glu Asp Ile Ile
        35                  40                  45

Leu Pro Ser Ser Phe Glu Arg Gly Ser Glu Val Val Ile His Trp Lys
    50                  55                  60

Tyr Gln Asp Ser Tyr Lys Val His Ser Tyr Tyr Lys Gly Ser Asp His
65                  70                  75                  80

Leu Glu Ser Gln Asp Pro Arg Tyr Ala Asn Arg Thr Ser Leu Phe Tyr
                85                  90                  95

Asn Glu Ile Gln Asn Gly Asn Ala Ser Leu Phe Phe Arg Arg Val Ser
            100                 105                 110

Leu Leu Asp Glu Gly Ile Tyr Thr Cys Tyr Val Gly Thr Ala Ile Gln
        115                 120                 125

Val Ile Thr Asn Lys Val Val Leu Lys Val Gly Val Phe Leu Thr Pro
    130                 135                 140

Val Met Lys Tyr Glu Lys Arg Asn Thr Asn Ser Phe Leu Ile Cys Ser
145                 150                 155                 160
```

```
Val Leu Ser Val Tyr Pro Arg Pro Ile Ile Thr Trp Lys Met Asp Asn
            165                 170                 175

Thr Pro Ile Ser Glu Asn Asn Met Glu Glu Thr Gly Ser Leu Asp Ser
        180                 185                 190

Phe Ser Ile Asn Ser Pro Leu Asn Ile Thr Gly Ser Asn Ser Ser Tyr
        195                 200                 205

Glu Cys Thr Ile Glu Asn Ser Leu Leu Lys Gln Thr Trp Thr Gly Arg
    210                 215                 220

Trp Thr Met Lys Asp Gly Leu His Lys Met Gln Ser Glu His Val Ser
225                 230                 235                 240

Leu Ser Cys Gln Pro Val Asn Asp Tyr Phe Ser Pro Asn Gln Asp Phe
                245                 250                 255

Lys Val Thr Trp Ser Arg Met Lys Ser Gly Thr Phe Ser Val Leu Ala
            260                 265                 270

Tyr Tyr Leu Ser Ser Ser Gln Asn Thr Ile Ile Asn Glu Ser Arg Phe
        275                 280                 285

Ser Trp Asn Lys Glu Leu Ile Asn Gln Ser Asp Phe Ser Met Asn Leu
    290                 295                 300

Met Asp Leu Asn Leu Ser Asp Ser Gly Glu Tyr Leu Cys Asn Ile Ser
305                 310                 315                 320

Ser Asp Glu Tyr Thr Leu Leu Thr Ile His Thr Val His Val Glu Pro
                325                 330                 335

Ser Gln Glu Thr Ala Ser His Asn Lys Gly Leu Trp Ile Leu Val Pro
            340                 345                 350

Ser Ala Ile Leu Ala Ala Phe Leu Leu Ile Trp Ser Val Lys Cys Cys
        355                 360                 365

Arg Ala Gln Leu Glu Ala Arg Arg Ser Arg His Pro Ala Asp Gly Ala
    370                 375                 380

Gln Gln Glu Arg Cys Cys Val Pro Pro Gly Glu Arg Cys Pro Ser Ala
385                 390                 395                 400

Pro Asp Asn Gly Glu Glu Asn Val Pro Leu Ser Gly Lys Val
                405                 410

<210> SEQ ID NO 5
<211> LENGTH: 2419
<212> TYPE: DNA
<213> ORGANISM: Homo sapiens

<400> SEQUENCE: 5
agtttactct acatcatagc agagaaaatg gacaaaacac agctgttttg catgtaggag      60
aatactaacc ctgcacagat tgtgatggtg atgtggaata tactaaagcc tagaacgcac     120
ctcctctgca tgactaatat gttctgcaca agacatgaag gcacagacag cactgtcttt     180
cttcctcatt ctcataacat ctctgagtgg atctcaaggc atattccctt tggctttctt     240
catttatgtt cctatgaatg aacaaatcgt cattggaaga cttgatgaag ataatattct     300
cccttcttca tttgagaggg gatccgaagt cgtaatacac tggaagtatc aagatagcta     360
taaggttcac agttactaca aaggcagtga ccatttggaa agccaagatc cagatatgc      420 aaacaggaca tccctttttct ataatgagat tcaaaatggg aatgcgtcgc tattttcag     480 aagagtaagc cttctggacg aaggaattta cacctgctat gtaggaacag caattcaagt     540
gattacaaac aaagtggtgc taaggtgggg agttttctc acacccgtga tgaagtatga     600
aaagaggaac acaaacagct tcttaatatg cagcgtgtta agtgtttatc ctcgtccaat     660
tatcacgtgg aaaatggaca acacaccttat ctctgaaaac aacatggaag aaacagggtc     720
```

```
tttggattct ttttctatta acagcccact gaatattaca ggatcaaatt catcttatga    780
atgtacaatt gaaaattcac tgctgaagca aacatggaca gggcgctgga cgatgaaaga    840
tggccttcat aaaatgcaaa gtgaacacgt tcactctca tgtcaacctg taaatgatta    900
tttttcacca aaccaagact tcaaagttac ttggtccaga atgaaaagtg ggactttctc    960
tgtcctggct tactatctga gctcctcaca aaatacaatt atcaatgaat cccgattctc   1020
atggaacaaa gagctgataa accagagtga cttctctatg aatttgatgg atcttaatct   1080
ttcagacagt ggggaatatt tatgcaatat ttcttcggat gaatatactt tacttaccat   1140
ccacacagtg catgtagaac cgagccaaga aacagcttcc cataacaaag cttatggat    1200 tttggtgccc tctgcgattt tggcagcttt tctgctgatt tggagcgtaa aatgttgcag   1260
agcccagcta aaagcagga ggagcagaca ccctgctgat ggagcccaac aagaaagatg    1320
ttgtgtccct cctggtgagc gctgtcccag tgcacccgat aatggcgaag aaaatgtgcc   1380
tctttcagga aaagtatagg aaatgagaga agactgtgac aactcatgac ctgcatcctt   1440
aatatccagt gacttcatct ccctttctt caccacaatt ccaggcaatg gcctgtcgga    1500
gcagacaatt ctaccactgc aaagagttgt aaccattttc tggtatcaca tttatttttc   1560
aagacatact tttcaagaca tcattcactg acccactacc tgcattgagt ataaatgcct   1620
ggatgttaag gattccaatt taactttgaa aagaactgtc tcattcattt acatttctgt   1680
tacagtcagc ccaggaggtt acagtgagct ctccactaag aatctggaag aaatgcatca   1740
ctaggggttg attcccaatc tgatcaactg ataatgggtg agagagcagg taagagccaa   1800
agtcacctta gtggaaaggt taaaaccag agcctggaaa ccaagatgat tgatttgaca    1860
aggtatttta gtctagtttt atatgaacgg ttgtatcagg gtaaccaact cgatttggga   1920
tgaatcttag ggcaccaaag actaagacag tatctttaag attgctaggg aaaagggccc   1980
tatgtgtcag gcctctgagc ccaagccaag catcgcatcc cctgtgattt gcacgtatac   2040
atccagatgg cctaaagtaa ctgaagatcc acaaaagaag taaaaatagc cttaactgat   2100
gacattccac cattgtgatt tgttcctgcc ccaccctaac tgatcaatgt actttgtaat   2160
ctcccccacc cttaagaagg tactttgtaa tcttccccac ccttaagaag gttctttgta   2220
attctcccca cccttgagaa tgtactttgt gagatccacc ctgcccacaa acattgctc    2280 ttaacttcac cgcctaaccc aaaacctata agaactaatg ataatccatc cccttcgct    2340 gactctcttt tcggactcag cccacctgca cccaggtgaa ataaacagct ttattgctca   2400
cacaaaaaaa aaaaaaaaa                                                2419
```

<210> SEQ ID NO 6
<211> LENGTH: 414
<212> TYPE: PRT
<213> ORGANISM: Homo sapiens

<400> SEQUENCE: 6

```
Met Lys Ala Gln Thr Ala Leu Ser Phe Phe Leu Ile Leu Ile Thr Ser
1               5                   10                  15

Leu Ser Gly Ser Gln Gly Ile Phe Pro Leu Ala Phe Phe Ile Tyr Val
            20                  25                  30

Pro Met Asn Glu Gln Ile Val Ile Gly Arg Leu Asp Glu Asp Ile Ile
        35                  40                  45

Leu Pro Ser Ser Phe Glu Arg Gly Ser Glu Val Val Ile His Trp Lys
    50                  55                  60
```

| | | | | | | | | | | | | | | |
|---|---|---|---|---|---|---|---|---|---|---|---|---|---|---|
|Tyr|Gln|Asp|Ser|Tyr|Lys|Val|His|Ser|Tyr|Tyr|Lys|Gly|Ser|Asp|His|
|65| | | |70| | | |75| | | |80| | | |

Tyr Gln Asp Ser Tyr Lys Val His Ser Tyr Tyr Lys Gly Ser Asp His
 65                  70                  75                  80

Leu Glu Ser Gln Asp Pro Arg Tyr Ala Asn Arg Thr Ser Leu Phe Tyr
                 85                  90                  95

Asn Glu Ile Gln Asn Gly Asn Ala Ser Leu Phe Phe Arg Arg Val Ser
            100                 105                 110

Leu Leu Asp Glu Gly Ile Tyr Thr Cys Tyr Val Gly Thr Ala Ile Gln
            115                 120                 125

Val Ile Thr Asn Lys Val Val Leu Lys Val Gly Phe Leu Thr Pro
            130                 135                 140

Val Met Lys Tyr Glu Lys Arg Asn Thr Asn Ser Phe Leu Ile Cys Ser
145                 150                 155                 160

Val Leu Ser Val Tyr Pro Arg Pro Ile Ile Thr Trp Lys Met Asp Asn
                165                 170                 175

Thr Pro Ile Ser Glu Asn Asn Met Glu Thr Gly Ser Leu Asp Ser
                180                 185                 190

Phe Ser Ile Asn Ser Pro Leu Asn Ile Thr Gly Ser Asn Ser Ser Tyr
                195                 200                 205

Glu Cys Thr Ile Glu Asn Ser Leu Leu Lys Gln Thr Trp Thr Gly Arg
    210                 215                 220

Trp Thr Met Lys Asp Gly Leu His Lys Met Gln Ser Glu His Val Ser
225                 230                 235                 240

Leu Ser Cys Gln Pro Val Asn Asp Tyr Phe Ser Pro Asn Gln Asp Phe
                    245                 250                 255

Lys Val Thr Trp Ser Arg Met Lys Ser Gly Thr Phe Ser Val Leu Ala
                260                 265                 270

Tyr Tyr Leu Ser Ser Ser Gln Asn Thr Ile Ile Asn Glu Ser Arg Phe
    275                 280                 285

Ser Trp Asn Lys Glu Leu Ile Asn Gln Ser Asp Phe Ser Met Asn Leu
    290                 295                 300

Met Asp Leu Asn Leu Ser Asp Ser Gly Glu Tyr Leu Cys Asn Ile Ser
305                 310                 315                 320

Ser Asp Glu Tyr Thr Leu Leu Thr Ile His Thr Val His Val Glu Pro
                325                 330                 335

Ser Gln Glu Thr Ala Ser His Asn Lys Gly Leu Trp Ile Leu Val Pro
                340                 345                 350

Ser Ala Ile Leu Ala Ala Phe Leu Leu Ile Trp Ser Val Lys Cys Cys
            355                 360                 365

Arg Ala Gln Leu Glu Ala Arg Arg Ser Arg His Pro Ala Asp Gly Ala
            370                 375                 380

Gln Gln Glu Arg Cys Cys Val Pro Pro Gly Glu Arg Cys Pro Ser Ala
385                 390                 395                 400

Pro Asp Asn Gly Glu Glu Asn Val Pro Leu Ser Gly Lys Val
                405                 410

<210> SEQ ID NO 7
<211> LENGTH: 2515
<212> TYPE: DNA
<213> ORGANISM: Homo sapiens

<400> SEQUENCE: 7
aaatcaaacg taccttggac tttactctct gagaaactca tagctgaatt caatgtttat      60
tcttatggac tacttagcat ttgactagac ggtatgaatt tctaagtaag cacatataga     120
actggatgcc cttgtggtac atctcaaggc tgatttgaaa gcttgagaga ccatcaagaa     180

-continued

```
ttggatttgg ggaagagcat gtaggagaat actaaccctg cacagattgt gatggtgatg      240
tggaatatac taaagcctag aacgcacctc ctctgcatga ctaatatgtt ctgcacaaga      300
catgaaggca cagacagcac tgtctttctt cctcattctc ataacatctc tgagtggatc      360
tcaaggcata ttccctttgg ctttcttcat ttatgttcct atgaatgaac aaatcgtcat      420
tggaagactt gatgaagata taattctccc ttcttcattt gagagggat ccgaagtcgt       480 aatacactgg aagtatcaag atagctataa ggttcacagt tactacaaag gcagtgacca     540
tttggaaagc caagatccca gatatgcaaa caggacatcc cttttctata atgagattca     600
aaatgggaat gcgtcgctat ttttcagaag agtaagcctt ctggacgaag gaatttacac     660
ctgctatgta ggaacagcaa ttcaagtgat tacaaacaaa gtggtgctaa aggtgggagt     720
ttttctcaca cccgtgatga agtatgaaaa aggaacacaa aacagcttct taatatgcag     780
cgtgttaagt gtttatcctc gtccaattat cacgtggaaa atggacaaca cacctatctc     840
tgaaaacaac atggaagaaa cagggtcttt ggattctttt tctattaaca gcccactgaa     900
tattacagga tcaaattcat cttatgaatg tacaattgaa aattcactgc tgaagcaaac     960
atggacaggg cgctggacga tgaaagatgg ccttcataaa atgcaaagtg aacacgtttc    1020
actctcatgt caacctgtaa atgattattt ttcaccaaac caagacttca aagttacttg    1080
gtccagaatg aaaagtggga cttttctctgt cctggcttac tatctgagct cctcacaaaa    1140
tacaattatc aatgaatccc gattctcatg gaacaaagag ctgataaacc agagtgactt    1200
ctctatgaat ttgatggatc ttaatctttc agacagtggg gaatatttat gcaatatttc    1260
ttcggatgaa tatactttac ttaccatcca cacagtgcat gtagaaccga gccaagaaac    1320
agcttcccat aacaaaggct tatgattttt ggtgccctct gcgattttgg cagcttttct    1380
gctgatttgg agcgtaaaat gttgcagaga aagatgttgt gtccctcctg gtgagcgctg    1440
tcccagtgca cccgataatg gcgaagaaaa tgtgcctctt tcaggaaaag tataggaaat    1500
gagagaagac tgtgacaact catgacctgc atccttaata tccagtgact tcatctcccc    1560
tttcttcacc acaattccag gcaatggcct gtcggagcag acaattctac cactgcaaag    1620
agttgtaacc attttctggt atcacattta tttttcaaga catactttc aagacatcat     1680 tcactgaccc actacctgca ttgagtataa atgcctggat gttaaggatt ccaatttaac    1740
tttgaaaaga actgtctcat tcatttacat ttctgttaca gtcagccag gaggttacag    1800 tgagctctcc actaagaatc tggaagaaat gcatcactag gggttgattc ccaatctgat    1860
caactgataa tgggtgagag agcaggtaag agccaaagtc accttagtgg aaaggttaaa    1920
aaccagagcc tggaaaccaa gatgattgat ttgacaaggt attttagtct agtttatat    1980 gaacggttgt atcagggtaa ccaactcgat ttgggatgaa tcttagggca ccaaagacta    2040
agacagtatc tttaagattg ctagggaaaa gggccctatg tgtcaggcct ctgagcccaa    2100
gccaagcatc gcatcccctg tgatttgcac gtatacatcc agatggccta agtaactga    2160 agatccacaa aagaagtaaa aatagcctta actgatgaca ttccaccatt gtgatttgtt    2220
cctgccccac cctaactgat caatgtactt tgtaatctcc cccacccttag agaaggtact   2280 ttgtaatctt ccccaccctt aagaaggttc tttgtaattc tccccacccct tgagaatgta   2340 ctttgtgaga tccaccctgc ccacaaaaca ttgctcttaa cttcaccgcc taacccaaaa    2400
cctataagaa ctaatgataa tccatcaccc ttcgctgact ctcttttcgg actcagccca    2460
cctgcaccca ggtgaaataa acagctttat tgctcacaca aaaaaaaaaa aaaaa         2515
```

```
<210> SEQ ID NO 8
<211> LENGTH: 397
<212> TYPE: PRT
<213> ORGANISM: Homo sapiens

<400> SEQUENCE: 8
```

| | | | | | | | | | | | | | | | |
|---|---|---|---|---|---|---|---|---|---|---|---|---|---|---|---|
| Met | Lys | Ala | Gln | Thr | Ala | Leu | Ser | Phe | Phe | Leu | Ile | Leu | Ile | Thr | Ser |
| 1 | | | | 5 | | | | | 10 | | | | | 15 | |

| Leu | Ser | Gly | Ser | Gln | Gly | Ile | Phe | Pro | Leu | Ala | Phe | Phe | Ile | Tyr | Val |
|---|---|---|---|---|---|---|---|---|---|---|---|---|---|---|---|
| | | | 20 | | | | | 25 | | | | | 30 | | |

| Pro | Met | Asn | Glu | Gln | Ile | Val | Ile | Gly | Arg | Leu | Asp | Glu | Asp | Ile | Ile |
|---|---|---|---|---|---|---|---|---|---|---|---|---|---|---|---|
| | | | 35 | | | | | 40 | | | | | 45 | | |

| Leu | Pro | Ser | Ser | Phe | Glu | Arg | Gly | Ser | Glu | Val | Val | Ile | His | Trp | Lys |
|---|---|---|---|---|---|---|---|---|---|---|---|---|---|---|---|
| | 50 | | | | | 55 | | | | | 60 | | | | |

| Tyr | Gln | Asp | Ser | Tyr | Lys | Val | His | Ser | Tyr | Tyr | Lys | Gly | Ser | Asp | His |
|---|---|---|---|---|---|---|---|---|---|---|---|---|---|---|---|
| 65 | | | | | 70 | | | | | 75 | | | | | 80 |

| Leu | Glu | Ser | Gln | Asp | Pro | Arg | Tyr | Ala | Asn | Arg | Thr | Ser | Leu | Phe | Tyr |
|---|---|---|---|---|---|---|---|---|---|---|---|---|---|---|---|
| | | | | 85 | | | | | 90 | | | | | 95 | |

| Asn | Glu | Ile | Gln | Asn | Gly | Asn | Ala | Ser | Leu | Phe | Phe | Arg | Arg | Val | Ser |
|---|---|---|---|---|---|---|---|---|---|---|---|---|---|---|---|
| | | | 100 | | | | | 105 | | | | | 110 | | |

| Leu | Leu | Asp | Glu | Gly | Ile | Tyr | Thr | Cys | Tyr | Val | Gly | Thr | Ala | Ile | Gln |
|---|---|---|---|---|---|---|---|---|---|---|---|---|---|---|---|
| | | | 115 | | | | | 120 | | | | | 125 | | |

| Val | Ile | Thr | Asn | Lys | Val | Val | Leu | Lys | Val | Gly | Val | Phe | Leu | Thr | Pro |
|---|---|---|---|---|---|---|---|---|---|---|---|---|---|---|---|
| | 130 | | | | | 135 | | | | | 140 | | | | |

| Val | Met | Lys | Tyr | Glu | Lys | Arg | Asn | Thr | Asn | Ser | Phe | Leu | Ile | Cys | Ser |
|---|---|---|---|---|---|---|---|---|---|---|---|---|---|---|---|
| 145 | | | | | 150 | | | | | 155 | | | | | 160 |

| Val | Leu | Ser | Val | Tyr | Pro | Arg | Pro | Ile | Ile | Thr | Trp | Lys | Met | Asp | Asn |
|---|---|---|---|---|---|---|---|---|---|---|---|---|---|---|---|
| | | | | 165 | | | | | 170 | | | | | 175 | |

| Thr | Pro | Ile | Ser | Glu | Asn | Asn | Met | Glu | Glu | Thr | Gly | Ser | Leu | Asp | Ser |
|---|---|---|---|---|---|---|---|---|---|---|---|---|---|---|---|
| | | | 180 | | | | | 185 | | | | | 190 | | |

| Phe | Ser | Ile | Asn | Ser | Pro | Leu | Asn | Ile | Thr | Gly | Ser | Asn | Ser | Ser | Tyr |
|---|---|---|---|---|---|---|---|---|---|---|---|---|---|---|---|
| | | | 195 | | | | | 200 | | | | | 205 | | |

| Glu | Cys | Thr | Ile | Glu | Asn | Ser | Leu | Leu | Lys | Gln | Thr | Trp | Thr | Gly | Arg |
|---|---|---|---|---|---|---|---|---|---|---|---|---|---|---|---|
| | 210 | | | | | 215 | | | | | 220 | | | | |

| Trp | Thr | Met | Lys | Asp | Gly | Leu | His | Lys | Met | Gln | Ser | Glu | His | Val | Ser |
|---|---|---|---|---|---|---|---|---|---|---|---|---|---|---|---|
| 225 | | | | | 230 | | | | | 235 | | | | | 240 |

| Leu | Ser | Cys | Gln | Pro | Val | Asn | Asp | Tyr | Phe | Ser | Pro | Asn | Gln | Asp | Phe |
|---|---|---|---|---|---|---|---|---|---|---|---|---|---|---|---|
| | | | | 245 | | | | | 250 | | | | | 255 | |

| Lys | Val | Thr | Trp | Ser | Arg | Met | Lys | Ser | Gly | Thr | Phe | Ser | Val | Leu | Ala |
|---|---|---|---|---|---|---|---|---|---|---|---|---|---|---|---|
| | | | 260 | | | | | 265 | | | | | 270 | | |

| Tyr | Tyr | Leu | Ser | Ser | Ser | Gln | Asn | Thr | Ile | Ile | Asn | Glu | Ser | Arg | Phe |
|---|---|---|---|---|---|---|---|---|---|---|---|---|---|---|---|
| | | | 275 | | | | | 280 | | | | | 285 | | |

| Ser | Trp | Asn | Lys | Glu | Leu | Ile | Asn | Gln | Ser | Asp | Phe | Ser | Met | Asn | Leu |
|---|---|---|---|---|---|---|---|---|---|---|---|---|---|---|---|
| | 290 | | | | | 295 | | | | | 300 | | | | |

| Met | Asp | Leu | Asn | Leu | Ser | Asp | Ser | Gly | Glu | Tyr | Leu | Cys | Asn | Ile | Ser |
|---|---|---|---|---|---|---|---|---|---|---|---|---|---|---|---|
| 305 | | | | | 310 | | | | | 315 | | | | | 320 |

| Ser | Asp | Glu | Tyr | Thr | Leu | Leu | Thr | Ile | His | Thr | Val | His | Val | Glu | Pro |
|---|---|---|---|---|---|---|---|---|---|---|---|---|---|---|---|
| | | | | 325 | | | | | 330 | | | | | 335 | |

| Ser | Gln | Glu | Thr | Ala | Ser | His | Asn | Lys | Gly | Leu | Trp | Ile | Leu | Val | Pro |
|---|---|---|---|---|---|---|---|---|---|---|---|---|---|---|---|
| | | | 340 | | | | | 345 | | | | | 350 | | |

| Ser | Ala | Ile | Leu | Ala | Ala | Phe | Leu | Leu | Ile | Trp | Ser | Val | Lys | Cys | Cys |
|---|---|---|---|---|---|---|---|---|---|---|---|---|---|---|---|
| | | | 355 | | | | | 360 | | | | | 365 | | |

| Arg | Glu | Arg | Cys | Cys | Val | Pro | Pro | Gly | Glu | Arg | Cys | Pro | Ser | Ala | Pro |
|---|---|---|---|---|---|---|---|---|---|---|---|---|---|---|---|
| | 370 | | | | | 375 | | | | | 380 | | | | |

Asp Asn Gly Glu Glu Asn Val Pro Leu Ser Gly Lys Val
385                 390                 395

<210> SEQ ID NO 9
<211> LENGTH: 2304
<212> TYPE: DNA
<213> ORGANISM: Homo sapiens

<400> SEQUENCE: 9

| | | | | | |
|---|---|---|---|---|---|
| aaatcaaacg | taccttggac | tttactctct | gagaaactca | tagctgaatt | caatgtttat | 60 |
| tcttatggac | tacttagcat | ttgactagac | ggtatgaatt | ctaagtaag | cacatataga | 120 |
| actggatgcc | cttgtggtac | atctcaaggc | tgatttgaaa | gcttgagaga | ccatcaagaa | 180 |
| ttggatttgg | ggaagagcat | gtaggagaat | actaaccctg | cacagattgt | gatggtgatg | 240 |
| tggaatatac | taaagcctag | aacgcacctc | ctctgcatga | ctaatatgtt | ctgcacaaga | 300 |
| catgaaggca | cagacagcac | tgtctttctt | cctcattctc | ataacatctc | tgagtggatc | 360 |
| tcaagaagag | taagccttct | ggacgaagga | atttacacct | gctatgtagg | aacagcaatt | 420 |
| caagtgatta | caaacaaagt | ggtgctaaag | gtgggagttt | ttctcacacc | cgtgatgaag | 480 |
| tatgaaaaga | ggaacacaaa | cagcttctta | atatgcagcg | tgttaagtgt | ttatcctcgt | 540 |
| ccaattatca | cgtggaaaat | ggacaacaca | cctatctctg | aaaacaacat | ggaagaaaca | 600 |
| gggtctttgg | attctttttc | tattaacagc | ccactgaata | ttacaggatc | aaattcatct | 660 |
| tatgaatgta | caattgaaaa | ttcactgctg | aagcaaacat | ggacagggcg | ctggacgatg | 720 |
| aaagatggcc | ttcataaaat | gcaaagtgaa | cacgtttcac | tctcatgtca | acctgtaaat | 780 |
| gattattttt | caccaaacca | agacttcaaa | gttacttggt | ccagaatgaa | agtgggact | 840 |
| ttctctgtcc | tggcttacta | tctgagctcc | tcacaaaata | caattatcaa | tgaatcccga | 900 |
| ttctcatgga | acaaagagct | gataaaccag | agtgacttct | ctatgaattt | gatggatctt | 960 |
| aatctttcag | acagtgggga | atatttatgc | aatatttctt | cggatgaata | tactttactt | 1020 |
| accatccaca | cagtgcatgt | agaaccgagc | caagaaacag | cttcccataa | caaaggctta | 1080 |
| tggatttttgg | tgccctctgc | gattttggca | gcttttctgc | tgatttggag | cgtaaaatgt | 1140 |
| tgcagagccc | agctagaagc | caggaggagc | agacaccctg | ctgatggagc | caacaagaa | 1200 |
| agatgttgtg | tccctcctgg | tgagcgctgt | cccagtgcac | ccgataatgg | cgaagaaaat | 1260 |
| gtgcctcttt | caggaaaagt | ataggaaatg | agagaagact | gtgacaactc | atgacctgca | 1320 |
| tccttaatat | ccagtgactt | catctccct | ttcttcacca | caattccagg | caatggcctg | 1380 |
| tcggagcaga | caattctacc | actgcaaaga | gttgtaacca | ttttctggta | tcacatttat | 1440 |
| ttttcaagac | atacttttca | agacatcatt | cactgaccca | ctacctgcat | tgagtataaa | 1500 |
| tgcctggatg | ttaaggattc | caatttaact | ttgaaaagaa | ctgtctcatt | catttacatt | 1560 |
| tctgttacag | tcagcccagg | aggttacagt | gagctctcca | ctaagaatct | ggaagaaatg | 1620 |
| catcactagg | ggttgattcc | caatctgatc | aactgataat | gggtgagaga | gcaggtaaga | 1680 |
| gccaaagtca | ccttagtgga | aaggttaaaa | accagagcct | ggaaaccaag | atgattgatt | 1740 |
| tgacaaggta | ttttagtcta | gttttatatg | aacggttgta | tcagggtaac | caactcgatt | 1800 |
| tgggatgaat | cttagggcac | caaagactaa | gacagtatct | ttaagattgc | tagggaaaag | 1860 |
| ggccctatgt | gtcaggcctc | tgagcccaag | ccaagcatcg | catcccctgt | gatttgcacg | 1920 |
| tatacatcca | gatggcctaa | agtaactgaa | gatccacaaa | agaagtaaaa | atagccttaa | 1980 |
| ctgatgacat | tccaccattg | tgatttgttc | ctgccccacc | ctaactgatc | aatgtactt | 2040 |

```
gtaatctccc ccaccct taa gaaggtactt tgtaatcttc cccaccctta agaaggttct    2100
ttgtaattct ccccaccctt gagaatgtac tttgtgagat ccaccctgcc cacaaaacat    2160
tgctcttaac ttcaccgcct aacccaaaac ctataagaac taatgataat ccatcaccct    2220
tcgctgactc tcttttcgga ctcagcccac ctgcacccag gtgaaataaa cagctttatt    2280
gctcacacaa aaaaaaaaaa aaaa                                           2304
```

<210> SEQ ID NO 10
<211> LENGTH: 350
<212> TYPE: PRT
<213> ORGANISM: Homo sapiens

<400> SEQUENCE: 10

```
Met Val Met Trp Asn Ile Leu Lys Pro Arg Thr His Leu Leu Cys Met
1               5                   10                  15

Thr Asn Met Phe Cys Thr Arg His Glu Gly Thr Asp Ser Thr Val Phe
            20                  25                  30

Leu Pro His Ser His Asn Ile Ser Glu Trp Ile Ser Arg Val Ser
        35                  40                  45

Leu Leu Asp Glu Gly Ile Tyr Thr Cys Tyr Val Gly Thr Ala Ile Gln
    50                  55                  60

Val Ile Thr Asn Lys Val Val Leu Lys Val Gly Val Phe Leu Thr Pro
65                  70                  75                  80

Val Met Lys Tyr Glu Lys Arg Asn Thr Asn Ser Phe Leu Ile Cys Ser
                85                  90                  95

Val Leu Ser Val Tyr Pro Arg Pro Ile Ile Thr Trp Lys Met Asp Asn
            100                 105                 110

Thr Pro Ile Ser Glu Asn Asn Met Glu Glu Thr Gly Ser Leu Asp Ser
        115                 120                 125

Phe Ser Ile Asn Ser Pro Leu Asn Ile Thr Gly Ser Asn Ser Ser Tyr
    130                 135                 140

Glu Cys Thr Ile Glu Asn Ser Leu Leu Lys Gln Thr Trp Thr Gly Arg
145                 150                 155                 160

Trp Thr Met Lys Asp Gly Leu His Lys Met Gln Ser Glu His Val Ser
                165                 170                 175

Leu Ser Cys Gln Pro Val Asn Asp Tyr Phe Ser Pro Asn Gln Asp Phe
            180                 185                 190

Lys Val Thr Trp Ser Arg Met Lys Ser Gly Thr Phe Ser Val Leu Ala
        195                 200                 205

Tyr Tyr Leu Ser Ser Ser Gln Asn Thr Ile Ile Asn Glu Ser Arg Phe
    210                 215                 220

Ser Trp Asn Lys Glu Leu Ile Asn Gln Ser Asp Phe Ser Met Asn Leu
225                 230                 235                 240

Met Asp Leu Asn Leu Ser Asp Ser Gly Glu Tyr Leu Cys Asn Ile Ser
                245                 250                 255

Ser Asp Glu Tyr Thr Leu Leu Thr Ile His Thr Val His Val Glu Pro
            260                 265                 270

Ser Gln Glu Thr Ala Ser His Asn Lys Gly Leu Trp Ile Leu Val Pro
        275                 280                 285

Ser Ala Ile Leu Ala Ala Phe Leu Leu Ile Trp Ser Val Lys Cys Cys
    290                 295                 300

Arg Ala Gln Leu Glu Ala Arg Arg Ser Arg His Pro Ala Asp Gly Ala
305                 310                 315                 320
```

Gln Gln Glu Arg Cys Cys Val Pro Pro Gly Glu Arg Cys Pro Ser Ala
            325                 330                 335

Pro Asp Asn Gly Glu Glu Asn Val Pro Leu Ser Gly Lys Val
            340                 345                 350

<210> SEQ ID NO 11
<211> LENGTH: 1282
<212> TYPE: DNA
<213> ORGANISM: Homo sapiens

<400> SEQUENCE: 11

| | | |
|---|---|---|
| ggaagtctgt caactgggag ggggagaggg gggtgatggg ccaggaatgg ggtccccggg | 60 |
| catggtgctg ggcctcctgg tgcagatctg ggccctgcaa gaagcctcaa gcctgagcgt | 120 |
| gcagcagggg cccaacttgc tgcaggtgag cagggcagt caggcgaccc tggtctgcca | 180 |
| ggtggaccag gccacagcct gggaacggct ccgtgttaag tggacaaagg atggggccat | 240 |
| cctgtgtcaa ccgtacatca ccaacggcag cctcagcctg ggggtctgcg ggccccaggg | 300 |
| acggctctcc tggcaggcac ccagccatct caccctgcag ctggaccctg tgagcctcaa | 360 |
| ccacagcggg gcgtacgtgt gctgggcggc cgtagagatt cctgagttgg aggaggctga | 420 |
| gggcaacata acaaggctct tgtggaccc agatgacccc acacagaaca gaaaccggat | 480 |
| cgcaagcttc ccaggattcc tcttcgtgct gctgggggtg ggaagcatgg gtgtggctgc | 540 |
| gatcgtgtgg ggtgcctggt tctggggccg ccgcagctgc cagcaaaggg actcaggtaa | 600 |
| cagcccagga aatgcattct acagcaacgt cctataccgg ccccgggggg ccccaaagaa | 660 |
| gagtgaggac tgctctggag aggggaagga ccagaggggc cagagcattt attcaacctc | 720 |
| cttcccgcaa ccggcccccc gccagccgca cctggcgtca agaccctgcc ccagcccgag | 780 |
| accctgcccc agcccaggc ccggccaccc cgtctctatg gtcagggtct ctcctagacc | 840 |
| aagcccacc cagcagccga ggccaaaagg gttccccaaa gtgggagagg agtgagagat | 900 |
| cccaggagac ctcaacagga ccccacccat aggtacacac aaaaaagggg ggatcgaggc | 960 |
| cagacacggt ggctcacgcc tgtaatccca gcagtttggg aagccgaggc gggtggaaca | 1020 |
| cttgaggtca ggggttttgag accagcctgg cttgaacctg ggaggcggag gttgcagtga | 1080 |
| gccgagattg cgccactgca ctccagcctg ggcgacagag tgagactccg tctcaaaaaa | 1140 |
| aacaaaaagc aggaggattg ggagcctgtc agcccatcc tgagaccccg tcctcatttc | 1200 |
| tgtaatgatg gatctcgctc ccactttccc ccaagaacct aataaaggct tgtgaagaaa | 1260 |
| aagcaaaaaa aaaaaaaaaa aa | 1282 |

<210> SEQ ID NO 12
<211> LENGTH: 282
<212> TYPE: PRT
<213> ORGANISM: Homo sapiens

<400> SEQUENCE: 12

Met Gly Ser Pro Gly Met Val Leu Gly Leu Leu Val Gln Ile Trp Ala
1               5                   10                  15

Leu Gln Glu Ala Ser Ser Leu Ser Val Gln Gln Gly Pro Asn Leu Leu
            20                  25                  30

Gln Val Arg Gln Gly Ser Gln Ala Thr Leu Val Cys Gln Val Asp Gln
        35                  40                  45

Ala Thr Ala Trp Glu Arg Leu Arg Val Lys Trp Thr Lys Asp Gly Ala
    50                  55                  60

Ile Leu Cys Gln Pro Tyr Ile Thr Asn Gly Ser Leu Ser Leu Gly Val

```
                65                  70                  75                  80
Cys Gly Pro Gln Gly Arg Leu Ser Trp Gln Ala Pro Ser His Leu Thr
                    85                  90                  95

Leu Gln Leu Asp Pro Val Ser Leu Asn His Ser Gly Ala Tyr Val Cys
                100                 105                 110

Trp Ala Ala Val Glu Ile Pro Glu Leu Glu Ala Glu Gly Asn Ile
            115                 120                 125

Thr Arg Leu Phe Val Asp Pro Asp Pro Thr Gln Asn Arg Asn Arg
        130                 135                 140

Ile Ala Ser Phe Pro Gly Phe Leu Phe Val Leu Leu Gly Val Gly Ser
145                 150                 155                 160

Met Gly Val Ala Ala Ile Val Trp Gly Ala Trp Phe Trp Gly Arg Arg
                165                 170                 175

Ser Cys Gln Gln Arg Asp Ser Gly Asn Ser Pro Gly Asn Ala Phe Tyr
                180                 185                 190

Ser Asn Val Leu Tyr Arg Pro Arg Gly Ala Pro Lys Lys Ser Glu Asp
                195                 200                 205

Cys Ser Gly Glu Gly Lys Asp Gln Arg Gly Gln Ser Ile Tyr Ser Thr
        210                 215                 220

Ser Phe Pro Gln Pro Ala Pro Arg Gln Pro His Leu Ala Ser Arg Pro
225                 230                 235                 240

Cys Pro Ser Pro Arg Pro Cys Pro Ser Pro Arg Pro Gly His Pro Val
                245                 250                 255

Ser Met Val Arg Val Ser Pro Arg Pro Ser Pro Thr Gln Gln Pro Arg
                260                 265                 270

Pro Lys Gly Phe Pro Lys Val Gly Glu Glu
        275                 280

<210> SEQ ID NO 13
<211> LENGTH: 1270
<212> TYPE: DNA
<213> ORGANISM: Homo sapiens

<400> SEQUENCE: 13
ggaagtctgt caactgggag ggggagaggg gggtgatggg ccaggaatgg ggtccccggg      60
catggtgctg ggcctcctgg tgcagatctg ggccctgcaa gaagcctcaa gcctgagcgt     120
gcagcagggg cccaacttgc tgcaggtgag cagggcagt caggcgaccc tggtctgcca     180
ggtggaccag gccacagcct gggaacggct ccgtgttaag tggacaaagg atggggccat     240
cctgtgtcaa ccgtacatca ccaacggcag cctcagcctg gggtctgcg ggccccaggg     300 acggctctcc tggcaggcac ccagccatct caccctgcag ctggaccctg tgagcctcaa     360
ccacagcggg gcgtacgtgt gctgggcggc cgtagagatt cctgagttgg aggaggctga     420
gggcaacata caaggctct ttgtggaccc agatgacccc acacagaaca gaaaccggat     480
cgcaagcttc ccaggattcc tcttcgtgct gctgggggtg ggaagcatgg gtgtggctgc     540
gatcgtgtgg ggtgcctggt tctggggccg ccgcagctgc cagcaaaggg actcaggaaa     600
tgcattctac agcaacgtcc tataccggcc cggggggcc ccaaagaaga gtgaggactg     660
ctctggagag gggaaggacc agaggggcca gagcatttat tcaacctcct tcccgcaacc     720
ggccccccgc cagccgcacc tggcgtcaag accctgcccc agcccgagac cctgccccag     780
ccccaggccc ggccacccg tctctatggt cagggtctct cctagaccaa gccccaccca     840
gcagccgagg ccaaaagggt tccccaaagt gggagaggag tgagagatcc caggagacct     900
```

```
caacaggacc ccacccatag gtacacacaa aaaaggggggg atcgaggcca gacacggtgg    960
ctcacgcctg taatcccagc agtttgggaa gccgaggcgg gtggaacact tgaggtcagg   1020
ggtttgagac cagcctggct tgaacctggg aggcggaggt tgcagtgagc cgagattgcg   1080
ccactgcact ccagcctggg cgacagagtg agactccgtc tcaaaaaaaa caaaaagcag   1140
gaggattggg agcctgtcag ccccatcctg agaccccgtc ctcatttctg taatgatgga   1200
tctcgctccc actttccccc aagaacctaa taaaggcttg tgaagaaaaa gcaaaaaaaa   1260
aaaaaaaaaa                                                          1270
```

<210> SEQ ID NO 14
<211> LENGTH: 278
<212> TYPE: PRT
<213> ORGANISM: Homo sapiens

<400> SEQUENCE: 14

```
Met Gly Ser Pro Gly Met Val Leu Gly Leu Leu Val Gln Ile Trp Ala
1               5                   10                  15

Leu Gln Glu Ala Ser Ser Leu Ser Val Gln Gln Gly Pro Asn Leu Leu
            20                  25                  30

Gln Val Arg Gln Gly Ser Gln Ala Thr Leu Val Cys Gln Val Asp Gln
        35                  40                  45

Ala Thr Ala Trp Glu Arg Leu Arg Val Lys Trp Thr Lys Asp Gly Ala
    50                  55                  60

Ile Leu Cys Gln Pro Tyr Ile Thr Asn Gly Ser Leu Ser Leu Gly Val
65                  70                  75                  80

Cys Gly Pro Gln Gly Arg Leu Ser Trp Gln Ala Pro Ser His Leu Thr
                85                  90                  95

Leu Gln Leu Asp Pro Val Ser Leu Asn His Ser Gly Ala Tyr Val Cys
            100                 105                 110

Trp Ala Ala Val Glu Ile Pro Glu Leu Glu Glu Ala Glu Gly Asn Ile
        115                 120                 125

Thr Arg Leu Phe Val Asp Pro Asp Pro Thr Gln Asn Arg Asn Arg
    130                 135                 140

Ile Ala Ser Phe Pro Gly Phe Leu Phe Val Leu Leu Gly Val Gly Ser
145                 150                 155                 160

Met Gly Val Ala Ala Ile Val Trp Gly Ala Trp Phe Trp Gly Arg Arg
                165                 170                 175

Ser Cys Gln Gln Arg Asp Ser Gly Asn Ala Phe Tyr Ser Asn Val Leu
            180                 185                 190

Tyr Arg Pro Arg Gly Ala Pro Lys Lys Ser Glu Asp Cys Ser Gly Glu
        195                 200                 205

Gly Lys Asp Gln Arg Gly Gln Ser Ile Tyr Ser Thr Ser Phe Pro Gln
    210                 215                 220

Pro Ala Pro Arg Gln Pro His Leu Ala Ser Arg Pro Cys Pro Ser Pro
225                 230                 235                 240

Arg Pro Cys Pro Ser Pro Arg Pro Gly His Pro Val Ser Met Val Arg
                245                 250                 255

Val Ser Pro Arg Pro Ser Pro Thr Gln Gln Pro Arg Pro Lys Gly Phe
            260                 265                 270

Pro Lys Val Gly Glu Glu
        275
```

<210> SEQ ID NO 15
<211> LENGTH: 918

```
<212> TYPE: DNA
<213> ORGANISM: Homo sapiens

<400> SEQUENCE: 15
ggaagtctgt caactgggag ggggagaggg gggtgatggg ccaggaatgg ggtccccggg      60
catggtgctg ggcctcctgg tgcagatctg ggatgacccc acacagaaca gaaaccggat     120
cgcaagcttc ccaggattcc tcttcgtgct gctgggggtg ggaagcatgg gtgtggctgc     180
gatcgtgtgg ggtgcctggt tctggggccg ccgcagctgc cagcaaaggg actcaggtaa     240
cagcccagga aatgcattct acagcaacgt cctataccgg ccccggggg ccccaaagaa      300
gagtgaggac tgctctggag aggggaagga ccagaggggc cagagcattt attcaacctc     360
cttcccgcaa ccggccccc gccagccgca cctggcgtca agaccctgcc ccagcccgag      420
accctgcccc agccccaggc ccggccaccc cgtctctatg gtcagggtct ctcctagacc     480
aagcccacc cagcagccga ggccaaaagg gttccccaaa gtgggagagg agtgagagat      540
cccaggagac ctcaacagga ccccacccat aggtacacac aaaaaagggg ggatcgaggc     600
cagacacggt ggctcacgcc tgtaatccca gcagtttggg aagccgaggc gggtggaaca     660
cttgaggtca ggggtttgag accagcctgg cttgaacctg ggaggcggag gttgcagtga     720
gccgagattg cgccactgca ctccagcctg ggcgacagag tgagactccg tctcaaaaaa     780
aacaaaaagc aggaggattg ggagcctgtc agccccatcc tgagacccg tcctcatttc      840
tgtaatgatg gatctcgctc ccactttccc ccaagaacct aataaaggct tgtgaagaaa     900
aagcaaaaaa aaaaaaaa                                                   918

<210> SEQ ID NO 16
<211> LENGTH: 162
<212> TYPE: PRT
<213> ORGANISM: Homo sapiens

<400> SEQUENCE: 16

Met Gly Ser Pro Gly Met Val Leu Gly Leu Leu Val Gln Ile Trp Asp
1               5                   10                  15

Asp Pro Thr Gln Asn Arg Asn Arg Ile Ala Ser Phe Pro Gly Phe Leu
                20                  25                  30

Phe Val Leu Leu Gly Val Gly Ser Met Gly Val Ala Ala Ile Val Trp
            35                  40                  45

Gly Ala Trp Phe Trp Gly Arg Arg Ser Cys Gln Gln Arg Asp Ser Gly
        50                  55                  60

Asn Ser Pro Gly Asn Ala Phe Tyr Ser Asn Val Leu Tyr Arg Pro Arg
65                  70                  75                  80

Gly Ala Pro Lys Lys Ser Glu Asp Cys Ser Gly Glu Gly Lys Asp Gln
                85                  90                  95

Arg Gly Gln Ser Ile Tyr Ser Thr Ser Phe Pro Gln Pro Ala Pro Arg
            100                 105                 110

Gln Pro His Leu Ala Ser Arg Pro Cys Pro Ser Pro Arg Pro Cys Pro
        115                 120                 125

Ser Pro Arg Pro Gly His Pro Val Ser Met Val Arg Val Ser Pro Arg
130                 135                 140

Pro Ser Pro Thr Gln Gln Pro Arg Pro Lys Gly Phe Pro Lys Val Gly
145                 150                 155                 160

Glu Glu

<210> SEQ ID NO 17
```

-continued

```
<211> LENGTH: 1723
<212> TYPE: DNA
<213> ORGANISM: Homo sapiens

<400> SEQUENCE: 17
tgctgctgaa ctgagctggg gcgcagccgc ctgtctgcac cggcagcacc atgtcgctca      60
tggtcgtcag catggcgtgt gttgggttct tcttgctgga ggggccctgg ccacatgtgg     120
gtggtcagga caagcccttc ctctctgcct ggcccggcac tgtggtgtct gaaggacaac     180
atgtgactct tcagtgtcgc tctcgtcttg ggtttaatga attcagtctg tccaaagaag     240
acgggatgcc tgtccctgag ctctacaaca gaatattccg gaacagcttt tcatgggcc      300
ctgtgacccc agcacatgca gggacctaca gatgttgcag ttcacaccca cactccccca     360
ctgggtggtc ggcacccagc aaccctgtgg tgatcatggt cacaggagtc cacagaaaac     420
cttccctcct ggcccaccca gtccctgg tgaaatcagg agagacggtc atcctgcaat       480
gttggtcaga tgtcaggttt gagcgcttcc ttctgcacag agaggggatc actgaggacc     540
ccttgcgcct cgttggacag ctccacgatg cgggttccca ggtcaactat tccatgggtc     600
ccatgacacc tgcccttgca gggacctaca gatgctttgg ttctgtcact cacttaccct     660
atgagttgtc ggctcccagt gaccctctgg acatcgtggt cgtaggtcta tatgggaaac     720
cttctctctc agcccagccg ggccccacgg ttcaggcagg agagaatgtg accttgtcct     780
gcagctcccg gagcttgttt gacatttacc atctatccag ggaggcggag gccggtgaac     840
ttaggctcac tgcagtgctg agggtcaatg gaacattcca ggccaacttc cctctgggcc     900
ctgtgaccca cggagggaac tacagatgct tcggctcttt ccgtgccctg ccccatgcgt     960
ggtcagaccc gagtgaccca ctgccgtttt ctgtcacagg taactccaga aacctgcacg    1020
ttctgattgg gacctcagtg gtcatcatcc cctttgctat cctcctcttc tttctccttc    1080
atcgctggtg tgccaacaaa agaatgctg ttgtaatgga ccaagagcct gcaggaaca     1140
gaacagtgaa cagggaggac tctgatgaac aagaccctca ggaggtgaca tacgcacagt    1200
tgaatcactg cgttttcaca cagagaaaaa tcactcgccc ttctcagagg cccaagacac    1260
ccccaacaga taccagcgtg taacacggaa cttccaaatg ctgagcgcag atccaaagtt    1320
gtcttctgtc cactagcacc acagtcaggc cttgatggga tcttctaggg agacaatagc    1380
cctgtctcaa aaccgggttg ccagctccca tgtaccagca gctggactct gaaggcgtga    1440
gtctgcatct tagggcatcg ctcttcctca caccacgaat ctgaacatgc ctctctcttg    1500
cttacaaatg tctaaggtcc ccactgcctg ctggagagaa aacacacttg cttagcccac    1560
aattctccat ttcacttgac ccctgcccac ctctccaacc taactggctt acttcctagt    1620
ctacttgagg ctgcgatcac actgaggaac tcacaattcc aaacatataa gaggctccct    1680
cttaacacgg cacttagata cgtgctattc acctttcct cag                       1723

<210> SEQ ID NO 18
<211> LENGTH: 410
<212> TYPE: PRT
<213> ORGANISM: Homo sapiens

<400> SEQUENCE: 18

Met Ser Leu Met Val Val Ser Met Ala Cys Val Gly Phe Phe Leu Leu
1               5                   10                  15

Glu Gly Pro Trp Pro His Val Gly Gly Gln Asp Lys Pro Phe Leu Ser
            20                  25                  30

Ala Trp Pro Gly Thr Val Val Ser Glu Gly Gln His Val Thr Leu Gln
```

```
                 35                  40                  45
Cys Arg Ser Arg Leu Gly Phe Asn Glu Phe Ser Leu Ser Lys Glu Asp
 50                  55                  60

Gly Met Pro Val Pro Glu Leu Tyr Asn Arg Ile Phe Arg Asn Ser Phe
 65                  70                  75                  80

Leu Met Gly Pro Val Thr Pro Ala His Ala Gly Thr Tyr Arg Cys Cys
                 85                  90                  95

Ser Ser His Pro His Ser Pro Thr Gly Trp Ser Ala Pro Ser Asn Pro
                100                 105                 110

Val Val Ile Met Val Thr Gly Val His Arg Lys Pro Ser Leu Leu Ala
                115                 120                 125

His Pro Gly Pro Leu Val Lys Ser Gly Glu Thr Val Ile Leu Gln Cys
130                 135                 140

Trp Ser Asp Val Arg Phe Glu Arg Phe Leu Leu His Arg Glu Gly Ile
145                 150                 155                 160

Thr Glu Asp Pro Leu Arg Leu Val Gly Gln Leu His Asp Ala Gly Ser
                165                 170                 175

Gln Val Asn Tyr Ser Met Gly Pro Met Thr Pro Ala Leu Ala Gly Thr
                180                 185                 190

Tyr Arg Cys Phe Gly Ser Val Thr His Leu Pro Tyr Glu Leu Ser Ala
                195                 200                 205

Pro Ser Asp Pro Leu Asp Ile Val Val Val Gly Leu Tyr Gly Lys Pro
210                 215                 220

Ser Leu Ser Ala Gln Pro Gly Pro Thr Val Gln Ala Gly Glu Asn Val
225                 230                 235                 240

Thr Leu Ser Cys Ser Ser Arg Ser Leu Phe Asp Ile Tyr His Leu Ser
                245                 250                 255

Arg Glu Ala Glu Ala Gly Glu Leu Arg Leu Thr Ala Val Leu Arg Val
                260                 265                 270

Asn Gly Thr Phe Gln Ala Asn Phe Pro Leu Gly Pro Val Thr His Gly
                275                 280                 285

Gly Asn Tyr Arg Cys Phe Gly Ser Phe Arg Ala Leu Pro His Ala Trp
                290                 295                 300

Ser Asp Pro Ser Asp Pro Leu Pro Val Ser Val Thr Gly Asn Ser Arg
305                 310                 315                 320

Asn Leu His Val Leu Ile Gly Thr Ser Val Val Ile Ile Pro Phe Ala
                325                 330                 335

Ile Leu Leu Phe Phe Leu Leu His Arg Trp Cys Ala Asn Lys Lys Asn
                340                 345                 350

Ala Val Val Met Asp Gln Glu Pro Ala Gly Asn Arg Thr Val Asn Arg
                355                 360                 365

Glu Asp Ser Asp Glu Gln Asp Pro Gln Glu Val Thr Tyr Ala Gln Leu
                370                 375                 380

Asn His Cys Val Phe Thr Gln Arg Lys Ile Thr Arg Pro Ser Gln Arg
385                 390                 395                 400

Pro Lys Thr Pro Pro Thr Asp Thr Ser Val
                405                 410

<210> SEQ ID NO 19
<211> LENGTH: 134
<212> TYPE: PRT
<213> ORGANISM: Artificial Sequence
<220> FEATURE:
<223> OTHER INFORMATION: Description of Artificial Sequence: Synthetic
      polypeptide
```

<400> SEQUENCE: 19

Met Leu Leu Gly Leu Lys Trp Ile Phe Phe Val Val Phe Tyr Gln Gly
1               5                   10                  15

Val His Cys Glu Val Gln Leu Val Glu Thr Gly Gly Gly Leu Val Gln
            20                  25                  30

Pro Lys Gly Ser Leu Lys Leu Ser Cys Ala Ala Ser Gly Phe Thr Phe
        35                  40                  45

Asn Thr Asn Val Met Asn Trp Val Arg Gln Ala Pro Gly Lys Gly Leu
    50                  55                  60

Glu Trp Val Gly Arg Ile Arg Thr Lys Thr Asn Asn Tyr Ala Thr Tyr
65                  70                  75                  80

Tyr Ala Asp Ser Val Lys Gly Arg Phe Thr Ile Ser Arg Asp Asp Ser
                85                  90                  95

Gln Ser Met Leu Tyr Leu Gln Met Asn Asn Leu Lys Thr Glu Asp Thr
            100                 105                 110

Ala Thr Tyr Phe Cys Val Gly Ala Met Asp Tyr Trp Gly Gln Gly Thr
        115                 120                 125

Ser Val Thr Val Ser Ser
    130

<210> SEQ ID NO 20
<211> LENGTH: 402
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 20
atgctgttgg ggctgaagtg gatttctttt gttgtttttt atcaaggtgt gcattgtgag      60
gtgcaacttg ttgagactgg tggaggattg gtgcagccta aagggtcatt gaaactctca     120
tgtgcagcct ctggattcac cttcaacacc aatgtcatga actgggtccg ccaggctcca     180
ggaaagggtt tggaatgggt tggtcgcata agaactaaaa ctaataatta tgcaacatat     240
tatgccgatt cagtgaaagg caggttcacc atctccagag atgattcaca agtatgctc     300 tatctgcaaa tgaacaactt gaaaactgag gacacagcca cgtatttctg tgtgggagct     360
atggactact ggggtcaagg aacctcagtc accgtctcct ca                        402

<210> SEQ ID NO 21
<211> LENGTH: 57
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 21
atgctgttgg ggctgaagtg gatttctttt gttgtttttt atcaaggtgt gcattgt        57

<210> SEQ ID NO 22
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Met Leu Leu Gly Leu Lys Trp Ile Phe Phe Val Val Phe Tyr Gln Gly
1               5                   10                  15

Val His Cys

<210> SEQ ID NO 23
<211> LENGTH: 75
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 23
gaggtgcaac ttgttgagac tggtggagga ttggtgcagc ctaaagggtc attgaaactc    60
tcatgtgcag cctct                                                    75

<210> SEQ ID NO 24
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Glu Val Gln Leu Val Glu Thr Gly Gly Gly Leu Val Gln Pro Lys Gly
1               5                   10                  15

Ser Leu Lys Leu Ser Cys Ala Ala Ser
            20                  25

<210> SEQ ID NO 25
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 25
ggattcacct tcaacaccaa t                                             21

<210> SEQ ID NO 26
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

Gly Phe Thr Phe Asn Thr Asn
1               5

<210> SEQ ID NO 27
<211> LENGTH: 57
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 27
gtcatgaact gggtccgcca ggctccagga aagggtttgg aatgggttgg tcgcata      57

<210> SEQ ID NO 28

```
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

Val Met Asn Trp Val Arg Gln Ala Pro Gly Lys Gly Leu Glu Trp Val
1               5                   10                  15

Gly Arg Ile

<210> SEQ ID NO 29
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 29
agaactaaaa ctaataatta tgca                                          24

<210> SEQ ID NO 30
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 30

Arg Thr Lys Thr Asn Asn Tyr Ala
1               5

<210> SEQ ID NO 31
<211> LENGTH: 123
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 31
acatattatg ccgattcagt gaaaggcagg ttcaccatct ccagagatga ttcacaaagt     60
atgctctatc tgcaaatgaa caacttgaaa actgaggaca cagccacgta tttctgtgtg    120
gga                                                                 123

<210> SEQ ID NO 32
<211> LENGTH: 41
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 32

Thr Tyr Tyr Ala Asp Ser Val Lys Gly Arg Phe Thr Ile Ser Arg Asp
1               5                   10                  15

Asp Ser Gln Ser Met Leu Tyr Leu Gln Met Asn Asn Leu Lys Thr Glu
                20                  25                  30

Asp Thr Ala Thr Tyr Phe Cys Val Gly
            35                  40
```

```
<210> SEQ ID NO 33
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 33
gctatggact ac                                                             12

<210> SEQ ID NO 34
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 34

Ala Met Asp Tyr
1

<210> SEQ ID NO 35
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 35
tggggtcaag gaacctcagt caccgtctcc tca                                      33

<210> SEQ ID NO 36
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 36

Trp Gly Gln Gly Thr Ser Val Thr Val Ser Ser
1               5                   10

<210> SEQ ID NO 37
<211> LENGTH: 131
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 37

Met Glu Thr Asp Thr Leu Leu Leu Trp Val Leu Leu Leu Trp Val Pro
1               5                   10                  15

Gly Ser Thr Gly Asp Ile Val Leu Thr Gln Ser Pro Ala Ser Leu Ala
            20                  25                  30

Val Ser Leu Gly Gln Arg Ala Thr Val Ser Cys Arg Ala Ser Glu Ser
        35                  40                  45

Val Asp Asn Ser Gly Ile Asn Phe Ile His Trp Tyr Gln Gln Lys Pro
    50                  55                  60

Gly Gln Ser Pro Lys Leu Leu Ile Tyr Arg Ala Ser Asn Leu Lys Ser
65                  70                  75                  80
```

Gly Ile Pro Ala Arg Phe Ser Gly Ser Gly Ser Arg Thr Asp Phe Thr
                85                  90                  95

Leu Thr Ile Asn Pro Val Glu Thr Gly Asp Val Ala Thr Tyr Tyr Cys
            100                 105                 110

Gln Gln Ser Tyr Lys Asp Pro Pro Thr Phe Gly Thr Gly Thr Lys Leu
        115                 120                 125

Glu Leu Lys
    130

<210> SEQ ID NO 38
<211> LENGTH: 393
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 38
atggagacag acacactcct gctatgggtg ctgctgctct ggttccagg ttccacaggt      60 gacattgtgc tgacccaatc tccagcttct ttggctgtgt ctctggggca gagggccacc    120
gtctcctgca gagccagcga aagtgttgat aattctggca taaatttat acactggtac    180 cagcagaaac caggacagtc acccaaactc ctcctctatc gtgcatccaa cctaaaatct    240
gggatccctg ccaggttcag tggcagtggg tctaggacag acttcaccct caccattaat    300
cctgtggaga ctggtgatgt tgcaacctat tactgtcagc aaagttataa ggatcctcct    360
acgttcggta ctgggaccaa gctggagctg aag                                 393

<210> SEQ ID NO 39
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 39
atggagacag acacactcct gctatgggtg ctgctgctct ggttccagg ttccacaggt      60

<210> SEQ ID NO 40
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 40

Met Glu Thr Asp Thr Leu Leu Leu Trp Val Leu Leu Leu Trp Val Pro
1               5                   10                  15

Gly Ser Thr Gly
            20

<210> SEQ ID NO 41
<211> LENGTH: 69
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 41
gacattgtgc tgacccaatc tccagcttct ttggctgtgt ctctggggca gagggccacc      60
gtctcctgc                                                           69

<210> SEQ ID NO 42
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 42

Asp Ile Val Leu Thr Gln Ser Pro Ala Ser Leu Ala Val Ser Leu Gly
1               5                   10                  15

Gln Arg Ala Thr Val Ser Cys
            20

<210> SEQ ID NO 43
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 43
agagccagcg aaagtgttga taattctggc ataaatttta tacac              45

<210> SEQ ID NO 44
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 44

Arg Ala Ser Glu Ser Val Asp Asn Ser Gly Ile Asn Phe Ile His
1               5                   10                  15

<210> SEQ ID NO 45
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 45
tggtaccagc agaaaccagg acagtcaccc aaactcctcc tctat              45

<210> SEQ ID NO 46
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 46

Trp Tyr Gln Gln Lys Pro Gly Gln Ser Pro Lys Leu Leu Leu Tyr
1               5                   10                  15

<210> SEQ ID NO 47
<211> LENGTH: 21
<212> TYPE: DNA
<213> ORGANISM: Artificial Sequence

```
<220> FEATURE:
<223> OTHER INFORMATION: Description of Artificial Sequence: Synthetic
      oligonucleotide

<400> SEQUENCE: 47
cgtgcatcca acctaaaatc t                                              21

<210> SEQ ID NO 48
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 48

Arg Ala Ser Asn Leu Lys Ser
1               5

<210> SEQ ID NO 49
<211> LENGTH: 96
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 49
gggatccctg ccaggttcag tggcagtggg tctaggacag acttcaccct caccattaat   60
cctgtggaga ctggtgatgt tgcaacctat tactgt                             96

<210> SEQ ID NO 50
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 50

Gly Ile Pro Ala Arg Phe Ser Gly Ser Gly Ser Arg Thr Asp Phe Thr
1               5                   10                  15

Leu Thr Ile Asn Pro Val Glu Thr Gly Asp Val Ala Thr Tyr Tyr Cys
                20                  25                  30

<210> SEQ ID NO 51
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 51
cagcaaagtt ataaggatcc tcctacg                                        27

<210> SEQ ID NO 52
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 52

Gln Gln Ser Tyr Lys Asp Pro Pro Thr
```

<210> SEQ ID NO 53
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 53
ttcggtactg ggaccaagct ggagctgaag                                        30

<210> SEQ ID NO 54
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 54

Phe Gly Thr Gly Thr Lys Leu Glu Leu Lys
1               5                   10

<210> SEQ ID NO 55
<211> LENGTH: 134
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 55

Met Leu Leu Gly Leu Lys Trp Ile Phe Phe Val Val Phe Tyr Gln Gly
1               5                   10                  15

Val His Cys Glu Val Gln Leu Val Glu Thr Gly Gly Gly Leu Val Gln
                20                  25                  30

Pro Lys Gly Ser Leu Lys Leu Ser Cys Ala Ala Ser Gly Phe Thr Phe
            35                  40                  45

Asn Thr Asn Val Met Asn Trp Val Arg Gln Ala Pro Gly Lys Gly Leu
        50                  55                  60

Glu Trp Val Ala Arg Ile Arg Thr Lys Thr Asn Asn Tyr Ala Thr Tyr
65                  70                  75                  80

Tyr Ala Asp Ser Val Lys Asp Arg Phe Thr Ile Phe Arg Asp Asp Ser
                85                  90                  95

Gln Ser Ile Leu Tyr Leu Gln Met Asn Asn Leu Lys Thr Glu Asp Thr
            100                 105                 110

Ala Met Tyr Tyr Cys Val Gly Ala Met Asp Tyr Trp Gly Gln Gly Thr
        115                 120                 125

Ser Val Thr Val Ser Ser
    130

<210> SEQ ID NO 56
<211> LENGTH: 402
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 56
atgctgttgg ggctgaagtg gattttcttt gttgtttttt atcaaggtgt gcattgtgag    60

```
gtgcagcttg ttgagactgg tggaggattg gtgcagccta aagggtcatt gaaactctca    120
tgtgcagcct ctggattcac cttcaatacc aatgtcatga actgggtccg ccaggctcca    180
ggaaagggtt tggaatgggt tgctcgcata agaactaaaa ctaataatta tgcaacatat    240
tatgccgatt cagtgaaaga caggttcacc atcttcagag atgattcaca aagcattctc    300
tatctgcaaa tgaacaactt gaaaactgag gacacagcca tgtattactg tgtgggagct    360
atggactact ggggtcaagg aacctcagtc accgtctcct ca                      402
```

<210> SEQ ID NO 57
<211> LENGTH: 57
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 57

```
atgctgttgg ggctgaagtg gatttctttt gttgtttttt atcaaggtgt gcattgt     57
```

<210> SEQ ID NO 58
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 58

```
Met Leu Leu Gly Leu Lys Trp Ile Phe Phe Val Val Phe Tyr Gln Gly
1               5                   10                  15

Val His Cys
```

<210> SEQ ID NO 59
<211> LENGTH: 75
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 59

```
gaggtgcagc ttgttgagac tggtggagga ttggtgcagc ctaaagggtc attgaaactc    60
tcatgtgcag cctct                                                     75
```

<210> SEQ ID NO 60
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 60

```
Glu Val Gln Leu Val Glu Thr Gly Gly Gly Leu Val Gln Pro Lys Gly
1               5                   10                  15

Ser Leu Lys Leu Ser Cys Ala Ala Ser
            20                  25
```

<210> SEQ ID NO 61
<211> LENGTH: 21
<212> TYPE: DNA
<213> ORGANISM: Artificial Sequence

```
<220> FEATURE:
<223> OTHER INFORMATION: Description of Artificial Sequence: Synthetic
      oligonucleotide

<400> SEQUENCE: 61
ggattcacct tcaataccaa t                                              21

<210> SEQ ID NO 62
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 62

Gly Phe Thr Phe Asn Thr Asn
1               5

<210> SEQ ID NO 63
<211> LENGTH: 57
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 63
gtcatgaact gggtccgcca ggctccagga aagggtttgg aatgggttgc tcgcata      57

<210> SEQ ID NO 64
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 64

Val Met Asn Trp Val Arg Gln Ala Pro Gly Lys Gly Leu Glu Trp Val
1               5                   10                  15

Ala Arg Ile

<210> SEQ ID NO 65
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 65
agaactaaaa ctaataatta tgca                                           24

<210> SEQ ID NO 66
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 66

Arg Thr Lys Thr Asn Asn Tyr Ala
1               5
```

<210> SEQ ID NO 67
<211> LENGTH: 123
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 67
acatattatg ccgattcagt gaaagacagg ttcaccatct tcagagatga ttcacaaagc    60
attctctatc tgcaaatgaa caacttgaaa actgaggaca cagccatgta ttactgtgtg   120
gga                                                                 123

<210> SEQ ID NO 68
<211> LENGTH: 41
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 68

Thr Tyr Tyr Ala Asp Ser Val Lys Asp Arg Phe Thr Ile Phe Arg Asp
1               5                   10                  15

Asp Ser Gln Ser Ile Leu Tyr Leu Gln Met Asn Asn Leu Lys Thr Glu
            20                  25                  30

Asp Thr Ala Met Tyr Tyr Cys Val Gly
        35                  40

<210> SEQ ID NO 69
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 69
gctatggact ac                                                        12

<210> SEQ ID NO 70
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 70

Ala Met Asp Tyr
1

<210> SEQ ID NO 71
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 71
tggggtcaag gaacctcagt caccgtctcc tca                                 33

<210> SEQ ID NO 72
<211> LENGTH: 11

<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 72

Trp Gly Gln Gly Thr Ser Val Thr Val Ser Ser
1               5                   10

<210> SEQ ID NO 73
<211> LENGTH: 131
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 73

Met Glu Thr Asp Thr Leu Leu Leu Trp Val Leu Leu Leu Trp Val Pro
1               5                   10                  15

Gly Ser Thr Gly Asp Ile Val Leu Thr Gln Ser Pro Ala Ser Leu Ala
            20                  25                  30

Val Ser Leu Gly Gln Arg Ala Thr Ile Ser Cys Arg Ala Ser Glu Ser
        35                  40                  45

Val Asp Asn Tyr Gly Ile Ser Phe Met His Trp Tyr Gln Gln Lys Pro
    50                  55                  60

Gly Gln Pro Pro Lys Leu Leu Ile Tyr Arg Ala Ser Asn Leu Lys Ser
65                  70                  75                  80

Gly Ile Pro Ala Arg Phe Ser Gly Ser Gly Ser Arg Thr Asp Phe Thr
                85                  90                  95

Leu Thr Ile Asn Pro Val Glu Thr Gly Asp Val Ala Thr Tyr Tyr Cys
            100                 105                 110

Gln Gln Ser Ser Lys Asp Pro Pro Thr Phe Gly Thr Gly Thr Lys Leu
        115                 120                 125

Glu Leu Lys
    130

<210> SEQ ID NO 74
<211> LENGTH: 393
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 74
atggagacag acacactcct gctatgggtg ctgctgctct gggttccagg ttccacaggt      60
gacattgtgc tgacccaatc tccagcttct ttggctgtgt ctctagggca gagggccacc     120
atctcctgca gagccagcga gagtgttgat aattatggca ttagttttat gcactggtac     180
cagcagaaac aggacagcc acccaaactc ctcatctatc gtgcatccaa cctaaaatct     240
gggatccctg ccaggttcag tggcagtggg tctaggacag acttcaccct caccattaat     300
cctgtggaga ctggtgatgt tgctacctat tactgtcagc aaagtagtaa ggatcctcct     360
acgttcggta ctgggaccaa gctagagctg aaa                                  393

<210> SEQ ID NO 75
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 75
atggagacag acacactcct gctatgggtg ctgctgctct ggttccagg ttccacaggt    60

<210> SEQ ID NO 76
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 76

Met Glu Thr Asp Thr Leu Leu Leu Trp Val Leu Leu Leu Trp Val Pro
1               5                   10                  15

Gly Ser Thr Gly
            20

<210> SEQ ID NO 77
<211> LENGTH: 69
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 77
gacattgtgc tgacccaatc tccagcttct ttggctgtgt ctctagggca gagggccacc    60
atctcctgc                                                            69

<210> SEQ ID NO 78
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 78

Asp Ile Val Leu Thr Gln Ser Pro Ala Ser Leu Ala Val Ser Leu Gly
1               5                   10                  15

Gln Arg Ala Thr Ile Ser Cys
            20

<210> SEQ ID NO 79
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 79
agagccagcg agagtgttga taattatggc attagtttta tgcac                    45

<210> SEQ ID NO 80
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 80

Arg Ala Ser Glu Ser Val Asp Asn Tyr Gly Ile Ser Phe Met His
1               5                   10                  15

<210> SEQ ID NO 81
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 81
tggtaccagc agaaaccagg acagccaccc aaactcctca tctat              45

<210> SEQ ID NO 82
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 82

Trp Tyr Gln Gln Lys Pro Gly Gln Pro Pro Lys Leu Leu Ile Tyr
1               5                   10                  15

<210> SEQ ID NO 83
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 83
cgtgcatcca acctaaaatc t                                        21

<210> SEQ ID NO 84
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 84

Arg Ala Ser Asn Leu Lys Ser
1               5

<210> SEQ ID NO 85
<211> LENGTH: 96
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 85
gggatccctg ccaggttcag tggcagtggg tctaggacag acttcaccct caccattaat    60
cctgtggaga ctggtgatgt tgctacctat tactgt                              96

<210> SEQ ID NO 86
<211> LENGTH: 32
<212> TYPE: PRT
<213> ORGANISM: Artificial Sequence
```

<220> FEATURE:
<223> OTHER INFORMATION: Description of Artificial Sequence: Synthetic
      polypeptide

<400> SEQUENCE: 86

```
Gly Ile Pro Ala Arg Phe Ser Gly Ser Gly Ser Arg Thr Asp Phe Thr
1               5                   10                  15

Leu Thr Ile Asn Pro Val Glu Thr Gly Asp Val Ala Thr Tyr Tyr Cys
            20                  25                  30
```

<210> SEQ ID NO 87
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 87
cagcaaagta gtaaggatcc tcctacg                                            27

<210> SEQ ID NO 88
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 88

```
Gln Gln Ser Ser Lys Asp Pro Pro Thr
1               5
```

<210> SEQ ID NO 89
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 89
ttcggtactg ggaccaagct agagctgaaa                                         30

<210> SEQ ID NO 90
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 90

```
Phe Gly Thr Gly Thr Lys Leu Glu Leu Lys
1               5                   10
```

<210> SEQ ID NO 91
<211> LENGTH: 135
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 91

```
Met Glu Arg His Trp Ile Phe Leu Phe Leu Leu Ser Val Thr Ala Gly
1               5                   10                  15
```

Val His Ser Gln Val His Leu Gln Gln Ser Ala Ala Glu Leu Ala Arg
         20                  25                  30

Pro Gly Ala Ser Val Lys Met Ser Cys Lys Ala Ser Gly Tyr Thr Phe
             35                  40                  45

Thr Thr Tyr Thr Met His Trp Val Lys Gln Arg Pro Gly Gln Gly Leu
 50                  55                  60

Glu Trp Ile Gly His Ile Asn Pro Ser Gly Tyr Thr Asp Tyr Asn
 65                  70                  75                  80

Gln Lys Phe Lys Asp Lys Thr Thr Leu Thr Ala Asp Lys Ser Ser Ser
                 85                  90                  95

Thr Ala Tyr Met Gln Leu Asn Ser Leu Thr Ser Glu Asp Ser Ala Val
             100                 105                 110

Tyr Tyr Cys Ala Arg His Pro Trp Asp Ser Asp Tyr Trp Gly Gln Gly
         115                 120                 125

Thr Thr Leu Thr Val Ser Ser
         130                 135

<210> SEQ ID NO 92
<211> LENGTH: 405
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 92
atggaaaggc actggatctt tctcttcctg ttgtcagtaa ctgcaggtgt ccactcccag     60
gtccacctgc agcagtctgc agctgaactg caagacctg  ggcctcagt gaagatgtcc    120 tgcaaggctt ctggctacac ctttactacc tacacgatgc actgggtaaa acagaggcct    180
ggacagggtc tggaatggat tggacacatt aatcctagca gtggatatac tgattacaat    240
cagaaattca aggacaagac cacattgact gcagacaaat cctccagtac agcctacatg    300
caactgaaca gcctgacatc tgaggactct gcggtctatt actgtgcaag acacccctgg    360
gactcggact actggggcca aggcaccact ctcacagtct cctca                    405

<210> SEQ ID NO 93
<211> LENGTH: 57
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 93
atggaaaggc actggatctt tctcttcctg ttgtcagtaa ctgcaggtgt ccactcc       57

<210> SEQ ID NO 94
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 94

Met Glu Arg His Trp Ile Phe Leu Phe Leu Leu Ser Val Thr Ala Gly
 1               5                  10                  15

Val His Ser

<210> SEQ ID NO 95
<211> LENGTH: 75
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 95
caggtccacc tgcagcagtc tgcagctgaa ctggcaagac ctggggcctc agtgaagatg    60
tcctgcaagg cttct    75

<210> SEQ ID NO 96
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 96

Gln Val His Leu Gln Gln Ser Ala Ala Glu Leu Ala Arg Pro Gly Ala
1               5                   10                  15

Ser Val Lys Met Ser Cys Lys Ala Ser
            20                  25

<210> SEQ ID NO 97
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 97
ggctacacct ttactaccta c    21

<210> SEQ ID NO 98
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 98

Gly Tyr Thr Phe Thr Thr Tyr
1               5

<210> SEQ ID NO 99
<211> LENGTH: 57
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 99
acgatgcact gggtaaaaca gaggcctgga cagggtctgg aatggattgg acacatt    57

<210> SEQ ID NO 100
<211> LENGTH: 19
<212> TYPE: PRT
<213> ORGANISM: Artificial Sequence
<220> FEATURE:
<223> OTHER INFORMATION: Description of Artificial Sequence: Synthetic peptide

<400> SEQUENCE: 100

Thr Met His Trp Val Lys Gln Arg Pro Gly Gln Gly Leu Glu Trp Ile
1               5                   10                  15

Gly His Ile

<210> SEQ ID NO 101
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 101
aatcctagca gtggatat                                                   18

<210> SEQ ID NO 102
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 102

Asn Pro Ser Ser Gly Tyr
1               5

<210> SEQ ID NO 103
<211> LENGTH: 123
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 103
actgattaca atcagaaatt caaggacaag accacattga ctgcagacaa atcctccagt      60
acagcctaca tgcaactgaa cagcctgaca tctgaggact ctgcggtcta ttactgtgca     120
aga                                                                  123

<210> SEQ ID NO 104
<211> LENGTH: 41
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 104

Thr Asp Tyr Asn Gln Lys Phe Lys Asp Lys Thr Thr Leu Thr Ala Asp
1               5                   10                  15

Lys Ser Ser Ser Thr Ala Tyr Met Gln Leu Asn Ser Leu Thr Ser Glu
            20                  25                  30

Asp Ser Ala Val Tyr Tyr Cys Ala Arg
        35                  40

<210> SEQ ID NO 105
<211> LENGTH: 21
<212> TYPE: DNA
<213> ORGANISM: Artificial Sequence
<220> FEATURE:

<223> OTHER INFORMATION: Description of Artificial Sequence: Synthetic
      oligonucleotide

<400> SEQUENCE: 105
cacccctggg actcggacta c                                              21

<210> SEQ ID NO 106
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 106

His Pro Trp Asp Ser Asp Tyr
1               5

<210> SEQ ID NO 107
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 107
tggggccaag gcaccactct cacagtctcc tca                                 33

<210> SEQ ID NO 108
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 108

Trp Gly Gln Gly Thr Thr Leu Thr Val Ser Ser
1               5                   10

<210> SEQ ID NO 109
<211> LENGTH: 127
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 109

Met Ser Val Pro Thr Gln Leu Leu Gly Leu Leu Leu Leu Trp Leu Thr
1               5                   10                  15

Asp Ala Arg Cys Asp Ile Gln Met Thr Gln Ser Pro Ala Ser Leu Ser
                20                  25                  30

Ala Ser Val Gly Glu Thr Val Thr Ile Thr Cys Arg Ala Ser Glu Asn
            35                  40                  45

Ile Asp Ser Tyr Leu Ala Trp Tyr Gln Gln Lys Gln Gly Arg Ser Pro
        50                  55                  60

Gln Leu Leu Val Tyr Ala Ala Thr Asn Leu Ala Asp Gly Val Pro Ser
65                  70                  75                  80

Arg Phe Ser Gly Ser Gly Ser Gly Thr Gln Phe Ser Leu Gln Ile Asn
                85                  90                  95

Arg Leu Gln Ser Glu Asp Val Ala Arg Tyr Tyr Cys Gln His Tyr Tyr
                100                 105                 110

Ile Thr Pro Phe Thr Phe Gly Ser Gly Thr Lys Leu Glu Ile Ala
        115                 120                 125

<210> SEQ ID NO 110
<211> LENGTH: 381
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 110
atgagtgtgc ccactcagct cctggggttg ctgctgctgt ggcttacaga tgccagatgt      60
gacatccaga tgactcagtc tccagcttcc ctgtctgcat ctgtgggaga aactgtcacc     120
atcacatgtc gagcaagtga gaatattgac agttatttag catggtatca gcagaaacag     180
ggaagatctc ctcagctcct ggtctatgct gcaacaaact tagcagatgg tgtgccatca     240
aggttcagtg gcagtggatc aggcacacag ttttctctcc agatcaaccg cctgcagtct     300
gaagatgttg cgagatatta ctgtcaacat tattatatta ctccattcac gttcggctcg     360
gggacaaaat tggaaatagc a                                                381

<210> SEQ ID NO 111
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 111
atgagtgtgc ccactcagct cctggggttg ctgctgctgt ggcttacaga tgccagatgt      60

<210> SEQ ID NO 112
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 112

Met Ser Val Pro Thr Gln Leu Leu Gly Leu Leu Leu Leu Trp Leu Thr
1               5                   10                  15

Asp Ala Arg Cys
            20

<210> SEQ ID NO 113
<211> LENGTH: 69
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 113
gacatccaga tgactcagtc tccagcttcc ctgtctgcat ctgtgggaga aactgtcacc      60
atcacatgt                                                              69

<210> SEQ ID NO 114
<211> LENGTH: 23
<212> TYPE: PRT
<213> ORGANISM: Artificial Sequence

```
<220> FEATURE:
<223> OTHER INFORMATION: Description of Artificial Sequence: Synthetic
      peptide

<400> SEQUENCE: 114

Asp Ile Gln Met Thr Gln Ser Pro Ala Ser Leu Ser Ala Ser Val Gly
1               5                   10                  15

Glu Thr Val Thr Ile Thr Cys
            20

<210> SEQ ID NO 115
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 115
cgagcaagtg agaatattga cagttattta gca                                 33

<210> SEQ ID NO 116
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 116

Arg Ala Ser Glu Asn Ile Asp Ser Tyr Leu Ala
1               5                   10

<210> SEQ ID NO 117
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 117
tggtatcagc agaaacaggg aagatctcct cagctcctgg tctat                    45

<210> SEQ ID NO 118
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 118

Trp Tyr Gln Gln Lys Gln Gly Arg Ser Pro Gln Leu Leu Val Tyr
1               5                   10                  15

<210> SEQ ID NO 119
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 119
gctgcaacaa acttagcaga t                                              21
```

<210> SEQ ID NO 120
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 120

Ala Ala Thr Asn Leu Ala Asp
1               5

<210> SEQ ID NO 121
<211> LENGTH: 96
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 121
ggtgtgccat caaggttcag tggcagtgga tcaggcacac agtttctct ccagatcaac      60 cgcctgcagt ctgaagatgt tgcgagatat tactgt                              96

<210> SEQ ID NO 122
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 122

Gly Val Pro Ser Arg Phe Ser Gly Ser Gly Ser Gly Thr Gln Phe Ser
1               5                   10                  15

Leu Gln Ile Asn Arg Leu Gln Ser Glu Asp Val Ala Arg Tyr Tyr Cys
            20                  25                  30

<210> SEQ ID NO 123
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 123
caacattatt atattactcc attcacg                                         27

<210> SEQ ID NO 124
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 124

Gln His Tyr Tyr Ile Thr Pro Phe Thr
1               5

<210> SEQ ID NO 125
<211> LENGTH: 30
<212> TYPE: DNA
<213> ORGANISM: Artificial Sequence
<220> FEATURE:

<223> OTHER INFORMATION: Description of Artificial Sequence: Synthetic
      oligonucleotide

<400> SEQUENCE: 125
ttcggctcgg ggacaaaatt ggaaatagca                                          30

<210> SEQ ID NO 126
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 126

Phe Gly Ser Gly Thr Lys Leu Glu Ile Ala
1               5                   10

<210> SEQ ID NO 127
<211> LENGTH: 134
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 127

Met Leu Leu Gly Leu Lys Trp Ile Phe Phe Val Val Phe Tyr Gln Gly
1               5                   10                  15

Val His Cys Glu Val Gln Leu Val Glu Thr Gly Gly Gly Leu Val Gln
            20                  25                  30

Pro Lys Gly Ser Leu Lys Leu Ser Cys Ala Ala Ser Gly Phe Thr Phe
        35                  40                  45

Asn Thr Asn Val Met Asn Trp Val Arg Gln Ala Pro Gly Lys Gly Leu
    50                  55                  60

Glu Trp Val Gly Arg Ile Arg Thr Lys Thr Asn Asn Tyr Ala Thr Tyr
65                  70                  75                  80

Tyr Ala Asp Ser Val Lys Gly Arg Phe Thr Ile Ser Arg Asp Asp Ser
                85                  90                  95

Gln Ser Met Leu Tyr Leu Gln Met Asn Asn Leu Lys Thr Glu Asp Thr
            100                 105                 110

Ala Thr Tyr Phe Cys Val Gly Ala Met Asp Tyr Trp Gly Gln Gly Thr
        115                 120                 125

Ser Val Thr Val Ser Ser
    130

<210> SEQ ID NO 128
<211> LENGTH: 402
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 128
atgctgttgg ggctgaagtg gatttttcttt gttgtttttt atcaaggtgt gcattgtgag        60
gtgcaacttg ttgagactgg tggaggattg gtgcagccta aagggtcatt gaaactctca       120
tgtgcagcct ctggattcac cttcaacacc aatgtcatga actgggtccg ccaggctcca       180
ggaaagggtt tggaatgggt tggtcgcata agaactaaaa ctaataatta tgcaacatat       240
tatgccgatt cagtgaaagg caggttcacc atctccagag atgattcaca agtatgctc        300

```
tatctgcaaa tgaacaactt gaaaactgag gacacagcca cgtatttctg tgtgggagct    360
atggactact ggggtcaagg aacctcagtc accgtctcct ca                      402
```

<210> SEQ ID NO 129
<211> LENGTH: 57
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 129

```
atgctgttgg ggctgaagtg gattttcttt gttgtttttt atcaaggtgt gcattgt       57
```

<210> SEQ ID NO 130
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 130

```
Met Leu Leu Gly Leu Lys Trp Ile Phe Phe Val Val Phe Tyr Gln Gly
1               5                   10                  15

Val His Cys
```

<210> SEQ ID NO 131
<211> LENGTH: 75
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 131

```
gaggtgcaac ttgttgagac tggtggagga ttggtgcagc ctaaagggtc attgaaactc    60
tcatgtgcag cctct                                                     75
```

<210> SEQ ID NO 132
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 132

```
Glu Val Gln Leu Val Glu Thr Gly Gly Gly Leu Val Gln Pro Lys Gly
1               5                   10                  15

Ser Leu Lys Leu Ser Cys Ala Ala Ser
            20                  25
```

<210> SEQ ID NO 133
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 133

```
ggattcacct tcaacaccaa t                                              21
```

```
<210> SEQ ID NO 134
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 134

Gly Phe Thr Phe Asn Thr Asn
1               5

<210> SEQ ID NO 135
<211> LENGTH: 57
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 135
gtcatgaact gggtccgcca ggctccagga aagggtttgg aatgggttgg tcgcata         57

<210> SEQ ID NO 136
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 136

Val Met Asn Trp Val Arg Gln Ala Pro Gly Lys Gly Leu Glu Trp Val
1               5                   10                  15

Gly Arg Ile

<210> SEQ ID NO 137
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 137
agaactaaaa ctaataatta tgca                                             24

<210> SEQ ID NO 138
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 138

Arg Thr Lys Thr Asn Asn Tyr Ala
1               5

<210> SEQ ID NO 139
<211> LENGTH: 123
<212> TYPE: DNA
<213> ORGANISM: Artificial Sequence
<220> FEATURE:
<223> OTHER INFORMATION: Description of Artificial Sequence: Synthetic
      polynucleotide
```

```
<400> SEQUENCE: 139
acatattatg ccgattcagt gaaaggcagg ttcaccatct ccagagatga ttcacaaagt    60
atgctctatc tgcaaatgaa caacttgaaa actgaggaca cagccacgta tttctgtgtg   120
gga                                                                 123

<210> SEQ ID NO 140
<211> LENGTH: 41
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 140

Thr Tyr Tyr Ala Asp Ser Val Lys Gly Arg Phe Thr Ile Ser Arg Asp
1               5                   10                  15

Asp Ser Gln Ser Met Leu Tyr Leu Gln Met Asn Asn Leu Lys Thr Glu
            20                  25                  30

Asp Thr Ala Thr Tyr Phe Cys Val Gly
        35                  40

<210> SEQ ID NO 141
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 141
gctatggact ac                                                        12

<210> SEQ ID NO 142
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 142

Ala Met Asp Tyr
1

<210> SEQ ID NO 143
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 143
tggggtcaag gaacctcagt caccgtctcc tca                                 33

<210> SEQ ID NO 144
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 144
```

```
Trp Gly Gln Gly Thr Ser Val Thr Val Ser Ser
1               5                   10
```

<210> SEQ ID NO 145
<211> LENGTH: 131
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 145

```
Met Glu Thr Asp Thr Leu Leu Leu Trp Val Leu Leu Leu Trp Val Pro
1               5                   10                  15

Gly Ser Thr Gly Asp Ile Val Leu Thr Gln Ser Pro Ala Ser Leu Ala
            20                  25                  30

Val Ser Leu Gly Gln Arg Ala Thr Val Ser Cys Arg Ala Ser Glu Ser
        35                  40                  45

Val Asp Asn Ser Gly Ile Asn Phe Ile His Trp Tyr Gln Gln Lys Pro
    50                  55                  60

Gly Gln Ser Pro Lys Leu Leu Leu Tyr Arg Ala Ser Asn Leu Lys Ser
65                  70                  75                  80

Gly Ile Pro Ala Arg Phe Ser Gly Ser Gly Ser Arg Thr Asp Phe Thr
                85                  90                  95

Leu Thr Ile Asn Pro Val Glu Thr Gly Asp Val Ala Thr Tyr Tyr Cys
            100                 105                 110

Gln Gln Ser Tyr Lys Asp Pro Pro Thr Phe Gly Thr Gly Thr Lys Leu
        115                 120                 125

Glu Leu Lys
    130
```

<210> SEQ ID NO 146
<211> LENGTH: 393
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 146

```
atggagacag acacactcct gctatgggtg ctgctgctct ggttccagg ttccacaggt      60 gacattgtgc tgacccaatc tccagcttct ttggctgtgt ctctggggca gagggccacc    120
gtctcctgca gagccagcga aagtgttgat aattctggca taaattttat acactggtac    180
cagcagaaac aggacagtc acccaaactc ctcctctatc gtgcatccaa cctaaaatct    240
gggatccctg ccaggttcag tggcagtggg tctaggacag acttcaccct caccattaat    300
cctgtggaga ctggtgatgt tgcaacctat tactgtcagc aaagttataa ggatcctcct    360
acgttcggta ctgggaccaa gctggagctg aag                                  393
```

<210> SEQ ID NO 147
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 147

```
atggagacag acacactcct gctatgggtg ctgctgctct ggttccagg ttccacaggt      60
```

<210> SEQ ID NO 148
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 148

Met Glu Thr Asp Thr Leu Leu Leu Trp Val Leu Leu Leu Trp Val Pro
1               5                   10                  15

Gly Ser Thr Gly
            20

<210> SEQ ID NO 149
<211> LENGTH: 69
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 149
gacattgtgc tgacccaatc tccagcttct ttggctgtgt ctctggggca gagggccacc      60
gtctcctgc                                                             69

<210> SEQ ID NO 150
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 150

Asp Ile Val Leu Thr Gln Ser Pro Ala Ser Leu Ala Val Ser Leu Gly
1               5                   10                  15

Gln Arg Ala Thr Val Ser Cys
            20

<210> SEQ ID NO 151
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 151
agagccagcg aaagtgttga taattctggc ataaatttta tacac                     45

<210> SEQ ID NO 152
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 152

Arg Ala Ser Glu Ser Val Asp Asn Ser Gly Ile Asn Phe Ile His
1               5                   10                  15

<210> SEQ ID NO 153
<211> LENGTH: 46

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 153
ctggtaccag cagaaaccag gacagtcacc caaactcctc ctctat                    46

<210> SEQ ID NO 154
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 154

Trp Tyr Gln Gln Lys Pro Gly Gln Ser Pro Lys Leu Leu Leu Tyr
1               5                   10                  15

<210> SEQ ID NO 155
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 155
cgtgcatcca acctaaaatc t                                               21

<210> SEQ ID NO 156
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 156

Arg Ala Ser Asn Leu Lys Ser
1               5

<210> SEQ ID NO 157
<211> LENGTH: 96
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 157
gggatccctg ccaggttcag tggcagtggg tctaggacag acttcaccct caccattaat    60
cctgtggaga ctggtgatgt tgcaacctat tactgt                               96

<210> SEQ ID NO 158
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 158

Gly Ile Pro Ala Arg Phe Ser Gly Ser Gly Ser Arg Thr Asp Phe Thr
1               5                   10                  15
```

Leu Thr Ile Asn Pro Val Glu Thr Gly Asp Val Ala Thr Tyr Tyr Cys
            20                  25                  30

<210> SEQ ID NO 159
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 159
cagcaaagtt ataaggatcc tcctacg                                         27

<210> SEQ ID NO 160
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 160

Gln Gln Ser Tyr Lys Asp Pro Pro Thr
1               5

<210> SEQ ID NO 161
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 161
ttcggtactg ggaccaagct ggagctgaag                                      30

<210> SEQ ID NO 162
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 162

Phe Gly Thr Gly Thr Lys Leu Glu Leu Lys
1               5                   10

<210> SEQ ID NO 163
<211> LENGTH: 135
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 163

Met Asn Phe Gly Leu Ser Leu Ile Phe Leu Val Leu Val Leu Lys Gly
1               5                   10                  15

Val Gln Cys Glu Val Met Leu Val Glu Ser Gly Gly Gly Leu Val Lys
            20                  25                  30

Pro Gly Gly Ser Leu Lys Leu Ser Cys Ala Val Ser Gly Leu Thr Phe
        35                  40                  45

Ser Ser Tyr Ala Met Ser Trp Val Arg Gln Thr Pro Glu Lys Arg Leu

```
                    50                  55                  60
Glu Trp Val Ala Thr Ile Ser Ser Gly Gly Ser His Thr Tyr Tyr Pro
 65                  70                  75                  80

Asp Ser Val Lys Gly Arg Phe Ile Ile Ser Arg Asp Asn Ala Lys Asn
                 85                  90                  95

Thr Leu Tyr Leu Gln Met Asn Ser Leu Arg Ser Glu Asp Thr Ala Met
            100                 105                 110

Tyr Tyr Cys Thr Arg Leu Gly Arg Ala Phe Asp Tyr Trp Gly Gln Gly
        115                 120                 125

Thr Thr Leu Thr Val Ser Ser
    130                 135

<210> SEQ ID NO 164
<211> LENGTH: 405
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 164
atgaacttcg ggctcagctt gattttcctt gtccttgttt taaaaggtgt ccagtgtgaa      60
gtgatgctgg tggagtcagg gggaggctta gtgaagcctg gaggatccct gaaactctcc    120
tgtgcagtct ctggattaac ttttagtagt tatgccatgt cttgggttcg ccagactccg    180
gagaagaggc tggagtgggt cgcaaccatt agtagtggtg gtagtcacac ctactatcca    240
gacagtgtga aggggcgatt catcatttct agagacaatg ccaagaacac cctgtacctg    300
caaatgaaca gtctgaggtc tgaggacacg gccatgtatt actgtacaag actgggacgg    360
gcctttgact actggggcca aggcaccact ctcacagtct cctca                    405

<210> SEQ ID NO 165
<211> LENGTH: 57
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 165
atgaacttcg ggctcagctt gattttcctt gtccttgttt taaaaggtgt ccagtgt         57

<210> SEQ ID NO 166
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 166

Met Asn Phe Gly Leu Ser Leu Ile Phe Leu Val Leu Val Leu Lys Gly
 1               5                  10                  15

Val Gln Cys

<210> SEQ ID NO 167
<211> LENGTH: 75
<212> TYPE: DNA
<213> ORGANISM: Artificial Sequence
<220> FEATURE:
<223> OTHER INFORMATION: Description of Artificial Sequence: Synthetic
      oligonucleotide
```

<400> SEQUENCE: 167
gaagtgatgc tggtggagtc aggggaggc ttagtgaagc ctggaggatc cctgaaactc      60
tcctgtgcag tctct                                                     75

<210> SEQ ID NO 168
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 168

Glu Val Met Leu Val Glu Ser Gly Gly Gly Leu Val Lys Pro Gly Gly
1               5                   10                  15

Ser Leu Lys Leu Ser Cys Ala Val Ser
            20                  25

<210> SEQ ID NO 169
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 169
ggattaactt ttagtagtta t                                              21

<210> SEQ ID NO 170
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 170

Gly Leu Thr Phe Ser Ser Tyr
1               5

<210> SEQ ID NO 171
<211> LENGTH: 57
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 171
gccatgtctt gggttcgcca gactccggag aagaggctgg agtgggtcgc aaccatt       57

<210> SEQ ID NO 172
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 172

Ala Met Ser Trp Val Arg Gln Thr Pro Glu Lys Arg Leu Glu Trp Val
1               5                   10                  15

Ala Thr Ile

<210> SEQ ID NO 173
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 173
agtagtggtg gtagtcac                                                   18

<210> SEQ ID NO 174
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 174

Ser Ser Gly Gly Ser His
1               5

<210> SEQ ID NO 175
<211> LENGTH: 123
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 175
acctactatc cagacagtgt gaagggcga ttcatcattt ctagagacaa tgccaagaac       60
accctgtacc tgcaaatgaa cagtctgagg tctgaggaca cggccatgta ttactgtaca      120
aga                                                                   123

<210> SEQ ID NO 176
<211> LENGTH: 41
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 176

Thr Tyr Tyr Pro Asp Ser Val Lys Gly Arg Phe Ile Ile Ser Arg Asp
1               5                   10                  15

Asn Ala Lys Asn Thr Leu Tyr Leu Gln Met Asn Ser Leu Arg Ser Glu
            20                  25                  30

Asp Thr Ala Met Tyr Tyr Cys Thr Arg
        35                  40

<210> SEQ ID NO 177
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 177
ctgggacggg cctttgacta c                                               21

```
<210> SEQ ID NO 178
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 178

Leu Gly Arg Ala Phe Asp Tyr
1               5

<210> SEQ ID NO 179
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 179
tggggccaag gcaccactct cacagtctcc tca                                    33

<210> SEQ ID NO 180
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 180

Trp Gly Gln Gly Thr Thr Leu Thr Val Ser Ser
1               5                   10

<210> SEQ ID NO 181
<211> LENGTH: 127
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 181

Met Glu Ser Gln Ile Gln Val Phe Val Phe Val Phe Leu Trp Leu Ser
1               5                   10                  15

Gly Val Asp Gly Asp Ile Val Met Thr Gln Ser His Lys Phe Met Ser
                20                  25                  30

Thr Ser Val Gly Asp Arg Val Ser Ile Thr Cys Lys Ala Ser Gln Asp
            35                  40                  45

Val Ser Thr Ala Val Ala Trp Tyr Gln Gln Lys Pro Gly Gln Ser Pro
        50                  55                  60

Lys Val Leu Ile Tyr Trp Ala Ser Thr Arg His Thr Gly Val Pro Asp
65                  70                  75                  80

Arg Phe Thr Gly Ser Gly Ser Gly Thr Asp Phe Thr Leu Thr Ile Ser
                85                  90                  95

Ser Val Gln Ala Glu Asp Leu Ala Leu Tyr Tyr Cys Gln Gln Asp Tyr
            100                 105                 110

Ser Thr Pro Trp Thr Phe Gly Gly Gly Thr Lys Leu Glu Ile Lys
        115                 120                 125

<210> SEQ ID NO 182
<211> LENGTH: 381
<212> TYPE: DNA
```

<213> ORGANISM: Artificial Sequence
<220> FEATURE:
<223> OTHER INFORMATION: Description of Artificial Sequence: Synthetic
      polynucleotide

<400> SEQUENCE: 182

```
atggagtcac agattcaggt ctttgtattc gtgtttctct ggttgtctgg tgttgacgga      60
gacattgtga tgacccagtc tcacaaattc atgtccacat cagtaggaga cagggtcagc     120
atcacctgca aggccagtca ggatgtgagt actgctgtag cctggtatca acaaaagcca     180
gggcaatctc ctaaagttct gatttactgg gcatccaccc ggcacactgg agtccctgat     240
cgcttcacag gcagtggatc tgggacagat tttactctca ccatcagcag tgtgcaggct     300
gaagacctgg cactttatta ctgtcagcaa gattatagca ctccgtggac gttcggtgga     360
ggcaccaagc tggaaatcaa a                                               381
```

<210> SEQ ID NO 183
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 183

```
atggagtcac agattcaggt ctttgtattc gtgtttctct ggttgtctgg tgttgacgga      60
```

<210> SEQ ID NO 184
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 184

```
Met Glu Ser Gln Ile Gln Val Phe Val Phe Val Phe Leu Trp Leu Ser
1               5                   10                  15

Gly Val Asp Gly
            20
```

<210> SEQ ID NO 185
<211> LENGTH: 69
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 185

```
gacattgtga tgacccagtc tcacaaattc atgtccacat cagtaggaga cagggtcagc      60
atcacctgc                                                             69
```

<210> SEQ ID NO 186
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 186

```
Asp Ile Val Met Thr Gln Ser His Lys Phe Met Ser Thr Ser Val Gly
1               5                   10                  15
```

Asp Arg Val Ser Ile Thr Cys
            20

<210> SEQ ID NO 187
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 187
aaggccagtc aggatgtgag tactgctgta gcc                                  33

<210> SEQ ID NO 188
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 188

Lys Ala Ser Gln Asp Val Ser Thr Ala Val Ala
1               5                   10

<210> SEQ ID NO 189
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 189
tggtatcaac aaaagccagg gcaatctcct aaagttctga tttac                     45

<210> SEQ ID NO 190
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 190

Trp Tyr Gln Gln Lys Pro Gly Gln Ser Pro Lys Val Leu Ile Tyr
1               5                   10                  15

<210> SEQ ID NO 191
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 191
tgggcatcca cccggcacac t                                               21

<210> SEQ ID NO 192
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 192

Trp Ala Ser Thr Arg His Thr
1               5

<210> SEQ ID NO 193
<211> LENGTH: 96
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 193
ggagtccctg atcgcttcac aggcagtgga tctgggacag attttactct caccatcagc    60
agtgtgcagg ctgaagacct ggcactttat tactgt                              96

<210> SEQ ID NO 194
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 194

Gly Val Pro Asp Arg Phe Thr Gly Ser Gly Ser Gly Thr Asp Phe Thr
1               5                   10                  15

Leu Thr Ile Ser Ser Val Gln Ala Glu Asp Leu Ala Leu Tyr Tyr Cys
            20                  25                  30

<210> SEQ ID NO 195
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 195
cagcaagatt atagcactcc gtggacg                                         27

<210> SEQ ID NO 196
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 196

Gln Gln Asp Tyr Ser Thr Pro Trp Thr
1               5

<210> SEQ ID NO 197
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 197
ttcggtggag gcaccaagct ggaaatcaaa                                      30

<210> SEQ ID NO 198
<211> LENGTH: 10
<212> TYPE: PRT
<213> ORGANISM: Artificial Sequence
<220> FEATURE:
<223> OTHER INFORMATION: Description of Artificial Sequence: Synthetic peptide

<400> SEQUENCE: 198

Phe Gly Gly Gly Thr Lys Leu Glu Ile Lys
1               5                   10

<210> SEQ ID NO 199
<211> LENGTH: 140
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 199

Met Gly Trp Thr Trp Ile Phe Ile Leu Ile Leu Ser Val Thr Thr Gly
1               5                   10                  15

Val His Ser Glu Val His Leu Gln Gln Ser Gly Pro Glu Leu Glu Lys
            20                  25                  30

Pro Gly Val Ser Val Lys Ile Ser Cys Lys Ala Ser Gly Phe Ser Phe
        35                  40                  45

Thr Asp Tyr Asn Met Asn Trp Val Lys Gln Ser Gly Lys Ser Leu
    50                  55                  60

Glu Trp Ile Gly Asn Ile Asp Pro Tyr Tyr Gly Arg Ile Asn Tyr Asn
65                  70                  75                  80

Gln Lys Phe Lys Gly Lys Ala Thr Leu Ser Val Asp Lys Ser Ser Ser
                85                  90                  95

Thr Ala Tyr Met His Leu Lys Ser Leu Thr Ser Glu Asp Ser Ala Val
            100                 105                 110

Tyr Tyr Cys Ala Thr Gly Ala Tyr Thr Ser Gly Tyr Ser Trp Phe Ala
        115                 120                 125

Tyr Trp Gly Gln Gly Thr Leu Val Thr Val Ser Ala
    130                 135                 140

<210> SEQ ID NO 200
<211> LENGTH: 420
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 200
atgggatgga cctggatctt tattttaatc ctgtcagtaa ctacaggtgt ccactctgag      60
gtccacctgc agcagtctgg acctgagctg gagaagcctg gcgtttcagt gaagatatcc     120
tgcaaggctt ctggtttctc attcactgac tacaacatga actgggtgaa acagagcagt     180
ggaaagagcc ttgagtggat tggaaatatt gatccttact atggacgtat taactataac     240
cagaaattca gggcaaggc cacattgagt gtagacaaat cctccagcac agcctacatg      300
cacctcaaga gcctgacatc tgaggactct gcagtctatt actgtgcaac tggggcctac     360
acctcgggct actcctggtt tgcttactgg ggccaaggga ctctggtcac tgtctctgca     420

<210> SEQ ID NO 201
<211> LENGTH: 57

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 201
atgggatgga cctggatctt tattttaatc ctgtcagtaa ctacaggtgt ccactct        57

<210> SEQ ID NO 202
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 202

Met Gly Trp Thr Trp Ile Phe Ile Leu Ile Leu Ser Val Thr Thr Gly
1               5                   10                  15

Val His Ser

<210> SEQ ID NO 203
<211> LENGTH: 75
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 203
gaggtccacc tgcagcagtc tggacctgag ctggagaagc ctggcgtttc agtgaagata    60
tcctgcaagg cttct                                                     75

<210> SEQ ID NO 204
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 204

Glu Val His Leu Gln Gln Ser Gly Pro Glu Leu Glu Lys Pro Gly Val
1               5                   10                  15

Ser Val Lys Ile Ser Cys Lys Ala Ser
            20                  25

<210> SEQ ID NO 205
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 205
ggtttctcat tcactgacta c                                              21

<210> SEQ ID NO 206
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
```

<400> SEQUENCE: 206

Gly Phe Ser Phe Thr Asp Tyr
1               5

<210> SEQ ID NO 207
<211> LENGTH: 57
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 207
aacatgaact gggtgaaaca gagcagtgga aagagccttg agtggattgg aaatatt       57

<210> SEQ ID NO 208
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 208

Asn Met Asn Trp Val Lys Gln Ser Ser Gly Lys Ser Leu Glu Trp Ile
1               5                   10                  15

Gly Asn Ile

<210> SEQ ID NO 209
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 209
gatccttact atggacgt                                                  18

<210> SEQ ID NO 210
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 210

Asp Pro Tyr Tyr Gly Arg
1               5

<210> SEQ ID NO 211
<211> LENGTH: 123
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 211
attaactata accagaaatt caagggcaag gccacattga gtgtagacaa atcctccagc    60
acagcctaca tgcacctcaa gagcctgaca tctgaggact ctgcagtcta ttactgtgca   120
act                                                                 123

<210> SEQ ID NO 212
<211> LENGTH: 41
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 212

Ile Asn Tyr Asn Gln Lys Phe Lys Gly Lys Ala Thr Leu Ser Val Asp
1               5                   10                  15

Lys Ser Ser Ser Thr Ala Tyr Met His Leu Lys Ser Leu Thr Ser Glu
            20                  25                  30

Asp Ser Ala Val Tyr Tyr Cys Ala Thr
        35                  40

<210> SEQ ID NO 213
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 213
ggggcctaca cctcgggcta ctcctggttt gcttac                              36

<210> SEQ ID NO 214
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 214

Gly Ala Tyr Thr Ser Gly Tyr Ser Trp Phe Ala Tyr
1               5                   10

<210> SEQ ID NO 215
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 215
tggggccaag ggactctggt cactgtctct gca                                 33

<210> SEQ ID NO 216
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 216

Trp Gly Gln Gly Thr Leu Val Thr Val Ser Ala
1               5                   10

<210> SEQ ID NO 217
<211> LENGTH: 130
<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 217

Met Gly Leu Gln Val Gln Val Ile Ser Phe Leu Leu Ile Ser Val Thr
1               5                   10                  15

Val Ile Met Ser Arg Gly Glu Asn Val Leu Thr Gln Ser Pro Gly Ile
            20                  25                  30

Met Ala Ala Ser Leu Gly Glu Lys Val Thr Met Thr Cys Ser Ala Ser
        35                  40                  45

Ser Ser Val Ser Ser Tyr Leu His Trp Tyr Gln Gln Arg Ser Gly
    50                  55                  60

Ala Ser Pro Lys Pro Leu Ile His Arg Thr Ser Asn Leu Ala Ser Gly
65                  70                  75                  80

Val Pro Ala Arg Phe Ser Gly Ser Gly Ser Gly Thr Ser Tyr Ser Leu
                85                  90                  95

Thr Ile Ser Ser Val Glu Ala Glu Asp Asp Ala Thr Tyr Tyr Cys Gln
            100                 105                 110

Gln Trp Ser Gly Tyr Pro Phe Thr Phe Gly Ser Gly Thr Lys Leu Glu
        115                 120                 125

Ile Lys
    130

<210> SEQ ID NO 218
<211> LENGTH: 390
<212> TYPE: DNA
<213> ORGANISM: Artificial Sequence
<220> FEATURE:
<223> OTHER INFORMATION: Description of Artificial Sequence: Synthetic
    polynucleotide

<400> SEQUENCE: 218
atgggtttac aggtgcaggt tatcagcttc ctgttaatca gtgtcacagt cataatgtcc      60
agaggagaaa atgtgctcac ccagtctcca ggaataatgg ctgcctctct gggggagaag     120
gtcaccatga cctgcagtgc cagctcaagt gtaagttcca gttacttgca ctggtaccag     180
cagaggtcag gcgcttcccc caaacccttg attcatagga catccaacct ggcttctggt     240
gtcccagctc gcttcagtgg cagtgggtct gggacctctt actctctcac aatcagcagc     300
gtggaggctg aagatgatgc aacttattac tgccagcagt ggagtggtta cccattcacg     360
ttcggctcgg gacaaagtt ggaaataaaa                                       390

<210> SEQ ID NO 219
<211> LENGTH: 66
<212> TYPE: DNA
<213> ORGANISM: Artificial Sequence
<220> FEATURE:
<223> OTHER INFORMATION: Description of Artificial Sequence: Synthetic
    oligonucleotide

<400> SEQUENCE: 219
atgggtttac aggtgcaggt tatcagcttc ctgttaatca gtgtcacagt cataatgtcc      60
agagga                                                                66

<210> SEQ ID NO 220
<211> LENGTH: 22
<212> TYPE: PRT
<213> ORGANISM: Artificial Sequence
<220> FEATURE:

<223> OTHER INFORMATION: Description of Artificial Sequence: Synthetic
      peptide

<400> SEQUENCE: 220

Met Gly Leu Gln Val Gln Val Ile Ser Phe Leu Leu Ile Ser Val Thr
1               5                   10                  15

Val Ile Met Ser Arg Gly
            20

<210> SEQ ID NO 221
<211> LENGTH: 69
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 221
gaaaatgtgc tcacccagtc tccaggaata atggctgcct ctctggggga gaaggtcacc    60
atgacctgc                                                            69

<210> SEQ ID NO 222
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 222

Glu Asn Val Leu Thr Gln Ser Pro Gly Ile Met Ala Ala Ser Leu Gly
1               5                   10                  15

Glu Lys Val Thr Met Thr Cys
            20

<210> SEQ ID NO 223
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 223
agtgccagct caagtgtaag ttccagttac ttgcac                              36

<210> SEQ ID NO 224
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 224

Ser Ala Ser Ser Ser Val Ser Ser Ser Tyr Leu His
1               5                   10

<210> SEQ ID NO 225
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

```
<400> SEQUENCE: 225
tggtaccagc agaggtcagg cgcttccccc aaacccttga ttcat          45

<210> SEQ ID NO 226
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 226

Trp Tyr Gln Gln Arg Ser Gly Ala Ser Pro Lys Pro Leu Ile His
1               5                   10                  15

<210> SEQ ID NO 227
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 227
aggacatcca acctggcttc t                                    21

<210> SEQ ID NO 228
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 228

Arg Thr Ser Asn Leu Ala Ser
1               5

<210> SEQ ID NO 229
<211> LENGTH: 96
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 229
ggtgtcccag ctcgcttcag tggcagtggg tctgggacct cttactctct cacaatcagc     60
agcgtggagg ctgaagatga tgcaacttat tactgc                              96

<210> SEQ ID NO 230
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 230

Gly Val Pro Ala Arg Phe Ser Gly Ser Gly Ser Gly Thr Ser Tyr Ser
1               5                   10                  15

Leu Thr Ile Ser Ser Val Glu Ala Glu Asp Asp Ala Thr Tyr Tyr Cys
            20                  25                  30

<210> SEQ ID NO 231
```

```
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 231
cagcagtgga gtggttaccc attcacg                                            27

<210> SEQ ID NO 232
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 232

Gln Gln Trp Ser Gly Tyr Pro Phe Thr
1               5

<210> SEQ ID NO 233
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 233
ttcggctcgg ggacaaagtt ggaaataaaa                                         30

<210> SEQ ID NO 234
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 234

Phe Gly Ser Gly Thr Lys Leu Glu Ile Lys
1               5                   10

<210> SEQ ID NO 235
<211> LENGTH: 138
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 235

Met Asp Trp Ser Cys Ile Ile Phe Phe Leu Val Ala Thr Ala Thr Gly
1               5                   10                  15

Val His Ser Gln Val Gln Leu Gln Gln Ser Gly Ala Glu Leu Val Arg
            20                  25                  30

Pro Gly Val Ser Val Lys Ile Ser Cys Lys Gly Ser Gly Tyr Thr Phe
        35                  40                  45

Thr Asp Tyr Ala Met His Trp Val Lys Gln Ser His Ala Lys Ser Leu
    50                  55                  60

Glu Trp Ile Gly Ser Ile Ser Thr Tyr Tyr Gly Asp Thr Asn Tyr Asn
65                  70                  75                  80

Gln Lys Phe Lys Gly Lys Ala Thr Met Thr Val Asp Lys Ser Ser Ser
```

```
                85                  90                  95
Thr Ala Tyr Met Glu Leu Ala Arg Leu Thr Ser Glu Asp Ser Ala Ile
                100                 105                 110

Tyr Tyr Cys Ala Arg Gly Asn Tyr Asp Asp Trp Tyr Phe Asn Val Trp
            115                 120                 125

Gly Ala Gly Thr Thr Val Thr Val Ser Ser
    130                 135
```

<210> SEQ ID NO 236
<211> LENGTH: 414
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 236

```
atggattgga gctgtatcat cttctttctg gtagcaacag ctacaggtgt gcactcccag    60
gtccagctgc agcagtctgg ggctgaactg gtgaggcctg ggtctcagt gaagatttcc    120 tgcaagggtt ctggctacac attcactgat tatgctatgc actgggtgaa gcagagtcat    180
gcaaagagtc tagagtggat tggaagtatt agtacttact atggtgatac taattacaac    240
cagaaattca gggcaaggc cacaatgact gtagacaaat cctccagcac agcctatatg    300
gaacttgcca gactgacatc tgaggattct gccatctatt actgtgcaag aggtaattac    360
gacgactggt acttcaatgt ctggggcgca gggaccacgg tcaccgtctc ctca         414
```

<210> SEQ ID NO 237
<211> LENGTH: 57
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 237

```
atggattgga gctgtatcat cttctttctg gtagcaacag ctacaggtgt gcactcc      57
```

<210> SEQ ID NO 238
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 238

```
Met Asp Trp Ser Cys Ile Ile Phe Phe Leu Val Ala Thr Ala Thr Gly
1               5                   10                  15

Val His Ser
```

<210> SEQ ID NO 239
<211> LENGTH: 75
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 239

```
caggtccagc tgcagcagtc tggggctgaa ctggtgaggc ctggggtctc agtgaagatt   60
tcctgcaagg gttct                                                    75
```

<210> SEQ ID NO 240
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 240

Gln Val Gln Leu Gln Gln Ser Gly Ala Glu Leu Val Arg Pro Gly Val
1               5                   10                  15

Ser Val Lys Ile Ser Cys Lys Gly Ser
            20                  25

<210> SEQ ID NO 241
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 241
ggctacacat tcactgatta t                                           21

<210> SEQ ID NO 242
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 242

Gly Tyr Thr Phe Thr Asp Tyr
1               5

<210> SEQ ID NO 243
<211> LENGTH: 57
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 243
gctatgcact gggtgaagca gagtcatgca aagagtctag agtggattgg aagtatt    57

<210> SEQ ID NO 244
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 244

Ala Met His Trp Val Lys Gln Ser His Ala Lys Ser Leu Glu Trp Ile
1               5                   10                  15

Gly Ser Ile

<210> SEQ ID NO 245
<211> LENGTH: 18
<212> TYPE: DNA
<213> ORGANISM: Artificial Sequence

```
<220> FEATURE:
<223> OTHER INFORMATION: Description of Artificial Sequence: Synthetic
      oligonucleotide

<400> SEQUENCE: 245
agtacttact atggtgat                                                    18

<210> SEQ ID NO 246
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 246

Ser Thr Tyr Tyr Gly Asp
1               5

<210> SEQ ID NO 247
<211> LENGTH: 123
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 247
actaattaca accagaaatt caagggcaag gccacaatga ctgtagacaa atcctccagc       60
acagcctata tggaacttgc cagactgaca tctgaggatt ctgccatcta ttactgtgca      120
aga                                                                   123

<210> SEQ ID NO 248
<211> LENGTH: 41
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 248

Thr Asn Tyr Asn Gln Lys Phe Lys Gly Lys Ala Thr Met Thr Val Asp
1               5                   10                  15

Lys Ser Ser Ser Thr Ala Tyr Met Glu Leu Ala Arg Leu Thr Ser Glu
            20                  25                  30

Asp Ser Ala Ile Tyr Tyr Cys Ala Arg
        35                  40

<210> SEQ ID NO 249
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 249
ggtaattacg acgactggta cttcaatgtc                                       30

<210> SEQ ID NO 250
<211> LENGTH: 10
<212> TYPE: PRT
<213> ORGANISM: Artificial Sequence
<220> FEATURE:
<223> OTHER INFORMATION: Description of Artificial Sequence: Synthetic
``` peptide

<400> SEQUENCE: 250

Gly Asn Tyr Asp Asp Trp Tyr Phe Asn Val
1               5                   10

<210> SEQ ID NO 251
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 251
tggggcgcag ggaccacggt caccgtctcc tca                                    33

<210> SEQ ID NO 252
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 252

Trp Gly Ala Gly Thr Thr Val Thr Val Ser Ser
1               5                   10

<210> SEQ ID NO 253
<211> LENGTH: 128
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 253

Met Arg Ile Pro Ala His Val Phe Gly Phe Leu Leu Leu Trp Phe Pro
1               5                   10                  15

Gly Ala Arg Cys Asp Ile Gln Met Thr Gln Ser Pro Ser Ser Leu Ser
            20                  25                  30

Ala Ser Leu Gly Glu Arg Val Ser Leu Thr Cys Arg Ala Ser Gln Asp
        35                  40                  45

Ile Ser Gly Tyr Leu Ser Trp Leu Gln Gln Lys Pro Asp Gly Thr Ile
    50                  55                  60

Lys Arg Leu Ile Tyr Ser Thr Ser Thr Leu Asp Ser Gly Val Pro Lys
65                  70                  75                  80

Arg Phe Ser Gly Ser Arg Ser Gly Ser Asp Tyr Ser Leu Thr Ile Ser
                85                  90                  95

Ser Leu Glu Ser Glu Asp Phe Ala Asp Tyr Tyr Cys Leu Gln Tyr Ala
            100                 105                 110

Ser Ser Pro Tyr Thr Phe Gly Gly Gly Ala Lys Leu Glu Ile Lys Arg
        115                 120                 125

<210> SEQ ID NO 254
<211> LENGTH: 381
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 254

```
atgaggattc ctgctcacgt ttttggcttc ttgttgctct ggtttccagg tgccagatgt    60
gacatccaaa tgacccagtc tccatcttcc ttatctgcct ctctgggaga aagagtcagt   120
ctcacttgtc gggcaagtca ggatattagt ggttacttaa gctggcttca gcagaaacca   180
gatggaacta ttaaacgtct gatttatagc acatccactt tagattctgg tgtcccaaaa   240
aggttcagtg gcagtaggtc tgggtcagat tattctctca ccatcagcag cctagagtct   300
gaagattttg cagactatta ctgtctacaa tatgctagtt ctccgtacac gttcggaggg   360
ggggccaagc tggaaataaa a                                             381
```

<210> SEQ ID NO 255
<211> LENGTH: 60
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 255

```
atgaggattc ctgctcacgt ttttggcttc ttgttgctct ggtttccagg tgccagatgt    60
```

<210> SEQ ID NO 256
<211> LENGTH: 20
<212> TYPE: PRT
<213> ORGANISM: Artificial Sequence
<220> FEATURE:
<223> OTHER INFORMATION: Description of Artificial Sequence: Synthetic peptide

<400> SEQUENCE: 256

Met Arg Ile Pro Ala His Val Phe Gly Phe Leu Leu Leu Trp Phe Pro
1               5                   10                  15

Gly Ala Arg Cys
            20

<210> SEQ ID NO 257
<211> LENGTH: 69
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 257

```
gacatccaaa tgacccagtc tccatcttcc ttatctgcct ctctgggaga aagagtcagt    60
ctcacttgt                                                           69
```

<210> SEQ ID NO 258
<211> LENGTH: 23
<212> TYPE: PRT
<213> ORGANISM: Artificial Sequence
<220> FEATURE:
<223> OTHER INFORMATION: Description of Artificial Sequence: Synthetic peptide

<400> SEQUENCE: 258

Asp Ile Gln Met Thr Gln Ser Pro Ser Ser Leu Ser Ala Ser Leu Gly
1               5                   10                  15

Glu Arg Val Ser Leu Thr Cys
            20

<210> SEQ ID NO 259

```
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 259
cgggcaagtc aggatattag tggttactta agc                                    33

<210> SEQ ID NO 260
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 260

Arg Ala Ser Gln Asp Ile Ser Gly Tyr Leu Ser
1               5                   10

<210> SEQ ID NO 261
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 261
tggcttcagc agaaaccaga tggaactatt aaacgtctga tttat                       45

<210> SEQ ID NO 262
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 262

Trp Leu Gln Gln Lys Pro Asp Gly Thr Ile Lys Arg Leu Ile Tyr
1               5                   10                  15

<210> SEQ ID NO 263
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 263
agcacatcca ctttagattc t                                                 21

<210> SEQ ID NO 264
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 264

Ser Thr Ser Thr Leu Asp Ser
1               5
```

<210> SEQ ID NO 265
<211> LENGTH: 96
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 265
ggtgtcccaa aaaggttcag tggcagtagg tctgggtcag attattctct caccatcagc    60
agcctagagt ctgaagattt tgcagactat tactgt                              96

<210> SEQ ID NO 266
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 266

Gly Val Pro Lys Arg Phe Ser Gly Ser Arg Ser Gly Ser Asp Tyr Ser
1               5                   10                  15

Leu Thr Ile Ser Ser Leu Glu Ser Glu Asp Phe Ala Asp Tyr Tyr Cys
            20                  25                  30

<210> SEQ ID NO 267
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 267
ctacaatatg ctagttctcc gtacacg                                        27

<210> SEQ ID NO 268
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 268

Leu Gln Tyr Ala Ser Ser Pro Tyr Thr
1               5

<210> SEQ ID NO 269
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 269
ttcggagggg gggccaagct ggaaataaaa                                     30

<210> SEQ ID NO 270
<211> LENGTH: 10
<212> TYPE: PRT
<213> ORGANISM: Artificial Sequence
<220> FEATURE:
<223> OTHER INFORMATION: Description of Artificial Sequence: Synthetic peptide

<400> SEQUENCE: 270

Phe Gly Gly Gly Ala Lys Leu Glu Ile Lys
1               5                   10

<210> SEQ ID NO 271
<211> LENGTH: 136
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 271

Met Lys Cys Ser Trp Ile Ile Phe Phe Leu Met Ala Val Val Thr Gly
1               5                   10                  15

Val Asn Ser Glu Val Gln Leu Gln Gln Ser Gly Ala Glu Leu Val Gln
            20                  25                  30

Pro Gly Ala Ser Val Lys Leu Ser Cys Thr Ala Ser Gly Phe Asn Ile
        35                  40                  45

Lys Asp Thr Tyr Met His Trp Val Lys Gln Arg Pro Glu Gln Gly Leu
    50                  55                  60

Glu Trp Ile Gly Arg Ile Asp Pro Ala Asn Gly Lys Thr Ile Phe Asp
65                  70                  75                  80

Pro Lys Phe Gln Val Lys Ala Thr Ile Thr Ala Asp Thr Ser Ser Asn
                85                  90                  95

Thr Val Tyr Leu His Leu Ser Ser Leu Thr Ser Glu Asp Thr Ala Ile
            100                 105                 110

Tyr Tyr Cys Ala Trp Leu Leu Pro Tyr Tyr Phe Asp Tyr Trp Gly Gln
        115                 120                 125

Gly Thr Thr Leu Thr Val Ser Ser
    130                 135

<210> SEQ ID NO 272
<211> LENGTH: 408
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 272
atgaaatgca gctggattat cttcttcctg atggctgtgg ttacaggggt caattcagag      60
gttcagctgc agcagtctgg ggcagaactt gtgcagccag ggcctcagt caagttgtcc      120 tgtacagctt ctggcttcaa tattaaagac acctatatgc actgggtaaa acagaggcct     180
gaacagggcc tggagtggat tggaaggatt gatcctgcga atggtaaaac tatttttgac     240
ccgaagttcc aggtcaaggc cactataact gccgacacat cctccaacac agtctacctg     300
catctcagca gcctgacatc tgaggacact gccatctatt actgtgcttg gttacttcct     360
tactactttg actactgggg ccaaggcacc actctcacag tctcctca               408

<210> SEQ ID NO 273
<211> LENGTH: 57
<212> TYPE: DNA
<213> ORGANISM: Artificial Sequence
<220> FEATURE:
<223> OTHER INFORMATION: Description of Artificial Sequence: Synthetic
      oligonucleotide

```
<400> SEQUENCE: 273
atgaaatgca gctggattat cttcttcctg atggctgtgg ttacagggt caattca        57

<210> SEQ ID NO 274
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 274

Met Lys Cys Ser Trp Ile Ile Phe Phe Leu Met Ala Val Val Thr Gly
1               5                   10                  15

Val Asn Ser

<210> SEQ ID NO 275
<211> LENGTH: 75
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 275
gaggttcagc tgcagcagtc tggggcagaa cttgtgcagc caggggcctc agtcaagttg    60
tcctgtacag cttct                                                     75

<210> SEQ ID NO 276
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 276

Glu Val Gln Leu Gln Gln Ser Gly Ala Glu Leu Val Gln Pro Gly Ala
1               5                   10                  15

Ser Val Lys Leu Ser Cys Thr Ala Ser
            20                  25

<210> SEQ ID NO 277
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 277
ggcttcaata ttaaagacac c                                              21

<210> SEQ ID NO 278
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 278

Gly Phe Asn Ile Lys Asp Thr
1               5
```

<210> SEQ ID NO 279
<211> LENGTH: 57
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 279
tatatgcact gggtaaaaca gaggcctgaa cagggcctgg agtggattgg aaggatt           57

<210> SEQ ID NO 280
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 280

Tyr Met His Trp Val Lys Gln Arg Pro Glu Gln Gly Leu Glu Trp Ile
1               5                   10                  15

Gly Arg Ile

<210> SEQ ID NO 281
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 281
gatcctgcga atggtaaa                                                     18

<210> SEQ ID NO 282
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 282

Asp Pro Ala Asn Gly Lys
1               5

<210> SEQ ID NO 283
<211> LENGTH: 123
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 283
actatttttg acccgaagtt ccaggtcaag gccactataa ctgccgacac atcctccaac       60
acagtctacc tgcatctcag cagcctgaca tctgaggaca ctgccatcta ttactgtgct      120
tgg                                                                    123

<210> SEQ ID NO 284
<211> LENGTH: 41
<212> TYPE: PRT
<213> ORGANISM: Artificial Sequence
<220> FEATURE:

<223> OTHER INFORMATION: Description of Artificial Sequence: Synthetic
polypeptide

<400> SEQUENCE: 284

Thr Ile Phe Asp Pro Lys Phe Gln Val Lys Ala Thr Ile Thr Ala Asp
1               5                   10                  15

Thr Ser Ser Asn Thr Val Tyr Leu His Leu Ser Ser Leu Thr Ser Glu
            20                  25                  30

Asp Thr Ala Ile Tyr Tyr Cys Ala Trp
        35                  40

<210> SEQ ID NO 285
<211> LENGTH: 24
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 285
ttacttcctt actactttga ctac                                              24

<210> SEQ ID NO 286
<211> LENGTH: 8
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 286

Leu Leu Pro Tyr Tyr Phe Asp Tyr
1               5

<210> SEQ ID NO 287
<211> LENGTH: 33
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 287
tggggccaag gcaccactct cacagtctcc tca                                    33

<210> SEQ ID NO 288
<211> LENGTH: 11
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 288

Trp Gly Gln Gly Thr Thr Leu Thr Val Ser Ser
1               5                   10

<210> SEQ ID NO 289
<211> LENGTH: 130
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 289

```
Met Asp Phe His Val Gln Ile Phe Ser Phe Met Leu Ile Ser Val Thr
1               5                   10                  15

Val Met Leu Ser Ser Gly Glu Ile Val Leu Thr Gln Ser Pro Ala Val
            20                  25                  30

Met Ala Ala Ser Pro Gly Glu Lys Val Thr Ile Thr Cys Ser Val Ser
            35                  40                  45

Ser Ser Ile Ser Ser Ser Asn Leu His Trp Tyr Gln Gln Lys Ser Gly
        50                  55                  60

Thr Ser Pro Lys Leu Trp Ile Tyr Gly Thr Ser Asn Leu Ala Ser Gly
65                  70                  75                  80

Val Pro Val Arg Phe Ser Gly Ser Gly Ser Gly Thr Ser Tyr Ser Leu
                85                  90                  95

Thr Ile Ser Ser Met Glu Ala Glu Asp Ala Ala Thr Tyr Tyr Cys Gln
            100                 105                 110

Lys Trp Ser His Tyr Pro Leu Thr Phe Gly Ala Gly Thr Lys Leu Glu
            115                 120                 125

Leu Lys
    130
```

<210> SEQ ID NO 290
<211> LENGTH: 390
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 290

```
atggattttc atgtgcagat tttcagcttc atgctaatca gtgtcacagt catgttgtcc        60
agtggggaaa ttgtactcac ccagtctcca gcagtcatgg ctgcatctcc aggggagaag       120
gtcaccatca cctgcagcgt cagttcaagt ataagttcca gcaacttgca ctggtaccag       180
cagaagtcag gaacctcgcc caaactctgg atttatggca catccaacct ggcttctgga       240
gtccctgttc gcttcagtgg cagtggatct gggacctctt attctctcac aatcagcagc       300
atggaggctg aagatgctgc cacttattac tgtcaaaagt ggagtcatta cccgctcacg       360
ttcggtgctg ggaccaagct ggagctgaaa                                         390
```

<210> SEQ ID NO 291
<211> LENGTH: 66
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 291

```
atggattttc atgtgcagat tttcagcttc atgctaatca gtgtcacagt catgttgtcc        60
agtggg                                                                   66
```

<210> SEQ ID NO 292
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 292

Met Asp Phe His Val Gln Ile Phe Ser Phe Met Leu Ile Ser Val Thr

Val Met Leu Ser Ser Gly
            20

<210> SEQ ID NO 293
<211> LENGTH: 69
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 293
gaaattgtac tcacccagtc tccagcagtc atggctgcat ctccagggga gaaggtcacc    60
atcacctgc                                                           69

<210> SEQ ID NO 294
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 294

Glu Ile Val Leu Thr Gln Ser Pro Ala Val Met Ala Ala Ser Pro Gly
1               5                   10                  15

Glu Lys Val Thr Ile Thr Cys
            20

<210> SEQ ID NO 295
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 295
agcgtcagtt caagtataag ttccagcaac ttgcac                              36

<210> SEQ ID NO 296
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 296

Ser Val Ser Ser Ser Ile Ser Ser Ser Asn Leu His
1               5                   10

<210> SEQ ID NO 297
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 297
tggtaccagc agaagtcagg aacctcgccc aaactctgga tttat                    45

<210> SEQ ID NO 298

```
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 298

Trp Tyr Gln Gln Lys Ser Gly Thr Ser Pro Lys Leu Trp Ile Tyr
1               5                   10                  15

<210> SEQ ID NO 299
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 299
ggcacatcca acctggcttc t                                            21

<210> SEQ ID NO 300
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 300

Gly Thr Ser Asn Leu Ala Ser
1               5

<210> SEQ ID NO 301
<211> LENGTH: 96
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 301
ggagtccctg ttcgcttcag tggcagtgga tctgggacct cttattctct cacaatcagc    60
agcatggagg ctgaagatgc tgccacttat tactgt                              96

<210> SEQ ID NO 302
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 302

Gly Val Pro Val Arg Phe Ser Gly Ser Gly Ser Gly Thr Ser Tyr Ser
1               5                   10                  15

Leu Thr Ile Ser Ser Met Glu Ala Glu Asp Ala Ala Thr Tyr Tyr Cys
            20                  25                  30

<210> SEQ ID NO 303
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide
```

<400> SEQUENCE: 303
caaaagtgga gtcattaccc gctcacg 27

<210> SEQ ID NO 304
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 304

Gln Lys Trp Ser His Tyr Pro Leu Thr
1               5

<210> SEQ ID NO 305
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 305
ttcggtgctg ggaccaagct ggagctgaaa 30

<210> SEQ ID NO 306
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 306

Phe Gly Ala Gly Thr Lys Leu Glu Leu Lys
1               5                   10

<210> SEQ ID NO 307
<211> LENGTH: 135
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 307

Met Glu Arg His Trp Ile Phe Leu Phe Leu Leu Ser Val Thr Ala Gly
1               5                   10                  15

Val His Ser Gln Val Gln Leu Gln Gln Ser Ala Ala Glu Leu Ala Arg
            20                  25                  30

Pro Gly Ala Ser Val Lys Met Ser Cys Lys Ala Ser Gly Tyr Thr Phe
        35                  40                  45

Thr Thr Tyr Thr Met His Trp Val Lys Gln Arg Pro Gly Gln Gly Leu
    50                  55                  60

Glu Trp Ile Gly His Ile Asn Pro Ser Ser Gly Tyr Thr Glu Tyr Asn
65                  70                  75                  80

Gln Lys Phe Lys Asp Lys Thr Thr Leu Thr Ala Asp Lys Ser Ser Ser
                85                  90                  95

Thr Ala His Met Gln Leu Ser Ser Leu Thr Ser Glu Asp Ser Ala Val
            100                 105                 110

Tyr Tyr Cys Ala Arg His Pro Trp Asp Ser Asn Tyr Trp Gly Gln Gly

Thr Thr Leu Thr Val Ser Ser
     130                 135

<210> SEQ ID NO 308
<211> LENGTH: 405
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 308
atggaaaggc actggatctt tctcttcctg ttgtcagtaa ctgcaggtgt ccactcccag    60
gtccagctgc agcagtctgc agctgaactg gcaagacctg gggcctcagt gaagatgtcc   120
tgcaaggctt ctggctacac ctttactacc tacacgatgc actgggtaaa acagaggcct   180
ggacagggtc tggagtggat tggacacatt aatcctagca gtggatatac tgagtacaat   240
cagaaattca aggacaagac cacactgact gcagacaaat cctccagcac agcccacatg   300
caactgagca gcctaacatc tgaggactct gcggtctatt actgtgcaag acacccctgg   360
gactcgaact actggggcca aggcaccact ctcacagtct cctca               405

<210> SEQ ID NO 309
<211> LENGTH: 57
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 309
atggaaaggc actggatctt tctcttcctg ttgtcagtaa ctgcaggtgt ccactcc       57

<210> SEQ ID NO 310
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 310

Met Glu Arg His Trp Ile Phe Leu Phe Leu Leu Ser Val Thr Ala Gly
1               5                   10                  15

Val His Ser

<210> SEQ ID NO 311
<211> LENGTH: 75
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 311
caggtccagc tgcagcagtc tgcagctgaa ctggcaagac ctggggcctc agtgaagatg    60
tcctgcaagg cttct                                                     75

<210> SEQ ID NO 312
<211> LENGTH: 25
<212> TYPE: PRT
<213> ORGANISM: Artificial Sequence

```
<220> FEATURE:
<223> OTHER INFORMATION: Description of Artificial Sequence: Synthetic
      peptide

<400> SEQUENCE: 312

Gln Val Gln Leu Gln Gln Ser Ala Ala Glu Leu Ala Arg Pro Gly Ala
1               5                   10                  15

Ser Val Lys Met Ser Cys Lys Ala Ser
            20                  25

<210> SEQ ID NO 313
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 313
ggctacacct ttactaccta c                                              21

<210> SEQ ID NO 314
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 314

Gly Tyr Thr Phe Thr Thr Tyr
1               5

<210> SEQ ID NO 315
<211> LENGTH: 57
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 315
acgatgcact gggtaaaaca gaggcctgga cagggtctgg agtggattgg acacatt      57

<210> SEQ ID NO 316
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 316

Thr Met His Trp Val Lys Gln Arg Pro Gly Gln Gly Leu Glu Trp Ile
1               5                   10                  15

Gly His Ile

<210> SEQ ID NO 317
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 317
```
aatcctagca gtggatat					18

<210> SEQ ID NO 318
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 318

Asn Pro Ser Ser Gly Tyr
1               5

<210> SEQ ID NO 319
<211> LENGTH: 123
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 319
actgagtaca atcagaaatt caaggacaag accacactga ctgcagacaa atcctccagc		60 acagcccaca tgcaactgag cagcctaaca tctgaggact ctgcggtcta ttactgtgca		120 aga					123

<210> SEQ ID NO 320
<211> LENGTH: 41
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 320

Thr Glu Tyr Asn Gln Lys Phe Lys Asp Lys Thr Thr Leu Thr Ala Asp
1               5                   10                  15

Lys Ser Ser Ser Thr Ala His Met Gln Leu Ser Ser Leu Thr Ser Glu
            20                  25                  30

Asp Ser Ala Val Tyr Tyr Cys Ala Arg
        35                  40

<210> SEQ ID NO 321
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 321
cacccctggg actcgaacta c					21

<210> SEQ ID NO 322
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 322

His Pro Trp Asp Ser Asn Tyr
1               5

<210> SEQ ID NO 323
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 323
tggggccaag gcaccactct cacagtctcc tca                                    33

<210> SEQ ID NO 324
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 324

Trp Gly Gln Gly Thr Thr Leu Thr Val Ser Ser
1               5                   10

<210> SEQ ID NO 325
<211> LENGTH: 127
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 325

Met Ser Val Pro Thr Gln Leu Leu Gly Leu Leu Leu Leu Trp Leu Thr
1               5                   10                  15

Asp Ala Arg Cys Asp Ile Gln Met Thr Gln Ser Pro Ala Ser Leu Ser
                20                  25                  30

Ala Ser Val Gly Glu Thr Val Thr Ile Thr Cys Arg Ala Ser Glu Asn
            35                  40                  45

Ile Asp Ser Tyr Leu Ala Trp Tyr Gln Gln Lys Gln Gly Arg Ser Pro
        50                  55                  60

Gln Leu Leu Val Tyr Ala Ala Thr Asn Leu Ala Asp Gly Val Pro Ser
65                  70                  75                  80

Arg Phe Ser Gly Ser Gly Ser Gly Thr Gln Tyr Ser Leu Lys Ile Asn
                85                  90                  95

Ser Leu Gln Ser Glu Asp Val Ala Arg Tyr Tyr Cys Gln His Tyr Tyr
            100                 105                 110

Ile Thr Pro Phe Thr Phe Gly Ser Gly Thr Lys Leu Glu Ile Lys
        115                 120                 125

<210> SEQ ID NO 326
<211> LENGTH: 381
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 326
atgagtgtgc ccactcagct cctggggttg ctgctgctgt ggcttacaga tgccagatgt     60
gacatccaga tgactcagtc tccagcttcc ctgtctgcat ctgtgggaga aactgtcacc    120
atcacatgtc gagcaagtga gaatattgac agttatttag catggtatca gcagaaacag    180

```
ggaagatctc ctcagctcct ggtctatgct gcaacaaact tagcagatgg tgtgccatca    240
aggttcagtg gcagtggatc aggcacacag tattctctca agatcaacag cctgcagtct    300
gaagatgttg cgagatatta ctgtcaacat tattatatta ctccattcac gttcggctcg    360
gggacaaagt tggaaataaa a                                               381

<210> SEQ ID NO 327
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 327
atgagtgtgc ccactcagct cctggggttg ctgctgctgt ggcttacaga tgccagatgt    60

<210> SEQ ID NO 328
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 328

Met Ser Val Pro Thr Gln Leu Leu Gly Leu Leu Leu Leu Trp Leu Thr
1               5                   10                  15

Asp Ala Arg Cys
            20

<210> SEQ ID NO 329
<211> LENGTH: 69
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 329
gacatccaga tgactcagtc tccagcttcc ctgtctgcat ctgtgggaga aactgtcacc    60
atcacatgt                                                             69

<210> SEQ ID NO 330
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 330

Asp Ile Gln Met Thr Gln Ser Pro Ala Ser Leu Ser Ala Ser Val Gly
1               5                   10                  15

Glu Thr Val Thr Ile Thr Cys
            20

<210> SEQ ID NO 331
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide
```

<400> SEQUENCE: 331
cgagcaagtg agaatattga cagttattta gca          33

<210> SEQ ID NO 332
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 332

Arg Ala Ser Glu Asn Ile Asp Ser Tyr Leu Ala
1               5                   10

<210> SEQ ID NO 333
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 333
tggtatcagc agaaacaggg aagatctcct cagctcctgg tctat          45

<210> SEQ ID NO 334
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 334

Trp Tyr Gln Gln Lys Gln Gly Arg Ser Pro Gln Leu Leu Val Tyr
1               5                   10                  15

<210> SEQ ID NO 335
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 335
gctgcaacaa acttagcaga t          21

<210> SEQ ID NO 336
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 336

Ala Ala Thr Asn Leu Ala Asp
1               5

<210> SEQ ID NO 337
<211> LENGTH: 96
<212> TYPE: DNA
<213> ORGANISM: Artificial Sequence
<220> FEATURE:

<223> OTHER INFORMATION: Description of Artificial Sequence: Synthetic
      oligonucleotide

<400> SEQUENCE: 337
ggtgtgccat caaggttcag tggcagtgga tcaggcacac agtattctct caagatcaac    60
agcctgcagt ctgaagatgt tgcgagatat tactgt                              96

<210> SEQ ID NO 338
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 338

Gly Val Pro Ser Arg Phe Ser Gly Ser Gly Ser Gly Thr Gln Tyr Ser
1               5                   10                  15

Leu Lys Ile Asn Ser Leu Gln Ser Glu Asp Val Ala Arg Tyr Tyr Cys
            20                  25                  30

<210> SEQ ID NO 339
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 339
caacattatt atattactcc attcacg                                        27

<210> SEQ ID NO 340
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 340

Gln His Tyr Tyr Ile Thr Pro Phe Thr
1               5

<210> SEQ ID NO 341
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 341
ttcggctcgg ggacaaagtt ggaaataaaa                                     30

<210> SEQ ID NO 342
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 342

Phe Gly Ser Gly Thr Lys Leu Glu Ile Lys
1               5                   10

<210> SEQ ID NO 343
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 343

Val Thr Tyr Ala Gln Leu
1               5

<210> SEQ ID NO 344
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 344

Gly Phe Thr Phe Asn Thr Asn Val
1               5

<210> SEQ ID NO 345
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 345

Ile Arg Thr Lys Thr Asn Asn Tyr Ala Thr
1               5                   10

<210> SEQ ID NO 346
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 346

Val Gly Ala Met Asp Tyr
1               5

<210> SEQ ID NO 347
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 347

Glu Ser Val Asp Asn Ser Gly Ile Asn Phe
1               5                   10

<210> SEQ ID NO 348
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 348

Glu Ser Val Asp Asn Tyr Gly Ile Ser Phe
1               5                   10

<210> SEQ ID NO 349
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 349

Gly Tyr Thr Phe Thr Thr Tyr Thr
1               5

<210> SEQ ID NO 350
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 350

Ile Asn Pro Ser Ser Gly Tyr Thr
1               5

<210> SEQ ID NO 351
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 351

Ala Arg His Pro Trp Asp Ser Asp Tyr
1               5

<210> SEQ ID NO 352
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 352

Glu Asn Ile Asp Ser Tyr
1               5

<210> SEQ ID NO 353
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 353

Gly Leu Thr Phe Ser Ser Tyr Ala
1               5

<210> SEQ ID NO 354
<211> LENGTH: 8

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 354

Ile Ser Ser Gly Gly Ser His Thr
1               5

<210> SEQ ID NO 355
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 355

Thr Arg Leu Gly Arg Ala Phe Asp Tyr
1               5

<210> SEQ ID NO 356
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 356

Gln Asp Val Ser Thr Ala
1               5

<210> SEQ ID NO 357
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 357

Gly Phe Ser Phe Thr Asp Tyr Asn
1               5

<210> SEQ ID NO 358
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 358

Ile Asp Pro Tyr Tyr Gly Arg Ile
1               5

<210> SEQ ID NO 359
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 359

Ala Thr Gly Ala Tyr Thr Ser Gly Tyr Ser Trp Phe Ala Tyr
```

<210> SEQ ID NO 360
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 360

Ser Ser Val Ser Ser Ser Tyr
1               5

<210> SEQ ID NO 361
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 361

Gly Tyr Thr Phe Thr Asp Tyr Ala
1               5

<210> SEQ ID NO 362
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 362

Ile Ser Thr Tyr Tyr Gly Asp Thr
1               5

<210> SEQ ID NO 363
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 363

Ala Arg Gly Asn Tyr Asp Asp Trp Tyr Phe Asn Val
1               5                   10

<210> SEQ ID NO 364
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 364

Gln Asp Ile Ser Gly Tyr
1               5

<210> SEQ ID NO 365
<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 365

Gly Phe Asn Ile Lys Asp Thr Tyr
1               5

<210> SEQ ID NO 366
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 366

Ile Asp Pro Ala Asn Gly Lys Thr
1               5

<210> SEQ ID NO 367
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 367

Ala Trp Leu Leu Pro Tyr Tyr Phe Asp Tyr
1               5                   10

<210> SEQ ID NO 368
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 368

Ser Ser Ile Ser Ser Ser Asn
1               5

<210> SEQ ID NO 369
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 369

Ala Arg His Pro Trp Asp Ser Asn Tyr
1               5

<210> SEQ ID NO 370
<211> LENGTH: 16
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 370
tgttctgcac aagaca                                                   16

<210> SEQ ID NO 371
<211> LENGTH: 21

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 371
gtaaggatgc aggtcatgag t                                              21
```

KIR3DL3 AS AN HHLA2 RECEPTOR, ANTI-HHLA2 ANTIBODIES, AND USES THEREOF

CROSS-REFERENCE TO RELATED APPLICATIONS

This application is the U.S. national phase of International Patent Application No. PCT/US2019/026034, filed on Apr. 5, 2019, which claims the benefit of priority to U.S. Provisional Application Ser. No. 62/654,068, filed on Apr. 6, 2018; the entire contents of each of said applications are incorporated herein in their entirety by this reference.

STATEMENT OF RIGHTS

This invention was made with government support under grant number P01 AI056299 awarded by The National Institutes of Health. The government has certain rights in the invention.

BACKGROUND OF THE INVENTION

Immune checkpoints, such as CTLA-4, PD-1, VISTA, B7-H2, B7-H3, PD-L1, B7-H4, B7-H6, ICOS, HVEM, PD-L2, CD160, gp49B, PIR-B, KIR family receptors, TIM-1, TIM-3, TIM-4, LAG-3, GITR, 4-IBB, OX-40, BTLA, SIRPalpha (CD47), CD48, 2B4 (CD244), B7.1, B7.2, ILT-2, ILT-4, TIGIT, butyrophilins, and A2aR, and many more, negatively regulate immune response progression based on complex and combinatorial interactions between numerous inputs. Inhibitors of immune checkpoints can modulate immune responses in some subjects, but immune checkpoint expression and interactions with natural binding partners vary between subjects and within tissues of a subject. Accordingly, a great need exists in the art to identify new immune checkpoints for use in interventions. HHLA2 is a newly identified B7 family member that modulates T-cell functions. HHLA2 was identified as a specific ligand for TMIGD2 and the HHLA2/TMIGD2 interaction selectively costimulates human T-cell growth and cytokine production via an AKT-dependent signaling cascade (Zhu et al. (2013) *Nat. Comm.* 4:2043; Janakiram et al. (2015) *Clin. Cancer Res.* 21:2359-2366). A second uncharacterized receptor for HHLA2 on activated T cells that exerts a coinhibitory function was suggested by several studies (Zhao et al. (2013) *Proc. Natl. Acad. Sci. USA* 110:9879-9884; Xiao and Freeman et al. (2015) *Clin. Cancer Res.* 21:2201-2203; Wang et al. (2014) *J. Immunol.* 192:126.11). HHLA2 is expressed on a variety of human cancers, and its co-inhibitory function makes it a candidate for cancer immunotherapy.

SUMMARY OF THE INVENTION

The present invention is based, at least in part, on the discovery that HHLA2, a B7 gene family member, is broadly expressed in a variety of tumors and antigen presenting cells and has been implicated as both an activating and inhibitory ligand for T cells. TMIGD2 expressed in naive T cells is an activating receptor for HHLA2 and transduces co-stimulatory signals following T cell antigen receptor (TCR) engagement. TMIGD2 is downregulated following repeated TCR stimulation. It is possible that a putative inhibitory receptor for HHLA2 is upregulated on activated T cells to modulate T cell activation. The present invention is based, at least in part, on the discovery that HHLA2 binds KIR3DL3, a receptor on T and NK cells, and a consequence of the HHLA2:KIR3DL3 interaction is inhibition of T cell activation. Based on the observations that HHLA2 is highly expressed in tumors and can serve as a checkpoint ligand, a panel of anti-HHLA2 human monoclonal antibodies (mAbs) were generated as candidate immune checkpoint inhibitor agents. Blocking and non-blocking anti-HHLA2 mAbs were identified by evaluating soluble human HHLA2-mIgG2a binding to TMIGD2 transfected 300.19 mouse pre-B leukemic cells or to KIR3DL3 transfected 300.19 mouse pre-B leukemic cells. Anti-HHLA2 mAbs that block HHLA2 binding to both TMIGD2 and KIR3DL3 or more selectively block KIR3DL3 but not TMIGD2 were shown to be checkpoint inhibitor antibodies in T cell assays.

In one aspect, a monoclonal antibody, or antigen-binding fragment thereof, wherein the monoclonal antibody comprises a) a heavy chain sequence with at least about 95% identity to a heavy chain sequence selected from the group consisting of the sequences listed in Table 2; and/or b) a light chain sequence with at least about 95% identity to a light chain sequence selected from the group consisting of the sequences listed in Table 2, is provided.

In another aspect, a monoclonal antibody, or antigen-binding fragment thereof, wherein the monoclonal antibody comprises a) a heavy chain CDR sequence with at least about 95% identity to a heavy chain CDR sequence selected from the group consisting of the sequences listed in Table 2; and/or b) a light chain CDR sequence with at least about 95% identity to a light chain CDR sequence selected from the group consisting of the sequences listed in Table 2, is provided.

In still another aspect, a monoclonal antibody, or antigen-binding fragment thereof, wherein the monoclonal antibody comprises a) a heavy chain sequence selected from the group consisting of the sequences listed in Table 2; and/or b) a light chain sequence selected from the group consisting of the sequences listed in Table 2, is provided.

In yet another aspect, a monoclonal antibody, or antigen-binding fragment thereof, wherein the monoclonal antibody comprises a) a heavy chain CDR sequence selected from the group consisting of the sequences listed in Table 2; and/or b) a light chain CDR sequence selected from the group consisting the sequences listed in Table 2, is provided.

Numerous embodiments are further provided that can be applied to any aspect of the present invention described herein. For example, in one embodiment, the monoclonal antibody, or antigen-binding fragment thereof, is chimeric, humanized, composite, murine, or human. In another embodiment, the monoclonal antibody, or antigen-binding fragment thereof, is detectably labeled, comprises an effector domain, comprises an Fc domain, and/or is selected from the group consisting of Fv, Fav, F(ab')2), Fab', dsFv, scFv, sc(Fv)2, and diabodies fragments. In yet another embodiment, the monoclonal antibody, or antigen-binding fragment thereof, inhibits a) the binding of HHLA2 to TMIGD2, b) the binding of HHLA2 to KIR3DL3, or c) the binding of HHLA2 to TMIGD2 and the binding of HHLA2 to KIR3DL3. HHLA2 mAbs that block HHLA2 binding to KIR3DL3 in T cell activation assays were shown to be checkpoint blockers. In another embodiment, the monoclonal antibody, or antigen-binding fragment thereof, specifically binds HHLA2.

In another aspect, an immunoglobulin heavy and/or light chain selected from the group consisting of immunoglobulin heavy and light chain sequences listed in Table 2, is provided.

In still another aspect, an isolated nucleic acid molecule that hybridizes, under stringent conditions, with the complement of a nucleic acid encoding a polypeptide selected from the group consisting of polypeptide sequences listed in Table 2, or a sequence with at least about 95% homology to a nucleic acid encoding a polypeptide selected from the group consisting of the polypeptide sequences listed in Table 2, is provided.

In yet another aspect, a vector comprising the isolated nucleic acid described herein, is provided.

In still another aspect, a device or kit comprising at least one monoclonal antibody, or antigen-binding fragment thereof, described herein, the device or kit optionally comprising a label to detect the at least one monoclonal antibody, or antigen-binding fragment thereof, or a complex comprising the monoclonal antibody, or antigen-binding fragment thereo, is provided.

In yet another aspect, a method of producing at least one monoclonal antibody, or antigen-binding fragment thereof, described herein, which method comprises the steps of: (i) culturing a transformed host cell which has been transformed by a nucleic acid comprising a sequence encoding at least one monoclonal antibody according to any one of claims 1-9 under conditions suitable to allow expression of said monoclonal antibody, or antigen-binding fragment thereof; and (ii) recovering the expressed monoclonal antibody, or antigen-binding fragment thereof, is provided.

In another aspect, a method of detecting the presence or level of an HHLA2 polypeptide comprising obtaining a sample and detecting said polypeptide in the sample by use of at least one monoclonal antibody, or antigen-binding fragment thereof, described herein.

As described above, certain embodiments are applicable to any method described herein. For example, in one embodiment, the at least one monoclonal antibody, or antigen-binding fragment thereof, forms a complex with an HHLA2 polypeptide and the complex is detected in the form of an enzyme linked immunosorbent assay (ELISA), radioimmune assay (RIA), immunochemically, Western blot, or using an intracellular flow assay.

In another aspect, a method for monitoring the progression of a disorder associated with aberrant HHLA2 expression in a subject, the method comprising a) detecting in a subject sample at a first point in time the level of HHLA2 using at least one monoclonal antibody, or antigen-binding fragment thereof, described herein; b) repeating step a) at a subsequent point in time; and c) comparing the level of HHLA2 detected in steps a) and b) to monitor the progression of the disorder in the subject, is provided.

As described above, certain embodiments are applicable to any method described herein. For example, in one embodiment, between the first point in time and the subsequent point in time, the subject has undergone treatment to ameliorate the disorder.

In another aspect, a method for predicting the clinical outcome of a subject afflicted with a disorder associated with aberrant HHLA2 expression, the method comprising a) determining the level of HHLA2 in a subject sample using at least one monoclonal antibody, or antigen-binding fragment thereof, described herein; b) determining the level of HHLA2 in a sample from a control subject having a good clinical outcome using the at least one monoclonal antibody, or antigen-binding fragment thereof; and c) comparing the level of HHLA2 in the subject sample and in the sample from the control subject; wherein a significantly higher level of HHLA2 in the subject sample as compared to the level in the sample from the control subject is an indication that the subject has a poor clinical outcome, is provided.

In still another aspect, a method of assessing the efficacy of a therapy for a disorder associated with aberrant HHLA2 expression in a subject, the method comprising a) determining the level of HHLA2 using at least one monoclonal antibody, or antigen-binding fragment thereof, described herein, in a first sample obtained from the subject prior to providing at least a portion of the therapy to the subject, and b) determining the level of HHLA2 in a second sample obtained from the subject following provision of the portion of the therapy, wherein a significantly lower level of HHLA2 in the second sample, relative to the first sample, is an indication that the therapy is efficacious for inhibiting the disorder in the subject, is provided.

In yet another aspect, a method of assessing the efficacy of a test compound for inhibiting a disorder associated with aberrant HHLA2 expression in a subject, the method comprising a) determining the level of HHLA2 using at least one monoclonal antibody, or antigen-binding fragment thereof, described herein, in a first sample obtained from the subject and exposed to the test compound; and b) determining the level of HHLA2 in a second sample obtained from the subject, wherein the second sample is not exposed to the test compound, and a significantly lower level of HHLA2, relative to the second sample, is an indication that the test compound is efficacious for inhibiting the disorder in the subject, is provided.

As described above, certain embodiments are applicable to any method described herein. For example, in one embodiment, the first and second samples are portions of a single sample obtained from the subject or portions of pooled samples obtained from the subject. In another embodiment, the disorder is a cancer. In yet another embodiment, the cancer is selected from the group consisting of lung cancer, renal cancer, pancreatic cancer, colorectal cancer, Acute myeloid leukemia, head and neck carcinoma, liver cancer, ovarian cancer, prostate cancer, uterine cancer, gliomas, glioblastoma, neuroblastoma, breast cancer, pancreatic ductal carcinoma, thymoma, B-CLL, leukemia, B cell lymphoma, and a cancer infiltrated with immune cells expressing a receptor to HHLA2. In another embodiment, the sample comprises cells, serum, peritumoral tissue, and/or intratumoral tissue obtained from the subject. In still another embodiment, the significantly higher level of HHLA2 comprises an at least twenty percent increase between the level of HHLA2 in the subject sample relative to the normal level of HHLA2 in the sample from the control subject. In another embodiment, the significantly lower level of HHLA2 comprises an at least twenty percent decrease of the level of HHLA2. In yet another embodiment, the subject is a human.

In yet another aspect, a method of treating a subject afflicted with cancer comprising administering to the subject at least one monoclonal antibody, or antigen-binding fragment thereof, described herein, is provided.

As described above, certain embodiments are applicable to any method described herein. For example, in one embodiment, the at least one monoclonal antibody, or antigen-binding fragment thereof, is conjugated to a cytotoxic agent. In another embodiment, the cytotoxic agent is selected from the group consisting of a chemotherapeutic agent, a biologic agent, a toxin, and a radioactive isotope. In yet another embodiment, the at least one monoclonal antibody, or antigen-binding fragment thereof, reduces the number of proliferating cells in the cancer and/or reduces the volume or size of a tumor of the cancer. In another embodiment, the at least one monoclonal antibody, or antigen-binding fragment thereof, is administered in a pharmaceutically acceptable formulation. In still another embodiment, the method described herein, further comprising administering to the subject a therapeutic agent or regimen for treating cancer. In yet another embodiment, the method described herein, further comprising administering to the subject an additional therapy selected from the group consisting of immunotherapy, checkpoint blockade, cancer vaccines, chimeric antigen receptors, chemotherapy, radiation, target therapy, and surgery. In another embodiment, cancer cells and/or tumor immune infiltrating cells in the subject express HHLA2. In yet another embodiment, the cancer is selected from the group consisting of lung cancer, renal cancer, pancreatic cancer, colorectal cancer, Acute myeloid leukemia, head and neck carcinoma, liver cancer, ovarian cancer, prostate cancer, uterine cancer, gliomas, glioblastoma, neuroblastoma, breast cancer, pancreatic ductal carcinoma, thymoma, B-CLL, leukemia, B cell lymphoma, and a cancer infiltrated with immune cells expressing a receptor to HHLA2. In another embodiment, the cancer is selected from the group consisting of lung cancer, renal cancer, pancreatic cancer, colorectal cancer, acute myeloid leukemia (AML), head and neck carcinoma, liver cancer, ovarian cancer, prostate cancer, and uterine cancer. In still another embodiment, the subject is an animal model of cancer. In yet another embodiment, the animal model is a mouse model, optionally wherein the mouse model is a humanized mouse model. In another embodiment, the subject is a mammal. In yet another embodiment, the mammal is a humanized mouse or a human. In still another embodiment, the mammal is a human.

In another aspect, a method of modulating an immune response by inhibiting the interaction between HHLA2 and its binding inhibitor receptor, KIRDL3, is provided.

In still another aspect, a method of modulating an immune response by selectively inhibiting the interaction between HHLA2 and its binding inhibitor receptor, KIR3DL3, without blocking or significantly inhibiting the interaction between HHLA2 and its binding stimulatory receptor, TMIGD2, is provided.

As described above, certain embodiments are applicable to any method described herein. For example, in one embodiment, the interaction between HHLA2 and KIRDL3 is blocked for use in checkpoint blockade cancer immunotherapy. In another embodiment, the interaction between HHLA2 and KIRDL3 is inhibited or blocked using an anti-HHLA2 antibody. In still another embodiment, the anti-HHLA2 antibody is a checkpoint inhibitor of T cell activation for cancer immunotherapy.

For any figure showing a bar histogram, curve, or other data associated with a legend, the bars, curve, or other data presented from left to right for each indication correspond directly and in order to the boxes from top to bottom, or from left to right, of the legend.

BRIEF DESCRIPTION OF FIGURES

FIG. 6C shows gene ID and NCBI accession information for relevant biomarkers.

DETAILED DESCRIPTION OF THE INVENTION

Figure 1A:
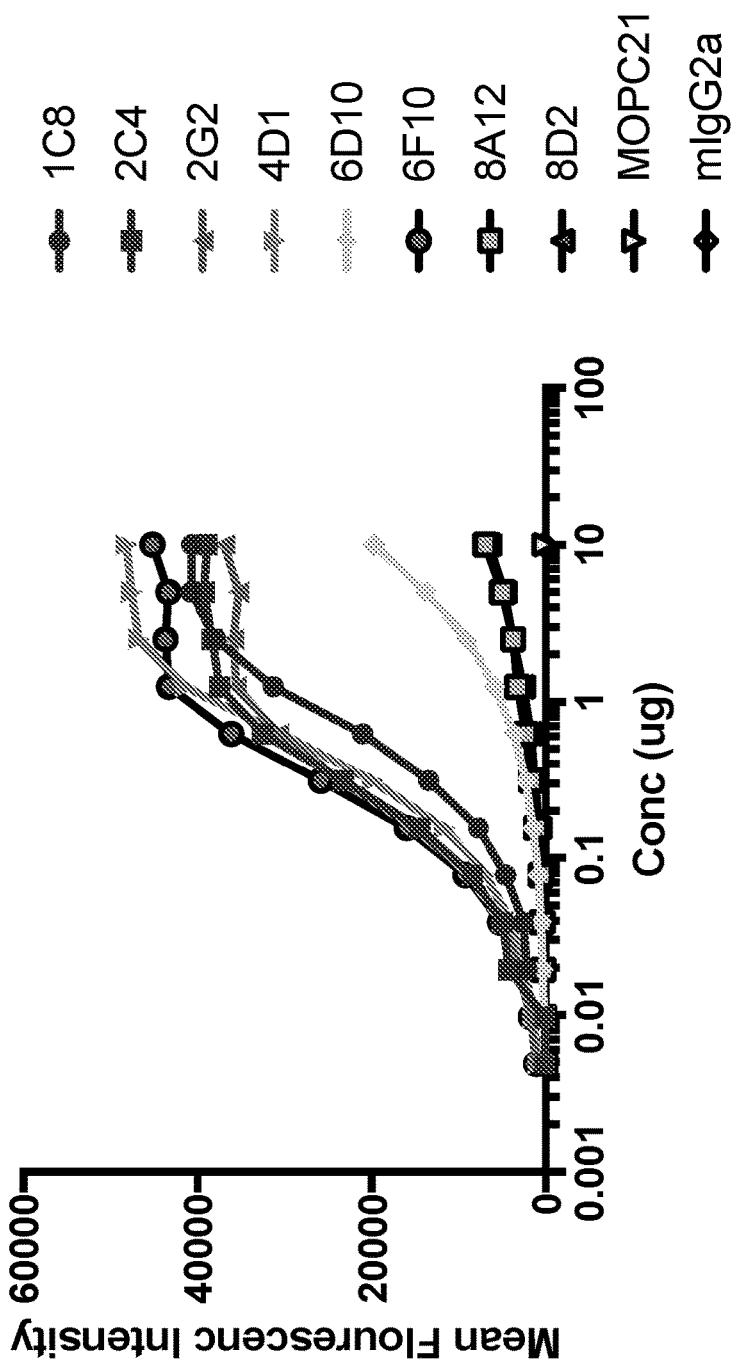
FIG. 1A shows binding affinity data for Anti-HHLA2 mAbs on HHLA2 transfected 300.19 mouse pre-B cell leukemic cell line by flow cytomtery

The present invention is based, at least in part, on the discovery that HHLA2, a B7 gene family member, is broadly expressed in a variety of tumors and antigen presenting cells and has been implicated as both an activating and inhibitory ligand for T cells. TMIGD2 expressed in naive T cells is an activating receptor for HHLA2 and transduces co-stimulatory signals following T cell antigen receptor (TCR) engagement. TMIGD2 is downregulated following repeated TCR stimulation. Based on the observations that HHLA2 is highly expressed in tumors and can serve as a checkpoint ligand, a panel of anti-HHLA2 human monoclonal antibodies (mAbs) were generated as candidate immune checkpoint inhibitor therapeutics. Given that the same ligand binding domains of B7 family members B7-1 and B7-2 are known to bind both activating and inhibitory receptors (e.g., CD28 and CTLA-4), anti-HHLA2 monoclonal antibodies that block TMIGD2 binding are believed to serve as good candidates for blocking binding to its putative inhibitory receptor. Evaluating soluble hHHLA2-mIgG2a binding to TMIGD2 transfected 300.19 mouse pre-B leukemic cells, both blocking and non-blocking anti-HHLA2 mAbs were identified. Anti-HHLA2 mAbs listed in Table 2 (e.g., 6F10, 4D1, 4E5 and 2G2) that blocked TMIGD2 binding and also bound HHLA2 transfected 300.19 cells with relative EC50 binding affinities of 0.25, 0.44 and 0.21 µg/ml (nanomolar range), respectively. Non-blocking antibodies listed in Table 2 (e.g., 1C8 and 6D10) bound HHLA2 with relative binding affinities of 0.63 and 22.49 µg/ml, respectively. The variable region heavy and light chain gene sequences for these candidate therapeutic anti-HHLA2 antibodies are described herein.

Anti-HHLA2 mAbs 1C8 and 6D10 were identified as good formalin-fixed paraffin-embedded immunohistochemistry or Western blotting reagents. HHLA2 in primary tumors from the TCGA database shows high expression in lung, renal, pancreatic and colorectal cancers and in AML and intermediate levels in head and neck, liver, ovarian, prostate and uterine cancers. HHLA2 mRNA expression in cancer is higher than corresponding normal tissues.

Screening a cell surface expressed human plasma protein library of >4500 full-length clones covering more than 3,500 different plasma membrane proteins with soluble human HHLA2-mIgG2a identified KIR3DL3 (killer cell immunoglobulin-like receptor, three domains, long cytoplasmic tail, 3) as a new receptor for HHLA2. The cytoplasmic tail of KIR3DL3 contains an ITIM motif comprised of the sequence "VTYAQL" indicating an inhibitory receptor for HHLA2 that can serve as a checkpoint receptor target for cancer immunotherapy. Selectivity of HHLA2 binding to KIR3DL3 was demonstrated because no binding against other KIRs receptors was observed using a panel of 14 KIR receptors (i.e., KIR3DL3, KIR2DL1, KIR2DL2, KIR2DL3, KIR2DL4, KIR2DL5A, KIR2DL5B, KIR2DS1, KIR2DS2, KIR2DS3, KIR2DS5, KIR3DL1, KIR3DS1, and KIR3DS1).

Since HHLA2 is expressed at high levels in multiple types of tumors, the anti-HHLA2 mAb check-point inhibitor therapeutics may increase the pool of patients that respond to check-point inhibitor treatment. Furthermore, patients who develop resistance to PD-1 therapy may express HHLA2 as an alternative immune evasion strategy and HHLA2 blockade may offer an avenue to overcome resistance to PD-1 immunotherapy.

Accordingly, the present invention provides monoclonal antibodies, and antigen-binding fragments thereof, that specifically bind to HHLA2, as well as immunoglobulins, polypeptides, nucleic acids thereof, and methods of using such antibodies for diagnostic, prognostic, and therapeutic purposes.

I. Definitions

The articles "a" and "an" are used herein to refer to one or to more than one (i.e. to at least one) of the grammatical object of the article. By way of example, "an element" means one element or more than one element.

The term "altered amount" of a marker refers to increased or decreased copy number of a marker and/or increased or decreased nucleic acid level of a particular marker gene or genes in a sample, as compared to that of the marker in a control sample. The term "altered amount" of a marker also includes an increased or decreased protein level of a marker in a sample, as compared to the protein level of the marker in a normal, control sample.

The term "altered activity" of a marker refers to an activity of a marker which is increased or decreased in a disease state, e.g., in a biological sample, as compared to the activity of the marker in a normal, control sample. Altered activity of a marker may be the result of, for example, altered expression of the marker, altered protein level of the marker, altered structure of the marker, or, e.g., an altered interaction with other proteins involved in the same or different pathway as the marker, or altered interaction with transcriptional activators or inhibitors.

The term "altered structure" of a marker refers to the presence of mutations or allelic variants within the marker gene or maker protein, e.g., mutations which affect expression or activity of the marker, as compared to the normal or wild-type gene or protein. For example, mutations include, but are not limited to substitutions, deletions, or addition mutations. Mutations may be present in the coding or non-coding region of the marker.

The term "activating receptor" includes immune cell receptors that bind antigen, complexed antigen (e.g., in the context of MHC polypeptides), or bind to antibodies. Such activating receptors include T cell receptors (TCR), B cell receptors (BCR), cytokine receptors, LPS receptors, complement receptors, and Fc receptors.

T cell receptors are present on T cells and are associated with CD3 polypeptides. T cell receptors are stimulated by antigen in the context of MHC polypeptides (as well as by polyclonal T cell activating reagents). T cell activation via the TCR results in numerous changes, e.g., protein phosphorylation, membrane lipid changes, ion fluxes, cyclic nucleotide alterations, RNA transcription changes, protein synthesis changes, and cell volume changes.

The term "chimeric antigen receptor" or "CAR" refers to engineered T cell receptors (TCR) having a desired antigen specificity. T lymphocytes recognize specific antigens through interaction of the T cell receptor (TCR) with short peptides presented by major histocompatibility complex (MHC) class I or II molecules. For initial activation and clonal expansion, naive T cells are dependent on professional antigen-presenting cells (APCs) that provide additional co-stimulatory signals. TCR activation in the absence of co-stimulation can result in unresponsiveness and clonal anergy. To bypass immunization, different approaches for the derivation of cytotoxic effector cells with grafted recognition specificity have been developed. CARs have been constructed that consist of binding domains derived from natural ligands or antibodies specific for cell-surface components of the TCR-associated CD3 complex. Upon antigen binding, such chimeric antigen receptors link to endogenous signaling pathways in the effector cell and generate activating signals similar to those initiated by the TCR complex. Since the first reports on chimeric antigen receptors, this concept has steadily been refined and the molecular design of chimeric receptors has been optimized and routinely use any number of well-known binding domains, such as scFV, Fav, and another protein binding fragments described herein.

Generally, CARs are one type of "cell therapy" (e.g., T cell therapy) contemplated for use according to the present invention. Although numerous representative embodiments of agents and methods for modulating immune cell activity by modulating the HHLA2 pathway, such as modulating the interaction between HHLA2 and a HHLA2 natural binding partner, such as TMIGD2 and/or KIR3DL3, immune cell-based therapies and methods are also encompassed. For example, T cells engineered to have a knockout, knockdown, or increased expression of TMIGD2 and/or KIR3DL3 are contemplated. Similarly, immune cells or other cells engineered to have a knockout, knockdown, or increased expression of a HHLA2 ligand, such as TMIGD2 and/or KIR3DL3, are also contemplated.

B cell receptors are present on B cells. B cell antigen receptors are a complex between membrane Ig (mIg) and other transmembrane polypeptides (e.g., Igα and Igβ). The signal transduction function of mIg is triggered by cross-linking of receptor polypeptides by oligomeric or multimeric antigens. B cells can also be activated by anti-immunoglobulin antibodies. Upon BCR activation, numerous changes occur in B cells, including tyrosine phosphorylation.

Fc receptors are found on many cells which participate in immune responses. Fc receptors (FcRs) are cell surface receptors for the Fc portion of immunoglobulin polypeptides (Igs). Among the human FcRs that have been identified so far are those which recognize IgG (designated FcγR), IgE (FcεR1), IgA (Fcα), and polymerized IgM/A (Fcμα R). FcRs are found in the following cell types: FcεR I (mast cells), Fcε R.II (many leukocytes), Fcα R (neutrophils), and Fcα R (glandular epithelium, hepatocytes) (Hogg, N. (1988) *Immunol. Today* 9:185-86). The widely studied FcγRs are central in cellular immune defenses, and are responsible for stimulating the release of mediators of inflammation and hydrolytic enzymes involved in the pathogenesis of autoimmune disease (Unkeless, J. C. et al. (1988) *Annu. Rev. Immunol.* 6:251-81). The FcγRs provide a crucial link between effector cells and the lymphocytes that secrete Ig, since the macrophage/monocyte, polymorphonuclear leukocyte, and natural killer (NK) cell FcγRs confer an element of specific recognition mediated by IgG. Human leukocytes have at least three different receptors for IgG: h Fcγ RI (found on monocytes/macrophages), hFcγ RII (on monocytes, neutrophils, eosinophils, platelets, possibly B cells, and the K562 cell line), and Fcγ III (on NK cells, neutrophils, eosinophils, and macrophages).

With respect to T cells, transmission of a costimulatory signal to a T cell involves a signaling pathway that is not inhibited by cyclosporin A. In addition, a costimulatory signal can induce cytokine secretion (e.g., IL-2 and/or IL-10) in a T cell and/or can prevent the induction of unresponsiveness to antigen, the induction of anergy, or the induction of cell death (deletion) in the T cell.

The term "activity," when used with respect to a polypeptide, e.g., HHLA2 and/or a HHLA2 natural binding partner, such as TMIGD2 and/or KIR3DL3, includes activities that are inherent in the structure of the protein. For example, with regard to a HHLA2 ligand, the term "activity" includes the ability to modulate immune cell inhibition by modulating an inhibitory signal in an immune cell (e.g., by engaging a natural receptor on an immune cell). Those of skill in the art will recognize that when an activating form of the HHLA2 ligannd polypeptide binds to an inhibitory receptor, an inhibitory signal is generated in the immune cell.

The term "inhibitory signal" refers to a signal transmitted via an inhibitory receptor (e.g., HHLA2, KLRB1, CTLA4, PD-1, and the like) for a polypeptide on a immune cell. Such a signal antagonizes a signal via an activating receptor (e.g., via a TCR, CD3, BCR, TMIGD2, or Fc polypeptide) and can result in, e.g., inhibition of second messenger generation; an inhibition of proliferation; an inhibition of effector function in the immune cell, e.g., reduced phagocytosis, reduced antibody production, reduced cellular cytotoxicity, the failure of the immune cell to produce mediators, (such as cytokines (e.g., IL-2) and/or mediators of allergic responses); or the development of anergy.

The amount of a biomarker in a subject is "significantly" higher or lower than the normal amount of the biomarker, if the amount of the biomarker is greater or less, respectively, than the normal or control level by an amount greater than the standard error of the assay employed to assess amount, and preferably at least 20%, 30%, 40%, 50%, 60%, 70%, 80%, 90%, 100%, 150%, 200%, 300%, 350%, 400%, 500%, 600%, 700%, 800%, 900%, 1000% or than that amount. Alternatively, the amount of the biomarker in the subject can be considered "significantly" higher or lower than the normal and/or control amount if the amount is at least about two, and preferably at least about 5%, 10%, 15%, 20%, 25%, 30%, 35%, 40%, 45%, 50%, 55%, 60%, 65%, 70%, 75%, 80%, 85%, 90%, 95%, 100%, 105%, 110%, 115%, 120%, 125%, 130%, 135%, 140%, 145%, 150%, 155%, 160%, 165%, 170%, 175%, 180%, 185%, 190%, 195%, two times, three times, four times, five times, or more, or any range in between, such as 5%-100%, higher or lower, respectively, than the normal and/or control amount of the biomarker. Such significant modulation values can be applied to any metric described herein, such as altered level of expression, altered activity, changes in cancer cell hyperproliferative growth, changes in cancer cell death, changes in biomarker inhibition, changes in test agent binding, and the like.

The "amount" of a marker, e.g., expression or copy number of a marker or MCR, or protein level of a marker, in a subject is "significantly" higher or lower than the normal amount of a marker, if the amount of the marker is greater or less, respectively, than the normal level by an amount greater than the standard error of the assay employed to assess amount, and preferably at least twice, and more preferably three, four, five, ten or more times that amount. Alternately, the amount of the marker in the subject can be considered "significantly" higher or lower than the normal amount if the amount is at least about two, and preferably at least about three, four, or five times, higher or lower, respectively, than the normal amount of the marker.

The term "altered level of expression" of a marker refers to an expression level or copy number of a marker in a test sample e.g., a sample derived from a subject suffering from cancer, that is greater or less than the standard error of the assay employed to assess expression or copy number, and is preferably at least twice, and more preferably three, four, five or ten or more times the expression level or copy number of the marker or chromosomal region in a control sample (e.g., sample from a healthy subject not having the associated disease) and preferably, the average expression level or copy number of the marker or chromosomal region in several control samples. The altered level of expression is greater or less than the standard error of the assay employed to assess expression or copy number, and is preferably at least twice, and more preferably three, four, five or ten or more times the expression level or copy number of the marker in a control sample (e.g., sample from a healthy subject not having the associated disease) and preferably, the average expression level or copy number of the marker in several control samples.

The term "immunotherapy" refers to a form of targeted therapy that may comprise, for example, the use of cancer vaccines and/or sensitized antigen presenting cells. For example, an oncolytic virus is a virus that is able to infect and lyse cancer cells, while leaving normal cells unharmed, making them potentially useful in immunomodulatory therapy. Replication of oncolytic viruses both facilitates tumor cell destruction and also produces dose amplification at the tumor site. They may also act as vectors for anticancer genes, allowing them to be specifically delivered to the tumor site. The immunotherapy can involve passive immunity for short-term protection of a host, achieved by the administration of pre-formed antibody directed against a cancer antigen or disease antigen (e.g., administration of a monoclonal antibody, optionally linked to a chemotherapeutic agent or toxin, to a tumor antigen). Immunotherapy can also focus on using the cytotoxic lymphocyte-recognized epitopes of cancer cell lines. Alternatively, antisense polynucleotides, ribozymes, RNA interference molecules, triple helix polynucleotides and the like, can be used to selectively modulate biomolecules that are linked to the initiation, progression, and/or pathology of a tumor or cancer. As described above, immunotherapy against immune checkpoint targets, such as HHLA2, TMIGD2, KIR3DL3, and the like are useful.

Unless otherwise specified here within, the terms "antibody" and "antibodies" broadly encompass naturally-occurring forms of antibodies (e.g. IgG, IgA, IgM, IgE) and recombinant antibodies such as single-chain antibodies, chimeric and humanized antibodies and multi-specific antibodies, as well as fragments and derivatives of all of the foregoing, which fragments and derivatives have at least an antigenic binding site. Antibody derivatives may comprise a protein or chemical moiety conjugated to an antibody. An "antibody" refers to a glycoprotein comprising at least two heavy (H) chains and two light (L) chains inter-connected by disulfide bonds, or an antigen binding portion thereof. Each heavy chain is comprised of a heavy chain variable region (abbreviated herein as $V_H$) and a heavy chain constant region. The heavy chain constant region is comprised of three domains, CH1, CH2 and CH3. Each light chain is comprised of a light chain variable region (abbreviated herein as $V_L$) and a light chain constant region. The light chain constant region is comprised of one domain, CL. The $V_H$ and $V_L$ regions can be further subdivided into regions of hypervariability, termed complementarity determining regions (CDR), interspersed with regions that are more conserved, termed framework regions (FR). Each $V_H$ and $V_L$ is composed of three CDRs and four FRs, arranged from amino-terminus to carboxyl-terminus in the following order: FR1, CDR1, FR2, CDR2, FR3, CDR3, FR4. The variable regions of the heavy and light chains contain a binding domain that interacts with an antigen. The term "inactivating antibodies" refers to antibodies that do not induce the complement system.

The term "antibody" as used herein also includes an "antigen-binding portion" of an antibody (or simply "antibody portion"). The term "antigen-binding portion", as used herein, refers to one or more fragments of an antibody that retain the ability to specifically bind to an antigen (e.g., HHLA2 polypeptide or fragment thereof). It has been shown that the antigen-binding function of an antibody can be performed by fragments of a full-length antibody. Examples of binding fragments encompassed within the term "antigen-binding portion" of an antibody include (i) a Fab fragment, a monovalent fragment consisting of the VL, VH, CL and CH1 domains; (ii) a F(ab')$_2$ fragment, a bivalent fragment comprising two Fab fragments linked by a disulfide bridge at the hinge region; (iii) a Fd fragment consisting of the VH and CH1 domains; (iv) a Fv fragment consisting of the $V_L$ and VH domains of a single arm of an antibody, (v) a dAb fragment (Ward et al., (1989) Nature 341:544-546), which consists of a VH domain; and (vi) an isolated complementarity determining region (CDR). Furthermore, although the two domains of the Fv fragment, $V_L$ and VH, are coded for by separate genes, they can be joined, using recombinant methods, by a synthetic linker that enables them to be made as a single protein chain in which the $V_L$ and VH regions pair to form monovalent polypeptides (known as single chain Fv (scFv); see e.g., Bird et al. (1988) *Science* 242:423-426; and Huston et al. (1988) *Proc. Natl. Acad. Sci. USA* 85:5879-5883; and Osbourn et al. 1998, Nature Biotechnology 16: 778). Such single chain antibodies are also intended to be encompassed within the term "antigen-binding portion" of an antibody. Any VH and $V_L$ sequences of specific scFv can be linked to human immunoglobulin constant region cDNA or genomic sequences, in order to generate expression vectors encoding complete IgG polypeptides or other isotypes. VH and $V_L$ can also be used in the generation of Fab, Fv or other fragments of immunoglobulins using either protein chemistry or recombinant DNA technology. Other forms of single chain antibodies, such as diabodies are also encompassed. Diabodies are bivalent, bispecific antibodies in which VH and $V_L$ domains are expressed on a single polypeptide chain, but using a linker that is too short to allow for pairing between the two domains on the same chain, thereby forcing the domains to pair with complementary domains of another chain and creating two antigen binding sites (see e.g., Holliger, P., et al. (1993) *Proc. Natl. Acad. Sci. USA* 90:6444-6448; Poljak, R. J., et al. (1994) *Structure* 2:1121-1123).

Still further, an antibody or antigen-binding portion thereof may be part of larger immunoadhesion polypeptides, formed by covalent or noncovalent association of the antibody or antibody portion with one or more other proteins or peptides. Examples of such immunoadhesion polypeptides include use of the streptavidin core region to make a tetrameric scFv polypeptide (Kipriyanov, S. M., et al. (1995) *Human Antibodies and Hybridomas* 6:93-101) and use of a cysteine residue, a marker peptide and a C-terminal polyhistidine tag to make bivalent and biotinylated scFv polypeptides (Kipriyanov, S. M., et al. (1994) *Mol. Immunol.* 31:1047-1058). Antibody portions, such as Fab and F(ab')$_2$ fragments, can be prepared from whole antibodies using conventional techniques, such as papain or pepsin digestion, respectively, of whole antibodies. Moreover, antibodies, antibody portions and immunoadhesion polypeptides can be obtained using standard recombinant DNA techniques, as described herein.

Antibodies may be polyclonal or monoclonal; xenogeneic, allogeneic, or syngeneic; or modified forms thereof (e.g., humanized, chimeric, etc.). Antibodies may also be fully human. In one embodiment, antibodies of the present invention bind specifically or substantially specifically to HHLA2 polypeptides or fragments thereof. The terms "monoclonal antibodies" and "monoclonal antibody composition", as used herein, refer to a population of antibody polypeptides that contain only one species of an antigen binding site capable of immunoreacting with a particular epitope of an antigen, whereas the term "polyclonal antibodies" and "polyclonal antibody composition" refer to a population of antibody polypeptides that contain multiple species of antigen binding sites capable of interacting with a particular antigen. A monoclonal antibody composition typically displays a single binding affinity for a particular antigen with which it immunoreacts.

The term "body fluid" refers to fluids that are excreted or secreted from the body as well as fluids that are normally not (e.g. amniotic fluid, aqueous humor, bile, blood and blood plasma, cerebrospinal fluid, cerumen and earwax, cowper's fluid or pre-ejaculatory fluid, chyle, chyme, stool, female ejaculate, interstitial fluid, intracellular fluid, lymph, menses, breast milk, mucus, pleural fluid, pus, saliva, sebum, semen, serum, sweat, synovial fluid, tears, urine, vaginal lubrication, vitreous humor, vomit).

The terms "cancer" or "tumor" or "hyperproliferative disorder" refer to the presence of cells possessing characteristics typical of cancer-causing cells, such as uncontrolled proliferation, immortality, metastatic potential, rapid growth and proliferation rate, and certain characteristic morphological features. Cancer cells are often in the form of a tumor, but such cells may exist alone within an animal, or may be a non-tumorigenic cancer cell, such as a leukemia cell. Cancers include, but are not limited to, B cell cancer, e.g., multiple myeloma, Waldenstram's macroglobulinemia, the heavy chain diseases, such as, for example, alpha chain disease, gamma chain disease, and mu chain disease, benign monoclonal gammopathy, and immunocytic amyloidosis, melanomas, breast cancer, lung cancer, bronchus cancer, colorectal cancer, prostate cancer, pancreatic cancer, stomach cancer, ovarian cancer, urinary bladder cancer, brain or central nervous system cancer, peripheral nervous system cancer, esophageal cancer, cervical cancer, uterine or endometrial cancer, cancer of the oral cavity or pharynx, liver cancer, kidney cancer, testicular cancer, biliary tract cancer, small bowel or appendix cancer, salivary gland cancer, thyroid gland cancer, adrenal gland cancer, osteosarcoma, chondrosarcoma, cancer of hematologic tissues, and the like. Other non-limiting examples of types of cancers applicable to the methods encompassed by the present invention include human sarcomas and carcinomas, e.g., fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, colorectal cancer, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, liver cancer, choriocarcinoma, seminoma, embryonal carcinoma, Wilms' tumor, cervical cancer, bone cancer, brain tumor, testicular cancer, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, melanoma, neuroblastoma, retinoblastoma; leukemias, e.g., acute lymphocytic leukemia and acute myelocytic leukemia (myeloblastic, promyelocytic, myelomonocytic, monocytic and erythroleukemia); chronic leukemia (chronic myelocytic (granulocytic) leukemia and chronic lymphocytic leukemia); and polycythemia vera, lymphoma (Hodgkin's disease and non-Hodgkin's disease), multiple myeloma, Waldenstrom's macroglobulinemia, and heavy chain disease. In some embodiments, cancers are epithlelial in nature and include but are not limited to, bladder cancer, breast cancer, cervical cancer, colon cancer, gynecologic cancers, renal cancer, laryngeal cancer, lung cancer, oral cancer, head and neck cancer, ovarian cancer, pancreatic cancer, prostate cancer, or skin cancer. In other embodiments, the cancer is breast cancer, prostate cancer, lung cancer, or colon cancer. In still other embodiments, the epithelial cancer is non-small-cell lung cancer, nonpapillary renal cell carcinoma, cervical carcinoma, ovarian carcinoma (e.g., serous ovarian carcinoma), or breast carcinoma. The epithelial cancers may be characterized in various other ways including, but not limited to, serous, endometrioid, mucinous, clear cell, Brenner, or undifferentiated.

The terms "CDR", and its plural "CDRs", refer to a complementarity determining region (CDR) of which three make up the binding character of a light chain variable region (CDR-L1, CDR-L2 and CDR-L3) and three make up the binding character of a heavy chain variable region (CDR-H1, CDR-H2 and CDR-H3). CDRs contribute to the functional activity of an antibody molecule and are separated by amino acid sequences that comprise scaffolding or framework regions. The exact definitional CDR boundaries and lengths are subject to different classification and numbering systems. CDRs may therefore be referred to by Kabat, Chothia, contact or any other boundary definitions. Despite differing boundaries, each of these systems has some degree of overlap in what constitutes the so called "hypervariable regions" within the variable sequences. CDR definitions according to these systems may therefore differ in length and boundary areas with respect to the adjacent framework region. See for example Kabat, Chothia, and/or MacCallum et al., (Kabat et al., in "Sequences of Proteins of Immunological Interest," $5^{th}$ Edition, U.S. Department of Health and Human Services, 1992; Chothia et al. (1987) J. Mol. Biol. 196, 901; and MacCallum et al., J. Mol. Biol. (1996) 262, 732, each of which is incorporated by reference in its entirety).

As used herein, the term "classifying" includes "to associate" or "to categorize" a sample with a disease state. In certain instances, "classifying" is based on statistical evidence, empirical evidence, or both. In certain embodiments, the methods and systems of classifying use of a so-called training set of samples having known disease states. Once established, the training data set serves as a basis, model, or template against which the features of an unknown sample are compared, in order to classify the unknown disease state of the sample. In certain instances, classifying the sample is akin to diagnosing the disease state of the sample. In certain other instances, classifying the sample is akin to differentiating the disease state of the sample from another disease state.

As used herein, the term "coding region" refers to regions of a nucleotide sequence comprising codons which are translated into amino acid residues, whereas the term "non-coding region" refers to regions of a nucleotide sequence that are not translated into amino acids (e.g., 5' and 3' untranslated regions).

"Complement [to]" or "complementary" refers to the broad concept of sequence complementarity between regions of two nucleic acid strands or between two regions of the same nucleic acid strand. It is known that an adenine residue of a first nucleic acid region is capable of forming specific hydrogen bonds ("base pairing") with a residue of a second nucleic acid region which is antiparallel to the first region if the residue is thymine or uracil. Similarly, it is known that a cytosine residue of a first nucleic acid strand is capable of base pairing with a residue of a second nucleic acid strand which is antiparallel to the first strand if the residue is guanine. A first region of a nucleic acid is complementary to a second region of the same or a different nucleic acid if, when the two regions are arranged in an antiparallel fashion, at least one nucleotide residue of the first region is capable of base pairing with a residue of the second region. In one embodiment, the first region comprises a first portion and the second region comprises a second portion, whereby, when the first and second portions are arranged in an antiparallel fashion, at least about 50%, and preferably at least about 75%, at least about 90%, or at least about 95% of the nucleotide residues of the first portion are capable of base pairing with nucleotide residues in the second portion. In another embodiment, all nucleotide residues of the first portion are capable of base pairing with nucleotide residues in the second portion.

As used herein, the term "composite antibody" refers to an antibody which has variable regions comprising germline or non-germline immunoglobulin sequences from two or more unrelated variable regions. Additionally, the term "composite, human antibody" refers to an antibody which has constant regions derived from human germline or non-germline immunoglobulin sequences and variable regions comprising human germline or non-germline sequences from two or more unrelated human variable regions. A composite, human antibody is useful as an effective component in a therapeutic agent according to the present invention since the antigenicity of the composite, human antibody in the human body is lowered.

The term "control" refers to any reference standard suitable to provide a comparison to the expression products in the test sample. In one embodiment, the control comprises obtaining a "control sample" from which expression product levels are detected and compared to the expression product levels from the test sample. Such a control sample may comprise any suitable sample, including but not limited to a sample from a control cancer patient (can be stored sample or previous sample measurement) with a known outcome; normal tissue or cells isolated from a subject, such as a normal patient or the cancer patient, cultured primary cells/tissues isolated from a subject such as a normal subject or the cancer patient, adjacent normal cells/tissues obtained from the same organ or body location of the cancer patient, a tissue or cell sample isolated from a normal subject, or a primary cells/tissues obtained from a depository. In another preferred embodiment, the control may comprise a reference standard expression product level from any suitable source, including but not limited to housekeeping genes, an expression product level range from normal tissue (or other previously analyzed control sample), a previously determined expression product level range within a test sample from a group of patients, or a set of patients with a certain outcome (for example, survival for one, two, three, four years, etc.) or receiving a certain treatment (for example, standard of care cancer therapy). It will be understood by those of skill in the art that such control samples and reference standard expression product levels can be used in combination as controls in the methods of the present invention. In one embodiment, the control may comprise normal or non-cancerous cell/tissue sample. In another preferred embodiment, the control may comprise an expression level for a set of patients, such as a set of cancer patients, or for a set of cancer patients receiving a certain treatment, or for a set of patients with one outcome versus another outcome. In the former case, the specific expression product level of each patient can be assigned to a percentile level of expression, or expressed as either higher or lower than the mean or average of the reference standard expression level. In another preferred embodiment, the control may comprise normal cells, cells from patients treated with combination chemotherapy, and cells from patients having benign cancer. In another embodiment, the control may also comprise a measured value for example, average level of expression of a particular gene in a population compared to the level of expression of a housekeeping gene in the same population. Such a population may comprise normal subjects, cancer patients who have not undergone any treatment (i.e., treatment naive), cancer patients undergoing standard of care therapy, or patients having benign cancer. In another preferred embodiment, the control comprises a ratio transformation of expression product levels, including but not limited to determining a ratio of expression product levels of two genes in the test sample and comparing it to any suitable ratio of the same two genes in a reference standard; determining expression product levels of the two or more genes in the test sample and determining a difference in expression product levels in any suitable control; and determining expression product levels of the two or more genes in the test sample, normalizing their expression to expression of housekeeping genes in the test sample, and comparing to any suitable control. In particularly preferred embodiments, the control comprises a control sample which is of the same lineage and/or type as the test sample. In another embodiment, the control may comprise expression product levels grouped as percentiles within or based on a set of patient samples, such as all patients with cancer. In one embodiment a control expression product level is established wherein higher or lower levels of expression product relative to, for instance, a particular percentile, are used as the basis for predicting outcome. In another preferred embodiment, a control expression product level is established using expression product levels from cancer control patients with a known outcome, and the expression product levels from the test sample are compared to the control expression product level as the basis for predicting outcome. As demonstrated by the data below, the methods of the invention are not limited to use of a specific cut-point in comparing the level of expression product in the test sample to the control.

As used herein, the term "Fc region" is used to define a C-terminal region of an immunoglobulin heavy chain, including native-sequence Fc regions and variant Fc regions. Although the boundaries of the Fc region of an immunoglobulin heavy chain might vary, the human IgG heavy-chain Fc region is usually defined to stretch from an amino acid residue at position Cys226, or from Pro230, to the carboxyl-terminus thereof. Suitable native-sequence Fc regions for use in the antibodies of the present invention include human IgG1, IgG2 (IgG2A, IgG2B), IgG3 and IgG4.

As used herein, "Fc receptor" or "FcR" describes a receptor that binds to the Fc region of an antibody. The preferred FcR is a native sequence human FcR. Moreover, a preferred FcR is one which binds an IgG antibody (a gamma receptor) and includes receptors of the FcγRI, FcγRII, and FcγRIII subclasses, including allelic variants and alternatively spliced forms of these receptors, FcγRII receptors include FcγRIIA (an "activating receptor") and FcγRIIB (an "inhibiting receptor"), which have similar amino acid sequences that differ primarily in the cytoplasmic domains thereof. Activating receptor FcγRIIA contains an immunoreceptor tyrosine-based activation motif (ITAM) in its cytoplasmic domain. Inhibiting receptor FcγRIIB contains an immunoreceptor tyrosine-based inhibition motif (ITIM) in its cytoplasmic domain (see M. Daëron, *Annu. Rev. Immunol.* 15:203-234 (1997). FcRs are reviewed in Ravetch and Kinet, *Annu. Rev. Immunol.* 9: 457-92 (1991); Capel et al., *Immunomethods* 4: 25-34 (1994); and de Haas et al., *J. Lab. Clin. Med.* 126: 330-41 (1995). Other FcRs, including those to be identified in the future, are encompassed by the term "FcR" herein.

A molecule is "fixed" or "affixed" to a substrate if it is covalently or non-covalently associated with the substrate such the substrate can be rinsed with a fluid (e.g. standard saline citrate, pH 7.4) without a substantial fraction of the molecule dissociating from the substrate.

As used herein, "framework" or "FR" residues are those variable-domain residues other than the HVR residues as herein defined.

"Function-conservative variants" are those in which a given amino acid residue in a protein or enzyme has been changed without altering the overall conformation and function of the polypeptide, including, but not limited to, replacement of an amino acid with one having similar properties (such as, for example, polarity, hydrogen bonding potential, acidic, basic, hydrophobic, aromatic, and the like). Amino acids other than those indicated as conserved may differ in a protein so that the percent protein or amino acid sequence similarity between any two proteins of similar function may vary and may be, for example, from 70% to 99% as determined according to an alignment scheme such as by the Cluster Method, wherein similarity is based on the MEGALIGN algorithm. A "function-conservative variant" also includes a polypeptide which has at least 60% amino acid identity as determined by BLAST or FASTA algorithms, preferably at least 75%, more preferably at least 85%, still preferably at least 90%, and even more preferably at least 95%, and which has the same or substantially similar properties or functions as the native or parent protein to which it is compared.

As used herein, the term "heterologous antibody" is defined in relation to the transgenic non-human organism producing such an antibody. This term refers to an antibody having an amino acid sequence or an encoding nucleic acid sequence corresponding to that found in an organism not consisting of the transgenic non-human animal, and generally from a species other than that of the transgenic non-human animal.

"Homologous" as used herein, refers to nucleotide sequence similarity between two regions of the same nucleic acid strand or between regions of two different nucleic acid strands. When a nucleotide residue position in both regions is occupied by the same nucleotide residue, then the regions are homologous at that position. A first region is homologous to a second region if at least one nucleotide residue position of each region is occupied by the same residue. Homology between two regions is expressed in terms of the proportion of nucleotide residue positions of the two regions that are occupied by the same nucleotide residue. By way of example, a region having the nucleotide sequence 5'-ATTGCC-3' and a region having the nucleotide sequence 5'-TATGGC-3' share 50% homology. Preferably, the first region comprises a first portion and the second region comprises a second portion, whereby, at least about 50%, and preferably at least about 75%, at least about 90%, or at least about 95% of the nucleotide residue positions of each of the portions are occupied by the same nucleotide residue. More preferably, all nucleotide residue positions of each of the portions are occupied by the same nucleotide residue.

As used herein, the term "host cell" is intended to refer to a cell into which a nucleic acid of the present invention, such as a recombinant expression vector of the present invention, has been introduced. The terms "host cell" and "recombinant host cell" are used interchangeably herein. It should be understood that such terms refer not only to the particular subject cell but to the progeny or potential progeny of such a cell. Because certain modifications may occur in succeeding generations due to either mutation or environmental influences, such progeny may not, in fact, be identical to the parent cell, but are still included within the scope of the term as used herein.

The term "humanized antibody", as used herein, is intended to include antibodies made by a non-human cell having variable and constant regions which have been altered to more closely resemble antibodies that would be made by a human cell. For example, by altering the non-human antibody amino acid sequence to incorporate amino acids found in human germline immunoglobulin sequences. Humanized antibodies may include amino acid residues not encoded by human germline immunoglobulin sequences (e.g., mutations introduced by random or site-specific mutagenesis in vitro or by somatic mutation in vivo), for example in the CDRs. The term "humanized antibody", as used herein, also includes antibodies in which CDR sequences derived from the germline of another mammalian species, such as a mouse, have been grafted onto human framework sequences.

A humanized mouse, as used herein, is a mouse carrying functioning human genes (e.g., HHLA2, TMIGD2, and/or KIR3DL3), cells, tissues, and/or organs. Humanized mice are commonly used as small animal models in biological and medical research for human therapeutics. The nude mouse and severe combined immunodeficiency (SCID) mouse may be used for this purpose. The NCG mouse, NOG mouse and the NSG mouse may be used to engraft human cells and tissues more efficiently than other models. Such humanized mouse models may be used to model the human immune system in scenarios of health and pathology, and may enable evaluation of therapeutic candidates in an in vivo setting relevant to human physiology.

As used herein, the term "hypervariable region," "HVR," or "HV," refers to the regions of an antibody-variable domain that are hypervariable in sequence and/or form structurally defined loops. Generally, antibodies comprise six HVRs; three in the VH (H1, H2, H3), and three in the VL (L1, L2, L3). In native antibodies, H3 and L3 display the most diversity of the six HVRs, and H3 in particular is believed to play a unique role in conferring fine specificity to antibodies. See, e.g., Xu et al. (2000) Immunity 13, 37-45; Johnson and Wu in Methods in Molecular Biology 248, 1-25 (Lo, ed., Human Press, Totowa, N J, 2003)). Indeed, naturally occurring camelid antibodies consisting of a heavy chain only are functional and stable in the absence of light chain (see, e.g., Hamers-Casterman et al. (1993) Nature 363:446-448 (1993) and Sheriff et al. (1996) Nature Struct. Biol. 3, 733-736).

As used herein, the term "immune cell" refers to cells that play a role in the immune response. Immune cells are of hematopoietic origin, and include lymphocytes, such as B cells and T cells; natural killer cells; myeloid cells, such as monocytes, macrophages, eosinophils, mast cells, basophils, and granulocytes.

As used herein, the term "immune disorder" includes immune diseases, conditions, and predispositions to, including, but not limited to, cancer, chronic inflammatory disease and disorders (including, e.g., Crohn's disease, inflammatory bowel disease, reactive arthritis, and Lyme disease), insulin-dependent diabetes, organ specific autoimmunity (including, e.g., multiple sclerosis, Hashimoto's thyroiditis, autoimmune uveitis, and Grave's disease), contact dermatitis, psoriasis, graft rejection, graft versus host disease, sarcoidosis, atopic conditions (including, e.g., asthma and allergy including, but not limited to, allergic rhinitis and gastrointestinal allergies such as food allergies), eosinophilia, conjunctivitis, glomerular nephritis, systemic lupus erythematosus, scleroderma, certain pathogen susceptibilities such as helminthic (including, e.g., leishmaniasis) and certain viral infections (including, e.g., HIV and bacterial infections such as tuberculosis and lepromatous leprosy) and malaria.

As used herein, the term "immune response" includes T cell mediated and/or B cell mediated immune responses. Exemplary immune responses include T cell responses, e.g., cytokine production, and cellular cytotoxicity. In addition, the term immune response includes immune responses that are indirectly effected by T cell activation, e.g., antibody production (humoral responses) and activation of cytokine responsive cells, e.g., macrophages.

The term "immunotherapeutic agent" can include any molecule, peptide, antibody or other agent which can stimulate a host immune system to generate an immune response to a tumor or cancer in the subject. Various immunotherapeutic agents are useful in the compositions and methods described herein.

The term "immune checkpoint" refers to a group of molecules on the cell surface of CD4+ and/or CD8+ T cells that fine-tune immune responses by down-modulating or inhibiting an anti-tumor immune response. Immune checkpoint proteins are well-known in the art and include, without limitation, CTLA-4, PD-1, VISTA, B7-H2, B7-H3, PD-L1, B7-H4, B7-H6, ICOS, HVEM, PD-L2, CD160, gp49B, PIR-B, KIR family receptors, TIM-1, TIM-3, TIM-4, LAG-3, GITR, 4-IBB, OX-40, BTLA, SIRPalpha (CD47), CD48, 2B4 (CD244), B7.1, B7.2, ILT-2, ILT-4, TIGIT, HHLA2, butyrophilins, and A2aR (see, for example, WO 2012/177624). The term further encompasses biologically active protein fragment, as well as nucleic acids encoding full-length immune checkpoint proteins and biologically active protein fragments thereof. In some embodiment, the term further encompasses any fragment according to homology descriptions provided herein.

Immune checkpoints and their sequences are well-known in the art and representative embodiments are described below. For example, the term "PD-1" refers to a member of the immunoglobulin gene superfamily that functions as a coinhibitory receptor having PD-L1 and PD-L2 as known ligands. PD-1 was previously identified using a subtraction cloning based approach to select for genes upregulated during TCR-induced activated T cell death. PD-1 is a member of the CD28/CTLA-4 family of molecules based on its ability to bind to PD-L1. Like CTLA-4, PD-1 is rapidly induced on the surface of T-cells in response to anti-CD3 (Agata et al. 25 (1996) *Int. Immunol.* 8:765). In contrast to CTLA-4, however, PD-1 is also induced on the surface of B-cells (in response to anti-IgM). PD-1 is also expressed on a subset of thymocytes and myeloid cells (Agata et al. (1996) supra; Nishimura et al. (1996) *Int. Immunol.* 8:773).

As used herein, the term "inhibiting" and grammatical equivalents thereof refer decrease, limiting, and/or blocking a particular action, function, or interaction. In one embodiment, the term refers to reducing the level of a given output or parameter to a quantity (e.g., background staining, HHLA2 signaling, HHLA2 immunoinhibitory function, and the like) which is at least 10%, 15%, 20%, 25%, 30%, 35%, 40%, 45%, 50%, 55%, 60%, 65%, 70%, 75%, 80%, 85%, 90%, 95%, 99% or less than the quantity in a corresponding control. A reduced level of a given output or parameter need not, although it may, mean an absolute absence of the output or parameter. The invention does not require, and is not limited to, methods that wholly eliminate the output or parameter. The given output or parameter can be determined using methods well-known in the art, including, without limitation, immunohistochemical, molecular biological, cell biological, clinical, and biochemical assays, as discussed herein and in the examples. The opposite terms "promoting," "increasing," and grammatical equivalents thereof refer to the increase in the level of a given output or parameter that is the reverse of that described for inhibition or decrease.

As used herein, the term "interaction", when referring to an interaction between two molecules, refers to the physical contact (e.g., binding) of the molecules with one another (e.g., binding of HHLA2 to TMIGD2 or binding of HHLA2 to KIR3DL3). Generally, such an interaction results in an activity (which produces a biological effect) of one or both of said molecules. The activity may be a direct activity of one or both of the molecules, (e.g., signal transduction). Alternatively, one or both molecules in the interaction may be prevented from binding their ligand, and thus be held inactive with respect to ligand binding activity (e.g., binding its ligand and triggering or inhibiting an immune response).

To inhibit such an interaction results in the disruption of the activity of one or more molecules involved in the interaction. To enhance such an interaction is to prolong or increase the likelihood of said physical contact, and prolong or increase the likelihood of said activity.

The term "neoadjuvant therapy" refers to a treatment given before the primary treatment. Examples of neoadjuvant therapy can include chemotherapy, radiation therapy, and hormone therapy.

As used herein, the term an "isolated antibody" is intended to refer to an antibody which is substantially free of other antibodies having different antigenic specificities (e.g., an isolated antibody that specifically binds to HHLA2 and is substantially free of antibodies that do not bind to HHLA2). An isolated antibody that specifically binds to a HHLA2 may, however, have cross-reactivity to other B7 family proteins, respectively, from different species. For example, in some embodiments, the antibody maintains specific binding affinity for at least two species, such as human and other animals, such as non-rodent animals, or other mammal or non-mammal species. However, in some embodiments, the antibody maintains higher or indeed specific affinity and selectivity for human HHLA2. In addition, an isolated antibody is typically substantially free of other cellular material and/or chemicals. In one embodiment of the present invention, a combination of "isolated" monoclonal antibodies having different specificities to human HHLA2 are combined in a well-defined composition.

As used herein, an "isolated protein" refers to a protein that is substantially free of other proteins, cellular material, separation medium, and culture medium when isolated from cells or produced by recombinant DNA techniques, or chemical precursors or other chemicals when chemically synthesized. An "isolated" or "purified" protein or biologically active portion thereof is substantially free of cellular material or other contaminating proteins from the cell or tissue source from which the antibody, polypeptide, peptide or fusion protein is derived, or substantially free from chemical precursors or other chemicals when chemically synthesized. The language "substantially free of cellular material" includes preparations of a target polypeptide (e.g., immunoglobulin) or fragment thereof, in which the protein is separated from cellular components of the cells from which it is isolated or recombinantly produced. In one embodiment, the language "substantially free of cellular material" includes preparations of target protein or fragment thereof, having less than about 30% (by dry weight) of non-target protein (also referred to herein as a "contaminating protein"), more preferably less than about 20% of non-target protein, still more preferably less than about 10% of non-target protein, and most preferably less than about 5% non-target protein. When antibody, polypeptide, peptide or fusion protein or fragment thereof, e.g., a biologically active fragment thereof, is recombinantly produced, it is also preferably substantially free of culture medium, i.e., culture medium represents less than about 20%, more preferably less than about 10%, and most preferably less than about 5% of the volume of the protein preparation.

As used herein, the term "isotype" refers to the antibody class (e.g., IgM or IgG1) that is encoded by heavy chain constant region genes.

As used herein, the term "$K_D$" is intended to refer to the dissociation equilibrium constant of a particular antibody-antigen interaction. The binding affinity of antibodies of the disclosed invention may be measured or determined by standard antibody-antigen assays, for example, competitive assays, saturation assays, or standard immunoassays such as ELISA or RIA.

As used herein, a "kit" is any manufacture (e.g. a package or container) comprising at least one reagent, e.g. a probe, for specifically detecting or modulating the expression of a marker of the present invention. The kit may be promoted, distributed, or sold as a unit for performing the methods of the present invention.

As used herein, the term "monoclonal antibody", refers to an antibody which displays a single binding specificity and affinity for a particular epitope. Accordingly, the term "human monoclonal antibody" refers to an antibody which displays a single binding specificity and which has variable and constant regions derived from human germline or non-germline immunoglobulin sequences. In one embodiment, human monoclonal antibodies are produced by a hybridoma which includes a B cell obtained from a transgenic non-human animal, e.g., a transgenic mouse, having a genome comprising a human heavy chain transgene and a light chain transgene fused to an immortalized cell.

A "marker" is a gene whose altered level of expression in a tissue or cell from its expression level in normal or healthy tissue or cell is associated with a disease state, such as cancer. A "marker nucleic acid" is a nucleic acid (e.g., mRNA, cDNA) encoded by or corresponding to a marker of the present invention. Such marker nucleic acids include DNA (e.g., cDNA) comprising the entire or a partial sequence of any of the nucleic acid sequences set forth in the Sequence Listing or the complement of such a sequence. The marker nucleic acids also include RNA comprising the entire or a partial sequence of any of the nucleic acid sequences set forth in the Sequence Listing or the complement of such a sequence, wherein all thymidine residues are replaced with uridine residues. A "marker protein" is a protein encoded by or corresponding to a marker of the present invention. A marker protein comprises the entire or a partial sequence of any of the sequences set forth in the Sequence Listing. In some embodiments, the overall HHLA2 is used as a marker. In other embodiments, a fragment of HHLA2 is used as a marker. The terms "protein" and "polypeptide" are used interchangeably.

As used herein, the term "modulate" includes up-regulation and down-regulation, e.g., enhancing or inhibiting a response.

The "normal" level of expression of a marker is the level of expression of the marker in cells of a subject, e.g., a human patient, not afflicted with a disease or disorder related to aberrant marker levels. An "over-expression" or "significantly higher level of expression" of a marker refers to an expression level in a test sample that is greater than the standard error of the assay employed to assess expression, and is preferably at least twice, and more preferably three, four, five or ten times the expression level of the marker in a control sample (e.g., sample from a healthy subjects not having the marker associated disease) and preferably, the average expression level of the marker in several control samples. A "significantly lower level of expression" of a marker refers to an expression level in a test sample that is at least twice, and more preferably three, four, five or ten times lower than the expression level of the marker in a control sample (e.g., sample from a healthy subject not having the marker associated disease) and preferably, the average expression level of the marker in several control samples.

Such "significance" levels can also be applied to any other measured parameter described herein, such as for expression, inhibition, cytotoxicity, cell growth, and the like.

The term "pre-determined" biomarker amount and/or activity measurement(s) may be a biomarker amount and/or activity measurement(s) used to, by way of example only, evaluate a subject that may be selected for a particular treatment, evaluate a response to a treatment such as one or more modulators of the HHLA2 pathway, such as a modulator of HHLA2 and one or more natural binding partners, such as TMIGD2 and/or KIR3DL3, either alone or in combination with one or more immunotherapies, and/or evaluate the disease state. A pre-determined biomarker amount and/or activity measurement(s) may be determined in populations of patients with or without cancer. The pre-determined biomarker amount and/or activity measurement(s) can be a single number, equally applicable to every patient, or the pre-determined biomarker amount and/or activity measurement(s) can vary according to specific subpopulations of patients. Age, weight, height, and other factors of a subject may affect the pre-determined biomarker amount and/or activity measurement(s) of the individual. Furthermore, the pre-determined biomarker amount and/or activity can be determined for each subject individually. In one embodiment, the amounts determined and/or compared in a method described herein are based on absolute measurements. In another embodiment, the amounts determined and/or compared in a method described herein are based on relative measurements, such as ratios (e.g., cell ratios or serum biomarker normalized to the expression of housekeeping or otherwise generally constant biomarker). The pre-determined biomarker amount and/or activity measurement(s) can be any suitable standard. For example, the pre-determined biomarker amount and/or activity measurement(s) can be obtained from the same or a different human for whom a patient selection is being assessed. In one embodiment, the pre-determined biomarker amount and/or activity measurement(s) can be obtained from a previous assessment of the same patient. In such a manner, the progress of the selection of the patient can be monitored over time. In addition, the control can be obtained from an assessment of another human or multiple humans, e.g., selected groups of humans, if the subject is a human. In such a manner, the extent of the selection of the human for whom selection is being assessed can be compared to suitable other humans, e.g., other humans who are in a similar situation to the human of interest, such as those suffering from similar or the same condition(s) and/or of the same ethnic group.

The term "predictive" includes the use of a biomarker nucleic acid and/or protein status, e.g., over- or under-activity, emergence, expression, growth, remission, recurrence or resistance of tumors before, during or after therapy, for determining the likelihood of response of a cancer to immunomodulatory therapy, such as HHLA2 pathway modulator therapy (e.g., modulator of the interaction between HHLA2 and one or more natural binding partners, such as TMIGD2 and/or KIR3DL3, either alone or in combination with an immunotherapy, such as an immune checkpoint inhibition therapy). Such predictive use of the biomarker may be confirmed by, e.g., (1) increased or decreased copy number (e.g., by FISH, FISH plus SKY, single-molecule sequencing, e.g., as described in the art at least at J. Biotechnol., 86:289-301, or qPCR), overexpression or underexpression of a biomarker nucleic acid (e.g., by ISH, Northern Blot, or qPCR), increased or decreased biomarker protein (e.g., by IHC) and/or biomarker target, or increased or decreased activity, e.g., in more than about 5%, 6%, 7%, 8%, 9%, 10%, 11%, 12%, 13%, 14%, 15%, 20%, 25%, 30%, 40%, 50%, 60%, 70%, 80%, 90%, 95%, 100%, or more of assayed human cancers types or cancer samples; (2) its absolute or relatively modulated presence or absence in a biological sample, e.g., a sample containing tissue, whole blood, serum, plasma, buccal scrape, saliva, cerebrospinal fluid, urine, stool, or bone marrow, from a subject, e.g. a human, afflicted with cancer; (3) its absolute or relatively modulated presence or absence in clinical subset of patients with cancer (e.g., those responding to a particular immunomodulatory therapy (e.g., HHLA2 pathway modulator therapy (e.g., modulator of the interaction between HHLA2 and one or more natural binding partners, such as TMIGD2 AND/OR KIR3DL3, either alone or in combination with an immunotherapy) or those developing resistance thereto).

The terms "prevent," "preventing," "prevention," "prophylactic treatment," and the like refer to reducing the probability of developing a disease, disorder, or condition in a subject, who does not have, but is at risk of or susceptible to developing a disease, disorder, or condition.

The term "prognosis" includes a prediction of the probable course and outcome of cancer or the likelihood of recovery from the disease. In some embodiments, the use of statistical algorithms provides a prognosis of cancer in an individual. For example, the prognosis can be surgery, development of a clinical subtype of cancer (e.g., solid tumors, such as lung cancer, melanoma, and renal cell carcinoma), development of one or more clinical factors, development of intestinal cancer, or recovery from the disease.

The term "response to therapy" (e.g., HHLA2 pathway modulator therapy (e.g., modulator of the interaction between HHLA2 and one or more natural binding partners, such as TMIGD2 and/or KIR3DL3, either alone or in combination with an immunotherapy, such as an immune checkpoint inhibition therapy) relates to any response to therapy (e.g., HHLA2 pathway modulator therapy (e.g., modulator of the interaction between HHLA2 and one or more natural binding partners, such as TMIGD2 and/or KIR3DL3, either alone or in combination with an immunotherapy, such as an immune checkpoint inhibition therapy), and, for cancer, preferably to a change in cancer cell numbers, tumor mass, and/or volume after initiation of neoadjuvant or adjuvant chemotherapy. Hyperproliferative disorder response may be assessed, for example for efficacy or in a neoadjuvant or adjuvant situation, where the size of a tumor after systemic intervention can be compared to the initial size and dimensions as measured by CT, PET, mammogram, ultrasound or palpation. Responses may also be assessed by caliper measurement or pathological examination of the tumor after biopsy or surgical resection. Response may be recorded in a quantitative fashion like percentage change in tumor volume or in a qualitative fashion like "pathological complete response" (pCR), "clinical complete remission" (cCR), "clinical partial remission" (cPR), "clinical stable disease" (cSD), "clinical progressive disease" (cPD) or other qualitative criteria. Assessment of hyperproliferative disorder response may be done early after the onset of neoadjuvant or adjuvant therapy, e.g., after a few hours, days, weeks or preferably after a few months. A typical endpoint for response assessment is upon termination of neoadjuvant chemotherapy or upon surgical removal of residual tumor cells and/or the tumor bed. This is typically three months after initiation of neoadjuvant therapy. In some embodiments, clinical efficacy of the therapeutic treatments described herein may be determined by measuring the clinical benefit rate (CBR). The clinical benefit rate is measured by determining the sum of the percentage of patients who are in complete remission (CR), the number of patients who are in partial remission (PR) and the number of patients having stable disease (SD) at a time point at least 6 months out from the end of therapy. The shorthand for this formula is CBR=CR+PR+SD over 6 months. In some embodiments, the CBR for a particular cancer therapeutic regimen is at least 25%, 30%, 35%, 40%, 45%, 50%, 55%, 60%, 65%, 70%, 75%, 80%, 85%, or more. Additional criteria for evaluating the response to cancer therapies are related to "survival," which includes all of the following: survival until mortality, also known as overall survival (wherein said mortality may be either irrespective of cause or tumor related); "recurrence-free survival" (wherein the term recurrence shall include both localized and distant recurrence); metastasis free survival; disease free survival (wherein the term disease shall include cancer and diseases associated therewith). The length of said survival may be calculated by reference to a defined start point (e.g., time of diagnosis or start of treatment) and end point (e.g., death, recurrence or metastasis). In addition, criteria for efficacy of treatment can be expanded to include response to chemotherapy, probability of survival, probability of metastasis within a given time period, and probability of tumor recurrence. For example, in order to determine appropriate threshold values, a particular cancer therapeutic regimen can be administered to a population of subjects and the outcome can be correlated to biomarker measurements that were determined prior to administration of any immunomodulatory therapy. The outcome measurement may be pathologic response to therapy given in the neoadjuvant setting. Alternatively, outcome measures, such as overall survival and disease-free survival can be monitored over a period of time for subjects following immunomodulatory therapy for whom biomarker measurement values are known. In certain embodiments, the doses administered are standard doses known in the art for cancer therapeutic agents. The period of time for which subjects are monitored can vary. For example, subjects may be monitored for at least 2, 4, 6, 8, 10, 12, 14, 16, 18, 20, 25, 30, 35, 40, 45, 50, 55, or 60 months.

The term "resistance" refers to an acquired or natural resistance of a cancer sample or a mammal to an immunomodulatory therapy (i.e., being nonresponsive to or having reduced or limited response to the therapeutic treatment), such as having a reduced response to a therapeutic treatment by 5% or more, for example, 10%, 15%, 20%, 25%, 30%, 35%, 40%, 45%, 50%, 55%, 60%, 65%, 70%, 75%, 80%, 85%, 90%, 95%, 100%, or more, to 2-fold, 3-fold, 4-fold, 5-fold, 10-fold, 15-fold, 20-fold or more. The reduction in response can be measured by comparing with the same cancer sample or mammal before the resistance is acquired, or by comparing with a different cancer sample or a mammal who is known to have no resistance to the therapeutic treatment. A typical acquired resistance to chemotherapy is called "multidrug resistance." The multidrug resistance can be mediated by P-glycoprotein or can be mediated by other mechanisms, or it can occur when a mammal is infected with a multi-drug-resistant microorganism or a combination of microorganisms. The determination of resistance to a therapeutic treatment is routine in the art and within the skill of an ordinarily skilled clinician, for example, can be measured by cell proliferative assays and cell death assays as described herein as "sensitizing." In some embodiments, the term "reverses resistance" means that the use of a second agent in combination with a primary cancer therapy (e.g., chemotherapeutic or radiation therapy) is able to produce a significant decrease in tumor volume at a level of statistical significance (e.g., p<0.05) when compared to tumor volume of untreated tumor in the circumstance where the primary cancer therapy (e.g., chemotherapeutic or radiation therapy) alone is unable to produce a statistically significant decrease in tumor volume compared to tumor volume of untreated tumor. This generally applies to tumor volume measurements made at a time when the untreated tumor is growing log rhythmically.

The terms "response" or "responsiveness" refers to response to therapy. For example, an anti-cancer response includes reduction of tumor size or inhibiting tumor growth. The terms can also refer to an improved prognosis, for example, as reflected by an increased time to recurrence, which is the period to first recurrence censoring for second primary cancer as a first event or death without evidence of recurrence, or an increased overall survival, which is the period from treatment to death from any cause. To respond or to have a response means there is a beneficial endpoint attained when exposed to a stimulus. Alternatively, a negative or detrimental symptom is minimized, mitigated or attenuated on exposure to a stimulus. It will be appreciated that evaluating the likelihood that a tumor or subject will exhibit a favorable response is equivalent to evaluating the likelihood that the tumor or subject will not exhibit favorable response (i.e., will exhibit a lack of response or be non-responsive).

The term "tolerance" or "unresponsiveness" includes refractivity of cells, such as immune cells, to stimulation, e.g., stimulation via an activating receptor or a cytokine. Unresponsiveness can occur, e.g., because of exposure to immunosuppressants or exposure to high doses of antigen. Several independent methods can induce tolerance. One mechanism is referred to as "anergy," which is defined as a state where cells persist in vivo as unresponsive cells rather than differentiating into cells having effector functions. Such refractivity is generally antigen-specific and persists after exposure to the tolerizing antigen has ceased. For example, anergy in T cells is characterized by lack of cytokine production, e.g., IL-2. T cell anergy occurs when T cells are exposed to antigen and receive a first signal (a T cell receptor or CD-3 mediated signal) in the absence of a second signal (a costimulatory signal). Under these conditions, reexposure of the cells to the same antigen (even if reexposure occurs in the presence of a costimulatory polypeptide) results in failure to produce cytokines and, thus, failure to proliferate. Anergic T cells can, however, proliferate if cultured with cytokines (e.g., IL-2). For example, T cell anergy can also be observed by the lack of IL-2 production by T lymphocytes as measured by ELISA or by a proliferation assay using an indicator cell line. Alternatively, a reporter gene construct can be used. For example, anergic T cells fail to initiate IL-2 gene transcription induced by a heterologous promoter under the control of the 5' IL-2 gene enhancer or by a multimer of the API sequence that can be found within the enhancer (Kang et al. (1992) Science 257:1134). Another mechanism is referred to as "exhaustion." T cell exhaustion is a state of T cell dysfunction that arises during many chronic infections and cancer. It is defined by poor effector function, sustained expression of inhibitory receptors and a transcriptional state distinct from that of functional effector or memory T cells.

As used herein, the term "nucleic acid molecule" is intended to include DNA molecules and RNA molecules. A nucleic acid molecule may be single-stranded or double-stranded, but preferably is double-stranded DNA. As used herein, the term "isolated nucleic acid molecule" in reference to nucleic acids encoding antibodies or antibody portions (e.g., VH, $V_L$, CDR3) that bind to HHLA2 (e.g., mAbs 2G2, 4D1, 8A12, 8D2, 1C8, 2C4, 6D10, 4E5, and 6F10 and polyclonal antibodies), is intended to refer to a nucleic acid molecule in which the nucleotide sequences encoding the antibody or antibody portion are free of other nucleotide sequences encoding antibodies or antibody portions that bind antigens other than HHLA2, which other sequences may naturally flank the nucleic acid in human genomic DNA.

A nucleic acid is "operably linked" when it is placed into a functional relationship with another nucleic acid sequence. For instance, a promoter or enhancer is operably linked to a coding sequence if it affects the transcription of the sequence. With respect to transcription regulatory sequences, operably linked means that the DNA sequences being linked are contiguous and, where necessary to join two protein coding regions, contiguous and in reading frame. For switch sequences, operably linked indicates that the sequences are capable of effecting switch recombination.

An "over-expression" or "significantly higher level of expression" of a marker refers to an expression level in a test sample that is greater than the standard error of the assay employed to assess expression, and is preferably at least twice, and more preferably 2.1, 2.2, 2.3, 2.4, 2.5, 2.6, 2.7, 2.8, 2.9, 3, 3.5, 4, 4.5, 5, 5.5, 6, 6.5, 7, 7.5, 8, 8.5, 9, 9.5, 10, 10.5, 11, 12, 13, 14, 15, 16, 17, 18, 19, 20 times or more higher than the expression activity or level of the marker in a control sample (e.g., sample from a healthy subject not having the marker associated disease) and preferably, the average expression level of the marker in several control samples. A "significantly lower level of expression" of a marker refers to an expression level in a test sample that is at least twice, and more preferably 2.1, 2.2, 2.3, 2.4, 2.5, 2.6, 2.7, 2.8, 2.9, 3, 3.5, 4, 4.5, 5, 5.5, 6, 6.5, 7, 7.5, 8, 8.5, 9, 9.5, 10, 10.5, 11, 12, 13, 14, 15, 16, 17, 18, 19, 20 times or more lower than the expression level of the marker in a control sample (e.g., sample from a healthy subject not having the marker associated disease) and preferably, the average expression level of the marker in several control samples.

Such antibodies, described herein, can be used in any one of well-known immunoassay forms, including, without limitation, a radioimmunoassay, a Western blot assay, an immunofluorescence assay, an enzyme immunoassay, an immunoprecipitation assay, a chemiluminescence assay, an immunohistochemical assay, a dot blot assay, or a slot blot assay. General techniques to be used in performing the various immunoassays noted above and other variations of the techniques, such as in situ proximity ligation assay (PLA), fluorescence polarization immunoassay (FPIA), fluorescence immunoassay (FIA), enzyme immunoassay (EIA), nephelometric inhibition immunoassay (NIA), enzyme linked immunosorbent assay (ELISA), and radioimmunoassay (RIA), ELISA, etc. alone or in combination or alternatively with NMR, MALDI-TOF, LC-MS/MS, are known to those of ordinary skill in the art.

Such reagents can also be used to monitor protein levels in a cell or tissue, e.g., white blood cells or lymphocytes, as part of a clinical testing procedure, e.g., in order to monitor an optimal dosage of an inhibitory agent. Detection can be facilitated by coupling (e.g., physically linking) the antibody to a detectable substance. Examples of detectable substances include various enzymes, prosthetic groups, fluorescent materials, luminescent materials, bioluminescent materials, and radioactive materials. Examples of suitable enzymes include horseradish peroxidase, alkaline phosphatase, P-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin, and examples of suitable radioactive material include $^{125}$I, $^{131}$I, $^{35}$S or $^3$H.

Such reagents can also be used with any number of biological samples. Biological samples can be collected from a variety of sources from a patient including a body fluid sample, cell sample, or a tissue sample comprising nucleic acids and/or proteins. In a preferred embodiment, the subject and/or control sample is selected from the group consisting of cells, cell lines, histological slides, paraffin embedded tissues, biopsies, whole blood, nipple aspirate, serum, plasma, buccal scrape, saliva, cerebrospinal fluid, urine, stool, and bone marrow. In one embodiment, the sample is serum, plasma, or urine. In another embodiment, the sample is serum.

The samples can be collected from individuals repeatedly over a longitudinal period of time (e.g., once or more on the order of days, weeks, months, annually, biannually, etc.). Obtaining numerous samples from an individual over a period of time can be used to verify results from earlier detections and/or to identify an alteration in biological pattern as a result of, for example, disease progression, drug treatment, etc. For example, subject samples can be taken and monitored every month, every two months, or combinations of one, two, or three month intervals according to the present invention. In addition, the biomarker amount and/or activity measurements of the subject obtained over time can be conveniently compared with each other, as well as with those of normal controls during the monitoring period, thereby providing the subject's own values, as an internal, or personal, control for long-term monitoring.

Samples can contain live cells/tissue, fresh frozen cells, fresh tissue, biopsies, fixed cells/tissue, cells/tissue embedded in a medium, such as paraffin, histological slides, or any combination thereof.

Sample preparation and separation can involve any of the procedures, depending on the type of sample collected and/or analysis of biomarker measurement(s). Such procedures include, by way of example only, concentration, dilution, adjustment of pH, removal of high abundance polypeptides (e.g., albumin, gamma globulin, and transferrin, etc.), addition of preservatives and calibrants, addition of protease inhibitors, addition of denaturants, desalting of samples, concentration of sample proteins, extraction and purification of lipids.

The sample preparation can also isolate molecules that are bound in non-covalent complexes to other protein (e.g., carrier proteins). This process may isolate those molecules bound to a specific carrier protein (e.g., albumin), or use a more general process, such as the release of bound molecules from all carrier proteins via protein denaturation, for example using an acid, followed by removal of the carrier proteins.

Removal of undesired proteins (e.g., high abundance, uninformative, or undetectable proteins) from a sample can be achieved using high affinity reagents, high molecular weight filters, ultracentrifugation and/or electrodialysis. High affinity reagents include antibodies or other reagents (e.g., aptamers) that selectively bind to high abundance proteins. Sample preparation could also include ion exchange chromatography, metal ion affinity chromatography, gel filtration, hydrophobic chromatography, chromatofocusing, adsorption chromatography, isoelectric focusing and related techniques. Molecular weight filters include membranes that separate molecules on the basis of size and molecular weight. Such filters may further employ reverse osmosis, nanofiltration, ultrafiltration and microfiltration.

The terms "polypeptide fragment" or "fragment", when used in reference to a reference polypeptide, refers to a polypeptide in which amino acid residues are deleted as compared to the reference polypeptide itself, but where the remaining amino acid sequence is usually identical to the corresponding positions in the reference polypeptide. Such deletions may occur at the amino-terminus, internally, or at the carboxyl-terminus of the reference polypeptide, or alternatively both. Fragments typically are at least 5, 6, 8 or 10 amino acids long, at least 14 amino acids long, at least 20, 30, 40 or 50 amino acids long, at least 75 amino acids long, or at least 100, 150, 200, 300, 500 or more amino acids long. They can be, for example, at least and/or including 10, 15, 20, 25, 30, 35, 40, 45, 50, 55, 60, 65, 70, 75, 80, 85, 90, 95, 100, 120, 140, 160, 180, 200, 220, 240, 260, 280, 300, 320, 340, 360, 380, 400, 420, 440, 460, 480, 500, 520, 540, 560, 580, 600, 620, 640, 660, 680, 700, 720, 740, 760, 780, 800, 820, 840, 860, 880, 900, 920, 940, 960, 980, 1000, 1020, 1040, 1060, 1080, 1100, 1120, 1140, 1160, 1180, 1200, 1220, 1240, 1260, 1280, 1300, 1320, 1340 or more long so long as they are less than the length of the full-length polypeptide. Alternatively, they can be no longer than and/or excluding such a range so long as they are less than the length of the full-length polypeptide.

The term "probe" refers to any molecule which is capable of selectively binding to a specifically intended target molecule, for example, a nucleotide transcript or protein encoded by or corresponding to a marker. Probes can be either synthesized by one skilled in the art, or derived from appropriate biological preparations. For purposes of detection of the target molecule, probes may be specifically designed to be labeled, as described herein. Examples of molecules that can be utilized as probes include, but are not limited to, RNA, DNA, proteins, antibodies, and organic molecules.

As used herein, the term "rearranged" refers to a configuration of a heavy chain or light chain immunoglobulin locus wherein a V segment is positioned immediately adjacent to a D-J or J segment in a conformation encoding essentially a complete $V_H$ and $V_L$ domain, respectively. A rearranged immunoglobulin gene locus can be identified by comparison to germline DNA; a rearranged locus will have at least one recombined heptamer/nonamer homology element.

As used herein, the term "recombinant host cell" (or simply "host cell"), is intended to refer to a cell into which a recombinant expression vector has been introduced. It should be understood that such terms are intended to refer not only to the particular subject cell but to the progeny of such a cell. Because certain modifications may occur in succeeding generations due to either mutation or environmental influences, such progeny may not, in fact, be identical to the parent cell, but are still included within the scope of the term "host cell" as used herein.

As used herein, the term "recombinant human antibody" includes all human antibodies that are prepared, expressed, created or isolated by recombinant means, such as (a) antibodies isolated from an animal (e.g., a mouse) that is transgenic or transchromosomal for human immunoglobulin genes or a hybridoma prepared therefrom (described further below), (b) antibodies isolated from a host cell transformed to express the antibody, e.g., from a transfectoma, (c)

antibodies isolated from a recombinant, combinatorial human antibody library, and (d) antibodies prepared, expressed, created or isolated by any other means that involve splicing of human immunoglobulin gene sequences to other DNA sequences. Such recombinant human antibodies have variable and constant regions derived from human germline and/or non-germline immunoglobulin sequences. In certain embodiments, however, such recombinant human antibodies can be subjected to in vitro mutagenesis (or, when an animal transgenic for human Ig sequences is used, in vivo somatic mutagenesis) and thus the amino acid sequences of the $V_H$ and $V_L$ regions of the recombinant antibodies are sequences that, while derived from and related to human germline VH and $V_L$ sequences, may not naturally exist within the human antibody germline repertoire in vivo.

The term "costimulate," as used with reference to activated immune cells, includes the ability of a costimulatory polypeptide to provide a second, non-activating receptor mediated signal (a "costimulatory signal") that induces proliferation or effector function. For example, a costimulatory signal can result in cytokine secretion, e.g., in a T cell that has received a T cell-receptor-mediated signal. Immune cells that have received a cell-receptor mediated signal, e.g., via an activating receptor are referred to herein as "activated immune cells."

The term "costimulatory receptor" includes receptors which transmit a costimulatory signal to a immune cell, e.g., CD28. As used herein, the term "inhibitory receptors" includes receptors which transmit a negative signal to an immune cell (e.g., CTLA4, KIR3DL3 or PD-1). An inhibitory signal as transduced by an inhibitory receptor can occur even if a costimulatory receptor (such as CD28) is not present on the immune cell and, thus, is not simply a function of competition between inhibitory receptors and costimulatory receptors for binding of costimulatory polypeptides (Fallarino et al. (1998) *J. Exp. Med.* 188:205). Transmission of an inhibitory signal to an immune cell can result in unresponsiveness or anergy or programmed cell death in the immune cell. Preferably transmission of an inhibitory signal operates through a mechanism that does not involve apoptosis. As used herein the term "apoptosis" includes programmed cell death which can be characterized using techniques which are known in the art. Apoptotic cell death can be characterized, e.g., by cell shrinkage, membrane blebbing and chromatin condensation culminating in cell fragmentation. Cells undergoing apoptosis also display a characteristic pattern of internucleosomal DNA cleavage. Depending upon the form of the polypeptide that binds to a receptor, a signal can either be transmitted (e.g., by a multivalent form of HHLA2 and/or KIR3DL3 polypeptide) or a signal can be inhibited (e.g., by a soluble, monovalent form of a HHLA2 and/or KIR3DL3), for instance by competing with activating forms of HHLA2 and/or KIR3DL3 for binding to one or more natural binding partners. However, there are instances in which a soluble polypeptide can be stimulatory. The effects of a modulatory agent can be easily demonstrated using routine screening assays as described herein.

The terms "high," "low," "intermediate," and "negative" in connection with cellular biomarker expression refers to the amount of the biomarker expressed relative to the cellular expression of the biomarker by one or more reference cells. Biomarker expression can be determined according to any method described herein including, without limitation, an analysis of the cellular level, activity, structure, and the like, of one or more biomarker genomic nucleic acids, ribonucleic acids, and/or polypeptides. In one embodiment, the terms refer to a defined percentage of a population of cells expressing the biomarker at the highest, intermediate, or lowest levels, respectively. Such percentages can be defined as the top 0.1%, 0.5%, 1.0%, 1.5%, 2.0%, 2.5%, 3.0%, 3.5%, 4.0%, 4.5%, 5.0%, 5.5%, 6.0%, 6.5%, 7.0%, 7.5%, 8.0%, 8.5%, 9.0%, 9.5%, 10%, 11%, 12%, 13%, 14%, 15% or more, or any range in between, inclusive, of a population of cells that either highly express or weakly express the biomarker. The term "low" excludes cells that do not detectably express the biomarker, since such cells are "negative" for biomarker expression. The term "intermediate" includes cells that express the biomarker, but at levels lower than the population expressing it at the "high" level. In another embodiment, the terms can also refer to, or in the alternative refer to, cell populations of biomarker expression identified by qualitative or statistical plot regions. For example, cell populations sorted using flow cytometry can be discriminated on the basis of biomarker expression level by identifying distinct plots based on detectable moiety analysis, such as based on mean fluorescence intensities and the like, according to well-known methods in the art. Such plot regions can be refined according to number, shape, overlap, and the like based on well-known methods in the art for the biomarker of interest. In still another embodiment, the terms can also be determined according to the presence or absence of expression for additional biomarkers.

As described above, the term "response" is generally related to for example, determining the effects on progression, efficacy, or outcome of a clinical intervention. In some embodiments, responses relate directly to a change in tumor mass and/or volume after initiation of clinical intervention (e.g., administration of an anti-HHLA2 monoclonal antibody, such as 2G2, 4D1, 8A12, 8D2, 1C8, 2C4, 6D10, 4E5, or 6F10 and polyclonal antibodies). For example, hyperproliferative disorder responses may be assessed according to the size of a tumor after systemic intervention compared to the initial size and dimensions as measured by CT, PET, mammogram, ultrasound or palpation. Response may also be assessed by caliper measurement or pathological examination of the tumor after biopsy or surgical resection. Response may be recorded in a quantitative fashion like percentage change in tumor volume or in a qualitative fashion like "pathological complete response" (pCR), "clinical complete remission" (cCR), "clinical partial remission" (cPR), "clinical stable disease" (cSD), "clinical progressive disease" (cPD) or other qualitative criteria. Assessment may be done early after the onset of the clinical intervention, e.g., after a few hours, days, weeks or preferably after a few months. A typical endpoint for response assessment is upon termination of the clinical intervention or upon surgical removal of residual tumor cells and/or the tumor bed.

As used herein, the term "specific binding" refers to antibody binding to a predetermined antigen. Typically, the antibody binds with an affinity ($K_D$) of approximately less than $10^{-7}$ M, such as approximately less than $10^{-8}$ M, $10^{-9}$ M or $10^{-10}$ M or even lower when determined by surface plasmon resonance (SPR) technology in a BIACORE® assay instrument using human HHLA2 as the analyte and the antibody as the ligand, and binds to the predetermined antigen with an affinity that is at least 1.1-, 1.2-, 1.3-, 1.4-, 1.5-, 1.6-, 1.7-, 1.8-, 1.9-, 2.0-, 2.5-, 3.0-, 3.5-, 4.0-, 4.5-, 5.0-, 6.0-, 7.0-, 8.0-, 9.0-, or 10.0-fold or greater than its affinity for binding to a non-specific antigen (e.g., BSA, casein) other than the predetermined antigen or a closely-related antigen. The phrases "an antibody recognizing an antigen" and "an antibody specific for an antigen" are used interchangeably herein with the term "an antibody which binds specifically to an antigen."

As used herein, "subject" refers to any healthy animal, mammal or human, or any animal, mammal or human afflicted with a disease or disorder related to aberrant marker levels. The term "subject" is interchangeable with "patient". The term "non-human animal"includes all vertebrates, e.g., mammals and non-mammals, such as non-human primates, sheep, dog, cow, chickens, amphibians, reptiles, etc.

The language "substantially free of chemical precursors or other chemicals" includes preparations of antibody, polypeptide, peptide or fusion protein in which the protein is separated from chemical precursors or other chemicals which are involved in the synthesis of the protein. In one embodiment, the language "substantially free of chemical precursors or other chemicals" includes preparations of antibody, polypeptide, peptide or fusion protein having less than about 30% (by dry weight) of chemical precursors or non-antibody, polypeptide, peptide or fusion protein chemicals, more preferably less than about 20% chemical precursors or non-antibody, polypeptide, peptide or fusion protein chemicals, still more preferably less than about 10% chemical precursors or non-antibody, polypeptide, peptide or fusion protein chemicals, and most preferably less than about 5% chemical precursors or non-antibody, polypeptide, peptide or fusion protein chemicals.

As used herein, the term "survival" includes all of the following: survival until mortality, also known as overall survival (wherein said mortality may be either irrespective of cause or tumor related); "recurrence-free survival" (wherein the term recurrence shall include both localized and distant recurrence); metastasis free survival; disease free survival (wherein the term disease shall include cancer and diseases associated therewith). The length of said survival may be calculated by reference to a defined start point (e.g. time of diagnosis or start of treatment) and end point (e.g. death, recurrence or metastasis). In addition, criteria for efficacy of treatment can be expanded to include response to chemotherapy, probability of survival, probability of metastasis within a given time period, and probability of tumor recurrence.

A "transcribed polynucleotide" or "nucleotide transcript" is a polynucleotide (e.g. an mRNA, hnRNA, a cDNA, or an analog of such RNA or cDNA) which is complementary to or homologous with all or a portion of a mature mRNA made by transcription of a marker of the present invention and normal post-transcriptional processing (e.g. splicing), if any, of the RNA transcript, and reverse transcription of the RNA transcript.

As used herein, the term "T cell"includes CD4+ T cells and CD8+ T cells. The term T cell also includes both T helper 1 type T cells and T helper 2 type T cells. The term "antigen presenting cell" includes professional antigen presenting cells (e.g., B lymphocytes, monocytes, dendritic cells, Langerhans cells) as well as other antigen presenting cells (e.g., keratinocytes, endothelial cells, astrocytes, fibroblasts, oligodendrocytes).

Conventional T cells, also known as Tconv or Teffs, have effector functions (e.g., cytokine secretion, cytotoxic activity, anti-self-recognition, and the like) to increase immune responses by virtue of their expression of one or more T cell receptors. Tcons or Teffs are generally defined as any T cell population that is not a Treg and include, for example, naive T cells, activated T cells, memory T cells, resting Tcons, or Tcons that have differentiated toward, for example, the Th1 or Th2 lineages. In some embodiments, Teffs are a subset of non-Treg T cells. In some embodiments, Teffs are CD4+ Teffs or CD8+Teffs, such as CD4+helper T lymphocytes (e.g., Th0, Th1, Tfh, or Th17) and CD8+cytotoxic T lymphocytes. As described further herein, cytotoxic T cells are CD8+T lymphocytes. "Naive Tcons" are CD4+ T cells that have differentiated in bone marrow, and successfully underwent a positive and negative processes of central selection in a thymus, but have not yet been activated by exposure to an antigen. Naive Tcons are commonly characterized by surface expression of L-selectin (CD62L), absence of activation markers such as CD25, CD44 or CD69, and absence of memory markers such as CD45RO. Naive Tcons are therefore believed to be quiescent and non-dividing, requiring interleukin-7 (IL-7) and interleukin-15 (IL-15) for homeostatic survival (see, at least WO 2010/101870). The presence and activity of such cells are undesired in the context of suppressing immune responses. Unlike Tregs, Tcons are not anergic and can proliferate in response to antigen-based T cell receptor activation (Lechler et al. (2001) *Philos. Trans. R. Soc. Lond. Biol. Sci.* 356:625-637). In tumors, exhausted cells can present hallmarks of anergy.

As used herein, the term "unrearranged" or "germline configuration" in reference to a V segment refers to the configuration wherein the V segment is not recombined so as to be immediately adjacent to a D or J segment.

As used herein, the term "vector" refers to a nucleic acid capable of transporting another nucleic acid to which it has been linked. One type of vector is a "plasmid", which refers to a circular double stranded DNA loop into which additional DNA segments may be ligated. Another type of vector is a viral vector, wherein additional DNA segments may be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors are capable of directing the expression of genes to which they are operatively linked. Such vectors are referred to herein as "recombinant expression vectors" or simply "expression vectors". In general, expression vectors of utility in recombinant DNA techniques are often in the form of plasmids. In the present specification, "plasmid" and "vector" may be used interchangeably as the plasmid is the most commonly used form of vector. However, the invention is intended to include such other forms of expression vectors, such as viral vectors (e.g., replication defective retroviruses, adenoviruses and adeno-associated viruses), which serve equivalent functions.

For nucleic acids, the term "substantial homology" indicates that two nucleic acids, or designated sequences thereof, when optimally aligned and compared, are identical, with appropriate nucleotide insertions or deletions, in at least about 80% of the nucleotides, usually at least about 81%, 82%, 83%, 84%, 85%, 86%, 87%, 88%, 89%, 90%, 91%, 92%, 93%, 94%, 95%, 96%, or more of the nucleotides, and more preferably at least about 97%, 98%, 99% or more of the nucleotides. Alternatively, substantial homology exists when the segments will hybridize under selective hybridization conditions, to the complement of the strand.

The percent identity between two sequences is a function of the number of identical positions shared by the sequences (i.e., % identity=# of identical positions/total # of positions× 100), taking into account the number of gaps, and the length of each gap, which need to be introduced for optimal alignment of the two sequences. The comparison of sequences and determination of percent identity between two sequences can be accomplished using a mathematical algorithm, as described in the non-limiting examples below.

The percent identity between two nucleotide sequences can be determined using the GAP program in the GCG software package (available on the world wide web at the GCG company website), using a NWSgapdna. CMP matrix and a gap weight of 40, 50, 60, 70, or 80 and a length weight of 1, 2, 3, 4, 5, or 6. The percent identity between two nucleotide or amino acid sequences can also be determined using the algorithm of E. Meyers and W. Miller (CABIOS, 4:11 17 (1989)) which has been incorporated into the ALIGN program (version 2.0), using a PAM120 weight residue table, a gap length penalty of 12 and a gap penalty of 4. In addition, the percent identity between two amino acid sequences can be determined using the Needleman and Wunsch (J. Mol. Biol. (48):444 453 (1970)) algorithm which has been incorporated into the GAP program in the GCG software package (available on the world wide web at the GCG company website), using either a Blosum 62 matrix or a PAM250 matrix, and a gap weight of 16, 14, 12, 10, 8, 6, or 4 and a length weight of 1, 2, 3, 4, 5, or 6.

The nucleic acid and protein sequences of the present invention can further be used as a "query sequence" to perform a search against public databases to, for example, identify related sequences. Such searches can be performed using the NBLAST and XBLAST programs (version 2.0) of Altschul, et al. (1990) J. Mol. Biol. 215:403 10. BLAST nucleotide searches can be performed with the NBLAST program, score=100, wordlength=12 to obtain nucleotide sequences homologous to the nucleic acid molecules of the present invention. BLAST protein searches can be performed with the XBLAST program, score=50, wordlength=3 to obtain amino acid sequences homologous to the protein molecules of the present invention. To obtain gapped alignments for comparison purposes, Gapped BLAST can be utilized as described in Altschul et al., (1997) Nucleic Acids Res. 25(17):3389 3402. When utilizing BLAST and Gapped BLAST programs, the default parameters of the respective programs (e.g., XBLAST and NBLAST) can be used (available on the world wide web at the NCBI website).

The nucleic acids may be present in whole cells, in a cell lysate, or in a partially purified or substantially pure form. A nucleic acid is "isolated" or "rendered substantially pure" when purified away from other cellular components or other contaminants, e.g., other cellular nucleic acids or proteins, by standard techniques, including alkaline/SDS treatment, CsCl banding, column chromatography, agarose gel electrophoresis and others well-known in the art (see, F. Ausubel, et al., ed. Current Protocols in Molecular Biology, Greene Publishing and Wiley Interscience, New York (1987)).

The term "determining a suitable treatment regimen for the subject" is taken to mean the determination of a treatment regimen (i.e., a single therapy or a combination of different therapies that are used for the prevention and/or treatment of the cancer in the subject) for a subject that is started, modified and/or ended based or essentially based or at least partially based on the results of the analysis according to the present invention. One example is determining whether to provide targeted therapy against a cancer to provide immunomodulatory therapy (e.g., HHLA2 pathway modulator therapy (e.g., modulator of the interaction between HHLA2 and one or more natural binding partners, such as TMIGD2 and/or KIR3DL3)). Another example is starting an adjuvant therapy after surgery whose purpose is to decrease the risk of recurrence, another would be to modify the dosage of a particular chemotherapy. The determination can, in addition to the results of the analysis according to the present invention, be based on personal characteristics of the subject to be treated. In most cases, the actual determination of the suitable treatment regimen for the subject will be performed by the attending physician or doctor.

II. Monoclonal Antibodies, Immunoglobulins, and Polypeptides

The present invention relates, in part, to isolated monoclonal antibodies or fragments thereof that are directed against HHLA2 (such as monoclonal antibodies and polyclonal antibodies listed herein). Such molecules, in part, are characterized in that they exhibit the ability to recognize HHLA2 protein in diagnostic assays, such as immunohistochemical (IHC), Western blot, intercellular flow, ELISA, and the like. Such molecules, in part, are characterized in that they exhibit the ability to inhibit HHLA2 binding to receptors, such as receptors expressed on T-cells (e.g. TMIGD2, and KIR3DL3)

The term "HHLA2", also known as human endogenous retrovirus-H long terminal repeat-associating protein 2, HERV-H LTR-associating 2, B7y, B7H7, B7-H5, B7-H7, refers to a member of the B7 family. HHLA2 protein has limited expression in normal human tissues but is widely expressed in human cancers. The HHLA2 protein is a membrane protein with three Ig-like domains (IgV-IgC-IgV), whereas other members of the B7 family generally have only two Ig domains (IgV-IgC). HHLA2 protein in normal human tissues is expressed in the epithelium of kidney, gut, gallbladder, and breast as well as placental trophoblast cells. In the immune system, HHLA2 protein is constitutively expressed on human monocytes/macrophages. HHLA2 regulates human T-cell functions including, for example, HHLA2 inhibits T-cell proliferation and cytokine production, and increases T-cell production and cytokine production. HHLA2 is expressed in higher levels in a wide range of human cancers from the colorectal, renal, lung, pancreas, ovary, and prostate. HHLA2 is also expressed in human cancers of thyroid, melanoma, liver, bladder, colon, kidney, breast, and esophagus.

HHLA2 structures and functions, are well-known in the art as described above (see, for example, Xiao et al. (2015) *Clin. Cancer Res.* 21:2201-2203, Janakiram et al. (2015) *Clin. Cancer Res.* 21:2359-2366, Mager et al. (1999) *Genomics* 21:2359-2366, Flajnik et al. (2012) *Immunogenet.* 64:571-590, Zhao et al. (2013) *Proc. Natl. Acad. Sci. U.S.A.* 110:9879-9884, and Zhu et al. (2013) Nat. Commun. 4:2043).

The term "HHLA2" is intended to include fragments, variants (e.g., allelic variants), and derivatives thereof. Representative human HHLA2 cDNA and human HHLA2 protein sequences are well-known in the art and are publicly available from the National Center for Biotechnology Information (NCBI). Human HHLA2 variants include variant 1 (NM_007072.3 and NP_009003.1, which represents the longest transcript and encodes the longest isoform a), variant 2 (NM_001282556.1 and NP_001269485.1, which represents the use of an alternate promoter and differs in the 5' UTR, compared to variant 1), vaiant 3 (NM_001282557.1 and NP_001269486.1, which represents the use of an alternate promoter and differs in the 5' UTR, compared to variant 1), variant 4 (NM_001282558.1 and NP_001269487.1, which encodes isoform b, represents the use of an alternate promoter, differs in the 5' UTR and lacks an alternate in-frame exon in the 3' coding region, compared to variant 1, resulting a shorter isoform than isoform a), and variant 5 (NM_001282559.1 and NP_001269488.1, which encodes isoform c, represents the use of an alternate promoter, and has multiple differences compared to variant 2, resulting in a distinct 5' UTR and causing translation initiation at an alternate start codon, compared to variant 1, resulting in a distinct N-terminus and a shorter isoform than isoform a). Nucleic acid and polypeptide sequences of HHLA2 orthologs in organisms other than humans are well-known and include, for example, frog HHLA2 (NM_001128644.1 and NP_001122116.1). Representative sequences of HHLA2 orthologs are presented below in Table 1.

Anti-HHLA2 antibodies suitable for detecting HHLA2 protein are well-known in the art and include, for example, antibodies Cat #: ab107119 and ab214327 (abcam), antibodies PA5-24146 and PA5-6313 (ThermoFisher Scientific), antibodies MAB80841, AF8084, FAB80841R, FAB80841T, and MAB8084 (R&D systems), antibody AP52042PU-N (Origene), antibodies NBP2-49187, MAB80842, H00011148-BO1P, and NBP2-32420 (Novus Biologicals), antibody GTX51981 (GeneTex), antibody HPA055478 (Atlas Antibodies), antibodies LS-C321945, LS-C308228, LS-C246742, LS-C246743, LS-C246744, LS-C236210, and LS-C249186 (LifeSpan Biosiences), etc. Moreover, multiple siRNA, shRNA, CRISPR constructs for reducing HHLA2 expression can be found in the commercial product lists of the above-referenced companies, such as shRNA product #TL312462, TF312462, TR312462, TG312462, and TL312462V, siRNA product #SR323358 from Origene Technologies, SiRNA product #i009616, i009616a, i009616b, i009616c, i009616d, iV009616, iV009616a, iV009616b, iV009616c, iV009616d, iAAV00961600, iAAV00961601, iAAV00961602, iAAV00961603, iAAV00961604, iAAV00961605, iAAV00961606, iAAV00961607, iAAV00961608, and iAAV00961609, CRISPR product #K0950321, K0950301, K0950302, K0950303, K0950304, K0950305, K0950306, K0950307, K0950308, and K0950311 (abm), siRNA product #sc-78498, shRNA product #sc-78498-V and sc-78498-SH, CRISPR product #sc-411576, sc-411576-HDR, sc-411576-NIC, sand c-411576-NIC-2 (Santa Cruz Biotechnology), etc. It is to be noted that the term can further be used to refer to any combination of features described herein regarding HHLA2 molecules. For example, any combination of sequence composition, percentage identify, sequence length, domain structure, functional activity, etc. can be used to describe an HHLA2 molecule of the present invention.

The term "HHLA2 pathway" includes HHLA2 and interactions of HHLA2 with one or more of its natural binding partners, such as TMIGD2 and KIR3DL3.

The term "TMIGD2" refers to transmembrane and immunoglobulin domain containing 2, CD28H, IGPR1, and IGPR-1, which is a membrane protein having ~10% amino acid identity with CD28, CTLA-4, ICOS, and PD-1. TMIGD2 has one extracellular IgV-like domain, a transmembrane region, and a proline-rich cytoplasmic domain with two tyrosine signaling motifs. TMIGD2 protein is constitutively expressed on all naive T cells and the majority of natural killer (NK) cells, but not on T regulatory cells or B cells. TMIGD2 expression is slowly lost with repetitive stimulation of T cells. Consistent with this, TMIGD2 is expressed on only about half of memory T cells, and TMIGD2-negative T cells have a terminally-differentiated, senescent phenotype. TMIGD2 has also been shown to be expressed in endothelial and epithelial cells and function to reduce cell migration and promote capillary tube formation during angiogenesis.

TMIGD2 structures and functions, are well-known in the art as described above (see, for example, Xiao et al. (2015) Clin. Cancer Res. 21:2201-2203, Janakiram et al. (2015) Clin. Cancer Res. 21:2359-2366, Zhu et al. (2013) Nat. Commun. 4:2043, and Rahimi (2012) Cell 23:1646-1656).

The term "TMIGD2" is intended to include fragments, variants (e.g., allelic variants), and derivatives thereof. Representative human TMIGD2 cDNA and human TMIGD2 protein sequences are well-known in the art and are publicly available from the National Center for Biotechnology Information (NCBI). Human TMIGD2 isoforms include isoform 1 (NM_144615.2 and NP_653216.2), isoform 2 (NM_001169126.1 and NP_001162597.1; which uses an alternate in-frame splice site in the 3' coding region, compared to variant 1, resulting a shorter isoform, compared to isoform 1), and isoform 3 (NM_001308232.1 and NP_001295161.1, which lacks an alternate in-frame exon in the 5' coding region compared to variant 1, resulting a shorter isoform, compared to isoform 1). Nucleic acid and polypeptide sequences of TMIGD2 orthologs in organisms other than humans are well-known and include, for example, chimpanzee TMIGD2 (XM_009434393.2 and XP_009432668.2, and XM_001138228.4 and XP_001138228.3), and cattle TMIGD2 (XM_005208980.3 and XP_005209037.1, XM_005208979.3 and XP_005209036.1, and XM_002688933.5 and XP_002688979.1). Representative sequences of TMIGD2 orthologs are presented below in Table 1.

Anti-TMIGD2 antibodies suitable for detecting TMIGD2 protein are well-known in the art and include, for example, antibodies Cat #MAB8316, MAB83162, FAB8316R, FAB83162R, FAB83162G, FAB83162N, FAB83162S, FAB83162T, FAB83162U, and FAB83162V (R&D systems), antibody TA326695 (Origene), antibodies PA5-52787, and PA5-38055 (ThermoFisher Scientific), antibodies MAB83161, and NBP1-81164 (Novus Biologicals), etc.. Moreover, multiple siRNA, shRNA, CRISPR constructs for reducing TMIGD2 expression can be found in the commercial product lists of the above-referenced companies, such as shRNA product #TF317829, TG317829, TL317829, TR317829, and TL317829V, siRNA product #SR314913, and CRISPR products #KN204938, KN204938LP, KN204938RB, and KN204938BN from Origene Technologies, siRNA products #i024914, i024914a, i024914b, i024914c, i024914d, iV024914, iV024914a, iV024914b, iV024914c, iV024914d, iAAV02491400, iAAV02491401, iAAV02491402, iAAV02491403, iAAV02491404, iAAV02491405, iAAV02491406, iAAV02491407, iAAV02491408, and iAAV02491409, and CRISPR products #K2409321, K2409301, K2409302, K2409303, K2409304, K2409305, K2409306, K2409307, K2409308, and K2409311 (Abm), siRNA product #sc-97757, shRNA products #sc-97757-SH, and sc-97757-V, and CRISPR products #sc-414261, sc-414261-HDR, sc-414261-NIC, and sc-414261-NIC-2 (Santa Cruz Biotechnology), shRNA products #SH888208, and SH874720 (Vigene Biosciences), etc.. Moreover, multiple CRISPR constructs for increasing TMIGD2 expression can be found in the commercial product lists of the above-referenced companies, such as CRISPR products #K2409378, K2409377, K2409376, K2409375, K2409374, K2409373, K2409372, and K2409371 (Abm), CRISPR products #sc-414261-ACT, sc-414261-ACT-2, sc-414261-LAC, and sc-414261-LAC-2 (Santa Cruz Biotechnology), etc.. It is to be noted that the term can further be used to refer to any combination of features described herein regarding TMIGD2 molecules. For example, any combination of sequence composition, percentage identify, sequence length, domain structure, functional activity, etc. can be used to describe an TMIGD2 molecule of the present invention.

Interactions between TMIGD2 and HHLA2 as well as their functions, are well-known in the art as described above (see, for example, Xiao et al. (2015) Clin. Cancer Res. 21:2201-2203 and Janakiram et al. (2015) Clin. Cancer Res. 21:2359-2366).

The term "KIR3DL3", also known as Killer cell immunoglobulin-like receptor 3DL3, CD158Z, KIR3DL7, KIR44, KIRC1, KIR2DS2, killer cell immunoglobulin like receptor, three Ig domains and long cytoplasmic tail 3, refers to a member of a transmembrane glycoprotein family expressed by natural killer cells and subsets of T cells. The killer cell immunoglobulin-like receptor (KIR) genes are polymorphic and highly homologous and they are found in a cluster on chromosome 19q13.4 within the 1 Mb leukocyte receptor complex (LRC). The gene content of the KIR gene cluster varies among haplotypes, although several "framework" genes are found in all haplotypes (KIR3DL3, KIR3DP1, KIR3DL4, KIR3DL2). The KIR proteins are classified by the number of extracellular immunoglobulin domains (2D or 3D) and by whether they have a long (L) or short (S) cytoplasmic domain. KIR proteins with the long cytoplasmic domain transduce inhibitory signals upon ligand binding via an immune tyrosine-based inhibitory motif (ITIM), while KIR proteins with the short cytoplasmic domain lack the ITIM motif and instead associate with the TYRO protein tyrosine kinase binding protein to transduce activating signals. The ligands for several KIR proteins are subsets of HLA class I molecules; thus, KIR proteins are thought to play an important role in regulation of the immune response. This gene is one of the "framework" loci that is present on all haplotypes. The KIR3DL3 protein has an N-terminal signal sequence, 3 Ig domains, a transmembrane region lacking a positively charged residue, and a long cytoplasmic tail containing an immunoreceptor tyrosine-based inhibitory motif (ITIM). KIR3DL3 lacks the stalk region found in other KIRs.

KIR3DL3 structures and functions, are well-known in the art as described above (see, for example, Hsu et al. (2002) *Immunol Rev.* 190:40-52, Trompeter et al. (2005) *J. Immunol.* 174:4135-4143, Trundley et al. (2006) *Immunogenet.* 57:904-916, and Jones et al. (2006) *Immunogenet.* 58:614-627).

The term "KIR3DL3" is intended to include fragments, variants (e.g., allelic variants), and derivatives thereof. Representative human KIR3DL3 cDNA and human KIR3DL3 protein sequences are well-known in the art and are publicly available from the National Center for Biotechnology Information (NCBI). For example, at least one human KIR3DL3 isoform is known: human KIR3DL3 (NM_153443.4) is encodable by the transcript (NP_703144.3). Nucleic acid and polypeptide sequences of KIR3DL3 orthologs in organisms other than humans are well-known and include, for example, chimpanzee KIR3DL3 (XM_003316679.3 and XP_003316727.3), Rhesus monkey KIR3DL3 (NM_001104552.2 and NP_001098022.1), mouse KIR3DL3 (NM_001310690.1 and NP_001297619.1, NM_177749.4 and NP_808417.2, NM_177748.2 and NP_808416.1), and rat KIR3DL3 (NM_181479.2 and NP_852144.1). Representative sequences of KIR3DL3 orthologs are presented below in Table 1.

Anti-KIR3DL3 antibodies suitable for detecting KIR3DL3 protein are well-known in the art and include, for example, antibodies Cat #: FAB8919R, MAB8919, FAB8919G, FAB8919N, FAB8919S, FAB8919T, FAB8919U, and FAB8919V (R&D systems), antibody AP52374PU-N(Origene), antibody PA5-26178 (ThermoFisher Scientific), antibodies OAAB05761, OAAF08125, OAAN04122, OACA09134, OACA09135, OACD04988, and OASG01190 (Aviva Systems Biology), etc.. Moreover, multiple siRNA, shRNA, CRISPR constructs for reducing KIR3DL3 expression can be found in the commercial product lists of the above-referenced companies, such as shRNA products #TF303684, TR303684, TG303684, TL303684, TL303684V, siRNA products #SR314516, and CRISPR products #KN224383, KN224383BN, KN224383RB, and KN224383LP from Origene Technologies, siRNA products #i011627, i011627a, i011627b, i011627c, i011627d, iV011627, iV011627a, iVO11627b, iVO11627c, iV011627d, iAAV01162700, iAAV01162701, iAAV01162702, iAAV01162703, iAAV01162704, iAAV01162705, iAAV01162706, iAAV01162707, iAAV01162708, and iAAV01162709, and CRISPR products #K1151421, K1151401, K1151402, K1151403, K1151404, K1151405, K1151406, K1151407, K1151408, and K1151411 (Abm), siRNA product #sc-60892, shRNA products #sc-60892-SH, and sc-60892-V, and CRISPR products #sc-406227, sc-406227-KO-2, sc-406227-HDR-2, sc-406227-NIC, and sc-406227-NIC-2 (Santa Cruz Biotechnology), etc.. It is to be noted that the term can further be used to refer to any combination of features described herein regarding KIR3DL3 molecules. For example, any combination of sequence composition, percentage identify, sequence length, domain structure, functional activity, etc. can be used to describe an KIR3DL3 molecule of the present invention.

The term "peripheral blood cell subtypes" refers to cell types normally found in the peripheral blood including, but is not limited to, eosinophils, neutrophils, T cells, monocytes, NK cells, granulocytes, and B cells.

The term "recombinant human antibody" includes all human antibodies that are prepared, expressed, created or isolated by recombinant means, such as (a) antibodies isolated from an animal (e.g., a mouse) that is transgenic or transchromosomal for human immunoglobulin genes or a hybridoma prepared therefrom (described further below), (b) antibodies isolated from a host cell transformed to express the antibody, e.g., from a transfectoma, (c) antibodies isolated from a recombinant, combinatorial human antibody library, and (d) antibodies prepared, expressed, created or isolated by any other means that involve splicing of human immunoglobulin gene sequences to other DNA sequences. Such recombinant human antibodies have variable and constant regions derived from human germline and/or non-germline immunoglobulin sequences. In certain embodiments, however, such recombinant human antibodies can be subjected to in vitro mutagenesis (or, when an animal transgenic for human Ig sequences is used, in vivo somatic mutagenesis) and thus the amino acid sequences of the VH and $V_L$ regions of the recombinant antibodies are sequences that, while derived from and related to human germline $V_H$ and $V_L$ sequences, may not naturally exist within the human antibody germline repertoire in vivo.

The term "sample" used for detecting or determining the presence or level of at least one biomarker is typically whole blood, plasma, serum, saliva, urine, stool (e.g., feces), tears, and any other bodily fluid (e.g., as described above under the definition of "body fluids"), or a tissue sample (e.g., biopsy) such as a small intestine, colon sample, or surgical resection tissue. In certain instances, the method of the present invention further comprises obtaining the sample from the individual prior to detecting or determining the presence or level of at least one marker in the sample.

An "RNA interfering agent" as used herein, is defined as any agent which interferes with or inhibits expression of a target biomarker gene by RNA interference (RNAi). Such RNA interfering agents include, but are not limited to, nucleic acid molecules including RNA molecules which are homologous to the target biomarker gene of the present invention, or a fragment thereof, short interfering RNA (siRNA), and small molecules which interfere with or inhibit expression of a target biomarker nucleic acid by RNA interference (RNAi). "RNA interference (RNAi)" is an evolutionarily conserved process whereby the expression or introduction of RNA of a sequence that is identical or highly similar to a target biomarker nucleic acid results in the sequence specific degradation or specific post-transcriptional gene silencing (PTGS) of messenger RNA (mRNA) transcribed from that targeted gene (see Coburn, G. and Cullen, B. (2002) *J. of Virology* 76(18):9225), thereby inhibiting expression of the target biomarker nucleic acid. In one embodiment, the RNA is double stranded RNA (dsRNA). This process has been described in plants, invertebrates, and mammalian cells. In nature, RNAi is initiated by the dsRNA-specific endonuclease Dicer, which promotes processive cleavage of long dsRNA into double-stranded fragments termed siRNAs. siRNAs are incorporated into a protein complex that recognizes and cleaves target mRNAs. RNAi can also be initiated by introducing nucleic acid molecules, e.g., synthetic siRNAs, shRNAs, or other RNA interfering agents, to inhibit or silence the expression of target biomarker nucleic acids. As used herein, "inhibition of target biomarker nucleic acid expression" or "inhibition of marker gene expression" includes any decrease in expression or protein activity or level of the target biomarker nucleic acid or protein encoded by the target biomarker nucleic acid. The decrease may be of at least 30%, 40%, 50%, 60%, 70%, 80%, 90%, 95% or 99% or more as compared to the expression of a target biomarker nucleic acid or the activity or level of the protein encoded by a target biomarker nucleic acid which has not been targeted by an RNA interfering agent.

In addition to RNAi, genome editing can be used to modulate the copy number or genetic sequence of a biomarker of interest, such as constitutive or induced knockout or mutation of a biomarker of interest, such as a HHLA2 pathway component like HHLA2, TMIGD2, and/or KIR3DL3. For example, the CRISPR-Cas system can be used for precise editing of genomic nucleic acids (e.g., for creating non-functional or null mutations). In such embodiments, the CRISPR guide RNA and/or the Cas enzyme may be expressed. For example, a vector containing only the guide RNA can be administered to an animal or cells transgenic for the Cas9 enzyme. Similar strategies may be used (e.g., designer zinc finger, transcription activator-like effectors (TALEs) or homing meganucleases). Such systems are well-known in the art (see, for example, U.S. Pat. No. 8,697,359; Sander and Joung (2014) Nat. Biotech. 32:347-355; Hale et al. (2009) *Cell* 139:945-956; Karginov and Hannon (2010) *Mol. Cell* 37:7; U.S. Pat. Publ. 2014/0087426 and 2012/0178169; Boch et al. (2011) *Nat. Biotech.* 29:135-136; Boch et al. (2009) *Science* 326:1509-1512; Moscou and Bogdanove (2009) *Science* 326:1501; Weber et al. (2011) *PLoS One* 6:e19722; Li et al. (2011) *Nucl. Acids Res.* 39:6315-6325; Zhang et al. (2011) *Nat. Biotech.* 29:149-153; Miller et al. (2011) *Nat. Biotech.* 29:143-148; Lin et al. (2014) *Nucl. Acids Res.* 42:e47). Such genetic strategies can use constitutive expression systems or inducible expression systems according to well-known methods in the art.

"Piwi-interacting RNA (piRNA)" is the largest class of small non-coding RNA molecules. piRNAs form RNA-protein complexes through interactions with piwi proteins. These piRNA complexes have been linked to both epigenetic and post-transcriptional gene silencing of retrotransposons and other genetic elements in germ line cells, particularly those in spermatogenesis. They are distinct from microRNA (miRNA) in size (26-31 nt rather than 21-24 nt), lack of sequence conservation, and increased complexity. However, like other small RNAs, piRNAs are thought to be involved in gene silencing, specifically the silencing of transposons. The majority of piRNAs are antisense to transposon sequences, suggesting that transposons are the piRNA target. In mammals it appears that the activity of piRNAs in transposon silencing is most important during the development of the embryo, and in both *C. elegans* and humans, piRNAs are necessary for spermatogenesis. piRNA has a role in RNA silencing via the formation of an RNA-induced silencing complex (RISC).

"Aptamers" are oligonucleotide or peptide molecules that bind to a specific target molecule. "Nucleic acid aptamers" are nucleic acid species that have been engineered through repeated rounds of in vitro selection or equivalently, SELEX (systematic evolution of ligands by exponential enrichment) to bind to various molecular targets such as small molecules, proteins, nucleic acids, and even cells, tissues and organisms. "Peptide aptamers" are artificial proteins selected or engineered to bind specific target molecules. These proteins consist of one or more peptide loops of variable sequence displayed by a protein scaffold. They are typically isolated from combinatorial libraries and often subsequently improved by directed mutation or rounds of variable region mutagenesis and selection. The "Affimer protein", an evolution of peptide aptamers, is a small, highly stable protein engineered to display peptide loops which provides a high affinity binding surface for a specific target protein. It is a protein of low molecular weight, 12-14 kDa, derived from the cysteine protease inhibitor family of cystatins. Aptamers are useful in biotechnological and therapeutic applications as they offer molecular recognition properties that rival that of the commonly used biomolecule, antibodies. In addition to their discriminate recognition, aptamers offer advantages over antibodies as they can be engineered completely in a test tube, are readily produced by chemical synthesis, possess desirable storage properties, and elicit little or no immunogenicity in therapeutic applications.

"Short interfering RNA" (siRNA), also referred to herein as "small interfering RNA" is defined as an agent which functions to inhibit expression of a target biomarker nucleic acid, e.g., by RNAi. An siRNA may be chemically synthesized, may be produced by in vitro transcription, or may be produced within a host cell. In one embodiment, siRNA is a double stranded RNA (dsRNA) molecule of about 15 to about 40 nucleotides in length, preferably about 15 to about 28 nucleotides, more preferably about 19 to about 25 nucleotides in length, and more preferably about 19, 20, 21, or 22 nucleotides in length, and may contain a 3' and/or 5' overhang on each strand having a length of about 0, 1, 2, 3, 4, or 5 nucleotides. The length of the overhang is independent between the two strands, i.e., the length of the overhang on one strand is not dependent on the length of the overhang on the second strand. Preferably the siRNA is capable of promoting RNA interference through degradation or specific post-transcriptional gene silencing (PTGS) of the target messenger RNA (mRNA).

In another embodiment, an siRNA is a small hairpin (also called stem loop) RNA (shRNA). In one embodiment, these shRNAs are composed of a short (e.g., 19-25 nucleotide) antisense strand, followed by a 5-9 nucleotide loop, and the analogous sense strand. Alternatively, the sense strand may precede the nucleotide loop structure and the antisense strand may follow. These shRNAs may be contained in plasmids, retroviruses, and lentiviruses and expressed from, for example, the pol III U6 promoter, or another promoter (see, e.g., Stewart, et al. (2003) *RNA* Apr; 9(4):493-501 incorporated by reference herein).

RNA interfering agents, e.g., siRNA molecules, may be administered to a patient having or at risk for having cancer, to inhibit expression of a biomarker gene which is overexpressed in cancer and thereby treat, prevent, or inhibit cancer in the subject.

The term "small molecule" is a term of the art and includes molecules that are less than about 1000 molecular weight or less than about 500 molecular weight. In one embodiment, small molecules do not exclusively comprise peptide bonds. In another embodiment, small molecules are not oligomeric. Exemplary small molecule compounds which can be screened for activity include, but are not limited to, peptides, peptidomimetics, nucleic acids, carbohydrates, small organic molecules (e.g., polyketides) (Cane et al. 1998. Science 282:63), and natural product extract libraries. In another embodiment, the compounds are small, organic non-peptidic compounds. In a further embodiment, a small molecule is not biosynthetic.

The term "selective modulator" or "selectively modulate" as applied to a biologically active agent refers to the agent's ability to modulate the target, such as a cell population, signaling activity, etc. as compared to off-target cell population, signaling activity, etc. via direct or interact interaction with the target. For example, an agent that selectively inhibits the interaction between HHLA2 and one or more natural binding partners, such as TMIGD2 and KIR3DL3, over another interaction between HHLA2 and another binding partner, and/or such interaction(s) on a cell population of interest may have an activity against the HHLA2 pathway modulator therapy (e.g., modulator of the interaction between HHLA2 and one or more natural binding partners, such as TMIGD2 and KIR3DL3, interaction that is at least 5%, 10%, 15%, 20%, 25%, 30%, 35%, 40%, 45%, 50%, 55%, 60%, 65%, 70%, 75%, 80%, 85%, 90%, 95%, 100%, 110%, 120%, 130%, 140%, 150%, 160%, 170%, 180%, 190%, 2× (times) or more than the agent's activity against at least one other binding partner (e.g., at least about 3×, 4×, 5×, 6×, 7×, 8×, 9×, 10×, 15×, 20×, 25×, 30×, 35×, 40×, 45×, 50×, 55×, 60×, 65×, 70×, 75×, 80×, 85×, 90×, 95×, 100×, 105×, 110×, 120×, 125×, 150×, 200×, 250×, 300×, 350×, 400×, 450×, 500×, 600×, 700×, 800×, 900×, 1000×, 1500×, 2000×, 2500×, 3000×, 3500×, 4000×, 4500×, 5000×, 5500×, 6000×, 6500×, 7000×, 7500×, 8000×, 8500×, 9000×, 9500×, 10000×, or greater, or any range in between, inclusive). Such metrics are typically expressed in terms of relative amounts of agent required to reduce the interaction/activity by half.

More generally, the term "selective" refers to a preferential action or function. The term "selective" can be quantified in terms of the preferential effect in a particular target of interest relative to other targets. For example, a measured variable (e.g., modulation of Tregs/Bregs versus other cells, such as other immune cells like Tcons) can be 10%, 20%, 25%, 30%, 35%, 40%, 45%, 50%, 55%, 60%, 65%, 70%, 75%, 80%, 85%, 90%, 95%, 1-fold, 1.5-fold, 2-fold, 2.5-fold, 3-fold, 3.5-fold, 4-fold, 4.5-fold, 5-fold, 5.5-fold, 6-fold, 6.5-fold, 7-fold, 7.5-fold, 8-fold, 8.5-fold, 9-fold, 9.5-fold, 10-fold, 11-fold, 12-fold, 13-fold, 14-fold, 15-fold, 16-fold, 17-fold, 18-fold, 19-fold, 20-fold, 25-fold, 30-fold, 35-fold, 40-fold, 45-fold, 50-fold, 55-fold, 60-fold, 70-fold, 80-fold, 90-fold, 100-fold, or greater or any range in between inclusive (e.g., 50% to 16-fold), different in a target of interest versus unintended or undesired targets. The same fold analysis can be used to confirm the magnitude of an effect in a given tissue, cell population, measured variable, measured effect, and the like, such as the Tregs:Tcons ratio, Bregs:Tcons ratio, hyperproliferative cell growth rate or volume, Tregs/Bregs proliferation rate or number, and the like.

By contrast, the term "specific" refers to an exclusionary action or function. For example, specific modulation of the HHLA2-TMIGD2 and HHLA2-KIR3DL3 interactions refers to the exclusive modulation of the HHLA2/TMIDG2 and HHLA2/KIR3DL3 interactions, respectively, and not modulation of HHLA2 with another ligand. In another example, specific binding of an antibody to a predetermined antigen refers to the ability of the antibody to bind to the antigen of interest without binding to other antigens. Typically, the antibody binds with an affinity ($K_D$) of approximately less than $1 \times 10^{-7}$ M, such as approximately less than $10^{-8}$ M, $10^{-9}$ M, $10^{-10}$ M, $10^{-11}$ M, or even lower when determined by surface plasmon resonance (SPR) technology in a BIACORE® assay instrument using an antigen of interest as the analyte and the antibody as the ligand, and binds to the predetermined antigen with an affinity that is at least 1.1-, 1.2-, 1.3-, 1.4-, 1.5-, 1.6-, 1.7-, 1.8-, 1.9-, 2.0-, 2.5-, 3.0-, 3.5-, 4.0-, 4.5-, 5.0-, 6.0-, 7.0-, 8.0-, 9.0-, or 10.0-fold or greater than its affinity for binding to a non-specific antigen (e.g., BSA, casein) other than the predetermined antigen or a closely-related antigen. In addition, $K_D$ is the inverse of $K_A$. The phrases "an antibody recognizing an antigen" and "an antibody specific for an antigen" are used interchangeably herein with the term "an antibody which binds specifically to an antigen." The term "sensitize" means to alter cells, such as cancer cells or tumor cells, in a way that allows for more effective treatment with a therapy (e.g., HHLA2 pathway modulator therapy (e.g., modulator of the interaction between HHLA2 and one or more natural binding partners, such as TMIGD2 and KIR3DL3), either alone or in combination with an immunotherapy, such as an immune checkpoint inhibition therapy). In some embodiments, normal cells are not affected to an extent that causes the normal cells to be unduly injured by the therapy (e.g., HHLA2 pathway modulator therapy (e.g., modulator of the interaction between HHLA2 and one or more natural binding partners, such as TMIGD2 and KIR3DL3), either alone or in combination with an immunotherapy, such as an immune checkpoint inhibition therapy). An increased sensitivity or a reduced sensitivity to a therapeutic treatment is measured according to a known method in the art for the particular treatment and methods described herein below, including, but not limited to, cell proliferative assays (Tanigawa N, Kern D H, Kikasa Y, Morton D L, Cancer Res 1982; 42: 2159-2164), cell death assays (Weisenthal L M, Shoemaker R H, Marsden J A, Dill P L, Baker J A, Moran E M, Cancer Res 1984; 94: 161-173; Weisenthal L M, Lippman M E, Cancer Treat Rep 1985; 69: 615-632; Weisenthal L M, In: Kaspers G J L, Pieters R, Twentyman P R, Weisenthal L M, Veerman A J P, eds. Drug Resistance in Leukemia and Lymphoma. Langhorne, P A: Harwood Academic Publishers, 1993: 415-432; Weisenthal L M, Contrib Gynecol Obstet 1994; 19: 82-90). The sensitivity or resistance may also be measured in animal by measuring the tumor size reduction over a period of time, for example, 6 months for human and 4-6 weeks for mouse. A composition or a method sensitizes response to a therapeutic treatment if the increase in treatment sensitivity or the reduction in resistance is 5% or more, for example, 10%, 15%, 20%, 25%, 30%, 35%, 40%, 45%, 50%, 55%, 60%, 65%, 70%, 75%, 80%, 85%, 90%, 95%, 100%, or more, to 2-fold, 3-fold, 4-fold, 5-fold, 10-fold, 15-fold, 20-fold or more, compared to treatment sensitivity or resistance in the absence of such composition or method. The determination of sensitivity or resistance to a therapeutic treatment is routine in the art and within the skill of an ordinarily skilled clinician. It is to be understood that any method described herein for enhancing the efficacy of an immunomodulatory can be equally applied to methods for sensitizing hyperproliferative or otherwise cancerous cells (e.g., resistant cells) to the therapy.

The term "synergistic effect" refers to the combined effect of two or more therapeutic agents, such as two or more HHLA2 pathway modulators, a HHLA2 pathway modulator and an immunotherapy, HHLA2 pathway modulators either alone or in combination with an immunotherapy, such as an immune checkpoint inhibition therapy, and the like, can be greater than the sum of the separate effects of the anticancer agents alone.

The term "subject" refers to any healthy animal, mammal or human, or any animal, mammal or human afflicted with a condition of interest (e.g., cancer). The term "subject" is interchangeable with "patient."

The term "survival" includes all of the following: survival until mortality, also known as overall survival (wherein said mortality may be either irrespective of cause or tumor related); "recurrence-free survival" (wherein the term recurrence shall include both localized and distant recurrence); metastasis free survival; disease free survival (wherein the term disease shall include cancer and diseases associated therewith). The length of said survival may be calculated by reference to a defined start point (e.g. time of diagnosis or start of treatment) and end point (e.g. death, recurrence or metastasis). In addition, criteria for efficacy of treatment can be expanded to include response to chemotherapy, probability of survival, probability of metastasis within a given time period, and probability of tumor recurrence.

The term "therapeutic effect" refers to a local or systemic effect in animals, particularly mammals, and more particularly humans, caused by a pharmacologically active substance. The term thus means any substance intended for use in the diagnosis, cure, mitigation, treatment or prevention of disease or in the enhancement of desirable physical or mental development and conditions in an animal or human. The phrase "therapeutically-effective amount" means that amount of such a substance that produces some desired local or systemic effect at a reasonable benefit/risk ratio applicable to any treatment. In certain embodiments, a therapeutically effective amount of a compound will depend on its therapeutic index, solubility, and the like. For example, certain compounds discovered by the methods of the present invention may be administered in a sufficient amount to produce a reasonable benefit/risk ratio applicable to such treatment.

The terms "therapeutically-effective amount" and "effective amount" as used herein means that amount of a compound, material, or composition comprising a compound of the present invention which is effective for producing some desired therapeutic effect in at least a sub-population of cells in an animal at a reasonable benefit/risk ratio applicable to any medical treatment. Toxicity and therapeutic efficacy of subject compounds may be determined by standard pharmaceutical procedures in cell cultures or experimental animals, e.g., for determining the $LD_{50}$ and the $ED_{50}$. Compositions that exhibit large therapeutic indices are preferred. In some embodiments, the $LD_{50}$ (lethal dosage) can be measured and can be, for example, at least 10%, 20%, 30%, 40%, 50%, 60%, 70%, 80%, 90%, 100%, 200%, 300%, 400%, 500%, 600%, 700%, 800%, 900%, 1000% or more reduced for the agent relative to no administration of the agent. Similarly, the $ED_{50}$ (i.e., the concentration which achieves a half-maximal inhibition of symptoms) can be measured and can be, for example, at least 10%, 20%, 30%, 40%, 50%, 60%, 70%, 80%, 90%, 100%, 200%, 300%, 400%, 500%, 600%, 700%, 800%, 900%, 1000% or more increased for the agent relative to no administration of the agent. Also, similarly, the $IC_{50}$ (i.e., the concentration which achieves half-maximal cytotoxic or cytostatic effect on cancer cells) can be measured and can be, for example, at least 10%, 20%, 30%, 40%, 50%, 60%, 70%, 80%, 90%, 100%, 200%, 300%, 400%, 500%, 600%, 700%, 800%, 900%, 1000% or more increased for the agent relative to no administration of the agent. In some embodiments, cancer cell growth in an assay can be inhibited by at least about 10%, 15%, 20%, 25%, 30%, 35%, 40%, 45%, 50%, 55%, 60%, 65%, 70%, 75%, 80%, 85%, 90%, 95%, or even 100%. Cancer cell death can be promoted by at least about 10%, 15%, 20%, 25%, 30%, 35%, 40%, 45%, 50%, 55%, 60%, 65%, 70%, 75%, 80%, 85%, 90%, 95%, or even 100%. In another embodiment, at least about a 10%, 15%, 20%, 25%, 30%, 35%, 40%, 45%, 50%, 55%, 60%, 65%, 70%, 75%, 80%, 85%, 90%, 95%, or even 100% decrease in cancer cell numbers and/or a solid malignancy can be achieved.

The term "substantially free of chemical precursors or other chemicals"includes preparations of antibody, polypeptide, peptide or fusion protein in which the protein is separated from chemical precursors or other chemicals which are involved in the synthesis of the protein. In one embodiment, the language "substantially free of chemical precursors or other chemicals" includes preparations of antibody, polypeptide, peptide or fusion protein having less than about 30% (by dry weight) of chemical precursors or non-antibody, polypeptide, peptide or fusion protein chemicals, more preferably less than about 20% chemical precursors or non-antibody, polypeptide, peptide or fusion protein chemicals, still more preferably less than about 10% chemical precursors or non-antibody, polypeptide, peptide or fusion protein chemicals, and most preferably less than about 5% chemical precursors or non-antibody, polypeptide, peptide or fusion protein chemicals.

A "transcribed polynucleotide" or "nucleotide transcript" is a polynucleotide (e.g. an mRNA, hnRNA, cDNA, mature miRNA, pre-miRNA, pri-miRNA, miRNA*, anti-miRNA, or a miRNA binding site, or a variant thereof or an analog of such RNA or cDNA) which is complementary to or homologous with all or a portion of a mature mRNA made by transcription of a marker of the present invention and normal post-transcriptional processing (e.g. splicing), if any, of the RNA transcript, and reverse transcription of the RNA transcript.

The term "vector" refers to a nucleic acid capable of transporting another nucleic acid to which it has been linked. One type of vector is a "plasmid", which refers to a circular double stranded DNA loop into which additional DNA segments may be ligated. Another type of vector is a viral vector, wherein additional DNA segments may be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors are capable of directing the expression of genes to which they are operatively linked. Such vectors are referred to herein as "recombinant expression vectors" or simply "expression vectors". In general, expression vectors of utility in recombinant DNA techniques are often in the form of plasmids. In the present specification, "plasmid" and "vector" may be used interchangeably as the plasmid is the most commonly used form of vector. However, the invention is intended to include such other forms of expression vectors, such as viral vectors (e.g., replication defective retroviruses, adenoviruses and adeno-associated viruses), which serve equivalent functions.

There is a known and definite correspondence between the amino acid sequence of a particular protein and the nucleotide sequences that can code for the protein, as defined by the genetic code (shown below). Likewise, there is a known and definite correspondence between the nucleotide sequence of a particular nucleic acid and the amino acid sequence encoded by that nucleic acid, as defined by the genetic code.

| GENETIC CODE | |
|---|---|
| Alanine (Ala, A) | GCA, GCC, GCG, GCT |
| Arginine (Arg, R) | AGA, ACG, CGA, CGC, CGG, CGT |
| Asparagine (Asn, N) | AAC, AAT |
| Aspartic acid (Asp, D) | GAC, GAT |
| Cysteine (Cys, C) | TGC, TGT |
| Glutamic acid (Glu, E) | GAA, GAG |
| Glutamine (Gln, Q) | CAA, CAG |
| Glycine (Gly, G) | GGA, GGC, GGG, GGT |
| Histidine (His, H) | CAC, CAT |
| Isoleucine (Ile, I) | ATA, ATC, ATT |
| Leucine (Leu, L) | CTA, CTC, CTG, CTT, TTA, TTG |
| Lysine (Lys, K) | AAA, AAG |
| Methionine (Met, M) | ATG |
| Phenylalanine (Phe, F) | TTC, TTT |
| Proline (Pro, P) | CCA, CCC, CCG, CCT |
| Serine (Ser, S) | AGC, AGT, TCA, TCC, TCG, TCT |
| Threonine (Thr, T) | ACA, ACC, ACG, ACT |
| Tryptophan (Trp, W) | TGG |
| Tyrosine (Tyr, Y) | TAC, TAT |
| Valine (Val, V) | GTA, GTC, GTG, GTT |
| Termination signal (end) | TAA, TAG, TGA |

An important and well-known feature of the genetic code is its redundancy, whereby, for most of the amino acids used to make proteins, more than one coding nucleotide triplet may be employed (illustrated above). Therefore, a number of different nucleotide sequences may code for a given amino acid sequence. Such nucleotide sequences are considered functionally equivalent since they result in the production of the same amino acid sequence in all organisms (although certain organisms may translate some sequences more efficiently than they do others). Moreover, occasionally, a methylated variant of a purine or pyrimidine may be found in a given nucleotide sequence. Such methylations do not affect the coding relationship between the trinucleotide codon and the corresponding amino acid.

In view of the foregoing, the nucleotide sequence of a DNA or RNA encoding a biomarker nucleic acid (or any portion thereof) can be used to derive the polypeptide amino acid sequence, using the genetic code to translate the DNA or RNA into an amino acid sequence. Likewise, for polypeptide amino acid sequence, corresponding nucleotide sequences that can encode the polypeptide can be deduced from the genetic code (which, because of its redundancy, will produce multiple nucleic acid sequences for any given amino acid sequence). Thus, description and/or disclosure herein of a nucleotide sequence which encodes a polypeptide should be considered to also include description and/or disclosure of the amino acid sequence encoded by the nucleotide sequence. Similarly, description and/or disclosure of a polypeptide amino acid sequence herein should be considered to also include description and/or disclosure of all possible nucleotide sequences that can encode the amino acid sequence.

Finally, nucleic acid and amino acid sequence information for nucleic acid and polypeptide molecules useful in the present invention are well-known in the art and readily available on publicly available databases, such as the National Center for Biotechnology Information (NCBI). For example, exemplary nucleic acid and amino acid sequences derived from publicly available sequence databases are provided in Table 1 below.

TABLE 1

```
Human HHLA2 Variant 1 cDNA Sequence (NM 007072.3, CDS
region from position 415-1659)
                                                    SEQ ID NO: 1
    1   agttctcttc  aagtcatgta  atcgactttt  ttgaattagt  tttcagtttc  attttgtttt 61   ccctaattca  agttgggaac  acttcatttt  ccccaattca  agttgggaac  acttccttgg 121   tatttccttg  ctacatggac  tttagcaaat  gctactttac  tctccttcca  gctactcagg 181   aggctgaggc  aggagaatcg  cttgaacccg  ggaggcggag  gttacagtga  gcctttcct 241   agttttactg  ttggaagcct  aactcacagg  agagattatg  caatacagtc  ctgaagtcaa 301   gggaggagag  catgtaggag  aatactaacc  ctgcacagat  tgtgatggtg  atgtggaata 361   tactaaagcc  tagaacgcac  ctcctctgca  tgactaatat  gttctgcaca  agacatgaag 421   gcacagacag  cactgtcttt  cttcctcatt  ctcataacat  ctctgagtgg  atctcaaggc 481   atattcccctt  tggctttctt  catttatgtt  cctatgaatg  aacaaatcgt  cattggaaga 541   cttgatgaag  atataattct  cccttcttca  tttgagaggg  gatccgaagt  cgtaatacac 601   tggaagtatc  aagatagcta  taaggttcac  agttactaca  aaggcagtga  ccatttggaa 661   agccaagatc  ccagatatgc  aaacaggaca  tcccttttct  ataatgagat  tcaaaatggg 721   aatgcgtcgc  tattttcag  aagagtaagc  cttctggacg  aaggaattta  cacctgctat
```

TABLE 1-continued

```
 781  gtaggaacag caattcaagt gattacaaac aaagtggtgc taaaggtggg agttttttctc
 841  acacccgtga tgaagtatga aagaggaac acaaacagct tcttaatatg cagcgtgtta
 901  agtgtttatc ctcgtccaat tatcacgtgg aaaatggaca acacacctat ctctgaaaac
 961  aacatggaag aaacagggtc tttggattct ttttctatta acagcccact gaatattaca
1021  ggatcaaatt catcttatga atgtacaatt gaaaattcac tgctgaagca aacatggaca
1081  gggcgctgga cgatgaaaga tggccttcat aaaatgcaaa gtgaacacgt ttcactctca
1141  tgtcaacctg taaatgatta ttttttcacca aaccaagact tcaaagttac ttggtccaga
1201  atgaaaagtg ggactttctc tgtcctggct tactatctga gctcctcaca aaatacaatt
1261  atcaatgaat cccgattctc atggaacaaa gagctgataa accagagtga cttctctatg
1321  aatttgatgg atcttaatct ttcagacagt ggggaatatt tatgcaatat ttcttcggat
1381  gaatatactt tacttaccat ccacacagtg catgtagaac cgagccaaga aacagcttcc
1441  cataacaaag gcttatggat tttggtgccc tctgcgattt ggcagctttt tctgctgatt
1501  tggagcgtaa aatgttgcag agcccagcta aagccagga ggagcagaca ccctgctgat
1561  ggagcccaac aagaaagatg ttgtgtccct cctggtgagc gctgtcccag tgcacccgat
1621  aatggcgaag aaaatgtgcc tctttcagga aaagtatagg aaatgagaga agactgtgac
1681  aactcatgac ctgcatcctt aatatccagt gacttcatct cccctttctt caccacaatt
1741  ccaggcaatg gcctgtcgga gcagacaatt ctaccactgc aaagagttgt aaccattttc
1801  tggtatcaca tttattttc aagacatact tttcaagaca tcattcactg acccactacc
1861  tgcattgagt ataaatgcct ggatgttaag gattccaatt taactttgaa aagaactgtc
1921  tcattcattt acatttctgt tacagtcagc ccaggaggtt acagtgagct ctccactaag
1981  aatctggaag aaatgcatca ctagggggttg attcccaatc tgatcaactg ataatgggtg
2041  agagagcagg taagagccaa agtcacctta gtggaaaggt taaaaaccag agcctggaaa
2101  ccaagatgat tgatttgaca aggtatttta gtctagtttt atatgaacgg ttgtatcagg
2161  gtaaccaact cgatttggga tgaatcttag ggcaccaaag actaagacag tatctttaag
2221  attgctaggg aaaagggccc tatgtgtcag gcctctgagc ccaagccaag catcgcatcc
2281  cctgtgattt gcacgtatac atccagatgg cctaaagtaa ctgaagatcc acaaaagaag
2341  taaaaatagc cttaactgat gacattccac cattgtgatt tgttcctgcc ccaccctaac
2401  tgatcaatgt actttgtaat ctcccccacc cttaagaagg tactttgtaa tcttccccac
2461  ccttaagaag gttctttgta attctcccca cccttgagaa tgtactttgt gagatccacc
2521  ctgcccacaa aacattgctc ttaacttcac cgcctaaccc aaaacctata agaactaatg
2581  ataatccatc acccttcgct gactctcttt tcggactcag cccacctgca cccaggtgaa
2641  ataaacagct ttattgctca cacaaaaaaa aaaaaaaaa
```

Human HHLA2 Variant 1 Amino Acid Sequence (NP 009003.1)

SEQ ID NO: 2

```
  1  MKAQTALSFF LILITSLSGS QGIFPLAFFI YVPMNEQIVI GRLDEDIILP SSFERGSEVV
 61  IHWKYQDSYK VHSYYKGSDH LESQDPRYAN RTSLFYNEIQ NGNASLFFRR VSLLDEGIYT
121  CYVGTAIQVI TNKVVLKVGV FLTPVMKYEK RNTNSFLICS VLSVYPRPII TWKMDNTPIS
181  ENNMEETGSL DSFSINSPLN ITGSNSSYEC TIENSLLKQT WTGRWTMKDG LHKMQSEHVS
241  LSCQPVNDYF SPNQDFKVTW SRMKSGTFSV LAYYLSSSQN TIINESRFSW NKELINQSDF
301  SMNLMDLNLS DSGEYLCNIS SDEYTLLTIH TVHVEPSQET ASHNKGLWIL VPSAILAAFL
361  LIWSVKCCRA QLEARRSRHP ADGAQQERCC VPPGERCPSA PDNGEENVPL SGKV
```

TABLE 1-continued

Human HHLA2 Variant 2 cDNA Sequence (NM 001282556.1,
CDS region from position 224-1468)

SEQ ID NO: 3

```
   1  aaatcaaacg taccttggac tttactctct gagaaactca tagctgaatt caatgtttat
  61  tcttatggac tacttagcat ttgactagac ggtatgaatt tctaagtaag cacatataga
 121  actggatgcc cttgtggtac atctcaaggc tgatttgaaa gcttgagaga ccatcaagaa
 181  ttggatttgg ggaagagcat gactaatatg ttctgcacaa gacatgaagg cacagacagc
 241  actgtctttc ttcctcattc tcataacatc tctgagtgga tctcaaggca tattcccttt
 301  ggctttcttc atttatgttc ctatgaatga acaaatcgtc attggaagac ttgatgaaga
 361  tataattctc ccttcttcat ttgagagggg atccgaagtc gtaatacact ggaagtatca
 421  agatagctat aaggttcaca gttactacaa aggcagtgac catttggaaa gccaagatcc
 481  cagatatgca aacaggacat ccctttttcta taatgagatt caaaatggga atgcgtcgct
 541  atttttcaga agagtaagcc ttctggacga aggaatttac acctgctatg taggaacagc
 601  aattcaagtg attacaaaca aagtggtgct aaaggtggga gttttctca cacccgtgat
 661  gaagtatgaa agaggaacca aaacagcttc ttaatatgc agcgtgttaa gtgtttatcc
 721  tcgtccaatt atcacgtgga aaatggacaa cacacctatc tctgaaaaca catggaaga
 781  aacagggtct ttggattctt tttctattaa cagcccactg aatattacag gatcaaattc
 841  atcttatgaa tgtacaattg aaaattcact gctgaagcaa acatggacag ggcgctggac
 901  gatgaaagat ggccttcata aaatgcaaag tgaacacgtt tcactctcat gtcaacctgt
 961  aaatgattat ttttcaccaa accaagactt caaagttact tggtccagaa tgaaaagtgg
1021  gactttctct gtcctggctt actatctgag ctcctcacaa aatacaatta tcaatgaatc
1081  ccgattctca tggaacaaag agctgataaa ccagagtgac ttctctatga atttgatgga
1141  tcttaatctt tcagacagtg gggaatattt atgcaatatt tcttcggatg aatatacttt
1201  acttaccatc cacacagtgc atgtagaacc gagccaagaa acagcttccc ataacaaagg
1261  cttatggatt ttggtgccct ctgcgatttt ggcagctttt ctgctgattt ggagcgtaaa
1321  atgttgcaga gcccagctag aagccaggag gagcagacac cctgctgatg gagcccaaca
1381  agaaagatgt tgtgtccctc ctggtgagcg ctgtcccagt gcacccgata tggcgaaga
1441  aaatgtgcct ctttcaggaa aagtatagga aatgagagaa gactgtgaca actcatgacc
1501  tgcatcctta atatccagtg acttcatctc ccctttcttc accacaattc caggcaatgg
1561  cctgtcggag cagacaattc taccactgca aagagttgta accatttttct ggtatcacat
1621  ttattttca agacatactt ttcaagacat cattcactga cccactacct gcattgagta
1681  taaatgcctg gatgttaagg attccaattt aactttgaaa agaactgtct cattcattta
1741  catttctgtt acagtcagcc caggaggtta cagtgagctc tccactaaga atctggaaga
1801  aatgcatcac taggggttga ttcccaatct gatcaactga taatgggtga gagagcaggt
1861  aagagccaaa gtcaccttag tggaaaggtt aaaaaccaga gcctggaaac caagatgatt
1921  gatttgacaa ggtattttag tctagttta tatgaacggt tgtatcaggg taaccaactc
1981  gatttgggat gaatcttagg gcaccaaaga ctaagacagt atctttaaga ttgctaggga
2041  aaagggccct atgtgtcagg cctctgagcc caagccaagc atcgcatccc ctgtgatttg
2101  cacgtataca tccagatggc ctaaagtaac tgaagatcca caaagaagt aaaaatagcc
2161  ttaactgatg acattccacc attgtgattt gttcctgccc caccctaact gatcaatgta
2221  ctttgtaatc tcccccaccc ttaagaaggt actttgtaat cttccccacc cttaagaagg
```

TABLE 1-continued

```
2281  ttctttgtaa ttctccccac ccttgagaat gtactttgtg agatccaccc tgcccacaaa
2341  acattgctct taacttcacc gcctaaccca aaacctataa gaactaatga taatccatca
2401  cccttcgctg actctctttt cggactcagc ccacctgcac ccaggtgaaa taaacagctt
2461  tattgctcac acaaaaaaaa aaaaaaaa
```

Human HHLA2 Variant 2 Amino Acid Sequence
(NP_001269485.1)

SEQ ID NO: 4

```
  1  MKAQTALSFF LILITSLSGS QGIFPLAFFI YVPMNEQIVI GRLDEDIILP SSFERGSEVV
 61  IHWKYQDSYK VHSYYKGSDH LESQDPRYAN RTSLFYNEIQ NGNASLFFRR VSLLDEGIYT
121  CYVGTAIQVI TNKVVLKVGV FLTPVMKYEK RNTNSFLICS VLSVYPRPII TWKMDNTPIS
181  ENNMEETGSL DSFSINSPLN ITGSNSSYEC TIENSLLKQT WTGRWTMKDG LHKMQSEHVS
241  LSCQPVNDYF SPNQDFKVTW SRMKSGTFSV LAYYLSSSQN TIINESRFSW NKELINQSDF
301  SMNLMDLNLS DSGEYLCNIS SDEYTLLTIH TVHVEPSQET ASHNKGLWIL VPSAILAAFL
361  LIWSVKCCRA QLEARRSRHP ADGAQQERCC VPPGERCPSA PDNGEENVPL SGKV
```

Human HHLA2 Variant 3 cDNA Sequence (NM_001282557.1,
CDS region from position 155-1399)

SEQ ID NO: 5

```
   1  agtttactct acatcatagc agagaaaatg gacaaaacac agctgttttg catgtaggag
  61  aatactaacc ctgcacagat tgtgatggtg atgtggaata tactaaagcc tagaacgcac
 121  ctcctctgca tgactaatat gttctgcaca agacatgaag gcacagacag cactgtcttt
 181  cttcctcatt ctcataacat ctctgagtgg atctcaaggc atattccctt ggctttctt
 241  catttatgtt cctatgaatg aacaaatcgt cattggaaga cttgatgaag atataattct
 301  cccttcttca tttgagaggg gatccgaagt cgtaatacac tggaagtatc aagatagcta
 361  taaggttcac agttactaca aaggcagtga ccatttggaa agccaagatc ccagatatgc
 421  aaacaggaca tccctttttct ataatgagat tcaaaatggg aatgcgtcgc tattttttcag
 481  aagagtaagc cttctggacg aaggaattta cacctgctat gtaggaacag caattcaagt
 541  gattacaaac aaagtggtgc taaaggtggg agttttttctc acaccgtga tgaagtatga
 601  aaagaggaac acaaacagct tcttaatatg cagcgtgtta agtgtttatc ctcgtccaat
 661  tatcacgtgg aaaatggaca acacacctat ctctgaaaac aacatggaag aaacagggtc
 721  tttggattct ttttctatta acagcccact gaatattaca ggatcaaatt catcttatga
 781  atgtacaatt gaaaattcac tgctgaagca acatggacag gggcgctgga cgatgaaaga
 841  tggccttcat aaaatgcaaa gtgaacacgt tcactctca tgtcaacctg taaatgatta
 901  tttttcacca aaccaagact tcaaagttac ttggtccaga atgaaaagtg ggactttctc
 961  tgtcctggct tactatctga gctcctcaca aaatacaatt atcaatgaat cccgattctc
1021  atggaacaaa gagctgataa accagagtga cttctctatg aatttgatgg atcttaatct
1081  ttcagacagt ggggaatatt tatgcaatat ttcttcggat gaatatactt tacttaccat
1141  ccacacagtg catgtagaac cgagccaaga aacagcttcc cataacaaag gcttatggat
1201  tttggtgccc tctgcgattt tggcagcttt tctgctgatt tggagcgtaa aatgttgcag
1261  agcccagcta gaagccagga ggagcagaca ccctgctgat ggagcccaac aagaaagatg
1321  ttgtgtccct cctggtgagc gctgtcccag tgcacccgat aatggcgaag aaaatgtgcc
1381  tctttcagga aaagtatagg aaatgagaga agactgtgac aactcatgac ctgcatcctt
1441  aatatccagt gacttcatct ccccttttctt caccacaatt ccaggcaatg gcctgtcgga
1501  gcagacaatt ctaccactgc aaagagttgt aaccattttc tggtatcaca tttattttc
```

TABLE 1-continued

```
1561  aagacatact tttcaagaca tcattcactg acccactacc tgcattgagt ataaatgcct
1621  ggatgttaag gattccaatt taactttgaa aagaactgtc tcattcattt acatttctgt
1681  tacagtcagc ccaggaggtt acagtgagct ctccactaag aatctggaag aaatgcatca
1741  ctaggggttg attcccaatc tgatcaactg ataatggggt agagagcagg taagagccaa
1801  agtcacctta gtggaaaggt taaaaaccag agcctggaaa ccaagatgat tgatttgaca
1861  aggtatttta gtctagtttt atatgaacgg ttgtatcagg gtaaccaact cgatttggga
1921  tgaatcttag ggcaccaaag actaagacag tatctttaag attgctaggg aaaagggccc
1981  tatgtgtcag gcctctgagc ccaagccaag catcgcatcc cctgtgattt gcacgtatac
2041  atccagatgg cctaaagtaa ctgaagatcc acaaaagaag taaaaatagc cttaactgat
2101  gacattccac cattgtgatt tgttcctgcc ccaccctaac tgatcaatgt actttgtaat
2161  ctcccccacc cttaagaagg tactttgtaa tcttccccac ccttaagaag gttctttgta
2221  attctcccca cccttgagaa tgtactttgt gagatccacc ctgcccacaa acattgctc
2281  ttaacttcac cgcctaaccc aaaacctata agaactaatg ataatccatc accctttcgct
2341  gactctcttt tcggactcag cccacctgca cccaggtgaa ataaacagct ttattgctca
2401  cacaaaaaaa aaaaaaaaa
```

Human HHLA2 Variant 3 Amino Acid Sequence
(NP 001269486.1)

SEQ ID NO: 6

```
  1  MKAQTALSFF LILITSLSGS QGIFPLAFFI YVPMNEQIVI GRLDEDIILP SSFERGSEVV
 61  IHWKYQDSYK VHSYYKGSDH LESQDPRYAN RTSLFYNEIQ NGNASLFFRR VSLLDEGIYT
121  CYVGTAIQVI TNKVVLKVGV FLTPVMKYEK RNTNSFLICS VLSVYPRPII TWKMDNTPIS
181  ENNMEETGSL DSFSINSPLN ITGSNSSYEC TIENSLLKQT WTGRWTMKDG LHKMQSEHVS
241  LSCQPVNDYF SPNQDFKVTW SRMKSGTFSV LAYYLSSSQN TIINESRFSW NKELINQSDF
301  SMNLMDLNLS DSGEYLCNIS SDEYTLLTIH TVHVEPSQET ASHNKGLWIL VPSAILAAFL
361  LIWSVKCCRA QLEARRSRHP ADGAQQERCC VPPGERCPSA PDNGEENVPL SGKV
```

Human HHLA2 Variant 4 cDNA Sequence (NM 001282558.1,
CDS region from position 302-1495)

SEQ ID NO: 7

```
  1  aaatcaaacg taccttggac tttactctct gagaaactca tagctgaatt caatgtttat
 61  tcttatggac tacttagcat ttgactagac ggtatgaatt ctaagtaag cacatataga
121  actggatgcc cttgtggtac atctcaaggc tgatttgaaa gcttgagaga ccatcaagaa
181  ttggatttgg ggaagagcat gtaggagaat actaaccctg cacagattgt gatggtgatg
241  tggaatatac taaagcctag aacgcacctc ctctgcatga ctaatatgtt ctgcacaaga
301  catgaaggca cagacagcac tgtctttctt cctcattctc ataacatctc tgagtggatc
361  tcaaggcata ttcccttttgg cttcttcat ttatgttcct atgaatgaac aaatcgtcat
421  tggaagactt gatgaagata taattctccc ttcttcattt gagaggggga ccgaagtcgt
481  aatacactgg aagtatcaag atagctataa ggttcacagt tactacaaag gcagtgacca
541  tttggaaagc caagatccca gatatgcaaa caggacatcc cttttctata tgagagattca
601  aaatgggaat gcgtcgctat ttttcagaag agtaagcctt ctggacgaag gaatttacac
661  ctgctatgta ggaacagcaa ttcaagtgat acaaacaaa gtggtgctaa aggtgggagt
721  ttttctcaca cccgtgatga agtatgaaaa gaggaacaca aacagcttct taatatgcag
781  cgtgttaagt gtttatcctc gtccaattat cacgtggaaa atggacaaca cacctatctc
841  tgaaaacaac atggaagaaa cagggtcttt ggattctttt tctattaaca gcccactgaa
```

TABLE 1-continued

```
 901   tattacagga tcaaattcat cttatgaatg tacaattgaa aattcactgc tgaagcaaac
 961   atggacaggg cgctggacga tgaaagatgg ccttcataaa atgcaaagtg aacacgtttc
1021   actctcatgt caacctgtaa atgattattt ttcaccaaac caagacttca aagttacttg
1081   gtccagaatg aaaagtggga ctttctctgt cctggcttac tatctgagct cctcacaaaa
1141   tacaattatc aatgaatccc gattctcatg gaacaaagag ctgataaacc agagtgactt
1201   ctctatgaat ttgatggatc ttaatctttc agacagtggg gaatatttat gcaatatttc
1261   ttcggatgaa tatactttac ttaccatcca cacagtgcat gtagaaccga gccaagaaac
1321   agcttcccat aacaaaggct tatggatttt ggtgccctct gcgattttgg cagcttttct
1381   gctgatttgg agcgtaaaat gttgcagaga agatgttgt gtccctcctg gtgagcgctg
1441   tcccagtgca cccgataatg gcgaagaaaa tgtgcctctt caggaaaag tataggaaat
1501   gagagaagac tgtgacaact catgacctgc atccttaata tccagtgact tcatctcccc
1561   tttcttcacc acaattccag gcaatggcct gtcggagcag acaattctac cactgcaaag
1621   agttgtaacc attttctggt atcacattta ttttcaaga catactttc aagacatcat
1681   tcactgaccc actacctgca ttgagtataa atgcctggat gttaaggatt ccaatttaac
1741   tttgaaaaga actgtctcat tcatttacat ttctgttaca gtcagcccag gaggttacag
1801   tgagctctcc actaagaatc tggaagaaat gcatcactag gggttgattc ccaatctgat
1861   caactgataa tgggtgagag agcaggtaag agccaaagtc accttagtgg aaaggttaaa
1921   aaccagagcc tggaaaccaa gatgattgat ttgacaaggt attttagtct agtttttatat
1981   gaacggttgt atcagggtaa ccaactcgat ttgggatgaa tcttagggca ccaaagacta
2041   agacagtatc tttaagattg ctagggaaaa gggccctatg tgtcaggcct ctgagcccaa
2101   gccaagcatc gcatcccctg tgatttgcac gtatacatcc agatggccta aagtaactga
2161   agatccacaa aagaagtaaa aatagccttaa actgatgaca ttccaccatt gtgatttgtt
2221   cctgccccac cctaactgat caatgtactt tgtaatctcc ccacccctta agaaggtact
2281   ttgtaatctt cccccacccctt aagaaggttc tttgtaattc tccccaccct tgagaatgta
2341   ctttgtgaga tccaccctgc ccacaaaaca ttgctcttaa cttcaccgcc taacccaaaa
2401   cctataagaa ctaatgataa tccatcaccc ttcgctgact ctcttttcgg actcagccca
2461   cctgcaccca ggtgaaataa acagctttat tgctcacaca aaaaaaaaaa aaaaa
```

Human HHLA2 Variant 4 Amino Acid Sequence
(NP 001269487.1)

SEQ ID NO: 8

```
  1   MKAQTALSFF LILITSLSGS QGIFPLAFFI YVPMNEQIVI GRLDEDIILP SSFERGSEVV
 61   IHWKYQDSYK VHSYYKGSDH LESQDPRYAN RTSLFYNEIQ NGNASLFFRR VSLLDEGIYT
121   CYVGTAIQVI TNKVVLKVGV FLTPVMKYEK RNTNSFLICS VLSVYPRPII TWKMDNTPIS
181   ENNMEETGSL DSFSINSPLN ITGSNSSYEC TIENSLLKQT WTGRWTMKDG LHKMQSEHVS
241   LSCQPVNDYF SPNQDFKVTW SRMKSGTFSV LAYYLSSSQN TIINESRFSW NKELINQSDF
301   SMNLMDLNLS DSGEYLCNIS SDEYTLLTIH TVHVEPSQET ASHNKGLWIL VPSAILAAFL
361   LIWSVKCCRE RCCVPPGERC PSAPDNGEEN VPLSGKV
```

Human HHLA2 Variant 5 cDNA Sequence (NM_001282559.1,
CDS region from position 232-1284)

SEQ ID NO: 9

```
  1   aaatcaaacg taccttggac tttactctct gagaaactca tagctgaatt caatgtttat
 61   tcttatggac tacttagcat ttgactagac ggtatgaatt tctaagtaag cacatataga
121   actggatgcc cttgtggtac atctcaaggc tgatttgaaa gcttgagaga ccatcaagaa
```

TABLE 1-continued

```
 181   ttggatttgg ggaagagcat gtaggagaat actaaccctg cacagattgt gatggtgatg
 241   tggaatatac taaagcctag aacgcacctc ctctgcatga ctaatatgtt ctgcacaaga
 301   catgaaggca cagacagcac tgtctttctt cctcattctc ataacatctc tgagtggatc
 361   tcaagaagag taagccttct ggacgaagga atttacacct gctatgtagg aacagcaatt
 421   caagtgatta caaacaaagt ggtgctaaag gtgggagttt tctcacacc cgtgatgaag
 481   tatgaaaaga ggaacacaaa cagcttctta atatgcagcg tgttaagtgt ttatcctcgt
 541   ccaattatca cgtggaaaat ggacaacaca cctatctctg aaaacaacat ggaagaaaca
 601   gggtctttgg attcttttc tattaacagc ccactgaata ttacaggatc aaattcatct
 661   tatgaatgta caattgaaaa ttcactgctg aagcaaacat ggacagggcg ctggacgatg
 721   aaagatggcc ttcataaaat gcaaagtgaa cacgtttcac tctcatgtca acctgtaaat
 781   gattatttt caccaaacca agacttcaaa gttacttggt ccagaatgaa aagtgggact
 841   ttctctgtcc tggcttacta tctgagctcc tcacaaaata caattatcaa tgaatcccga
 901   ttctcatgga acaaagagct gataaaccag agtgacttct ctatgaattt gatggatctt
 961   aatctttcag acagtgggga atatttatgc aatatttctt cggatgaata tactttactt
1021   accatccaca cagtgcatgt agaaccgagc caagaaacag cttcccataa caaaggctta
1081   tggattttgg tgccctctgc gattttggca gcttttctgc tgatttggag cgtaaaatgt
1141   tgcagagccc agctagaagc caggaggagc agacaccctg ctgatggagc ccaacaagaa
1201   agatgttgtg tccctcctgg tgagcgctgt cccagtgcac ccgataatgg cgaagaaaat
1261   gtgcctcttt caggaaaagt ataggaaatg agagaagact gtgacaactc atgacctgca
1321   tccttaatat ccagtgactt catctcccct ttcttccacca caattccagg caatggcctg
1381   tcggagcaga caattctacc actgcaaaga gttgtaacca ttttctggta tcacatttat
1441   ttttcaagac atacttttca agcatcatt cactgaccca ctacctgcat tgagtataaa
1501   tgcctggatg ttaaggattc caatttaact ttgaaaagaa ctgtctcatt catttacatt
1561   tctgttacag tcagcccagg aggttacagt gagctctcca ctaagaatct ggaagaaatg
1621   catcactagg ggttgattcc caatctgatc aactgataat gggtgagaga gcaggtaaga
1681   gccaaagtca ccttagtgga aaggttaaaa accagagcct ggaaaccaag atgattgatt
1741   tgacaaggta ttttagtcta gttttatatg aacggttgta tcagggtaac caactcgatt
1801   tgggatgaat cttagggcac caaagactaa gacagtatct ttaagattgc tagggaaaag
1861   ggccctatgt gtcaggcctc tgagcccaag ccaagcatcg catcccctgt gatttgcacg
1921   tatacatcca gatggcctaa agtaactgaa gatccacaaa agaagtaaaa atagccttaa
1981   ctgatgacat tccaccattg tgatttgttc ctgccccacc taactgatc aatgtacttt
2041   gtaatctccc ccaccccttaa gaaggtactt tgtaatcttc cccacccttta agaaggttct
2101   ttgtaattct ccccacccctt gagaatgtac tttgtgagat ccacccctgcc cacaaaacat
2161   tgctcttaac ttcaccgcct aacccaaaac ctataagaac taatgataat ccatcaccct
2221   tcgctgactc tcttttcgga ctcagcccac ctgcacccag gtgaaataaa cagctttatt
2281   gctcacacaa aaaaaaaaaa aaaa
```

Human HHLA2 Variant 5 Amino Acid Sequence
(NP 001269488.1)

SEQ ID NO: 10

```
  1   MVMWNILKPR THLLCMTNMF CTRHEGTDST VFLPHSHNIS EWISRRVSLL DEGIYTCYVG
 61   TAIQVITNKV VLKVGVFLTP VMKYEKRNTN SFLICSVLSV YPRPIITWKM DNTPISENNM
121   EETGSLDSFS INSPLNITGS NSSYECTIEN SLLKQTWTGR WTMKDGLHKM QSEHVSLSCQ
```

TABLE 1-continued

```
181  PVNDYFSPNQ DFKVTWSRMK SGTFSVLAYY LSSSQNTIIN ESRFSWNKEL INQSDFSMNL

241  MDLNLSDSGE YLCNISSDEY TLLTIHTVHV EPSQETASHN KGLWILVPSA ILAAFLLIWS

301  VKCCRAQLEA RRSRHPADGA QQERCCVPPG ERCPSAPDNG EENVPLSGKV
```

Human TMIGD2 Isoform 1 cDNA Sequence (NM 144615.2,
CDS region from position 47-895)
SEQ ID NO: 11
```
   1  ggaagtctgt caactgggag ggggagaggg gggtgatggg ccaggaatgg ggtccccggg 61  catggtgctg ggcctcctgg tgcagatctg ggccctgcaa gaagcctcaa gcctgagcgt 121  gcagcagggg cccaacttgc tgcaggtgag gcagggcagt caggcgaccc tggtctgcca 181  ggtggaccag gccacagcct gggaacggct ccgtgttaag tggacaaagg atggggccat 241  cctgtgtcaa ccgtacatca ccaacggcag cctcagcctg ggggtctgcg gccccaggg 301  acggctctcc tggcaggcac ccagccatct caccctgcag ctggaccctg tgagcctcaa 361  ccacagcggg gcgtacgtgt gctgggcggc cgtagagatt cctgagttgg aggaggctga 421  gggcaacata caaggctct ttgtggaccc agatgacccc acacagaaca gaaaccggat 481  cgcaagcttc caggattcc tcttcgtgct gctgggggtg ggaagcatgg gtgtggctgc 541  gatcgtgtgg ggtgcctggt tctgggccg ccgcagctgc agcaaaggg actcaggtaa 601  cagcccagga aatgcattct acagcaacgt cctataccgg ccccgggggg ccccaaagaa 661  gagtgaggac tgctctggag aggggaagga ccagagggc cagagcattt attcaacctc 721  cttcccgcaa ccggcccccc gccagccgca cctggcgtca gaccctgcc ccagcccgag 781  accctgcccc agccccaggc ccggccaccc cgtctctatg gtcagggtct ctcctagacc 841  aagccccacc cagcagccga ggccaaaagg ttccccaaa gtgggagagg agtgagagat 901  cccaggagac ctcaacagga ccccacccat aggtacacac aaaaaagggg ggatcgaggc 961  cagacacggt ggctcacgcc tgtaatccca gcagtttggg aagccgaggc gggtggaaca 1021  cttgaggtca ggggtttgag accagcctgg cttgaacctg ggaggcggag gttgcagtga 1081  gccgagattg cgccactgca ctccagcctg ggcgacagag tgagactccg tctcaaaaaa 1141  aacaaaaagc aggaggattg ggagcctgtc agccccatcc tgagaccccg tcctcatttc 1201  tgtaatgatg gatctcgctc ccactttccc ccaagaacct aataaaggct tgtgaagaaa 1261  aagcaaaaaa aaaaaaaaaa aa
```

Human TMIGD2 Isoform 1 Amino Acid Sequence
(NP 653216.2)
SEQ ID NO: 12
```
   1  MGSPGMVLGL LVQIWALQEA SSLSVQQGPN LLQVRQGSQA TLVCQVDQAT AWERLRVKWT

61  KDGAILCQPY ITNGSLSLGV CGPQGRLSWQ APSHLTLQLD PVSLNHSGAY VCWAAVEIPE

121  LEEAEGNITR LFVDPDDPTQ NRNRIASFPG FLFVLLGVGS MGVAAIVWGA WFWGRRSCQQ

181  RDSGNSPGNA FYSNVLYRPR GAPKKSEDCS GEGKDQRGQS IYSTSFPQPA PRQPHLASRP

241  CPSPRPCPSP RPGHPVSMVR VSPRPSPTQQ PRPKGFPKVG EE
```

Human TMIGD2 Isoform 2 cDNA Sequence (NM 001169126.1,
CDS region from position 47-883)
SEQ ID NO: 13
```
   1  ggaagtctgt caactgggag ggggagaggg gggtgatggg ccaggaatgg ggtccccggg 61  catggtgctg ggcctcctgg tgcagatctg ggccctgcaa gaagcctcaa gcctgagcgt 121  gcagcagggg cccaacttgc tgcaggtgag gcagggcagt caggcgaccc tggtctgcca 181  ggtggaccag gccacagcct gggaacggct ccgtgttaag tggacaaagg atggggccat 241  cctgtgtcaa ccgtacatca ccaacggcag cctcagcctg ggggtctgcg gccccaggg
```

TABLE 1-continued

```
 301  acggctctcc tggcaggcac ccagccatct caccctgcag ctggaccctg tgagcctcaa
 361  ccacagcggg gcgtacgtgt gctgggcggc cgtagagatt cctgagttgg aggaggctga
 421  gggcaacata caaggctct tgtggaccc agatgacccc acacagaaca gaaaccggat
 481  cgcaagcttc ccaggattcc tcttcgtgct gctggggtg ggaagcatgg gtgtggctgc
 541  gatcgtgtgg ggtgcctggt tctggggccg ccgcagctgc cagcaaaggg actcaggaaa
 601  tgcattctac agcaacgtcc tataccggcc cgggggcc caaagaaga gtgaggactg
 661  ctctggagag gggaaggacc agaggggcca gagcatttat tcaacctcct tcccgcaacc
 721  ggccccccgc cagccgcacc tggcgtcaag accctgcccc agcccgagac cctgccccag
 781  ccccaggccc ggccacccg tctctatggt cagggtctct cctagaccaa gccccaccca
 841  gcagccgagg ccaaaagggt tccccaaagt gggagaggag tgagagatcc caggagacct
 901  caacaggacc ccacccatag gtacacacaa aaaggggg atcgaggcca gacacggtgg
 961  ctcacgcctg taatcccagc agtttgggaa gccgaggcgg gtggaacact tgaggtcagg
1021  ggtttgagac cagcctggct tgaacctggg aggcggaggt tgcagtgagc cgagattgcg
1081  ccactgcact ccagcctggg cgacagagtg agactccgtc tcaaaaaaaa caaaaagcag
1141  gaggattggg agcctgtcag ccccatcctg agaccccgtc ctcatttctg taatgatgga
1201  tctcgctccc actttccccc aagaacctaa taaaggcttg tgaagaaaaa gcaaaaaaaa
1261  aaaaaaaaaa
```

Human TMIGD2 Isoform 2 Amino Acid Sequence  
(NP 001162597.1)

SEQ ID NO: 14

```
   1  MGSPGMVLGL LVQIWALQEA SSLSVQQGPN LLQVRQGSQA TLVCQVDQAT AWERLRVKWT
  61  KDGAILCQPY ITNGSLSLGV CGPQGRLSWQ APSHLTLQLD PVSLNHSGAY VCWAAVEIPE
 121  LEEAEGNITR LFVDPDDPTQ NRNRIASFPG FLFVLLGVGS MGVAAIVWGA WFWGRRSCQQ
 181  RDSGNAFYSN VLYRPRGAPK KSEDCSGEGK DQRGQSIYST SFPQPAPRQP HLASRPCPSP
 241  RPCPSPRPGH PVSMVRVSPR PSPTQQPRPK GFPKVGEE
```

Human TMIGD2 Isoform 3 cDNA Sequence (NM 001308232.1,  
CDS region from position 47-535)

SEQ ID NO: 15

```
   1  ggaagtctgt caactgggag ggggagaggg gggtgatggg ccaggaatgg ggtccccggg
  61  catggtgctg ggcctcctgg tgcagatctg ggatgacccc acacagaaca gaaaccggat
 121  cgcaagcttc ccaggattcc tcttcgtgct gctggggtg ggaagcatgg gtgtggctgc
 181  gatcgtgtgg ggtgcctggt tctggggccg ccgcagctgc cagcaaaggg actcaggtaa
 241  cagcccagga aatgcattct acagcaacgt cctataccgg ccccggggg ccccaaagaa
 301  gagtgaggac tgctctggag aggggaagga ccagagggggc cagagcattt attcaacctc
 361  cttcccgcaa ccggccccc gccagccgca cctggcgtca gacccctgcc cagcccgag
 421  accctgcccc agccccaggc ccggccaccc cgtctctatg gtcagggtct ctcctagacc
 481  aagccccacc cagcagccga ggccaaaagg gttccccaaa gtgggagagg agtgagagat
 541  cccaggagac ctcaacagga ccccacccat aggtacacac aaaaaagggg ggatcgaggc
 601  cagacacggt ggctcacgcc tgtaatccca gcagtttggg aagccgaggc gggtggaaca
 661  cttgaggtca ggggtttgag accagcctgg cttgaacctg ggaggcggag gttgcagtga
 721  gccgagattg cgccactgca ctccagcctg ggcgacagag tgagactccg tctcaaaaaa
 781  aacaaaaagc aggaggattg ggagcctgtc agccccatcc tgagaccccg tcctcatttc
```

TABLE 1-continued

```
841  tgtaatgatg gatctcgctc ccactttccc ccaagaacct aataaaggct tgtgaagaaa 901  aagcaaaaaa aaaaaaaa
```

Human TMIGD2 Isoform 3 Amino Acid Sequence
(NP 001295161.1)

SEQ ID NO: 16

```
  1  MGSPGMVLGL LVQIWDDPTQ NRNRIASFPG FLFVLLGVGS MGVAAIVWGA WFWGRRSCQQ

61  RDSGNSPGNA FYSNVLYRPR GAPKKSEDCS GEGKDQRGQS IYSTSFPQPA PRQPHLASRP

121  CPSPRPCPSP RPGHPVSMVR VSPRPSPTQQ PRPKGFPKVG EE
```

Human KIR3DL3 cDNA Sequence (NM_153443.4, CDS region
from position 51-1283)

SEQ ID NO: 17

```
   1  tgctgctgaa ctgagctggg gcgcagccgc ctgtctgcac cggcagcacc atgtcgctca 61  tggtcgtcag catggcgtgt gttgggttct tcttgctgga ggggccctgg ccacatgtgg 121  gtggtcagga caagcccttc ctctctgcct ggcccggcac tgtggtgtct gaaggacaac 181  atgtgactct tcagtgtcgc tctcgtcttg gtttaatga attcagtctg ccaaagaag 241  acgggatgcc tgtccctgag ctctacaaca gaatattccg gaacagcttt tcatgggcc 301  ctgtgacccc agcacatgca gggacctaca gatgttgcag ttcacaccca cactccccca 361  ctgggtggtc ggcacccagc aaccctgtgg tgatcatggt cacaggagtc cacagaaaac 421  cttccctcct ggcccaccca gtcccctgg tgaaatcagg agagacggtc atcctgcaat 481  gttggtcaga tgtcaggttt gagcgcttcc ttctgcacag agagggatc actgaggacc 541  ccttgcgcct cgttggacag ctccacgatg cgggttccca ggtcaactat tccatgggtc 601  ccatgacacc tgcccttgca gggacctaca gatgctttgg ttctgtcact cacttaccct 661  atgagttgtc ggctcccagt gaccctctgg acatcgtggt cgtaggtcta tatgggaaac 721  cttctctctc agcccagccg ggcccacgg ttcaggcagg agagaatgtg accttgtcct 781  gcagctcccg gagcttgttt gacatttacc atctatccag ggaggcggag gccggtgaac 841  ttaggctcac tgcagtgctg agggtcaatg aacattcca ggccaacttc cctctgggcc 901  ctgtgaccca cggagggaac tacagatgct tcggtctttt ccgtgccctg cccatgcgt 961  ggtcagaccc gagtgaccca ctgccgtttt ctgtcacagg taactccaga aacctgcacg 1021  ttctgattgg gacctcagtg gtcatcatcc cctttgctat cctcctcttc tttctccttc 1081  atcgctggtg tgccaacaaa aagaatgctg ttgtaatgga ccaagagcct gcagggaaca 1141  gaacagtgaa cagggaggac tctgatgaac aagaccctca ggaggtgaca tacgcacagt 1201  tgaatcactg cgttttcaca cagagaaaaa tcactcgccc ttctcagagg cccaagacac 1261  ccccaacaga taccagcgtg taacacgaa cttccaaatg ctgagcgcag atccaaagtt 1321  gtcttctgtc cactagcacc acagtcaggc cttgatggga tcttctaggg agacaatagc 1381  cctgtctcaa aaccgggttg ccagctccca tgtaccagca gctggactct gaaggcgtga 1441  gtctgcatct tagggcatcg ctcttcctca caccacgaat ctgaacatgc ctctctcttg 1501  cttacaaatg tctaaggtcc ccactgcctg ctggagaaa aacacacttg cttagcccac 1561  aattctccat ttcacttgac ccctgcccac ctctccaacc taactggctt acttcctagt 1621  ctacttgagg ctgcgatcac actgaggaac tcacaattcc aaacatataa gaggctccct 1681  cttaacacgg cacttagata cgtgctattc cacctttcct cag
```

Human KIR3DL3 Amino Acid Sequence (NP 703144.3)

SEQ ID NO: 18

```
  1  MSLMVVSMAC VGFFLLEGPW PHVGGQDKPF LSAWPGTVVS EGQHVTLQCR SRLGFNEFSL

61  SKEDGMPVPE LYNRIFRNSF LMGPVTPAHA GTYRCCSSHP HSPTGWSAPS NPVVIMVTGV
```

TABLE 1-continued

```
121   HRKPSLLAHP GPLVKSGETV ILQCWSDVRF ERFLLHREGI TEDPLRLVGQ LHDAGSQVNY

181   SMGPMTPALA GTYRCFGSVT HLPYELSAPS DPLDIVVVGL YGKPSLSAQP GPTVQAGENV

241   TLSCSSRSLF DIYHLSREAE AGELRLTAVL RVNGTFQANF PLGPVTHGGN YRCFGSFRAL

301   PHAWSDPSDP LPVSVTGNSR NLHVLIGTSV VIIPFAILLF FLLHRWCANK KNAVVMDQEP

361   AGNRTVNRED SDEQDPQEVT YAQLNHCVFT QRKITRPSQR PKTPPTDTSV
```

\* Included in Table 1 are RNA nucleic acid molecules (e.g., thymines replaced with uridines), nucleic acid molecules encoding orthologs of the encoded proteins, as well as DNA or RNA nucleic acid sequences comprising a nucleic acid sequence having at least 80%, 81%, 82%, 83%, 84%, 85%, 86%, 87%, 88%, 89%, 90%, 91%, 92%, 93%, 94%, 95%, 96%, 97%, 98%, 99%, 99.5%, or more identity across their full length with the nucleic acid sequence of any SEQ ID NO listed in Table 1, or a portion thereof. Such nucleic acid molecules can have a function of the full-length nucleic acid as described further herein.
\* Included in Table 1 are orthologs of the proteins, as well as polypeptide molecules comprising an amino acid sequence having at least 80%, 81%, 82%, 83%, 84%, 85%, 86%, 87%, 88%, 89%, 90%, 91%, 92%, 93%, 94%, 95%, 96%, 97%, 98%,99%, 99.5%, or more identity across their full length with an amino acid sequence of any SEQ ID NO listed in Table 1, or a portion thereof. Such polypeptides can have a function of the full-length polypeptide as described further herein.
\* Included in Table 1 are other known HHLA2, TMIGD2, and KIR3DL3 nucleic acid and amino acid sequences.

In addition to being stimulatory receptors (i.e. transmitting a costimulatory signal to an immune cell), HHLA2 polypeptides are inhibitory receptors capable of transmitting an inhibitory signal to an immune cell to thereby inhibit immune cell effector function, or are capable of promoting costimulation of immune cells, e.g., when bound to inhibitory receptors or stimulatory receptors. HHLA2 bind to one or more receptors, e.g., TMIGD2, KIR3DL3, and/or other polypeptides on T-cells.

The term "HHLA2 activity," includes the ability of a HHLA2 polypeptide to modulate an inhibitory signal in an activated immune cell, e.g., by engaging a natural HHLA2 ligand on a T-cell. Modulation of an inhibitory signal in an immune cell results in modulation of proliferation of, and/or cytokine secretion by, an immune cell. Thus, the term "HHLA2 activity" includes the ability of a HHLA2 polypeptide to bind its natural ligand(s), the ability to modulate immune cell costimulatory or inhibitory signals, and the ability to modulate the immune response.

In some embodiments, a condition such as cancer is responsive to HHLA2 blockade alone. In other embodiments, a condition such as cancer is responsive to HHLA2 blockade alone, but is significantly or synergistically more responsive when treated with HHLA2 blockade and another therapy in combination. Many conditions responsive to HHLA2 blockade alone or in combination include, without limitation, melanoma (e.g., advanced or metastatic melanoma), lung cancer (e.g., non-small cell lung cancer and small cell lung cancer), breast cancer (e.g., HER-2 negative breast cancer, estrogen-receptor+/HER-2-breast cancer, and triple negative breast cancer), pancreatic cancer (e.g., pancreatic adenocarcinoma), and Hodgkin lymphoma, as well as bladder, gastric, head and neck, renal, prostate, gynecologic, colorectal, ovary, and hematologic cancers.

Preferred B7 polypeptides are capable of providing costimulatory or inhibitory signals to immune cells to thereby promote or inhibit immune cell responses. For example, B7 family members that bind to costimulatory receptors increase T cell activation and proliferation, while B7 family members that bind to inhibitory receptors reduce costimulation. Moreover, the same B7 family member may increase or decrease T cell costimulation. For example, when bound to a costimulatory receptor, HHLA2 can induce costimulation of immune cells or when bound to an inhibitory receptor, HHLA2 can inhibit immune cells. When bound to an inhibitory receptor, HHLA2 can transmit an inhibitory signal to an immune cell. Preferred B7 family members include HHLA2, B7-1, B7-2, B7h, PD-L1 or PD-L2 and soluble fragments or derivatives thereof. In one embodiment, B7 family members bind to one or more receptors on an immune cell, e.g., TMIGD2, KIR3DL3, CTLA4, CD28, ICOS, PD-1 and/or other receptors, and, depending on the receptor, have the ability to transmit an inhibitory signal or a costimulatory signal to an immune cell, preferably a T cell.

Modulation of a costimulatory signal results in modulation of effector function of an immune cell. Thus, the term "HHLA2 ligand activity" includes the ability of a HHLA2 ligand polypeptide to bind its natural receptor(s) (e.g. HHLA2), the ability to modulate immune cell costimulatory or inhibitory signals, and the ability to modulate the immune response.

It is demonstrated herein that the HHLA2 pathway is a negative regulator or a positive regulator of immune function, such that modulating the interaction between HHLA2 and one or more natural binding partners, such as TMIGD2 and/or KIR3DL3 can modulate immune function. HHLA2 binding to TMIGD2 can be a positive regulator of immune function. HHLA2 binding to inhibitory receptors is a negative regulator of immune function. HHLA2 binding to TMIGD2 is believed to be similar to HHLA2 binding to inhibitory receptors. Therefore, inhibiting HHLA2 binding to TMIGD2 is believed to inhibit HHLA2 binding to inhibitory receptors. Thus, the agents of the present invention described herein that are HHLA2 pathway modulators (e.g., modulator of the interaction between HHLA2 and one or more natural binding partners, such as TMIGD2 and/or KIR3DL3) modulate the interaction between HHLA2 and one or more natural binding partners, whether directly or indirectly, can upregulate or downregulate the immune system and, thereby, upregulate or downregulate an immune response. Agents that modulate such an interaction can do so either directly or indirectly.

The interaction between HHLA2 and one or more HHLA2 natural binding partners, such as TMIGD2 and/or KIR3DL3, results in the delivery of a co-stimulatory or co-inhibitory immune signal. Thus, in one embodiment, agents which directly block such an interaction(s) (e.g., anti-HHLA2, anti-TMIGD2, and/or anti-KIR3DL3 blocking antibodies) can prevent inhibitory or stimulatory signaling and upregulate or downregulate an immune response. Alternatively, agents that indirectly block the interaction(s) can prevent inhibitory signaling and upregulate an immune response. Exemplary agents for upregulating an immune response include antibodies against HHLA2 or KIR3DL3 that block the interaction between HHLA2 and KIR3DL3; a non-activating form of HHLA2 or KIR3DL3 (e.g., a dominant negative polypeptide), small molecules or peptides that block the interaction between HHLA2 and KIR3DL3; fusion proteins (e.g., the extracellular portion of HHLA2 or KIR3DL3 fused to the Fc portion of an antibody or immunoglobulin) that bind to HHLA2 or KIR3DL3, respectively, and inhibit the interaction between HHLA2 and KIR3DL3; nucleic acid molecules and/or genetic modifications that block HHLA2 and/or KIR3DL3 transcription or translation; a non-activating form of a natural HHLA2 ligand, and a soluble form of a natural KIR3DL3 ligand.

In other exemplary embodiments, agents that promote the binding of a HHLA2 polypeptide to one or more natural binding partners, such as KIR3DL3 polypeptide, promote an inhibitory signal to an immune cell. Agents that modulate such an interaction can do so either directly or indirectly. Thus, in one embodiment, agents which directly enhance the interaction between HHLA2 and KIR3DL3 (HHLA2 agonists and/or KIR3DL3 agonists) can promote inhibitory signaling and downregulate an immune response. Alternatively, agents that block KIR3DL3 binding to other targets increase the effective concentration of KIR3DL3 available to bind to HHLA2. Exemplary agents for downregulating an immune response include antibodies against HHLA2 or KIR3DL3 that activate or promote the interaction between HHLA2 and KIR3DL3; small molecules or peptides that activate or promote the interaction between HHLA2 and KIR3DL3; and blocking antibodies that bind natural binding partners of HHLA2 and KIR3DL3 other than HHLA2 and KIR3DL3, respectively. These relationships also apply for HHLA2 and TMIGD2 interactions.

Additional agents useful in the methods of the present invention include antibodies, small molecules, peptides, peptidomimetics, natural ligands, and derivatives of natural ligands, that can either bind and/or activate or inhibit protein biomarkers of the present invention, including the biomarkers listed in Table 1, or fragments thereof; RNA interference, antisense, nucleic acid aptamers, etc. that can downregulate the expression and/or activity of the biomarkers of the present invention, including the biomarkers listed in Table 1, or fragments thereof.

Isolated monoclonal antibodies or fragments thereof that are directed against HHLA2 are provided.

Since it is well-known in the art that antibody heavy and light chain CDR3 domains play a particularly important role in the binding specificity/affinity of an antibody for an antigen, the recombinant monoclonal antibodies of the present invention prepared as set forth above preferably comprise the heavy and light chain CDR3s of variable regions of the present invention (e.g., including the sequences of Table 2, or portions thereof). The antibodies further can comprise the CDR2s of variable regions of the present invention (e.g., including the sequences of Table 2, or portions thereof). The antibodies further can comprise the CDR1s of variable regions of the present invention (e.g., including the sequences of Table 2, or portions thereof). In other embodiments, the antibodies can comprise any combinations of the CDRs.

The CDR1, 2, and/or 3 regions of the engineered antibodies described above can comprise the exact amino acid sequence(s) as those of variable regions of the present invention (e.g., including the sequences of Table 2, or portions thereof) disclosed herein. However, the ordinarily skilled artisan will appreciate that some deviation from the exact CDR sequences may be possible while still retaining the ability of the antibody to bind HHLA2 effectively (e.g., conservative sequence modifications). Accordingly, in another embodiment, the engineered antibody may be composed of one or more CDRs that are, for example, 50%, 60%, 70%, 80%, 85%, 90%, 91%, 92%, 93%, 94%, 95%, 96%, 97%, 98%, 99%, or 99.5% identical to one or more CDRs of the present invention (e.g., including the sequences of Table 2, or portions thereof).

The structural features of known, non-human or human antibodies (e.g., a mouse or a non-rodent anti-human HHLA2 antibody) can be used to create structurally related human anti-human HHLA2 antibodies that retain at least one functional property of the antibodies of the present invention, such as binding of HHLA2 (such as mAb 8A12 and polyclonal antibodies 1.2 and 2.2). Another functional property includes inhibiting binding of the original known, non-human or human antibodies in a competition ELISA assay.

In some embodiments, monoclonal antibodies capable of binding human HHLA2 (such as mAb 8A12 and polyclonal antibodies 1.2 and 2.2) are provided, comprising a heavy chain wherein the variable domain comprises at least a CDR having a sequence that is at least 80%, 85%, 90%, 91%, 92%, 93%, 94%, 95%, 96%, 97%, 98%, 99%, 99.5% or 100% identical from the group of heavy chain variable domain CDRs presented in Table 2.

Similarly, monoclonal antibodies capable of binding human HHLA2 (such as mAb 8A12 and polyclonal antibodies 1.2 and 2.2), comprising a light chain wherein the variable domain comprises at least a CDR having a sequence that is at least 80%, 85%, 90%, 91%, 92%, 93%, 94%, 95%, 96%, 97%, 98%, 99%, 99.5% or 100% identical from the group of light chain variable domain CDRs presented in Table 2, are also provided.

Monoclonal antibodies capable of binding human HHLA2 (such as mAb 8A12 and polyclonal antibodies 1.2 and 2.2), comprising a heavy chain wherein the variable domain comprises at least a CDR having a sequence that is at least 80%, 85%, 90%, 91%, 92%, 93%, 94%, 95%, 96%, 97%, 98%, 99%, 99.5% or 100% identical from the group of heavy chain variable domain CDRs presented in Table 2; and comprising a light chain wherein the variable domain comprises at least a CDR having a sequence that is at least 80%, 85%, 90%, 91%, 92%, 93%, 94%, 95%, 96%, 97%, 98%, 99%, 99.5% or 100% identical from the group of light chain variable domain CDRs presented in Table 2, are also provided.

A skilled artisan will note that such percentage homology is equivalent to and can be achieved by introducing 1, 2, 3, 4, 5, 6, 7, 8, 9, 10, or more conservative amino acid substitutions within a given CDR.

The monoclonal antibodies of the present invention can comprise a heavy chain, wherein the variable domain comprises at least a CDR having a sequence selected from the group consisting of the heavy chain variable domain CDRs presented in Table 2 and a light chain, wherein the variable domain comprises at least a CDR having a sequence selected from the group consisting of the light chain variable domain CDRs presented in Table 2.

Such monoclonal antibodies can comprise a light chain, wherein the variable domain comprises at least a CDR having a sequence selected from the group consisting of CDR-L1, CDR-L2, and CDR-L3, as described herein; and/ or a heavy chain, wherein the variable domain comprises at least a CDR having a sequence selected from the group consisting of CDR-H1, CDR-H2, and CDR-H3, as described herein. In some embodiments, the monoclonal antibodies capable of binding human HHLA2 comprises or consists of CDR-L1, CDR-L2, CDR-L3, CDR-H1, CDR-H2, and CDR-H3, as described herein.

The heavy chain variable domain of the monoclonal antibodies of the present invention can comprise or consist of the vH amino acid sequence set forth in Table 2 and/or the light chain variable domain of the monoclonal antibodies of the present invention can comprise or consist of the vκ amino acid sequence set forth in Table 2.

The monoclonal antibodies of the present invention can be produced and modified by any technique well-known in the art. Similarly, such monoclonal antibodies can be chimeric, preferably chimeric mouse/human antibodies. In some embodiments, the monoclonal antibodies are humanized antibodies such that the variable domain comprises human acceptor frameworks regions, and optionally human constant domain where present, and non-human donor CDRs, such as mouse or non-rodent CDRs as defined above.

The present invention further provides fragments of said monoclonal antibodies which include, but are not limited to, Fv, Fab, F(ab')2, Fab', dsFv, scFv, sc(Fv)2 and diabodies; and multispecific antibodies formed from antibody fragments. For example, a number of immunoinhibitory molecules, such as HHLA2, PD-L2, PD-L1, CTLA-4, KIR3DL3, and the like, can be detected in a bispecific or multispecific manner in order to efficiently characterize the expression of such molecules.

Other fragments of the monoclonal antibodies of the present invention are also contemplated. For example, individual immunoglobulin heavy and/or light chains are provided, wherein the variable domains thereof comprise at least a CDR presented in Table 2. In one embodiment, the immunoglobulin heavy chain comprises at least a CDR having a sequence that is at least 80%, 85%, 90%, 91%, 92%, 93%, 94%, 95%, 96%, 97%, 98%, 99%, 99.5% or 100% identical from the group of heavy chain or light chain variable domain CDRs presented in Table 2. In another embodiment, an immunoglobulin light chain comprises at least a CDR having a sequence that is at least 80%, 85%, 90%, 91%, 92%, 93%, 94%, 95%, 96%, 97%, 98%, 99%, 99.5% or 100% identical from the group of light chain or heavy chain variable domain CDRs described herein (e.g., presented in Table 2).

In some embodiments, the immunoglobulin heavy and/or light chain comprises a variable domain comprising at least one of CDR-L1, CDR-L2, CDR-L3, CDR-H1, CDR-H2, or CDR-H3 described herein. Such immunoglobulin heavy chains can comprise or consist of at least one of CDR-H1, CDR-H2, and CDR-H3. Such immunoglobulin light chains can comprise or consist of at least one of CDR-L1, CDR-L2, and CDR-L3.

In other embodiments, an immunoglobulin heavy and/or light chain according to the present invention comprises or consists of a vH or vκ variable domain sequence, respectively, provided in Table 2.

The present invention further provides polypeptides which have a sequence selected from the group consisting of vH variable domain, vκ variable domain, CDR-L1, CDR-L2, CDR-L3, CDR-H1, CDR-H2, and CDR-H3 sequences described herein.

Antibodies, immunoglobulins, and polypeptides of the invention can be use in an isolated (e.g., purified) form or contained in a vector, such as a membrane or lipid vesicle (e.g. a liposome).

TABLE 2

Identification and sequencing of the leader and variable regions of anti-HHLA2 monoclonal antibodies including mAbs 8A12, 6D10, 6F10, 8D2, 2G2, 2C4, 4D1, 1C8, and 4E5

8A12 Heavy Chain Variable (vH) DNA and Amino Acid Sequences*

```
MHC2554HC.1;M13 499.5.8A12.11.10.5
CDR Analysis
GFTFNTNV....___IRTKTNNYAT___VGAMDY
Amino Acid Sequence in FASTA format (MHC2554HC.1\;M13F)
> MHC2554HC.1\;M13F LOCUS  8A12_vH 402 bp DNA linear FEATURES      Location/Qualifiers
J_segment     370..402
              /label = FWR4

V_segment     358..369
              /label = CDR3

V_region      235..357
              /label = FWR3

V_segment     211..234
              /label = CDR2

V_region      154..210
              /label = FWR2

V_segment     133..153
              /label = CDR1

V_region       58..132
              /label = FWR1
```

TABLE 2-continued

Identification and sequencing of the leader and variable regions of anti-HHLA2 monoclonal antibodies including mAbs 8A12, 6D10, 6F10, 8D2, 2G2, 2C4, 4D1, 1C8, and 4E5

```
sig_peptide    1..57
               /label = LS

CDS            1..402
               /label = 8A12_vH

8A12_vH
/translation = "MLLGLKWIFFVVFYQGVHCEVQLVETGGGLVQPKGSLKLSCAASGFTFNTNVMNWV
RQAPGKGLEWVGRIRTKTNNYATYYADSVKGRFTISRDDSQSMLYLQMNNLKTEDTATYFCVGAMDYWGQ
GTSVTVSS" (SEQ ID NO: 19)

Nucleotide Sequence in FASTA format (MHC2554HC.1\;M13F)
> MHC2554HC.1\;M13F. 499.5.8A12.11.10.5
ORIGIN
    1       ATGCTGTTGG GGCTGAAGTG GATTTTCTTT GTTGTTTTTT ATCAAGGTGT GCATTGTGAG

61       GTGCAACTTG TTGAGACTGG TGGAGGATTG GTGCAGCCTA AAGGGTCATT GAAACTCTCA

121       TGTGCAGCCT CTGGATTCAC CTTCAACACC AATGTCATGA ACTGGGTCCG CCAGGCTCCA

181       GGAAAGGGTT TGGAATGGGT TGGTCGCATA AGAACTAAAA CTAATAATTA TGCAACATAT

241       TATGCCGATT CAGTGAAAGG CAGGTTCACC ATCTCCAGAG ATGATTCACA AAGTATGCTC

301       TATCTGCAAA TGAACAACTT GAAAACTGAG GACACAGCCA CGTATTTCTG TGTGGGAGCT

361       ATGGACTACT GGGGTCAAGG AACCTCAGTC ACCGTCTCCT CA (SEQ ID NO: 20)

Signal Peptide (base pairs 1-57):
    1       ATGCTGTTGG GGCTGAAGTG GATTTTCTTT GTTGTTTTTT ATCAAGGTGT GCATTGT          57
            (SEQ ID NO: 21)
/translation = "MLLGLKWIFFVVFYQGVHC" (SEQ ID NO: 22)

Framework 1 (base pairs 58-132):
   58       GAG GTGCAACTTG TTGAGACTGG TGGAGGATTG GTGCAGCCTA AAGGGTCATT
            GAAACTCTCA TGTGCAGCCT CT (SEQ ID NO: 23)                               132
/translation = "EVQLVETGGGLVQPKGSLKLSCAAS" (SEQ ID NO: 24)

CDR-H1 (base pairs 133-153):
  133       GGATTCAC CTTCAACACC AAT (SEQ ID NO: 25)                                153
/translation = "GFTFNTN" (SEQ ID NO: 26)

Framework 2 (base pairs 154-210):
  154       GTCATGA ACTGGGTCCG CCAGGCTCCA GGAAAGGGTT TGGAATGGGT TGGTCGCATA         210
            (SEQ ID NO: 27)
/translation = "VMNWVRQAPGKGLEWVGRI" (SEQ ID NO: 28)

CDR-H2 (base pairs 211-234):
  211       AGAACTAAAA CTAATAATTA TGCA (SEQ ID NO: 29)                             234
/translation = "RTKTNNYA" (SEQ ID NO: 30)

Framework 3 (base pairs 235-357):
  235       ACATAT TATGCCGATT CAGTGAAAGG CAGGTTCACC ATCTCCAGAG ATGATTCACA
            AAGTATGCTC TATCTGCAAA TGAACAACTT GAAAACTGAG GACACAGCCA CGTATTTCTG
            TGTGGGA (SEQ ID NO: 31)                                                357
/translation = "TYYADSVKGRFTISRDDSQSMLYLQMNNLKTEDTATYFCVG" (SEQ ID
NO: 32)

CDR-H3 (base pairs 358-369):
  358       GCT ATGGACTAC (SEQ ID NO: 33)                                          369
/translation = "AMDY" (SEQ ID NO: 34)

Framework 4 (base pairs 370-402):
  370       T GGGGTCAAGG AACCTCAGTC ACCGTCTCCT CA (SEQ ID NO: 35)                  402
/translation = "WGQGTSVTVSS" (SEQ ID NO: 36)
```

MHC2554HC.1 499.5.8A12.11.10.5

| Region | Sequence Fragment | Residues | Length |
|---|---|---|---|
| Leader | MLLGLKWIFFVVFYQGVHC | 1-19 | 19 |
| HFR1 | EVQLVETGGGLVQPKGSLKLSCAAS | 20-44 | 25 |
| CDR-H1 | GFTFNTN | 45-51 | 7 |

TABLE 2-continued

Identification and sequencing of the leader and variable regions of
anti-HHLA2 monoclonal antibodies including mAbs 8A12, 6D10, 6F10, 8D2,
2G2, 2C4, 4D1, 1C8, and 4E5

| | | | |
|---|---|---|---|
| HFR2 | VMNWVRQAPGKGLEWVGRI | 52-70 | 19 |
| CDR-H2 | RTKTNNYA | 71-78 | 8 |
| HFR3 | TYYADSVKGRFTISRDDSQSMLYLQMNNLKTEDTATYFCVG | 79-119 | 41 |
| CDR-H3 | AMDY | 120-123 | 4 |
| HFR4 | WGQGTSVTVSS | 124-134 | 11 |

8A12 Light Chain Variable (vL) DNA and Amino Acid Sequences*

```
MHC2554LC.2;M13. 499.5.8A12.11.10.5
CDR Analysis
ESVDNSGINF..___RAS.......___QQSYKDPPT
Amino Acid Sequence in FASTA format (MHC2554LC.2\;M13F)
> MHC2554LC.2\;M13F LOCUS  8A12_vL  393 bp DNA linear FEATURES        Location/Qualifiers
J_segment       364..393
                /label = FWR4

V_segment       337..363
                /label = CDR3

V_region        241..336
                /label = FWR3

V_segment       220..240
                /label = CDR2

V_region        175..219
                /label = FWR2

V_segment       130..174
                /label = CDR1

V_region         61..129
                /label = FWR1 sig_peptide      1..60
                /label = LS

CDS              1..393
                /label = 8A12_vL

8A12_vL
/translation = "METDTLLLWVLLLWVPGSTGDIVLTQSPASLAVSLGQRATVSCRASESVDNSGINF
IHWYQQKPGQSPKLLLYRASNLKSGIPARFSGSGSRTDFTLTINPVETGDVATYYCQQSYKDPPTFGTGT
KLELK" (SEQ ID NO: 37)

Nucleotide Sequence in FASTA format (MHC2554LC.2\;M13F)
> MHC2554LC.2\;M13F. 499.5.8A12.11.10.5
ORIGIN
    1      ATGGAGACAG ACACACTCCT GCTATGGGTG CTGCTGCTCT GGGTTCCAGG TTCCACAGGT

61      GACATTGTGC TGACCCAATC TCCAGCTTCT TTGGCTGTGT CTCTGGGGCA GAGGGCCACC

121      GTCTCCTGCA GAGCCAGCGA AAGTGTTGAT AATTCTGGCA TAAATTTTAT ACACTGGTAC

181      CAGCAGAAAC CAGGACAGTC ACCCAAACTC CTCCTCTATC GTGCATCCAA CCTAAAATCT

241      GGGATCCCTG CCAGGTTCAG TGGCAGTGGG TCTAGGACAG ACTTCACCCT CACCATTAAT

301      CCTGTGGAGA CTGGTGATGT TGCAACCTAT TACTGTCAGC AAAGTTATAA GGATCCTCCT

361      ACGTTCGGTA CTGGGACCAA GCTGGAGCTG AAG (SEQ ID NO: 38)

Signal Peptide (base pairs 1-60):
    1      ATGGAGACAG ACACACTCCT GCTATGGGTG CTGCTGCTCT GGGTTCCAGG TTCCACAGGT      60
           (SEQ ID NO: 39)
/translation = "METDTLLLWVLLLWVPGSTG" (SEQ ID NO: 40)
```

TABLE 2-continued

Identification and sequencing of the leader and variable regions of anti-HHLA2 monoclonal antibodies including mAbs 8A12, 6D10, 6F10, 8D2, 2G2, 2C4, 4D1, 1C8, and 4E5

```
Framework 1 (base pairs 61-129):
 61       GACATTGTGC TGACCCAATC TCCAGCTTCT TTGGCTGTGT CTCTGGGGCA GAGGGCCACC
          GTCTCCTGC (SEQ ID NO: 41)                                              129
/translation = "DIVLTQSPASLAVSLGQRATVSC" (SEQ ID NO: 42)

CDR-L1 (base pairs 130-174):
130       A GAGCCAGCGA AAGTGTTGAT AATTCTGGCA TAAATTTTAT ACAC (SEQ ID NO: 43)     174
/translation = "RASESVDNSGINFIH" (SEQ ID NO: 44)

Framework 2 (base pairs 175-219):
175       TGGTAC CAGCAGAAAC CAGGACAGTC ACCCAAACTC CTCCTCTAT (SEQ ID NO: 45)     219
/translation = "WYQQKPGQSPKLLLY" (SEQ ID NO: 46)

CDR-L2 (base pairs 220-240):
220       C GTGCATCCAA CCTAAAATCT (SEQ ID NO: 47)                               240
/translation = "RASNLKS" (SEQ ID NO: 48)

Framework 3 (base pairs 241-336):
241       GGGATCCCTG CCAGGTTCAG TGGCAGTGGG TCTAGGACAG ACTTCACCCT CACCATTAAT
          CCTGTGGAGA CTGGTGATGT TGCAACCTAT TACTGT (SEQ ID NO: 49)                336
/translation = "GIPARFSGSGSRTDFTLTINPVETGDVATYYC" (SEQ ID NO: 50)

CDR-L3 (base pairs 337-363):
337       CAGC AAAGTTATAA GGATCCTCCT ACG (SEQ ID NO: 51)                        363
/translation = "QQSYKDPPT" (SEQ ID NO: 52)

Framework 4 (base pairs 364-393):
364       TTCGGTA CTGGGACCAA GCTGGAGCTG AAG (SEQ ID NO: 53)                     393
/translation = "FGTGTKLELK" (SEQ ID NO: 54)
```

MHC2554LC.2. 499.5.8A12.11.10.5

| Region  | Sequence Fragment                  | Residues | Length |
|---------|------------------------------------|----------|--------|
| Leader  | METDTLLLWVLLLWVPGSTG               | 1-20     | 20     |
| LFR1    | DIVLTQSPASLAVSLGQRATVSC            | 21-43    | 23     |
| CDR-L1  | RASESVDNSGINFIH                    | 44-58    | 15     |
| LFR2    | WYQQKPGQSPKLLLY                    | 59-73    | 15     |
| CDR-L2  | RASNLKS                            | 74-80    | 7      |
| LFR3    | GIPARFSGSGSRTDFTLTINPVETGDVATYYC   | 81-112   | 32     |
| CDR-L3  | QQSYKDPPT                          | 113-121  | 9      |
| LFR4    | FGTGTKLELK                         | 122-131  | 10     |

6D10 Heavy Chain Variable (vH) DNA and Amino Acid Sequences*

```
MHC2555HC.1;M13. 499.5.6D10.11.11.7
CDR Analysis
GFTFNTNV....___IRTKTNNYAT___VGAMDY
Amino Acid Sequence in FASTA format (MHC2555HC.1\;M13F)
> MHC2555HC.1\;M13F 499.5.6D10.11.11.7

LOCUS 6D10_vH 402 bp DNA linear

FEATURES        Location/Qualifiers
J_segment       370..402
                /label = FWR4

V_segment       358..369
                /label = CDR3

V_region        235..357
                /label = FWR3

V_segment       211..234
                /label = CDR2

V_region        154..210
                /label = FWR2
```

TABLE 2-continued

Identification and sequencing of the leader and variable regions of anti-HHLA2 monoclonal antibodies including mAbs 8A12, 6D10, 6F10, 8D2, 2G2, 2C4, 4D1, 1C8, and 4E5

```
V_segment    133..153
             /label = CDR1

V_region     58..132
             /label = FWR1 sig_peptide  1..57
             /label = LS

CDS          1..402
             /label = 6D10_vH
```

6D10_vH
/translation = "MLLGLKWIFFVVFYQGVHCEVQLVETGGGLVQPKGSLKLSCAASGFTFNTNVMNWV
RQAPGKGLEWVARIRTKTNNYATYYADSVKDRFTIFRDDSQSILYLQMNNLKTEDTAMYYCVGAMDYWGQ
GTSVTVSS" (SEQ ID NO: 55)

Nucleotide Sequence in FASTA format (MHC2555HC.1\;M13F)
> MHC2555HC.1\;M13F. 499.5.6D10.11.11.7
ORIGIN

```
   1    ATGCTGTTGG GGCTGAAGTG GATTTTCTTT GTTGTTTTTT ATCAAGGTGT GCATTGTGAG

61    GTGCAGCTTG TTGAGACTGG TGGAGGATTG GTGCAGCCTA AGGGTCATT GAAACTCTCA

121    TGTGCAGCCT CTGGATTCAC CTTCAATACC AATGTCATGA ACTGGGTCCG CCAGGCTCCA

181    GGAAAGGGTT TGGAATGGGT TGCTCGCATA AGAACTAAAA CTAATAATTA TGCAACATAT

241    TATGCCGATT CAGTGAAAGA CAGGTTCACC ATCTTCAGAG ATGATTCACA AAGCATTCTC

301    TATCTGCAAA TGAACAACTT GAAAACTGAG GACACAGCCA TGTATTACTG TGTGGGAGCT

361    ATGGACTACT GGGGTCAAGG AACCTCAGTC ACCGTCTCCT CA(SEQ ID NO: 56)
```

Signal Peptide (base pairs 1-57):
```
   1    ATGCTGTTGG GGCTGAAGTG GATTTTCTTT GTTGTTTTTT ATCAAGGTGT GCATTGT    57
        (SEQ ID NO: 57)
```
/translation = "MLLGLKWIFFVVFYQGVHC" (SEQ ID NO: 58)

Framework 1 (base pairs 58-132):
```
  58    GAG GTGCAGCTTG TTGAGACTGG TGGAGGATTG GTGCAGCCTA AGGGTCATT
        GAAACTCTCA TGTGCAGCCT CT (SEQ ID NO: 59)                           132
```
/translation = "EVQLVETGGGLVQPKGSLKLSCAAS" (SEQ ID NO: 60)

CDR-H1 (base pairs 133-153):
```
 133    GGATTCAC CTTCAATACC AAT (SEQ ID NO: 61)                           153
```
/translation = "GFTFNTN" (SEQ ID NO: 62)

Framework 2 (base pairs 154-210):
```
 154    GTCATGA ACTGGGTCCG CCAGGCTCCA GGAAAGGGTT TGGAATGGGT TGCTCGCATA     210
        (SEQ ID NO: 63)
```
/translation = "VMNWVRQAPGKGLEWVARI" (SEQ ID NO: 64)

CDR-H2 (base pairs 211-234):
```
 211    AGAACTAAAA CTAATAATTA TGCA (SEQ ID NO: 65)                        234
```
/translation = "RTKTNNYA" (SEQ ID NO: 66)

Framework 3 (base pairs 235-357):
```
 235    ACATAT TATGCCGATT CAGTGAAAGA CAGGTTCACC ATCTTCAGAG ATGATTCACA
        AAGCATTCTC TATCTGCAAA TGAACAACTT GAAAACTGAG GACACAGCCA TGTATTACTG
        TGTGGGA (SEQ ID NO: 67)                                           357
```
/translation = "TYYADSVKDRFTIFRDDSQSILYLQMNNLKTEDTAMYYCVG" (SEQ ID NO: 68)

CDR-H3 (base pairs 358-369):
```
 358    GCT ATGGACTAC (SEQ ID NO: 69)                                     369
```
/translation = "AMDY" (SEQ ID NO: 70)

Framework 4 (base pairs 370-402):
```
 370    T GGGGTCAAGG AACCTCAGTC ACCGTCTCCT CA (SEQ ID NO: 71)              402
```
/translation = "WGQGTSVTVSS" (SEQ ID NO: 72)

MHC2555HC.1;M13. 499.5.6D10.11.11.7

TABLE 2-continued

Identification and sequencing of the leader and variable regions of anti-HHLA2 monoclonal antibodies including mAbs 8A12, 6D10, 6F10, 8D2, 2G2, 2C4, 4D1, 1C8, and 4E5

| Region | Sequence Fragment | Residues | Length |
|---|---|---|---|
| Leader | MLLGLKWIFFVVFYQGVHC | 1-19 | 19 |
| HFR1 | EVQLVETGGGLVQPKGSLKLSCAAS | 20-44 | 25 |
| CDR-H1 | GFTFNTN | 45-51 | 7 |
| HFR2 | VMNWVRQAPGKGLEWVARI | 52-70 | 19 |
| CDR-H2 | RTKTNNYA | 71-78 | 8 |
| HFR3 | TYYADSVKDRFTIFRDDSQSILYLQMNNLKTEDTAMYYCVG | 79-119 | 41 |
| CDR-H3 | AMDY | 120-123 | 4 |
| HFR4 | WGQGTSVTVSS | 124-134 | 11 |

6D10 Light Chain Variable (vL) DNA and Amino Acid Sequences*

MHC2555LC.1;M13. 499.5.6D10.11.11.7
CDR Analysis
ESVDNYGISF.. ___RAS....... ___QQSSKDPPT
Amino Acid Sequence in FASTA format (MHC2555LC.1\;M13F)
> MHC2555LC.1\;M13F. 499.5.6D10.11.11.7

```
LOCUS    6D10_vL 393 bp DNA linear

FEATURES       Location/Qualifiers
J_segment      364..393
               /label = FWR4

V_segment      337..363
               /label = CDR3

V_region       241..336
               /label = FWR3

V_segment      220..240
               /label = CDR2

V_region       175..219
               /label = FWR2

V_segment      130..174
               /label = CDR1

V_region        61..129
               /label = FWR1 sig_peptide     1..60
               /label = LS

CDS             1..393
               /label = 6D10_vL

6D10_vL
/translation =
"METDTLLLWVLLLWVPGSTGDIVLTQSPASLAVSLGQRATISCRASESVDNYGISFMHWYQQKPGQPPKL
LIYRASNLKSGIPARFSGSGSRTDFTLTINPVETGDVATYYCQQSSKDPPTFGTGTKLELK" (SEQ ID
NO: 73)
```

Nucleotide Sequence in FASTA format (MHC2555LC.1\;M13F)
>MHC2555LC.1\;M13F. 499.5.6D10.11.11.7
ORIGIN

```
  1    ATGGAGACAG ACACACTCCT GCTATGGGTG CTGCTGCTCT GGGTTCCAGG TTCCACAGGT
 61    GACATTGTGC TGACCCAATC TCCAGCTTCT TTGGCTGTGT CTCTAGGGCA GAGGGCCACC
121    ATCTCCTGCA GAGCCAGCGA GAGTGTTGAT AATTATGGCA TTAGTTTTAT GCACTGGTAC
181    CAGCAGAAAC CAGGACAGCC ACCCAAACTC CTCATCTATC GTGCATCCAA CCTAAAATCT
241    GGGATCCCTG CCAGGTTCAG TGGCAGTGGG TCTAGGACAG ACTTCACCCT CACCATTAAT
301    CCTGTGGAGA CTGGTGATGT TGCTACCTAT TACTGTCAGC AAAGTAGTAA GGATCCTCCT
```

TABLE 2-continued

Identification and sequencing of the leader and variable regions of
anti-HHLA2 monoclonal antibodies including mAbs 8A12, 6D10, 6F10, 8D2,
2G2, 2C4, 4D1, 1C8, and 4E5

```
361        ACGTTCGGTA CTGGGACCAA GCTAGAGCTG AAA (SEQ ID NO: 74)

Signal Peptide (base pairs 1-60):
  1        ATGGAGACAG ACACACTCCT GCTATGGGTG CTGCTGCTCT GGGTTCCAGG TTCCACAGGT    60
           (SEQ ID NO: 75)
/translation = "METDTLLLWVLLLWVPGSTG" (SEQ ID NO: 76)

Framework 1 (base pairs 61-129):
 61        GACATTGTGC TGACCCAATC TCCAGCTTCT TTGGCTGTGT CTCTAGGGCA GAGGGCCACC
           ATCTCCTGC (SEQ ID NO: 77)                                            129
/translation = "DIVLTQSPASLAVSLGQRATISC" (SEQ ID NO: 78)

CDR-L1 (base pairs 130-174):
130        A GAGCCAGCGA GAGTGTTGAT AATTATGGCA TTAGTTTTAT GCAC (SEQ ID NO: 79)  174
/translation = "RASESVDNYGISFMH" (SEQ ID NO: 80)

Framework 2 (base pairs 175-219):
175        TGGTAC CAGCAGAAAC CAGGACAGCC ACCCAAACTC CTCATCTAT (SEQ ID NO: 81)   219
/translation = "WYQQKPGQPPKLLIY" (SEQ ID NO: 82)

CDR-L2 (base pairs 220-240):
220        C GTGCATCCAA CCTAAAATCT (SEQ ID NO: 83)                             240
/translation = "RASNLKS" (SEQ ID NO: 84)

Framework 3 (base pairs 241-336):
241        GGGATCCCTG CCAGGTTCAG TGGCAGTGGG TCTAGGACAG ACTTCACCCT CACCATTAAT
           CCTGTGGAGA CTGGTGATGT TGCTACCTAT TACTGT (SEQ ID NO: 85)              336
/translation = "GIPARFSGSGSRTDFTLTINPVETGDVATYYC" (SEQ ID NO: 86)

CDR-L3 (base pairs 337-363):
337        CAGC AAAGTAGTAA GGATCCTCCT ACG (SEQ ID NO: 87)                      363
/translation = "QQSSKDPPT" (SEQ ID NO: 88)

Framework 4 (base pairs 364-393):
364        TTCGGTA CTGGGACCAA GCTAGAGCTG AAA (SEQ ID NO: 89)                   393
/translation = "FGTGTKLELK" (SEQ ID NO: 90)
```

MHC2555LC.1 499.5.6D10.11.11.7

| Region | Sequence Fragment | Residues | Length |
|---|---|---|---|
| Leader | METDTLLLWVLLLWVPGSTG | 1-20 | 20 |
| LFR1 | DIVLTQSPASLAVSLGQRATISC | 21-43 | 23 |
| CDR-L1 | RASESVDNYGISFMH | 44-58 | 15 |
| LFR2 | WYQQKPGQPPKLLIY | 59-73 | 15 |
| CDR-L2 | RASNLKS | 74-80 | 7 |
| LFR3 | GIPARFSGSGSRTDFTLTINPVETGDVATYYC | 81-112 | 32 |
| CDR-L3 | QQSSKDPPT | 113-121 | 9 |
| LFR4 | FGTGTKLELK | 122-131 | 10 |

6F10 Heavy Chain Variable (vH) DNA and Amino Acid Sequences*

```
MHC2557HCO.1;M13. 499.5.6F10.A4.10
CDR Analysis
GYTFTTYT....___INPSSGYT..___ARHPWDSDY
Amino Acid Sequence in FASTA format (MHC2557HCO.1\;M13F)
> MHC2557HCO.1\;M13F. 499.5.6F10.A4.10

LOCUS 6F10_vH 405 bp DNA linear

FEATURES    Location/Qualifiers
J_segment   373..405
            /label = FWR4

V_segment   352..372
            /label = CDR3
```

TABLE 2-continued

Identification and sequencing of the leader and variable regions of
anti-HHLA2 monoclonal antibodies including mAbs 8A12, 6D10, 6F10, 8D2,
2G2, 2C4, 4D1, 1C8, and 4E5

```
V_region        229..351
                /label = FWR3

V_segment       211..228
                /label = CDR2

V_region        154..210
                /label = FWR2

V_segment       133..153
                /label = CDR1

V_region        58..132
                /label = FWR1 sig_peptide     1..57
                /label = LS

CDS             1..405
                /label = 6F10_vH
```

6F10_vH
/translation = "MERHWIFLFLLSVTAGVHSQVHLQQSAAELARPGASVKMSCKAS<u>GYTFTTYTMHWV</u>
KQRPGQGLEWIGHI<u>NPSSGY</u>TDYNQKFKDKTTLTADKSSSTAYMQLNSLTSEDSAVYYCAR<u>HPWDSDY</u>WG
QGTTLTVSS" (SEQ ID NO: 91)

Nucleotide Sequence in FASTA format (MHC2557HC0.1\;M13F)
>MHC2557HC0.1\;M13F. 499.5.6F10.A4.10
ORIGIN
```
  1     ATGGAAAGGC ACTGGATCTT TCTCTTCCTG TTGTCAGTAA CTGCAGGTGT CCACTCCCAG

61     GTCCACCTGC AGCAGTCTGC AGCTGAACTG GCAAGACCTG GGGCCTCAGT GAAGATGTCC

121     TGCAAGGCTT CTGGCTACAC CTTTACTACC TACACGATGC ACTGGGTAAA ACAGAGGCCT

181     GGACAGGGTC TGGAATGGAT TGGACACATT AATCCTAGCA GTGGATATAC TGATTACAAT

241     CAGAAATTCA AGGACAAGAC CACATTGACT GCAGACAAAT CCTCCAGTAC AGCCTACATG

301     CAACTGAACA GCCTGACATC TGAGGACTCT GCGGTCTATT ACTGTGCAAG ACACCCCTGG

361     GACTCGGACT ACTGGGGCCA AGGCACCACT CTCACAGTCT CCTCA (SEQ ID NO: 92)
```

Signal Peptide (base pairs 1-57):
```
  1     ATGGAAAGGC ACTGGATCTT TCTCTTCCTG TTGTCAGTAA CTGCAGGTGT CCACTCC              57
        (SEQ ID NO: 93)
```
/translation = "MERHWIFLFLLSVTAGVHS" (SEQ ID NO: 94)

Framework 1 (base pairs 58-132):
```
 58     CAG GTCCACCTGC AGCAGTCTGC AGCTGAACTG GCAAGACCTG GGGCCTCAGT
        GAAGATGTCC TGCAAGGCTT CT (SEQ ID NO: 95)                                  132
```
/translation = "QVHLQQSAAELARPGASVKMSCKAS" (SEQ ID NO: 96)

CDR-H1 (base pairs 133-153):
```
133     GGCTACAC CTTTACTACC TAC (SEQ ID NO: 97)                                   153
```
/translation = "GYTFTTY" (SEQ ID NO: 98)

Framework 2 (base pairs 154-210):
```
154     ACGATGC ACTGGGTAAA ACAGAGGCCT
181     GGACAGGGTC TGGAATGGAT TGGACACATT (SEQ ID NO: 99)                          210
```
/translation = "TMHWVKQRPGQGLEWIGHI" (SEQ ID NO: 100)

CDR-H2 (base pairs 211-228):
```
211     AATCCTAGCA GTGGATAT (SEQ ID NO: 101)                                     228
```
/translation = "NPSSGY" (SEQ ID NO: 102)

Framework 3 (base pairs 229-351):
```
229     AC TGATTACAAT CAGAAATTCA AGGACAAGAC CACATTGACT GCAGACAAAT
        CCTCCAGTAC AGCCTACATG CAACTGAACA GCCTGACATC TGAGGACTCT GCGGTCTATT
        ACTGTGCAAG A (SEQ ID NO: 103)                                            351
```
/translation = "TDYNQKFKDKTTLTADKSSSTAYMQLNSLTSEDSAVYYCAR" (SEQ
ID NO: 104)

TABLE 2-continued

Identification and sequencing of the leader and variable regions of anti-HHLA2 monoclonal antibodies including mAbs 8A12, 6D10, 6F10, 8D2, 2G2, 2C4, 4D1, 1C8, and 4E5

```
CDR-H3 (base pairs 352-372):
352         CACCCCTGG GACTCGGACT AC (SEQ ID NO: 105)                     372
/translation = "HPWDSDY" (SEQ ID NO: 106)

Framework 4 (base pairs 373-405):
373         TGGGGCCA AGGCACCACT CTCACAGTCT CCTCA (SEQ ID NO: 107)        405
/translation = "WGQGTTLTVSS" (SEQ ID NO: 108)

MHC2557HCO.1 499.5.6F10.A4.10
```

| Region | Sequence Fragment | Residues | Length |
| --- | --- | --- | --- |
| Leader | MERHWIFLFLLSVTAGVHS | 1-19 | 19 |
| HFR1 | QVHLQQSAAELARPGASVKMSCKAS | 20-44 | 25 |
| CDR-H1 | GYTFTTY | 45-51 | 7 |
| HFR2 | TMHWVKQRPGQGLEWIGHI | 52-70 | 19 |
| CDR-H2 | NPSSGY | 71-76 | 6 |
| HFR3 | TDYNQKFKDKTTLTADKSSSTAYMQLNSLTSEDSAVYYCAR | 77-117 | 41 |
| CDR-H3 | HPWDSDY | 118-124 | 7 |
| HFR4 | WGQGTTLTVSS | 125-135 | 11 |

6F10 Light Chain Variable (vL) DNA and Amino Acid Sequences*

```
MHC2557LC.1;M13.
CDR Analysis
ENIDSY......___AAT.......___QHYYITPFT
Amino Acid Sequence in FASTA format (MHC2557LC.1\;M13F)
>MHC2557LC.1\;M13F. 499.5.6F10.A4.10

LOCUS 6F10_vL 381 bp DNA linear

FEATURES     Location/Qualifiers
J_segment    352..381
             /label = FWR4

V_segment    325..351
             /label = CDR3

V_region     229..324
             /label = FWR3

V_segment    208..228
             /label = CDR2

V_region     163..207
             /label = FWR2

V_segment    130..162
             /label = CDR1

V_region      61..129
             /label = FWR1 sig_peptide   1..60
             /label = LS

CDS           1..381
             /label = 6F10_vL

6F10_vL
/translation = "MSVPTQLLGLLLLWLTDARCDIQMTQSPASLSASVGETVTITCRASENIDSYLAWY
QQKQGRSPQLLVYAATNLADGVPSRFGSGSGTQFSLQINRLQSEDVARYYCQHYYITPFTFGSGTKLEI
A" (SEQ ID NO: 109)
```

TABLE 2-continued

Identification and sequencing of the leader and variable regions of
anti-HHLA2 monoclonal antibodies including mAbs 8A12, 6D10, 6F10, 8D2,
2G2, 2C4, 4D1, 1C8, and 4E5

```
Nucleotide Sequence in FASTA format (MHC2557LC.1\;M13F)
>MHC2557LC.1\;M13F. 499.5.6F10.A4.10
ORIGIN
    1       ATGAGTGTGC CCACTCAGCT CCTGGGGTTG CTGCTGCTGT GGCTTACAGA TGCCAGATGT

61       GACATCCAGA TGACTCAGTC TCCAGCTTCC CTGTCTGCAT CTGTGGGAGA AACTGTCACC

121       ATCACATGTC GAGCAAGTGA GAATATTGAC AGTTATTTAG CATGGTATCA GCAGAAACAG

181       GGAAGATCTC CTCAGCTCCT GGTCTATGCT GCAACAAACT TAGCAGATGG TGTGCCATCA

241       AGGTTCAGTG GCAGTGGATC AGGCACACAG TTTTCTCTCC AGATCAACCG CCTGCAGTCT

301       GAAGATGTTG CGAGATATTA CTGTCAACAT TATTATATTA CTCCATTCAC GTTCGGCTCG

361       GGGACAAAAT TGGAAATAGC A (SEQ ID NO: 110)

Signal Peptide (base pairs 1-60):
    1       ATGAGTGTGC CCACTCAGCT CCTGGGGTTG CTGCTGCTGT GGCTTACAGA TGCCAGATGT        60
            (SEQ ID NO: 111)
/translation = "MSVPTQLLGLLLLWLTDARC" (SEQ ID NO: 112)

Framework 1 (base pairs 61-129):
   61       GACATCCAGA TGACTCAGTC TCCAGCTTCC CTGTCTGCAT CTGTGGGAGA AACTGTCACC
            ATCACATGT (SEQ ID NO: 113)                                            129
/translation = "DIQMTQSPASLSASVGETVTITC" (SEQ ID NO: 114)

CDR-L1 (base pairs 130-162):
  130       C GAGCAAGTGA GAATATTGAC AGTTATTTAG CA (SEQ ID NO: 115)                162
/translation = "RASENIDSYLA" (SEQ ID NO: 116)

Framework 2 (base pairs 163-207):
  163       TGGTATCA GCAGAAACAG GGAAGATCTC CTCAGCTCCT GGTCTAT (SEQ ID NO: 117)    207
/translation = "WYQQKQGRSPQLLVY" (SEQ ID NO: 118)

CDR-L2 (base pairs 208-228):
  208       GCT GCAACAAACT TAGCAGAT (SEQ ID NO: 119)                              228
/translation = "AATNLAD" (SEQ ID NO: 120)

Framework 3 (base pairs 229-324):
  229       GG TGTGCCATCA AGGTTCAGTG GCAGTGGATC AGGCACACAG TTTTCTCTCC
            AGATCAACCG CCTGCAGTCT GAAGATGTTG CGAGATATTA CTGT (SEQ ID NO: 121)     324
/translation = "GVPSRFSGSGSGTQFSLQINRLQSEDVARYYC" (SEQ ID NO: 122)

CDR-L3 (base pairs 325-351):
  325       CAACAT TATTATATTA CTCCATTCAC G (SEQ ID NO: 123)                       351
/translation = "QHYYITPFT" (SEQ ID NO: 124)

Framework 4 (base pairs 352-381):
  352       TTCGGCTCG GGGACAAAAT TGGAAATAGC A (SEQ ID NO: 125)                    381
/translation = "FGSGTKLEIA" (SEQ ID NO: 126)
```

MHC2557LC.1 499.5.6F10.A4.10

| Region | Sequence Fragment | Residues | Length |
|---|---|---|---|
| Leader | MSVPTQLLGLLLLWLTDARC | 1-20 | 20 |
| LFR1 | DIQMTQSPASLSASVGETVTITC | 21-43 | 23 |
| CDR-L1 | RASENIDSYLA | 44-54 | 11 |
| LFR2 | WYQQKQGRSPQLLVY | 55-69 | 15 |
| CDR-L2 | AATNLAD | 70-76 | 7 |
| LFR3 | GVPSRFSGSGSGTQFSLQINRLQSEDVARYYC | 77-108 | 32 |
| CDR-L3 | QHYYITPFT | 109-117 | 9 |
| LFR4 | FGSGTKLEIA | 118-127 | 10 |

TABLE 2-continued

Identification and sequencing of the leader and variable regions of anti-HHLA2 monoclonal antibodies including mAbs 8A12, 6D10, 6F10, 8D2, 2G2, 2C4, 4D1, 1C8, and 4E5

8D2 Heavy Chain Variable (vH) DNA and Amino Acid Sequences*

MHC2558HC.1;M13. 499.8D2.6.8
CDR Analysis
GFTFNTNV....___IRTKTNNYAT___VGAMDY
Amino Acid Sequence in FASTA format (MHC2558HC.1\;M13F)
> MHC2558HC.1\;M13F. 499.8D2.6.8

LOCUS 8D2_vH 402 bp DNA linear

```
FEATURES         Location/Qualifiers
J_segment        370..402
                 /label = FWR4

V_segment        358..369
                 /label = CDR3

V_region         235..357
                 /label = FWR3

V_segment        211..234
                 /label = CDR2

V_region         154..210
                 /label = FWR2

V_segment        133..153
                 /label = CDR1

V_region         58..132
                 /label = FWR1 sig_peptide      1..57
                 /label = LS

CDS              1..402
                 /label = 8D2_vH
```

8D2_vH
/translation = "MLLGLKWIFFVVFYQGVHCEVQLVETGGGLVQPKGSLKLSCAASGFTFNTNVMNWV
RQAPGKGLEWVGRIRTKTNNYATYYADSVKGRFTISRDDSQSMLYLQMNNLKTEDTATYFCVGAMDYWGQ
GTSVTVSS" (SEQ ID NO: 127)

Nucleotide Sequence in FASTA format (MHC2558HC.1\;M13F)
> MHC2558HC.1\;M13F. 499.8D2.6.8
ORIGIN
  1    ATGCTGTTGG GGCTGAAGTG GATTTTCTTT GTTGTTTTTT ATCAAGGTGT GCATTGTGAG

61    GTGCAACTTG TTGAGACTGG TGGAGGATTG GTGCAGCCTA AAGGGTCATT GAAACTCTCA

121    TGTGCAGCCT CTGGATTCAC CTTCAACACC AATGTCATGA ACTGGGTCCG CCAGGCTCCA

181    GGAAAGGGTT TGGAATGGGT TGGTCGCATA AGAACTAAAA CTAATAATTA TGCAACATAT

241    TATGCCGATT CAGTGAAAGG CAGGTTCACC ATCTCCAGAG ATGATTCACA AAGTATGCTC

301    TATCTGCAAA TGAACAACTT GAAAACTGAG GACACAGCCA CGTATTTCTG TGTGGGAGCT

361    ATGGACTACT GGGGTCAAGG AACCTCAGTC ACCGTCTCCT CA (SEQ ID NO: 128)

Signal Peptide (base pairs 1-57):
  1    ATGCTGTTGG GGCTGAAGTG GATTTTCTTT GTTGTTTTTT ATCAAGGTGT GCATTGT        57
       (SEQ ID NO: 129)
/translation = "MLLGLKWIFFVVFYQGVHC" (SEQ ID NO: 130)

Framework 1 (base pairs 58-132):
 58    GAG GTGCAACTTG TTGAGACTGG TGGAGGATTG GTGCAGCCTA AAGGGTCATT
       GAAACTCTCA TGTGCAGCCT CT (SEQ ID NO: 131)                            132
/translation = "EVQLVETGGGLVQPKGSLKLSCAAS" (SEQ ID NO: 132)

CDR-H1 (base pairs 133-153):
133           GGATTCAC CTTCAACACC AAT (SEQ ID NO: 133)                      153
/translation = "GFTFNTN" (SEQ ID NO: 134)

TABLE 2-continued

Identification and sequencing of the leader and variable regions of anti-HHLA2 monoclonal antibodies including mAbs 8A12, 6D10, 6F10, 8D2, 2G2, 2C4, 4D1, 1C8, and 4E5

```
Framework 2 (base pairs 154-210):
154     GTCATGA ACTGGGTCCG CCAGGCTCCA GGAAAGGGTT TGGAATGGGT TGGTCGCATA       210
        (SEQ ID NO: 135)
/translation = "VMNWVRQAPGKGLEWVGRI" (SEQ ID NO: 136)

CDR-H2 (base pairs 211-234):
211     AGAACTAAAA CTAATAATTA TGCA (SEQ ID NO: 137)                          234
/translation = "RTKTNNYA" (SEQ ID NO: 138)

Framework 3 (base pairs 235-357):
235     ACATAT TATGCCGATT CAGTGAAAGG CAGGTTCACC ATCTCCAGAG ATGATTCACA
        AAGTATGCTC TATCTGCAAA TGAACAACTT GAAAACTGAG GACACAGCCA CGTATTTCTG
        TGTGGGA (SEQ ID NO: 139)                                              357
/translation = "TYYADSVKGRFTISRDDSQSMLYLQMNNLKTEDTATYFCVG" (SEQ ID
NO: 140)

CDR-H3 (base pairs 358-369):
358     GCT ATGGACTAC (SEQ ID NO: 141)                                       369
/translation = "AMDY" (SEQ ID NO: 142)

Framework 4 (base pairs 370-402):
370     T GGGGTCAAGG AACCTCAGTC ACCGTCTCCT CA (SEQ ID NO: 143)                402
/translation = "WGQGTSVTVSS" (SEQ ID NO: 144)
```

MHC2558HC.1 499.8D2.6.8

| Region | Sequence Fragment | Residues | Length |
|---|---|---|---|
| Leader | MLLGLKWIFFVVFYQGVHC | 1-19 | 19 |
| HFR1 | EVQLVETGGGLVQPKGSLKLSCAAS | 20-44 | 25 |
| CDR-H1 | GFTFNTN | 45-51 | 7 |
| HFR2 | VMNWVRQAPGKGLEWVGRI | 52-70 | 19 |
| CDR-H2 | RTKTNNYA | 71-78 | 8 |
| HFR3 | TYYADSVKGRFTISRDDSQSMLYLQMNNLKTEDTATYFCVG | 79-119 | 41 |
| CDR-H3 | AMDY | 120-123 | 4 |
| HFR4 | WGQGTSVTVSS | 124-134 | 11 |

8D2 Light Chain Variable (vL) DNA and Amino Acid Sequences*

```
MHC2558LC.2;M13. 499.8D2.6.8
CDR Analysis
ESVDNSGINF..___RAS.......___QQSYKDPPT
Amino Acid Sequence in FASTA format (MHC2558LC.2\;M13F)
> MHC2558LC.2\;M13F. 499.8D2.6.8

LOCUS       8D2_vL      393 bp     DNA     linear

FEATURES        Location/Qualifiers
J_segment       364..393
                /label = FWR4

V_segment       337..363
                /label = CDR3

V_region        241..336
                /label = FWR3

V_segment       220..240
                /label = CDR2

V_region        175..219
                /label = FWR2

V_segment       130..174
                /label = CDR1

V_region         61..129
                /label = FWR1
```

TABLE 2-continued

Identification and sequencing of the leader and variable regions of anti-HHLA2 monoclonal antibodies including mAbs 8A12, 6D10, 6F10, 8D2, 2G2, 2C4, 4D1, 1C8, and 4E5

```
sig_peptide     1..60
                /label = LS

CDS             1..393
                /label = 8D2_vL

8D2_vL
/translation = "METDTLLLWVLLLWVPGSTGDIVLTQSPASLAVSLGQRATVSCRASESVDNSGINF
IHWYQQKPGQSPKLLLYRASNLKSGIPARFSGSGSRTDFTLTINPVETGDVATYYCQQSYKDPPTFGTGT
KLELK" (SEQ ID NO: 145)

Nucleotide Sequence in FASTA format (MHC2558LC.2\;M13F)
> MHC2558LC.2\;M13F. 499.8D2.6.8
ORIGIN
    1       ATGGAGACAG ACACACTCCT GCTATGGGTG CTGCTGCTCT GGGTTCCAGG TTCCACAGGT

61       GACATTGTGC TGACCCAATC TCCAGCTTCT TTGGCTGTGT CTCTGGGGCA GAGGGCCACC

121       GTCTCCTGCA GAGCCAGCGA AAGTGTTGAT AATTCTGGCA TAAATTTTAT ACACTGGTAC

181       CAGCAGAAAC CAGGACAGTC ACCCAAACTC CTCCTCTATC GTGCATCCAA CCTAAAATCT

241       GGGATCCCTG CCAGGTTCAG TGGCAGTGGG TCTAGGACAG ACTTCACCCT CACCATTAAT

301       CCTGTGGAGA CTGGTGATGT TGCAACCTAT TACTGTCAGC AAAGTTATAA GGATCCTCCT

361       ACGTTCGGTA CTGGGACCAA GCTGGAGCTG AAG (SEQ ID NO: 146)
```

Signal Peptide (base pairs 1-60):
```
    1       ATGGAGACAG ACACACTCCT GCTATGGGTG CTGCTGCTCT GGGTTCCAGG TTCCACAGGT    60
            (SEQ ID NO: 147)
```
/translation = "METDTLLLWVLLLWVPGSTG" (SEQ ID NO: 148)

Framework 1 (base pairs 61-129):
```
   61       GACATTGTGC TGACCCAATC TCCAGCTTCT TTGGCTGTGT CTCTGGGGCA GAGGGCCACC
            GTCTCCTGC (SEQ ID NO: 149)                                            129
```
/translation = "DIVLTQSPASLAVSLGQRATVSC" (SEQ ID NO: 150)

CDR-L1 (base pairs 130-174):
```
  130       A GAGCCAGCGA AAGTGTTGAT AATTCTGGCA TAAATTTTAT ACAC (SEQ ID NO: 151)   174
```
/translation = "RASESVDNSGINFIH" (SEQ ID NO: 152)

Framework 2 (base pairs 175-219):
```
  175       CTGGTAC CAGCAGAAAC CAGGACAGTC ACCCAAACTC CTCCTCTAT (SEQ ID NO: 153)  219
```
/translation = "WYQQKPGQSPKLLLY" (SEQ ID NO: 154)

CDR-L2 (base pairs 220-240):
```
  220       C GTGCATCCAA CCTAAAATCT (SEQ ID NO: 155)                             240
```
/translation = "RASNLKS" (SEQ ID NO: 156)

Framework 3 (base pairs 241-336):
```
  241       GGGATCCCTG CCAGGTTCAG TGGCAGTGGG TCTAGGACAG ACTTCACCCT CACCATTAAT
            CCTGTGGAGA CTGGTGATGT TGCAACCTAT TACTGT (SEQ ID NO: 157)             336
```
/translation = "GIPARFSGSGSRTDFTLTINPVETGDVATYYC" (SEQ ID NO: 158)

CDR-L3 (base pairs 337-363):
```
  337       CAGC AAAGTTATAA GGATCCTCCT ACG (SEQ ID NO: 159)                      363
```
/translation = "QQSYKDPPT" (SEQ ID NO: 160)

Framework 4 (base pairs 364-393):
```
  364       TTCGGTA CTGGGACCAA GCTGGAGCTG AAG (SEQ ID NO: 161)                   393
```
/translation = "FGTGTKLELK" (SEQ ID NO: 162)

MHC2558LC.2 499.8D2.6.8

| Region | Sequence Fragment | Residues | Length |
| --- | --- | --- | --- |
| Leader | METDTLLLWVLLLWVPGSTG | 1-20 | 20 |
| LFR1 | DIVLTQSPASLAVSLGQRATVSC | 21-43 | 23 |
| CDR-L1 | RASESVDNSGINFIH | 44-58 | 15 |
| LFR2 | WYQQKPGQSPKLLLY | 59-73 | 15 |

TABLE 2-continued

Identification and sequencing of the leader and variable regions of anti-HHLA2 monoclonal antibodies including mAbs 8A12, 6D10, 6F10, 8D2, 2G2, 2C4, 4D1, 1C8, and 4E5

| | | | |
|---|---|---|---|
| CDR-L2 | RASNLKS | 74-80 | 7 |
| LFR3 | GIPARFSGSGSRTDFTLTINPVETGDVATYYC | 81-112 | 32 |
| CDR-L3 | QQSYKDPPT | 113-121 | 9 |
| LFR4 | FGTGTKLELK | 122-131 | 10 |

2G2 Heavy Chain Variable (vH) DNA and Amino Acid Sequences*

MHC2561HC.1;M13. 499.5.2G2.13.3.10
CDR Analysis
GLTFSSYA....___ISSGGSHT..___TRLGRAFDY
Amino Acid Sequence in FASTA format (MHC2561HC.1\;M13F)
> MHC2561HC.1\;M13F. 499.5.2G2.13.3.10

```
LOCUS     2G2_vH 405 bp DNA linear

FEATURES         Location/Qualifiers
J_segment        373..405
                 /label = FWR4

V_segment        352..372
                 /label = CDR3

V_region         229..351
                 /label = FWR3

V_segment        211..228
                 /label = CDR2

V_region         154..210
                 /label = FWR2

V_segment        133..153
                 /label = CDR1

V_region         58..132
                 /label = FWR1 sig_peptide      1..57
                 /label = LS

CDS              1..405
                 /label = 2G2_vH
```

2G2_vH
/translation = "MNFGLSLIFLVLVLKGVQCEVMLVESGGGLVKPGGSLKLSCAVSGLTFSSYAMSWV
RQTPEKRLEWVATISSGGSHTYYPDSVKGRFIISRDNAKNTLYLQMNSLRSEDTAMYYCTRLGRAFDYWG
QGTTLTVSS" (SEQ ID NO: 163)

Nucleotide Sequence in FASTA format (MHC2561HC.1\;M13F)
> MHC2561HC.1\;M13F. 499.5.2G2.13.3.10
ORIGIN
```
  1    ATGAACTTCG GGCTCAGCTT GATTTTCCTT GTCCTTGTTT TAAAAGGTGT CCAGTGTGAA

61    GTGATGCTGG TGGAGTCAGG GGGAGGCTTA GTGAAGCCTG GAGGATCCCT GAAACTCTCC

121    TGTGCAGTCT CTGGATTAAC TTTTAGTAGT TATGCCATGT CTTGGGTTCG CCAGACTCCG

181    GAGAAGAGGC TGGAGTGGGT CGCAACCATT AGTAGTGGTG GTAGTCACAC CTACTATCCA

241    GACAGTGTGA AGGGGCGATT CATCATTTCT AGAGACAATG CCAAGAACAC CCTGTACCTG

301    CAAATGAACA GTCTGAGGTC TGAGGACACG GCCATGTATT ACTGTACAAG ACTGGGACGG

361    GCCTTTGACT ACTGGGGCCA AGGCACCACT CTCACAGTCT CCTCA (SEQ ID NO: 164)
```

TABLE 2-continued

Identification and sequencing of the leader and variable regions of anti-HHLA2 monoclonal antibodies including mAbs 8A12, 6D10, 6F10, 8D2, 2G2, 2C4, 4D1, 1C8, and 4E5

```
Signal Peptide (base pairs 1-57):
  1        ATGAACTTCG GGCTCAGCTT GATTTTCCTT GTCCTTGTTT TAAAAGGTGT CCAGTGT        57
           (SEQ ID NO: 165)
/translation = "MNFGLSLIFLVLVLKGVQC" (SEQ ID NO: 166)

Framework 1 (base pairs 58-132):
  58       GAA GTGATGCTGG TGGAGTCAGG GGGAGGCTTA GTGAAGCCTG GAGGATCCCT
           GAAACTCTCC TGTGCAGTCT CT (SEQ ID NO: 167)                          132
/translation = "EVMLVESGGGLVKPGGSLKLSCAVS" (SEQ ID NO: 168)

CDR-H1 (base pairs 133-153):
  133      GGATTAAC TTTTAGTAGT TAT (SEQ ID NO: 169)                           153
/translation = "GLTFSSY" (SEQ ID NO: 170)

Framework 2 (base pairs 154-210):
  154      GCCATGT CTTGGGTTCG CCAGACTCCG GAGAAGAGGC TGGAGTGGGT CGCAACCATT      210
           (SEQ ID NO: 171)
/translation = "AMSWVRQTPEKRLEWVATI" (SEQ ID NO: 172)

CDR-H2 (base pairs 211-228):
  211      AGTAGTGGTG GTAGTCAC (SEQ ID NO: 173)                                228
/translation = "SSGGSH" (SEQ ID NO: 174)

Framework 3 (base pairs 229-351):
  229      AC TACTATCCA GACAGTGTGA AGGGGCGATT CATCATTTCT AGAGACAATG
           CCAAGAACAC CCTGTACCTG CAAATGAACA GTCTGAGGTC TGAGGACACG GCCATGTATT
           ACTGTACAAG A (SEQ ID NO: 175)                                       351
/translation = "TYYPDSVKGRFIISRDNAKNTLYLQMNSLRSEDTAMYYCTR" (SEQ ID
NO: 176)

CDR-H3 (base pairs 352-372):
  352      CTGGGACGG GCCTTTGACT AC (SEQ ID NO: 177)                            372
/translation = "LGRAFDY" (SEQ ID NO: 178)

Framework 4 (base pairs 373-405):
  373      TGGGGCCA AGGCACCACT CTCACAGTCT CCTCA (SEQ ID NO: 179)               405
/translation = "WGQGTTLTVSS" (SEQ ID NO: 180)
```

MHC2561HC.1 499.5.2G2.13.3.10

| Region | Sequence Fragment | Residues | Length |
| --- | --- | --- | --- |
| Leader | MNFGLSLIFLVLVLKGVQC | 1-19 | 19 |
| HFR1 | EVMLVESGGGLVKPGGSLKLSCAVS | 20-44 | 25 |
| CDR-H1 | GLTFSSY | 45-51 | 7 |
| HFR2 | AMSWVRQTPEKRLEWVATI | 52-70 | 19 |
| CDR-H2 | SSGGSH | 71-76 | 6 |
| HFR3 | TYYPDSVKGRFIISRDNAKNTLYLQMNSLRSEDTAMYYCTR | 77-117 | 41 |
| CDR-H3 | LGRAFDY | 118-124 | 7 |
| HFR4 | WGQGTTLTVSS | 125-135 | 11 |

2G2 Light Chain Variable (vL) DNA and Amino Acid Sequences*

MHC2561LC.1;M13. 499.5.2G2.13.3.10
CDR Analysis
QDVSTA......___WAS.......___QQDYSTPWT
Amino Acid Sequence in FASTA format (MHC2561LC.1\;M13F)
> MHC2561LC.1\;M13F. 499.5.2G2.13.3.10

LOCUS 2G2_vL 381 bp DNA linear

```
FEATURES        Location/Qualifiers
J_segment       352..381
                /label = FWR4

V_segment       325..351
                /label = CDR3
```

TABLE 2-continued

Identification and sequencing of the leader and variable regions of anti-HHLA2 monoclonal antibodies including mAbs 8A12, 6D10, 6F10, 8D2, 2G2, 2C4, 4D1, 1C8, and 4E5

```
V_region        229..324
                /label = FWR3

V_segment       208..228
                /label = CDR2

V_region        163..207
                /label = FWR2

V_segment       130..162
                /label = CDR1

V_region         61..129
                /label = FWR1 sig_peptide       1..60
                /label = LS

CDS               1..381
                /label = 2G2_vL
```

2G2_vL
/translation = "MESQIQVFVFVFLWLSGVDGDIVMTQSHKFMSTSVGDRVSITCKASQDVSTAVAWY
QQKPGQSPKVLIYWASTRHTGVPDRFTGSGSGTDFTLTISSVQAEDLALYYCQQDYSTPWTFGGGTKLEI
K" (SEQ ID NO: 181)

Nucleotide Sequence in FASTA format (MHC2561LC.1\;M13F)
> MHC2561LC.1\;M13F. 499.5.2G2.13.3.10
ORIGIN

```
    1       ATGGAGTCAC AGATTCAGGT CTTTGTATTC GTGTTTCTCT GGTTGTCTGG TGTTGACGGA

61       GACATTGTGA TGACCCAGTC TCACAAATTC ATGTCCACAT CAGTAGGAGA CAGGGTCAGC

121       ATCACCTGCA AGGCCAGTCA GGATGTGAGT ACTGCTGTAG CCTGGTATCA ACAAAAGCCA

181       GGGCAATCTC CTAAAGTTCT GATTTACTGG GCATCCACCC GGCACACTGG AGTCCCTGAT

241       CGCTTCACAG GCAGTGGATC TGGGACAGAT TTTACTCTCA CCATCAGCAG TGTGCAGGCT

301       GAAGACCTGG CACTTTATTA CTGTCAGCAA GATTATAGCA CTCCGTGGAC GTTCGGTGGA

361       GGCACCAAGC TGGAAATCAA A  (SEQ ID NO: 182)
```

Signal Peptide (base pairs 1-60):
```
    1       ATGGAGTCAC AGATTCAGGT CTTTGTATTC GTGTTTCTCT GGTTGTCTGG TGTTGACGGA      60
            (SEQ ID NO: 183)
```
/translation = "MESQIQVFVFVFLWLSGVDG" (SEQ ID NO: 184)

Framework 1 (base pairs 61-129):
```
   61       GACATTGTGA TGACCCAGTC TCACAAATTC ATGTCCACAT CAGTAGGAGA CAGGGTCAGC
            ATCACCTGC  (SEQ ID NO: 185)                                           129
```
/translation = "DIVMTQSHKFMSTSVGDRVSITC" (SEQ ID NO: 186)

CDR-L1 (base pairs 130-162):
```
  130       A AGGCCAGTCA GGATGTGAGT ACTGCTGTAG CC (SEQ ID NO: 187)                162
```
/translation = "KASQDVSTAVA" (SEQ ID NO: 188)

Framework 2 (base pairs 163-207):
```
  163       TGGTATCA ACAAAAGCCA GGGCAATCTC CTAAAGTTCT GATTTAC (SEQ ID NO: 189)    207
```
/translation = "WYQQKPGQSPKVLIY" (SEQ ID NO: 190)

CDR-L2 (base pairs 208-228):
```
  208       TGG GCATCCACCC GGCACACT (SEQ ID NO: 191)                              228
```
/translation = "WASTRHT" (SEQ ID NO: 192)

Framework 3 (base pairs 229-324):
```
  229       GG AGTCCCTGAT CGCTTCACAG GCAGTGGATC TGGGACAGAT TTTACTCTCA
            CCATCAGCAG TGTGCAGGCT GAAGACCTGG CACTTTATTA CTGT (SEQ ID NO: 193)     324
```
/translation = "GVPDRFTGSGSGTDFTLTISSVQAEDLALYYC" (SEQ ID NO: 194)

CDR-L3 (base pairs 325-351):
```
  325       CAGCAA GATTATAGCA CTCCGTGGAC G (SEQ ID NO: 195)                       351
```
/translation = "QQDYSTPWT" (SEQ ID NO: 196)

TABLE 2-continued

Identification and sequencing of the leader and variable regions of anti-HHLA2 monoclonal antibodies including mAbs 8A12, 6D10, 6F10, 8D2, 2G2, 2C4, 4D1, 1C8, and 4E5

```
Framework 4 (base pairs 352-381):
352            TTCGGTGGA GGCACCAAGC TGGAAATCAA A (SEQ ID NO: 197)            381
/translation = "FGGGTKLEIK" (SEQ ID NO: 198)
```

MHC2561LC.1 499.5.2G2.13.3.10

| Region | Sequence Fragment | Residues | Length |
|---|---|---|---|
| Leader | MESQIQVFVFVFLWLSGVDG | 1-20 | 20 |
| LFR1 | DIVMTQSHKFMSTSVGDRVSITC | 21-43 | 23 |
| CDR-L1 | KASQDVSTAVA | 44-54 | 11 |
| LFR2 | WYQQKPGQSPKVLIY | 55-69 | 15 |
| CDR-L2 | WASTRHT | 70-76 | 7 |
| LFR3 | GVPDRFTGSGSGTDFTLTISSVQAEDLALYYC | 77-108 | 32 |
| CDR-L3 | QQDYSTPWT | 109-117 | 9 |
| LFR4 | FGGGTKLEIK | 118-127 | 10 |

2C4 Heavy Chain Variable (vH) DNA and Amino Acid Sequences*

```
MHC2562HC.1;M13. 499.5.2C4.E6.6.8.1
CDR Analysis
GFSFTDYN....___IDPYYGRI..___ATGAYTSGYSWFAY
Amino Acid Sequence in FASTA format (MHC2562HC.1\;M13F)
> MHC2562HC.1\;M13F. 499.5.2C4.E6.6.8.1

LOCUS 2C4_vH 420 bp DNA linear

FEATURES      Location/Qualifiers
J_segment     388..420
              /label = FWR4

V_segment     352..387
              /label = CDR3

V_region      229..351
              /label = FWR3

V_segment     211..228
              /label = CDR2

V_region      154..210
              /label = FWR2

V_segment     133..153
              /label = CDR1

V_region      58..132
              /label = FWR1 sig_peptide   1..57
              /label = LS

CDS           1..420
              /label = 2C4_vH

2C4_vH
/translation = "MGWTWIFILILSVTTGVHSEVHLQQSGPELEKPGVSVKISCKASGFSFTDYNMNWV
KQSSGKSLEWIGNIDPYYGRINYNQKFKGKATLSVDKSSTAYMHLKSLTSEDSAVYYCATGAYTSGYSW
FAYWGQGTLVTVSA" (SEQ ID NO: 199)

Nucleotide Sequence in FASTA format (MHC2562HC.1\;M13F)
> MHC2562HC.1\;M13F. 499.5.2C4.E6.6.8.1
ORIGIN
      1       ATGGGATGGA CCTGGATCTT TATTTTAATC CTGTCAGTAA CTACAGGTGT CCACTCTGAG

61       GTCCACCTGC AGCAGTCTGG ACCTGAGCTG GAGAAGCCTG GCGTTTCAGT GAAGATATCC

121       TGCAAGGCTT CTGGTTTCTC ATTCACTGAC TACAACATGA ACTGGGTGAA ACAGAGCAGT
```

TABLE 2-continued

Identification and sequencing of the leader and variable regions of anti-HHLA2 monoclonal antibodies including mAbs 8A12, 6D10, 6F10, 8D2, 2G2, 2C4, 4D1, 1C8, and 4E5

```
181        GGAAAGAGCC TTGAGTGGAT TGGAAATATT GATCCTTACT ATGGACGTAT TAACTATAAC

241        CAGAAATTCA AGGGCAAGGC CACATTGAGT GTAGACAAAT CCTCCAGCAC AGCCTACATG

301        CACCTCAAGA GCCTGACATC TGAGGACTCT GCAGTCTATT ACTGTGCAAC TGGGGCCTAC

361        ACCTCGGGCT ACTCCTGGTT TGCTTACTGG GGCCAAGGGA CTCTGGTCAC TGTCTCTGCA (SEQ ID NO: 200)
```

Signal Peptide (base pairs 1-57):
```
  1        ATGGGATGGA CCTGGATCTT TATTTTAATC CTGTCAGTAA CTACAGGTGT
           CCACTCT (SEQ ID NO: 201)                                                    57
```
/translation = "MGWTWIFILILSVTTGVHS" (SEQ ID NO: 202)

Framework 1 (base pairs 58-132):
```
 58        GAG GTCCACCTGC AGCAGTCTGG ACCTGAGCTG GAGAAGCCTG GCGTTTCAGT
           GAAGATATCC TGCAAGGCTT CT (SEQ ID NO: 203)                                  132
```
/translation = "EVHLQQSGPELEKPGVSVKISCKAS" (SEQ ID NO: 204)

CDR-H1 (base pairs 133-153):
```
133        GGTTTCTC ATTCACTGAC TAC (SEQ ID NO: 205)                                  153
```
/translation = "GFSFTDY" (SEQ ID NO: 206)

Framework 2 (base pairs 154-210):
```
154        AACATGA ACTGGGTGAA ACAGAGCAGT GGAAAGAGCC TTGAGTGGAT TGGAAATATT           210
           (SEQ ID NO: 207)
```
/translation = "NMNWVKQSSGKSLEWIGNI" (SEQ ID NO: 208)

CDR-H2 (base pairs 211-228):
```
211        GATCCTTACT ATGGACGT (SEQ ID NO: 209)                                      228
```
/translation = "DPYYGR" (SEQ ID NO: 210)

Framework 3 (base pairs 229-351):
```
229        AT TAACTATAAC CAGAAATTCA AGGGCAAGGC CACATTGAGT GTAGACAAAT
           CCTCCAGCAC AGCCTACATG CACCTCAAGA GCCTGACATC TGAGGACTCT GCAGTCTATT
           ACTGTGCAAC T (SEQ ID NO: 211)                                              351
```
/translation = "INYNQKFKGKATLSVDKSSSTAYMHLKSLTSEDSAVYYCAT" (SEQ ID NO: 212)

CDR-H3 (base pairs 352-387):
```
352        GGGGCCTAC ACCTCGGGCT ACTCCTGGTT TGCTTAC (SEQ ID NO: 213)                  387
```
/translation = "GAYTSGYSWFAY" (SEQ ID NO: 214)

Framework 4 (base pairs 388-420):
```
388        TGG GGCCAAGGGA CTCTGGTCAC TGTCTCTGCA (SEQ ID NO: 215)                     420
```
/translation = "WGQGTLVTVSA" (SEQ ID NO: 216)

MHC2562HC.1 499.5.2C4.E6.6.8.1

| Region | Sequence Fragment | Residues | Length |
| --- | --- | --- | --- |
| Leader | MGWTWIFILILSVTTGVHS | 1-19 | 19 |
| HFR1 | EVHLQQSGPELEKPGVSVKISCKAS | 20-44 | 25 |
| CDR-H1 | GFSFTDY | 45-51 | 7 |
| HFR2 | NMNWVKQSSGKSLEWIGNI | 52-70 | 19 |
| CDR-H2 | DPYYGR | 71-76 | 6 |
| HFR3 | INYNQKFKGKATLSVDKSSSTAYMHLKSLTSEDSAVYYCAT | 77-117 | 41 |
| CDR-H3 | GAYTSGYSWFAY | 118-129 | 12 |
| HFR4 | WGQGTLVTVSA | 130-140 | 11 |

TABLE 2-continued

Identification and sequencing of the leader and variable regions of anti-HHLA2 monoclonal antibodies including mAbs 8A12, 6D10, 6F10, 8D2, 2G2, 2C4, 4D1, 1C8, and 4E5

2C4 Light Chain Variable (vL) DNA and Amino Acid Sequences*

```
MHC2562LC.2;M13. 499.5.2C4.E6.6.8.1
CDR Analysis
SSVSSSY.....___RTS.......___QQWSGYPFT
Amino Acid Sequence in FASTA format (MHC2562LC.2\;M13F)
> MHC2562LC.2\;M13F. 499.5.2C4.E6.6.8.1

LOCUS 2C4_vL 390 bp DNA linear

FEATURES        Location/Qualifiers
J_segment       361..390
                /label = FWR4

V_segment       334..360
                /label = CDR3

V_region        238..333
                /label = FWR3

V_segment       217..237
                /label = CDR2

V_region        172..216
                /label = FWR2

V_segment       136..171
                /label = CDR1

V_region         67..135
                /label = FWR1 sig_peptide       1..66
                /label = LS

CDS               1..390
                /label = 2C4_vL

2C4_vL
/translation = "MGLQVQVISFLLISVTVIMSRGENVLTQSPGIMAASLGEKVTMTCSASSSVSSSYL
HWYQQRSGASPKPLIHRTSNLASGVPARFSGSGSGTSYSLTISSVEAEDDATYYCQQWSGYPFTFGSGTK
LEIK" (SEQ ID NO: 217)

Nucleotide Sequence in FASTA format (MHC2562LC.2\;M13F)
> MHC2562LC.2\;M13F. 499.5.2C4.E6.6.8.1
ORIGIN
     1      ATGGGTTTAC AGGTGCAGGT TATCAGCTTC CTGTTAATCA GTGTCACAGT CATAATGTCC

61      AGAGGAGAAA ATGTGCTCAC CCAGTCTCCA GGAATAATGG CTGCCTCTCT GGGGGAGAAG

121      GTCACCATGA CCTGCAGTGC CAGCTCAAGT GTAAGTTCCA GTTACTTGCA CTGGTACCAG

181      CAGAGGTCAG GCGCTTCCCC CAAACCCTTG ATTCATAGGA CATCCAACCT GGCTTCTGGT

241      GTCCCAGCTC GCTTCAGTGG CAGTGGGTCT GGGACCTCTT ACTCTCTCAC AATCAGCAGC

301      GTGGAGGCTG AAGATGATGC AACTTATTAC TGCCAGCAGT GGAGTGGTTA CCCATTCACG

361      TTCGGCTCGG GGACAAAGTT GGAAATAAAA (SEQ ID NO: 218)

Signal Peptide (base pairs 1-66):
     1      ATGGGTTTAC AGGTGCAGGT TATCAGCTTC CTGTTAATCA GTGTCACAGT CATAATGTCC
            AGAGGA (SEQ ID NO: 219)                                                     66
/translation = "MGLQVQVISFLLISVTVIMSRG" (SEQ ID NO: 220)

Framework 1 (base pairs 67-135):
    67             GAAA ATGTGCTCAC CCAGTCTCCA GGAATAATGG CTGCCTCTCT GGGGGAGAAG
            GTCACCATGA CCTGC (SEQ ID NO: 221)                                           135
/translation = "ENVLTQSPGIMAASLGEKVTMTC" (SEQ ID NO: 222)

CDR-L1 (base pairs 136-171):
   136            AGTGC CAGCTCAAGT GTAAGTTCCA GTTACTTGCA C (SEQ ID NO: 223)             171
/translation = "SASSSVSSSYLH" (SEQ ID NO: 224)
```

TABLE 2-continued

Identification and sequencing of the leader and variable regions of
anti-HHLA2 monoclonal antibodies including mAbs 8A12, 6D10, 6F10, 8D2,
2G2, 2C4, 4D1, 1C8, and 4E5

```
Framework 2 (base pairs 172-216):
172        TGGTACCAG CAGAGGTCAG GCGCTTCCCC CAAACCCTTG ATTCAT (SEQ ID NO: 225)     216
/translation = "WYQQRSGASPKPLIH" (SEQ ID NO: 226)

CDR-L2 (base pairs 217-237):
217        AGGA CATCCAACCT GGCTTCT (SEQ ID NO: 227)                               237
/translation = "RTSNLAS" (SEQ ID NO: 228)

Framework 3 (base pairs 238-333):
238        GGT GTCCCAGCTC GCTTCAGTGG CAGTGGGTCT GGGACCTCTT ACTCTCTCAC
           AATCAGCAGC GTGGAGGCTG AAGATGATGC AACTTATTAC TGC (SEQ ID NO: 229)       333
/translation = "GVPARFSGSGSGTSYSLTISSVEAEDDATYYC" (SEQ ID NO: 230)

CDR-L3 (base pairs 334-360):
334        CAGCAGT GGAGTGGTTA CCCATTCACG (SEQ ID NO: 231)                         360
/translation = "QQWSGYPFT" (SEQ ID NO: 232)

Framework 4 (base pairs 361-390):
361        TTCGGCTCGG GGACAAAGTT GGAAATAAAA (SEQ ID NO: 233)                       390
/translation = "FGSGTKLEIK" (SEQ ID NO: 234)
```

MHC2562LC.2 499.5.2C4.E6.6.8.1

| Region | Sequence Fragment | Residues | Length |
|---|---|---|---|
| Leader | MGLQVQVISFLLISVTVIMSRG | 1-22 | 22 |
| LFR1 | ENVLTQSPGIMAASLGEKVTMTC | 23-45 | 23 |
| CDR-L1 | SASSSVSSSYLH | 46-57 | 12 |
| LFR2 | WYQQRSGASPKPLIH | 58-72 | 15 |
| CDR-L2 | RTSNLAS | 73-79 | 7 |
| LFR3 | GVPARFSGSGSGTSYSLTISSVEAEDDATYYC | 80-111 | 32 |
| CDR-L3 | QQWSGYPFT | 112-120 | 9 |
| LFR4 | FGSGTKLEIK | 121-130 | 10 |

4D1 Heavy Chain Variable (vH) DNA and Amino Acid Sequences*

```
MHC2563HC.1;M13. 499.5.4D1.5.16
CDR Analysis
GYTFTDYA....___ISTYYGDT..___ARGNYDDWYFNV
Amino Acid Sequence in FASTA format (MHC2563HC.1\;M13F)
> MHC2563HC.1\;M13F. 499.5.4D1.5.16

LOCUS 4D1_vH 414 bp DNA linear

FEATURES       Location/Qualifiers
J_segment      382..414
               /label = FWR4

V_segment      352..381
               /label = CDR3

V_region       229..351
               /label = FWR3

V_segment      211..228
               /label = CDR2

V_region       154..210
               /label = FWR2

V_segment      133..153
               /label = CDR1

V_region        58..132
               /label = FWR1
```

TABLE 2-continued

Identification and sequencing of the leader and variable regions of anti-HHLA2 monoclonal antibodies including mAbs 8A12, 6D10, 6F10, 8D2, 2G2, 2C4, 4D1, 1C8, and 4E5

```
sig_peptide     1..57
                /label = LS

CDS             1..414
                /label = 4D1_vH

4D1_vH
/translation = "MDWSCIIFFLVATATGVHSQVQLQQSGAELVRPGVSVKISCKGSGYTFTDYAMHWV
KQSHAKSLEWIGSISTYYGDTNYNQKFKGKATMTVDKSSSTAYMELARLTSEDSAIYYCARGNYDDWYFN
VWGAGTTVTSS" (SEQ ID NO: 235)

Nucleotide Sequence in FASTA format (MHC2563HC.1\;M13F)
> MHC2563HC.1\;M13F. 499.5.4D1.5.16
ORIGIN
    1       ATGGATTGGA GCTGTATCAT CTTCTTTCTG GTAGCAACAG CTACAGGTGT GCACTCCCAG

61       GTCCAGCTGC AGCAGTCTGG GGCTGAACTG GTGAGGCCTG GGTCTCAGT GAAGATTTCC

121       TGCAAGGGTT CTGGCTACAC ATTCACTGAT TATGCTATGC ACTGGGTGAA GCAGAGTCAT

181       GCAAAGAGTC TAGAGTGGAT TGGAAGTATT AGTACTTACT ATGGTGATAC TAATTACAAC

241       CAGAAATTCA AGGGCAAGGC CACAATGACT GTAGACAAAT CCTCCAGCAC AGCCTATATG

301       GAACTTGCCA GACTGACATC TGAGGATTCT GCCATCTATT ACTGTGCAAG AGGTAATTAC

361       GACGACTGGT ACTTCAATGT CTGGGGCGCA GGGACCACGG TCACCGTCTC CTCA (SEQ ID NO: 236)

Signal Peptide (base pairs 1-57):
    1       ATGGATTGGA GCTGTATCAT CTTCTTTCTG GTAGCAACAG CTACAGGTGT GCACTCC        57
            (SEQ ID NO: 237)
/translation = "MDWSCIIFFLVATATGVHS" (SEQ ID NO: 238)

Framework 1 (base pairs 58-132):
   58       CAG GTCCAGCTGC AGCAGTCTGG GGCTGAACTG GTGAGGCCTG GGTCTCAGT
            GAAGATTTCC TGCAAGGGTT CT (SEQ ID NO: 239)                            132
/translation = "QVQLQQSGAELVRPGVSVKISCKGS" (SEQ ID NO: 240)

CDR-H1 (base pairs 133-153):
  133       GGCTACAC ATTCACTGAT TAT (SEQ ID NO: 241)                            153
/translation = "GYTFTDY" (SEQ ID NO: 242)

Framework 2 (base pairs 154-210):
  154       GCTATGC ACTGGGTGAA GCAGAGTCAT GCAAAGAGTC TAGAGTGGAT TGGAAGTATT       210
            (SEQ ID NO: 243)
/translation = "AMHWVKQSHAKSLEWIGSI" (SEQ ID NO: 244)

CDR-H2 (base pairs 211-228):
  211       AGTACTTACT ATGGTGAT (SEQ ID NO: 245)                                228
/translation = "STYYGD" (SEQ ID NO: 246)

Framework 3 (base pairs 229-351):
  229       AC TAATTACAAC CAGAAATTCA AGGGCAAGGC CACAATGACT GTAGACAAAT
            CCTCCAGCAC AGCCTATATG GAACTTGCCA GACTGACATC TGAGGATTCT GCCATCTATT
            ACTGTGCAAG A (SEQ ID NO: 247)                                       351
/translation = "TNYNQKFKGKATMTVDKSSSTAYMELARLTSEDSAIYYCAR" (SEQ ID
NO: 248)

CDR-H3 (base pairs 352-381):
  352       GGTAATTAC GACGACTGGT ACTTCAATGT C (SEQ ID NO: 249)                  381
/translation = "GNYDDWYFNV" (SEQ ID NO: 250)

Framework 4 (base pairs 382-414):
  382       TGGGGCGCA GGGACCACGG TCACCGTCTC CTCA (SEQ ID NO: 251)               414
/translation = "WGAGTTVTSS" (SEQ ID NO: 252)
```

MHC2563HC.1 499.5.4D1.5.16

| Region | Sequence Fragment | Residues | Length |
|---|---|---|---|
| Leader | MDWSCIIFFLVATATGVHS | 1-19 | 19 |
| HFR1 | QVQLQQSGAELVRPGVSVKISCKGS | 20-44 | 25 |
| CDR-H1 | GYTFTDY | 45-51 | 7 |

TABLE 2-continued

Identification and sequencing of the leader and variable regions of anti-HHLA2 monoclonal antibodies including mAbs 8A12, 6D10, 6F10, 8D2, 2G2, 2C4, 4D1, 1C8, and 4E5

| | | | |
|---|---|---|---|
| HFR2 | AMHWVKQSHAKSLEWIGSI | 52-70 | 19 |
| CDR-H2 | STYYGD | 71-76 | 6 |
| HFR3 | TNYNQKFKGKATMTVDKSSSTAYMELARLTSEDSAIYYCAR | 77-117 | 41 |
| CDR-H3 | GNYDDWYFNV | 118-127 | 10 |
| HFR4 | WGAGTTVTVSS | 128-138 | 11 |

4D1 Light Chain Variable (vL) DNA and Amino Acid Sequences*

MHC2563LC.1;M13. 499.5.4D1.5.16
CDR Analysis
QDISGY......___STS.......___LQYASSPYT
Amino Acid Sequence in FASTA format (MHC2563LC.1\;M13F)
> MHC2563LC.1\;M13F. 499.5.4D1.5.16

LOCUS 4D1_vL 381 bp DNA linear

FEATURES    Location/Qualifiers
J_segment   352..381
            /label = FWR4

V_segment   325..351
            /label = CDR3

V_region    229..324
            /label = FWR3

V_segment   208..228
            /label = CDR2

V_region    163..207
            /label = FWR2

V_segment   130..162
            /label = CDR1

V_region    61..129
            /label = FWR1 sig_peptide 1..60
            /label = LS

CDS         1..381
            /label = 4D1_vL

4D1_vL
/translation = "MRIPAHVFGFLLLWFPGARCDIQMTQSPSSLSASLGERVSLTCRASQDISGYLSWL
QQKPDGTIKRLIYSTSTLDSGVPKRFSGSRSGSDYSLTISSLESEDFADYYCLQYASSPYTFGGGAKLEI
KR" (SEQ ID NO: 253)

Nucleotide Sequence in FASTA format (MHC2563LC.1\;M13F)
> MHC2563LC.1\;M13F. 499.5.4D1.5.16
ORIGIN
   1    ATGAGGATTC CTGCTCACGT TTTTGGCTTC TTGTTGCTCT GGTTTCCAGG TGCCAGATGT
  61    GACATCCAAA TGACCCAGTC TCCATCTTCC TTATCTGCCT CTCTGGGAGA AAGAGTCAGT
 121    CTCACTTGTC GGGCAAGTCA GGATATTAGT GGTTACTTAA GCTGGCTTCA GCAGAAACCA
 181    GATGGAACTA TTAAACGTCT GATTTATAGC ACATCCACTT TAGATTCTGG TGTCCCAAAA
 241    AGGTTCAGTG GCAGTAGGTC TGGGTCAGAT TATTCTCTCA CCATCAGCAG CCTAGAGTCT
 301    GAAGATTTTG CAGACTATTA CTGTCTACAA TATGCTAGTT CTCCGTACAC GTTCGGAGGG
 361    GGGGCCAAGC TGGAAATAAA A (SEQ ID NO: 254)

TABLE 2-continued

Identification and sequencing of the leader and variable regions of anti-HHLA2 monoclonal antibodies including mAbs 8A12, 6D10, 6F10, 8D2, 2G2, 2C4, 4D1, 1C8, and 4E5

```
Signal Peptide (base pairs 1-60):
  1         ATGAGGATTC CTGCTCACGT TTTTGGCTTC TTGTTGCTCT GGTTTCCAGG TGCCAGATGT        60
            (SEQ ID NO: 255)
/translation = "MRIPAHVFGFLLLWFPGARC" (SEQ ID NO: 256)

Framework 1 (base pairs 61-129):
 61         GACATCCAAA TGACCCAGTC TCCATCTTCC TTATCTGCCT CTCTGGGAGA AAGAGTCAGT
            CTCACTTGT (SEQ ID NO: 257)                                             129
/translation = "DIQMTQSPSSLSASLGERVSLTC" (SEQ ID NO: 258)

CDR-L1 (base pairs 130-162):
130         C GGGCAAGTCA GGATATTAGT GGTTACTTAA GC (SEQ ID NO: 259)                 162
/translation = "RASQDISGYLS" (SEQ ID NO: 260)

Framework 2 (base pairs 163-207):
163         TGGCTTCA GCAGAAACCA GATGGAACTA TTAAACGTCT GATTTAT (SEQ ID NO: 261)     207
/translation = "WLQQKPDGTIKRLIY" (SEQ ID NO: 262)

CDR-L2 (base pairs 208-228):
208         AGC ACATCCACTT TAGATTCT (SEQ ID NO: 263)                               228
/translation = "STSTLDS" (SEQ ID NO: 264)

Framework 3 (base pairs 229-324):
229         GG TGTCCCAAAA AGGTTCAGTG GCAGTAGGTC TGGGTCAGAT TATTCTCTCA
            CCATCAGCAG CCTAGAGTCT GAAGATTTTG CAGACTATTA CTGT (SEQ ID NO: 265)      324
/translation = "GVPKRFSGSRSGSDYSLTISSLESEDFADYYC" (SEQ ID NO: 266)

CDR-L3 (base pairs 325-351):
325         CTACAA TATGCTAGTT CTCCGTACAC G (SEQ ID NO: 267)                        351
/translation = "LQYASSPYT" (SEQ ID NO: 268)

Framework 4 (base pairs 352-381):
352         TTCGGAGGG GGGGCCAAGC TGGAAATAAA A (SEQ ID NO: 269)                     381
/translation = "FGGGAKLEIK" (SEQ ID NO: 270)
```

MHC2563LC.1 499.5.4D1.5.16

| Region | Sequence Fragment | Residues | Length |
| --- | --- | --- | --- |
| Leader | MRIPAHVFGFLLLWFPGARC | 1-20 | 20 |
| LFR1 | DIQMTQSPSSLSASLGERVSLTC | 21-43 | 23 |
| CDR-L1 | RASQDISGYLS | 44-54 | 11 |
| LFR2 | WLQQKPDGTIKRLIY | 55-69 | 15 |
| CDR-L2 | STSTLDS | 70-76 | 7 |
| LFR3 | GVPKRFSGSRSGSDYSLTISSLESEDFADYYC | 77-108 | 32 |
| CDR-L3 | LQYASSPYT | 109-117 | 9 |
| LFR4 | FGGGAKLEIK | 118-127 | 10 |

1C8 Heavy Chain Variable (vH) DNA and Amino Acid Sequences*

```
MHC2564HC.1;M13. 499.5.1C8.9.12.2
CDR Analysis
GFNIKDTY....___IDPANGKT..___AWLLPYYFDY
Amino Acid Sequence in FASTA format (MHC2564HC.1\;M13F)
> MHC2564HC.1\;M13F. 499.5.1C8.9.12.2

LOCUS 1C8_vH 408 bp DNA linear

FEATURES       Location/Qualifiers
J_segment      376..408
               /label = FWR4

V_segment      352..375
               /label = CDR3

V_region       229..351
               /label = FWR3
```

TABLE 2-continued

Identification and sequencing of the leader and variable regions of
anti-HHLA2 monoclonal antibodies including mAbs 8A12, 6D10, 6F10, 8D2,
2G2, 2C4, 4D1, 1C8, and 4E5

```
V_segment       211..228
                /label = CDR2

V_region        154..210
                /label = FWR2

V_segment       133..153
                /label = CDR1

V_region        58..132
                /label = FWR1 sig_peptide     1..57
                /label = LS

CDS             1..408
                /label = 1C8_vH

1C8_vH
/translation = "MKCSWIIFFLMAVVTGVNSEVQLQQSGAELVQPGASVKLSCTASGFNIKDTYMHWV
KQRPEQGLEWIGRIDPANGKTIFDPKFQVKATITADTSSNTVYLHLSSLTSEDTAIYYCAWLLPYYFDYW
GQGTTLTVSS" (SEQ ID NO: 271)

Nucleotide Sequence in FASTA format (MHC2564HC.1\;M13F)
> MHC2564HC.1\;M13F. 499.5.1C8.9.12.2
ORIGIN
     1       ATGAAATGCA GCTGGATTAT CTTCTTCCTG ATGGCTGTGG TTACAGGGGT CAATTCAGAG

61       GTTCAGCTGC AGCAGTCTGG GGCAGAACTT GTGCAGCCAG GGGCCTCAGT CAAGTTGTCC

121       TGTACAGCTT CTGGCTTCAA TATTAAAGAC ACCTATATGC ACTGGGTAAA ACAGAGGCCT

181       GAACAGGGCC TGGAGTGGAT TGGAAGGATT GATCCTGCGA ATGGTAAAAC TATTTTTGAC

241       CCGAAGTTCC AGGTCAAGGC CACTATAACT GCCGACACAT CCTCCAACAC AGTCTACCTG

301       CATCTCAGCA GCCTGACATC TGAGGACACT GCCATCTATT ACTGTGCTTG GTTACTTCCT

361       TACTACTTTG ACTACTGGGG CCAAGGCACC ACTCTCACAG TCTCCTCA (SEQ ID NO: 272)

Signal Peptide (base pairs 1-57):
     1       ATGAAATGCA GCTGGATTAT CTTCTTCCTG ATGGCTGTGG TTACAGGGGT CAATTCA        57
             (SEQ ID NO: 273)
/translation = "MKCSWIIFFLMAVVTGVNS" (SEQ ID NO: 274)

Framework 1 (base pairs 58-132):
    58       GAG GTTCAGCTGC AGCAGTCTGG GGCAGAACTT GTGCAGCCAG GGGCCTCAGT
             CAAGTTGTCC TGTACAGCTT CT (SEQ ID NO: 275)                          132
/translation = "EVQLQQSGAELVQPGASVKLSCTAS" (SEQ ID NO: 276)

CDR-H1 (base pairs 133-153):
   133       GGCTTCAA TATTAAAGAC ACC (SEQ ID NO: 277)                           153
/translation = "GFNIKDT" (SEQ ID NO: 278)

Framework 2 (base pairs 154-210):
   154       TATATGC ACTGGGTAAA ACAGAGGCCT GAACAGGGCC TGGAGTGGAT TGGAAGGATT     210
             (SEQ ID NO: 279)
/translation = "YMHWVKQRPEQGLEWIGRI" (SEQ ID NO: 280)

CDR-H2 (base pairs 211-228):
   211       GATCCTGCGA ATGGTAAA (SEQ ID NO: 281)                               228
/translation = "DPANGK" (SEQ ID NO: 282)

Framework 3 (base pairs 229-351):
   229       AC TATTTTTGAC CCGAAGTTCC AGGTCAAGGC CACTATAACT GCCGACACAT
             CCTCCAACAC AGTCTACCTG CATCTCAGCA GCCTGACATC TGAGGACACT GCCATCTATT
             ACTGTGCTTG G (SEQ ID NO: 283)                                      351
/translation = "TIFDPKFQVKATITADTSSNTVYLHLSSLTSEDTAIYYCAW" (SEQ ID
NO: 284)

CDR-H3 (base pairs 352-375):
   352       TTACTTCCT TACTACTTTG ACTAC (SEQ ID NO: 285)                        375
/translation = "LLPYYFDY" (SEQ ID NO: 286)
```

TABLE 2-continued

Identification and sequencing of the leader and variable regions of anti-HHLA2 monoclonal antibodies including mAbs 8A12, 6D10, 6F10, 8D2, 2G2, 2C4, 4D1, 1C8, and 4E5

Framework 4 (base pairs 376-408):
376        TGGGG CCAAGGCACC ACTCTCACAG TCTCCTCA (SEQ ID NO: 287)        408
/translation = "WGQGTTLTVSS" (SEQ ID NO: 288)

MHC2564HC.1 499.5.1C8.9.12.2

| Region | Sequence Fragment | Residues | Length |
| --- | --- | --- | --- |
| Leader | MKCSWIIFFLMAVVTGVNS | 1-19 | 19 |
| HFR1 | EVQLQQSGAELVQPGASVKLSCTAS | 20-44 | 25 |
| CDR-H1 | GFNIKDT | 45-51 | 7 |
| HFR2 | YMHWVKQRPEQGLEWIGRI | 52-70 | 19 |
| CDR-H2 | DPANGK | 71-76 | 6 |
| HFR3 | TIFDPKFQVKATITADTSSNTVYLHLSSLTSEDTAIYYCAW | 77-117 | 41 |
| CDR-H3 | LLPYYFDY | 118-125 | 8 |
| HFR4 | WGQGTTLTVSS | 126-136 | 11 |

1C8 Light Chain Variable (vL) DNA and Amino Acid Sequences*

MHC2564LCB.4;M13. 499.5.1C8.9.12.2
CDR Analysis
SSISSSN.....___GTS.......___QKWSHYPLT
Amino Acid Sequence in FASTA format (MHC2564LCB.4\;M13F)
> MHC2564LCB.4\;M13F. 499.5.1C8.9.12.2

LOCUS 1C8_vL 390 bp DNA linear

FEATURES     Location/Qualifiers
J_segment    361..390
              /label = FWR4

V_segment    334..360
              /label = CDR3

V_region     238..333
              /label = FWR3

V_segment    217..237
              /label = CDR2

V_region     172..216
              /label = FWR2

V_segment    136..171
              /label = CDR1

V_region     67..135
              /label = FWR1 sig_peptide  1..66
              /label = LS

CDS           1..390
              /label = 1C8_vL

1C8_vL
/translation = "MDFHVQIFSFMLISVTVMLSSGEIVLTQSPAVMAASPGEKVTITCSVSSSISSSNL
HWYQQKSGTSPKLWIYGTSNLASGVPVRFSGSGSGTSYSLTISSMEAEDAATYYCQKWSHYPLTFGAGTK
LELK" (SEQ ID NO: 289)

Nucleotide Sequence in FASTA format (MHC2564LCB.4\;M13F)
> MHC2564LCB.4\;M13F. 499.5.1C8.9.12.2
ORIGIN
    1        ATGGATTTTC ATGTGCAGAT TTTCAGCTTC ATGCTAATCA GTGTCACAGT CATGTTGTCC

61       AGTGGGGAAA TTGTACTCAC CCAGTCTCCA GCAGTCATGG CTGCATCTCC AGGGGAGAAG

121       GTCACCATCA CCTGCAGCGT CAGTTCAAGT ATAAGTTCCA GCAACTTGCA CTGGTACCAG

TABLE 2-continued

Identification and sequencing of the leader and variable regions of anti-HHLA2 monoclonal antibodies including mAbs 8A12, 6D10, 6F10, 8D2, 2G2, 2C4, 4D1, 1C8, and 4E5

```
181        CAGAAGTCAG GAACCTCGCC CAAACTCTGG ATTTATGGCA CATCCAACCT GGCTTCTGGA

241        GTCCCTGTTC GCTTCAGTGG CAGTGGATCT GGGACCTCTT ATTCTCTCAC AATCAGCAGC

301        ATGGAGGCTG AAGATGCTGC CACTTATTAC TGTCAAAAGT GGAGTCATTA CCCGCTCACG

361        TTCGGTGCTG GGACCAAGCT GGAGCTGAAA (SEQ ID NO: 290)
```

Signal Peptide (base pairs 1-66):
```
  1        ATGGATTTTC ATGTGCAGAT TTTCAGCTTC ATGCTAATCA GTGTCACAGT CATGTTGTCC
           AGTGGG (SEQ ID NO: 291)                                                66
```
/translation = "MDFHVQIFSFMLISVTVMLSSG" (SEQ ID NO: 292)

Framework 1 (base pairs 67-135):
```
 67        GAAA TTGTACTCAC CCAGTCTCCA GCAGTCATGG CTGCATCTCC AGGGGAGAAG
           GTCACCATCA CCTGC (SEQ ID NO: 293)                                      135
```
/translation = "EIVLTQSPAVMAASPGEKVTITC" (SEQ ID NO: 294)

CDR-L1 (base pairs 136-171):
```
136        AGCGT CAGTTCAAGT ATAAGTTCCA GCAACTTGCA C (SEQ ID NO: 295)              171
```
/translation = "SVSSSISSSNLH" (SEQ ID NO: 296)

Framework 2 (base pairs 172-216):
```
172        TGGTACCAG CAGAAGTCAG GAACCTCGCC CAAACTCTGG ATTTAT (SEQ ID NO: 297)     216
```
/translation = "WYQQKSGTSPKLWIY" (SEQ ID NO: 298)

CDR-L2 (base pairs 217-237):
```
217        GGCA CATCCAACCT GGCTTCT (SEQ ID NO: 299)                               237
```
/translation = "GTSNLAS" (SEQ ID NO: 300)

Framework 3 (base pairs 238-333):
```
238        GGA GTCCCTGTTC GCTTCAGTGG CAGTGGATCT GGGACCTCTT ATTCTCTCAC
           AATCAGCAGC ATGGAGGCTG AAGATGCTGC CACTTATTAC TGT (SEQ ID NO: 301)       333
```
/translation = "GVPVRFSGSGSGTSYSLTISSMEAEDAATYYC" (SEQ ID NO: 302)

CDR-L3 (base pairs 334-360):
```
334        CAAAAGT GGAGTCATTA CCCGCTCACG (SEQ ID NO: 303)                         360
```
/translation = "QKWSHYPLT" (SEQ ID NO: 304)

Framework 4 (base pairs 361-390):
```
361        TTCGGTGCTG GGACCAAGCT GGAGCTGAAA (SEQ ID NO: 305)                      390
```
/translation = "FGAGTKLELK" (SEQ ID NO: 306)

MHC2564LCB.4 499.5.1C8.9.12.2

| Region | Sequence Fragment | Residues | Length |
| --- | --- | --- | --- |
| Leader | MDFHVQIFSFMLISVTVMLSSG | 1-22 | 22 |
| LFR1 | EIVLTQSPAVMAASPGEKVTITC | 23-45 | 23 |
| CDR-L1 | SVSSSISSSNLH | 46-57 | 12 |
| LFR2 | WYQQKSGTSPKLWIY | 58-72 | 15 |
| CDR-L2 | GTSNLAS | 73-79 | 7 |
| LFR3 | GVPVRFSGSGSGTSYSLTISSMEAEDAATYYC | 80-111 | 32 |
| CDR-L3 | QKWSHYPLT | 112-120 | 9 |
| LFR4 | FGAGTKLELK | 121-130 | 10 |

TABLE 2-continued

Identification and sequencing of the leader and variable regions of
anti-HHLA2 monoclonal antibodies including mAbs 8A12, 6D10, 6F10, 8D2,
2G2, 2C4, 4D1, 1C8, and 4E5

4E5 Heavy Chain Variable (vH) DNA and Amino Acid Sequences*

MHC2556HCN.1;M13.499.5.4E5.20.22
CDRAnalysis
GYTFTTYT....___INPSSGYT..___ARHPWDSNY
AminoAcidSequenceinFASTAformat(MHC2556HCN.1\;M13F)
>MHC2556HCN.1\;M13F LOCUS 4E5_vH 405 bp DNA linear FEATURES     Location/Qualifiers
J_segment    373..405
             /label = FWR4

V_segment    352..372
             /label = CDR3

V_region     229..351
             /label = FWR3

V_segment    211..228
             /label = CDR2

V_region     154..210
             /label = FWR2

V_segment    133..153
             /label = CDR1

V_region     58..132
             /label = FWR1 sig_peptide  1..57
             /label = LS

CDS          1..405
             /label = 4E5_vH

4E5_vH
/translation = "MERHWIFLFLLSVTAGVHSQVQLQQSAAELARPGASVKMSCKASGYTFTTYTMHWV
KQRPGQGLEWIGHINPSSGYTEYNQKFKDKTTLTADKSSSTAHMQLSSLTSEDSAVYYCARHPWDSNYWG
QGTTLTVSS" (SEQ ID NO: 307)

NucleotideSequenceinFASTAformat(MHC2556HCN.1\;M13F)
>MHC2556HCN.1\;M13F
ORIGIN
    1        ATGGAAAGGC ACTGGATCTT TCTCTTCCTG TTGTCAGTAA CTGCAGGTGT CCACTCCCAG

61        GTCCAGCTGC AGCAGTCTGC AGCTGAACTG GCAAGACCTG GGGCCTCAGT GAAGATGTCC

121        TGCAAGGCTT CTGGCTACAC CTTTACTACC TACACGATGC ACTGGGTAAA ACAGAGGCCT

181        GGACAGGGTC TGGAGTGGAT TGGACACATT AATCCTAGCA GTGGATATAC TGAGTACAAT

241        CAGAAATTCA AGGACAAGAC CACACTGACT GCAGACAAAT CCTCCAGCAC AGCCCACATG

301        CAACTGAGCA GCCTAACATC TGAGGACTCT GCGGTCTATT ACTGTGCAAG ACACCCCTGG

361        GACTCGAACT ACTGGGGCCA AGGCACCACT CTCACAGTCT CCTCA (SEQ ID NO: 308)

Signal Peptide (base pairs 1-57):
    1        ATGGAAAGGC ACTGGATCTT TCTCTTCCTG TTGTCAGTAA CTGCAGGTGT CCACTCC      57
             (SEQ ID NO: 309)
/translation = "MERHWIFLFLLSVTAGVHS" (SEQ ID NO: 310)

Framework 1 (base pairs 58-132):
   58        CAG GTCCAGCTGC AGCAGTCTGC AGCTGAACTG GCAAGACCTG GGGCCTCAGT
             GAAGATGTCC TGCAAGGCTT CT (SEQ ID NO: 311)                           132
/translation = "QVQLQQSAAELARPGASVKMSCKAS" (SEQ ID NO: 312)

TABLE 2-continued

Identification and sequencing of the leader and variable regions of anti-HHLA2 monoclonal antibodies including mAbs 8A12, 6D10, 6F10, 8D2, 2G2, 2C4, 4D1, 1C8, and 4E5

```
CDR-H1 (base pairs 133-153):
133        GGCTACAC CTTTACTACC TAC (SEQ ID NO: 313)                    153
/translation = "GYTFTTY" (SEQ ID NO: 314)

Framework 2 (base pairs 154-210):
154        ACGATGC ACTGGGTAAA ACAGAGGCCT GGACAGGGTC TGGAGTGGAT TGGACACATT    210
           (SEQ ID NO: 315)
/translation = "TMHWVKQRPGQGLEWIGHI" (SEQ ID NO: 316)

CDR-H2 (base pairs 211-228):
211        AATCCTAGCA GTGGATAT (SEQ ID NO: 317)                         228
/translation = "NPSSGY" (SEQ ID NO: 318)

Framework 3 (base pairs 229-351):
229        AC TGAGTACAAT CAGAAATTCA AGGACAAGAC CACACTGACT GCAGACAAAT
           CCTCCAGCAC AGCCCACATG CAACTGAGCA GCCTAACATC TGAGGACTCT GCGGTCTATT
           ACTGTGCAAG A (SEQ ID NO: 319)                                351
/translation = "TEYNQKFKDKTTLTADKSSSTAHMQLSSLTSEDSAVYYCAR" (SEQ ID
NO: 320)

CDR-H3 (base pairs 352-372):
352        CACCCCTGG GACTCGAACT AC (SEQ ID NO: 321)                     372
/translation = "HPWDSNY" (SEQ ID NO: 322)

Framework 4 (base pairs 373-405):
373        TGGGGCCA AGGCACCACT CTCACAGTCT CCTCA (SEQ ID NO: 323)         405
/translation = "WGQGTTLTVSS" (SEQ ID NO: 324)
```

MHC2556HCN.1 499.5.4E5.20.22

| Region | Sequence Fragment | Residues | Length |
|---|---|---|---|
| Leader | MERHWIFLFLLSVTAGVHS | 1-19 | 19 |
| HFR1 | QVQLQQSAAELARPGASVKMSCKAS | 20-44 | 25 |
| CDR-H1 | GYTFTTY | 45-51 | 7 |
| HFR2 | TMHWVKQRPGQGLEWIGHI | 52-70 | 19 |
| CDR-H2 | NPSSGY | 71-76 | 6 |
| HFR3 | TEYNQKFKDKTTLTADKSSSTAHMQLSSLTSEDSAVYYCAR | 77-117 | 41 |
| CDR-H3 | HPWDSNY | 118-124 | 7 |
| HFR4 | WGQGTTLTVSS | 125-135 | 11 |

4E5 Light Chain Variable (vL) DNA and Amino Acid Sequences*

```
MHC2556LCN.2;M13. 499.5.4E5.20.22
CDR Analysis
ENIDSY......___AAT.......___QHYYITPFT
Amino Acid Sequence in FASTA format (MHC2556LCN.2\;M13F)
> MHC2556LCN.2\;M13F LOCUS 4E5_vL 381 bp DNA linear FEATURES        Location/Qualifiers
J_segment       352..381
                /label = FWR4

V_segment       325..351
                /label = CDR3

V_region        229..324
                /label = FWR3

V_segment       208..229
                /label = CDR2

V_region        163..207
                /label = FWR2
```

TABLE 2-continued

Identification and sequencing of the leader and variable regions of anti-HHLA2 monoclonal antibodies including mAbs 8A12, 6D10, 6F10, 8D2, 2G2, 2C4, 4D1, 1C8, and 4E5

```
V_segment      130..162
               /label = CDR1

V_region       61..129
               /label = FWR1 sig_peptide    1..60
               /label = LS

CDS            1..381
               /label = 4E5_vL
```

4E5_vL
/translation = "MSVPTQLLGLLLLWLTDARCDIQMTQSPASLSASVGETVTITCRASENIDSYLAWY
QQKQGRSPQLLVYAATNLADGVPSRFSGSGSGTQYSLKINSLQSEDVARYYCQHYYITPFTFGSGTKLEI
K" (SEQ ID NO: 325)

Nucleotide Sequence in FASTA format (MHC2556LCN.2\;M13F)
> MHC2556LCN.2\;M13F
ORIGIN
```
  1       ATGAGTGTGC CCACTCAGCT CCTGGGGTTG CTGCTGCTGT GGCTTACAGA TGCCAGATGT

61       GACATCCAGA TGACTCAGTC TCCAGCTTCC CTGTCTGCAT CTGTGGGAGA AACTGTCACC

121       ATCACATGTC GAGCAAGTGA GAATATTGAC AGTTATTTAG CATGGTATCA GCAGAAACAG

181       GGAAGATCTC CTCAGCTCCT GGTCTATGCT GCAACAAACT TAGCAGATGG TGTGCCATCA

241       AGGTTCAGTG GCAGTGGATC AGGCACACAG TATTCTCTCA AGATCAACAG CCTGCAGTCT

301       GAAGATGTTG CGAGATATTA CTGTCAACAT TATTATATTA CTCCATTCAC GTTCGGCTCG

361       GGGACAAAGT TGGAAATAAA A (SEQ ID NO: 326)
```

Signal Peptide (base pairs 1-60):
```
  1       ATGAGTGTGC CCACTCAGCT CCTGGGGTTG CTGCTGCTGT GGCTTACAGA TGCCAGATGT    60
          (SEQ ID NO: 327)
```
/translation = "MSVPTQLLGLLLLWLTDARC" (SEQ ID NO: 328)

Framework 1 (base pairs 61-129):
```
 61       GACATCCAGA TGACTCAGTC TCCAGCTTCC CTGTCTGCAT CTGTGGGAGA AACTGTCACC
          ATCACATGT (SEQ ID NO: 329)                                           129
```
/translation = "DIQMTQSPASLSASVGETVTITC" (SEQ ID NO: 330)

CDR-L1 (base pairs 130-162):
```
130       C GAGCAAGTGA GAATATTGAC AGTTATTTAG CA (SEQ ID NO: 331)               162
```
/translation = "RASENIDSYLA" (SEQ ID NO: 332)

Framework 2 (base pairs 163-207):
```
163       TGGTATCA GCAGAAACAG GGAAGATCTC CTCAGCTCCT GGTCTAT (SEQ ID NO: 333)  207
```
/translation = "WYQQKQGRSPQLLVY" (SEQ ID NO: 334)

CDR-L2 (base pairs 208-228):
```
208       GCT GCAACAAACT TAGCAGAT (SEQ ID NO: 335)                            228
```
/translation = "AATNLAD" (SEQ ID NO: 336)

Framework 3 (base pairs 229-324):
```
229       GG TGTGCCATCA AGGTTCAGTG GCAGTGGATC AGGCACACAG TATTCTCTCA
          AGATCAACAG CCTGCAGTCT GAAGATGTTG CGAGATATTA CTGT (SEQ ID NO: 337)   324
```
/translation = "GVPSRFSGSGSGTQYSLKINSLQSEDVARYYC" (SEQ ID NO: 338)

CDR-L3 (base pairs 325-351):
```
325       CAACAT TATTATATTA CTCCATTCAC G (SEQ ID NO: 339)                     351
```
/translation = "QHYYITPFT" (SEQ ID NO: 340)

Framework 4 (base pairs 352-381):
```
352       TTCGGCTCG GGGACAAAGT TGGAAATAAA A (SEQ ID NO: 341)                  381
```
/translation = "FGSGTKLEIK" (SEQ ID NO: 342)

MHC2556LCN.2 499.5.4E5.20.22

TABLE 2-continued

Identification and sequencing of the leader and variable regions of
anti-HHLA2 monoclonal antibodies including mAbs 8A12, 6D10, 6F10, 8D2,
2G2, 2C4, 4D1, 1C8, and 4E5

| Region | Sequence Fragment | Residues | Length |
| --- | --- | --- | --- |
| Leader | MSVPTQLLGLLLLWLTDARC | 1-20 | 20 |
| LFR1 | DIQMTQSPASLSASVGETVTITC | 21-43 | 23 |
| CDR-L1 | RASENIDSYLA | 44-54 | 11 |
| LFR2 | WYQQKQGRSPQLLVY | 55-69 | 15 |
| CDR-L2 | AATNLAD | 70-76 | 7 |
| LFR3 | GVPSRFSGSGSGTQYSLKINSLQSEDVARYYC | 77-108 | 32 |
| CDR-L3 | QHYYITPFT | 109-117 | 9 |
| LFR4 | FGSGTKLEIK | 118-127 | 10 |

*CDR definitions and protein sequence numbering according to Kabat. CDR amino acid sequences are underlined in order of CDR1, CDR2, and CDR3, respectively.

TABLE 3

Summary of Anti-HHLA2 mAb binding and ligand blocking characteristics

| HHLA2 mAb (Isotype) | 8A12 (IgG2a) | 6DI0 (IgG1) | 6F10 (IgG1) | 8D2 (IgG2a) | 2G2 (IgG1) | 2C4 (IgG1) | 4D1 (IgG1) | 1C8 (IgG2a) | 4E5 (IgG1) |
| --- | --- | --- | --- | --- | --- | --- | --- | --- | --- |
| [1]Binding EC50 (ug/ml) | [3]nd | 22.49 | 0.25 | [3]nd | 0.21 | 0.24 | 0.44 | 0.63 | [3]nd |
| [2]Function | IHC, WB | Non Blocker | Blocker | IHC, WB | Weak Blocker | Augments Binding | Blocker | Non Blocker | Blocker |

[1]Binding to HHLA2 transfected 300.19 mouse pre-B cell leukemic cell line by flow cytometry
[2]Blockade of HHLA2-mIgG2a binding to TMIGD2 transfected 300.19 mouse pre-B cell leukemic cell line by flow cytometry
[3]not determined: 8A12-not measurable due to low binding; 4E5 -culture supernatants III. Nucleic Acids, Vectors, and Recombinant Host Cells A further object of the invention relates to nucleic acid sequences encoding monoclonal antibodies and fragments thereof, immunoglobulins, and polypeptides of the present invention.

For example, in a particular embodiment, the present invention relates, in part, to a nucleic acid sequence encoding the vH domain of mAb 8A12, or the vL domain of mAb 8A12. In another particular embodiment, the present invention relates, in part, to a nucleic acid sequence encoding the vH domain or the vL domain of at least one effective anti-HHLA2 mAb isolated from the polyclonal antibodies 1.2 and/or 2.2.

Typically, said nucleic acid is a DNA or RNA molecule, which may be included in any suitable vector, such as a plasmid, cosmid, episome, artificial chromosome, phage or a viral vector.

The terms "vector", "cloning vector" and "expression vector" mean the vehicle by which a DNA or RNA sequence (e.g. a foreign gene) can be introduced into a host cell, so as to transform the host and promote expression (e.g. transcription and translation) of the introduced sequence. Thus, a further object of the invention relates to a vector comprising a nucleic acid of the present invention.

Such vectors may comprise regulatory elements, such as a promoter, enhancer, terminator and the like, to cause or direct expression of said polypeptide upon administration to a subject. Examples of promoters and enhancers used in the expression vector for animal cell include early promoter and enhancer of SV40 (Mizukami T. et al. 1987), LTR promoter and enhancer of Moloney mouse leukemia virus (Kuwana Y et al. 1987), promoter (Mason J O et al. 1985) and enhancer (Gillies S D et al. 1983) of immunoglobulin H chain and the like.

Any expression vector for animal cell can be used. Examples of suitable vectors include pAGE107 (Miyaji H et al. 1990), pAGE103 (Mizukami T et al. 1987), pHSG274 (Brady G et al. 1984), pKCR (O'Hare K et al. 1981), pSG1 beta d2-4-(Miyaji H et al. 1990) and the like. Other representative examples of plasmids include replicating plasmids comprising an origin of replication, or integrative plasmids, such as for instance pUC, pcDNA, pBR, and the like. Representative examples of viral vector include adenoviral, retroviral, herpes virus and AAV vectors. Such recombinant viruses may be produced by techniques known in the art, such as by transfecting packaging cells or by transient transfection with helper plasmids or viruses. Typical examples of virus packaging cells include PA317 cells, PsiCRIP cells, GPenv-positive cells, 293 cells, etc. Detailed protocols for producing such replication-defective recombinant viruses may be found for instance in WO 95/14785, WO 96/22378, U.S. Pat. Nos. 5,882,877, 6,013,516, 4,861, 719, 5,278,056 and WO 94/19478.

A further object of the present invention relates to a cell which has been transfected, infected or transformed by a nucleic acid and/or a vector according to the invention. The term "transformation" means the introduction of a "foreign" (i.e. extrinsic or extracellular) gene, DNA or RNA sequence to a host cell, so that the host cell will express the introduced gene or sequence to produce a desired substance, typically a protein or enzyme coded by the introduced gene or sequence. A host cell that receives and expresses introduced DNA or RNA has been "transformed."

The nucleic acids of the present invention may be used to produce a recombinant polypeptide of the invention in a suitable expression system. The term "expression system" means a host cell and compatible vector under suitable conditions, e.g. for the expression of a protein coded for by foreign DNA carried by the vector and introduced to the host cell.

Common expression systems include E. coli host cells and plasmid vectors, insect host cells and Baculovirus vectors, and mammalian host cells and vectors. Other examples of host cells include, without limitation, prokaryotic cells (such as bacteria) and eukaryotic cells (such as yeast cells, mammalian cells, insect cells, plant cells, etc.). Specific examples include E. coli, Kluyveromyces or Saccharomyces yeasts, mammalian cell lines (e.g., Vero cells, CHO cells, 3T3 cells, COS cells, etc.) as well as primary or established mammalian cell cultures (e.g., produced from lymphoblasts, fibroblasts, embryonic cells, epithelial cells, nervous cells, adipocytes, etc.). Examples also include mouse SP2/0-Ag14 cell (ATCC CRL1581), mouse P3X63-Ag8.653 cell (ATCC CRL1580), CHO cell in which a dihydrofolate reductase gene (hereinafter referred to as "DHFR gene") is defective (Urlaub G et al; 1980), rat YB2/3HL.P2.G11.16Ag. 20 cell (ATCC CRL 1662, hereinafter referred to as "YB2/0 cell"), and the like. The YB2/0 cell is preferred, since ADCC activity of chimeric or humanized antibodies is enhanced when expressed in this cell.

The present invention also relates to a method of producing a recombinant host cell expressing an antibody or a polypeptide of the invention according to the invention, said method comprising the steps consisting of (i) introducing in vitro or ex vivo a recombinant nucleic acid or a vector as described above into a competent host cell, (ii) culturing in vitro or ex vivo the recombinant host cell obtained and (iii), optionally, selecting the cells which express and/or secrete said antibody or polypeptide. Such recombinant host cells can be used for the production of antibodies and polypeptides of the invention.

In another aspect, the present invention provides isolated nucleic acids that hybridize under selective hybridization conditions to a polynucleotide disclosed herein. Thus, the polynucleotides of this embodiment can be used for isolating, detecting, and/or quantifying nucleic acids comprising such polynucleotides. For example, polynucleotides of the present invention can be used to identify, isolate, or amplify partial or full-length clones in a deposited library. In some embodiments, the polynucleotides are genomic or cDNA sequences isolated, or otherwise complementary to, a cDNA from a human or mammalian nucleic acid library. Preferably, the cDNA library comprises at least 80% full-length sequences, preferably, at least 85% or 90% full-length sequences, and, more preferably, at least 95% full-length sequences. The cDNA libraries can be normalized to increase the representation of rare sequences. Low or moderate stringency hybridization conditions are typically, but not exclusively, employed with sequences having a reduced sequence identity relative to complementary sequences. Moderate and high stringency conditions can optionally be employed for sequences of greater identity. Low stringency conditions allow selective hybridization of sequences having about 70% sequence identity and can be employed to identify orthologous or paralogous sequences. Optionally, polynucleotides of this invention will encode at least a portion of an antibody encoded by the polynucleotides described herein. The polynucleotides of this invention embrace nucleic acid sequences that can be employed for selective hybridization to a polynucleotide encoding an antibody of the present invention. See, e.g., Ausubel, supra; Colligan, supra, each entirely incorporated herein by reference.

IV. Methods of Producing Antibodies

Antibodies and fragments thereof, immunoglobulins, and polypeptides of the present invention may be produced by any technique known in the art, such as, without limitation, any chemical, biological, genetic or enzymatic technique, either alone or in combination.

Knowing the amino acid sequence of the desired sequence, one skilled in the art can readily produce said antibodies or polypeptides, by standard techniques for production of polypeptides. For instance, they can be synthesized using well-known solid phase method, preferably using a commercially available peptide synthesis apparatus (such as that made by Applied Biosystems, Foster City, Calif.) and following the manufacturer's instructions. Alternatively, antibodies and other polypeptides of the present invention can be synthesized by recombinant DNA techniques as is well-known in the art. For example, these fragments can be obtained as DNA expression products after incorporation of DNA sequences encoding the desired (poly) peptide into expression vectors and introduction of such vectors into suitable eukaryotic or prokaryotic hosts that will express the desired polypeptide, from which they can be later isolated using well-known techniques.

In particular, the present invention further relates to a method of producing an antibody or a polypeptide of the invention, which method comprises the steps consisting of: (i) culturing a transformed host cell according to the invention under conditions suitable to allow expression of said antibody or polypeptide; and (ii) recovering the expressed antibody or polypeptide.

Antibodies and other polypeptides of the present invention are suitably separated from the culture medium by conventional immunoglobulin purification procedures such as, for example, protein A-Sepharose, hydroxylapatite chromatography, gel electrophoresis, dialysis, affinity chromatography, ammonium sulfate or ethanol precipitation, acid extraction, anion or cation exchange chromatography, phosphocellulose chromatography, hydrophobic interaction chromatography, hydroxylapatite chromatography and lectin chromatography. High performance liquid chromatography ("HPLC") can also be employed for purification. See, e.g., Colligan, Current Protocols in Immunology, or Current Protocols in Protein Science, John Wiley & Sons, NY, N.Y., (1997-2001), e.g., Chapters 1, 4, 6, 8, 9, 10, each entirely incorporated herein by reference.

Chimeric antibodies (e.g., mouse-human chimeras or non-rodent-human chimeras) of the present invention can be produced by obtaining nucleic sequences encoding $V_L$ and VH domains as previously described, constructing a human chimeric antibody expression vector by inserting them into an expression vector for animal cell having genes encoding human antibody CH and human antibody CL, and expressing the coding sequence by introducing the expression vector into an animal cell. The CH domain of a human chimeric antibody can be any region which belongs to human immunoglobulin, such as the IgG class or a subclass thereof, such as IgG1, IgG2, IgG3 and IgG4. Similarly, the CL of a human chimeric antibody can be any region which belongs to Ig, such as the kappa class or lambda class. chimeric and humanized monoclonal antibodies, comprising both human and non-human portions, which can be made using standard recombinant DNA techniques, are within the scope of the invention. Such chimeric and humanized monoclonal antibodies can be produced by recombinant DNA techniques known in the art, for example using methods described in Robinson et al. International Patent Publication PCT/US86/02269; Akira et al. European Patent Application 184,187; Taniguchi, M. European Patent Application 171, 496; Morrison et al. European Patent Application 173,494; Neuberger et al. PCT Application WO 86/01533; Cabilly et al. U.S. Pat. No. 4,816,567; Cabilly et al. European Patent Application 125,023; Better et al. (1988) Science 240:1041-1043; Liu et al. (1987) Proc. Natl. Acad. Sci. USA 84:3439-3443; Liu et al. (1987) J. Immunol. 139:3521-3526; Sun et al. (1987) Proc. Natl. Acad. Sci. 84:214-218; Nishimura et al. (1987) Cancer Res. 47:999-1005; Wood et al. (1985) Nature 314:446-449; Shaw et al. (1988) J. Natl. Cancer Inst. 80:1553-1559); Morrison, S. L. (1985) Science 229:1202-1207; Oi et al. (1986) Biotechniques 4:214; Winter U.S. Pat. No. 5,225,539; Jones et al. (1986) Nature 321:552-525; Verhoeyan et al. (1988) Science 239:1534; and Beidler et al. (1988) J. Immunol. 141:4053-4060.

In addition, humanized antibodies can be made according to standard protocols such as those disclosed in U.S. Pat. No. 5,565,332. In another embodiment, antibody chains or specific binding pair members can be produced by recombination between vectors comprising nucleic acid molecules encoding a fusion of a polypeptide chain of a specific binding pair member and a component of a replicable generic display package and vectors containing nucleic acid molecules encoding a second polypeptide chain of a single binding pair member using techniques known in the art, e.g., as described in U.S. Pat. Nos. 5,565,332, 5,871,907, or 5,733,743. Humanized antibodies of the present invention can be produced by obtaining nucleic acid sequences encoding CDR domains, as previously described, constructing a humanized antibody expression vector by inserting them into an expression vector for animal cell having genes encoding (i) a heavy chain constant region identical to that of a human antibody and (ii) a light chain constant region identical to that of a human antibody, and expressing the genes by introducing the expression vector into an animal cell. The humanized antibody expression vector may be either of a type in which a gene encoding an antibody heavy chain and a gene encoding an antibody light chain exists on separate vectors or of a type in which both genes exist on the same vector (tandem type).

Methods for producing humanized antibodies based on conventional recombinant DNA and gene transfection techniques are well-known in the art (See, e.g., Riechmann L. et al. 1988; Neuberger M S. et al. 1985). Antibodies can be humanized using a variety of techniques known in the art including, for example, CDR-grafting (EP 239,400; PCT publication WO91/09967; U.S. Pat. Nos. 5,225,539; 5,530, 101; and 5,585,089), veneering or resurfacing (EP 592,106; EP 519,596; Padlan EA (1991); Studnicka G M et al. (1994); Roguska M A. et al. (1994)), and chain shuffling (U.S. Pat. No. 5,565,332). The general recombinant DNA technology for preparation of such antibodies is also known (see European Patent Application EP 125023 and International Patent Application WO 96/02576).

Similarly, bispecific or multispecific antibodies described herein can be made according to standard procedures. For example, triomas and hybrid hybridomas are two examples of cell lines that can secrete bispecific or multispecific antibodies. Examples of bispecific and multispecific antibodies produced by a hybrid hybridoma or a trioma are disclosed in U.S. Pat. No. 4,474,893. Such antibodies can also be constructed by chemical means (Staerz et al. (1985) Nature 314:628, and Perez et al. (1985) Nature 316:354) and hybridoma technology (Staerz and Bevan (1986) Proc. Natl. Acad. Sci. USA, 83:1453, and Staerz and Bevan (1986) Immunol. Today 7:241). Alternatively, such antibodiescan also be generated by making heterohybridomas by fusing hybridomas or other cells making different antibodies, followed by identification of clones producing and co-assembling the desired antibodies. They can also be generated by chemical or genetic conjugation of complete immunoglobulin chains or portions thereof such as Fab and Fv sequences. The antibody component can bind to a polypeptide or a fragment thereof of one or more biomarkers of the invention, including one or more immunoinhibitory biomarkers described herein.

In addition, methods for producing antibody fragments are well-known. For example, Fab fragments of the present invention can be obtained by treating an antibody which specifically reacts with human HHLA2 (such as mAb 8A12 and polyclonal antibodies 1.2 and 2.2) with a protease such as papain. Also, Fabs can be produced by inserting DNA encoding Fabs of the antibody into a vector for prokaryotic expression system, or for eukaryotic expression system, and introducing the vector into a procaryote or eucaryote (as appropriate) to express the Fabs.

Similarly, F(ab')2 fragments of the present invention can be obtained treating an antibody which specifically reacts with HHLA2 with a protease, pepsin. Also, the F(ab')2 fragment can be produced by binding Fab' described below via a thioether bond or a disulfide bond.

Fab' fragments of the present invention can be obtained treating F(ab')2 which specifically reacts with human HHLA2 with a reducing agent, dithiothreitol. Also, the Fab' fragments can be produced by inserting DNA encoding a Fab' fragment of the antibody into an expression vector for prokaryote, or an expression vector for eukaryote, and introducing the vector into a prokaryote or eukaryote (as appropriate) to perform its expression.

In addition, scFvs of the present invention can be produced by obtaining cDNA encoding the VH and $V_L$ domains as previously described, constructing DNA encoding scFv, inserting the DNA into an expression vector for prokaryote, or an expression vector for eukaryote, and then introducing the expression vector into a prokaryote or eukaryote (as appropriate) to express the scFv. To generate a humanized scFv fragment, a well-known technology called CDR grafting may be used, which involves selecting the complementary determining regions (CDRs) from a donor scFv fragment, and grafting them onto a human scFv fragment framework of known three dimensional structure (see, e.g., WO98/45322; WO 87/02671; U.S. Pat. Nos. 5,859,205; 5,585,089; 4,816,567; EP0173494).

V. Modification of Antibodies, Immunoglobulins, and Polypeptides

Amino acid sequence modification(s) of the antibodies described herein are contemplated. For example, it may be desirable to improve the binding affinity and/or other biological properties of the antibody. It is known that when a humanized antibody is produced by simply grafting only CDRs in VH and VL of an antibody derived from a non-human animal in FRs of the VH and VL of a human antibody, the antigen binding activity is reduced in comparison with that of the original antibody derived from a non-human animal. It is considered that several amino acid residues of the VH and VL of the non-human antibody, not only in CDRs but also in FRs, are directly or indirectly associated with the antigen binding activity. Hence, substitution of these amino acid residues with different amino acid residues derived from FRs of the VH and VL of the human antibody would reduce binding activity and can be corrected by replacing the amino acids with amino acid residues of the original antibody derived from a non-human animal.

Modifications and changes may be made in the structure of the antibodies of the present invention, and in the DNA sequences encoding them, and still obtain a functional molecule that encodes an antibody and polypeptide with desirable characteristics. For example, certain amino acids may be substituted by other amino acids in a protein structure without appreciable loss of activity. Since the interactive capacity and nature of a protein define the protein's biological functional activity, certain amino acid substitutions can be made in a protein sequence, and, of course, in its DNA encoding sequence, while nevertheless obtaining a protein with like properties. It is thus contemplated that various changes may be made in the antibodies sequences of the invention, or corresponding DNA sequences which encode said polypeptides, without appreciable loss of their biological activity.

In one embodiment, amino acid changes may be achieved by changing codons in the DNA sequence to encode conservative substitutions based on conservation of the genetic code. Specifically, there is a known and definite correspondence between the amino acid sequence of a particular protein and the nucleotide sequences that can code for the protein, as defined by the genetic code (shown below). Likewise, there is a known and definite correspondence between the nucleotide sequence of a particular nucleic acid and the amino acid sequence encoded by that nucleic acid, as defined by the genetic code (see genetic code chart above).

As described above, an important and well-known feature of the genetic code is its redundancy, whereby, for most of the amino acids used to make proteins, more than one coding nucleotide triplet may be employed (illustrated above). Therefore, a number of different nucleotide sequences may code for a given amino acid sequence. Such nucleotide sequences are considered functionally equivalent since they result in the production of the same amino acid sequence in all organisms (although certain organisms may translate some sequences more efficiently than they do others). Moreover, occasionally, a methylated variant of a purine or pyrimidine may be found in a given nucleotide sequence. Such methylations do not affect the coding relationship between the trinucleotide codon and the corresponding amino acid.

In making the changes in the amino sequences of polypeptide, the hydropathic index of amino acids may be considered. The importance of the hydropathic amino acid index in conferring interactive biologic function on a protein is generally understood in the art. It is accepted that the relative hydropathic character of the amino acid contributes to the secondary structure of the resultant protein, which in turn defines the interaction of the protein with other molecules, for example, enzymes, substrates, receptors, DNA, antibodies, antigens, and the like. Each amino acid has been assigned a hydropathic index on the basis of their hydrophobicity and charge characteristics these are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophane (−0.9); tyrosine (−1.3); proline (−1.6); histidine (−3.2); glutamate (−3.5); glutamine (−3.5); aspartate (<RTI 3.5); asparagine (−3.5); lysine (−3.9); and arginine (−4.5).

It is known in the art that certain amino acids may be substituted by other amino acids having a similar hydropathic index or score and still result in a protein with similar biological activity, i.e. still obtain a biological functionally equivalent protein.

As outlined above, amino acid substitutions are generally therefore based on the relative similarity of the amino acid side-chain substituents, for example, their hydrophobicity, hydrophilicity, charge, size, and the like. Exemplary substitutions which take various of the foregoing characteristics into consideration are well-known to those of skill in the art and include: arginine and lysine; glutamate and aspartate; serine and threonine; glutamine and asparagine; and valine, leucine and isoleucine.

Another type of amino acid modification of the antibody of the invention may be useful for altering the original glycosylation pattern of the antibody to, for example, increase stability. By "altering" is meant deleting one or more carbohydrate moieties found in the antibody, and/or adding one or more glycosylation sites that are not present in the antibody. Glycosylation of antibodies is typically N-linked. "N-linked" refers to the attachment of the carbohydrate moiety to the side chain of an asparagine residue. The tripeptide sequences asparagine-X-serine and asparagines-X-threonine, where X is any amino acid except proline, are the recognition sequences for enzymatic attachment of the carbohydrate moiety to the asparagine side chain. Thus, the presence of either of these tripeptide sequences in a polypeptide creates a potential glycosylation site. Addition of glycosylation sites to the antibody is conveniently accomplished by altering the amino acid sequence such that it contains one or more of the above-described tripeptide sequences (for N-linked glycosylation sites). Another type of covalent modification involves chemically or enzymatically coupling glycosides to the antibody. These procedures are advantageous in that they do not require production of the antibody in a host cell that has glycosylation capabilities for N- or O-linked glycosylation. Depending on the coupling mode used, the sugar(s) may be attached to (a) arginine and histidine, (b) free carboxyl groups, (c) free sulfhydryl groups such as those of cysteine, (d) free hydroxyl groups such as those of serine, threonine, orhydroxyproline, (e) aromatic residues such as those of phenylalanine, tyrosine, or tryptophan, or (f) the amide group of glutamine. For example, such methods are described in WO87/05330.

Similarly, removal of any carbohydrate moieties present on the antibody may be accomplished chemically or enzymatically. Chemical deglycosylation requires exposure of the antibody to the compound trifluoromethanesulfonic acid, or an equivalent compound. This treatment results in the cleavage of most or all sugars except the linking sugar (N-acetylglucosamine or N-acetylgalactosamine), while leaving the antibody intact. Chemical deglycosylation is described by Sojahr H. et al. (1987) and by Edge, A S. et al. (1981). Enzymatic cleavage of carbohydrate moieties on antibodies can be achieved by the use of a variety of endo- and exo-glycosidases as described by Thotakura, N R. et al. (1987).

Other modifications can involve the formation of immunoconjugates. For example, in one type of covalent modification, antibodies or proteins are covalently linked to one of a variety of non proteinaceous polymers, e.g., polyethylene glycol, polypropylene glycol, or polyoxyalkylenes, in the manner set forth in U.S. Pat. Nos. 4,640,835; 4,496,689; 4,301,144; 4,670,417; 4,791,192 or 4,179,337.

Conjugation of antibodies or other proteins of the present invention with heterologous agents can be made using a variety of bifunctional protein coupling agents including but not limited to N-succinimidyl (2-pyridyldithio) propionate (SPDP), succinimidyl (N-maleimidomethyl)cyclohexane-1-carboxylate, iminothiolane (IT), bifunctional derivatives of imidoesters (such as dimethyl adipimidate HCL), active esters (such as disuccinimidyl suberate), aldehydes (such as glutaraldehyde), bis-azido compounds (such as bis (p-azidobenzoyl) hexanediamine), bis-diazonium derivatives (such as bis-(p-diazoniumbenzoyl)-ethylenediamine), diisocyanates (such as toluene 2,6 diisocyanate), and bis-active fluorine compounds (such as 1,5-difluoro-2,4-dinitrobenzene). For example, carbon labeled 1-isothiocyanatobenzyl methyldiethylene triaminepentaacetic acid (MX-DTPA) is an exemplary chelating agent for conjugation of radionucleotide to the antibody (WO 94/11026).

In another aspect, the present invention features antibodies that specifically bind HHLA2 conjugated to a therapeutic moiety, such as a cytotoxin, a drug, and/or a radioisotope. When conjugated to a cytotoxin, these antibody conjugates are referred to as "immunotoxins." A cytotoxin or cytotoxic agent includes any agent that is detrimental to (e.g., kills) cells. Examples include taxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof. Therapeutic agents include, but are not limited to, antimetabolites (e.g., methotrexate, 6-mercaptopurine, 6-thioguanine, cytarabine, 5-fluorouracil decarbazine), alkylating agents (e.g., mechlorethamine, thioepa chlorambucil, melphalan, carmustine (BSNU) and lomustine (CCNU), cyclothosphamide, busulfan, dibromomannitol, streptozotocin, mitomycin C, and cis-dichlorodiamine platinum (II) (DDP) cisplatin), anthracyclines (e.g., daunorubicin (formerly daunomycin) and doxorubicin), antibiotics (e.g., dactinomycin (formerly actinomycin), bleomycin, mithramycin, and anthramycin (AMC)), and anti-mitotic agents (e.g., vincristine and vinblastine). An antibody of the present invention can be conjugated to a radioisotope, e.g., radioactive iodine, to generate cytotoxic radiopharmaceuticals for treating a related disorder, such as a cancer.

Conjugated anti-HHLA2 antibodies can be used diagnostically or prognostically to monitor polypeptide levels in tissue as part of a clinical testing procedure, e.g., to determine the efficacy of a given treatment regimen or to select patients most likely to response to an immunotherapy. For example, cells can be permeabilized in a flow cytometry assay to allow antibodies that bind HHLA2 (such as mAb 8A12 and polyclonal antibodies 1.2 and 2.2) to target its recognized intracellular epitope and allow detection of the binding by analyzing signals emanating from the conjugated molecules. Detection can be facilitated by coupling (i.e., physically linking) the antibody to a detectable substance. Examples of detectable substances include various enzymes, prosthetic groups, fluorescent materials, luminescent materials, bioluminescent materials, and radioactive materials. Examples of suitable enzymes include horseradish peroxidase, alkaline phosphatase, 0-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate (FITC), rhodamine, dichlorotriazinylamine fluorescein, dansyl chloride or phycoerythrin (PE); an example of a luminescent material includes luminol; examples of bioluminescent materials include luciferase, luciferin, and aequorin, and examples of suitable radioactive material include $^{125}$I, $^{131}$I, $^{35}$S, or $^{3}$H. As used herein, the term "labeled", with regard to the antibody, is intended to encompass direct labeling of the antibody by coupling (i.e., physically linking) a detectable substance, such as a radioactive agent or a fluorophore (e.g. fluorescein isothiocyanate (FITC) or phycoerythrin (PE) or indocyanine (Cy5)) to the antibody, as well as indirect labeling of the antibody by reactivity with a detectable substance.

The antibody conjugates of the present invention can be used to modify a given biological response. The therapeutic moiety is not to be construed as limited to classical chemical therapeutic agents. For example, the drug moiety may be a protein or polypeptide possessing a desired biological activity. Such proteins may include, for example, an enzymatically active toxin, or active fragment thereof, such as abrin, ricin A, *pseudomonas* exotoxin, or diphtheria toxin; a protein such as tumor necrosis factor or interferon-.gamma.; or, biological response modifiers such as, for example, lymphokines, interleukin-1 ("IL-1"), interleukin-2 ("IL-2"), interleukin-6 ("IL-6"), granulocyte macrophage colony stimulating factor ("GM-CSF"), granulocyte colony stimulating factor ("G-CSF"), or other cytokines or growth factors.

Techniques for conjugating such therapeutic moiety to antibodies are well-known, see, e.g., Arnon et al., "Monoclonal Antibodies For Immunotargeting Of Drugs In Cancer Therapy", in Monoclonal Antibodies And Cancer Therapy, Reisfeld et al. (eds.), pp. 243 56 (Alan R. Liss, Inc. 1985); Hellstrom et al., "Antibodies For Drug Delivery", in Controlled Drug Delivery (2nd Ed.), Robinson et al. (eds.), pp. 623 53 (Marcel Dekker, Inc. 1987); Thorpe, "Antibody Carriers Of Cytotoxic Agents In Cancer Therapy: A Review", in Monoclonal Antibodies '84: Biological And Clinical Applications, Pinchera et al. (eds.), pp. 475 506 (1985); "Analysis, Results, And Future Prospective Of The Therapeutic Use Of Radiolabeled Antibody In Cancer Therapy", in Monoclonal Antibodies For Cancer Detection And Therapy, Baldwin et al. (eds.), pp. 303 16 (Academic Press 1985), and Thorpe et al., "The Preparation And Cytotoxic Properties Of Antibody-Toxin Conjugates", Immunol. Rev., 62:119 58 (1982).

In some embodiments, conjugations can be made using a "cleavable linker" facilitating release of the cytotoxic agent or growth inhibitory agent in a cell. For example, an acid-labile linker, peptidase-sensitive linker, photolabile linker, dimethyl linker or disulfide-containing linker (See e.g. U.S. Pat. No. 5,208,020) may be used. Alternatively, a fusion protein comprising the antibody and cytotoxic agent or growth inhibitory agent may be made, by recombinant techniques or peptide synthesis. The length of DNA may comprise respective regions encoding the two portions of the conjugate either adjacent one another or separated by a region encoding a linker peptide which does not destroy the desired properties of the conjugate.

VI. Uses and Methods of the Present Invention

The anti-HHLA2 antibodies, immunoglobulins, polypeptides, and nucleic acids of the present invention described herein can be used in numerous predictive medicine assays (e.g., diagnostic assays, prognostic assays, and monitoring clinical trials) based on detection of HHLA2 levels and, in some embodiments and can be useful for therapeutic purposes (e.g., therapeutic and prophylactic) either alone or when conjugated to toxic compounds or other therapeutics.

The term "detection" as used herein includes qualitative and/or quantitative detection (measuring levels) with or without reference to a control. As described herein, a HHLA2 polypeptide or fragment thereof of the present invention has one or more of the following activities: 1) binds to and/or modulates the activity of its natural binding partner(s), such as TMIGD2 and/or KIR3DL3; 2) modulates intra- or intercellular signaling, such as co-immunoinhibitory signaling; 3) modulates activation and/or proliferation of lymphocytes; 4) modulates the immune response of an organism, e.g., a mammalian organism, such as a mouse, a non-rodent animal, or human; and 5) modulates immune cell anergy.

Thus, one aspect of the present invention relates to diagnostic assays for determining HHLA2 polypeptide levels in the context of a biological sample (e.g., blood, serum, cells, or tissue) to thereby determine the level of HHLA2 polypeptide in the sample, to determine whether an individual is afflicted with a disorder and/or to determine the state of such a disorder, indicated by such HHLA2 levels. For example, antibodies of the present invention are useful for staging cancer diseases associated with HHLA2.

The present invention also provides for prognostic (or predictive) assays for determining whether an individual is at risk of developing such a disorder. Another aspect of the present invention pertains to monitoring the influence of agents (e.g., drugs, compounds) on the expression or activity of HHLA2 in clinical trials.

The present invention also provides for detection of HHLA2 as a means to identify agents that transduce a HHLA2 signal. Agents that transduce a HHLA2 signal would attenuate immune responses and might be useful in autoimmune diseases, asthma, and for the establishment of tolerance.

In any method described herein, HHLA2 can be detected either alone or in combination with the expression of other molecules, such as other immune checkpoint and/or costimulatory molecules. Combinatorial detection (e.g., sequentially or simultaneously) of several molecules can provide useful information regarding synergies of therapeutic intervention and/or personalized, higher-resolution diagnoses of disorder subtypes. In some embodiments, HHLA2 is combinatorially detected with one more markers.

1. Diagnostic Assays

The present invention provides, in part, methods, systems, and code for accurately classifying whether a biological sample expresses cell-restricted HHLA2 and/or whether the levels of cell-restricted HHLA2 are modulated (e.g., upregulated or downregulated), thereby indicative of the state of a disorder of interest, such as cancer. In some embodiments, the present invention is useful for classifying a sample (e.g., from a subject) as associated with or at risk for cancer or a subtype thereof, mediated by HHLA2 using a statistical algorithm and/or empirical data (e.g., the presence, absence, or level of HHLA2).

An exemplary method for detecting the level of HHLA2 or fragments thereof, and thus useful for classifying whether a sample is associated with a disease or disorder mediated by an aberrant expression (e.g., upregulation or downregulation) of HHLA2 or a clinical subtype thereof involves obtaining a biological sample from a test subject and contacting the biological sample with an antibody or antigen-binding fragment thereof of the present invention capable of detecting HHLA2 such that the level of HHLA2 is detected in the biological sample. In some embodiments, at least one antibody or antigen-binding fragment thereof is used, wherein two, three, four, five, six, seven, eight, nine, ten, or more such antibodies or antibody fragments can be used in combination (e.g., in sandwich ELISAs) or in serial. In certain instances, the statistical algorithm is a single learning statistical classifier system. For example, a single learning statistical classifier system can be used to classify a sample as a HHLA2 sample based upon a prediction or probability value and the presence or level of HHLA2. The use of a single learning statistical classifier system typically classifies the sample as a HHLA2 sample with a sensitivity, specificity, positive predictive value, negative predictive value, and/or overall accuracy of at least about 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99%.

Other suitable statistical algorithms are well-known to those of skill in the art. For example, learning statistical classifier systems include a machine learning algorithmic technique capable of adapting to complex data sets (e.g., panel of markers of interest) and making decisions based upon such data sets. In some embodiments, a single learning statistical classifier system such as a classification tree (e.g., random forest) is used. In other embodiments, a combination of 2, 3, 4, 5, 6, 7, 8, 9, 10, or more learning statistical classifier systems are used, preferably in tandem. Examples of learning statistical classifier systems include, but are not limited to, those using inductive learning (e.g., decision/classification trees such as random forests, classification and regression trees (C&RT), boosted trees, etc.), Probably Approximately Correct (PAC) learning, connectionist learning (e.g., neural networks (NN), artificial neural networks (ANN), neuro fuzzy networks (NFN), network structures, perceptrons such as multi-layer perceptrons, multi-layer feed-forward networks, applications of neural networks, Bayesian learning in belief networks, etc.), reinforcement learning (e.g., passive learning in a known environment such as naive learning, adaptive dynamic learning, and temporal difference learning, passive learning in an unknown environment, active learning in an unknown environment, learning action-value functions, applications of reinforcement learning, etc.), and genetic algorithms and evolutionary programming. Other learning statistical classifier systems include support vector machines (e.g., Kernel methods), multivariate adaptive regression splines (MARS), Levenberg-Marquardt algorithms, Gauss-Newton algorithms, mixtures of Gaussians, gradient descent algorithms, and learning vector quantization (LVQ). In certain embodiments, the method of the present invention further comprises sending the HLA2 sample classification results to a clinician, e.g., a histopathologist or an oncologist.

In another embodiment, the method of the present invention further provides a diagnosis in the form of a probability that the individual has a condition or disorder associated with HHLA2. For example, the individual can have about a 0%, 5%, 10%, 15%, 20%, 25%, 30%, 35%, 40%, 45%, 50%, 55%, 60%, 65%, 70%, 75%, 80%, 85%, 90%, 95%, or greater probability of having the condition or disorder. In yet another embodiment, the method of the present invention further provides a prognosis of the condition or disorder in the individual. In some instances, the method of classifying a sample as a HHLA2 sample is further based on the symptoms (e.g., clinical factors) of the individual from which the sample is obtained. The symptoms or group of symptoms can be, for example, lymphocyte count, white cell count, erythrocyte sedimentation rate, diarrhea, abdominal pain, cramping, fever, anemia, weight loss, anxiety, depression, and combinations thereof. In some embodiments, the diagnosis of an individual as having a condition or disorder associated with HHLA2 is followed by administering to the individual a therapeutically effective amount of a drug useful for treating one or more symptoms associated with the condition or disorder (e.g., chemotherapeutic agents).

In one embodiment, the methods further involve obtaining a control biological sample (e.g., biological sample from a subject who does not have a condition or disorder mediated by HHLA2), a biological sample from the subject during remission or before developing a condition or disorder mediated by HHLA2, or a biological sample from the subject during treatment for developing a condition or disorder mediated by HHLA2.

An exemplary method for detecting the presence or absence of HHLA2 polypeptide or fragments thereof is an antibody of the present invention, or fragment thereof, capable of binding to a HHLA2 polypeptide, preferably an antibody with a detectable label. Antibodies can be polyclonal, or more preferably, monoclonal. Such agents can be labeled. The term "labeled", with regard to the antibody, is intended to encompass direct labeling of the probe or antibody by coupling (i.e., physically linking) a detectable substance to the probe or antibody, as well as indirect labeling of the probe or antibody by reactivity with another reagent that is directly labeled. Examples of indirect labeling include detection of a primary antibody using a fluorescently labeled secondary antibody. The term "biological sample" is intended to include tissues, cells, and biological fluids isolated from a subject, such as serum, as well as tissues, cells, and fluids present within a subject. That is, the detection method of the present invention can be used to detect HHLA2, or fragments thereof, in a biological sample in vitro as well as in vivo. In vitro techniques for detection of HHLA2 polypeptide include enzyme linked immunosorbent assays (ELISAs), Western blots, immunoprecipitations, immunohistochemistry (IHC), intracellular flow cytometry and related techniques, and immunofluorescence. Furthermore, in vivo techniques for detection of a HHLA2 polypeptide or a fragment thereof include introducing into a subject a labeled anti-HHLA2 antibody. For example, the antibody can be labeled with a radioactive, luminescent, fluorescent, or other similar marker whose presence and location in a subject can be detected by standard imaging techniques, either alone or in combination with imaging for other molecules, such as markers of cell type (e.g., CD8+ T cell markers).

In one embodiment, the biological sample contains polypeptide molecules from the test subject. A preferred biological sample is a serum, tumor microenvironment, peritumoral, or intratumoral, isolated by conventional means from a subject.

In another embodiment, the methods further involve obtaining a control biological sample from a control subject, contacting the control sample with a compound or agent capable of detecting HHLA2 polypeptide, or fragments thereof, such that the presence of HHLA2 polypeptide, or fragments thereof, is detected in the biological sample, and comparing the presence of HHLA2 polypeptide, or fragments thereof, in the control sample with the presence of HHLA2 polypeptide, or fragments thereof in the test sample.

In still other embodiments, the antibodies can be associated with a component or device for the use of the antibodies in an ELISA or RIA. Non-limiting examples include antibodies immobilized on solid surfaces for use in these assays (e.g., linked and/or conjugated to a detectable label based on light or radiation emission as described above). In other embodiments, the antibodies are associated with a device or strip for detection of HHLA2 by use of an immunochromatographic or immunochemical assay, such as in a "sandwich" or competitive assay, immunohistochemistry, immunofluorescence microscopy, and the like. Additional examples of such devices or strips are those designed for home testing or rapid point of care testing. Further examples include those that are designed for the simultaneous analysis of multiple analytes in a single sample. For example, an unlabeled antibody of the invention may be applied to a "capture" HHLA2 polypeptides in a biological sample and the captured (or immobilized) HHLA2 polypeptides may be bound to a labeled form of an anti-HHLA2 antibody of the invention for detection. Other standard embodiments of immunoassays are well-known the skilled artisan, including assays based on, for example, immunodiffusion, immunoelectrophoresis, immunohistopathology, immunohistochemistry, and histopathology.

2. Prognostic Assays

The diagnostic methods described herein can furthermore be utilized to identify subjects having or at risk of developing a disorder associated with HHLA2. As used herein, the term "aberrant" includes a HHLA2 upregulation or downregulation which deviates from the normal HHLA2 levels. Aberrant expression or activity includes increased or decreased expression or activity, as well as expression or activity which does not follow the normal developmental pattern of expression or the subcellular pattern of expression. For example, aberrant HHLA2 levels is intended to include the cases in which a mutation in the HHLA2 gene or regulatory sequence, or amplification of the chromosomal HHLA2 gene, thereof causes upregulation or downregulation of HHLA2. As used herein, the term "unwanted" includes an unwanted phenomenon involved in a biological response such as immune cell activation. For example, the term unwanted includes a HHLA2 which is undesirable in a subject.

Many disorders associated with HHLA2 are known to the skilled artisan, as explained further in the Examples. HHLA2 is expressed by multiple tumor types, including select lymphoid malignancies, virally-induced cancers, and many solid tumors. Generally, HHLA2 is an adverse prognostic marker because it activates immune checkpoint regulators that inhibit strong immune responses against conditions in need thereof. However, immunoinhibition is desired for downregulating immune responses in treating a number of disorders, such as autoimmune diseases, inflammatory diseases, and the like.

The assays described herein, such as the preceding diagnostic assays or the following assays, can be utilized to identify a subject having or at risk of developing a disorder associated with a misregulation of HHLA2 activation. Thus, the present invention provides a method for identifying a disorder associated with aberrant or unwanted HHLA2 activation in which a test sample is obtained from a subject and HHLA2 is detected, wherein the presence of HHLA2 polypeptide is diagnostic for a subject having or at risk of developing the disorder associated with aberrant or unwanted HHLA2 activity. As used herein, a "test sample" refers to a biological sample obtained from a subject of interest. For example, a test sample can be a biological fluid (e.g., cerebrospinal fluid or serum), cell sample, or tissue, such as a histopathological slide of the tumor microenvironment, peritumoral area, and/or intratumoral area. In a preferred embodiment, the sample comprises cells expressing mature membrane-bound HHLA2 and/or HHLA2 fragments.

Furthermore, the prognostic assays described herein can be used to determine whether a subject can be administered an agent (e.g., an agonist, antagonist, peptidomimetic, polypeptide, peptide, nucleic acid, small molecule, or other drug candidate) to treat such a disorder associated with aberrant or unwanted HHLA2 activity. For example, such methods can be used to determine whether a subject can be effectively treated with one or a combination of agents. Thus, the present invention provides methods for determining whether a subject can be effectively treated with one or more agents for treating a disorder associated with aberrant or unwanted HHLA2 activation in which a test sample is obtained and HHLA2 is detected (e.g., wherein the abundance of HHLA2 polypeptide is diagnostic for a subject that can be administered the agent to treat the disorder associated with aberrant or unwanted HHLA2 activation).

The methods described herein may be performed, for example, by utilizing pre-packaged diagnostic kits comprising at least one antibody reagent described herein, which may be conveniently used, e.g., in clinical settings to diagnose patients exhibiting symptoms or family history of a disease or illness involving HHLA2.

Furthermore, any cell type or tissue in which HHLA2 is expressed may be utilized in the prognostic assays described herein.

Another aspect of the present invention includes uses of the compositions and methods described herein for association and/or stratification analyses in which the HHLA2 in biological samples from individuals with a disorder associated with aberrant HHLA2 activation, are analyzed and the information is compared to that of controls (e.g., individuals who do not have the disorder; controls may be also referred to as "healthy" or "normal" individuals or at early timepoints in a given time lapse study) who are preferably of similar age and race. The appropriate selection of patients and controls is important to the success of association and/or stratification studies. Therefore, a pool of individuals with well-characterized phenotypes is extremely desirable. Criteria for disease diagnosis, disease predisposition screening, disease prognosis, determining drug responsiveness (pharmacogenomics), drug toxicity screening, etc. are described herein.

Different study designs may be used for genetic association and/or stratification studies (Modern Epidemiology, Lippincott Williams & Wilkins (1998), 609-622). Observational studies are most frequently carried out in which the response of the patients is not interfered with. The first type of observational study identifies a sample of persons in whom the suspected cause of the disease is present and another sample of persons in whom the suspected cause is absent, and then the frequency of development of disease in the two samples is compared. These sampled populations are called cohorts, and the study is a prospective study. The other type of observational study is case-control or a retrospective study. In typical case-control studies, samples are collected from individuals with the phenotype of interest (cases) such as certain manifestations of a disease, and from individuals without the phenotype (controls) in a population (target population) that conclusions are to be drawn from. Then the possible causes of the disease are investigated retrospectively. As the time and costs of collecting samples in case-control studies are considerably less than those for prospective studies, case-control studies are the more commonly used study design in genetic association studies, at least during the exploration and discovery stage.

After all relevant phenotypic and/or genotypic information has been obtained, statistical analyses are carried out to determine if there is any significant correlation between the presence of an allele or a genotype with the phenotypic characteristics of an individual. Preferably, data inspection and cleaning are first performed before carrying out statistical tests for genetic association. Epidemiological and clinical data of the samples can be summarized by descriptive statistics with tables and graphs well-known in the art. Data validation is preferably performed to check for data completion, inconsistent entries, and outliers. Chi-squared tests and t-tests (Wilcoxon rank-sum tests if distributions are not normal) may then be used to check for significant differences between cases and controls for discrete and continuous variables, respectively.

An important decision in the performance of genetic association tests is the determination of the significance level at which significant association can be declared when the p-value of the tests reaches that level. In an exploratory analysis where positive hits will be followed up in subsequent confirmatory testing, an unadjusted p-value <0.2 (a significance level on the lenient side), for example, may be used for generating hypotheses for significant association of a HHLA2 level with certain phenotypic characteristics of a disease. It is preferred that a p-value <0.05 (a significance level traditionally used in the art) is achieved in order for the level to be considered to have an association with a disease. When hits are followed up in confirmatory analyses in more samples of the same source or in different samples from different sources, adjustment for multiple testing will be performed as to avoid excess number of hits while maintaining the experiment-wise error rates at 0.05. While there are different methods to adjust for multiple testing to control for different kinds of error rates, a commonly used but rather conservative method is Bonferroni correction to control the experiment-wise or family-wise error rate (Multiple comparisons and multiple tests, Westfall et al, SAS Institute (1999)). Permutation tests to control for the false discovery rates, FDR, can be more powerful (Benjamini and Hochberg, Journal of the Royal Statistical Society, Series B 57, 1289-1300, 1995, Resampling-based Multiple Testing, Westfall and Young, Wiley (1993)). Such methods to control for multiplicity would be preferred when the tests are dependent and controlling for false discovery rates is sufficient as opposed to controlling for the experiment-wise error rates.

Once individual risk factors, genetic or non-genetic, have been found for the predisposition to disease, a classification/prediction scheme can be set up to predict the category (for instance, disease or no-disease) that an individual will be in depending on his phenotype and/or genotype and other non-genetic risk factors. Logistic regression for discrete trait and linear regression for continuous trait are standard techniques for such tasks (Applied Regression Analysis, Draper and Smith, Wiley (1998)). Moreover, other techniques can also be used for setting up classification. Such techniques include, but are not limited to, MART, CART, neural network, and discriminant analyses that are suitable for use in comparing the performance of different methods (The Elements of Statistical Learning, Hastie, Tibshirani & Friedman, Springer (2002)).

3. Monitoring of Effects During Clinical Trials

Monitoring the influence of agents (e.g., compounds, drugs or small molecules) on the HHLA2 polypeptide or a fragment thereof (e.g., the modulation of cell proliferation and/or migration) can be applied not only in basic drug screening, but also in clinical trials. For example, the effectiveness of an agent determined by a screening assay as described herein to decrease HHLA2 gene expression, polypeptide levels, or downregulate HHLA2 activity, can be monitored in clinical trials of subjects exhibiting decreased HHLA2 gene expression, polypeptide levels, or downregulated HHLA2 activity, or can be monitored in clinical trails of subjects exhibiting decreased HHLA2 expression, detectable by the anti-HHLA2 antibodies or fragments described herein. In such clinical trials, the expression or activity of a HHLA2 gene and/or symptoms or markers of the disorder of interest, can be used as a "read out" or marker of the phenotype of a particular cell, tissue, or system. Similarly, the effectiveness of an agent determined by a screening assay as described herein to increase HHLA2 gene expression, polypeptide levels, or increase HHLA2 activity, can be monitored in clinical trials of subjects exhibiting increased HHLA2 gene expression, polypeptide levels, or increased HHLA2 activity, or can be monitored in clinical trails of subjects exhibiting increased HHLA2, detectable by the anti-HHLA2 antibodies or fragments described herein. In such clinical trials, the expression or activity of a HHLA2 gene and/or symptoms or markers of the disorder of interest, can be used as a "read out" or marker of the phenotype of a particular cell, tissue, or system, such as for an autoimmune disorder.

For example, and not by way of limitation, genes, including HHLA2, that are modulated in cells by treatment with an agent (e.g., compound, drug or small molecule) which modulates HHLA2 activity (e.g., identified in a screening assay as described herein) can be identified. Thus, to study the effect of agents on a disorder associated with aberrant HHLA2 activation, for example, in a clinical trial, cells can be isolated and nucleic acids and/or protein prepared and analyzed for the levels of HHLA2 and/or other genes implicated in the disorder associated with aberrant HHLA2 activation. The levels of gene expression (e.g., a gene expression pattern) analyzed by measuring the amount of polypeptide produced, by one of the methods as described herein, or by measuring the levels of HHLA2 or other genes. In this way, the gene expression pattern can serve as a marker, indicative of the physiological response of the cells to the agent. Accordingly, this response state may be determined before, and at various points during treatment of the individual with the agent.

In a preferred embodiment, the present invention provides a method for monitoring the effectiveness of treatment of a subject with an agent (e.g., an agonist, antagonist, peptidomimetic, polypeptide, peptide, nucleic acid, small molecule, or other drug candidate identified by the screening assays described herein) including the steps of (i) obtaining a pre-administration sample from a subject prior to administration of the agent; (ii) detecting the level of HHLA2 polypeptides, or fragments thereof, in the preadministration sample; (iii) obtaining one or more post-administration samples from the subject; (iv) detecting the level of HHLA2 polypeptides, or fragments thereof, in the post-administration samples; (v) comparing the level of the HHLA2 polypeptide, or fragments thereof, in the pre-administration sample with the HHLA2 polypeptide in the post administration sample or samples; and (vi) altering the administration of the agent to the subject accordingly. For example, increased administration of the agent may be desirable to decrease the HHLA2 to lower levels than detected, i.e., to increase the effectiveness of the agent. According to such an embodiment, HHLA2 may be used as an indicator of the effectiveness of an agent, even in the absence of an observable phenotypic response. Similarly, HHLA2 analysis, such as by immunohistochemistry (IHC), can also be used to select patients who will receive HHLA2 immunotherapy to inhibit one ore more immune checkpoints. Patients whose tumors having HHLA2 activation are more likely to respond to HHLA2 mAb immunotherapy, as described herein. The immunotherapy will initially result in immune activation and the activated T cells will express IFN-gamma which in turn will upregulate HHLA2 activation. Normally this would result in HHLA2 engagement and down regulation of the immune response, but because HHLA2 may be blocked by the anti-HHLA2 mAb as described herein, the immune response continues until a desired condition, such as a tumor, is eliminated. By contrast, mAbs that actively signal through HHLA2 directly downregulate an immune response.

4. Therapeutic Methods and Uses

In some embodiments, antibodies, fragments or immunoconjugates of the present invention (e.g., anti-HHLA2 antibodies alone or conjugated to therapeutic moieties) are useful for treating any disorder (e.g., a cancer) associated with aberrant or undesired activation of HHLA2. In certain embodiments, the treatment is of a mammal, such as a human. Such antibodies of the invention may be used alone or in combination with any suitable agent or appropriate therapy to treat the disorder of interest. For example, therapeutic synergies are believed to become manifested when treating a cell comprising HHLA2 and another immune checkpoint or costimulatory molecule.

It is well-known that therapeutic monoclonal antibodies can lead to the depletion of cells extracellularly bearing the antigen specifically recognized by the antibody. This depletion can be mediated through at least three mechanisms: antibody mediated cellular cytotoxicity (ADCC), complement dependent lysis, and direct anti-tumour inhibition of tumour growth through signals given via the antigen targeted by the antibody.

"Complement dependent cytotoxicity" or "CDC" refers to the lysis of a target cell in the presence of complement. Activation of the classical complement pathway is initiated by the binding of the first component of the complement system to antibodies which are bound to their cognate antigen. To assess complement activation, a CDC assay, e.g. as described in Gazzano-Santoro et al. (1997) may be performed.

"Antibody-dependent cell-mediated cytotoxicity" or "ADCC" refers to a form of cytotoxicity in which secreted antibodies bound onto Fc receptors (FcRs) present on certain cytotoxic cells (e.g. Natural Killer (NK) cells, neutrophils, and macrophages) enable these cytotoxic effector cells to bind specifically to an antigen-bearing target cell and subsequently kill the target cell. To assess ADCC activity of a molecule of interest, an in vitro ADCC assay, such as that described in U.S. Pat. No. 5,500,362 or 5,821,337 may be performed. As is well-known in the art, the Fc portions can be engineered to effect a desired interaction or lack thereof with Fc receptors.

For antibody-mediated binding, neutralization, and/or modulation of intracellular targets, certain modifications should be made. As described herein, certain antibody formats, such as sFvs and Fabs, are amenable to intracellular expression of antibody-like molecules. Methods of rmaking and using such adapted antibody-like molecules for targeting expression in different compartments of the cell, including the nucleus, ER, cytoplasm, golgi, plasma membrane, mitochondria, where they counteract antigens or molecules in a specific pathway, are well-known (see, at least U.S. Pat. Publs. 2008-0233110 and 2003-0104402; Marasco et al. (1993) *Proc. Natl. Acad. Sci. U.S.A.* 90:7889-7893; Chen et al. (1994) *Human Gene Therapy* 5:595-601; Chen et al. (1994) *Proc. Natl. Acad. Sci. U.S.A.* 91:5932-5936; Mhashilkar et al. (1995) *EMBO J.* 14:1542-1551; Marasco et al. (1997) *Gene Therapy* 4:11-15; Richardson et al. (1995) *Proc. Natl. Acad. Sci. U.S.A.* 92:3137-3141; and Duan et al. (1994) *Human Gene Therapy* 5:1315-1324).

As used herein, the term "intracellular immunoglobulin molecule" is a complete immunoglobulin which is the same as a naturally-occurring secreted immunoglobulin, but which remains inside of the cell following synthesis. An "intracellular immunoglobulin fragment" refers to any fragment, including single-chain fragments of an intracellular immunoglobulin molecule. Thus, an intracellular immunoglobulin molecule or fragment thereof is not secreted or expressed on the outer surface of the cell. Single-chain intracellular immunoglobulin fragments are referred to herein as "single-chain immunoglobulins." As used herein, the term "intracellular immunoglobulin molecule or fragment thereof" is understood to encompass an "intracellular immunoglobulin," a "single-chain intracellular immunoglobulin" (or fragment thereof), an "intracellular immunoglobulin fragment," an "intracellular antibody" (or fragment thereof), and an "intrabody" (or fragment thereof). As such, the terms "intracellular immunoglobulin," "intracellular Ig," "intracellular antibody," and "intrabody" may be used interchangeably herein, and are all encompassed by the generic definition of an "intracellular immunoglobulin molecule, or fragment thereof." An intracellular immunoglobulin molecule, or fragment thereof of the present invention may, in some embodiments, comprise two or more subunit polypeptides, e.g., a "first intracellular immunoglobulin subunit polypeptide" and a "second intracellular immunoglobulin subunit polypeptide." However, in other embodiments, an intracellular immunoglobulin may be a "single-chain intracellular immunoglobulin" including only a single polypeptide. As used herein, a "single-chain intracellular immunoglobulin" is defined as any unitary fragment that has a desired activity, for example, intracellular binding to an antigen. Thus, single-chain intracellular immunoglobulins encompass those which comprise both heavy and light chain variable regions which act together to bind antigen, as well as single-chain intracellular immunoglobulins which only have a single variable region which binds antigen, for example, a "camelized" heavy chain variable region as described herein. An intracellular immunoglobulin or Ig fragment may be expressed anywhere substantially within the cell, such as in the cytoplasm, on the inner surface of the cell membrane, or in a subcellular compartment (also referred to as cell subcompartment or cell compartment) such as the nucleus, golgi, endoplasmic reticulum, endosome, mitochondria, etc. Additional cell subcompartments include those that are described herein and well-known in the art.

Such intracellular immunoglobulins are expressed in a recipient cell or host cell containing the antigen to be targeted. A host cell of the present invention is preferably a eukaryotic cell or cell line, preferably a plant, animal, vertebrate, mammalian, rodent, mouse, primate, or human cell or cell line.

Without being bound by theory, it is believed that intracellular expression of the immunoglobulin polypeptides described herein allow for the intracellular targeting and binding to HHLA2 to thereby sterically modulate the molecule's ability to signal by, for example, modulating its ability to propagate signaling upon activation by binding to inhibitory receptors, and the like and/or to modulate signaling upon increasing the local effective concentration of multiple HHLA2 molecules.

In some embodiments, antibodies of the present invention can be conjugated to a therapeutic moiety, such as a growth inhibitory agent, cytotoxic agent, or a prodrug-activating enzyme as previously described. Antibodies of the invention can be useful for targeting said growth inhibitory agent, cytotoxic agent, or a prodrug to a cell that under- or over-expresses the desired amount of HHLA2.

Thus, an object of the invention relates to a method for treating a disorder associated with aberrant HHLA2 activation comprising administering a subject in need thereof with a therapeutically effective amount of an antibody, fragment or immunoconjugate of the present invention.

Alternatively, in some embodiments, the antibodies or the antigen-binding fragments of the present invention are useful for therapeutic applications, in addition to diagnostic, prognostic, and prevention applications regarding upregulating an immune response. Upregulation of immune responses can be in the form of enhancing an existing immune response or eliciting an initial immune response. For instance, enhancing an immune response using the subject compositions and methods is useful in cases of improving an immunological defense against cancer and infections with microbes (e.g., bacteria, viruses, or parasites). For example, upregulation or enhancement of an immune response function, as described herein, is useful in the induction of tumor immunity.

In another embodiment, the immune response can be stimulated by the methods described herein, such that pre-existing tolerance, clonal deletion, and/or exhaustion (e.g., T cell exhaustion) is overcome. For example, immune responses against antigens to which a subject cannot mount a significant immune response, e.g., to an autologous antigen, such as a tumor specific antigens can be induced by administering appropriate agents described herein that upregulate the immune response. In one embodiment, an autologous antigen, such as a tumor-specific antigen, can be coadministered. In another embodiment, an immune response can be stimulated against an antigen (e.g., an autologous antigen) to treat a neurological disorder. In another embodiment, the subject agents can be used as adjuvants to boost responses to foreign antigens in the process of active immunization.

In certain instances, it may be desirable to further administer other agents that upregulate immune responses, for example, forms of other B7 family members that transduce signals via costimulatory receptors, in order to further augment the immune response. Also, agents that upregulate an immune response can be used prophylactically in vaccines against various polypeptides (e.g., polypeptides derived from pathogens). Immunity against a pathogen (e.g., a virus) can be induced by vaccinating with a viral protein along with an agent that upregulates an immune response, in an appropriate adjuvant.

Alternatively, in some embodiments, the antibodies and the antigen-binding fragments of the present invention are useful for therapeutic applications, in addition to diagnostic, prognostic, and prevention applications (such as treating, and delaying the onset or progression of the diseases), to inhibit diseases that upregulate the immune reaction, for example, asthma, autoimmune diseases (glomerular nephritis, arthritis, dilated cardiomyopathy-like disease, ulceous colitis, Sjogren syndrome, Crohn disease, systemic erythematodes, chronic rheumatoid arthritis, multiple sclerosis, psoriasis, allergic contact dermatitis, polymyosiis, *pachyderma*, periarteritis nodosa, rheumatic fever, vitiligo vulgaris, insulin dependent diabetes mellitus, Behcet disease, Hashimoto disease, Addison disease, dermatomyositis, myasthenia gravis, Reiter syndrome, Graves' disease, anaemia perniciosa, Goodpasture syndrome, sterility disease, chronic active hepatitis, pemphigus, autoimmune thrombopenic purpura, and autoimmune hemolytic anemia, active chronic hepatitis, Addison's disease, anti-phospholipid syndrome, atopic allergy, autoimmune atrophic gastritis, achlorhydra autoimmune, celiac disease, Cushing's syndrome, dermatomyositis, discoid lupus, erythematosis, Goodpasture's syndrome, Hashimoto's thyroiditis, idiopathic adrenal atrophy, idiopathic thrombocytopenia, insulin-dependent diabetes, Lambert-Eaton syndrome, lupoid hepatitis, some cases of lymphopenia, mixed connective tissue disease, pemphigoid, pemphigus vulgaris, pernicious anema, phacogenic uveitis, polyarteritis nodosa, polyglandular autosyndromes, primary biliary cirrhosis, primary sclerosing cholangitis, Raynaud's syndrome, relapsing polychondritis, Schmidt's syndrome, limited scleroderma (or crest syndrome), sympathetic ophthalmia, systemic lupus erythematosis, Takayasu's arteritis, temporal arteritis, thyrotoxicosis, type b insulin resistance, ulcerative colitis and Wegener's granulomatosis).

Similarly, the antibodies and the antigen-binding fragments of the present invention are useful for therapeutic applications, in addition to diagnostic, prognostic, and prevention applications (such as treating, and delaying the onset or progression of the diseases) for persistent infectious disease (e.g., viral infectious diseases including HPV, HBV, hepatitis C Virus (HCV), retroviruses such as human immunodeficiency virus (HIV-1 and HIV-2), herpes viruses such as Epstein Barr Virus (EBV), cytomegalovirus (CMV), HSV-1 and HSV-2, and influenza virus. Other antigens associated with pathogens that can be used as described herein are antigens of various parasites, includes malaria, preferably malaria peptide based on repeats of NANP. In addition, bacterial, fungal and other pathogenic diseases are included, such as *Aspergillus, Brugia, Candida, Chlamydia, Coccidia, Cryptococcus, Dirofilaria, Gonococcus, Histoplasma, Leishmania, Mycobacterium, Mycoplasma*, Paramecium, Pertussis, *Plasmodium, Pneumococcus, Pneumocystis, Rickettsia, Salmonella, Shigella, Staphylococcus, Streptococcus, Toxoplasma* and Vibriocholerae. Exemplary species include *Neisseria* gonorrhea, *Mycobacterium tuberculosis, Candida albicans, Candida tropicalis, Trichomonas vaginalis, Haemophilus vaginalis*, Group B *Streptococcus* sp., Microplasma *hominis*, Hemophilus ducreyi, Granuloma inguinale, Lymphopathia venereum, *Treponema pallidum, Brucella abortus. Brucella melitensis, Brucella suis, Brucella canis, Campylobacter fetus, Campylobacter fetus* intestinalis, Leptospira pomona, *Listeria monocytogenes, Brucella ovis, Chlamydia psittaci, Trichomonas foetus, Toxoplasma gondii, Escherichia coli, Actinobacillus equuli, Salmonella abortus ovis, Salmonella abortus equi, Pseudomonas aeruginosa, Corynebacterium equi, Corynebacterium pyogenes, Actinobaccilus seminis, Mycoplasma bovigenitalium, Aspergillus fumigatus, Absidia ramosa, Trypanosoma equiperdum, Babesia caballi, Clostridium tetani, Clostridium botulinum*; or, a fungus, such as, e.g., *Paracoccidioides brasiliensis*; or other pathogen, e.g., *Plasmodium falciparum*. Also included are National Institute of Allergy and Infectious Diseases (NIAID) priority pathogens. These include Category A agents, such as variola major (smallpox), *Bacillus anthracis* (anthrax), *Yersinia pestis* (plague), *Clostridium botulinum* toxin (botulism), *Francisella tularensis* (tularaemia), filoviruses (Ebola hemorrhagic fever, Marburg hemorrhagic fever), arenaviruses (Lassa (Lassa fever), Junin (Argentine hemorrhagic fever) and related viruses); Category B agents, such as *Coxiella burnetti* (Q fever), *Brucella* species (brucellosis), *Burkholderia mallei* (glanders), alphaviruses (Venezuelan encephalomyelitis, eastern & western equine encephalomyelitis), ricin toxin from *Ricinus communis* (castor beans), epsilon toxin of *Clostridium perfringens; Staphylococcus* enterotoxin B, *Salmonella* species, *Shigella dysenteriae, Escherichia coli* strain O157:H7, *Vibrio cholerae, Cryptosporidium parvum*; Category C agents, such as nipah virus, hantaviruses, tickborne hemorrhagic fever viruses, tickborne encephalitis viruses, yellow fever, and multidrug-resistant tuberculosis; helminths, such as *Schistosoma* and *Taenia*; and protozoa, such as *Leishmania* (e.g., *L. mexicana*) and *Plasmodium.*

In still another embodiment, the antibodies or the antigen-binding fragments of the present invention are useful for therapeutic applications, in addition to diagnostic, prognostic, and prevention applications regarding induction of immunological tolerance, organ graft rejection, graft-versus-host disease (GVHD), allergic disease, and diseases caused by attenuation of immune reactions mediated by HHLA2.

In the context of the invention, the term "treating" or "treatment", as used herein, means reversing, alleviating, inhibiting the progress of, or preventing the disorder or condition to which such term applies, or one or more symptoms of such disorder or condition. By the term "treating cancer" as used herein is meant the inhibition of the growth and/or proliferation of cancer cells. Preferably such treatment also leads to the regression of tumor growth (i.e., the decrease in size of a measurable tumor). Most preferably, such treatment leads to the complete regression of the tumor.

In some embodiments, the term "patient" or "patient in need thereof" is intended for a human or non-human mammal affected or likely to be affected with a cancer associated with aberrant activation of HHLA2.

By a "therapeutically effective amount" of the polypeptide of the invention is meant a sufficient amount of the antibody to treat the disorder of interest, such as cancer, at a reasonable benefit/risk ratio applicable to any medical treatment. It will be understood, however, that the total daily usage of the antibodies and compositions of the present invention will be decided by the attending physician within the scope of sound medical judgment. The specific therapeutically effective dose level for any particular patient will depend upon a variety of factors including the disorder being treated and the severity of the disorder; activity of the specific antibody employed; the specific composition employed, the age, body weight, general health, sex and diet of the patient; the time of administration, route of administration, and rate of excretion of the specific antibody employed; the duration of the treatment; drugs used in combination or coincidental with the specific polypeptide employed; and like factors well-known in the medical arts. For example, it is well-known within the skill of the art to start doses of the compound at levels lower than those required to achieve the desired therapeutic effect and to gradually increase the dosage until the desired effect is achieved.

Therapeutic formulations comprising one or more antibodies of the invention are prepared for storage by mixing the antibody having the desired degree of purity with optional physiologically acceptable carriers, excipients or stabilizers (Remington's Pharmaceutical Sciences 16th edition, Osol, A. Ed. (1980)), in the form of lyophilized formulations or aqueous solutions. The antibody composition will be formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners.

The therapeutic dose can be at least about 0.01 µg/kg body weight, at least about 0.05 µg/kg body weight; at least about 0.1 µg/kg body weight, at least about 0.5 µg/kg body weight, at least about 1 µg/kg body weight, at least about 2.5 µg/kg body weight, at least about 5 µg/kg body weight, and not more than about 100 µg/kg body weight. It will be understood by one of skill in the art that such guidelines will be adjusted for the molecular weight of the active agent, e.g. in the use of antibody fragments, or in the use of antibody conjugates. The dosage may also be varied for localized administration, e.g. intranasal, inhalation, etc., or for systemic administration, e.g. i.m., i.p., i.v., and the like.

The composition need not be, but is optionally formulated with one or more agents that potentiate activity, or that otherwise increase the therapeutic effect. These are generally used in the same dosages and with administration routes as used hereinbefore or about from 1 to 99% of the heretofore employed dosages.

Acceptable carriers, excipients, or stabilizers are nontoxic to recipients at the dosages and concentrations employed, and include buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN™ PLURONICS™ or polyethylene glycol (PEG). Formulations to be used for in vivo administration must be sterile. This is readily accomplished by filtration through sterile filtration membranes.

The active ingredients can also be entrapped in microcapsule prepared, for example, by coacervation techniques or by interfacial polymerization, for example, hydroxymethylcellulose or gelatin-microcapsule and poly-(methylmethacylate) microcapsule, respectively, in colloidal drug delivery systems (for example, liposomes, albumin microspheres, microemulsions, nano-particles and nanocapsules) or in macroemulsions. Such techniques are disclosed in Remington's Pharmaceutical Sciences 16th edition, Osol, A. Ed. (1980).

The compositions described herein can be administered by any suitable means, including parenteral, subcutaneous, intraperitoneal, intrapulmonary, and intranasal. Parenteral infusions include intramuscular, intravenous, intraarterial, intraperitoneal, or subcutaneous administration. In addition, the compositions can be suitably administered by pulse infusion, particularly with declining doses of the antibody.

For the prevention or treatment of disease, the appropriate dosage of antibody will depend on the type of disease to be treated, as defined above, the severity and course of the disease, whether the antibody is administered for preventive purposes, previous therapy, the patient's clinical history and response to the antibody, and the discretion of the attending physician. The antibody is suitably administered to the patient at one time or over a series of treatments.

The therapeutic agents of the present invention can be used alone or can be administered in combination therapy with, e.g., chemotherapeutic agents, hormones, antiangiogens, radiolabelled, compounds, or with surgery, cryotherapy, and/or radiotherapy. The preceding treatment methods can be administered in conjunction with other forms of conventional therapy (e.g., standard-of-care treatments for cancer well-known to the skilled artisan), either consecutively with, pre- or post-conventional therapy. For example, agents of the present invention can be administered with a therapeutically effective dose of chemotherapeutic agent. In another embodiment, agents of the present invention are administered in conjunction with chemotherapy to enhance the activity and efficacy of the chemotherapeutic agent. The Physicians' Desk Reference (PDR) discloses dosages of chemotherapeutic agents that have been used in the treatment of various cancers. The dosing regimen and dosages of these aforementioned chemotherapeutic drugs that are therapeutically effective will depend on the particular cancer being treated, the extent of the disease and other factors familiar to the physician of skill in the art, and can be determined by the physician.

The cancer vaccine can also be administered in combination with targeted therapy, e.g., immunotherapy. The term "targeted therapy" refers to administration of agents that selectively interact with a chosen biomolecule to thereby treat cancer. For example, targeted therapy regarding the inhibition of immune checkpoint inhibitor is useful in combination with the methods of the present invention. The term "immune checkpoint inhibitor" means a group of molecules on the cell surface of CD4+ and/or CD8+ T cells that fine-tune immune responses by down-modulating or inhibiting an anti-tumor immune response. Immune checkpoint proteins are well-known in the art and include, without limitation, CTLA-4, PD-1, VISTA, B7-H2, B7-H3, PD-L1, B7-H4, B7-H6, 2B4, ICOS, HVEM, PD-L2, CD160, gp49B, PIR-B, KIR family receptors, TIM-1, TIM-3, TIM-4, LAG-3, BTLA, SIRPalpha (CD47), CD48, 2B4 (CD244), B7.1, B7.2, ILT-2, ILT-4, TIGIT, HHLA2, TMIDG2, KIR3DL3, and A2aR (see, for example, WO 2012/177624). Inhibition of one or more immune checkpoint inhibitors can block or otherwise neutralize inhibitory signaling to thereby upregulate an immune response in order to more efficaciously treat cancer. In some embodiments, the cancer vaccine is administered in combination with one or more inhibitors of immune checkpoints, such as PD1, PD-L1, and/or CD47 inhibitors.

Immunotherapy is one form of targeted therapy that may comprise, for example, the use of additional cancer vaccines and/or sensitized antigen presenting cells. For example, an oncolytic virus is a virus that is able to infect and lyse cancer cells, while leaving normal cells unharmed, making them potentially useful in cancer therapy. Replication of oncolytic viruses both facilitates tumor cell destruction and also produces dose amplification at the tumor site. They may also act as vectors for anticancer genes, allowing them to be specifically delivered to the tumor site. The immunotherapy can involve passive immunity for short-term protection of a host, achieved by the administration of pre-formed antibody directed against a cancer antigen or disease antigen (e.g., administration of a monoclonal antibody, optionally linked to a chemotherapeutic agent or toxin, to a tumor antigen). For example, anti-VEGF and mTOR inhibitors are known to be effective in treating renal cell carcinoma. Immunotherapy can also focus on using the cytotoxic lymphocyte-recognized epitopes of cancer cell lines. Alternatively, antisense polynucleotides, ribozymes, RNA interference molecules, triple helix polynucleotides and the like, can be used to selectively modulate biomolecules that are linked to the initiation, progression, and/or pathology of a tumor or cancer.

The term "untargeted therapy" refers to administration of agents that do not selectively interact with a chosen biomolecule yet treat cancer. Representative examples of untargeted therapies include, without limitation, chemotherapy, gene therapy, and radiation therapy.

In one embodiment, chemotherapy is used. Chemotherapy includes the administration of a chemotherapeutic agent. Such a chemotherapeutic agent may be, but is not limited to, those selected from among the following groups of compounds: platinum compounds, cytotoxic antibiotics, antimetabolites, anti-mitotic agents, alkylating agents, arsenic compounds, DNA topoisomerase inhibitors, taxanes, nucleoside analogues, plant alkaloids, and toxins; and synthetic derivatives thereof. Exemplary compounds include, but are not limited to, alkylating agents: cisplatin, treosulfan, and trofosfamide; plant alkaloids: vinblastine, paclitaxel, docetaxol; DNA topoisomerase inhibitors: teniposide, crisnatol, and mitomycin; anti-folates: methotrexate, mycophenolic acid, and hydroxyurea; pyrimidine analogs: 5-fluorouracil, doxifluridine, and cytosine arabinoside; purine analogs: mercaptopurine and thioguanine; DNA antimetabolites: 2'-deoxy-5-fluorouridine, aphidicolin glycinate, and pyrazoloimidazole; and antimitotic agents: halichondrin, colchicine, and rhizoxin. Compositions comprising one or more chemotherapeutic agents (e.g., FLAG, CHOP) may also be used. FLAG comprises fludarabine, cytosine arabinoside (Ara-C) and G-CSF. CHOP comprises cyclophosphamide, vincristine, doxorubicin, and prednisone. The foregoing examples of chemotherapeutic agents are illustrative, and are not intended to be limiting.

In another embodiment, radiation therapy is used. The radiation used in radiation therapy can be ionizing radiation. Radiation therapy can also be gamma rays, X-rays, or proton beams. Examples of radiation therapy include, but are not limited to, external-beam radiation therapy, interstitial implantation of radioisotopes (I-125, palladium, iridium), radioisotopes such as strontium-89, thoracic radiation therapy, intraperitoneal P-32 radiation therapy, and/or total abdominal and pelvic radiation therapy. For a general overview of radiation therapy, see Hellman, Chapter 16: Principles of Cancer Management: Radiation Therapy, 6th edition, 2001, DeVita et al., eds., J. B. Lippencott Company, Philadelphia. The radiation therapy can be administered as external beam radiation or teletherapy wherein the radiation is directed from a remote source. The radiation treatment can also be administered as internal therapy or brachytherapy wherein a radioactive source is placed inside the body close to cancer cells or a tumor mass. Also encompassed is the use of photodynamic therapy comprising the administration of photosensitizers, such as hematoporphyrin and its derivatives, Vertoporfin (BPD-MA), phthalocyanine, photosensitizer Pc4, demethoxy-hypocrellin A; and 2BA-2-DMHA.

In another embodiment, hormone therapy is used. Hormonal therapeutic treatments can comprise, for example, hormonal agonists, hormonal antagonists (e.g., flutamide, bicalutamide, tamoxifen, raloxifene, leuprolide acetate (LUPRON), LH-RH antagonists), inhibitors of hormone biosynthesis and processing, and steroids (e.g., dexamethasone, retinoids, deltoids, betamethasone, cortisol, cortisone, prednisone, dehydrotestosterone, glucocorticoids, mineralocorticoids, estrogen, testosterone, progestins), vitamin A derivatives (e.g., all-trans retinoic acid (ATRA)); vitamin D3 analogs; antigestagens (e.g., mifepristone, onapristone), or antiandrogens (e.g., cyproterone acetate).

5. Assays and Screening Methods

Another aspect of the present invention relates to screening assays, including non-cell based assays and xenograft animal model assays. In one embodiment, the assays provide a method for identifying agents that modulate HHLA2 signaling, such as in a human or an animal model assay, in order to identify agents that reduce HHLA2 signaling thereby increasing immune responses and/or identify agents that increase HHLA2 signaling thereby decreasing immune responses.

In one embodiment, the present invention relates to assays for screening test agents which bind to, or modulate the biological activity of, at least one biomarker described herein (e.g., in the tables, figures, examples, or otherwise in the specification), such as HHLA2, TMIGD2, and KIR3DL3. In one embodiment, a method for identifying such an agent entails determining the ability of the agent to modulate, e.g. inhibit, the at least one biomarker described herein.

In one embodiment, an assay is a cell-free or cell-based assay, comprising contacting at least one biomarker described herein, with a test agent, and determining the ability of the test agent to modulate (e.g., inhibit) the enzymatic activity of the biomarker, such as by measuring direct binding of substrates or by measuring indirect parameters as described below.

For example, in a direct binding assay, biomarker protein (or their respective target polypeptides or molecules) can be coupled with a radioisotope or enzymatic label such that binding can be determined by detecting the labeled protein or molecule in a complex. For example, the targets can be labeled with $^{125}I$, $^{35}S$, $^{14}C$, or $^{3}H$, either directly or indirectly, and the radioisotope detected by direct counting of radioemmission or by scintillation counting. Alternatively, the targets can be enzymatically labeled with, for example, horseradish peroxidase, alkaline phosphatase, or luciferase, and the enzymatic label detected by determination of conversion of an appropriate substrate to product. Determining the interaction between biomarker and substrate can also be accomplished using standard binding or enzymatic analysis assays. In one or more embodiments of the above described assay methods, it may be desirable to immobilize polypeptides or molecules to facilitate separation of complexed from uncomplexed forms of one or both of the proteins or molecules, as well as to accommodate automation of the assay.

Binding of a test agent to a target can be accomplished in any vessel suitable for containing the reactants. Non-limiting examples of such vessels include microtiter plates, test tubes, and micro-centrifuge tubes. Immobilized forms of the antibodies described herein can also include antibodies bound to a solid phase like a porous, microporous (with an average pore diameter less than about one micron) or macroporous (with an average pore diameter of more than about 10 microns) material, such as a membrane, cellulose, nitrocellulose, or glass fibers; a bead, such as that made of agarose or polyacrylamide or latex; or a surface of a dish, plate, or well, such as one made of polystyrene.

In an alternative embodiment, determining the ability of the agent to modulate the interaction between the biomarker and a substrate or a biomarker and its natural binding partner can be accomplished by determining the ability of the test agent to modulate the activity of a polypeptide or other product that functions downstream or upstream of its position within the signaling pathway (e.g., feedback loops). Such feedback loops are well-known in the art (see, for example, Chen and Guillemin (2009) Int. J. Tryptophan Res. 2:1-19).

HHLA2 status can be measured using the anti-HHLA2 antibodies described herein. A reduction in HHLA2 expression indicates that the agent inhibits HHLA2 activity/signaling and identifies an agent as useful for inhibiting HHLA2 activity/signaling and for increasing immune responses. A reduction in HHLA2 binding to TMIGD2, KIR3DL3, and/or inhibitory receptors indicates that the agent inhibits HHLA2 activity/signaling and identifies an agent as useful for inhibiting HHLA2 activity/signaling and for increasing immune responses. By contrast, an increase in HHLA2 expression indicates that the agent promotes HHLA2 activity/signaling and identifies an agent as useful for promoting HHLA2 activity/signaling and for reducing immune responses. an increase in HHLA2 binding to TMIGD2, KIR3DL3, and/or inhibitory receptors indicates that the agent promotes HHLA2 activity/signaling and identifies an agent as useful for promoting HHLA2 activity/signaling and for reducing immune responses.

The present invention further pertains to novel agents identified by the above-described screening assays. Accordingly, it is within the scope of this invention to further use an agent identified as described herein, such as in an appropriate animal model. For example, an agent identified as described herein can be used in an animal model to determine the efficacy, toxicity, or side effects of treatment with such an agent. Alternatively, an antibody identified as described herein can be used in an animal model to determine the mechanism of action of such an agent.

One aspect of the present invention relates to screening assays, including non-cell based assays and xenograft animal model assays. In one embodiment, the assays provide a method for identifying whether a cancer is likely to respond to anti-HHLA2 antibody therapy, such as in a human by using a xenograft animal model assay, and/or whether an agent can inhibit the growth of or kill a cancer cell that is unlikely to respond to anti-HHLA2 antibody therapy.

6. Prophylactic Methods

In one aspect, the present invention provides a method for preventing in a subject, a disease or condition associated with an unwanted or less than desirable immune response. Subjects at risk for a disease that would benefit from treatment with the claimed agents or methods can be identified, for example, by any or a combination of diagnostic or prognostic assays known in the art. Administration of a prophylactic agent can occur prior to the manifestation of symptoms associated with an unwanted or less than desirable immune response. The appropriate agent used for treatment (e.g. antibodies, peptides, fusion proteins or small molecules) can be determined based on clinical indications and can be identified, e.g., using screening assays described herein.

VII. Pharmaceutical Compositions

Agents that modulate (e.g., inhibit or promote) the interaction between HHLA2 and one or more natural binding partners, such as TMIGD2 and/or KIR3DL3, including, e.g., blocking antibodies, peptides, fusion proteins, or small molecules, can be incorporated into pharmaceutical compositions suitable for administration to a subject. Such compositions typically comprise the antibody, peptide, fusion protein or small molecule and a pharmaceutically acceptable carrier. As used herein the language "pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances is well-known in the art. Except insofar as any conventional media or agent is incompatible with the active compound, use thereof in the compositions is contemplated. Supplementary active compounds can also be incorporated into the compositions.

A pharmaceutical composition of the present invention is formulated to be compatible with its intended route of administration. Examples of routes of administration include parenteral, e.g., intravenous, intradermal, subcutaneous, oral (e.g., inhalation), transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerin, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, NJ) or phosphate buffered saline (PBS). In all cases, the composition should be sterile and should be fluid to the extent that easy syringeability exists. It must be stable under the conditions of manufacture and storage and should be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it is preferable to include isotonic agents, for example, sugars, polyalcohols such as manitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The compounds can also be prepared in the form of suppositories (e.g., with conventional suppository bases such as cocoa butter and other glycerides) or retention enemas for rectal delivery.

In one embodiment, modulatory agents are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations should be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the present invention are dictated by, and directly dependent on, the unique characteristics of the active compound, the particular therapeutic effect to be achieved, and the limitations inherent in the art of compounding such an active compound for the treatment of individuals.

Toxicity and therapeutic efficacy of such compounds can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compounds which exhibit large therapeutic indices are preferred. While compounds that exhibit toxic side effects can be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. The dosage of such compounds lies preferably within a range of circulating concentrations that include the ED50 with little or no toxicity. The dosage may vary within this range depending upon the dosage form employed and the route of administration utilized. For any compound used in the method of the present invention, the therapeutically effective dose can be estimated initially from cell culture assays. A dose can be formulated in animal models to achieve a circulating plasma concentration range that includes the IC50 (i.e., the concentration of the test compound which achieves a half-maximal inhibition of symptoms) as determined in cell culture. Such information can be used to more accurately determine useful doses in humans. Levels in plasma can be measured, for example, by high performance liquid chromatography.

The above described modulating agents may be administered it he form of expressible nucleic acids which encode said agents. Such nucleic acids and compositions in which they are contained, are also encompassed by the present invention. For instance, the nucleic acid molecules of the present invention can be inserted into vectors and used as gene therapy vectors. Gene therapy vectors can be delivered to a subject by, for example, intravenous injection, local administration (see U.S. Pat. No. 5,328,470) or by stereotactic injection (see e.g., Chen et al. (1994) *Proc. Natl. Acad. Sci. USA* 91:3054-3057). The pharmaceutical preparation of the gene therapy vector can include the gene therapy vector in an acceptable diluent, or can comprise a slow release matrix in which the gene delivery vehicle is imbedded. Alternatively, where the complete gene delivery vector can be produced intact from recombinant cells, e.g., retroviral vectors, the pharmaceutical preparation can include one or more cells which produce the gene delivery system.

The pharmaceutical compositions can be included in a container, pack, or dispenser together with instructions for administration.

VIII. Administration of Agents

The immune modulating agents of the present invention are administered to subjects in a biologically compatible form suitable for pharmaceutical administration in vivo, to either enhance or suppress immune cell mediated immune responses. By "biologically compatible form suitable for administration in vivo" is meant a form of the protein to be administered in which any toxic effects are outweighed by the therapeutic effects of the protein. The term "subject" is intended to include living organisms in which an immune response can be elicited, e.g., mammals. Examples of subjects include humans, dogs, cats, mice, rats, and transgenic species thereof. Administration of an agent as described herein can be in any pharmacological form including a therapeutically active amount of an agent alone or in combination with a pharmaceutically acceptable carrier.

Administration of a therapeutically active amount of the therapeutic composition of the present invention is defined as an amount effective, at dosages and for periods of time necessary, to achieve the desired result. For example, a therapeutically active amount of an agent may vary according to factors such as the disease state, age, sex, and weight of the individual, and the ability of peptide to elicit a desired response in the individual. Dosage regimens can be adjusted to provide the optimum therapeutic response. For example, several divided doses can be administered daily or the dose can be proportionally reduced as indicated by the exigencies of the therapeutic situation.

The agents or the invention described herein can be administered in a convenient manner such as by injection (subcutaneous, intravenous, etc.), oral administration, inhalation, transdermal application, or rectal administration. Depending on the route of administration, the active compound can be coated in a material to protect the compound from the action of enzymes, acids and other natural conditions which may inactivate the compound. For example, for administration of agents, by other than parenteral administration, it may be desirable to coat the agent with, or co-administer the agent with, a material to prevent its inactivation.

An agent can be administered to an individual in an appropriate carrier, diluent or adjuvant, co-administered with enzyme inhibitors or in an appropriate carrier such as liposomes. Pharmaceutically acceptable diluents include saline and aqueous buffer solutions. Adjuvant is used in its broadest sense and includes any immune stimulating compound such as interferon. Adjuvants contemplated herein include resorcinols, non-ionic surfactants such as polyoxyethylene oleyl ether and n-hexadecyl polyethylene ether. Enzyme inhibitors include pancreatic trypsin inhibitor, diisopropylfluorophosphate (DEEP) and trasylol. Liposomes include water-in-oil-in-water emulsions as well as conventional liposomes (Sterna et al. (1984) *J. Neuroimmunol.* 7:27).

The agent may also be administered parenterally or intraperitoneally. Dispersions can also be prepared in glycerol, liquid polyethylene glycols, and mixtures thereof, and in oils. Under ordinary conditions of storage and use, these preparations may contain a preservative to prevent the growth of microorganisms.

Pharmaceutical compositions of agents suitable for injectable use include sterile aqueous solutions (where water soluble) or dispersions and sterile powders for the extemporaneous preparation of sterile injectable solutions or dispersion. In all cases the composition will preferably be sterile and must be fluid to the extent that easy syringeability exists. It will preferably be stable under the conditions of manufacture and storage and preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it is preferable to include isotonic agents, for example, sugars, polyalcohols such as manitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating an agent of the present invention (e.g., an antibody, peptide, fusion protein or small molecule) in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the agent plus any additional desired ingredient from a previously sterile-filtered solution thereof.

When the agent is suitably protected, as described above, the protein can be orally administered, for example, with an inert diluent or an assimilable edible carrier. As used herein "pharmaceutically acceptable carrier" includes any and all solvents, dispersion media, coatings, antibacterial and antifungal agents, isotonic and absorption delaying agents, and the like. The use of such media and agents for pharmaceutically active substances is well-known in the art. Except insofar as any conventional media or agent is incompatible with the active compound, use thereof in the therapeutic compositions is contemplated. Supplementary active compounds can also be incorporated into the compositions.

It is especially advantageous to formulate parenteral compositions in dosage unit form for ease of administration and uniformity of dosage. "Dosage unit form ", as used herein, refers to physically discrete units suited as unitary dosages for the mammalian subjects to be treated; each unit containing a predetermined quantity of active compound calculated to produce the desired therapeutic effect in association with the required pharmaceutical carrier. The specification for the dosage unit forms of the present invention are dictated by, and directly dependent on, (a) the unique characteristics of the active compound and the particular therapeutic effect to be achieved, and (b) the limitations inherent in the art of compounding such an active compound for the treatment of sensitivity in individuals.

In one embodiment, an agent of the present invention is an antibody. As defined herein, a therapeutically effective amount of antibody (i.e., an effective dosage) ranges from about 0.001 to 30 mg/kg body weight, preferably about 0.01 to 25 mg/kg body weight, more preferably about 0.1 to 20 mg/kg body weight, and even more preferably about 1 to 10 mg/kg, 2 to 9 mg/kg, 3 to 8 mg/kg, 4 to 7 mg/kg, or 5 to 6 mg/kg body weight. The skilled artisan will appreciate that certain factors may influence the dosage required to effectively treat a subject, including but not limited to the severity of the disease or disorder, previous treatments, the general health and/or age of the subject, and other diseases present. Moreover, treatment of a subject with a therapeutically effective amount of an antibody can include a single treatment or, preferably, can include a series of treatments. In a preferred example, a subject is treated with antibody in the range of between about 0.1 to 20 mg/kg body weight, one time per week for between about 1 to 10 weeks, preferably between 2 to 8 weeks, more preferably between about 3 to 7 weeks, and even more preferably for about 4, 5, or 6 weeks. It will also be appreciated that the effective dosage of antibody used for treatment may increase or decrease over the course of a particular treatment. Changes in dosage may result from the results of diagnostic assays.

As described above, in some embodiments, agents for administration are cell-based. Cell-based agents have an immunocompatibility relationship to a subject host and any such relationship is contemplated for use according to the present invention. For example, the cells, such as adoptive T cells, can be syngeneic. The term "syngeneic" can refer to the state of deriving from, originating in, or being members of the same species that are genetically identical, particularly with respect to antigens or immunological reactions. These include identical twins having matching MHC types. Thus, a "syngeneic transplant" refers to transfer of cells from a donor to a recipient who is genetically identical to the donor or is sufficiently immunologically compatible as to allow for transplantation without an undesired adverse immunogenic response (e.g., such as one that would work against interpretation of immunological screen results described herein).

A syngeneic transplant can be "autologous" if the transferred cells are obtained from and transplanted to the same subject. An "autologous transplant" refers to the harvesting and reinfusion or transplant of a subject's own cells or organs. Exclusive or supplemental use of autologous cells may eliminate or reduce many adverse effects of administration of the cells back to the host, particular graft versus host reaction.

A syngeneic transplant can be "matched allogeneic" if the transferred cells are obtained from and transplanted to different members of the same species yet have sufficiently matched major histocompatibility complex (MHC) antigens to avoid an adverse immunogenic response. Determining the degree of MHC mismatch may be accomplished according to standard tests known and used in the art. For instance, there are at least six major categories of MHC genes in humans, identified as being important in transplant biology. HLA-A, HLA-B, HLA-C encode the HLA class I proteins while HLA-DR, HLA-DQ, and HLA-DP encode the HLA class II proteins. Genes within each of these groups are highly polymorphic, as reflected in the numerous HLA alleles or variants found in the human population, and differences in these groups between individuals is associated with the strength of the immune response against transplanted cells. Standard methods for determining the degree of MHC match examine alleles within HLA-B and HLA-DR, or HLA-A, HLA-B and HLA-DR groups. Thus, tests may be made of at least 4, and even 5 or 6 MHC antigens within the two or three HLA groups, respectively. In serological MHC tests, antibodies directed against each HLA antigen type are reacted with cells from one subject (e.g., donor) to determine the presence or absence of certain MHC antigens that react with the antibodies. This is compared to the reactivity profile of the other subject (e.g., recipient). Reaction of the antibody with an MHC antigen is typically determined by incubating the antibody with cells, and then adding complement to induce cell lysis (i.e., lymphocytotoxicity testing). The reaction is examined and graded according to the amount of cells lysed in the reaction (see, for example, Mickelson and Petersdorf (1999) *Hematopoietic Cell Transplantation*, Thomas, E. D. et al. eds., pg 28-37, Blackwell Scientific, Malden, Mass.). Other cell-based assays include flow cytometry using labeled antibodies or enzyme linked immunoassays (ELISA). Molecular methods for determining MHC type are well-known and generally employ synthetic probes and/or primers to detect specific gene sequences that encode the HLA protein. Synthetic oligonucleotides may be used as hybridization probes to detect restriction fragment length polymorphisms associated with particular HLA types (Vaughn (2002) *Method. Mol. Biol. MHC Protocol.* 210:45-60). Alternatively, primers may be used for amplifying the HLA sequences (e.g., by polymerase chain reaction or ligation chain reaction), the products of which may be further examined by direct DNA sequencing, restriction fragment polymorphism analysis (RFLP), or hybridization with a series of sequence specific oligonucleotide primers (SSOP) (Petersdorf et al. (1998) *Blood* 92:3515-3520; Morishima et al. (2002) *Blood* 99:4200-4206; and Middleton and Williams (2002) *Method. Mol. Biol. MHC Protocol.* 210:67-112).

A syngeneic transplant can be "congenic" if the transferred cells and cells of the subject differ in defined loci, such as a single locus, typically by inbreeding. The term "congenic" refers to deriving from, originating in, or being members of the same species, where the members are genetically identical except for a small genetic region, typically a single genetic locus (i.e., a single gene). A "congenic transplant" refers to transfer of cells or organs from a donor to a recipient, where the recipient is genetically identical to the donor except for a single genetic locus. For example, CD45 exists in several allelic forms and congenic mouse lines exist in which the mouse lines differ with respect to whether the CD45.1 or CD45.2 allelic versions are expressed.

By contrast, "mismatched allogeneic" refers to deriving from, originating in, or being members of the same species having non-identical major histocompatibility complex (MHC) antigens (i.e., proteins) as typically determined by standard assays used in the art, such as serological or molecular analysis of a defined number of MHC antigens, sufficient to elicit adverse immunogenic responses. A "partial mismatch" refers to partial match of the MHC antigens tested between members, typically between a donor and recipient. For instance, a "half mismatch" refers to 50% of the MHC antigens tested as showing different MHC antigen type between two members. A "full" or "complete" mismatch refers to all MHC antigens tested as being different between two members.

Similarly, in contrast, "xenogeneic" refers to deriving from, originating in, or being members of different species, e.g., human and rodent, human and swine, human and chimpanzee, etc. A "xenogeneic transplant" refers to transfer of cells or organs from a donor to a recipient where the recipient is a species different from that of the donor.

In addition, cells can be obtained from a single source or a plurality of sources (e.g., a single subject or a plurality of subjects). A plurality refers to at least two (e.g., more than one). In still another embodiment, the non-human mammal is a mouse. The animals from which cell types of interest are obtained may be adult, newborn (e.g., less than 48 hours old), immature, or in utero. Cell types of interest may be primary cancer cells, cancer stem cells, established cancer cell lines, immortalized primary cancer cells, and the like. In certain embodiments, the immune systems of host subjects can be engineered or otherwise elected to be immunological compatible with transplanted cancer cells. For example, in one embodiment, the subject may be "humanized" in order to be compatible with human cancer cells. The term "immune-system humanized" refers to an animal, such as a mouse, comprising human HSC lineage cells and human acquired and innate immune cells, survive without being rejected from the host animal, thereby allowing human hematopoiesis and both acquired and innate immunity to be reconstituted in the host animal. Acquired immune cells include T cells and B cells. Innate immune cells include macrophages, granulocytes (basophils, eosinophils, neutrophils), DCs, NK cells and mast cells. Representative, non-limiting examples include SCID-hu, Hu-PBL-SCID, Hu-SRC-SCID, NSG (NOD-SCID IL2r-gamma(null) lack an innate immune system, B cells, T cells, and cytokine signaling), NOG (NOD-SCID IL2r-gamma(truncated)), BRG (BALB/c-Rag2(null)IL2r-gamma(null)), and H2dRG (Stock-H2d-Rag2(null)IL2r-gamma(null)) mice (see, for example, Shultz et al. (2007) Nat. Rev. Immunol. 7:118; Pearson et al. (2008) Curr. Protocol. Immunol. 15:21; Brehm et al. (2010) Clin. Immunol. 135:84-98; McCune et al. (1988) Science 241:1632-1639, U.S. Pat. No. 7,960,175, and U.S. Pat. Publ. 2006/0161996), as well as related null mutants of immune-related genes like Rag1 (lack B and T cells), Rag2 (lack B and T cells), TCR alpha (lack T cells), perforin (cD8+ T cells lack cytotoxic function), FoxP3 (lack functional CD4+T regulatory cells), IL2rg, or Prf1, as well as mutants or knockouts of HHLA2, KIR3DL3, TMIGD2, PD-1, PD-L1, Tim3, and/or 2B4, allow for efficient engraftment of human immune cells in and/or provide compartment-specific models of immunocompromised animals like mice (see, for example, PCT Publ. WO2013/062134). In addition, NSG-CD34+(NOD-SCID IL2r-gamma(null) CD34+) humanized mice are useful for studying human gene and tumor activity in animal models like mice.

As used herein, "obtained" from a biological material source means any conventional method of harvesting or partitioning a source of biological material from a donor. For example, biological material may obtained from a solid tumor, a blood sample, such as a peripheral or cord blood sample, or harvested from another body fluid, such as bone marrow or amniotic fluid. Methods for obtaining such samples are well-known to the artisan. In the present invention, the samples may be fresh (i.e., obtained from a donor without freezing). Moreover, the samples may be further manipulated to remove extraneous or unwanted components prior to expansion. The samples may also be obtained from a preserved stock. For example, in the case of cell lines or fluids, such as peripheral or cord blood, the samples may be withdrawn from a cryogenically or otherwise preserved bank of such cell lines or fluid. Such samples may be obtained from any suitable donor.

The obtained populations of cells may be used directly or frozen for use at a later date. A variety of mediums and protocols for cryopreservation are known in the art. Generally, the freezing medium will comprise DMSO from about 5-10%, 10-90% serum albumin, and 50-90% culture medium. Other additives useful for preserving cells include, by way of example and not limitation, disaccharides such as trehalose (Scheinkonig et. al.. (2004) Bone Marrow Transplant. 34:531-536), or a plasma volume expander, such as hetastarch (i.e., hydroxyethyl starch). In some embodiments, isotonic buffer solutions, such as phosphate-buffered saline, may be used. An exemplary cryopreservative composition has cell-culture medium with 4% HSA, 7.5% dimethyl sulfoxide (DMSO), and 2% hetastarch. Other compositions and methods for cryopreservation are well-known and described in the art (see, e.g., Broxmeyer et al. (2003) Proc. Natl. Acad. Sci. U.S.A. 100:645-650). Cells are preserved at a final temperature of less than about −135° C.

Cells can be administered at $0.1 \times 10^6$, $0.2 \times 10^6$, $0.3 \times 10^6$, $0.4 \times 10^6$, $0.5 \times 10^6$, $0.6 \times 10^6$, $0.7 \times 10^6$, $0.8 \times 10^6$, $0.9 \times 10^6$, $1.0 \times 10^6$, $5.0 \times 10^6$, $1.0 \times 10^7$, $5.0 \times 10^7$, $1.0 \times 10^8$, $5.0 \times 10^8$, or more, or any range in between or any value in between, cells per kilogram of subject body weight. The number of cells transplanted may be adjusted based on the desired level of engraftment in a given amount of time. Generally, $1 \times 10^5$ to about $1 \times 10^9$ cells/kg of body weight, from about $1 \times 10^6$ to about $1 \times 10^8$ cells/kg of body weight, or about $1 \times 10^7$ cells/kg of body weight, or more cells, as necessary, may be transplanted. In some embodiment, transplantation of at least about $0.1 \times 10^6$, $0.5 \times 10^6$, $1.0 \times 10^6$, $2.0 \times 10^6$, $3.0 \times 10^6$, $4.0 \times 10^6$, or $5.0 \times 10^6$ total cells relative to an average size mouse is effective.

Cells can be administered in any suitable route as described herein, such as by infusion. Cells can also be administered before, concurrently with, or after, other anticancer agents.

Administration can be accomplished using methods generally known in the art. Agents, including cells, may be introduced to the desired site by direct injection, or by any other means used in the art including, but are not limited to, intravascular, intracerebral, parenteral, intraperitoneal, intravenous, epidural, intraspinal, intrasternal, intra-articular, intra-synovial, intrathecal, intra-arterial, intracardiac, or intramuscular administration. For example, subjects of interest may be engrafted with the transplanted cells by various routes. Such routes include, but are not limited to, intravenous administration, subcutaneous administration, administration to a specific tissue (e.g., focal transplantation), injection into the femur bone marrow cavity, injection into the spleen, administration under the renal capsule of fetal liver, and the like. In certain embodiment, the cancer vaccine of the present invention is injected to the subject intratumorally or subcutaneously. Cells may be administered in one infusion, or through successive infusions over a defined time period sufficient to generate a desired effect. Exemplary methods for transplantation, engraftment assessment, and marker phenotyping analysis of transplanted cells are well-known in the art (see, for example, Pearson et al. (2008) Curr. Protoc. Immunol. 81:15.21.1-15.21.21; Ito et al. (2002) Blood 100:3175-3182; Traggiai et al. (2004) Science 304:104-107; Ishikawa et al. Blood (2005) 106:1565-1573; Shultz et al. (2005) J. Immunol. 174:6477-6489; and Holyoake et al. (1999) Exp. Hematol. 27:1418-1427).

Two or more cell types can be combined and administered, such as cell-based therapy and adoptive cell transfer of stem cells, cancer vaccines and cell-based therapy, and the like. For example, adoptive cell-based immunotherapies can be combined with the cell-based therapies of the present invention. Well-known adoptive cell-based immunotherapeutic modalities, including, without limitation, irradiated autologous or allogeneic tumor cells, tumor lysates or apoptotic tumor cells, antigen-presenting cell-based immunotherapy, dendritic cell-based immunotherapy, adoptive T cell transfer, adoptive CAR T cell therapy, autologous immune enhancement therapy (AIET), cancer vaccines, and/or antigen presenting cells. Such cell-based immunotherapies can be further modified to express one or more gene products to further modulate immune responses, such as expressing cytokines like GM-CSF, and/or to express tumor-associated antigen (TAA) antigens, such as Mage-1, gp-100, and the like. The ratio of cancer cells in the cancer vaccine described herein to other cell types can be 1:1, but can modulated in any amount desired (e.g., 1:1, 1.1:1, 1.2:1, 1.3:1, 1.4:1, 1.5:1, 2:1, 2.5:1, 3:1, 3.5:1, 4:1, 4.5:1, 5:1, 5.5:1, 6:1, 6.5:1, 7:1, 7.5:1, 8:1, 8.5:1, 9:1, 9.5:1, 10:1, or greater).

Engraftment of transplanted cells may be assessed by any of various methods, such as, but not limited to, tumor volume, cytokine levels, time of administration, flow cytometric analysis of cells of interest obtained from the subject at one or more time points following transplantation, and the like. For example, a time-based analysis of waiting 1, 2, 3, 4, 5, 6, 7, 8, 9, 10, 11, 12, 13, 14, 15, 16, 17, 18, 19, 20, 21, 22, 23, 24, 25, 26, 27, 28 days or can signal the time for tumor harvesting. Any such metrics are variables that can be adjusted according to well-known parameters in order to determine the effect of the variable on a response to anti-cancer immunotherapy. In addition, the transplanted cells can be co-transplanted with other agents, such as cytokines, extracellular matrices, cell culture supports, and the like.

The present invention is further illustrated by the following examples which should not be construed as limiting. The contents of all references, patents and published patent applications cited throughout this application, as well as the Figures, are incorporated herein by reference.

IX. Subjects

In one embodiment, the subject for whom predicted likelihood of efficacy of a HHLA2 antibodies therapy is determined, is a mammal (e.g., mouse, humanized mouse, rat, primate, non-human mammal, domestic animal, such as a dog, cat, cow, horse, and the like), and is preferably a human. In another embodiment, the subject is an animal model of cancer. For example, the animal model can be an orthotopic xenograft animal model of a human-derived cancer.

In another embodiment of the methods of the present invention, the subject has not undergone treatment, such as chemotherapy, radiation therapy, targeted therapy, and/or anti-immune checkpoint therapy. In still another embodiment, the subject has undergone treatment, such as chemotherapy, radiation therapy, targeted therapy, and/or anti-immune checkpoint therapy.

In certain embodiments, the subject has had surgery to remove cancerous or precancerous tissue. In other embodiments, the cancerous tissue has not been removed, e.g., the cancerous tissue may be located in an inoperable region of the body, such as in a tissue that is essential for life, or in a region where a surgical procedure would cause considerable risk of harm to the patient.

The methods of the present invention can be used to determine the responsiveness to HHLA2 inhibitor therapies of many different cancers in subjects such as those described herein.

X. Sample Collection, Preparation and Separation

In some embodiments, biomarker amount and/or activity measurement(s) in a sample from a subject is compared to a predetermined control (standard) sample. The sample from the subject is typically from a diseased tissue, such as cancer cells or tissues. The control sample can be from the same subject or from a different subject. The control sample is typically a normal, non-diseased sample. However, in some embodiments, such as for staging of disease or for evaluating the efficacy of treatment, the control sample can be from a diseased tissue. The control sample can be a combination of samples from several different subjects. In some embodiments, the biomarker amount and/or activity measurement(s) from a subject is compared to a pre-determined level. This pre-determined level is typically obtained from normal samples. As described herein, a "pre-determined" biomarker amount and/or activity measurement(s) may be a biomarker amount and/or activity measurement(s) used to, by way of example only, evaluate a subject that may be selected for treatment (e.g., based on the number of genomic mutations and/or the number of genomic mutations causing non-functional proteins for DNA repair genes), evaluate a response to an anti-HHLA2 antibody therapy, and/or evaluate a response to an anti-HHLA2 antibody therapy with one or more additional anti-cancer therapies. A pre-determined biomarker amount and/or activity measurement(s) may be determined in populations of patients with or without cancer. The pre-determined biomarker amount and/or activity measurement(s) can be a single number, equally applicable to every patient, or the pre-determined biomarker amount and/or activity measurement(s) can vary according to specific subpopulations of patients. Age, weight, height, and other factors of a subject may affect the pre-determined biomarker amount and/or activity measurement(s) of the individual. Furthermore, the pre-determined biomarker amount and/or activity can be determined for each subject individually. In one embodiment, the amounts determined and/or compared in a method described herein are based on absolute measurements.

In another embodiment, the amounts determined and/or compared in a method described herein are based on relative measurements, such as ratios (e.g., biomarker copy numbers, level, and/or activity before a treatment vs. after a treatment, such biomarker measurements relative to a spiked or man-made control, such biomarker measurements relative to the expression of a housekeeping gene, and the like). For example, the relative analysis can be based on the ratio of pre-treatment biomarker measurement as compared to post-treatment biomarker measurement. Pre-treatment biomarker measurement can be made at any time prior to initiation of anti-cancer therapy. Post-treatment biomarker measurement can be made at any time after initiation of anti-cancer therapy. In some embodiments, post-treatment biomarker measurements are made 1, 2, 3, 4, 5, 6, 7, 8, 9, 10, 11, 12, 13, 14, 15, 16, 17, 18, 19, 20 weeks or more after initiation of anti-cancer therapy, and even longer toward indefinitely for continued monitoring. Treatment can comprise anti-cancer therapy, such as a therapeutic regimen comprising one or more anti-HHLA2 antibodies alone or in combination with other anti-cancer agents, such as with immune checkpoint inhibitors.

The pre-determined biomarker amount and/or activity measurement(s) can be any suitable standard. For example, the pre-determined biomarker amount and/or activity measurement(s) can be obtained from the same or a different human for whom a patient selection is being assessed. In one embodiment, the pre-determined biomarker amount and/or activity measurement(s) can be obtained from a previous assessment of the same patient. In such a manner, the progress of the selection of the patient can be monitored over time. In addition, the control can be obtained from an assessment of another human or multiple humans, e.g., selected groups of humans, if the subject is a human. In such a manner, the extent of the selection of the human for whom selection is being assessed can be compared to suitable other humans, e.g., other humans who are in a similar situation to the human of interest, such as those suffering from similar or the same condition(s) and/or of the same ethnic group.

In some embodiments of the present invention the change of biomarker amount and/or activity measurement(s) from the pre-determined level is about 0.1, 0.2, 0.3, 0.4, 0.5, 0.6, 0.7, 0.8, 0.9, 1.0, 1.5, 2.0, 2.5, 3.0, 3.5, 4.0, 4.5, or 5.0 fold or greater, or any range in between, inclusive. Such cutoff values apply equally when the measurement is based on relative changes, such as based on the ratio of pre-treatment biomarker measurement as compared to post-treatment biomarker measurement.

Biological samples can be collected from a variety of sources from a patient including a body fluid sample, cell sample, or a tissue sample comprising nucleic acids and/or proteins. "Body fluids" refer to fluids that are excreted or secreted from the body as well as fluids that are normally not (e.g., amniotic fluid, aqueous humor, bile, blood and blood plasma, cerebrospinal fluid, cerumen and earwax, cowper's fluid or pre-ejaculatory fluid, chyle, chyme, stool, female ejaculate, interstitial fluid, intracellular fluid, lymph, menses, breast milk, mucus, pleural fluid, pus, saliva, sebum, semen, serum, sweat, synovial fluid, tears, urine, vaginal lubrication, vitreous humor, vomit). In a preferred embodiment, the subject and/or control sample is selected from the group consisting of cells, cell lines, histological slides, paraffin embedded tissues, biopsies, whole blood, nipple aspirate, serum, plasma, buccal scrape, saliva, cerebrospinal fluid, urine, stool, and bone marrow. In one embodiment, the sample is serum, plasma, or urine. In another embodiment, the sample is serum.

The samples can be collected from individuals repeatedly over a longitudinal period of time (e.g., once or more on the order of days, weeks, months, annually, biannually, etc.). Obtaining numerous samples from an individual over a period of time can be used to verify results from earlier detections and/or to identify an alteration in biological pattern as a result of, for example, disease progression, drug treatment, etc. For example, subject samples can be taken and monitored every month, every two months, or combinations of one, two, or three month intervals according to the present invention. In addition, the biomarker amount and/or activity measurements of the subject obtained over time can be conveniently compared with each other, as well as with those of normal controls during the monitoring period, thereby providing the subject's own values, as an internal, or personal, control for long-term monitoring.

Sample preparation and separation can involve any of the procedures, depending on the type of sample collected and/or analysis of biomarker measurement(s). Such procedures include, by way of example only, concentration, dilution, adjustment of pH, removal of high abundance polypeptides (e.g., albumin, gamma globulin, and transferrin, etc.), addition of preservatives and calibrants, addition of protease inhibitors, addition of denaturants, desalting of samples, and concentration of sample proteins, extraction and purification of lipids.

The sample preparation can also isolate molecules that are bound in non-covalent complexes to other protein (e.g., carrier proteins). This process may isolate those molecules bound to a specific carrier protein (e.g., albumin), or use a more general process, such as the release of bound molecules from all carrier proteins via protein denaturation, for example using an acid, followed by removal of the carrier proteins.

Removal of undesired proteins (e.g., high abundance, uninformative, or undetectable proteins) from a sample can be achieved using high affinity reagents, high molecular weight filters, ultracentrifugation and/or electrodialysis. High affinity reagents include antibodies or other reagents (e.g., aptamers) that selectively bind to high abundance proteins. Sample preparation could also include ion exchange chromatography, metal ion affinity chromatography, gel filtration, hydrophobic chromatography, chromatofocusing, adsorption chromatography, isoelectric focusing and related techniques. Molecular weight filters include membranes that separate molecules on the basis of size and molecular weight. Such filters may further employ reverse osmosis, nanofiltration, ultrafiltration and microfiltration.

Ultracentrifugation is a method for removing undesired polypeptides from a sample. Ultracentrifugation is the centrifugation of a sample at about 15,000-60,000 rpm while monitoring with an optical system the sedimentation (or lack thereof) of particles. Electrodialysis is a procedure which uses an electromembrane or semipermable membrane in a process in which ions are transported through semi-permeable membranes from one solution to another under the influence of a potential gradient. Since the membranes used in electrodialysis may have the ability to selectively transport ions having positive or negative charge, reject ions of the opposite charge, or to allow species to migrate through a semipermable membrane based on size and charge, it renders electrodialysis useful for concentration, removal, or separation of electrolytes.

Separation and purification in the present invention may include any procedure known in the art, such as capillary electrophoresis (e.g., in capillary or on-chip) or chromatography (e.g., in capillary, column or on a chip). Electrophoresis is a method which can be used to separate ionic molecules under the influence of an electric field. Electrophoresis can be conducted in a gel, capillary, or in a microchannel on a chip. Examples of gels used for electrophoresis include starch, acrylamide, polyethylene oxides, agarose, or combinations thereof. A gel can be modified by its cross-linking, addition of detergents, or denaturants, immobilization of enzymes or antibodies (affinity electrophoresis) or substrates (zymography) and incorporation of a pH gradient. Examples of capillaries used for electrophoresis include capillaries that interface with an electrospray.

Capillary electrophoresis (CE) is preferred for separating complex hydrophilic molecules and highly charged solutes. CE technology can also be implemented on microfluidic chips. Depending on the types of capillary and buffers used, CE can be further segmented into separation techniques such as capillary zone electrophoresis (CZE), capillary isoelectric focusing (CIEF), capillary isotachophoresis (cITP) and capillary electrochromatography (CEC). An embodiment to couple CE techniques to electrospray ionization involves the use of volatile solutions, for example, aqueous mixtures containing a volatile acid and/or base and an organic such as an alcohol or acetonitrile.

Capillary isotachophoresis (cITP) is a technique in which the analytes move through the capillary at a constant speed but are nevertheless separated by their respective mobilities. Capillary zone electrophoresis (CZE), also known as free-solution CE (FSCE), is based on differences in the electrophoretic mobility of the species, determined by the charge on the molecule, and the frictional resistance the molecule encounters during migration which is often directly proportional to the size of the molecule. Capillary isoelectric focusing (CIEF) allows weakly-ionizable amphoteric molecules, to be separated by electrophoresis in a pH gradient. CEC is a hybrid technique between traditional high performance liquid chromatography (HPLC) and CE.

Separation and purification techniques used in the present invention include any chromatography procedures known in the art. Chromatography can be based on the differential adsorption and elution of certain analytes or partitioning of analytes between mobile and stationary phases. Different examples of chromatography include, but not limited to, liquid chromatography (LC), gas chromatography (GC), high performance liquid chromatography (HPLC), etc.

XI. Biomarker Polypeptides

Another aspect of the present invention pertains to the use of biomarker proteins and biologically active portions thereof. In one embodiment, the native polypeptide corresponding to a marker can be isolated from cells or tissue sources by an appropriate purification scheme using standard protein purification techniques. In another embodiment, polypeptides corresponding to a marker of the present invention are produced by recombinant DNA techniques.

Alternative to recombinant expression, a polypeptide corresponding to a marker of the present invention can be synthesized chemically using standard peptide synthesis techniques.

Biologically active portions of a biomarker polypeptide include polypeptides comprising amino acid sequences sufficiently identical to or derived from a biomarker protein amino acid sequence described herein, but which includes fewer amino acids than the full length protein, and exhibit at least one activity of the corresponding full-length protein. Typically, biologically active portions comprise a domain or motif with at least one activity of the corresponding protein. A biologically active portion of a protein of the present invention can be a polypeptide which is, for example, 10, 25, 50, 100 or more amino acids in length. Moreover, other biologically active portions, in which other regions of the protein are deleted, can be prepared by recombinant techniques and evaluated for one or more of the functional activities of the native form of a polypeptide of the present invention.

Preferred polypeptides have an amino acid sequence of a biomarker protein encoded by a nucleic acid molecule described herein. Other useful proteins are substantially identical (e.g., at least about 40%, preferably 50%, 60%, 70%, 75%, 80%, 83%, 85%, 88%, 90%, 91%, 92%, 93%, 94%, 95%, 96%, 97%, 98%, or 99%) to one of these sequences and retain the functional activity of the protein of the corresponding naturally-occurring protein yet differ in amino acid sequence due to natural allelic variation or mutagenesis.

To determine the percent identity of two amino acid sequences or of two nucleic acids, the sequences are aligned for optimal comparison purposes (e.g., gaps can be introduced in the sequence of a first amino acid or nucleic acid sequence for optimal alignment with a second amino or nucleic acid sequence). The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position. The percent identity between the two sequences is a function of the number of identical positions shared by the sequences (i.e., % identity=# of identical positions/total # of positions (e.g., overlapping positions)×100). In one embodiment the two sequences are the same length.

The determination of percent identity between two sequences can be accomplished using a mathematical algorithm. A preferred, non-limiting example of a mathematical algorithm utilized for the comparison of two sequences is the algorithm of Karlin and Altschul (1990) *Proc. Natl. Acad. Sci. USA* 87:2264-2268, modified as in Karlin and Altschul (1993) *Proc. Natl. Acad. Sci. USA* 90:5873-5877. Such an algorithm is incorporated into the NBLAST and XBLAST programs of Altschul, et al. (1990) *J. Mol. Biol.* 215:403-410. BLAST nucleotide searches can be performed with the NBLAST program, score=100, wordlength=12 to obtain nucleotide sequences homologous to a nucleic acid molecules of the present invention. BLAST protein searches can be performed with the XBLAST program, score=50, wordlength=3 to obtain amino acid sequences homologous to a protein molecules of the present invention. To obtain gapped alignments for comparison purposes, Gapped BLAST can be utilized as described in Altschul et al. (1997) *Nucleic Acids Res.* 25:3389-3402. Alternatively, PSI-Blast can be used to perform an iterated search which detects distant relationships between molecules. When utilizing BLAST, Gapped BLAST, and PSI-Blast programs, the default parameters of the respective programs (e.g., XBLAST and NBLAST) can be used. See http://www.ncbi.nlm.nih.gov. Another preferred, non-limiting example of a mathematical algorithm utilized for the comparison of sequences is the algorithm of Myers and Miller, (1988) *Comput Appl Biosci*, 4:11-7. Such an algorithm is incorporated into the ALIGN program (version 2.0) which is part of the GCG sequence alignment software package. When utilizing the ALIGN program for comparing amino acid sequences, a PAM120 weight residue table, a gap length penalty of 12, and a gap penalty of 4 can be used. Yet another useful algorithm for identifying regions of local sequence similarity and alignment is the FASTA algorithm as described in Pearson and Lipman (1988) *Proc. Natl. Acad. Sci. USA* 85:2444-2448. When using the FASTA algorithm for comparing nucleotide or amino acid sequences, a PAM120 weight residue table can, for example, be used with a k-tuple value of 2.

The percent identity between two sequences can be determined using techniques similar to those described above, with or without allowing gaps. In calculating percent identity, only exact matches are counted.

The present invention also provides chimeric or fusion proteins corresponding to a biomarker protein. As used herein, a "chimeric protein" or "fusion protein" comprises all or part (preferably a biologically active part) of a polypeptide corresponding to a marker of the present invention operably linked to a heterologous polypeptide (i.e., a polypeptide other than the polypeptide corresponding to the marker). Within the fusion protein, the term "operably linked" is intended to indicate that the polypeptide of the present invention and the heterologous polypeptide are fused in-frame to each other. The heterologous polypeptide can be fused to the amino-terminus or the carboxyl-terminus of the polypeptide of the present invention.

One useful fusion protein is a GST fusion protein in which a polypeptide corresponding to a marker of the present invention is fused to the carboxyl terminus of GST sequences. Such fusion proteins can facilitate the purification of a recombinant polypeptide of the present invention.

In another embodiment, the fusion protein contains a heterologous signal sequence, immunoglobulin fusion protein, toxin, or other useful protein sequence. Chimeric and fusion proteins of the present invention can be produced by standard recombinant DNA techniques. In another embodiment, the fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed and re-amplified to generate a chimeric gene sequence (see, e.g., Ausubel et al., supra). Moreover, many expression vectors are commercially available that already encode a fusion moiety (e.g., a GST polypeptide). A nucleic acid encoding a polypeptide of the present invention can be cloned into such an expression vector such that the fusion moiety is linked in-frame to the polypeptide of the present invention.

A signal sequence can be used to facilitate secretion and isolation of the secreted protein or other proteins of interest. Signal sequences are typically characterized by a core of hydrophobic amino acids which are generally cleaved from the mature protein during secretion in one or more cleavage events. Such signal peptides contain processing sites that allow cleavage of the signal sequence from the mature proteins as they pass through the secretory pathway. Thus, the present invention pertains to the described polypeptides having a signal sequence, as well as to polypeptides from which the signal sequence has been proteolytically cleaved (i.e., the cleavage products). In one embodiment, a nucleic acid sequence encoding a signal sequence can be operably linked in an expression vector to a protein of interest, such as a protein which is ordinarily not secreted or is otherwise difficult to isolate. The signal sequence directs secretion of the protein, such as from a eukaryotic host into which the expression vector is transformed, and the signal sequence is subsequently or concurrently cleaved. The protein can then be readily purified from the extracellular medium by art recognized methods. Alternatively, the signal sequence can be linked to the protein of interest using a sequence which facilitates purification, such as with a GST domain.

The present invention also pertains to variants of the biomarker polypeptides described herein. Such variants have an altered amino acid sequence which can function as either agonists (mimetics) or as antagonists. Variants can be generated by mutagenesis, e.g., discrete point mutation or truncation. An agonist can retain substantially the same, or a subset, of the biological activities of the naturally occurring form of the protein. An antagonist of a protein can inhibit one or more of the activities of the naturally occurring form of the protein by, for example, competitively binding to a downstream or upstream member of a cellular signaling cascade which includes the protein of interest. Thus, specific biological effects can be elicited by treatment with a variant of limited function. Treatment of a subject with a variant having a subset of the biological activities of the naturally occurring form of the protein can have fewer side effects in a subject relative to treatment with the naturally occurring form of the protein.

Variants of a biomarker protein which function as either agonists (mimetics) or as antagonists can be identified by screening combinatorial libraries of mutants, e.g., truncation mutants, of the protein of the present invention for agonist or antagonist activity. In one embodiment, a variegated library of variants is generated by combinatorial mutagenesis at the nucleic acid level and is encoded by a variegated gene library. A variegated library of variants can be produced by, for example, enzymatically ligating a mixture of synthetic oligonucleotides into gene sequences such that a degenerate set of potential protein sequences is expressible as individual polypeptides, or alternatively, as a set of larger fusion proteins (e.g., for phage display). There are a variety of methods which can be used to produce libraries of potential variants of the polypeptides of the present invention from a degenerate oligonucleotide sequence. Methods for synthesizing degenerate oligonucleotides are known in the art (see, e.g., Narang, 1983, *Tetrahedron* 39:3; Itakura et al., 1984, *Annu. Rev. Biochem.* 53:323; Itakura et al., 1984, *Science* 198:1056; Ike et al., 1983 *Nucleic Acid Res.* 11:477).

In addition, libraries of fragments of the coding sequence of a polypeptide corresponding to a marker of the present invention can be used to generate a variegated population of polypeptides for screening and subsequent selection of variants. For example, a library of coding sequence fragments can be generated by treating a double stranded PCR fragment of the coding sequence of interest with a nuclease under conditions wherein nicking occurs only about once per molecule, denaturing the double stranded DNA, renaturing the DNA to form double stranded DNA which can include sense/antisense pairs from different nicked products, removing single stranded portions from reformed duplexes by treatment with S1 nuclease, and ligating the resulting fragment library into an expression vector. By this method, an expression library can be derived which encodes amino terminal and internal fragments of various sizes of the protein of interest.

Several techniques are known in the art for screening gene products of combinatorial libraries made by point mutations or truncation, and for screening cDNA libraries for gene products having a selected property. The most widely used techniques, which are amenable to high throughput analysis, for screening large gene libraries typically include cloning the gene library into replicable expression vectors, transforming appropriate cells with the resulting library of vectors, and expressing the combinatorial genes under conditions in which detection of a desired activity facilitates isolation of the vector encoding the gene whose product was detected. Recursive ensemble mutagenesis (REM), a technique which enhances the frequency of functional mutants in the libraries, can be used in combination with the screening assays to identify variants of a protein of the present invention (Arkin and Yourvan, 1992, *Proc. Natl. Acad. Sci. USA* 89:7811-7815; Delgrave et al., 1993, *Protein Engineering* 6(3):327-331).

An isolated polypeptide or a fragment thereof (or a nucleic acid encoding such a polypeptide) corresponding to one or more biomarkers of the invention, including the biomarkers listed in Table 1 or fragments thereof, can be used as an immunogen to generate antibodies that bind to said immunogen, using standard techniques for polyclonal and monoclonal antibody preparation according to well-known methods in the art. An antigenic peptide comprises at least 8 amino acid residues and encompasses an epitope present in the respective full length molecule such that an antibody raised against the peptide forms a specific immune complex with the respective full length molecule. Preferably, the antigenic peptide comprises at least 10 amino acid residues. In one embodiment such epitopes can be specific for a given polypeptide molecule from one species, such as mouse or human (i.e., an antigenic peptide that spans a region of the polypeptide molecule that is not conserved across species is used as immunogen; such non conserved residues can be determined using an alignment such as that provided herein).

In one embodiment, an antibody binds substantially specifically to HHLA2 and inhibits or blocks its function, such as by interrupting its interaction with a HHLA2 receptor (e.g., TMIGD2 and/or KIR3DL3). In another embodiment, an antibody binds substantially specifically to one or more HHLA2 receptors and inhibits or blocks its function, such as by interrupting its interaction with HHLA2 and at least one of its receptors.

For example, a polypeptide immunogen typically is used to prepare antibodies by immunizing a suitable subject (e.g., rabbit, goat, mouse, humanized mouse or other mammal) with the immunogen. An appropriate immunogenic preparation can contain, for example, a recombinantly expressed or chemically synthesized molecule or fragment thereof to which the immune response is to be generated. The preparation can further include an adjuvant, such as Freund's complete or incomplete adjuvant, or similar immunostimulatory agent. Immunization of a suitable subject with an immunogenic preparation induces a polyclonal antibody response to the antigenic peptide contained therein.

Polyclonal antibodies can be prepared as described above by immunizing a suitable subject with a polypeptide immunogen. The polypeptide antibody titer in the immunized subject can be monitored over time by standard techniques, such as with an enzyme linked immunosorbent assay (ELISA) using immobilized polypeptide. If desired, the antibody directed against the antigen can be isolated from the mammal (e.g., from the blood) and further purified by well-known techniques, such as protein A chromatography, to obtain the IgG fraction. At an appropriate time after immunization, e.g., when the antibody titers are highest, antibody-producing cells can be obtained from the subject and used to prepare monoclonal antibodies by standard techniques, such as the hybridoma technique (originally described by Kohler and Milstein (1975) *Nature* 256:495-497) (see also Brown et al. (1981) *J. Immunol.* 127:539-46; Brown et al. (1980) *J. Biol. Chem.* 255:4980-83; Yeh et al. (1976) *Proc. Natl. Acad. Sci.* 76:2927-31; Yeh et al. (1982) *Int. J. Cancer* 29:269-75), the more recent human B cell hybridoma technique (Kozbor et al. (1983) *Immunol. Today* 4:72), the EBV-hybridoma technique (Cole et al. (1985) *Monoclonal Antibodies and Cancer Therapy*, Alan R. Liss, Inc., pp. 77-96) or trioma techniques. The technology for producing monoclonal antibody hybridomas is well-known (see generally Kenneth, R. H. in Monoclonal Antibodies: A New Dimension In Biological Analyses, Plenum Publishing Corp., New York, New York (1980); Lerner, E. A. (1981) *Yale J. Biol. Med.* 54:387-402; Gefter, M. L. et al. (1977) *Somatic Cell Genet.* 3:231-36). Briefly, an immortal cell line (typically a myeloma) is fused to lymphocytes (typically splenocytes) from a mammal immunized with an immunogen as described above, and the culture supernatants of the resulting hybridoma cells are screened to identify a hybridoma producing a monoclonal antibody that binds to the polypeptide antigen, preferably specifically. In some embodiments, the immunization is performed in a cell or animal host that has a knockout of a target antigen of interest (e.g., does not produce the antigen prior to immunization).

Any of the many well-known protocols used for fusing lymphocytes and immortalized cell lines can be applied for the purpose of generating a monoclonal antibody against one or more biomarkers of the invention, including the biomarkers listed in Table 1, or a fragment thereof (see, e.g., Galfre, G. et al. (1977) *Nature* 266:55052; Gefter et al. (1977) supra; Lerner (1981) supra; Kenneth (1980) supra). Moreover, the ordinary skilled worker will appreciate that there are many variations of such methods which also would be useful. Typically, the immortal cell line (e.g., a myeloma cell line) is derived from the same mammalian species as the lymphocytes. For example, murine hybridomas can be made by fusing lymphocytes from a mouse immunized with an immunogenic preparation of the present invention with an immortalized mouse cell line. Preferred immortal cell lines are mouse myeloma cell lines that are sensitive to culture medium containing hypoxanthine, aminopterin and thymidine ("HAT medium"). Any of a number of myeloma cell lines can be used as a fusion partner according to standard techniques, e.g., the P3-NS1/1-Ag4-1, P3-x63-Ag8.653 or Sp2/O-Ag14 myeloma lines. These myeloma lines are available from the American Type Culture Collection (ATCC), Rockville, MD. Typically, HAT-sensitive mouse myeloma cells are fused to mouse splenocytes using polyethylene glycol ("PEG"). Hybridoma cells resulting from the fusion are then selected using HAT medium, which kills unfused and unproductively fused myeloma cells (unfused splenocytes die after several days because they are not transformed). Hybridoma cells producing a monoclonal antibody of the invention are detected by screening the hybridoma culture supernatants for antibodies that bind a given polypeptide, e.g., using a standard ELISA assay.

As an alternative to preparing monoclonal antibody-secreting hybridomas, a monoclonal specific for one of the above described polypeptides can be identified and isolated by screening a recombinant combinatorial immunoglobulin library (e.g., an antibody phage display library) with the appropriate polypeptide to thereby isolate immunoglobulin library members that bind the polypeptide. Kits for generating and screening phage display libraries are commercially available (e.g., the Pharmacia *Recombinant Phage Antibody System*, Catalog No. 27-9400-01; and the Stratagene SurfZAP™ *Phage Display Kit*, Catalog No. 240612). Additionally, examples of methods and reagents particularly amenable for use in generating and screening an antibody display library can be found in, for example, Ladner et al. U.S. Pat. No. 5,223,409; Kang et al. International Publication No. WO 92/18619; Dower et al. International Publication No. WO 91/17271; Winter et al. International Publication WO 92/20791; Markland et al. International Publication No. WO 92/15679; Breitling et al. International Publication WO 93/01288; McCafferty et al. International Publication No. WO 92/01047; Garrard et al. International Publication No. WO 92/09690; Ladner et al. International Publication No. WO 90/02809; Fuchs et al. (1991) *Biotechnology* (NY) 9:1369-1372; Hay et al. (1992) *Hum. Antibod. Hybridomas* 3:81-85; Huse et al. (1989) *Science* 246:1275-1281; Griffiths et al. (1993) *EMBO J.* 12:725-734; Hawkins et al. (1992) *J. Mol. Biol.* 226:889-896; Clarkson et al. (1991) *Nature* 352:624-628; Gram et al. (1992) *Proc. Natl. Acad. Sci. USA* 89:3576-3580; Garrard et al. (1991) *Biotechnology* (NY) 9:1373-1377; Hoogenboom et al. (1991) *Nucleic Acids Res.* 19:4133-4137; Barbas et al. (1991) *Proc. Natl. Acad. Sci. USA* 88:7978-7982; and McCafferty et al. (1990) *Nature* 348:552-554.

The structural features of non-human or human antibodies (e.g., a rat anti-mouse/anti-human antibody) can be used to create structurally related human antibodies that retain at least one functional property of the antibodies of the present invention, such as binding to one or more of HHLA2, a HHLA2 receptor, TMIGD2, and/or KIR3DL3. Another functional property includes inhibiting binding of the original known, non-human or human antibodies in a competition ELISA assay.

In some embodiments, monoclonal antibodies capable of binding and inhibiting/blocking one or more of HHLA2, a HHLA2 receptor, TMIGD2, and/or KIR3DL3 are provided, comprising a heavy chain wherein the variable domain comprises at least a CDR having a sequence that is at least 80%, 85%, 90%, 91%, 92%, 93%, 94%, 95%, 96%, 97%, 98%, 99%, 99.5% or 100% identical from the group of heavy chain variable domain CDRs presented herein or otherwise publicly available.

Similarly, monoclonal antibodies binding and inhibiting/blocking one or more of HHLA2, a HHLA2 receptor, TMIGD2, and/or KIR3DL3, comprising a light chain wherein the variable domain comprises at least a CDR having a sequence that is at least 80%, 85%, 90%, 91%, 92%, 93%, 94%, 95%, 96%, 97%, 98%, 99%, 99.5% or 100% identical from the group of light chain variable domain CDRs presented herein or otherwise publicly available, are also provided.

Monoclonal antibodies capable of binding and inhibiting/blocking one or more of HHLA2, a HHLA2 receptor, TMIGD2, and/or KIR3DL3, comprising a heavy chain wherein the variable domain comprises at least a CDR having a sequence that is at least 80%, 85%, 90%, 91%, 92%, 93%, 94%, 95%, 96%, 97%, 98%, 99%, 99.5% or 100% identical from the group of heavy chain variable domain CDRs presented herein or otherwise publicly available; and comprising a light chain wherein the variable domain comprises at least a CDR having a sequence that is at least 80%, 85%, 90%, 91%, 92%, 93%, 94%, 95%, 96%, 97%, 98%, 99%, 99.5% or 100% identical from the group of light chain variable domain CDRs presented herein or otherwise publicly available, are also provided.

A skilled artisan will note that such percentage homology is equivalent to and can be achieved by introducing 1, 2, 3, 4, 5, 6, 7, 8, 9, 10, or more conservative amino acid substitutions within a given CDR.

Additionally, fully human antibodies could be made against biomarkers of the invention, including the biomarkers listed in Table 1, or fragments thereof. Fully human antibodies can be made in mice that are transgenic for human immunoglobulin genes, e.g. according to Hogan, et al., "Manipulating the Mouse Embryo: A Laboratory Manuel," Cold Spring Harbor Laboratory. Briefly, transgenic mice are immunized with purified immunogen. Spleen cells are harvested and fused to myeloma cells to produce hybridomas.

Hybridomas are selected based on their ability to produce antibodies which bind to the immunogen. Fully human antibodies would reduce the immunogenicity of such antibodies in a human.

In one embodiment, an antibody for use in the instant invention is a bispecific or multispecific antibody. A bispecific antibody has binding sites for two different antigens within a single antibody polypeptide. Antigen binding may be simultaneous or sequential. Triomas and hybrid hybridomas are two examples of cell lines that can secrete bispecific antibodies. Examples of bispecific antibodies produced by a hybrid hybridoma or a trioma are disclosed in U.S. Pat. No. 4,474,893. Bispecific antibodies have been constructed by chemical means (Staerz et al. (1985) Nature 314:628, and Perez et al. (1985) Nature 316:354) and hybridoma technology (Staerz and Bevan (1986) Proc. Natl. Acad. Sci. USA, 83:1453, and Staerz and Bevan (1986) Immunol. Today 7:241). Bispecific antibodies are also described in U.S. Pat. No. 5,959,084. Fragments of bispecific antibodies are described in U.S. Pat. No. 5,798,229.

Bispecific agents can also be generated by making heterohybridomas by fusing hybridomas or other cells making different antibodies, followed by identification of clones producing and co-assembling both antibodies. They can also be generated by chemical or genetic conjugation of complete immunoglobulin chains or portions thereof such as Fab and Fv sequences. The antibody component can bind to a polypeptide or a fragment thereof of one or more biomarkers of the invention, including one or more biomarkers listed in Table 1, or a fragment thereof. In one embodiment, the bispecific antibody could specifically bind to both a polypeptide or a fragment thereof and its natural binding partner(s) or a fragment(s) thereof.

In another aspect of this invention, peptides or peptide mimetics can be used to antagonize the activity of one or more biomarkers of the invention, including one or more biomarkers listed in Table 1, or a fragment(s) thereof. In one embodiment, variants of one or more biomarkers listed in Table 1 which function as a modulating agent for the respective full length protein, can be identified by screening combinatorial libraries of mutants, e.g., truncation mutants, for antagonist activity. In one embodiment, a variegated library of variants is generated by combinatorial mutagenesis at the nucleic acid level and is encoded by a variegated gene library. A variegated library of variants can be produced, for instance, by enzymatically ligating a mixture of synthetic oligonucleotides into gene sequences such that a degenerate set of potential polypeptide sequences is expressible as individual polypeptides containing the set of polypeptide sequences therein. There are a variety of methods which can be used to produce libraries of polypeptide variants from a degenerate oligonucleotide sequence. Chemical synthesis of a degenerate gene sequence can be performed in an automatic DNA synthesizer, and the synthetic gene then ligated into an appropriate expression vector. Use of a degenerate set of genes allows for the provision, in one mixture, of all of the sequences encoding the desired set of potential polypeptide sequences. Methods for synthesizing degenerate oligonucleotides are known in the art (see, e.g., Narang, S. A. (1983) Tetrahedron 39:3; Itakura et al. (1984) Annu. Rev. Biochem. 53:323; Itakura et al. (1984) Science 198:1056; Ike et al. (1983) Nucleic Acid Res. 11:477.

In addition, libraries of fragments of a polypeptide coding sequence can be used to generate a variegated population of polypeptide fragments for screening and subsequent selection of variants of a given polypeptide. In one embodiment, a library of coding sequence fragments can be generated by treating a double stranded PCR fragment of a polypeptide coding sequence with a nuclease under conditions wherein nicking occurs only about once per polypeptide, denaturing the double stranded DNA, renaturing the DNA to form double stranded DNA which can include sense/antisense pairs from different nicked products, removing single stranded portions from reformed duplexes by treatment with S1 nuclease, and ligating the resulting fragment library into an expression vector. By this method, an expression library can be derived which encodes N-terminal, C-terminal and internal fragments of various sizes of the polypeptide.

Several techniques are known in the art for screening gene products of combinatorial libraries made by point mutations or truncation, and for screening cDNA libraries for gene products having a selected property. Such techniques are adaptable for rapid screening of the gene libraries generated by the combinatorial mutagenesis of polypeptides. The most widely used techniques, which are amenable to high through-put analysis, for screening large gene libraries typically include cloning the gene library into replicable expression vectors, transforming appropriate cells with the resulting library of vectors, and expressing the combinatorial genes under conditions in which detection of a desired activity facilitates isolation of the vector encoding the gene whose product was detected. Recursive ensemble mutagenesis (REM), a technique which enhances the frequency of functional mutants in the libraries, can be used in combination with the screening assays to identify variants of interest (Arkin and Youvan (1992) Proc. Natl. Acad. Sci. USA 89:7811-7815; Delagrave et al. (1993) Protein Eng. 6(3): 327-331). In one embodiment, cell based assays can be exploited to analyze a variegated polypeptide library. For example, a library of expression vectors can be transfected into a cell line which ordinarily synthesizes one or more biomarkers of the invention, including one or more biomarkers listed in Table 1, or a fragment thereof. The transfected cells are then cultured such that the full length polypeptide and a particular mutant polypeptide are produced and the effect of expression of the mutant on the full length polypeptide activity in cell supernatants can be detected, e.g., by any of a number of functional assays. Plasmid DNA can then be recovered from the cells which score for inhibition, or alternatively, potentiation of full length polypeptide activity, and the individual clones further characterized.

Systematic substitution of one or more amino acids of a polypeptide amino acid sequence with a D-amino acid of the same type (e.g., D-lysine in place of L-lysine) can be used to generate more stable peptides. In addition, constrained peptides comprising a polypeptide amino acid sequence of interest or a substantially identical sequence variation can be generated by methods known in the art (Rizo and Gierasch (1992) *Annu. Rev. Biochem.* 61:387, incorporated herein by reference); for example, by adding internal cysteine residues capable of forming intramolecular disulfide bridges which cyclize the peptide.

The amino acid sequences disclosed herein will enable those of skill in the art to produce polypeptides corresponding peptide sequences and sequence variants thereof. Such polypeptides can be produced in prokaryotic or eukaryotic host cells by expression of polynucleotides encoding the peptide sequence, frequently as part of a larger polypeptide. Alternatively, such peptides can be synthesized by chemical methods. Methods for expression of heterologous proteins in recombinant hosts, chemical synthesis of polypeptides, and in vitro translation are well-known in the art and are described further in Maniatis et al. *Molecular Cloning: A Laboratory Manual* (1989), 2nd Ed., Cold Spring Harbor, N.Y.; Berger and Kimmel, Methods in Enzymology, Volume 152, *Guide to Molecular Cloning Techniques* (1987), Academic Press, Inc., San Diego, Calif.; Merrifield, J. (1969) *J. Am. Chem. Soc.* 91:501; Chaiken I. M. (1981) *CRC Crit. Rev. Biochem.* 11: 255; Kaiser et al. (1989) *Science* 243:187; Merrifield, B. (1986) *Science* 232:342; Kent, S. B. H. (1988) *Annu. Rev. Biochem.* 57:957; and Offord, R. E. (1980) *Semisynthetic Proteins*, Wiley Publishing, which are incorporated herein by reference).

Peptides can be produced, typically by direct chemical synthesis. Peptides can be produced as modified peptides, with nonpeptide moieties attached by covalent linkage to the N-terminus and/or C-terminus. In certain preferred embodiments, either the carboxy-terminus or the amino-terminus, or both, are chemically modified. The most common modifications of the terminal amino and carboxyl groups are acetylation and amidation, respectively. Amino-terminal modifications such as acylation (e.g., acetylation) or alkylation (e.g., methylation) and carboxy-terminal-modifications such as amidation, as well as other terminal modifications, including cyclization, can be incorporated into various embodiments of the invention. Certain amino-terminal and/or carboxy-terminal modifications and/or peptide extensions to the core sequence can provide advantageous physical, chemical, biochemical, and pharmacological properties, such as: enhanced stability, increased potency and/or efficacy, resistance to serum proteases, desirable pharmacokinetic properties, and others. Peptides disclosed herein can be used therapeutically to treat disease, e.g., by altering costimulation in a patient.

Peptidomimetics (Fauchere (1986) *Adv. Drug Res.* 15:29; Veber and Freidinger (1985) TINS p. 392; and Evans et al. (1987) *J. Med. Chem.* 30:1229, which are incorporated herein by reference) are usually developed with the aid of computerized molecular modeling. Peptide mimetics that are structurally similar to therapeutically useful peptides can be used to produce an equivalent therapeutic or prophylactic effect. Generally, peptidomimetics are structurally similar to a paradigm polypeptide (i.e., a polypeptide that has a biological or pharmacological activity), but have one or more peptide linkages optionally replaced by a linkage selected from the group consisting of: —CH2NH—, —CH$_2$S—, —CH2-CH2-, —CH═CH— (cis and trans), —COCH2-, —CH(OH)CH2-, and —CH2SO—, by methods known in the art and further described in the following references: Spatola, A. F. in "*Chemistry and Biochemistry of Amino Acids, Peptides, and Proteins*" Weinstein, B., ed., Marcel Dekker, New York, p. 267 (1983); Spatola, A. F., Vega Data (March 1983), Vol. 1, Issue 3, "Peptide Backbone Modifications" (general review); Morley, J. S. (1980) *Trends Pharm. Sci.* pp. 463-468 (general review); Hudson, D. et al. (1979) *Int. J. Pept. Prot. Res.* 14:177-185 (—CH2NH—, CH2CH2-); Spatola, A. F. et al. (1986) *Life Sci.* 38:1243-1249 (—CH2-S); Hann, M. M. (1982) *J. Chem. Soc. Perkin Trans. I.* 307-314 (—CH═CH—, cis and trans); Almquist, R. G. et al. (190) *J. Med. Chem.* 23:1392-1398 (—COCH2-); Jennings-White, C. et al. (1982) *Tetrahedron Lett.* 23:2533 (—COCH2-); Szelke, M. et al. *European Appln.* EP 45665 (1982) CA: 97:39405 (1982)(—CH(OH) CH2-); Holladay, M. W. et al. (1983) *Tetrahedron Lett.* (1983) 24:4401-4404 (—C(OH)CH2-); and Hruby, V. J. (1982) *Life Sci.* (1982) 31:189-199 (—CH2-S—); each of which is incorporated herein by reference. A particularly preferred non-peptide linkage is —CH2NH—. Such peptide mimetics may have significant advantages over polypeptide embodiments, including, for example: more economical production, greater chemical stability, enhanced pharmacological properties (half-life, absorption, potency, efficacy, etc.), altered specificity (e.g., a broad-spectrum of biological activities), reduced antigenicity, and others. Labeling of peptidomimetics usually involves covalent attachment of one or more labels, directly or through a spacer (e.g., an amide group), to non-interfering position(s) on the peptidomimetic that are predicted by quantitative structure-activity data and/or molecular modeling. Such non-interfering positions generally are positions that do not form direct contacts with the macropolypeptides(s) to which the peptidomimetic binds to produce the therapeutic effect. Derivatization (e.g., labeling) of peptidomimetics should not substantially interfere with the desired biological or pharmacological activity of the peptidomimetic.

Also encompassed by the present invention are small molecules which can modulate (either enhance or inhibit) interactions, e.g., between biomarkers described herein or listed in Table 1 and their natural binding partners. The small molecules of the present invention can be obtained using any of the numerous approaches in combinatorial library methods known in the art, including: spatially addressable parallel solid phase or solution phase libraries; synthetic library methods requiring deconvolution; the 'one-bead one-compound' library method; and synthetic library methods using affinity chromatography selection. (Lam, K. S. (1997) *Anti-cancer Drug Des.* 12:145).

Examples of methods for the synthesis of molecular libraries can be found in the art, for example in: DeWitt et al. (1993) *Proc. Natl. Acad. Sci. USA* 90:6909; Erb et al. (1994) *Proc. Natl. Acad. Sci. USA* 91:11422; Zuckermann et al. (1994) *J. Med. Chem.* 37:2678; Cho et al. (1993) *Science* 261:1303; Carrell et al. (1994) *Angew. Chem. Int. Ed. Engl.* 33:2059; Carell et al. (1994) *Angew. Chem. Int. Ed. Engl.* 33:2061; and in Gallop et al. (1994) *J. Med. Chem.* 37:1233.

Libraries of compounds can be presented in solution (e.g., Houghten (1992) *Biotechniques* 13:412-421), or on beads (Lam (1991) *Nature* 354:82-84), chips (Fodor (1993) *Nature* 364:555-556), bacteria (Ladner U.S. Pat. No. 5,223,409), spores (Ladner USP '409), plasmids (Cull et al. (1992) *Proc. Natl. Acad. Sci. USA* 89:1865-1869) or on phage (Scott and Smith (1990) *Science* 249:386-390); (Devlin (1990) *Science* 249:404-406); (Cwirla et al. (1990) *Proc. Natl. Acad. Sci. USA* 87:6378-6382); (Felici (1991) *J. Mol. Biol.* 222:301-310); (Ladner supra.). Compounds can be screened in cell based or non-cell based assays. Compounds can be screened in pools (e.g. multiple compounds in each testing sample) or as individual compounds.

The invention also relates to chimeric or fusion proteins of the biomarkers of the invention, including the biomarkers listed in Table 1, or fragments thereof. As used herein, a "chimeric protein" or "fusion protein" comprises one or more biomarkers of the invention, including one or more biomarkers listed in Table 1, or a fragment thereof, operatively linked to another polypeptide having an amino acid sequence corresponding to a protein which is not substantially homologous to the respective biomarker. In a preferred embodiment, the fusion protein comprises at least one biologically active portion of one or more biomarkers of the invention, including one or more biomarkers listed in Table 1, or fragments thereof. Within the fusion protein, the term "operatively linked" is intended to indicate that the biomarker sequences and the non-biomarker sequences are fused in-frame to each other in such a way as to preserve functions exhibited when expressed independently of the fusion. The "another" sequences can be fused to the N-terminus or C-terminus of the biomarker sequences, respectively.

Such a fusion protein can be produced by recombinant expression of a nucleotide sequence encoding the first peptide and a nucleotide sequence encoding the second peptide. The second peptide may optionally correspond to a moiety that alters the solubility, affinity, stability or valency of the first peptide, for example, an immunoglobulin constant region. In another preferred embodiment, the first peptide consists of a portion of a biologically active molecule (e.g. the extracellular portion of the polypeptide or the ligand binding portion). The second peptide can include an immunoglobulin constant region, for example, a human Cγ1 domain or Cγ4 domain (e.g., the hinge, CH2 and CH3 regions of human IgCγ 1, or human IgCγ4, see e.g., Capon et al. U.S. Pat. Nos. 5,116,964; 5,580,756; 5,844,095 and the like, incorporated herein by reference). Such constant regions may retain regions which mediate effector function (e.g. Fc receptor binding) or may be altered to reduce effector function. A resulting fusion protein may have altered solubility, binding affinity, stability and/or valency (i.e., the number of binding sites available per polypeptide) as compared to the independently expressed first peptide, and may increase the efficiency of protein purification. Fusion proteins and peptides produced by recombinant techniques can be secreted and isolated from a mixture of cells and medium containing the protein or peptide. Alternatively, the protein or peptide can be retained cytoplasmically and the cells harvested, lysed and the protein isolated. A cell culture typically includes host cells, media and other byproducts. Suitable media for cell culture are well-known in the art. Protein and peptides can be isolated from cell culture media, host cells, or both using techniques known in the art for purifying proteins and peptides. Techniques for transfecting host cells and purifying proteins and peptides are known in the art.

Preferably, a fusion protein of the invention is produced by standard recombinant DNA techniques. For example, DNA fragments coding for the different polypeptide sequences are ligated together in-frame in accordance with conventional techniques, for example employing blunt-ended or stagger-ended termini for ligation, restriction enzyme digestion to provide for appropriate termini, filling-in of cohesive ends as appropriate, alkaline phosphatase treatment to avoid undesirable joining, and enzymatic ligation. In another embodiment, the fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed and reamplified to generate a chimeric gene sequence (see, for example, *Current Protocols in Molecular Biology*, eds. Ausubel et al. John Wiley & Sons: 1992).

Particularly preferred Ig fusion proteins include the extracellular domain portion or variable region-like domain of one or more biomarker listed in Table 1, coupled to an immunoglobulin constant region (e.g., the Fc region). The immunoglobulin constant region may contain genetic modifications which reduce or eliminate effector activity inherent in the immunoglobulin structure. For example, DNA encoding the extracellular portion of a polypeptide of interest can be joined to DNA encoding the hinge, CH2 and CH3 regions of human IgGγ1 and/or IgGγ4 modified by site directed mutagenesis, e.g., as taught in WO 97/28267.

In another embodiment, the fusion protein contains a heterologous signal sequence at its N-terminus. In certain host cells (e.g., mammalian host cells), expression and/or secretion of a polypeptide can be increased through use of a heterologous signal sequence.

The fusion proteins of the invention can be used as immunogens to produce antibodies in a subject. Such antibodies may be used to purify the respective natural polypeptides from which the fusion proteins were generated, or in screening assays to identify polypeptides which inhibit the interactions between one or more biomarkers polypeptide or a fragment thereof and its natural binding partner(s) or a fragment(s) thereof.

The modulatory agents described herein (e.g., antibodies, small molecules, peptides, fusion proteins, or small nucleic acids) can be incorporated into pharmaceutical compositions and administered to a subject in vivo. The compositions may contain a single such molecule or agent or any combination of agents described herein. "Single active agents" described herein can be combined with other pharmacologically active compounds ("second active agents") known in the art according to the methods and compositions provided herein.

The production and use of biomarker nucleic acid and/or biomarker polypeptide molecules described herein can be facilitated by using standard recombinant techniques. In some embodiments, such techniques use vectors, preferably expression vectors, containing a nucleic acid encoding a biomarker polypeptide or a portion of such a polypeptide. As used herein, the term "vector" refers to a nucleic acid molecule capable of transporting another nucleic acid to which it has been linked. One type of vector is a "plasmid", which refers to a circular double stranded DNA loop into which additional DNA segments can be ligated. Another type of vector is a viral vector, wherein additional DNA segments can be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors, namely expression vectors, are capable of directing the expression of genes to which they are operably linked. In general, expression vectors of utility in recombinant DNA techniques are often in the form of plasmids (vectors). However, the present invention is intended to include such other forms of expression vectors, such as viral vectors (e.g., replication defective retroviruses, adenoviruses and adeno-associated viruses), which serve equivalent functions.

The recombinant expression vectors of the present invention comprise a nucleic acid of the present invention in a form suitable for expression of the nucleic acid in a host cell. This means that the recombinant expression vectors include one or more regulatory sequences, selected on the basis of the host cells to be used for expression, which is operably linked to the nucleic acid sequence to be expressed. Within a recombinant expression vector, "operably linked" is intended to mean that the nucleotide sequence of interest is linked to the regulatory sequence(s) in a manner which allows for expression of the nucleotide sequence (e.g., in an in vitro transcription/translation system or in a host cell when the vector is introduced into the host cell). The term "regulatory sequence" is intended to include promoters, enhancers and other expression control elements (e.g., polyadenylation signals). Such regulatory sequences are described, for example, in Goeddel, *Methods in Enzymology: Gene Expression Technology* vol. 185, Academic Press, San Diego, CA (1991). Regulatory sequences include those which direct constitutive expression of a nucleotide sequence in many types of host cell and those which direct expression of the nucleotide sequence only in certain host cells (e.g., tissue-specific regulatory sequences). It will be appreciated by those skilled in the art that the design of the expression vector can depend on such factors as the choice of the host cell to be transformed, the level of expression of protein desired, and the like. The expression vectors of the present invention can be introduced into host cells to thereby produce proteins or peptides, including fusion proteins or peptides, encoded by nucleic acids as described herein.

The recombinant expression vectors for use in the present invention can be designed for expression of a polypeptide corresponding to a marker of the present invention in prokaryotic (e.g., *E. coli*) or eukaryotic cells (e.g., insect cells {using baculovirus expression vectors}, yeast cells or mammalian cells). Suitable host cells are discussed further in Goeddel, supra. Alternatively, the recombinant expression vector can be transcribed and translated in vitro, for example using T7 promoter regulatory sequences and T7 polymerase.

Expression of proteins in prokaryotes is most often carried out in *E. coli* with vectors containing constitutive or inducible promoters directing the expression of either fusion or non-fusion proteins. Fusion vectors add a number of amino acids to a protein encoded therein, usually to the amino terminus of the recombinant protein. Such fusion vectors typically serve three purposes: 1) to increase expression of recombinant protein; 2) to increase the solubility of the recombinant protein; and 3) to aid in the purification of the recombinant protein by acting as a ligand in affinity purification. Often, in fusion expression vectors, a proteolytic cleavage site is introduced at the junction of the fusion moiety and the recombinant protein to enable separation of the recombinant protein from the fusion moiety subsequent to purification of the fusion protein. Such enzymes, and their cognate recognition sequences, include Factor Xa, thrombin and enterokinase. Typical fusion expression vectors include pGEX (Pharmacia Biotech Inc; Smith and Johnson, 1988, *Gene* 67:31-40), pMAL (New England Biolabs, Beverly, MA) and pRIT5 (Pharmacia, Piscataway, NJ) which fuse glutathione S-transferase (GST), maltose E binding protein, or protein A, respectively, to the target recombinant protein.

Examples of suitable inducible non-fusion *E. coli* expression vectors include pTrc (Amann et al., 1988, *Gene* 69:301-315) and pET 11d (Studier et al., p. 60-89, In *Gene Expression Technology: Methods in Enzymology* vol. 185, Academic Press, San Diego, C A, 1991). Target biomarker nucleic acid expression from the pTrc vector relies on host RNA polymerase transcription from a hybrid trp-lac fusion promoter. Target biomarker nucleic acid expression from the pET 11d vector relies on transcription from a T7 gn10-lac fusion promoter mediated by a co-expressed viral RNA polymerase (T7 gn1). This viral polymerase is supplied by host strains BL21 (DE3) or HMS174(DE3) from a resident prophage harboring a T7 gn1 gene under the transcriptional control of the lacUV 5 promoter.

One strategy to maximize recombinant protein expression in *E. coli* is to express the protein in a host bacterium with an impaired capacity to proteolytically cleave the recombinant protein (Gottesman, p. 119-128, In Gene Expression Technology: *Methods in Enzymology* vol. 185, Academic Press, San Diego, C A, 1990. Another strategy is to alter the nucleic acid sequence of the nucleic acid to be inserted into an expression vector so that the individual codons for each amino acid are those preferentially utilized in *E. coli* (Wada et al., 1992, *Nucleic Acids Res.* 20:2111-2118). Such alteration of nucleic acid sequences of the present invention can be carried out by standard DNA synthesis techniques. In another embodiment, the expression vector is a yeast expression vector.

Examples of vectors for expression in yeast *S. cerevisiae* include pYepSec1 (Baldari et al., 1987, *EMBO J.* 6:229-234), pMFa (Kurjan and Herskowitz, 1982, *Cell* 30:933-943), pJRY88 (Schultz et al., 1987, *Gene* 54:113-123), pYES2 (Invitrogen Corporation, San Diego, CA), and pPicZ (Invitrogen Corp, San Diego, CA).

Alternatively, the expression vector is a baculovirus expression vector. Baculovirus vectors available for expression of proteins in cultured insect cells (e.g., Sf 9 cells) include the pAc series (Smith et al., 1983, *Mol. Cell Biol.* 3:2156-2165) and the pVL series (Lucklow and Summers, 1989, *Virology* 170:31-39).

In yet another embodiment, a nucleic acid of the present invention is expressed in mammalian cells using a mammalian expression vector. Examples of mammalian expression vectors include pCDM8 (Seed, 1987, *Nature* 329:840) and pMT2PC (Kaufman et al., 1987, *EMBO J.* 6:187-195). When used in mammalian cells, the expression vector's control functions are often provided by viral regulatory elements. For example, commonly used promoters are derived from polyoma, Adenovirus 2, cytomegalovirus and Simian Virus 40. For other suitable expression systems for both prokaryotic and eukaryotic cells see chapters 16 and 17 of Sambrook et al., supra.

In another embodiment, the recombinant mammalian expression vector is capable of directing expression of the nucleic acid preferentially in a particular cell type (e.g., tissue-specific regulatory elements are used to express the nucleic acid). Tissue-specific regulatory elements are known in the art. Non-limiting examples of suitable tissue-specific promoters include the albumin promoter (liver-specific; Pinkert et al., 1987, *Genes Dev.* 1:268-277), lymphoid-specific promoters (Calame and Eaton, 1988, *Adv. Immunol.* 43:235-275), in particular promoters of T cell receptors (Winoto and Baltimore, 1989, *EMBO J.* 8:729-733) and immunoglobulins (Banerji et al., 1983, *Cell* 33:729-740; Queen and Baltimore, 1983, *Cell* 33:741-748), neuron-specific promoters (e.g., the neurofilament promoter; Byrne and Ruddle, 1989, *Proc. Natl. Acad. Sci. USA* 86:5473-5477), pancreas-specific promoters (Edlund et al., 1985, *Science* 230:912-916), and mammary gland-specific promoters (e.g., milk whey promoter; U.S. Pat. No. 4,873,316 and European Application Publication No. 264,166). Developmentally-regulated promoters are also encompassed, for example the murine hox promoters (Kessel and Gruss, 1990, *Science* 249:374-379) and the a-fetoprotein promoter (Camper and Tilghman, 1989, *Genes Dev.* 3:537-546).

The present invention further provides a recombinant expression vector comprising a DNA molecule cloned into the expression vector in an antisense orientation. That is, the DNA molecule is operably linked to a regulatory sequence in a manner which allows for expression (by transcription of the DNA molecule) of an RNA molecule which is antisense to the mRNA encoding a polypeptide of the present invention. Regulatory sequences operably linked to a nucleic acid cloned in the antisense orientation can be chosen which direct the continuous expression of the antisense RNA molecule in a variety of cell types, for instance viral promoters and/or enhancers, or regulatory sequences can be chosen which direct constitutive, tissue-specific or cell type specific expression of antisense RNA. The antisense expression vector can be in the form of a recombinant plasmid, phagemid, or attenuated virus in which antisense nucleic acids are produced under the control of a high efficiency regulatory region, the activity of which can be determined by the cell type into which the vector is introduced. For a discussion of the regulation of gene expression using antisense genes (see Weintraub et al., 1986, *Trends in Genetics*, Vol. 1(1)).

Another aspect of the present invention pertains to host cells into which a recombinant expression vector of the present invention has been introduced. The terms "host cell" and "recombinant host cell" are used interchangeably herein. It is understood that such terms refer not only to the particular subject cell but to the progeny or potential progeny of such a cell. Because certain modifications may occur in succeeding generations due to either mutation or environmental influences, such progeny may not, in fact, be identical to the parent cell, but are still included within the scope of the term as used herein.

A host cell can be any prokaryotic (e.g., *E. coli*) or eukaryotic cell (e.g., insect cells, yeast or mammalian cells).

Vector DNA can be introduced into prokaryotic or eukaryotic cells via conventional transformation or transfection techniques. As used herein, the terms "transformation" and "transfection" are intended to refer to a variety of art-recognized techniques for introducing foreign nucleic acid into a host cell, including calcium phosphate or calcium chloride co-precipitation, DEAE-dextran-mediated transfection, lipofection, or electroporation. Suitable methods for transforming or transfecting host cells can be found in Sambrook, et al. (supra), and other laboratory manuals.

For stable transfection of mammalian cells, it is known that, depending upon the expression vector and transfection technique used, only a small fraction of cells may integrate the foreign DNA into their genome. In order to identify and select these integrants, a gene that encodes a selectable marker (e.g., for resistance to antibiotics) is generally introduced into the host cells along with the gene of interest. Preferred selectable markers include those which confer resistance to drugs, such as G418, hygromycin and methotrexate. Cells stably transfected with the introduced nucleic acid can be identified by drug selection (e.g., cells that have incorporated the selectable marker gene will survive, while the other cells die).

XII. Analyzing Biomarker Nucleic Acids and Polypeptides

Biomarker nucleic acids and/or biomarker polypeptides can be analyzed according to the methods described herein and techniques known to the skilled artisan to identify such genetic or expression alterations useful for the present invention including, but not limited to, 1) an alteration in the level of a biomarker transcript or polypeptide, 2) a deletion or addition of one or more nucleotides from a biomarker gene, 4) a substitution of one or more nucleotides of a biomarker gene, 5) aberrant modification of a biomarker gene, such as an expression regulatory region, and the like.

a. Methods for Detection of Copy Number

Methods of evaluating the copy number of a biomarker nucleic acid are well-known to those of skill in the art. The presence or absence of chromosomal gain or loss can be evaluated simply by a determination of copy number of the regions or markers identified herein.

In one embodiment, a biological sample is tested for the presence of copy number changes in genomic loci containing the genomic marker. A copy number of at least 3, 4, 5, 6, 7, 8, 9, or 10 is predictive of poorer outcome of an anti-HHLA2 antibody therapy.

Methods of evaluating the copy number of a biomarker locus include, but are not limited to, hybridization-based assays. Hybridization-based assays include, but are not limited to, traditional "direct probe" methods, such as Southern blots, in situ hybridization (e.g., FISH and FISH plus SKY) methods, and "comparative probe" methods, such as comparative genomic hybridization (CGH), e.g., cDNA-based or oligonucleotide-based CGH. The methods can be used in a wide variety of formats including, but not limited to, substrate (e.g. membrane or glass) bound methods or array-based approaches.

In one embodiment, evaluating the biomarker gene copy number in a sample involves a Southern Blot. In a Southern Blot, the genomic DNA (typically fragmented and separated on an electrophoretic gel) is hybridized to a probe specific for the target region. Comparison of the intensity of the hybridization signal from the probe for the target region with control probe signal from analysis of normal genomic DNA (e.g., a non-amplified portion of the same or related cell, tissue, organ, etc.) provides an estimate of the relative copy number of the target nucleic acid. Alternatively, a Northern blot may be utilized for evaluating the copy number of encoding nucleic acid in a sample. In a Northern blot, mRNA is hybridized to a probe specific for the target region. Comparison of the intensity of the hybridization signal from the probe for the target region with control probe signal from analysis of normal RNA (e.g., a non-amplified portion of the same or related cell, tissue, organ, etc.) provides an estimate of the relative copy number of the target nucleic acid. Alternatively, other methods well-known in the art to detect RNA can be used, such that higher or lower expression relative to an appropriate control (e.g., a non-amplified portion of the same or related cell tissue, organ, etc.) provides an estimate of the relative copy number of the target nucleic acid.

An alternative means for determining genomic copy number is in situ hybridization (e.g., Angerer (1987) *Meth. Enzymol* 152: 649). Generally, in situ hybridization comprises the following steps: (1) fixation of tissue or biological structure to be analyzed; (2) prehybridization treatment of the biological structure to increase accessibility of target DNA, and to reduce nonspecific binding; (3) hybridization of the mixture of nucleic acids to the nucleic acid in the biological structure or tissue; (4) post-hybridization washes to remove nucleic acid fragments not bound in the hybridization and (5) detection of the hybridized nucleic acid fragments. The reagent used in each of these steps and the conditions for use vary depending on the particular application. In a typical in situ hybridization assay, cells are fixed to a solid support, typically a glass slide. If a nucleic acid is to be probed, the cells are typically denatured with heat or alkali. The cells are then contacted with a hybridization solution at a moderate temperature to permit annealing of labeled probes specific to the nucleic acid sequence encoding the protein. The targets (e.g., cells) are then typically washed at a predetermined stringency or at an increasing stringency until an appropriate signal to noise ratio is obtained. The probes are typically labeled, e.g., with radioisotopes or fluorescent reporters. In one embodiment, probes are sufficiently long so as to specifically hybridize with the target nucleic acid(s) under stringent conditions. Probes generally range in length from about 200 bases to about 1000 bases. In some applications it is necessary to block the hybridization capacity of repetitive sequences. Thus, in some embodiments, tRNA, human genomic DNA, or Cot-I DNA is used to block non-specific hybridization.

An alternative means for determining genomic copy number is comparative genomic hybridization. In general, genomic DNA is isolated from normal reference cells, as well as from test cells (e.g., tumor cells) and amplified, if necessary. The two nucleic acids are differentially labeled and then hybridized in situ to metaphase chromosomes of a reference cell. The repetitive sequences in both the reference and test DNAs are either removed or their hybridization capacity is reduced by some means, for example by prehybridization with appropriate blocking nucleic acids and/or including such blocking nucleic acid sequences for said repetitive sequences during said hybridization. The bound, labeled DNA sequences are then rendered in a visualizable form, if necessary. Chromosomal regions in the test cells which are at increased or decreased copy number can be identified by detecting regions where the ratio of signal from the two DNAs is altered. For example, those regions that have decreased in copy number in the test cells will show relatively lower signal from the test DNA than the reference compared to other regions of the genome. Regions that have been increased in copy number in the test cells will show relatively higher signal from the test DNA. Where there are chromosomal deletions or multiplications, differences in the ratio of the signals from the two labels will be detected and the ratio will provide a measure of the copy number. In another embodiment of CGH, array CGH (aCGH), the immobilized chromosome element is replaced with a collection of solid support bound target nucleic acids on an array, allowing for a large or complete percentage of the genome to be represented in the collection of solid support bound targets. Target nucleic acids may comprise cDNAs, genomic DNAs, oligonucleotides (e.g., to detect single nucleotide polymorphisms) and the like. Array-based CGH may also be performed with single-color labeling (as opposed to labeling the control and the possible tumor sample with two different dyes and mixing them prior to hybridization, which will yield a ratio due to competitive hybridization of probes on the arrays). In single color CGH, the control is labeled and hybridized to one array and absolute signals are read, and the possible tumor sample is labeled and hybridized to a second array (with identical content) and absolute signals are read. Copy number difference is calculated based on absolute signals from the two arrays. Methods of preparing immobilized chromosomes or arrays and performing comparative genomic hybridization are well-known in the art (see, e.g., U.S. Pat. Nos. 6,335, 167; 6,197,501; 5,830,645; and 5,665,549 and Albertson (1984) *EMBO J.* 3: 1227-1234; Pinkel (1988) *Proc. Natl. Acad. Sci. USA* 85: 9138-9142; EPO Pub. No. 430,402; Methods in Molecular Biology, Vol. 33: In situ Hybridization Protocols, Choo, ed., Humana Press, Totowa, N.J. (1994), etc.) In another embodiment, the hybridization protocol of Pinkel, et al. (1998) *Nature Genetics* 20: 207-211, or of Kallioniemi (1992) *Proc. Natl Acad Sci USA* 89:5321-5325 (1992) is used.

In still another embodiment, amplification-based assays can be used to measure copy number. In such amplification-based assays, the nucleic acid sequences act as a template in an amplification reaction (e.g., Polymerase Chain Reaction (PCR). In a quantitative amplification, the amount of amplification product will be proportional to the amount of template in the original sample. Comparison to appropriate controls, e.g. healthy tissue, provides a measure of the copy number.

Methods of "quantitative" amplification are well-known to those of skill in the art. For example, quantitative PCR involves simultaneously co-amplifying a known quantity of a control sequence using the same primers. This provides an internal standard that may be used to calibrate the PCR reaction. Detailed protocols for quantitative PCR are provided in Innis, et al. (1990) PCR Protocols, *A Guide to Methods and Applications*, Academic Press, Inc. N.Y.). Measurement of DNA copy number at microsatellite loci using quantitative PCR analysis is described in Ginzonger, et al. (2000) *Cancer Research* 60:5405-5409. The known nucleic acid sequence for the genes is sufficient to enable one of skill in the art to routinely select primers to amplify any portion of the gene. Fluorogenic quantitative PCR may also be used in the methods of the present invention. In fluorogenic quantitative PCR, quantitation is based on amount of fluorescence signals, e.g., TaqMan and SYBR green.

Other suitable amplification methods include, but are not limited to, ligase chain reaction (LCR) (see Wu and Wallace (1989) *Genomics* 4: 560, Landegren, et al. (1988) *Science* 241:1077, and Barringer et al. (1990) *Gene* 89: 117), transcription amplification (Kwoh, et al. (1989) *Proc. Natl. Acad. Sci. USA* 86: 1173), self-sustained sequence replication (Guatelli, et al. (1990) *Proc. Nat. Acad. Sci. USA* 87: 1874), dot PCR, and linker adapter PCR, etc.

Loss of heterozygosity (LOH) and major copy proportion (MCP) mapping (Wang, Z. C., et al. (2004) *Cancer Res* 64(1):64-71; Seymour, A. B., et al. (1994) *Cancer Res* 54, 2761-4; Hahn, S. A., et al. (1995) *Cancer Res* 55, 4670-5; Kimura, M., et al. (1996) *Genes Chromosomes Cancer* 17, 88-93; Li et al., (2008) *MBC Bioinform.* 9, 204-219) may also be used to identify regions of amplification or deletion.

b. Methods for Detection of Biomarker Nucleic Acid Expression

Biomarker expression may be assessed by any of a wide variety of well-known methods for detecting expression of a transcribed molecule or protein. Non-limiting examples of such methods include immunological methods for detection of secreted, cell-surface, cytoplasmic, or nuclear proteins, protein purification methods, protein function or activity assays, nucleic acid hybridization methods, nucleic acid reverse transcription methods, and nucleic acid amplification methods.

In preferred embodiments, activity of a particular gene is characterized by a measure of gene transcript (e.g. mRNA), by a measure of the quantity of translated protein, or by a measure of gene product activity. Marker expression can be monitored in a variety of ways, including by detecting mRNA levels, protein levels, or protein activity, any of which can be measured using standard techniques. Detection can involve quantification of the level of gene expression (e.g., genomic DNA, cDNA, mRNA, protein, or enzyme activity), or, alternatively, can be a qualitative assessment of the level of gene expression, in particular in comparison with a control level. The type of level being detected will be clear from the context.

In another embodiment, detecting or determining expression levels of a biomarker and functionally similar homologs thereof, including a fragment or genetic alteration thereof (e.g., in regulatory or promoter regions thereof) comprises detecting or determining RNA levels for the marker of interest. In one embodiment, one or more cells from the subject to be tested are obtained and RNA is isolated from the cells. In a preferred embodiment, a sample of breast tissue cells is obtained from the subject.

In one embodiment, RNA is obtained from a single cell. For example, a cell can be isolated from a tissue sample by laser capture microdissection (LCM). Using this technique, a cell can be isolated from a tissue section, including a stained tissue section, thereby assuring that the desired cell is isolated (see, e.g., Bonner et al. (1997) *Science* 278: 1481; Emmert-Buck et al. (1996) *Science* 274:998; Fend et al. (1999) *Am. J. Path.* 154: 61 and Murakami et al. (2000) *Kidney Int.* 58:1346). For example, Murakami et al., supra, describe isolation of a cell from a previously immunostained tissue section.

It is also be possible to obtain cells from a subject and culture the cells in vitro, such as to obtain a larger population of cells from which RNA can be extracted. Methods for establishing cultures of non-transformed cells, i.e., primary cell cultures, are known in the art.

When isolating RNA from tissue samples or cells from individuals, it may be important to prevent any further changes in gene expression after the tissue or cells has been removed from the subject. Changes in expression levels are known to change rapidly following perturbations, e.g., heat shock or activation with lipopolysaccharide (LPS) or other reagents. In addition, the RNA in the tissue and cells may quickly become degraded. Accordingly, in a preferred embodiment, the tissue or cells obtained from a subject is snap frozen as soon as possible.

RNA can be extracted from the tissue sample by a variety of methods, e.g., the guanidium thiocyanate lysis followed by CsCl centrifugation (Chirgwin et al., 1979, *Biochemistry* 18:5294-5299). RNA from single cells can be obtained as described in methods for preparing cDNA libraries from single cells, such as those described in Dulac, C. (1998) *Curr. Top. Dev. Biol.* 36, 245 and Jena et al. (1996) *J. Immunol. Methods* 190:199. Care to avoid RNA degradation must be taken, e.g., by inclusion of RNAsin.

The RNA sample can then be enriched in particular species. In one embodiment, poly(A)+RNA is isolated from the RNA sample. In general, such purification takes advantage of the poly-A tails on mRNA. In particular and as noted above, poly-T oligonucleotides may be immobilized within on a solid support to serve as affinity ligands for mRNA. Kits for this purpose are commercially available, e.g., the MessageMaker kit (Life Technologies, Grand Island, NY).

In a preferred embodiment, the RNA population is enriched in marker sequences. Enrichment can be undertaken, e.g., by primer-specific cDNA synthesis, or multiple rounds of linear amplification based on cDNA synthesis and template-directed in vitro transcription (see, e.g., Wang et al. (1989) *PNAS* 86, 9717; Dulac et al., supra, and Jena et al., supra).

The population of RNA, enriched or not in particular species or sequences, can further be amplified. As defined herein, an "amplification process" is designed to strengthen, increase, or augment a molecule within the RNA. For example, where RNA is mRNA, an amplification process such as RT-PCR can be utilized to amplify the mRNA, such that a signal is detectable or detection is enhanced. Such an amplification process is beneficial particularly when the biological, tissue, or tumor sample is of a small size or volume.

Various amplification and detection methods can be used. For example, it is within the scope of the present invention to reverse transcribe mRNA into cDNA followed by polymerase chain reaction (RT-PCR); or, to use a single enzyme for both steps as described in U.S. Pat. No. 5,322,770, or reverse transcribe mRNA into cDNA followed by symmetric gap ligase chain reaction (RT-AGLCR) as described by R. L. Marshall, et al., *PCR Methods and Applications* 4: 80-84 (1994). Real time PCR may also be used.

Other known amplification methods which can be utilized herein include but are not limited to the so-called "NASBA" or "3SR" technique described in *PNAS* USA 87: 1874-1878 (1990) and also described in Nature 350 (No. 6313): 91-92 (1991); Q-beta amplification as described in published European Patent Application (EPA) No. 4544610; strand displacement amplification (as described in G. T. Walker et al., *Clin. Chem.* 42: 9-13 (1996) and European Patent Application No. 684315; target mediated amplification, as described by PCT Publication WO9322461; PCR; ligase chain reaction (LCR) (see, e.g., Wu and Wallace, Genomics 4, 560 (1989), Landegren et al., *Science* 241, 1077 (1988)); self-sustained sequence replication (SSR) (see, e.g., Guatelli et al., *Proc. Nat. Acad. Sci.* USA, 87, 1874 (1990)); and transcription amplification (see, e.g., Kwoh et al., *Proc. Natl. Acad. Sci. USA* 86, 1173 (1989)).

Many techniques are known in the state of the art for determining absolute and relative levels of gene expression, commonly used techniques suitable for use in the present invention include Northern analysis, RNase protection assays (RPA), microarrays and PCR-based techniques, such as quantitative PCR and differential display PCR. For example, Northern blotting involves running a preparation of RNA on a denaturing agarose gel, and transferring it to a suitable support, such as activated cellulose, nitrocellulose or glass or nylon membranes. Radiolabeled cDNA or RNA is then hybridized to the preparation, washed and analyzed by autoradiography.

In situ hybridization visualization may also be employed, wherein a radioactively labeled antisense RNA probe is hybridized with a thin section of a biopsy sample, washed, cleaved with RNase and exposed to a sensitive emulsion for autoradiography. The samples may be stained with hematoxylin to demonstrate the histological composition of the sample, and dark field imaging with a suitable light filter shows the developed emulsion. Non-radioactive labels such as digoxigenin may also be used.

Alternatively, mRNA expression can be detected on a DNA array, chip or a microarray. Labeled nucleic acids of a test sample obtained from a subject may be hybridized to a solid surface comprising biomarker DNA. Positive hybridization signal is obtained with the sample containing biomarker transcripts. Methods of preparing DNA arrays and their use are well-known in the art (see, e.g., U.S. Pat. Nos: 6,618,6796; 6,379,897; 6,664,377; 6,451,536; 548,257; U.S. 20030157485 and Schena et al. (1995) *Science* 20, 467-470; Gerhold et al. (1999) *Trends In Biochem. Sci.* 24, 168-173; and Lennon et al. (2000) *Drug Discovery Today* 5, 59-65, which are herein incorporated by reference in their entirety). Serial Analysis of Gene Expression (SAGE) can also be performed (See for example U.S. Patent Application 20030215858).

To monitor mRNA levels, for example, mRNA is extracted from the biological sample to be tested, reverse transcribed, and fluorescently-labeled cDNA probes are generated. The microarrays capable of hybridizing to marker cDNA are then probed with the labeled cDNA probes, the slides scanned and fluorescence intensity measured. This intensity correlates with the hybridization intensity and expression levels.

Types of probes that can be used in the methods described herein include cDNA, riboprobes, synthetic oligonucleotides and genomic probes. The type of probe used will generally be dictated by the particular situation, such as riboprobes for in situ hybridization, and cDNA for Northern blotting, for example. In one embodiment, the probe is directed to nucleotide regions unique to the RNA. The probes may be as short as is required to differentially recognize marker mRNA transcripts, and may be as short as, for example, 15 bases; however, probes of at least 17, 18, 19 or 20 or more bases can be used. In one embodiment, the primers and probes hybridize specifically under stringent conditions to a DNA fragment having the nucleotide sequence corresponding to the marker. As herein used, the term "stringent conditions" means hybridization will occur only if there is at least 95% identity in nucleotide sequences. In another embodiment, hybridization under "stringent conditions" occurs when there is at least 97% identity between the sequences.

The form of labeling of the probes may be any that is appropriate, such as the use of radioisotopes, for example, $^{32}P$ and $^{35}S$. Labeling with radioisotopes may be achieved, whether the probe is synthesized chemically or biologically, by the use of suitably labeled bases.

In one embodiment, the biological sample contains polypeptide molecules from the test subject. Alternatively, the biological sample can contain mRNA molecules from the test subject or genomic DNA molecules from the test subject.

In another embodiment, the methods further involve obtaining a control biological sample from a control subject, contacting the control sample with a compound or agent capable of detecting marker polypeptide, mRNA, genomic DNA, or fragments thereof, such that the presence of the marker polypeptide, mRNA, genomic DNA, or fragments thereof, is detected in the biological sample, and comparing the presence of the marker polypeptide, mRNA, genomic DNA, or fragments thereof, in the control sample with the presence of the marker polypeptide, mRNA, genomic DNA, or fragments thereof in the test sample.

c. Methods for Detection of Biomarker Protein Expression

The activity or level of a biomarker protein can be detected and/or quantified by detecting or quantifying the expressed polypeptide. The polypeptide can be detected and quantified by any of a number of means well-known to those of skill in the art. Aberrant levels of polypeptide expression of the polypeptides encoded by a biomarker nucleic acid and functionally similar homologs thereof, including a fragment or genetic alteration thereof (e.g., in regulatory or promoter regions thereof) are associated with the likelihood of response of a cancer to anti-HHLA2 antibody therapy. Any method known in the art for detecting polypeptides can be used. Such methods include, but are not limited to, immunodiffusion, immunoelectrophoresis, radioimmunoassay (RIA), enzyme-linked immunosorbent assays (ELISAs), immunofluorescent assays, Western blotting, binder-ligand assays, immunohistochemical techniques, agglutination, complement assays, high performance liquid chromatography (HPLC), thin layer chromatography (TLC), hyperdiffusion chromatography, and the like (e.g., Basic and Clinical Immunology, Sites and Terr, eds., Appleton and Lange, Norwalk, Conn. pp 217-262, 1991 which is incorporated by reference). Preferred are binder-ligand immunoassay methods including reacting antibodies with an epitope or epitopes and competitively displacing a labeled polypeptide or derivative thereof. In certain embodiments, the antibodies listed in table 2 are used to detect and/or quantify the biomarkers listed in table 1.

For example, ELISA and RIA procedures may be conducted such that a desired biomarker protein standard is labeled (with a radioisotope such as $^{125}I$ or $^{35}S$, or an assayable enzyme, such as horseradish peroxidase or alkaline phosphatase), and, together with the unlabeled sample, brought into contact with the corresponding antibody, whereon a second antibody is used to bind the first, and radioactivity or the immobilized enzyme assayed (competitive assay). Alternatively, the biomarker protein in the sample is allowed to react with the corresponding immobilized antibody, radioisotope- or enzyme-labeled anti-biomarker protein antibody is allowed to react with the system, and radioactivity or the enzyme assayed (ELISA-sandwich assay). Other conventional methods may also be employed as suitable.

The above techniques may be conducted essentially as a "one-step" or "two-step" assay. A "one-step" assay involves contacting antigen with immobilized antibody and, without washing, contacting the mixture with labeled antibody. A "two-step" assay involves washing before contacting, the mixture with labeled antibody. Other conventional methods may also be employed as suitable.

In one embodiment, a method for measuring biomarker protein levels comprises the steps of: contacting a biological specimen with an antibody or variant (e.g., fragment) thereof which selectively binds the biomarker protein, and detecting whether said antibody or variant thereof is bound to said sample and thereby measuring the levels of the biomarker protein.

Enzymatic and radiolabeling of biomarker protein and/or the antibodies may be effected by conventional means. Such means will generally include covalent linking of the enzyme to the antigen or the antibody in question, such as by glutaraldehyde, specifically so as not to adversely affect the activity of the enzyme, by which is meant that the enzyme must still be capable of interacting with its substrate, although it is not necessary for all of the enzyme to be active, provided that enough remains active to permit the assay to be effected. Indeed, some techniques for binding enzyme are non-specific (such as using formaldehyde), and will only yield a proportion of active enzyme.

It is usually desirable to immobilize one component of the assay system on a support, thereby allowing other components of the system to be brought into contact with the component and readily removed without laborious and time-consuming labor. It is possible for a second phase to be immobilized away from the first, but one phase is usually sufficient.

It is possible to immobilize the enzyme itself on a support, but if solid-phase enzyme is required, then this is generally best achieved by binding to antibody and affixing the antibody to a support, models and systems for which are well-known in the art. Simple polyethylene may provide a suitable support.

Enzymes employable for labeling are not particularly limited, but may be selected from the members of the oxidase group, for example. These catalyze production of hydrogen peroxide by reaction with their substrates, and glucose oxidase is often used for its good stability, ease of availability and cheapness, as well as the ready availability of its substrate (glucose). Activity of the oxidase may be assayed by measuring the concentration of hydrogen peroxide formed after reaction of the enzyme-labeled antibody with the substrate under controlled conditions well-known in the art.

Other techniques may be used to detect biomarker protein according to a practitioner's preference based upon the present disclosure. One such technique is Western blotting (Towbin et at., *Proc. Nat. Acad. Sci.* 76:4350 (1979)), wherein a suitably treated sample is run on an SDS-PAGE gel before being transferred to a solid support, such as a nitrocellulose filter. Anti-biomarker protein antibodies (unlabeled) are then brought into contact with the support and assayed by a secondary immunological reagent, such as labeled protein A or anti-immunoglobulin (suitable labels including $^{125}$I, horseradish peroxidase and alkaline phosphatase). Chromatographic detection may also be used.

Immunohistochemistry may be used to detect expression of biomarker protein, e.g., in a biopsy sample. A suitable antibody is brought into contact with, for example, a thin layer of cells, washed, and then contacted with a second, labeled antibody. Labeling may be by fluorescent markers, enzymes, such as peroxidase, avidin, or radiolabeling. The assay is scored visually, using microscopy.

Anti-biomarker protein antibodies (e.g., listed in table 2), such as intrabodies, may also be used for imaging purposes, for example, to detect the presence of biomarker protein in cells and tissues of a subject. Suitable labels include radioisotopes, iodine ($^{125}$I, $^{121}$I), carbon ($^{14}$C), sulphur ($^{35}$S), tritium (3H), indium ($^{112}$In), and technetium ($^{99}$mTc), fluorescent labels, such as fluorescein and rhodamine, and biotin.

For in vivo imaging purposes, antibodies are not detectable, as such, from outside the body, and so must be labeled, or otherwise modified, to permit detection. Markers for this purpose may be any that do not substantially interfere with the antibody binding, but which allow external detection. Suitable markers may include those that may be detected by X-radiography, NMR or MRI. For X-radiographic techniques, suitable markers include any radioisotope that emits detectable radiation but that is not overtly harmful to the subject, such as barium or cesium, for example. Suitable markers for NMR and MRI generally include those with a detectable characteristic spin, such as deuterium, which may be incorporated into the antibody by suitable labeling of nutrients for the relevant hybridoma, for example.

The size of the subject, and the imaging system used, will determine the quantity of imaging moiety needed to produce diagnostic images. In the case of a radioisotope moiety, for a human subject, the quantity of radioactivity injected will normally range from about 5 to 20 millicuries of technetium-99. The labeled antibody or antibody fragment will then preferentially accumulate at the location of cells which contain biomarker protein. The labeled antibody or antibody fragment can then be detected using known techniques.

Antibodies that may be used to detect biomarker protein include any antibody (e.g., listed in table 2), whether natural or synthetic, full length or a fragment thereof, monoclonal or polyclonal, that binds sufficiently strongly and specifically to the biomarker protein to be detected. An antibody may have a $K_d$ of at most about $10^{-6}$M, $10^{-7}$M, $10^{-8}$M, $10^{-9}$M, $10^{-10}$M, $10^{-11}$M, $10^{-12}$M. The phrase "specifically binds" refers to binding of, for example, an antibody to an epitope or antigen or antigenic determinant in such a manner that binding can be displaced or competed with a second preparation of identical or similar epitope, antigen or antigenic determinant. An antibody may bind preferentially to the biomarker protein relative to other proteins, such as related proteins.

Antibodies are commercially available or may be prepared according to methods known in the art.

Antibodies and derivatives thereof that may be used encompass polyclonal or monoclonal antibodies, chimeric, human, humanized, primatized (CDR-grafted), veneered or single-chain antibodies as well as functional fragments, i.e., biomarker protein binding fragments, of antibodies. For example, antibody fragments capable of binding to a biomarker protein or portions thereof, including, but not limited to, Fv, Fab, Fab' and F(ab') 2 fragments can be used. Such fragments can be produced by enzymatic cleavage or by recombinant techniques. For example, papain or pepsin cleavage can generate Fab or F(ab') 2 fragments, respectively. Other proteases with the requisite substrate specificity can also be used to generate Fab or F(ab') 2 fragments. Antibodies can also be produced in a variety of truncated forms using antibody genes in which one or more stop codons have been introduced upstream of the natural stop site. For example, a chimeric gene encoding a F(ab') 2 heavy chain portion can be designed to include DNA sequences encoding the CH, domain and hinge region of the heavy chain.

Synthetic and engineered antibodies are described in, e.g., Cabilly et al., U.S. Pat. No. 4,816,567 Cabilly et al., European Patent No. 0,125,023 B1; Boss et al., U.S. Pat. No. 4,816,397; Boss et al., European Patent No. 0,120,694 B1; Neuberger, M. S. et al., WO 86/01533; Neuberger, M. S. et al., European Patent No. 0,194,276 B1; Winter, U.S. Pat. No. 5,225,539; Winter, European Patent No. 0,239,400 B1; Queen et al., European Patent No. 0451216 B1; and Padlan, E. A. et al., EP 0519596 A1. See also, Newman, R. et al., BioTechnology, 10: 1455-1460 (1992), regarding primatized antibody, and Ladner et al., U.S. Pat. No. 4,946,778 and Bird, R. E. et al., Science, 242: 423-426 (1988)) regarding single-chain antibodies. Antibodies produced from a library, e.g., phage display library, may also be used.

In some embodiments, agents that specifically bind to a biomarker protein other than antibodies are used, such as peptides. Peptides that specifically bind to a biomarker protein can be identified by any means known in the art. For example, specific peptide binders of a biomarker protein can be screened for using peptide phage display libraries.

d. Methods for Detection of Biomarker Structural Alterations

The following illustrative methods can be used to identify the presence of a structural alteration in a biomarker nucleic acid and/or biomarker polypeptide molecule in order to, for example, identify HHLA2, TMIGD2, KIR3DL3 that are overexpressed, overfunctional, and the like.

In certain embodiments, detection of the alteration involves the use of a probe/primer in a polymerase chain reaction (PCR) (see, e.g., U.S. Pat. Nos. 4,683,195 and 4,683,202), such as anchor PCR or RACE PCR, or, alternatively, in a ligation chain reaction (LCR) (see, e.g., Landegran et al. (1988) Science 241:1077-1080; and Nakazawa et al. (1994) Proc. Natl. Acad. Sci. USA 91:360-364), the latter of which can be particularly useful for detecting point mutations in a biomarker nucleic acid such as a biomarker gene (see Abravaya et al. (1995) Nucleic Acids Res. 23:675-682). This method can include the steps of collecting a sample of cells from a subject, isolating nucleic acid (e.g., genomic, mRNA or both) from the cells of the sample, contacting the nucleic acid sample with one or more primers which specifically hybridize to a biomarker gene under conditions such that hybridization and amplification of the biomarker gene (if present) occurs, and detecting the presence or absence of an amplification product, or detecting the size of the amplification product and comparing the length to a control sample. It is anticipated that PCR and/or LCR may be desirable to use as a preliminary amplification step in conjunction with any of the techniques used for detecting mutations described herein.

Alternative amplification methods include: self-sustained sequence replication (Guatelli, J. C. et al. (1990) Proc. Natl. Acad. Sci. USA 87:1874-1878), transcriptional amplification system (Kwoh, D. Y. et al. (1989) Proc. Natl. Acad. Sci. USA 86:1173-1177), Q-Beta Replicase (Lizardi, P. M. et al. (1988) Bio-Technology 6:1197), or any other nucleic acid amplification method, followed by the detection of the amplified molecules using techniques well-known to those of skill in the art. These detection schemes are especially useful for the detection of nucleic acid molecules if such molecules are present in very low numbers.

In an alternative embodiment, mutations in a biomarker nucleic acid from a sample cell can be identified by alterations in restriction enzyme cleavage patterns. For example, sample and control DNA is isolated, amplified (optionally), digested with one or more restriction endonucleases, and fragment length sizes are determined by gel electrophoresis and compared. Differences in fragment length sizes between sample and control DNA indicates mutations in the sample DNA. Moreover, the use of sequence specific ribozymes (see, for example, U.S. Pat. No. 5,498,531) can be used to score for the presence of specific mutations by development or loss of a ribozyme cleavage site.

In other embodiments, genetic mutations in biomarker nucleic acid can be identified by hybridizing a sample and control nucleic acids, e.g., DNA or RNA, to high density arrays containing hundreds or thousands of oligonucleotide probes (Cronin, M. T. et al. (1996) Hum. Mutat. 7:244-255; Kozal, M. J. et al. (1996) Nat. Med. 2:753-759). For example, biomarker genetic mutations can be identified in two dimensional arrays containing light-generated DNA probes as described in Cronin et al. (1996) supra. Briefly, a first hybridization array of probes can be used to scan through long stretches of DNA in a sample and control to identify base changes between the sequences by making linear arrays of sequential, overlapping probes. This step allows the identification of point mutations. This step is followed by a second hybridization array that allows the characterization of specific mutations by using smaller, specialized probe arrays complementary to all variants or mutations detected. Each mutation array is composed of parallel probe sets, one complementary to the wild-type gene and the other complementary to the mutant gene. Such biomarker genetic mutations can be identified in a variety of contexts, including, for example, germline and somatic mutations.

In yet another embodiment, any of a variety of sequencing reactions known in the art can be used to directly sequence a biomarker gene and detect mutations by comparing the sequence of the sample biomarker with the corresponding wild-type (control) sequence. Examples of sequencing reactions include those based on techniques developed by Maxam and Gilbert (1977) Proc. Natl. Acad. Sci. USA 74:560 or Sanger (1977) Proc. Natl. Acad Sci. USA 74:5463. It is also contemplated that any of a variety of automated sequencing procedures can be utilized when performing the diagnostic assays (Naeve (1995) Biotechniques 19:448-53), including sequencing by mass spectrometry (see, e.g., PCT International Publication No. WO 94/16101; Cohen et al. (1996) Adv. Chromatogr. 36:127-162; and Griffin et al. (1993) Appl. Biochem. Biotechnol. 38:147-159).

Other methods for detecting mutations in a biomarker gene include methods in which protection from cleavage agents is used to detect mismatched bases in RNA/RNA or RNA/DNA heteroduplexes (Myers et al. (1985) Science 230:1242). In general, the art technique of "mismatch cleavage" starts by providing heteroduplexes formed by hybridizing (labeled) RNA or DNA containing the wild-type biomarker sequence with potentially mutant RNA or DNA obtained from a tissue sample. The double-stranded duplexes are treated with an agent which cleaves single-stranded regions of the duplex such as which will exist due to base pair mismatches between the control and sample strands. For instance, RNA/DNA duplexes can be treated with RNase and DNA/DNA hybrids treated with SI nuclease to enzymatically digest the mismatched regions. In other embodiments, either DNA/DNA or RNA/DNA duplexes can be treated with hydroxylamine or osmium tetroxide and with piperidine in order to digest mismatched regions. After digestion of the mismatched regions, the resulting material is then separated by size on denaturing polyacrylamide gels to determine the site of mutation. See, for example, Cotton et al. (1988) Proc. Natl. Acad. Sci. USA 85:4397 and Saleeba et al. (1992) Methods Enzymol. 217:286-295. In a preferred embodiment, the control DNA or RNA can be labeled for detection.

In still another embodiment, the mismatch cleavage reaction employs one or more proteins that recognize mismatched base pairs in double-stranded DNA (so called "DNA mismatch repair" enzymes) in defined systems for detecting and mapping point mutations in biomarker cDNAs obtained from samples of cells. For example, the mutY enzyme of E. coli cleaves A at G/A mismatches and the thymidine DNA glycosylase from HeLa cells cleaves T at G/T mismatches (Hsu et al. (1994) Carcinogenesis 15:1657-1662). According to an exemplary embodiment, a probe based on a biomarker sequence, e.g., a wild-type biomarker treated with a DNA mismatch repair enzyme, and the cleavage products, if any, can be detected from electrophoresis protocols or the like (e.g., U.S. Pat. No. 5,459,039.)

In other embodiments, alterations in electrophoretic mobility can be used to identify mutations in biomarker genes. For example, single strand conformation polymorphism (SSCP) may be used to detect differences in electrophoretic mobility between mutant and wild type nucleic acids (Orita et al. (1989) Proc Natl. Acad. Sci USA 86:2766; see also Cotton (1993) Mutat. Res. 285:125-144 and Hayashi (1992) Genet. Anal. Tech. Appl. 9:73-79). Single-stranded DNA fragments of sample and control biomarker nucleic acids will be denatured and allowed to renature. The secondary structure of single-stranded nucleic acids varies according to sequence, the resulting alteration in electrophoretic mobility enables the detection of even a single base change. The DNA fragments may be labeled or detected with labeled probes. The sensitivity of the assay may be enhanced by using RNA (rather than DNA), in which the secondary structure is more sensitive to a change in sequence. In a preferred embodiment, the subject method utilizes heteroduplex analysis to separate double stranded heteroduplex molecules on the basis of changes in electrophoretic mobility (Keen et al. (1991) Trends Genet. 7:5).

In yet another embodiment the movement of mutant or wild-type fragments in polyacrylamide gels containing a gradient of denaturant is assayed using denaturing gradient gel electrophoresis (DGGE) (Myers et al. (1985) Nature 313:495). When DGGE is used as the method of analysis, DNA will be modified to ensure that it does not completely denature, for example by adding a GC clamp of approximately 40 bp of high-melting GC-rich DNA by PCR. In a further embodiment, a temperature gradient is used in place of a denaturing gradient to identify differences in the mobility of control and sample DNA (Rosenbaum and Reissner (1987) *Biophys. Chem.* 265:12753).

Examples of other techniques for detecting point mutations include, but are not limited to, selective oligonucleotide hybridization, selective amplification, or selective primer extension. For example, oligonucleotide primers may be prepared in which the known mutation is placed centrally and then hybridized to target DNA under conditions which permit hybridization only if a perfect match is found (Saiki et al. (1986) *Nature* 324:163; Saiki et al. (1989) *Proc. Natl. Acad. Sci. USA* 86:6230). Such allele specific oligonucleotides are hybridized to PCR amplified target DNA or a number of different mutations when the oligonucleotides are attached to the hybridizing membrane and hybridized with labeled target DNA.

Alternatively, allele specific amplification technology which depends on selective PCR amplification may be used in conjunction with the instant invention. Oligonucleotides used as primers for specific amplification may carry the mutation of interest in the center of the molecule (so that amplification depends on differential hybridization) (Gibbs et al. (1989) *Nucleic Acids Res.* 17:2437-2448) or at the extreme 3' end of one primer where, under appropriate conditions, mismatch can prevent, or reduce polymerase extension (Prossner (1993) *Tibtech* 11:238). In addition it may be desirable to introduce a novel restriction site in the region of the mutation to create cleavage-based detection (Gasparini et al. (1992) *Mol. Cell Probes* 6:1). It is anticipated that in certain embodiments amplification may also be performed using Taq ligase for amplification (Barany (1991) *Proc. Natl. Acad. Sci USA* 88:189). In such cases, ligation will occur only if there is a perfect match at the 3' end of the 5' sequence making it possible to detect the presence of a known mutation at a specific site by looking for the presence or absence of amplification.

Anti-Cancer Therapies

The efficacy of anti-HHLA2 antibody therapy is predicted according to biomarker amount and/or activity associated with a cancer in a subject according to the methods described herein. In one embodiment, such anti-HHLA2 antibody therapy or combinations of therapies (e.g., one or more anti-HHLA2 antibody therapy in combination with one or more additional anti-cancer therapies, such as another immune checkpoint inhibitor) can be administered, particularly if a subject has first been indicated as being a likely responder to anti-HHLA2 antibody therapy. In another embodiment, such anti-HHLA2 antibody therapy can be avoided once a subject is indicated as not being a likely responder to anti-HHLA2 antibody therapy and an alternative treatment regimen, such as targeted and/or untargeted anti-cancer therapies can be administered. Combination therapies are also contemplated and can comprise, for example, one or more chemotherapeutic agents and radiation, one or more chemotherapeutic agents and immunotherapy, or one or more chemotherapeutic agents, radiation and chemotherapy, each combination of which can be with anti-immune checkpoint therapy. In addition, any representative embodiment of an agent to modulate a particular target can be adapted to any other target described herein and below by the ordinarily skilled artisn (e.g., direct and indirect HHLA2 inhibitors described herein can be applied to other immune checkpoint inhibitors and/or HHLA2, such as monospecific antibodies, bispecific antibodies, non-activating forms, small molecules, peptides, interfering nucleic acids, and the like).

The term "targeted therapy" refers to administration of agents that selectively interact with a chosen biomolecule to thereby treat cancer. One example includes immune checkpoint inhibitors, which are well-known in the art. For example, anti-CTLA-4 pathway agents, such as therapeutic monoclonal blocking antibodies, which are well-known in the art and described above, can be used to target tumor microenvironments and cells expressing unwanted components of the CTLA-4 pathway, such as CTLA-4 ligands (e.g., CD80 and CD86).

For example, the term "CTLA-4 pathway" refers to the CTLA-4 receptor and its ligands, e.g., CD80 and CD86. "CTLA-4 pathway inhibitors" block or otherwise reduce the interaction between CTLA-4 and one or both of its ligands such that the immunoinhibitory signaling otherwise generated by the interaction is blocked or otherwise reduced. Anti-immune checkpoint inhibitors can be direct or indirect. Direct anti-immune checkpoint inhibitors block or otherwise reduce the interaction between an immune checkpoint and at least one of its ligands. For example, CTLA-4 inhibitors can block CTLA-4 binding with one or both of its ligands. Direct CTLA-4 combination inhibitors are well-known in the art, especially since the natural binding partners of CTLA-4 (e.g., CD80 and CD86) are known.

For example, agents which directly block the interaction between CTLA-4 and one or more CTLA-4 ligands and/or binding partners, such as a bispecific antibody, can prevent inhibitory signaling and upregulate an immune response (i.e., as a CTLA-4 pathway inhibitor). Alternatively, agents that indirectly block the interaction between CTLA-4 and one or both of its ligands can prevent inhibitory signaling and upregulate an immune response. For example, B7-1 or a soluble form thereof, by binding to a CTLA-4 polypeptide indirectly reduces the effective concentration of PD-L1 polypeptide available to bind to CTLA-4. Exemplary agents include monospecific or bispecific blocking antibodies against CTLA-4 and one or more CTLA-4 ligands and/or binding partners that block the interaction between the receptor and ligand(s); a non-activating form of CTLA-4 and one or more CTLA-4 ligands and/or binding partners (e.g., a dominant negative or soluble polypeptide), small molecules or peptides that block the interaction between CTLA-4 and one or more CTLA-4 ligands and/or binding partners; fusion proteins (e.g. the extracellular portion of CTLA-4 and one or more CTLA-4 ligands and/or binding partners, fused to the Fc portion of an antibody or immunoglobulin) that bind CTLA-4 and one or more CTLA-4 ligands and/or binding partners and inhibit the interaction between the receptor and ligand(s); a non-activating form of a natural CTLA-4 and one or more CTLA-4 ligands and/or binding partners, and a soluble form of a natural CTLA-4 and one or more CTLA-4 ligands and/or binding partners.

Indirect anti-immune checkpoint inhibitors block or otherwise reduce the immunoinhibitory signaling generated by the interaction between the immune checkpoint and at least one of its ligands. For example, an inhibitor can block the interaction between CTLA-4 and one or both of its ligands without necessarily directly blocking the interaction between CTLA-4 and one or both of its ligands. For example, indirect inhibitors include intrabodies that bind the intracellular portion of CTLA-4 and/or one or more CTLA-4 ligands and/or binding partners required to signal to block or otherwise reduce the immunoinhibitory signaling. Similarly, nucleic acids that reduce the expression of CTLA-4 and/or one or more CTLA-4 ligands and/or binding partners can indirectly inhibit the interaction between CTLA-4 and one or both of its ligands by removing the availability of components for interaction. Such nucleic acid molecules can block CTLA-4 and/or one or more CTLA-4 ligands and/or binding partners transcription or translation.

Similarly, agents which directly block the interaction between HHLA2 and HHLA2 receptor(s)/co-receptor(s), such as an anti-HHLA2 antibody, an antibody recognizing one or more HHLA2 receptor(s)/co-receptor(s), an anti-HHLA2/anti-immune checkpoint bispecific antibody, and the like, can prevent the HHLA2 and/or its receptor(s)/co-receptor(s) signaling and its downstream immune responses. Alternatively, agents that indirectly block the interaction between HHLA2 and/or its receptor(s)/co-receptor(s) can prevent the HHLA2 and/or its receptor(s)/co-receptor(s) signaling and its downstream immune responses. For example, a soluble form HHLA2, such as an extracellular domain of HHLA2, by binding to its receptor(s)/co-receptor(s) indirectly reduces the effective concentration of its receptor(s)/co-receptor(s) available to bind to HHLA2 on cell surface. Exemplary agents include monospecific or bispecific blocking antibodies against HHLA2 and/or its receptor(s)/co-receptor(s) that block the interaction between the receptor and ligand(s); a non-activating form of HHLA2 and/or its receptor(s)/co-receptor(s) (e.g., a dominant negative or soluble polypeptide), small molecules or peptides that block the interaction between HHLA2 and/or its receptor(s)/co-receptor(s); fusion proteins (e.g. the extracellular portion of HHLA2 and/or its receptor(s)/co-receptor(s), fused to the Fc portion of an antibody or immunoglobulin) that bind to HHLA2 and/or its receptor(s)/co-receptor(s) and inhibit the interaction between the receptor and ligand(s); a non-activating form of a natural HHLA2 and/or its receptor(s)/co-receptor(s), and a soluble form of a natural HHLA2 and/or its receptor(s)/co-receptor(s).

Immunotherapies that are designed to elicit or amplify an immune response are referred to as "activation immunotherapies." Immunotherapies that are designed to reduce or suppress an immune response are referred to as "suppression immunotherapies." Any agent believed to have an immune system effect on the genetically modified transplanted cancer cells can be assayed to determine whether the agent is an immunotherapy and the effect that a given genetic modification has on the modulation of immune response. In some embodiments, the immunotherapy is cancer cell-specific. In some embodiments, immunotherapy can be "untargeted," which refers to administration of agents that do not selectively interact with immune system cells, yet modulates immune system function. Representative examples of untargeted therapies include, without limitation, chemotherapy, gene therapy, and radiation therapy.

Immunotherapy can involve passive immunity for short-term protection of a host, achieved by the administration of pre-formed antibody directed against a cancer antigen or disease antigen (e.g., administration of a monoclonal antibody, optionally linked to a chemotherapeutic agent or toxin, to a tumor antigen). Immunotherapy can also focus on using the cytotoxic lymphocyte-recognized epitopes of cancer cell lines. Alternatively, antisense polynucleotides, ribozymes, RNA interference molecules, triple helix polynucleotides and the like, can be used to selectively modulate biomolecules that are linked to the initiation, progression, and/or pathology of a tumor or cancer.

In one embodiment, immunotherapy comprises adoptive cell-based immunotherapies. Well-known adoptive cell-based immunotherapeutic modalities, including, without limitation, Irradiated autologous or allogeneic Lunor cells, tumor lysates or apoptotic tumor cells, antigen-presenting cell-based immunotherapy, dendritic cell-based immunotherapy, adoptive T cell transfer, adoptive CAR T cell therapy, autologous immune enhancement therapy (AIET), cancer vaccines, and/or antigen presenting cells. Such cell-based immunotherapies can be further modified to express one or more gene products to further modulate immune responses, such as expressing cytokines like GM-CSF, and/or to express tumor-associated antigen (TAA) antigens, such as Mage-1, gp-100, patient-specific neoantigen vaccines, and the like.

In another embodiment, immunotherapy comprises non-cell-based immunotherapies. In one embodiment, compositions comprising antigens with or without vaccine-enhancing adjuvants are used. Such compositions exist in many well-known forms, such as peptide compositions, oncolytic viruses, recombinant antigen comprising fusion proteins, and the like. In still another embodiment, immunomodulatory interleukins, such as IL-2, IL-6, IL-7, IL-12, IL-17, IL-23, and the like, as well as modulators thereof (e.g., blocking antibodies or more potent or longer lasting forms) are used. In yet another embodiment, immunomodulatory cytokines, such as interferons, G-CSF, imiquimod, TNFalpha, and the like, as well as modulators thereof (e.g., blocking antibodies or more potent or longer lasting forms) are used. In another embodiment, immunomodulatory chemokines, such as CCL3, CCL26, and CXCL7, and the like, as well as modulators thereof (e.g., blocking antibodies or more potent or longer lasting forms) are used. In another embodiment, immunomodulatory molecules targeting immunosuppression, such as STAT3 signaling modulators, NFkappaB signaling modulators, and immune checkpoint modulators, are used. The terms "immune checkpoint" and "anti-immune checkpoint therapy" are described above.

In still another embodiment, immunomodulatory drugs, such as immunocytostatic drugs, glucocorticoids, cytostatics, immunophilins and modulators thereof (e.g., rapamycin, a calcineurin inhibitor, tacrolimus, ciclosporin (cyclosporin), pimecrolimus, abetimus, gusperimus, ridaforolimus, everolimus, temsirolimus, zotarolimus, etc.), hydrocortisone (cortisol), cortisone acetate, prednisone, prednisolone, methylprednisolone, dexamethasone, betamethasone, triamcinolone, beclometasone, fludrocortisone acetate, deoxycorticosterone acetate (doca) aldosterone, a non-glucocorticoid steroid, a pyrimidine synthesis inhibitor, leflunomide, teriflunomide, a folic acid analog, methotrexate, anti-thymocyte globulin, anti-lymphocyte globulin, thalidomide, lenalidomide, pentoxifylline, bupropion, curcumin, catechin, an opioid, an IMPDH inhibitor, mycophenolic acid, myriocin, fingolimod, an NF-xB inhibitor, raloxifene, drotrecogin alfa, denosumab, an NF-xB signaling cascade inhibitor, disulfiram, olmesartan, dithiocarbamate, a proteasome inhibitor, bortezomib, MG132, Prol, NPI-0052, curcumin, genistein, resveratrol, parthenolide, thalidomide, lenalidomide, flavopiridol, non-steroidal anti-inflammatory drugs (NSAIDs), arsenic trioxide, dehydroxymethylepoxyquinomycin (DHMEQ), I3C(indole-3-carbinol)/DIM(di-indolmethane) (13C/DIM), Bay 11-7082, luteolin, cell permeable peptide SN-50, IKBa.-super repressor overexpression, NFKB decoy oligodeoxynucleotide (ODN), or a derivative or analog of any thereo, are used. In yet another embodiment, immunomodulatory antibodies or protein are used. For example, antibodies that bind to CD40, Toll-like receptor (TLR), OX40, GITR, CD27, or to 4-1BB, T-cell bispecific antibodies, an anti-IL-2 receptor antibody, an anti-CD3 antibody, OKT3 (muromonab), otelixizumab, teplizumab, visilizumab, an anti-CD4 antibody, clenoliximab, keliximab, zanolimumab, an anti-CD11 a antibody, efalizumab, an anti-CD18 antibody, erlizumab, rovelizumab, an anti-CD20 antibody, afutuzumab, ocrelizumab, ofatumumab, pascolizumab, rituximab, an anti-CD23 antibody, lumiliximab, an anti-CD40 antibody, teneliximab, toralizumab, an anti-CD40L antibody, ruplizumab, an anti-CD62L antibody, aselizumab, an anti-CD80 antibody, galiximab, an anti-CD147 antibody, gavilimomab, a B-Lymphocyte stimulator (BLyS) inhibiting antibody, belimumab, an CTLA4-Ig fusion protein, abatacept, belatacept, an anti-CTLA4 antibody, ipilimumab, tremelimumab, an anti-eotaxin 1 antibody, bertilimumab, an anti-a4-integrin antibody, natalizumab, an anti-IL-6R antibody, tocilizumab, an anti-LFA-1 antibody, odulimomab, an anti-CD25 antibody, basiliximab, daclizumab, inolimomab, an anti-CD5 antibody, zolimomab, an anti-CD2 antibody, siplizumab, nerelimomab, faralimomab, atlizumab, atorolimumab, cedelizumab, dorlimomab aritox, dorlixizumab, fontolizumab, gantenerumab, gomiliximab, lebrilizumab, maslimomab, morolimumab, pexelizumab, reslizumab, rovelizumab, talizumab, telimomab aritox, vapaliximab, vepalimomab, aflibercept, alefacept, rilonacept, an IL-1 receptor antagonist, anakinra, an anti-IL-5 antibody, mepolizumab, an IgE inhibitor, omalizumab, talizumab, an IL12 inhibitor, an IL23 inhibitor, ustekinumab, and the like.

Nutritional supplements that enhance immune responses, such as vitamin A, vitamin E, vitamin C, and the like, are well-known in the art (see, for example, U.S. Pat. Nos. 4,981,844 and 5,230,902 and PCT Publ. No. WO 2004/004483) can be used in the methods described herein.

Similarly, agents and therapies other than immunotherapy or in combination thereof can be used with in combination with an anti-HHLA2 antibodies to stimulate an immune response to thereby treat a condition that would benefit therefrom. For example, chemotherapy, radiation, epigenetic modifiers (e.g., histone deacetylase (HDAC) modifiers, methylation modifiers, phosphorylation modifiers, and the like), targeted therapy, and the like are well-known in the art.

The term "untargeted therapy" refers to administration of agents that do not selectively interact with a chosen biomolecule yet treat cancer. Representative examples of untargeted therapies include, without limitation, chemotherapy, gene therapy, and radiation therapy.

In one embodiment, chemotherapy is used. Chemotherapy includes the administration of a chemotherapeutic agent. Such a chemotherapeutic agent may be, but is not limited to, those selected from among the following groups of compounds: platinum compounds, cytotoxic antibiotics, antimetabolites, anti-mitotic agents, alkylating agents, arsenic compounds, DNA topoisomerase inhibitors, taxanes, nucleoside analogues, plant alkaloids, and toxins; and synthetic derivatives thereof. Exemplary compounds include, but are not limited to, alkylating agents: cisplatin, treosulfan, and trofosfamide; plant alkaloids: vinblastine, paclitaxel, docetaxol; DNA topoisomerase inhibitors: teniposide, crisnatol, and mitomycin; anti-folates: methotrexate, mycophenolic acid, and hydroxyurea; pyrimidine analogs: 5-fluorouracil, doxifluridine, and cytosine arabinoside; purine analogs: mercaptopurine and thioguanine; DNA antimetabolites: 2'-deoxy-5-fluorouridine, aphidicolin glycinate, and pyrazoloimidazole; and antimitotic agents: halichondrin, colchicine, and rhizoxin. Compositions comprising one or more chemotherapeutic agents (e.g., FLAG, CHOP) may also be used. FLAG comprises fludarabine, cytosine arabinoside (Ara-C) and G-CSF. CHOP comprises cyclophosphamide, vincristine, doxorubicin, and prednisone. In another embodiments, PARP (e.g., PARP-1 and/or PARP-2) inhibitors are used and such inhibitors are well-known in the art (e.g., Olaparib, ABT-888, BSI-201, BGP-15 (N-Gene Research Laboratories, Inc.); INO-1001 (Inotek Pharmaceuticals Inc.); PJ34 (Soriano et al., 2001; Pacher et al., 2002b); 3-aminobenzamide (Trevigen); 4-amino-1,8-naphthalimide; (Trevigen); 6(5H)-phenanthridinone (Trevigen); benzamide (U.S. Pat. Re. 36,397); and NU1025 (Bowman et al.). The mechanism of action is generally related to the ability of PARP inhibitors to bind PARP and decrease its activity. PARP catalyzes the conversion of .beta.-nicotinamide adenine dinucleotide (NAD+) into nicotinamide and poly-ADP-ribose (PAR). Both poly (ADP-ribose) and PARP have been linked to regulation of transcription, cell proliferation, genomic stability, and carcinogenesis (Bouchard V. J. et. al. Experimental Hematology, Volume 31, Number 6, June 2003, pp. 446-454(9); Herceg Z.; Wang Z.-Q. Mutation Research/Fundamental and Molecular Mechanisms of Mutagenesis, Volume 477, Number 1, 2 Jun. 2001, pp. 97-110(14)). Poly(ADP-ribose) polymerase 1 (PARP1) is a key molecule in the repair of DNA single-strand breaks (SSBs) (de Murcia J. et al. 1997. Proc Natl Acad Sci USA 94:7303-7307; Schreiber V, Dantzer F, Ame J C, de Murcia G (2006) Nat Rev Mol Cell Biol 7:517-528; Wang Z Q, et al. (1997) Genes Dev 11:2347-2358). Knockout of SSB repair by inhibition of PARP1 function induces DNA double-strand breaks (DSBs) that can trigger synthetic lethality in cancer cells with defective homology-directed DSB repair (Bryant H E, et al. (2005) Nature 434:913-917; Farmer H, et al. (2005) Nature 434:917-921). The foregoing examples of chemotherapeutic agents are illustrative, and are not intended to be limiting.

In another embodiment, radiation therapy is used. The radiation used in radiation therapy can be ionizing radiation. Radiation therapy can also be gamma rays, X-rays, or proton beams. Examples of radiation therapy include, but are not limited to, external-beam radiation therapy, interstitial implantation of radioisotopes (I-125, palladium, iridium), radioisotopes such as strontium-89, thoracic radiation therapy, intraperitoneal P-32 radiation therapy, and/or total abdominal and pelvic radiation therapy. For a general overview of radiation therapy, see Hellman, Chapter 16: Principles of Cancer Management: Radiation Therapy, 6th edition, 2001, DeVita et al., eds., J. B. Lippencott Company, Philadelphia. The radiation therapy can be administered as external beam radiation or teletherapy wherein the radiation is directed from a remote source. The radiation treatment can also be administered as internal therapy or brachytherapy wherein a radioactive source is placed inside the body close to cancer cells or a tumor mass. Also encompassed is the use of photodynamic therapy comprising the administration of photosensitizers, such as hematoporphyrin and its derivatives, Vertoporfin (BPD-MA), phthalocyanine, photosensitizer Pc4, demethoxy-hypocrellin A; and 2BA-2-DMHA.

In another embodiment, surgical intervention can occur to physically remove cancerous cells and/or tissues.

In still another embodiment, hormone therapy is used. Hormonal therapeutic treatments can comprise, for example, hormonal agonists, hormonal antagonists (e.g., flutamide, bicalutamide, tamoxifen, raloxifene, leuprolide acetate (LUPRON), LH-RH antagonists), inhibitors of hormone biosynthesis and processing, and steroids (e.g., dexamethasone, retinoids, deltoids, betamethasone, cortisol, cortisone, prednisone, dehydrotestosterone, glucocorticoids, mineralocorticoids, estrogen, testosterone, progestins), vitamin A derivatives (e.g., all-trans retinoic acid (ATRA)); vitamin D3 analogs; antigestagens (e.g., mifepristone, onapristone), or antiandrogens (e.g., cyproterone acetate).

In yet another embodiment, hyperthermia, a procedure in which body tissue is exposed to high temperatures (up to 106° F.) is used. Heat may help shrink tumors by damaging cells or depriving them of substances they need to live. Hyperthermia therapy can be local, regional, and whole-body hyperthermia, using external and internal heating devices. Hyperthermia is almost always used with other forms of therapy (e.g., radiation therapy, chemotherapy, and biological therapy) to try to increase their effectiveness. Local hyperthermia refers to heat that is applied to a very small area, such as a tumor. The area may be heated externally with high-frequency waves aimed at a tumor from a device outside the body. To achieve internal heating, one of several types of sterile probes may be used, including thin, heated wires or hollow tubes filled with warm water; implanted microwave antennae; and radiofrequency electrodes. In regional hyperthermia, an organ or a limb is heated. Magnets and devices that produce high energy are placed over the region to be heated. In another approach, called perfusion, some of the patient's blood is removed, heated, and then pumped (perfused) into the region that is to be heated internally. Whole-body heating is used to treat metastatic cancer that has spread throughout the body. It can be accomplished using warm-water blankets, hot wax, inductive coils (like those in electric blankets), or thermal chambers (similar to large incubators). Hyperthermia does not cause any marked increase in radiation side effects or complications. Heat applied directly to the skin, however, can cause discomfort or even significant local pain in about half the patients treated. It can also cause blisters, which generally heal rapidly.

In still another embodiment, photodynamic therapy (also called PDT, photoradiation therapy, phototherapy, or photochemotherapy) is used for the treatment of some types of cancer. It is based on the discovery that certain chemicals known as photosensitizing agents can kill one-celled organisms when the organisms are exposed to a particular type of light. PDT destroys cancer cells through the use of a fixed-frequency laser light in combination with a photosensitizing agent. In PDT, the photosensitizing agent is injected into the bloodstream and absorbed by cells all over the body. The agent remains in cancer cells for a longer time than it does in normal cells. When the treated cancer cells are exposed to laser light, the photosensitizing agent absorbs the light and produces an active form of oxygen that destroys the treated cancer cells. Light exposure must be timed carefully so that it occurs when most of the photosensitizing agent has left healthy cells but is still present in the cancer cells. The laser light used in PDT can be directed through a fiber-optic (a very thin glass strand). The fiber-optic is placed close to the cancer to deliver the proper amount of light. The fiber-optic can be directed through a bronchoscope into the lungs for the treatment of lung cancer or through an endoscope into the esophagus for the treatment of esophageal cancer. An advantage of PDT is that it causes minimal damage to healthy tissue. However, because the laser light currently in use cannot pass through more than about 3 centimeters of tissue (a little more than one and an eighth inch), PDT is mainly used to treat tumors on or just under the skin or on the lining of internal organs. Photodynamic therapy makes the skin and eyes sensitive to light for 6 weeks or more after treatment. Patients are advised to avoid direct sunlight and bright indoor light for at least 6 weeks. If patients must go outdoors, they need to wear protective clothing, including sunglasses. Other temporary side effects of PDT are related to the treatment of specific areas and can include coughing, trouble swallowing, abdominal pain, and painful breathing or shortness of breath. In December 1995, the U.S. Food and Drug Administration (FDA) approved a photosensitizing agent called porfimer sodium, or Photofrin®, to relieve symptoms of esophageal cancer that is causing an obstruction and for esophageal cancer that cannot be satisfactorily treated with lasers alone. In January 1998, the FDA approved porfimer sodium for the treatment of early non-small cell lung cancer in patients for whom the usual treatments for lung cancer are not appropriate. The National Cancer Institute and other institutions are supporting clinical trials (research studies) to evaluate the use of photodynamic therapy for several types of cancer, including cancers of the bladder, brain, larynx, and oral cavity.

In yet another embodiment, laser therapy is used to harness high-intensity light to destroy cancer cells. This technique is often used to relieve symptoms of cancer such as bleeding or obstruction, especially when the cancer cannot be cured by other treatments. It may also be used to treat cancer by shrinking or destroying tumors. The term "laser" stands for light amplification by stimulated emission of radiation. Ordinary light, such as that from a light bulb, has many wavelengths and spreads in all directions. Laser light, on the other hand, has a specific wavelength and is focused in a narrow beam. This type of high-intensity light contains a lot of energy. Lasers are very powerful and may be used to cut through steel or to shape diamonds. Lasers also can be used for very precise surgical work, such as repairing a damaged retina in the eye or cutting through tissue (in place of a scalpel). Although there are several different kinds of lasers, only three kinds have gained wide use in medicine: Carbon dioxide (CO2) laser—This type of laser can remove thin layers from the skin's surface without penetrating the deeper layers. This technique is particularly useful in treating tumors that have not spread deep into the skin and certain precancerous conditions. As an alternative to traditional scalpel surgery, the $CO_2$ laser is also able to cut the skin. The laser is used in this way to remove skin cancers.

Neodymium:yttrium-aluminum-garnet (Nd:YAG) laser—Light from this laser can penetrate deeper into tissue than light from the other types of lasers, and it can cause blood to clot quickly. It can be carried through optical fibers to less accessible parts of the body. This type of laser is sometimes used to treat throat cancers. Argon laser—This laser can pass through only superficial layers of tissue and is therefore useful in dermatology and in eye surgery. It also is used with light-sensitive dyes to treat tumors in a procedure known as photodynamic therapy (PDT). Lasers have several advantages over standard surgical tools, including: Lasers are more precise than scalpels. Tissue near an incision is protected, since there is little contact with surrounding skin or other tissue. The heat produced by lasers sterilizes the surgery site, thus reducing the risk of infection. Less operating time may be needed because the precision of the laser allows for a smaller incision. Healing time is often shortened; since laser heat seals blood vessels, there is less bleeding, swelling, or scarring. Laser surgery may be less complicated. For example, with fiber optics, laser light can be directed to parts of the body without making a large incision. More procedures may be done on an outpatient basis. Lasers can be used in two ways to treat cancer: by shrinking or destroying a tumor with heat, or by activating a chemical—known as a photosensitizing agent—that destroys cancer cells. In PDT, a photosensitizing agent is retained in cancer cells and can be stimulated by light to cause a reaction that kills cancer cells. $CO_2$ and Nd:YAG lasers are used to shrink or destroy tumors. They may be used with endoscopes, tubes that allow physicians to see into certain areas of the body, such as the bladder. The light from some lasers can be transmitted through a flexible endoscope fitted with fiber optics. This allows physicians to see and work in parts of the body that could not otherwise be reached except by surgery and therefore allows very precise aiming of the laser beam. Lasers also may be used with low-power microscopes, giving the doctor a clear view of the site being treated. Used with other instruments, laser systems can produce a cutting area as small as 200 microns in diameter—less than the width of a very fine thread. Lasers are used to treat many types of cancer. Laser surgery is a standard treatment for certain stages of glottis (vocal cord), cervical, skin, lung, vaginal, vulvar, and penile cancers. In addition to its use to destroy the cancer, laser surgery is also used to help relieve symptoms caused by cancer (palliative care). For example, lasers may be used to shrink or destroy a tumor that is blocking a patient's trachea (windpipe), making it easier to breathe. It is also sometimes used for palliation in colorectal and anal cancer. Laser-induced interstitial thermotherapy (LITT) is one of the most recent developments in laser therapy. LITT uses the same idea as a cancer treatment called hyperthermia; that heat may help shrink tumors by damaging cells or depriving them of substances they need to live. In this treatment, lasers are directed to interstitial areas (areas between organs) in the body. The laser light then raises the temperature of the tumor, which damages or destroys cancer cells.

The duration and/or dose of treatment with therapies may vary according to the particular therapeutic agent or combination thereof. An appropriate treatment time for a particular cancer therapeutic agent will be appreciated by the skilled artisan. The present invention contemplates the continued assessment of optimal treatment schedules for each cancer therapeutic agent, where the phenotype of the cancer of the subject as determined by the methods of the present invention is a factor in determining optimal treatment doses and schedules.

Any means for the introduction of a polynucleotide into mammals, human or non-human, or cells thereof may be adapted to the practice of this invention for the delivery of the various constructs of the present invention into the intended recipient. In one embodiment of the present invention, the DNA constructs are delivered to cells by transfection, i.e., by delivery of "naked" DNA or in a complex with a colloidal dispersion system. A colloidal system includes macromolecule complexes, nanocapsules, microspheres, beads, and lipid-based systems including oil-in-water emulsions, micelles, mixed micelles, and liposomes. The preferred colloidal system of this invention is a lipid-complexed or liposome-formulated DNA. In the former approach, prior to formulation of DNA, e.g., with lipid, a plasmid containing a transgene bearing the desired DNA constructs may first be experimentally optimized for expression (e.g., inclusion of an intron in the 5' untranslated region and elimination of unnecessary sequences (Felgner, et al., Ann NY Acad Sci 126-139, 1995). Formulation of DNA, e.g. with various lipid or liposome materials, may then be effected using known methods and materials and delivered to the recipient mammal. See, e.g., Canonico et al, Am J Respir Cell Mol Biol 10:24-29, 1994; Tsan et al, Am J Physiol 268; Alton et al., Nat Genet. 5:135-142, 1993 and U.S. Pat. No. 5,679,647 by Carson et al.

The targeting of liposomes can be classified based on anatomical and mechanistic factors. Anatomical classification is based on the level of selectivity, for example, organ-specific, cell-specific, and organelle-specific. Mechanistic targeting can be distinguished based upon whether it is passive or active. Passive targeting utilizes the natural tendency of liposomes to distribute to cells of the reticuloendothelial system (RES) in organs, which contain sinusoidal capillaries. Active targeting, on the other hand, involves alteration of the liposome by coupling the liposome to a specific ligand such as a monoclonal antibody, sugar, glycolipid, or protein, or by changing the composition or size of the liposome in order to achieve targeting to organs and cell types other than the naturally occurring sites of localization.

The surface of the targeted delivery system may be modified in a variety of ways. In the case of a liposomal targeted delivery system, lipid groups can be incorporated into the lipid bilayer of the liposome in order to maintain the targeting ligand in stable association with the liposomal bilayer. Various linking groups can be used for joining the lipid chains to the targeting ligand. Naked DNA or DNA associated with a delivery vehicle, e.g., liposomes, can be administered to several sites in a subject (see below). Nucleic acids can be delivered in any desired vector. These include viral or non-viral vectors, including adenovirus vectors, adeno-associated virus vectors, retrovirus vectors, lentivirus vectors, and plasmid vectors. Exemplary types of viruses include HSV (herpes simplex virus), AAV (adeno associated virus), HIV (human immunodeficiency virus), BIV (bovine immunodeficiency virus), and MLV (murine leukemia virus). Nucleic acids can be administered in any desired format that provides sufficiently efficient delivery levels, including in virus particles, in liposomes, in nanoparticles, and complexed to polymers.

The nucleic acids encoding a protein or nucleic acid of interest may be in a plasmid or viral vector, or other vector as is known in the art. Such vectors are well-known and any can be selected for a particular application. In one embodiment of the present invention, the gene delivery vehicle comprises a promoter and a demethylase coding sequence. Preferred promoters are tissue-specific promoters and promoters which are activated by cellular proliferation, such as the thymidine kinase and thymidylate synthase promoters. Other preferred promoters include promoters which are activatable by infection with a virus, such as the α- and β-interferon promoters, and promoters which are activatable by a hormone, such as estrogen. Other promoters which can be used include the Moloney virus LTR, the CMV promoter, and the mouse albumin promoter. A promoter may be constitutive or inducible.

In another embodiment, naked polynucleotide molecules are used as gene delivery vehicles, as described in WO 90/11092 and U.S. Pat. No. 5,580,859. Such gene delivery vehicles can be either growth factor DNA or RNA and, in certain embodiments, are linked to killed adenovirus. Curiel et al., Hum. Gene. Ther. 3:147-154, 1992. Other vehicles which can optionally be used include DNA-ligand (Wu et al., J. Biol. Chem. 264:16985-16987, 1989), lipid-DNA combinations (Felgner et al., Proc. Natl. Acad. Sci. USA 84:7413 7417, 1989), liposomes (Wang et al., Proc. Natl. Acad. Sci. 84:7851-7855, 1987) and microprojectiles (Williams et al., Proc. Natl. Acad. Sci. 88:2726-2730, 1991).

A gene delivery vehicle can optionally comprise viral sequences such as a viral origin of replication or packaging signal. These viral sequences can be selected from viruses such as astrovirus, coronavirus, orthomyxovirus, papovavirus, paramyxovirus, parvovirus, picornavirus, poxvirus, retrovirus, togavirus or adenovirus. In a preferred embodiment, the growth factor gene delivery vehicle is a recombinant retroviral vector. Recombinant retroviruses and various uses thereof have been described in numerous references including, for example, Mann et al., Cell 33:153, 1983, Cane and Mulligan, Proc. Nat'l. Acad. Sci. USA 81:6349, 1984, Miller et al., Human Gene Therapy 1:5-14, 1990, U.S. Pat. Nos. 4,405,712, 4,861,719, and 4,980,289, and PCT Application Nos. WO 89/02,468, WO 89/05,349, and WO 90/02,806. Numerous retroviral gene delivery vehicles can be utilized in the present invention, including for example those described in EP 0,415,731; WO 90/07936; WO 94/03622; WO 93/25698; WO 93/25234; U.S. Pat. No. 5,219,740; WO 9311230; WO 9310218; Vile and Hart, Cancer Res. 53:3860-3864, 1993; Vile and Hart, Cancer Res. 53:962-967, 1993; Ram et al., Cancer Res. 53:83-88, 1993; Takamiya et al., J. Neurosci. Res. 33:493-503, 1992; Baba et al., J. Neurosurg. 79:729-735, 1993 (U.S. Pat. No. 4,777,127, GB 2,200,651, EP 0,345,242 and WO91/02805).

Other viral vector systems that can be used to deliver a polynucleotide of the present invention have been derived from herpes virus, e.g., Herpes Simplex Virus (U.S. Pat. No. 5,631,236 by Woo et al., issued May 20, 1997 and WO 00/08191 by Neurovex), vaccinia virus (Ridgeway (1988) Ridgeway, "Mammalian expression vectors," In: Rodriguez R L, Denhardt D T, ed. Vectors: A survey of molecular cloning vectors and their uses. Stoneham: Butterworth; Baichwal and Sugden (1986) "Vectors for gene transfer derived from animal DNA viruses: Transient and stable expression of transferred genes," In: Kucherlapati R, ed. Gene transfer. New York: Plenum Press; Coupar et al. (1988) Gene, 68:1-10), and several RNA viruses. Preferred viruses include an alphavirus, a poxivirus, an arena virus, a vaccinia virus, a polio virus, and the like. They offer several attractive features for various mammalian cells (Friedmann (1989) Science, 244:1275-1281; Ridgeway, 1988, supra; Baichwal and Sugden, 1986, supra; Coupar et al., 1988; Horwich et al.(1990) J.Virol., 64:642-650).

In other embodiments, target DNA in the genome can be manipulated using well-known methods in the art. For example, the target DNA in the genome can be manipulated by deletion, insertion, and/or mutation are retroviral insertion, artificial chromosome techniques, gene insertion, random insertion with tissue specific promoters, gene targeting, transposable elements and/or any other method for introducing foreign DNA or producing modified DNA/modified nuclear DNA. Other modification techniques include deleting DNA sequences from a genome and/or altering nuclear DNA sequences. Nuclear DNA sequences, for example, may be altered by site-directed mutagenesis.

In other embodiments, recombinant biomarker polypeptides, and fragments thereof, can be administered to subjects. In some embodiments, fusion proteins can be constructed and administered which have enhanced biological properties. In addition, the biomarker polypeptides, and fragment thereof, can be modified according to well-known pharmacological methods in the art (e.g., pegylation, glycosylation, oligomerization, etc.) in order to further enhance desirable biological activities, such as increased bioavailability and decreased proteolytic degradation.

Clinical Efficacy

Clinical efficacy can be measured by any method known in the art. For example, the response to a therapy, such as anti-HHLA2 antibody therapy, relates to any response of the cancer, e.g., a tumor, to the therapy, preferably to a change in tumor mass and/or volume after initiation of neoadjuvant or adjuvant chemotherapy. Tumor response may be assessed in a neoadjuvant or adjuvant situation where the size of a tumor after systemic intervention can be compared to the initial size and dimensions as measured by CT, PET, mammogram, ultrasound or palpation and the cellularity of a tumor can be estimated histologically and compared to the cellularity of a tumor biopsy taken before initiation of treatment. Response may also be assessed by caliper measurement or pathological examination of the tumor after biopsy or surgical resection. Response may be recorded in a quantitative fashion like percentage change in tumor volume or cellularity or using a semi-quantitative scoring system such as residual cancer burden (Symmans et al., *J. Clin. Oncol.* (2007) 25:4414-4422) or Miller-Payne score (Ogston et al., (2003) Breast (Edinburgh, Scotland) 12:320-327) in a qualitative fashion like "pathological complete response" (pCR), "clinical complete remission" (cCR), "clinical partial remission" (cPR), "clinical stable disease" (cSD), "clinical progressive disease" (cPD) or other qualitative criteria. Assessment of tumor response may be performed early after the onset of neoadjuvant or adjuvant therapy, e.g., after a few hours, days, weeks or preferably after a few months. A typical endpoint for response assessment is upon termination of neoadjuvant chemotherapy or upon surgical removal of residual tumor cells and/or the tumor bed.

In some embodiments, clinical efficacy of the therapeutic treatments described herein may be determined by measuring the clinical benefit rate (CBR). The clinical benefit rate is measured by determining the sum of the percentage of patients who are in complete remission (CR), the number of patients who are in partial remission (PR) and the number of patients having stable disease (SD) at a time point at least 6 months out from the end of therapy. The shorthand for this formula is CBR=CR+PR+SD over 6 months. In some embodiments, the CBR for a particular anti-immune checkpoint therapeutic regimen is at least 25%, 30%, 35%, 40%, 45%, 50%, 55%, 60%, 65%, 70%, 75%, 80%, 85%, or more.

Additional criteria for evaluating the response to anti-immune checkpoint therapies are related to "survival," which includes all of the following: survival until mortality, also known as overall survival (wherein said mortality may be either irrespective of cause or tumor related); "recurrence-free survival" (wherein the term recurrence shall include both localized and distant recurrence); metastasis free survival; disease free survival (wherein the term disease shall include cancer and diseases associated therewith). The length of said survival may be calculated by reference to a defined start point (e.g., time of diagnosis or start of treatment) and end point (e.g., death, recurrence or metastasis). In addition, criteria for efficacy of treatment can be expanded to include response to chemotherapy, probability of survival, probability of metastasis within a given time period, and probability of tumor recurrence.

For example, in order to determine appropriate threshold values, a particular anti-cancer therapeutic regimen can be administered to a population of subjects and the outcome can be correlated to biomarker measurements that were determined prior to administration of any anti-immune checkpoint therapy. The outcome measurement may be pathologic response to therapy given in the neoadjuvant setting. Alternatively, outcome measures, such as overall survival and disease-free survival can be monitored over a period of time for subjects following anti-immune checkpoint therapy for whom biomarker measurement values are known. In certain embodiments, the same doses of anti-immune checkpoint agents are administered to each subject. In related embodiments, the doses administered are standard doses known in the art for anti-immune checkpoint agents. The period of time for which subjects are monitored can vary. For example, subjects may be monitored for at least 2, the Examples section.

XIII. Kits

In addition, the present invention also encompasses kits for detecting the presence of a HHLA2 polypeptide, or fragments thereof, in a biological sample. For example, the kit can comprise a labeled compound or agent capable of detecting a HHLA2 polypeptide, or fragments thereof, in a biological sample; means for determining the amount of the HHLA2 polypeptide, or fragments thereof, in the sample; and means for comparing the amount of the HHLA2 polypeptide, or fragments thereof, in the sample with a standard. The compound or agent can be packaged in a suitable container. For example, the present invention provides kits comprising at least one antibody described herein. Kits containing antibodies of the invention find use in detecting HHLA2, or in therapeutic or diagnostic assays. Kits of the invention can contain an antibody coupled to a solid support, e.g., a tissue culture plate or beads (e.g., sepharose beads).

A kit can include additional components to facilitate the particular application for which the kit is designed. For example, kits can be provided which contain antibodies for detection and quantification of HHLA2 in vitro, e.g. in an ELISA or a Western blot. Additional, exemplary agents that kits can contain include means of detecting the label (e.g., enzyme substrates for enzymatic labels, filter sets to detect fluorescent labels, appropriate secondary labels such as a sheep anti-mouse-HRP, etc.) and reagents necessary for controls (e.g., control biological samples or HHLA2 protein standards). A kit may additionally include buffers and other reagents recognized for use in a method of the disclosed invention. Non-limiting examples include agents to reduce non-specific binding, such as a carrier protein or a detergent. A kit of the present invention can also include instructional materials disclosing or describing the use of the kit or an antibody of the disclosed invention in a method of the disclosed invention as provided herein.

This invention is further illustrated by the following examples which should not be construed as limiting. The contents of all references, patents and published patent applications cited throughout this application, as well as the Figures, are incorporated herein by reference.

EXAMPLES

Example 1: Derivation of Anti-Human HHLA2 Monoclonal Antibodies

A number of anti-HHLA2 monoclonal antibodies were generated and analyzed. Briefly, human HHLA2-mIgG2a fusion protein was produced before the immunization and generation of mouse monoclonal antibodies. The coding region of human HHLA2 was PCR-amplified using the primers 5'-TGTTCTGCACAAGACA-3' (sense primer located just 5' of ATG start) and 5'-GTAAGGATGCAGGT-CATGAGT-3' (anti-sense primer located just 3' to stop codon) and introduced into the pEF6 vector by TA cloning. The HHLA2-mIgG2a fusion protein was made by fusing cDNA's for the HHLA2 extracellular domain to the mouse IgG2a hinge and Fc domains (with mutations to reduce binding to Fc receptors) and cloning into the pEF6 vector. The construct was introduced into CHO cells and HHLA2-mIgG2a fusion protein was purified by affinity chromatography on a protein G column.

Five mice (Balb/c; C57B1/6; Swiss-Webster), 4-6 weeks old, were obtained from Charles River Laboratories (Wilmington, MA). All animals were acquired and maintained according to the guidelines of the Institutional Animal Care and Use Committee of Harvard Standing Committee on Animals.

For the initial immunization, fifty micrograms of recombinant HHLA2-mIgG2a fusion protein was suspended in Dulbecco's phosphate buffered saline (PBS; GIBCO, Grand Island, NY) and emulsified with an equal volume of complete Freund's adjuvant (Sigma Chemical Co., St. Louis, MO). Mice were immunized by injection of the emulsion at five subcutaneous sites where lymph nodes could be found (inguinal, brachial, axillary and superficial cervical) and intraperitoneally. Fourteen days after the initial immunization, the mice were given booster immunization with fifty micrograms of recombinant HHLA2-mIgG2a fusion protein emulsified with an equal volume of incomplete Freund's adjuvant intraperitoneally. Fourteen days later, the mice were boosted with fifty micrograms recombinant HHLA2-mIgG2a fusion protein emulsified with an equal volume of incomplete Freund's adjuvant intraperitoneally. Forty-two days later, the mice were boosted with fifty micrograms recombinant HHLA2-mIgG2a fusion protein emulsified with an equal volume of incomplete Freund's adjuvant and fifty micrograms denatured recombinant HHLA2-mIgG2a fusion protein intraperitoneally. Protein was denatured by boiling for 5 minutes in the presence of 0.1% sodium dodecyl sulfate. Thirteen days later, the mice were boosted with fifty micrograms recombinant HHLA2-mIgG2a fusion protein emulsified with an equal volume of incomplete Freund's adjuvant and fifty micrograms denatured recombinant HHLA2-mIgG2a fusion protein intraperitoneally. A small amount of blood was collected 10-12 days after the boosts. The serum activity against HHLA2 was titred by flow cytometry on 300.19 cells transfected with HHLA2 cDNA and untransfected 300.19 cells. Thirty-six days, the mice were boosted a final time intraperitoneally and intravenously with fifty micrograms denatured recombinant HHLA2-mIgG2a fusion protein.

The mouse #5 with the highest titre was selected for fusion 4 days later. The harvested spleen and lymph nodes were made into a cell suspension and then washed with DMEM. The spleen/lymph node cells were counted and mixed with SP 2/0 myeloma cells that are incapable of secreting either heavy or light chain immunoglobulin chains (Kearney et al. (1979) *J. Immunol.* 123:1548-1550 and Kilpatrick et al. (1997) *Hybridoma* 16:381-389) using a spleen:myeloma ratio of 2:1. Cells were fused with polyethylene glycol 1450 in eight 96-well tissue culture plates in HAT selection medium according to standard procedures (Kohler and Milstein (1975) *Nature* 256:495-497).

Between 10 and 21 days after fusion, hybridoma colonies became visible and culture supernatants were harvested then screened against HHLA2 by flow cytometry on 300.19 cells transfected with HHLA2 cDNA and lack of reactivity on untransfected 300.19 cells.

Example 2: Anti-HHLA2 Antibodies

A number of anti-HHLA2 mAbs were sequenced to analyze their CDR regions. Briefly, RACE (Rapid Amplification of cDNA Ends) was performed to amplify DNA for vH and vL (mRNA denaturing, cDNA synthesis, 5' RACE Reaction, and Analyzed PCR results). To identify positive clones, PCR reaction samples were analyzed on an agarose gel to visualize the amplified DNA fragments. The correct antibody variable region DNA fragments should have a size between 500-700 base pairs. PCR-positive bands were TOPO cloned and then PCR-amplified, followed by gel electrophoresis, recovery from agarose gel, and sequencing. CDR analysis was performed using sequencing data (CDR regions were defined using VBASE2, see the World Wide Web at vbase2.org/)

Table 2 lists the results of mAb sequencing. The light chains of the antibodies are kappa type. The mouse antibodies 8A12, 8D2, and 1C8 are IgG2a isotype while 2C4, 5H4, 6G8, 6D10, 2G2, 4D1, 4E5, and 6F10 are IgG1 isotype.

The newly identified anti-HHLA2 antibodies were characterized for in vitro binding and TMIGD2 blocking.

In particular, binding affinity for each anti-HHLA2 antibody was assayed. The HHLA2 cDNA and a vector encoding puromycin resistance were co-transfected by electroporation (300 volts, 1600 microfarads) into mouse 300.19 cells and selected with media containing 5 µg/ml puromycin. Cells expressing HHLA2 were identified by staining with TMIGD2-human Fc fusion protein and goat anti-human Fc antibody conjugated to phycoerythrin and single cell sorted by flow cytometry. Expression of HHLA2 in individual clones was confirmed by flow cytometry as described above. HHLA2-transfected 300.19 cells were titrated with anti-HHLA2 mAbs (FIG. 1A).

Figure 1B:
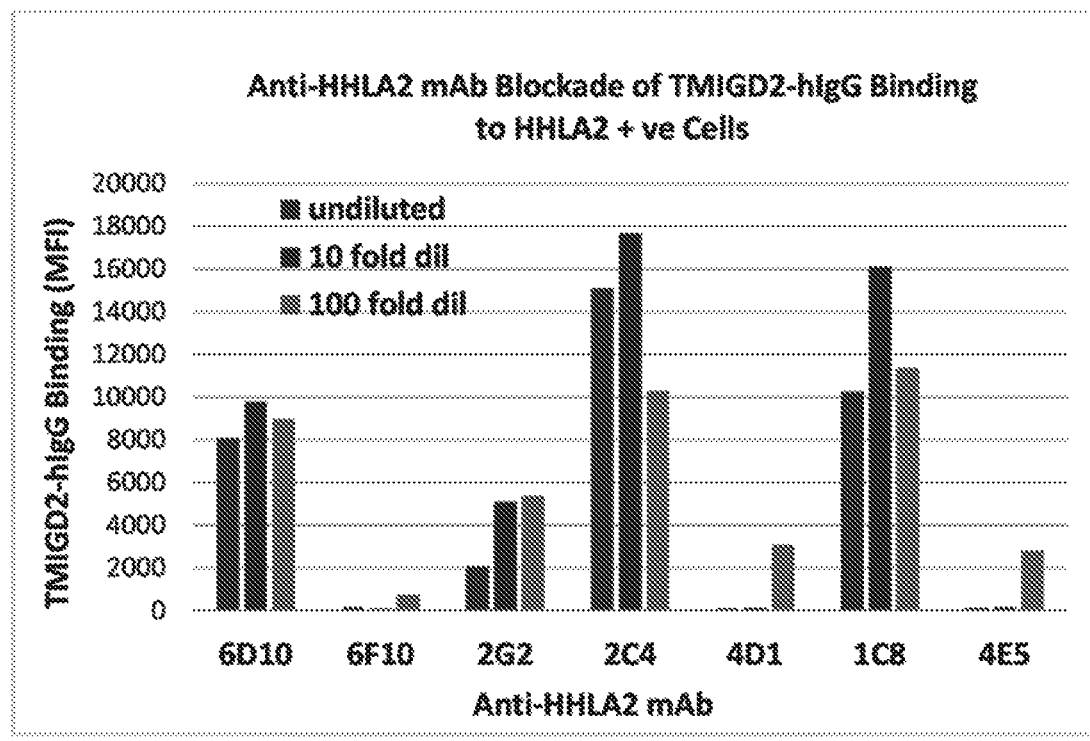
FIG. 1B shows Anti-HHLA2 mAb blockade of TMIGD2-human IgG binding to HHLA2 transfected 300.19 mouse pre-B cell leukemic cell line by flow cytomtery

FIG. 1B shows the results of evaluation of TMIGD2 blockade by flow cytometry. Briefly, assays for anti-HHLA2 mAb blocking of TMIGD2-human IgG binding to 300.19 cells transfected with human HHLA2 cells were performed. For example, 20 µl (equivalent to 25,000 of 300.19 cells) of stably transfected with human HHLA2 were added per well of a 96 well, round-bottom plate. Fifty 50 µl of antibody was per well. Undiluted, 1 to 10, and 1 to 100 dilutions were assayed. Cells were pipetted up and down to resuspend cells in mAb and incubated at 4° C. for 30 min with mixing on a rotating platform. Twenty 1 of 2 g/ml human TMIGD2-human IgG1 fusion protein (R&D Systems catalog #8316-TR-050) in FACS buffer (PBS plus 2% FBS, 0.02% azide) was added to each well. A negative control well of cells with no TMIGD2-hIgG and a positive control of TMIGD2 with mouse IgG isotype control were included. The plate was incubated at 4° C. for 30 min with mixing. Cells were washed twice in FACS buffer, and supernatant was removed. Fifty 1 of 2.5 µg/ml second antibody (Fab$_2$ goat anti-human-IgG-PE, cross-absorbed against mouse Ig; Southern Biotech 2043-09) was added per well. Cells were pipetted up and down 3 times to resuspend cells in Ab and incubate at 4° C. for 30 min with mixing. Cells were washed twice in FACS buffer and supernatant was removed. Cells were resuspended in 80 µl of PBS plus 2% formaldehyde and binding was analyzed on FACS machine. The FACS buffer (PBS plus 2% FBS, 0.02% azide) was used.

Figure 2:
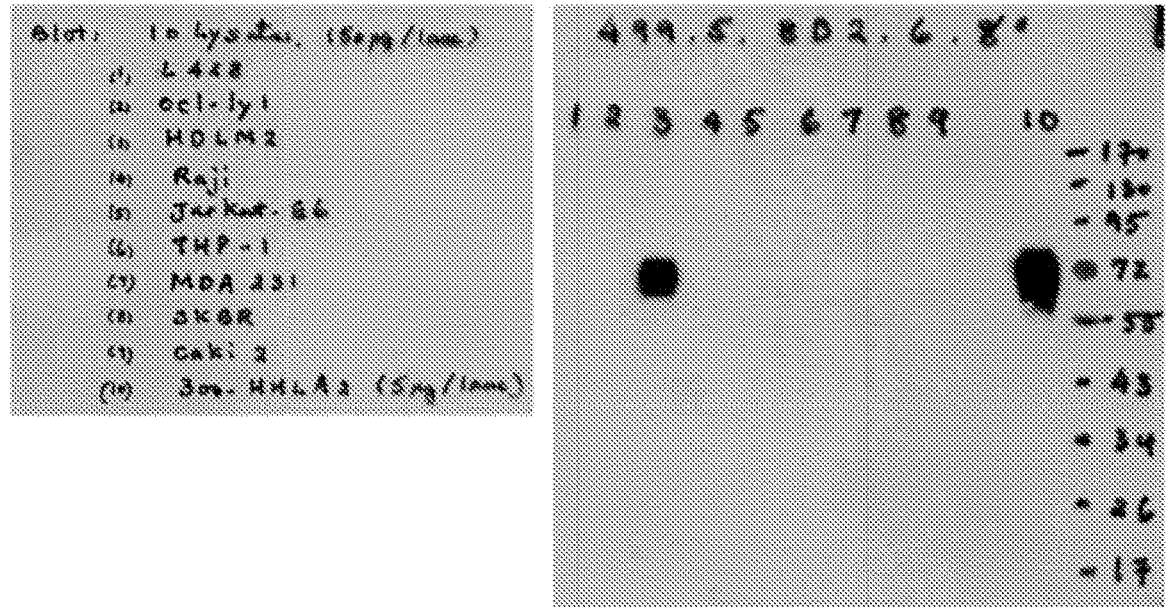
FIG. 2 shows Western blot data of protein from nine human tumor cell lines probed with anti-HHLA2 mAb 8D2 (IHC mAb).

FIG. 2 shows Western blotting results of human tumor cell lines analyzed using anti-HHLA2 monoclonal antibody, 8D2. Briefly, protein lysates were prepared with RIPA buffer per manufacturer's instructions (Thermo Scientific), and protease inhibitor cocktail was added to the buffer (complete Ultra tablets, mini, EDTA-free, Roche) prior to lysate preparation. Protein lysates were made from 300.19 cells stably transfected with human HHLA2 and from the indicated human tumor cell lines. L428 and HDLM2 are Hodgkin lymphoma cell lines, OC1-Ly1 is a B-cell non-Hodgkin lymphoma (diffuse large cell) cell line, Raji is a Burkitt's lymphoma cell line, Jurkat E6 is a T cell leukemia cell line, THP-1 is an acute monocytic leukemia cell line, MDA231 and SKBR are breast tumor cell lines, CAKI2 is a human clear cell renal cell carcinoma (ccRCC) cell line. Eighty pg of lysates were loaded into a 4-15% gradient mini-Protean TGX gel (BioRad) and transferred by a semi-dry method. Membranes were blocked with Tris-buffered saline with Tween20 (TBST) with 12% non-fat milk and 1% normal goat serum for 1 hour at room temperature. The membrane was washed with TBST and incubated with the primary antibody (final concentration of 1 µg/ml anti-HHLA2 mAb 499.5.8D2 in TBST and 1% BSA) at 4° C. overnight. Membranes were washed with TBST three times at room temperature and incubated with secondary antibody (1:4000, horseradish-conjugated goat anti-mouse IgG HRP antibody, Southern Biotech Catalog #1030-05) in TBST, 6% non-fat milk, and 0.5% normal goat serum for 30 min. After 3 additional washes with TBST, a 1:1 ratio of ECL substrate: enhancer was added to the membrane (SuperSignal West Pico Stable Peroxide Solution, Supersignal West Pico Luminol/Enhancer Solution, ThermoScientific) and imaged on Hyblot CL autoradiography film (Denville Scientific).

Example 3: HHLA2 mRNA Expression in Normal and Cancer Tissue

Figure 3:
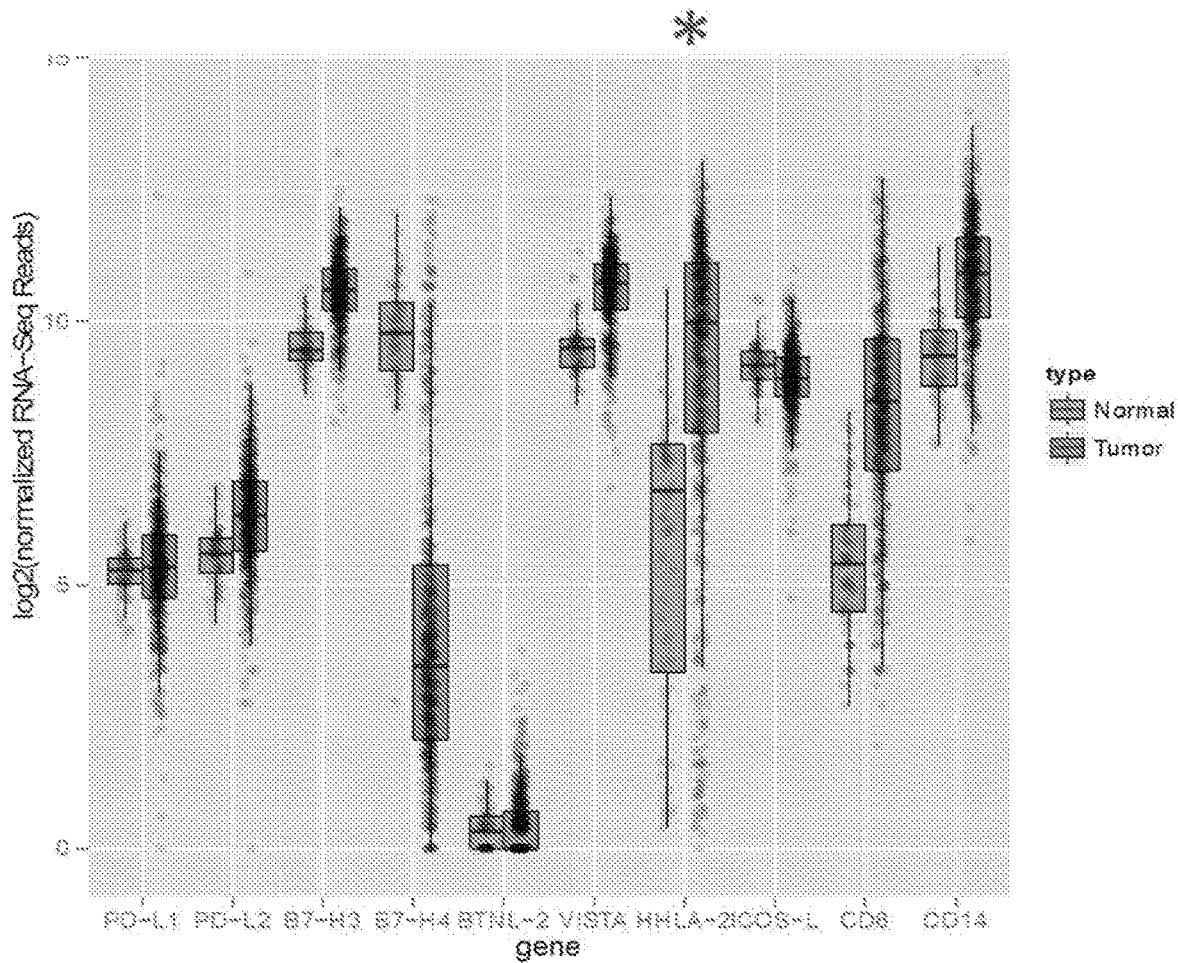
FIG. 3 shows HHLA2 mRNA expression compared to other checkpoint inhibitors in normal kidney versus clear cell renal carcinoma (ccRCC).

FIG. 3 shows the results of HHLA2 mRNA expression compared to other checkpoint inhibitors in normal kidney versus renal cancers. Expression of the indicated B7 family member immune receptors and tumor infiltrating leukocytes in normal kidney and kidney tumors were evaluated by normalizing RNA seq data from the TCGA database. Increased receptor expression in tumors compared to normal tissues was observed for PD-L1, PD-L2, B7-H3, VISTA and HHLA2. Increased levels were also observed for CD8+ and CD14+tumor infiltrating cells in tumors compared to normal tissue.

Figure 4:
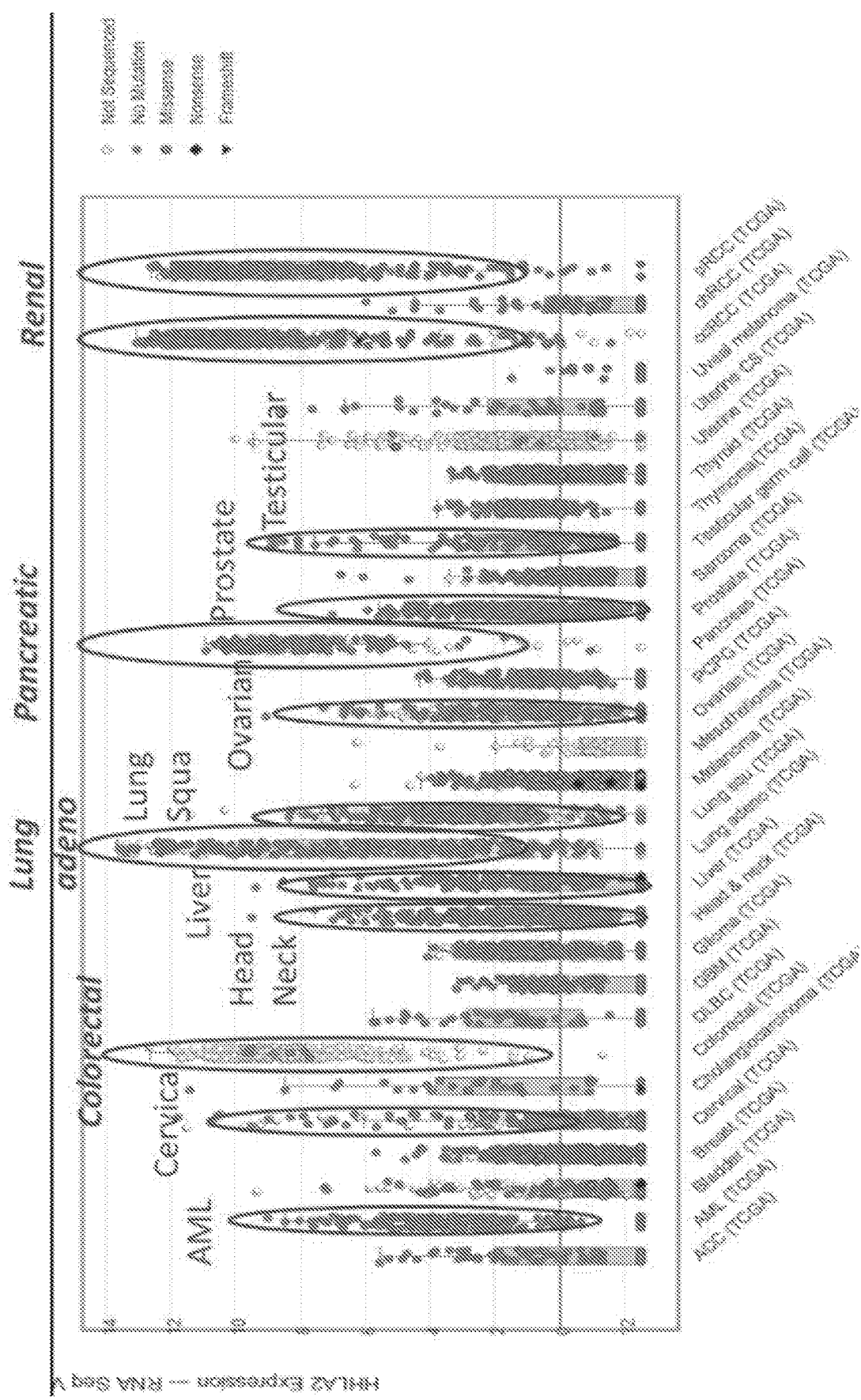
FIG. 4 depicts HHLA2 expression in various cancers from the TCGA database.
Figure 5A:
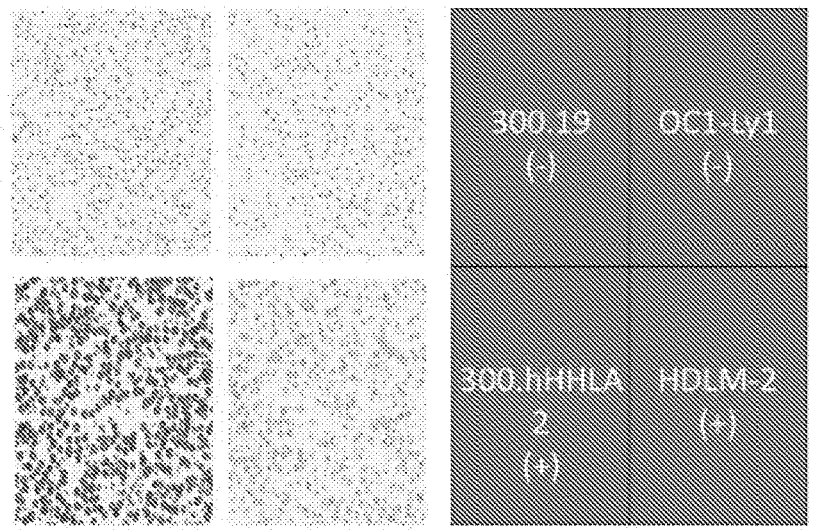
FIG. 5A shows HHLA2 immunohistochemistry (IHC) results on negative control cells (300.19), HHLA-2 transfected 300.19 cells (positive control), OC1-Ly1 cells (negative tumor) and HDLM2 (positive Hodgkon's lymphoma cell line) HHLA2 control cells.
Figure 5B:
FIG. 5B shows HHLA2 expression in normal kidney.
Figure 5C:
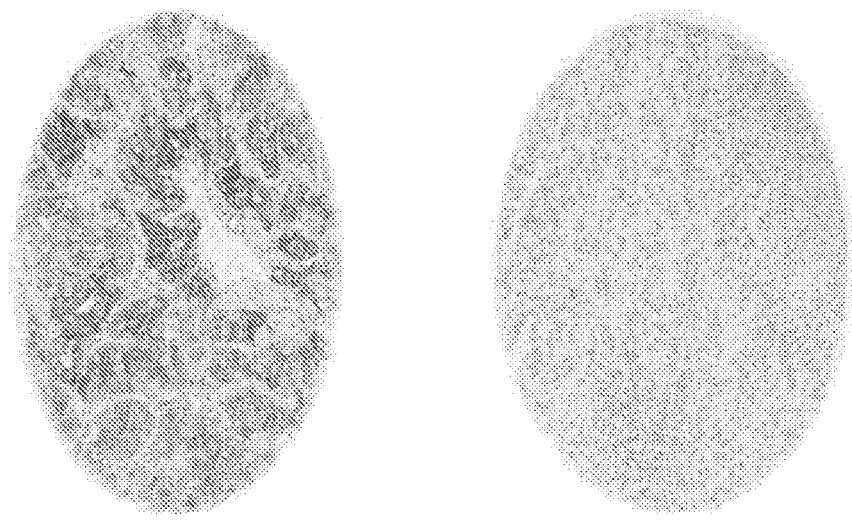
FIG. 5C shows a representative image of HHLA2 expression in a ccRCC from a microarray (TMA).
Figure 5D:
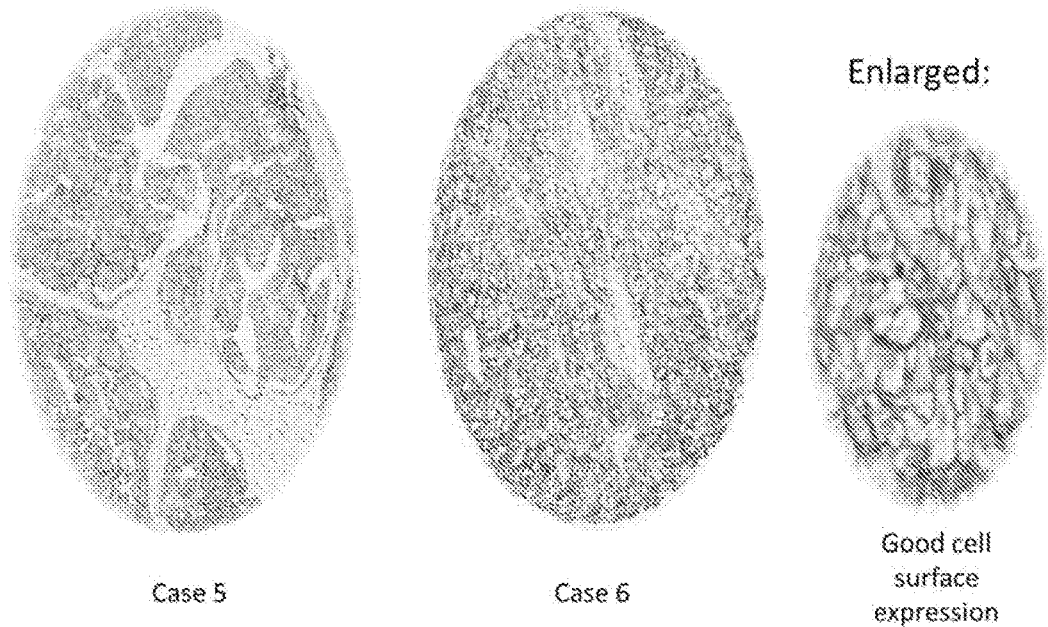
FIG. 5D shows a representative image of lack of HHLA2 expression in a different ccRCC from a tumor microarray (TMA).

Similarly, FIG. 4 shows the results of HHLA2 expression in various cancers from the TCGA database (FIG. 4). Briefly, the expression profile for HHLA2 in various cancer types were investigated using the database of TCGA (supervised by the National Cancer Institute's Center for Cancer Genomics and the National Human Genome Research Institute) by RNAseq analysis. As shown in FIG. 4, HHLA2 is expressed at high levels (bold italicized) in clear cell and papillary renal cell carcinoma, lung adenocarcinoma, colorectal and pancreatic cancers and moderately expressed in AML, cervical, head and neck, liver, ovarian, prostate, testicular cancers and lung squamous cell carcinoma.

FIG. 5 shows the results of HHLA2 expression by immunohistochemistry, such as on HHLA2-positive and negative cell lines renal cancer tumor arrays. HHLA2 expression in renal cancer tumor arrays and cell lines was detected by immunohistochemistry. Rehydrated paraffin embedded tissue sections and cell line sections were boiled in EDTA buffer pH 8 (Life Technologies) with a pressure cooker (Biocare Medical) for 30 seconds at 125° C. After cooling down at room temperature (RT), tissue sections were successively incubated with a peroxidase block (Dual Endogenous Enzyme Block, Dako) and a protein block (Serum Free Block, Dako) for 5 minutes each at RT. Sections were next incubated for 1 hour at RT with a mouse anti-HHLA-2 antibody (1/100, clone 8D2) diluted in antibody diluent with background reducing components (Dako). Tissue sections were then incubated for 30 minutes at RT with the EnVision® anti-mouse horseradish (HRP)-conjugated antibody (Dako). HRP visualization was performed by applying 3,3-diaminobenzidine substrate (DAB+, Dako). Between each step, at the exemption of the protein block and primary antibody incubation steps, tissue sections were washed for 5 minutes in washing buffer (0.1 mM Tris, pH7.4+0.05% Tween 20). Nuclei were counterstained with hematoxylin (FIGS. 5A-5D).

Figure 11:
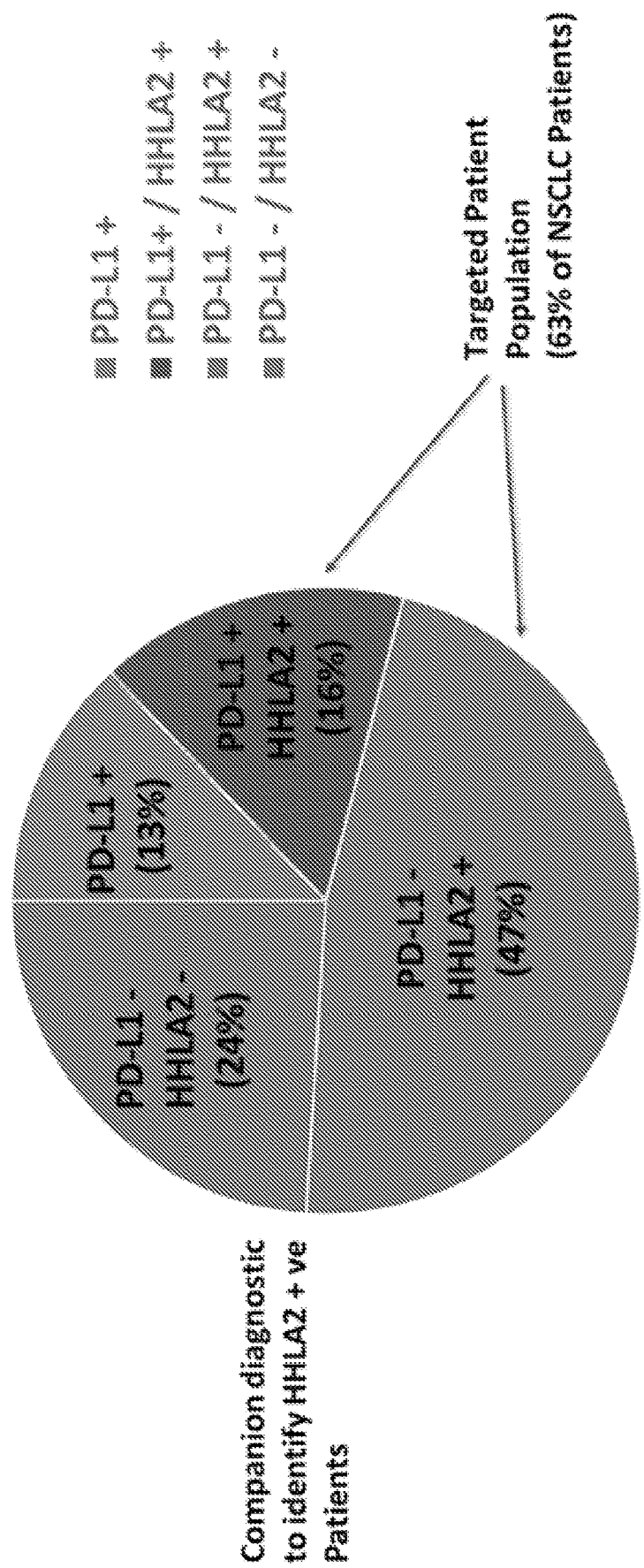
FIG. 11 shows HHLA2+ve (i.e., lung cancer tissues that expressed HHLA2 based on immunohistochemistry (IHC) staining with an HHLA2 mAb) patient stratification in non-small cell lung cancer. The percentage of HHLA2 expression in PD-L1 positive and negative non-small cell lung cancers was calculated based on the HHLA2 and PD-L1 immunostaining study (Cheng et al. (2018) *Clin. Cancer Res.* 24:1954-1964).

FIG. 11 shows the percentage of HHLA2 expression in PD-L1 positive and negative non-small cell lung cancers calculated based on the HHLA2 and PD-L1 immunostaining study (Cheng et al. (2018) Clin. Cancer Res. 24:1954-1964). It was shown that 63% of the total NSCLC population is targetable with HHLA2.

Example 4: HHLA2 Receptor Identification

HHLA2 was identified as a specific ligand for TMIGD2 and the HHLA2/TMIGD2 interaction selectively costimulates human T-cell growth and cytokine production via an AKT-dependent signalling cascade (Zhu et al. (2013) Nat. Comm. 4:2043; Janakiram et al. (2015) Clin. Cancer Res. 21:2359-2366). A second receptor for HHLA2 on activated T cells that exerts a coinhibitory function was suggested by several studies (Zhao et al. (2013) Proc. Natl. Acad. Sci. USA 110:9879-9884; Xiao and Freeman et al. (2015) Clin. Cancer Res. 21:2201-2203; Wang et al. (2014) J. Immunol. 192:126.11). In the present study, TMIGD2 binding to HHLA2 was confirmed and a new HHLA2 receptor, KIR3DL3, was identified. Briefly, a library of >4500 full length clones covering more than 3,500 different plasma membrane proteins expressed on HEK293 cells and imprinted on slides using the cell microarray technology (Retrogenix, Whaley Bridge, UK) was evaluated for binding to soluble human HHLA2-mIg fusion proteins.

Assay conditions for binding were developed first prior to initiation of the full screen. Slides imprinted with positive control receptor TMIGD2 or negative control EGFR transfected cells or untransfected cells were evaluated for specific binding to soluble HHLA2-mIgG2a at 2, 10 and 20 µg/ml concentration, and the protein was detected with an AF647 labeled anti-mouse IgG detection antibody. Two replicate slides were screened for each of the 13 slide sets. Fluorescent images were analyzed and quantitated (for transfection efficiency) using ImageQuant software (GE). A protein 'hit' was defined as duplicate spots showing a raised signal compared to background levels. This was achieved by visual inspection using the images gridded on the ImageQuant software.

Hits were classified as 'strong, medium, weak or very weak', depending on the intensity of the duplicate spots. All the vectors encoding the hits identified in one or both of the two primary screens were sequenced to double-check their identities.

In order to determine which hit(s), if any, were reproducible and specific to human HHLA2, all vectors encoding the primary hits, plus appropriate control KIR receptors, were arrayed on new slides. Identical slides were screened with each test ligand, using the doses and incubation conditions used in the primary screens, and appropriate positive and negative controls (n=2 slides per treatment).

Figure 6A:
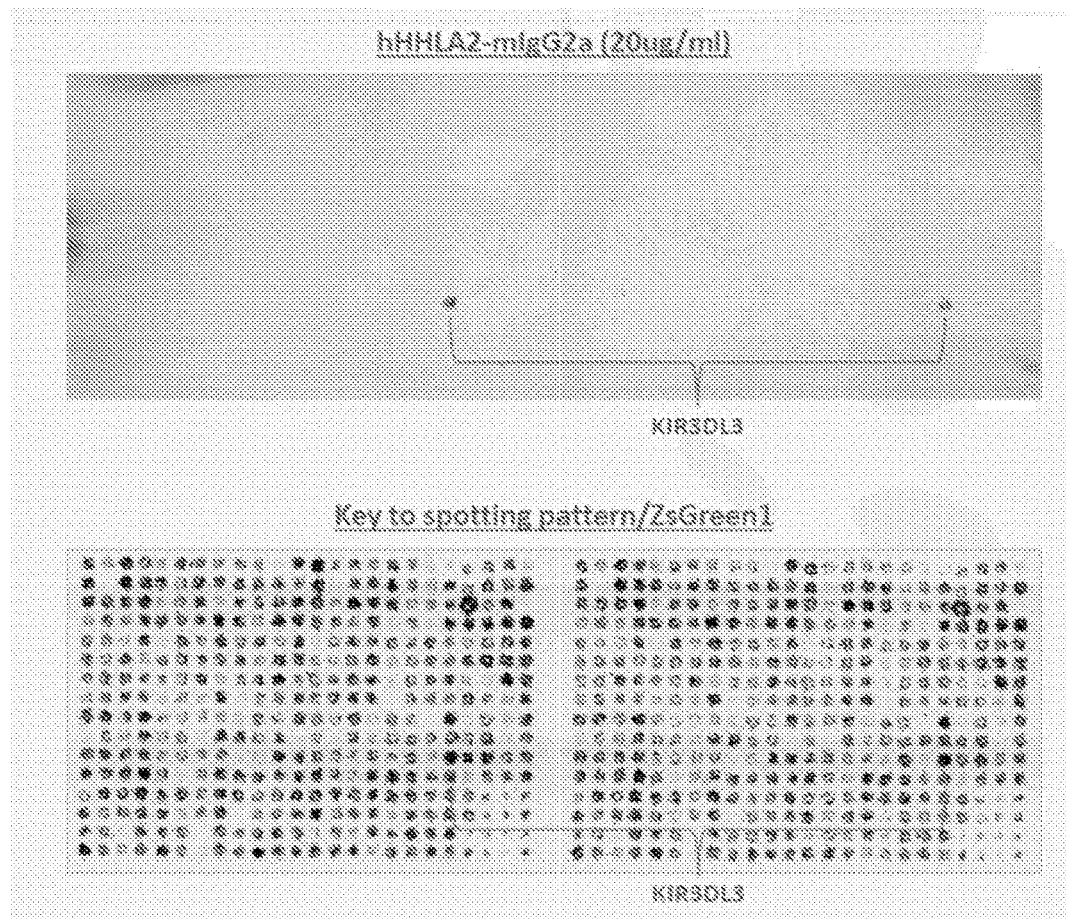
FIG. 6A shows screening results of a representative set of~300 plasma membrane clones in duplicate, as well as a confirmatory screen showing HHLA2 binding to KIR3DL3. A total 5682 cell surface receptor membrane clones were screened

Screening of more than >4500 full length cell surface receptor clones using soluble HHLA2-mIgG2a identified KIR3DL3 as a hit for HHLA2 binding. The screening results of a representative set of~300 plasma membrane clones in duplicates is shown in FIG. 6A. The addition of the AF647 labeled anti-mouse IgG detection antibody in the absence of HHLA2-mIgG2a produced no signal.

Figure 6B:
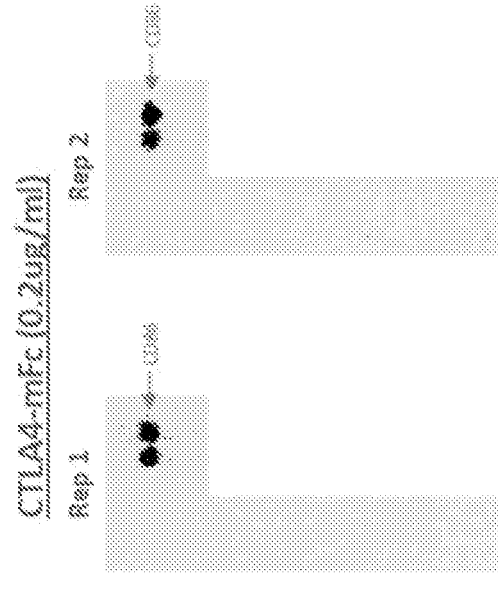
FIG. 6B shows selective binding of HHLA2 to KIR3DL3
Figure 6B:
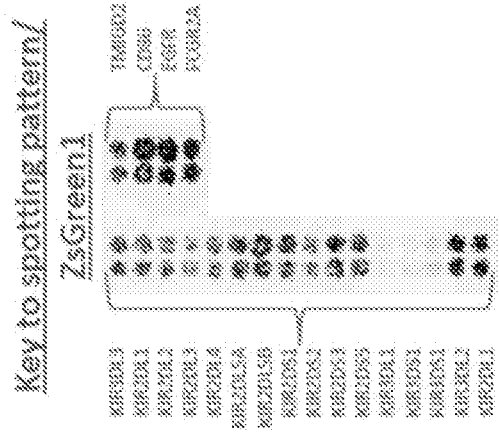
Figure 6B:
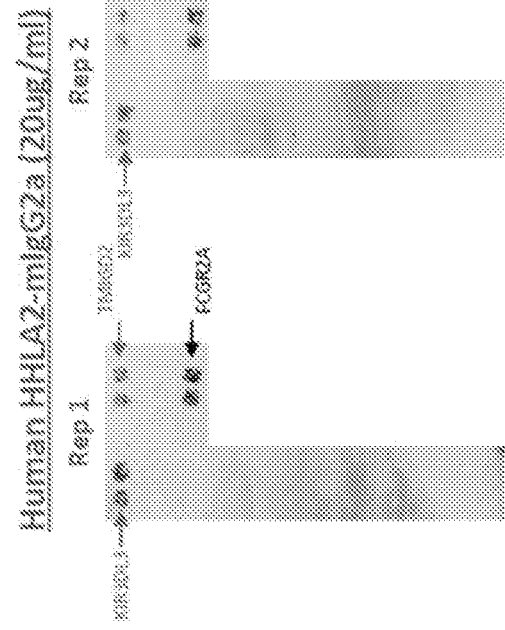
Figure 6B:
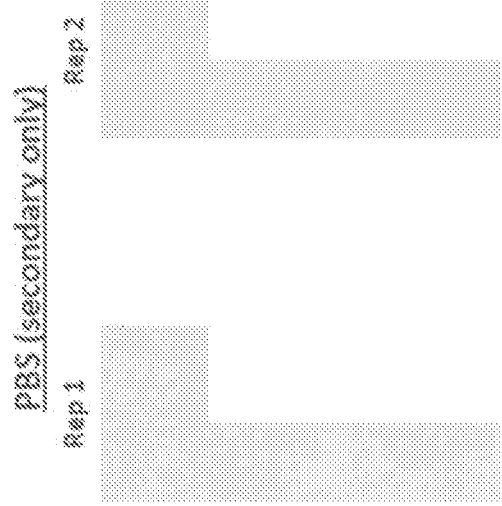

The confirmatory screen on newly arrayed slides showed HHLA2 binding to KIR3DL3 (FIG. 6A). Addition of the AF647 labeled anti-mouse IgG detection antibody alone in the absence of HHLA2-mIgG2a produced no signal. The selectivity of HHLA2 binding to KIR3DL3 was evaluated using a panel of 14 KIR receptors arrayed on slides. Selective binding of HHLA2 to KIR3DL3 was demonstrated (Table 4 and FIGS. 6B-6C).

TABLE 4

| | KIR Receptor | | | | | | |
| --- | --- | --- | --- | --- | --- | --- | --- |
| | KIR3DL3 | KIR2DL1 | KIR2DL2 | KIR2DL3 | KIR2DL4 | KIR2DL5A | KIR2DL5B |
| HHLA2 Binding | + | − | − | − | − | − | − |

| | KIR Receptor | | | | | | |
| --- | --- | --- | --- | --- | --- | --- | --- |
| | KIR2DS1 | KIR2DS2 | KIR2DS3 | KIR2DS5 | KIR3DL1 | KIR3DS1 | KIR3DL2 |
| HHLA2 Binding | − | − | − | − | − | − | − | concentrations as detected with a AF647 labeled anti-mouse IgG detection antibody either pre-complexed with HHLA2-mIgG2a at a 2:1 molar ratio or added sequentially.

For primary screening, 4,500+expression vectors, each encoding a full-length human plasma membrane protein, were arrayed in duplicate across 13 microarray slides ("slide-sets"), respectively.

An expression vector (pIRES-hEGFR-IRES-ZsGreenl) was spotted in quadruplicate on every slide, and was used to ensure that a minimal threshold of transfection efficiency had been achieved or exceeded on every slide. This minimal threshold (mean ZsGreen1 signal from the pIRES-EGFR-ZsGreenl vector over background of 1.5) has been previously defined.

Human HHLA2-mIgG2a fusion protein was added to slides of fixed, transfected HEK293 cell slides at a 20 µg/ml Example 5: T Cell Activation Assays to Confirm Immune Checkpoint Inhibition of Anti-Human HHLA2 mAbs A. Plasmid Construction The TCR activator, a membrane-anchored chimeric antibody, was constructed by fusing the single chain variable fragment (scFv) of an anti-human CD3 mAb OKT3 (Kipriyanov et al. (1997) PEDS 10:445-453) to the C-terminal domain (residues 113-220) of mouse CD8u (accession number: NP_001074579.1) which includes hinge, transmembrane and cytoplasmic domains. By doing so, anti-CD3 scFv was anchored to CHO-K1 cell surface as a T cell activator. The DNA sequence encoding TCR activator was synthesized and inserted into pIRES-hyg3 vector (ClonTech) to make resulting construct TCRαpIREShyg3.

The DNA sequence of human HHLA2 (accession number:NP_009003.1 and TMIGD2 (accession number: NM_144615.2) were cloned into pIRES-Hyg3 or pIRES-Neo3 individually to make HHLA2_pIRESneo3 and TMIGD2_pIREShyg3, respectively. The DNA sequence of KIR3DL3 (accession number: BC143802.1 from Genecopoeia) was synthesized and inserted into puroEIF2 vector.

The NFAT reporter contains a firefly luciferase gene under the control of four copies of NFAT response element followed by a minimal promoter. The IL2 reporter contains a firefly luciferase gene under the control of an endogenous IL2 promoter. The DNA sequence encoding the reporters was inserted into pcDNA 3.1 to generate NFAT-Luc-pcDNA and IL2-Luc-pcDNA.

B. Cell Lines and Cell Culture

Parental Jurkat (clone E6-1)(ATCC #TIB-152) and CHO-K1 (ATCC #CCL-61) cells were obtained from ATCC. Jurkat cells were cultured at 37° C. with 5% CO2 using RPMI1640 medium (Life Technologies #A10491-01) supplemented with 10% FBS (Life Technologies #26140-079) and 1% Penicillin/Streptomycin (Hyclone #SV30010.01).

TMIGD2-NFAT-Jurkat stable cell line culture was supplemented with 1000 μg/ml of Geneticin (Life Technologies #11811031), and 200 μg/ml Hygromycin (Invitrogen #10687010) to ensure the recombinant expression of TMIGD2 and NFAT reporter was maintained.

KIR3DL3-IL2-Jurkat stable cell line culture was supplemented with 1000 μg/ml of Geneticin, and 250 ng/ml puromycin (InvivoGen #ant-pr-1) to ensure the recombinant expression of KIR3DL3 and IL-2 reporter was maintained.

CHO cells were maintained in F12-K (Hyclone #SH30526.01) medium supplemented with 10% FBS and 1% Penicillin/Streptomycin. HHLA2-TCR-CHO stable cell line culture was supplemented with 1000 μg/ml of Geneticin, and 500 μg/ml Hygromycin to ensure the recombinant expression of HHLA2 and TCR activator was maintained.

C. Generation of Jurkat Reporter and CHO Stable Cell Lines

Jurkat Clones: To make TMIGD2-NFAT-Jurkat stable cell line, Jurkat cells (clone E6-1) were co-transfected sequentially with NFAT_Luc_pcDNA and TMIGD2_pIREShyg3 by electroporation. Stable clones were generated by hygromycin and G418 double selection and limiting dilution. The chosen stable cell clone was maintained with complete cell culture medium supplemented with hygromycin and G418. Cells were maintained in RPMI+10% FBS+1% P/S+1000 μg/mL G418+200 μg/mL Hygromycin.

To make KIR3DL3-IL2-Jurkat stable cell line, Jurkat cells (clone E6-1) were co-transfected sequentially with IL2_Luc_pcDNA and KIR3DL3_puro by electroporation. Stable clones were generated by puromycin and G418 double selection and limiting dilution. The chosen stable cell clone was maintained with complete cell culture medium supplemented with puromycin and G418. Cells were maintained in RPMI+10% FBS+1% P/S+1000 μg/mL G418+250 ng/mL Puromycin.

Parental Jurkat clones expressing only the NFAT (Jurkat-Luciferase) or IL-2 promoter (Jurkat-IL-2) were maintained in RPMI+10% FBS+1% P/S+1000 μg/mL G418 (BPS Biosciences).

CHO cell Clones: To make HHLA2-TCR-CHO stable cell line, CHO-K1 cells were co-transfected sequentially with TCRa_pIREShyg3 and HHLA2 pIRESneo3 by Lipofectamine® 2000 (Invitrogen). Stable clones were generated by hygromycin and G418 double selection and limiting dilution. The chosen stable cell clone was maintained with complete cell culture medium supplemented with hygromycin and G418. Cells were maintained in F12-K+10% FBS+1% P/S+1000 μg/mL G418+500 μg/mL Hygromycin. Parental CHO clones expressing anti-CD3 scFv were maintained in F12-K+10% FBS+1% P/S+500 μg/mL Hygromycin (BPS Biosciences).

D. Jurkat Reporter Gene Assays

TMIGD2 NFAT Jurkat reporter gene co-stimulation assay and inhibition by HHLA2 antibodies: HHLA2-TCR-CHO cells were seeded at 2×10$^4$ cells/well density in CHOK1 growth medium in a white opaque bottom 96-well plate. The cells attached the plate after overnight incubation at 37° C. with 5% CO2. The next day, medium was carefully removed from each well, anti-HHLA2 antibody was added in 50 μl Jurkat cell medium and HHLA2-TCR-CHO cells were incubated for one hour before the addition of TMIGD2_NFAT_Jurkat reporter cell line at 4-5×10$^4$ cells/well in 50 μl Jurkat cell medium. The plate well was mixed and incubated for approximately 3-6 hours. To develop the luciferase signal, 100 μl of the ONE-Step™ Luciferase Assay System (BPS Bioscience, Cat. #60690) was added to each well, according to recommended protocol. Luminescence was read using a luminometer.

KIR3DL3 IL2 Jurkat reporter gene inhibition assay and reversal by HHLA2 antibodies: HHLA2-TCR-CHO cells were seeded at 2×10$^4$ cells/well density in CHOK1 growth medium in a white opaque bottom 96-well plate. The cells attached the plate after overnight incubation at 37° C. with 5% $CO_2$. The next day, medium was carefully removed from each well, anti-HHLA2 antibody was added in 50 μl Jurkat cell medium and HHLA2-TCR-CHO cells were incubated for one hour before the addition of KIR3DL3_IL2_Jurkat reporter cell line at 4-5×10$^4$ cells/well in 50 μl Jurkat cell medium, plus 2 μg/mL anti CD28 antibody (BPS Bioscience #100186) (final concentration at 1 μg/mL in 100 μL assay mixture per well). The plate well was mixed and incubated for approximately 5 hours. To develop the luciferase signal 100 μl of the ONE-Step™ Luciferase Assay System (BPS Bioscience, Cat. #60690) was added to each well, according to recommended protocol. Luminescence was read using a luminometer.

Figure 14:
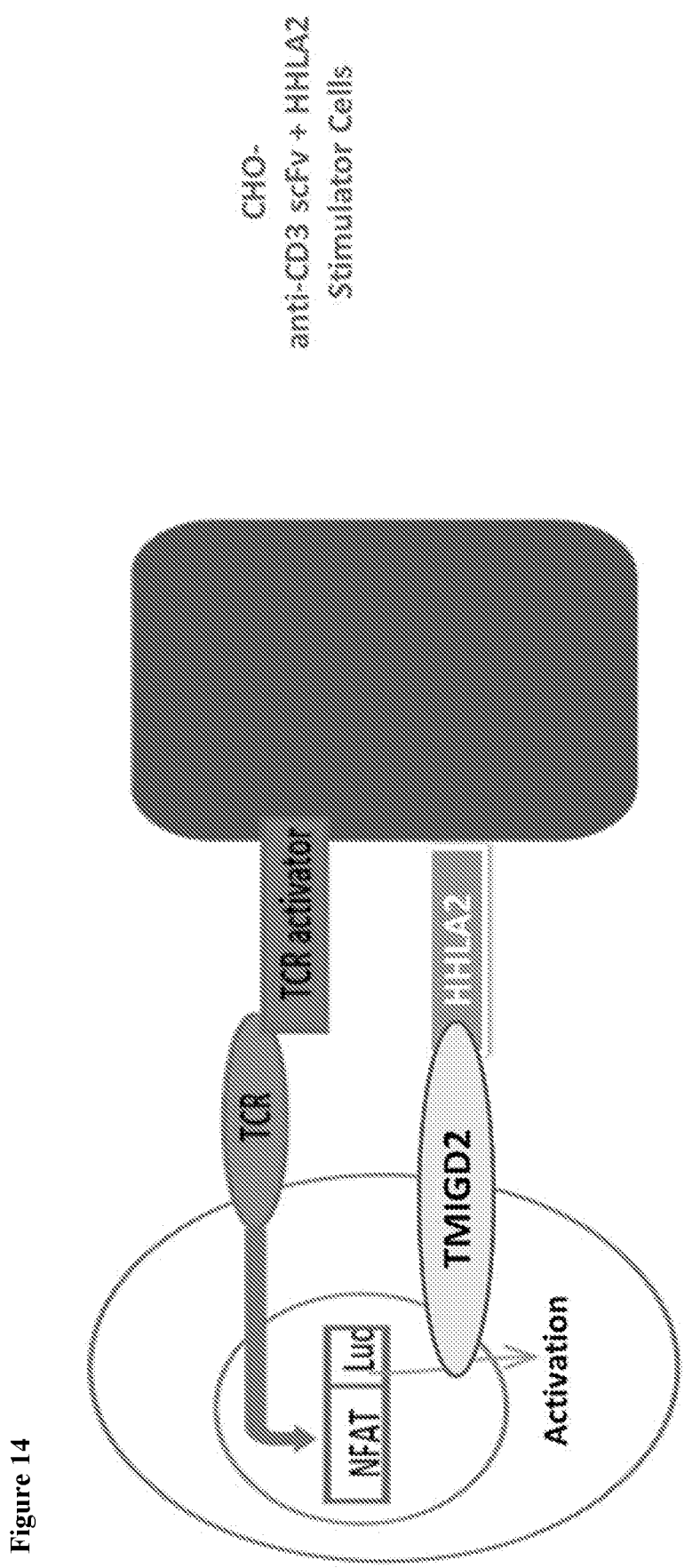
FIG. 14 shows a schematic of TMIGD2/HHLA2 T cell co-stimulation assay. TMIGD2 Jurkat T cell NFAT-luciferase reporter gene cells were stimulated with CHO cells transfected with anti-CD3 scFV or anti-CD3 scFV+HHLA2.

Using these materials and methods, HHLA2 mAbs or isotype control antibodies were evaluated for co-stimulation blockade in TMIGD2/HHLA2 T cell co-stimulation assay as shown in FIG. 14 and outlined in Table 9 below.

TABLE 9 study outline for evaluation of HHLA2 mAbs in TMIGD2/HHLA2 T cell co-stimulation assay

| Responder Jurkat NFAT Cells | Stimulating CHO cell | Expected Response |
|---|---|---|
| Jurkat NFAT/TMIGD2 | CHO-parental cell | None |
| Jurkat NFAT/TMIGD2 | CHO-Anti-CD3 Fv | Activation |
| Jurkat NFAT/TMIGD2 | CHO-Anti-CD3 Fv/ HHLA2 | Enhanced Activation |
| Jurkat NFAT/TMIGD2 | CHO-Anti-CD3 Fv/ HHLA2 + HHLA2 mAb | Reversal of Enhanced Activation |

Figure 15:
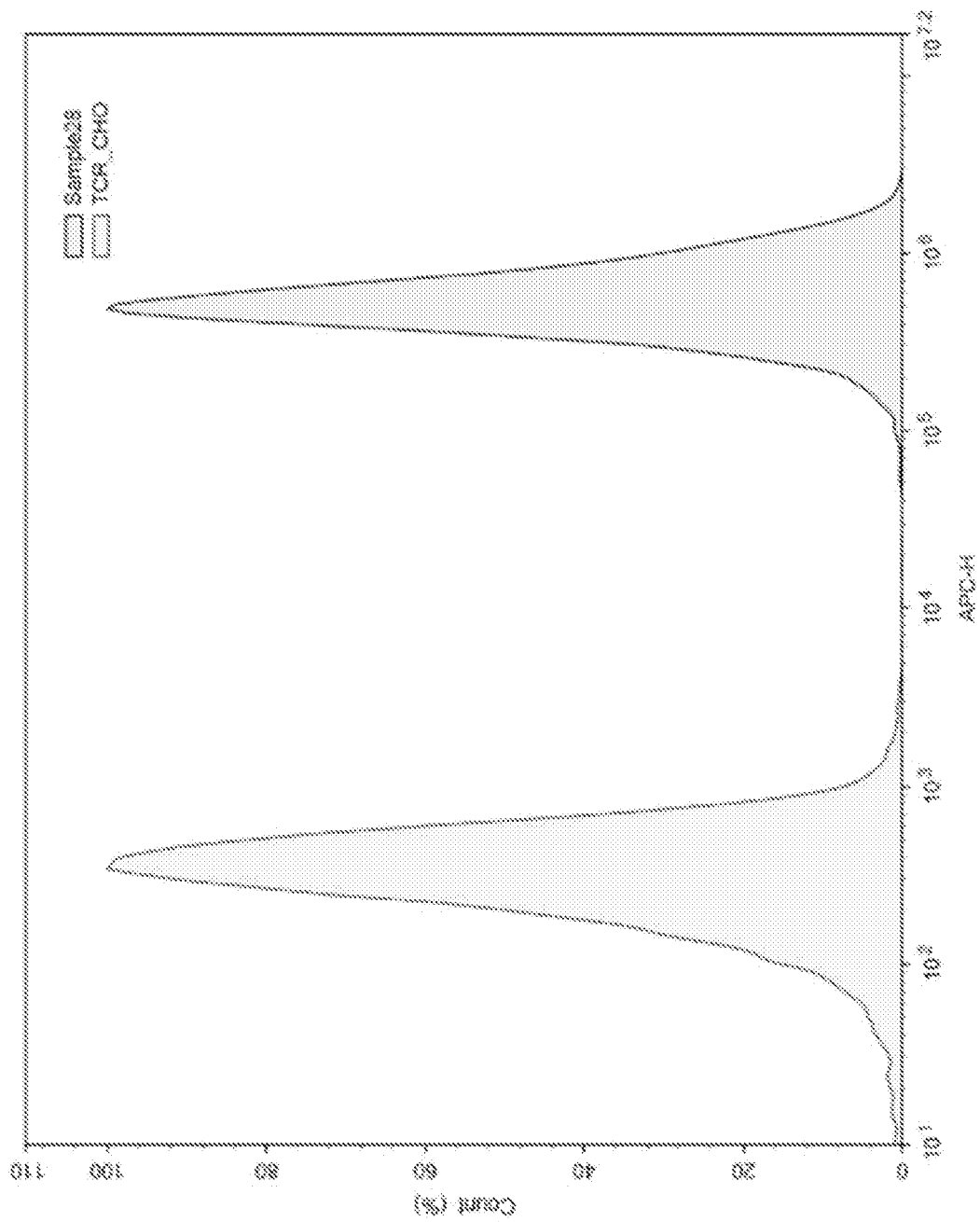
FIG. 15 shows HHLA2 expression in CHO-anti-CD3 scFV Cells. HHLA2 expression on CHO cells (clone #28) transfected with anti-CD3 scFV+HHLA2 was detected with PE-conjugated 6F10 HHLA2 mAb by flow cytometry.
Figure 16:
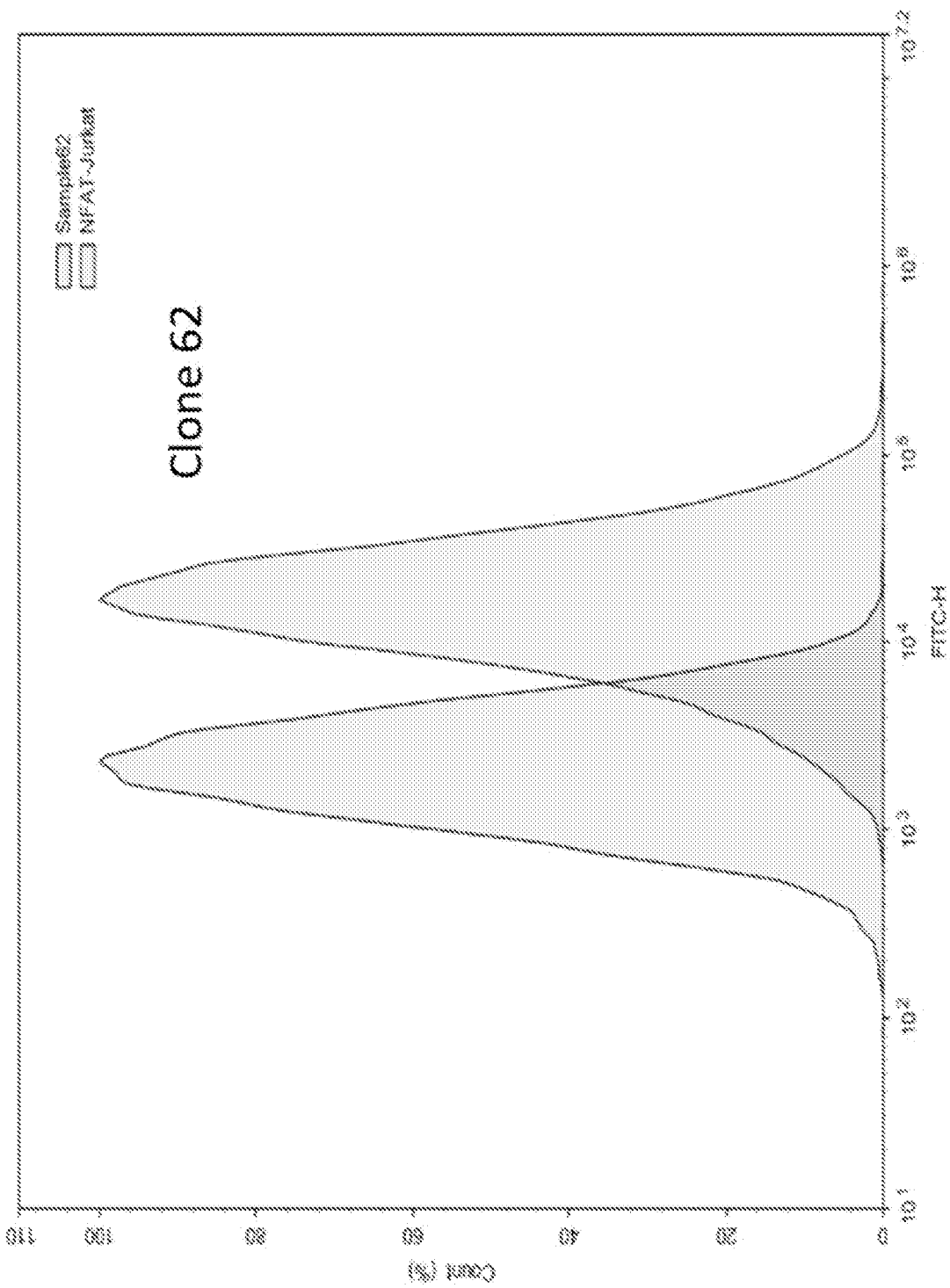
FIG. 16 shows TMIGD2 expression in Jurkat NFAT reporter cells. TMIGD2 expression in TMIGD2-transfected Jurkat NFAT reporter cells (clone #62) is shown.
Figure 17:
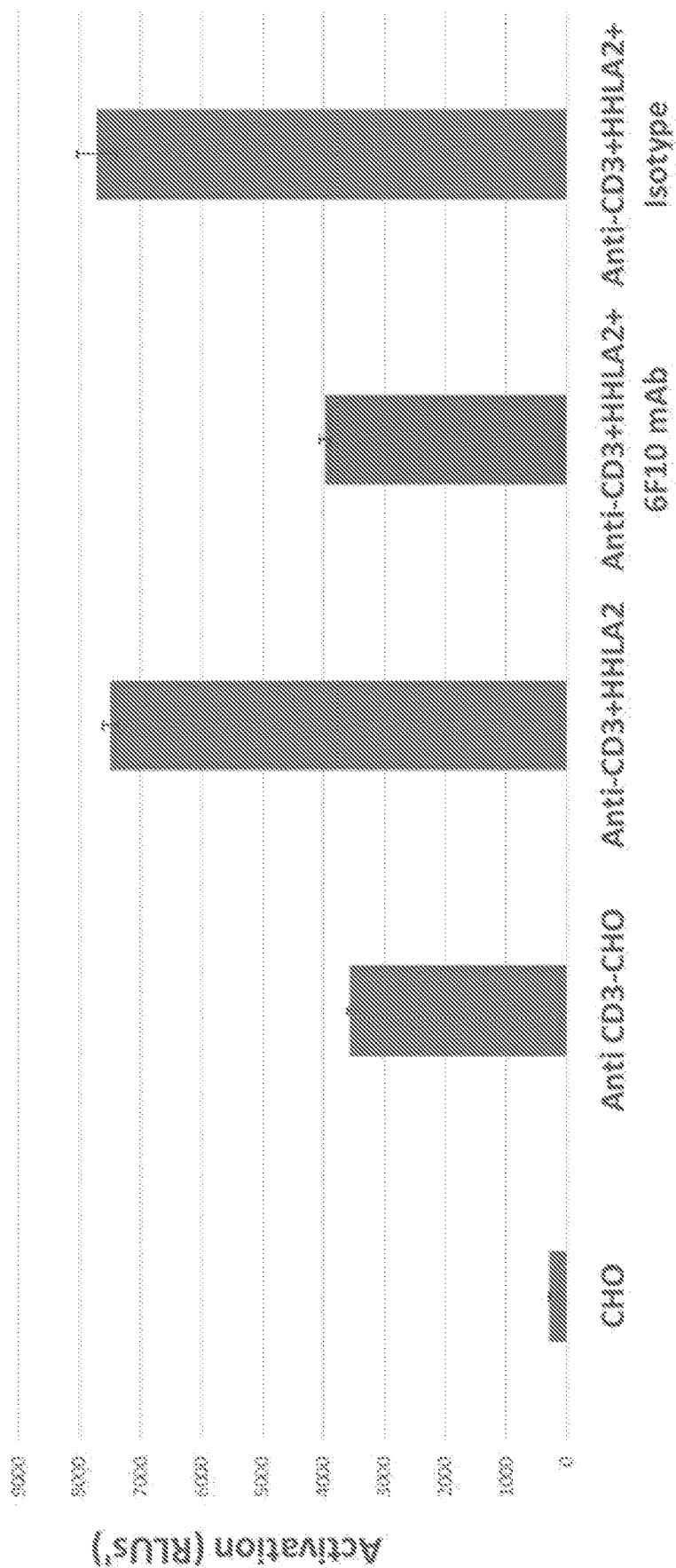
FIG. 17 shows HHLA2 mAb blockade of TMIGD2-mediated T cell co-stimulation. HHLA2-TCR-CHO cells were seeded at $2 \times 10^4$ cells/well density in CHOK1 growth medium in a white opaque bottom 96-well plate. Cells attached to the plate after overnight incubation at 37° C. with 5% $CO_2$. The next day, medium was carefully removed from each well, anti HHLA2 antibody in 50 µl Jurkat cell medium was added, and HHLA2-TCR-CHO cells were incubated for one hour before the addition of MIGD2 NFAT Jurkat reporter cell line at $4$-$5 \times 10^4$ cells/well in 50 µl Jurkat cell medium. The plate well was mixed and incubated for approximately 3-6 hours. To develop the luciferase signal, 100 µl of the ONE-Step™ Luciferase Assay System (BPS Bioscience, Cat. #60690) was added to each well, according to the manufacturer's recommended protocol. Luminescence was read using a luminometer.

Expression of HHLA2 on CHO cells transfected with anti-CD3 scFV and HHLA2 was detected (FIG. 15). Expression of TMIGD2 on Jurkat NFAT reporter cells transfected with TMIGD2 was also detected (FIG. 16). CHO cells expressing anti-CD3 scFV and HHLA2 and Jurkat NFAT reporter cells expressing TMIGD2 were used in the T cell co-stimulation assay. It was found that HHLA2 mAb (6F10)

reversed the enhanced activation induced by HHLA2 whereas the isotype control antibody did not have such effect (FIG. 17).

Figure 18:
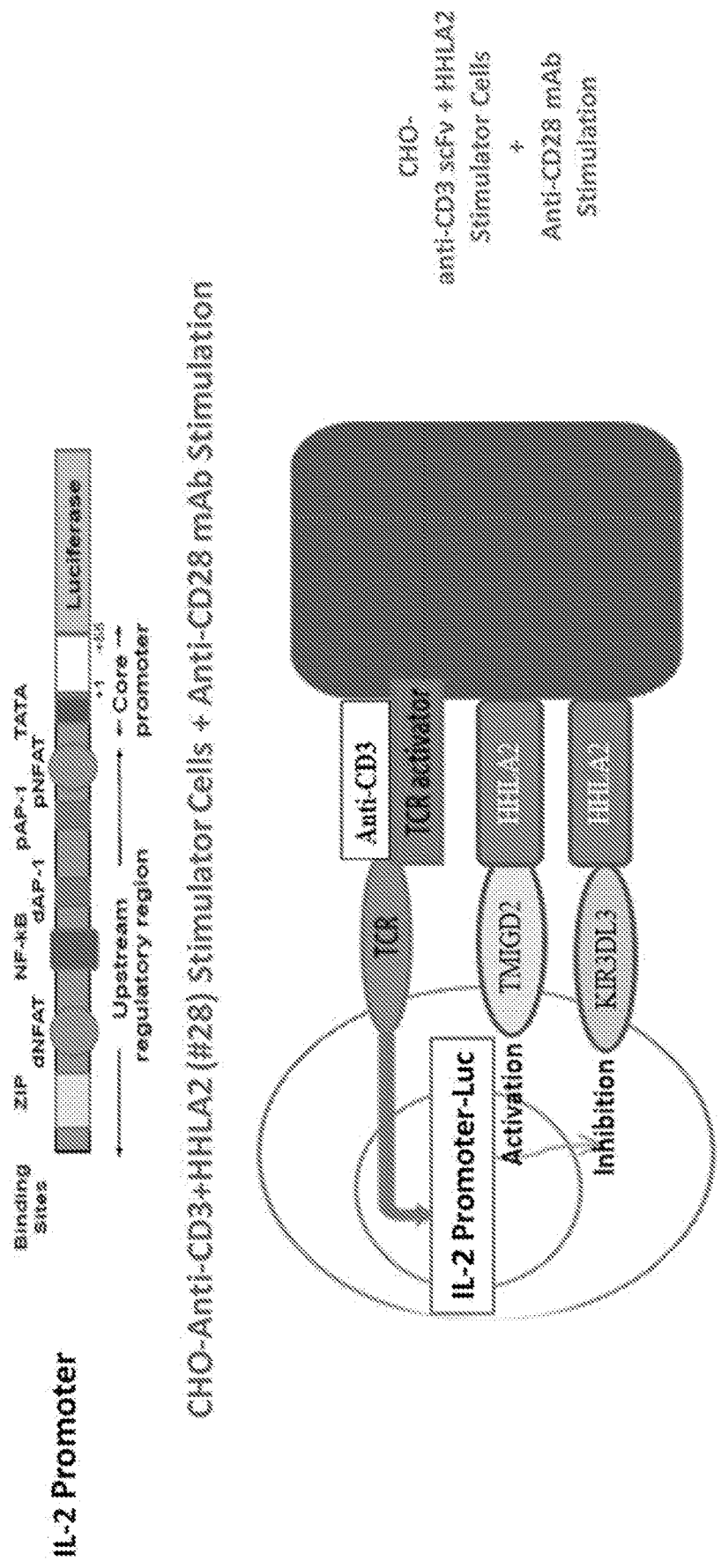
FIG. 18 shows a schematic of KIR3DL3/HHLA2 checkpoint T cell assay. KIR3DL3 Jurkat T cell IL-2 promoter luciferase reporter gene cells were stimulated with CHO cells transfected with anti-CD3 scFV or anti-CD3 scFV+HHLA2.

HHLA2 mAbs or isotype control antibodies were also evaluated for checkpoint blockade in the KIR3DL3/HHLA2 T cell inhibition assay as shown in FIG. 18 and outlined below in Table 10.

TABLE 10 study outline of KIR3DL3/HHLA2 T cell checkpoint assay (Jurkat T Cell IL-2 reporter gene assay)

| Responder Jurkat NFAT cell | Stimulating CHO cell | Expected Response |
| --- | --- | --- |
| Jurkat IL-2/KIR3DL3 | CHO-parental cell | None |
| Jurkat IL-2/KIR3DL3 | CHO-Anti-CD3 Fv | Activation |
| Jurkat IL-2/KIR3DL3 | CHO-Anti-CD3 Fv/HHLA2 | Inhibition |
| Jurkat IL-2/KIR3DL3 | CHO-Anti-CD3 Fv/HHLA2 + HHLA2 mAb | Reversal of Inhibition |

Figure 19A:
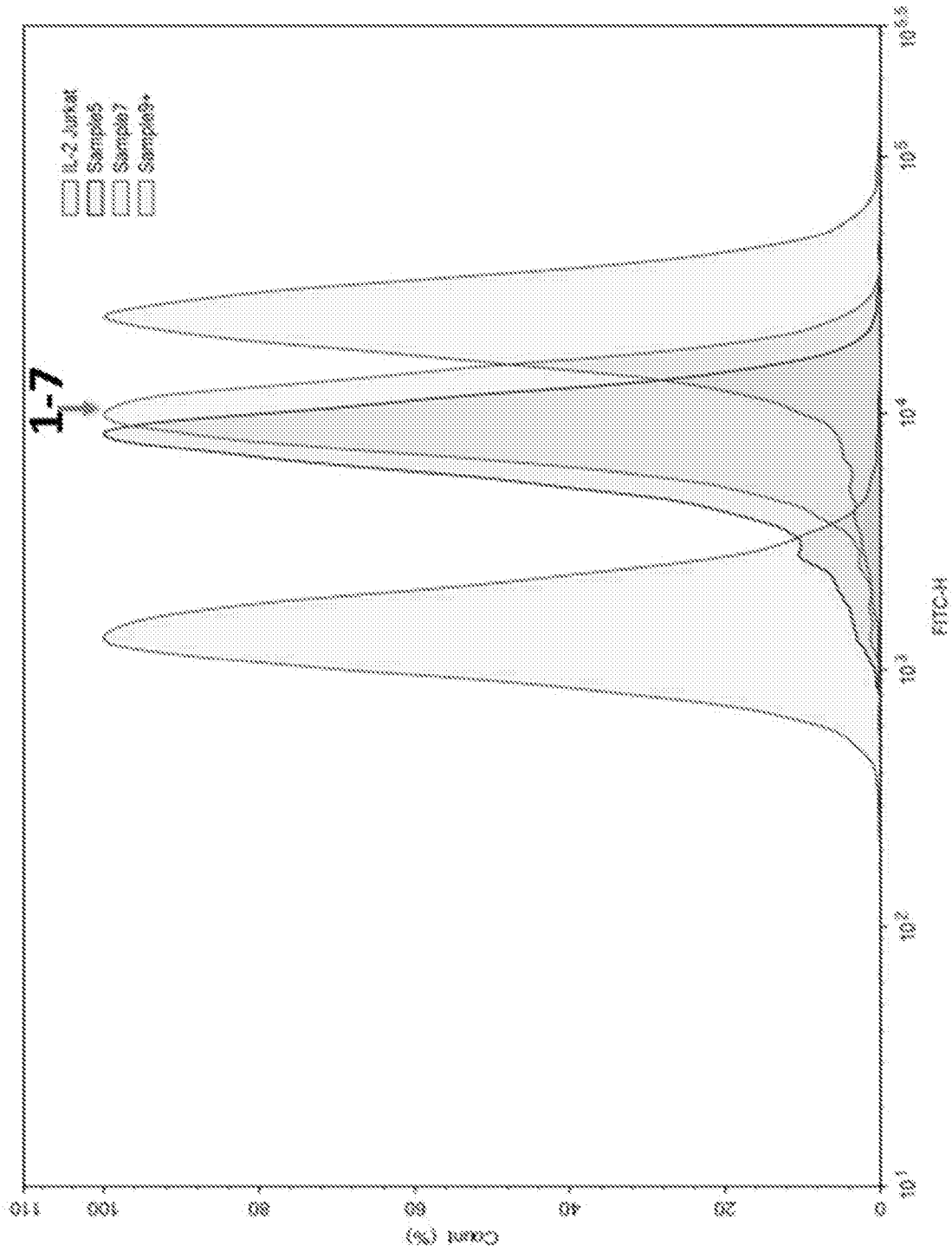
FIG. 19 shows KIR3DL3 expression in Jurkat-IL-2 reporter clones. KIR3DL3 expression was detected in KIR3DL3-transfected Jurkat IL-2 reporter cell clones 1-6, 1-7 and 2-12.
Figure 19B:
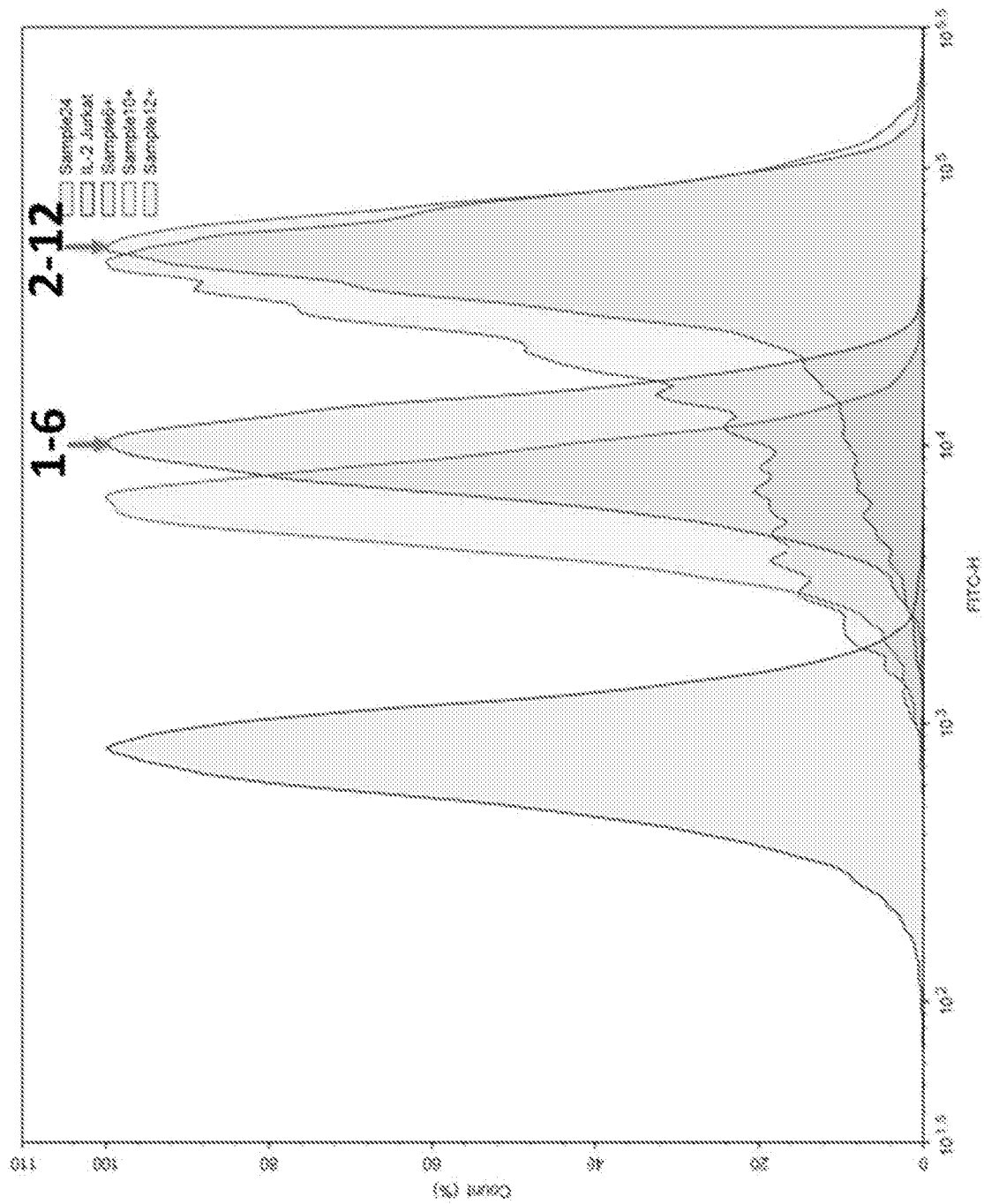
Figure 20A:
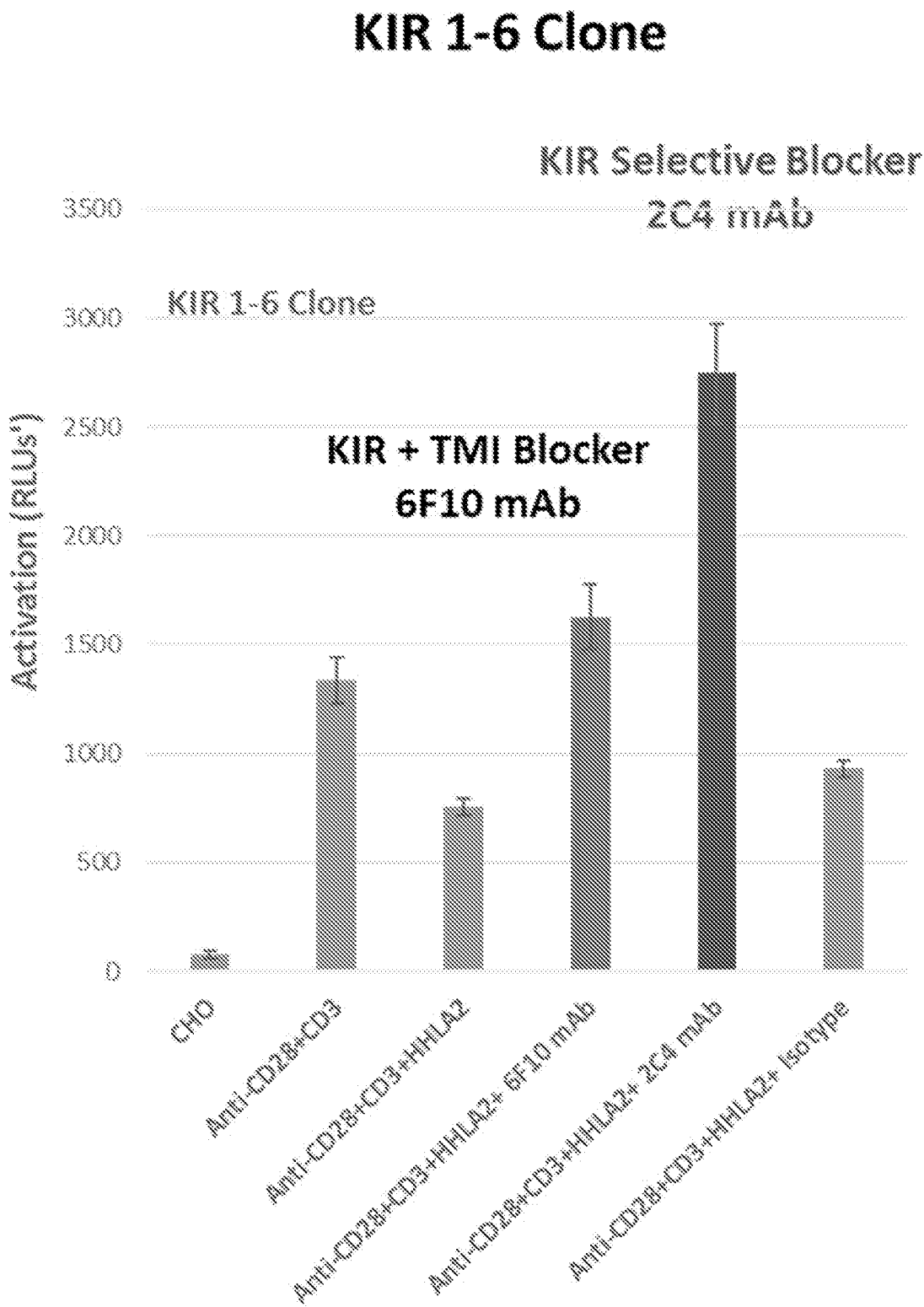
FIGS. 20A-20C show HHLA2 mAb checkpoint blockade of KIR3DL3-mediated T cell inhibition. HHLA2-TCR-CHO cells were seeded at $2 \times 10^4$ cells/well density in CHOK1 growth medium in a white opaque bottom 96-well plate. Cells attached to the plate after overnight incubation at 37° C. with 5% $CO_2$. The next day, medium was carefully removed from each well, anti HHLA2 antibody in 50 µl Jurkat cell medium was added, and HHLA2-TCR-CHO cells were incubated for one hour before the addition of KIR3DL3_IL2_Jurkat reporter cell line at $4$-$5 \times 10^4$ cells/well in 50 µl Jurkat cell medium, plus 2 µg/mL anti CD28 antibody (BPS Bioscience #100186) (final concentration at 1 µg/mL in 100 µL assay mixture per well. The plate well was mixed and incubated for approximately 5 hours. To develop the luciferase signal, 100 µl of the ONE-Step™ Luciferase Assay System (BPS Bioscience, Cat. #60690) was added to each well, according to recommended protocol. Luminescence was read using a luminometer.
Figure 20B:
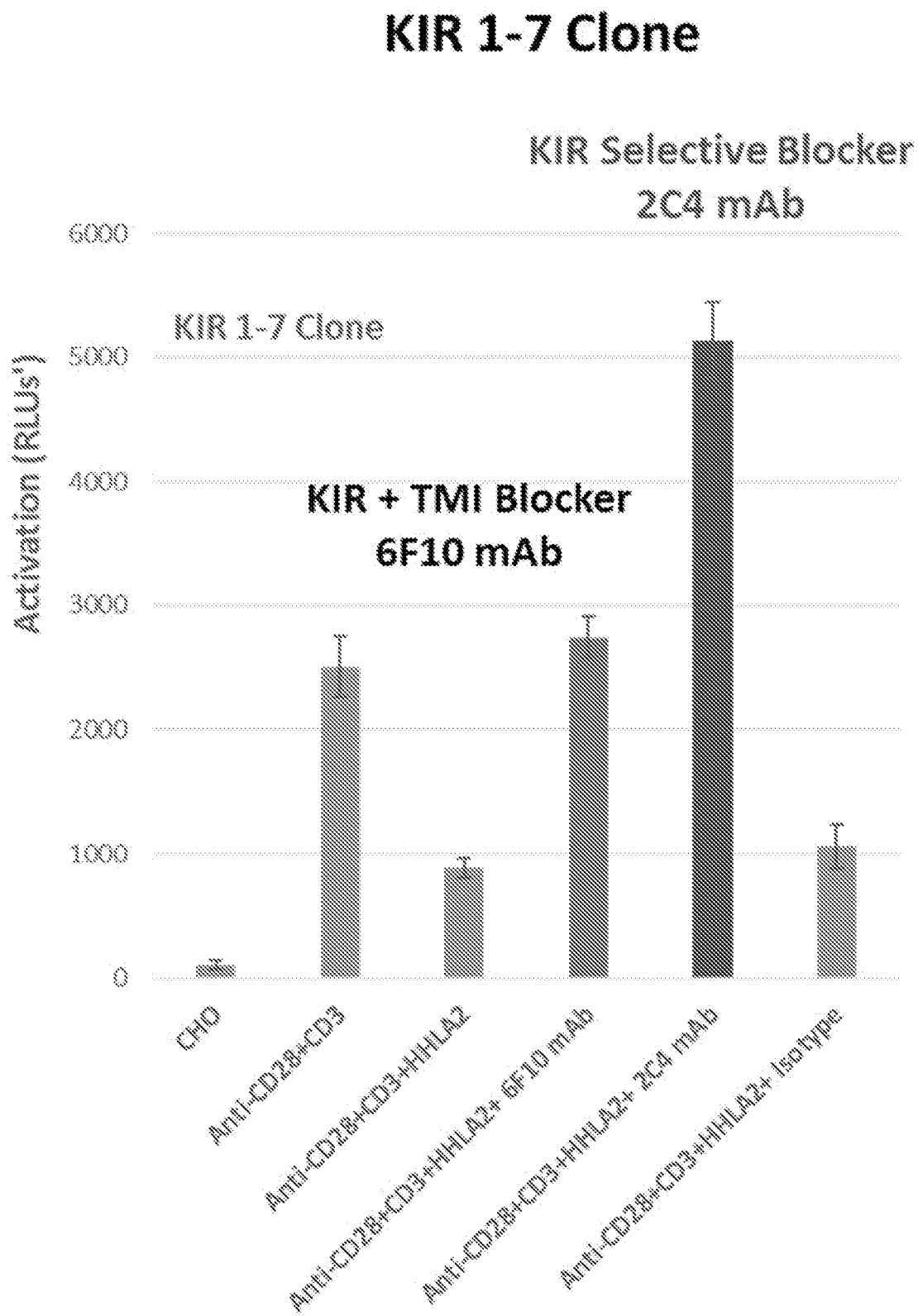
Figure 20C:
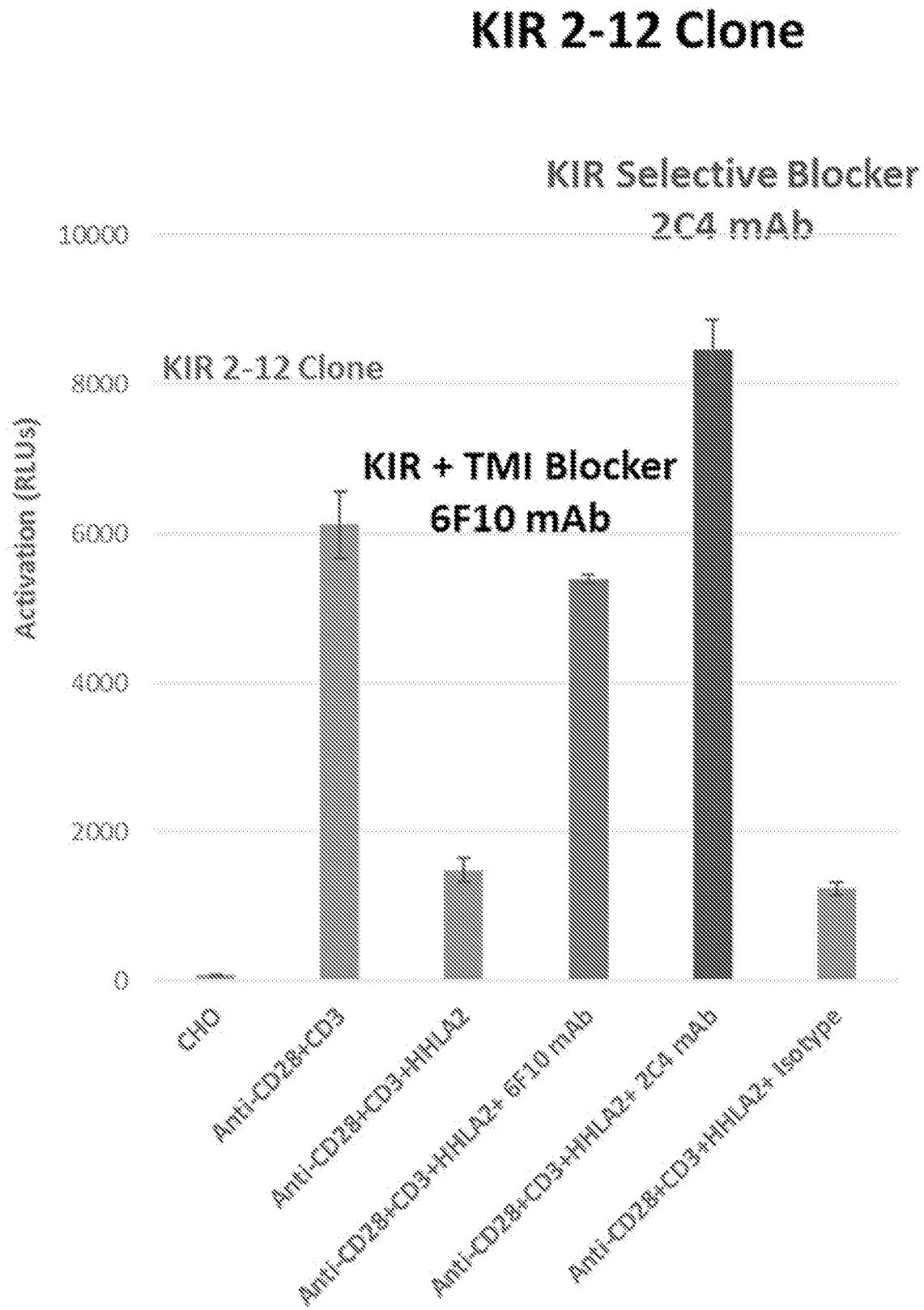
Figure 21A:
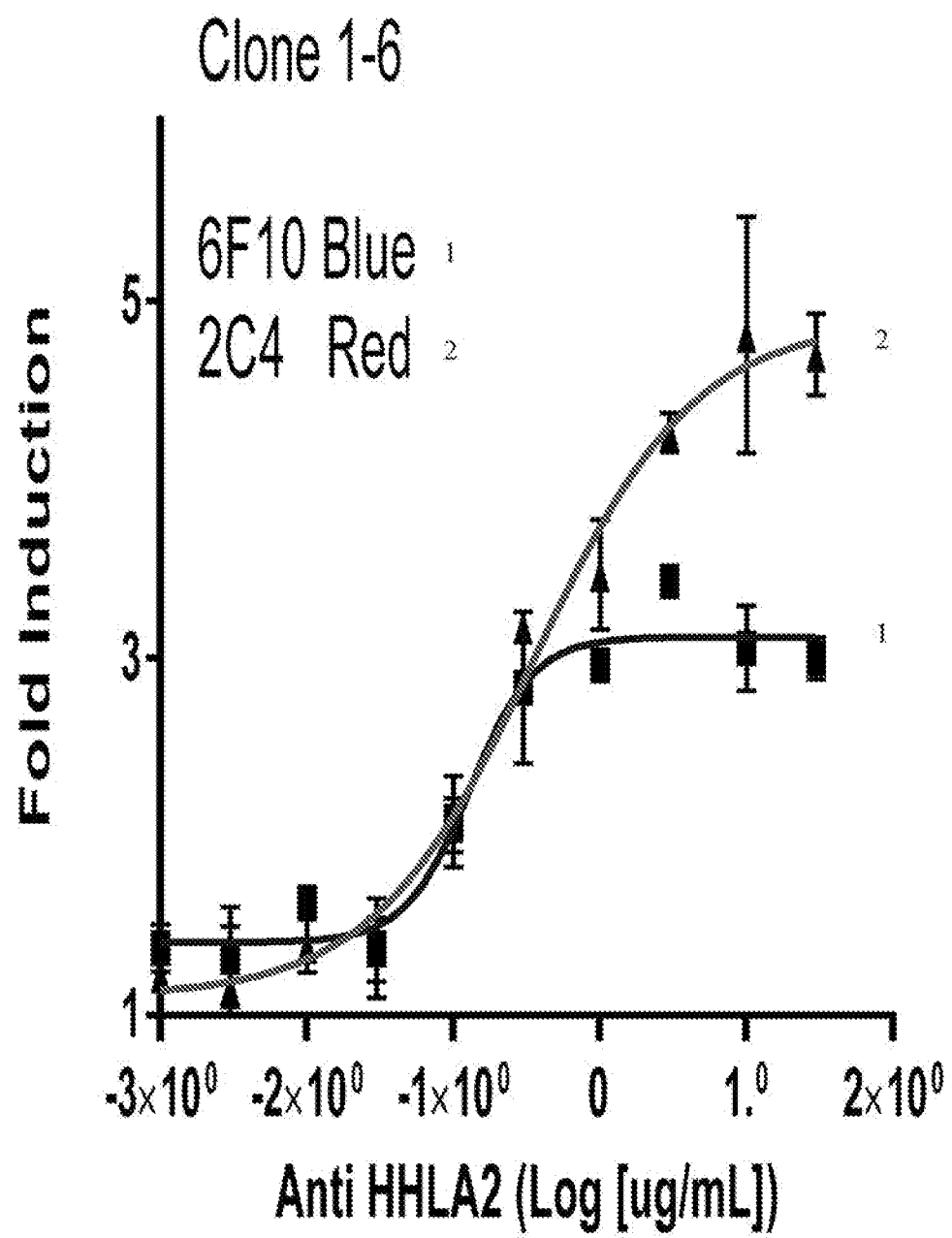
FIGS. 21A-21C show titration of HHLA2 mAb in Jurkat KIR3DL3 inhibition assay. Different concentrations of HHLA2 mAbs 2C4 and 6F10 were evaluated in Jurkat IL-2 reporter luciferase assay using Jurkat IL-2 luciferase clones 1-6, 1-7 and 2-12.
Figure 21B:
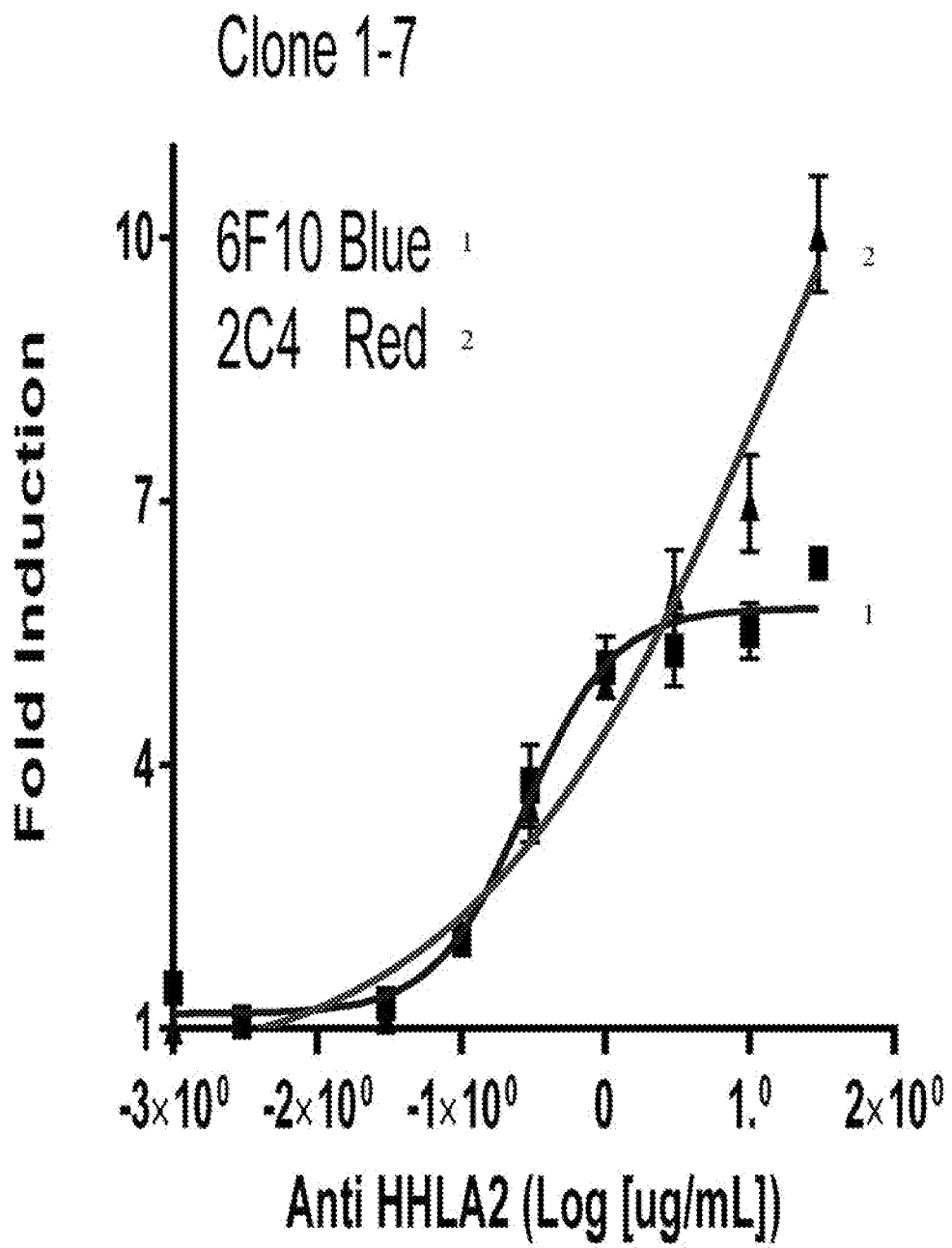
Figure 21C:
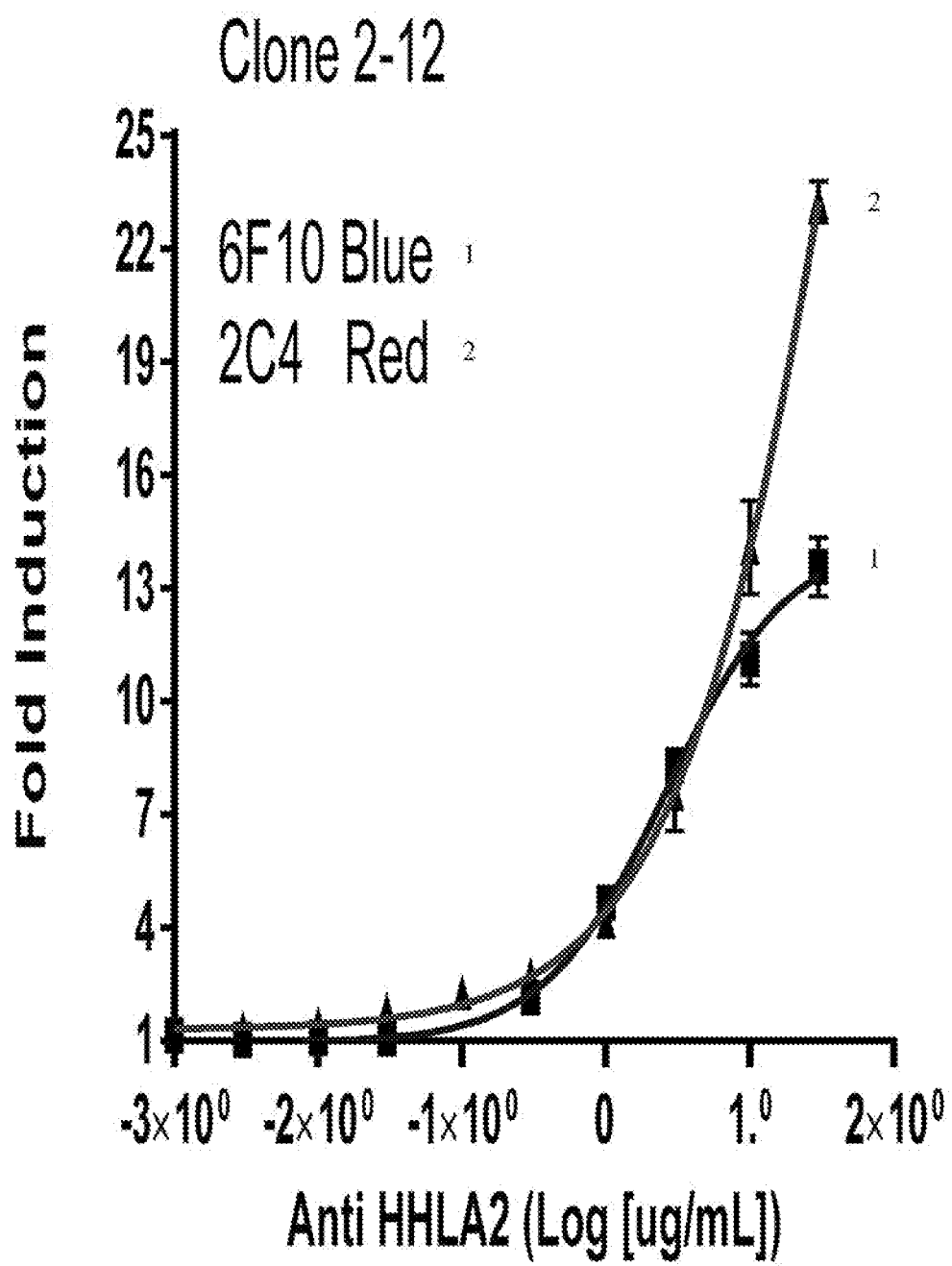
Figure 22:
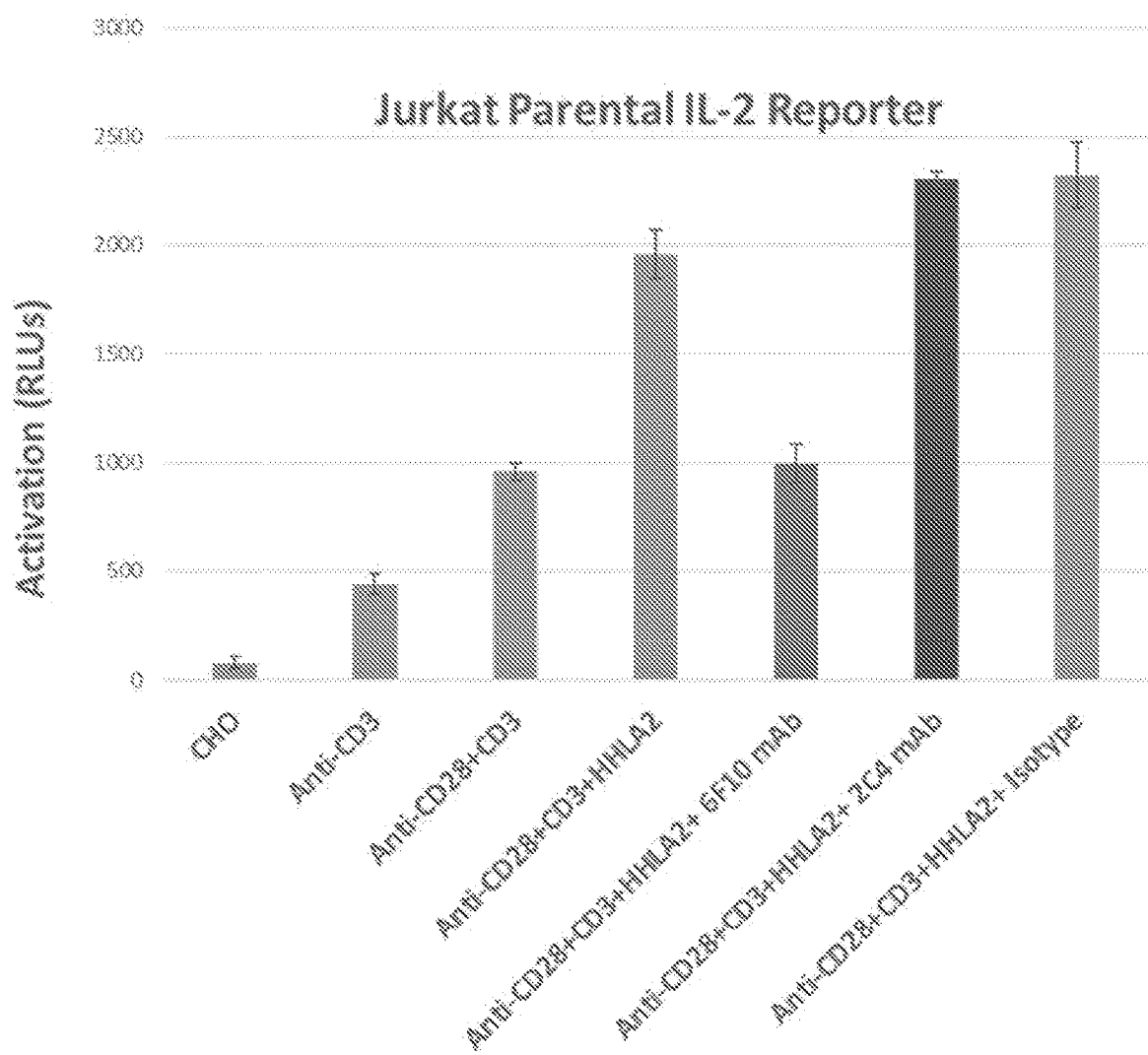
FIG. 22 shows KIR3DL3-selective HHLA2 mAb 2C4 does not block TMIGD2-mediated co-stimulation. HHLA2 mAb 2C4 at a concentration 30 µg/ml was evaluated in Jurkat parental NFAT reporter cells. HHLA2-TCR-CHO cells were seeded at $2 \times 10^4$ cells/well density in CHOK1 growth medium in a white opaque bottom 96-well plate. Cells attached to the plate after overnight incubation at 37° C. with 5% $CO_2$. The next day, medium was carefully removed from each well, anti HHLA2 antibody in 50 µl Jurkat cell medium was added, and HHLA2-TCR-CHO cells were incubated for one hour before the addition of Jurkat parental_NFAT_Jurkat reporter cell line at $4$-$5 \times 10^4$ cells/well in 50 µl Jurkat cell medium. The plate well was mixed and incubated for approximately 3-6 hours. To develop the luciferase signal, 100 µl of the ONE-Step™ Luciferase Assay System (BPS Bioscience, Cat. #60690) was added to each well, according to recommended protocol. Luminescence was read using a luminometer.

Expression of KIR3DL3 on Jurkat-IL-2 reporter cells transfected with KIR3DL3 was detected (FIGS. 19A and 19B). CHO cells expressing anti-CD3 scFV and HHLA2 and Jurkat-IL-2 reporter cells expressing KIR3DL3 were used in the T cell inhibition assay. It was found that HHLA2 mAbs (clone 6F10 and clone 2C4) reversed the inhibition by HHLA2 whereas the isotype control antibody did not have such effect (FIGS. 20A-20C and 21A-21C). KIR3DL3 selective HHLA2 mAb clone 2C4 did not block co-stimulation mediated by TMIGD2 (FIG. 22).

The data described herein demonstrate TMIGD2 as a T cell co-stimulatory receptor for HHLA2, and HHLA2 mAbs that block TMIGD2 co-stimulation were identified. These data also demonstrate KIR3DL3 as a T cell inhibitory receptor for HHLA2, and HHLA2 mAb check-point blockers were identified.

Additional assays can be used to evaluate HHLA2 mAbs. For example, allo-stimulation T cell assays, such as those using CD4 T cells and allogenic monocyte-derived DC's or macrophages can be used to confirm immune checkpoint inhibition of anti-human HHLA2 mAbs. Such methods are well-known in the art, such as described in Wang et al. (2014) *Cancer Immunol. Res.* 2:846 and Brown et al. (2003) *J. Immunol.* 170:1257.

In some embodiments, HHLA2 is expressed in dendritic cells and macrophages. Methods of deriving dendritic cell cultures are well-known in the art such as in, for example, Zhao et al. (2013) *Proc. Natl. Acad. Sci. U.S.A.* 110:9879 and Zhu et al. (2013) *Nat. Comm.* 4:2043.

In some embodiments, monocyte-derived immature DC's (iDC's) are generated by culturing monocytes isolated from PBMC's using a monocyte purification kit (Miltenyi Biotec) and culturing for 7 days with 50 ng/ml IL-4 and 100 ng/ml GM-CSF (R&D Systems). Monocyte-derived activated DC's can be generated by culturing monocytes isolated from PBMC's using a monocyte purification kit (Miltenyi Biotec) and culturing for 7 days with 1 µg/ml LPS and 100 ng/ml IFN-gamma or poly IC.

In some embodiments, macrophages are generated by culturing monocytes isolated from PBMC's using a monocyte purification kit (Miltenyi Biotec) and are cultured for 3 days in the presence of 100 ng/ml LPS plus 100 ng/ml IFN-g or Poly IC.

Dendritic cell and macrophage cultures can be evaluated for expression of HHLA2, TMIGD2 (CD28H), and PD-L1 by flow cytometry using antibodies against these antigens.

Allo-stimulation T cell activation assays can be used to measure T cell proliferation. Briefly, in some embodiments, CD4+ T cells ($1 \times 10^5$) and allogeneic DC's ($1 \times 10^4$) or macrophages derived as described above are co-cultured at a 10:1 (T/DC) ratio with and without anti-human HHLA-2, PD-1 (nivolumab) and isotype control antibodies for 6 days. IFN-gamma secretion in culture supernatants at day 5 is measured by ELISA (BD biosciences or R&D systems kits). T cell proliferation at day 6 is measured by CFSE dilution using flow cytometry.

In some embodiments, IL-2 and IFN-gamma levels can be used to confirm T cell activation, such as using SEB-stimulated PBMC activation assays (see, for example, Wang et al. (2014) *Cancer Immunol. Res.* 2:846). For example, PBMC's ($10^5$ cells) from healthy donors can be co-cultured with or without saturating concentrations of anti-human HHLA-2, PD-1 (nivolumab) and isotype control antibodies for 3 days in the presence of Staphylococcal enterotoxin B (SEB; Toxin Technology) concentrations at 1, 0.1 and 0.01 ug/ml. IL-2 and IFN-gamma levels in culture supernatants can be measured by ELISA or multiplex analysis (BD Biosciences).

In other embodiments, CMV lysate-stimulated PBMC activation recall assays can be used to confirm T cell activation (see, for example, Sinclair et al. (2004) *Viral Immunol.* 17:445 and Wang et al. (2014) *Cancer Immunol. Res.* 2:846). For example, PBMC's ($2 \times 10^5$ cells) from CMV-positive donors can be co-cultured with and without anti-human HHLA-2, PD-1 (nivolumab), and isotype control antibodies and are stimulated with lysate from CMV-infected cells (3 µg/ml, Advanced Biotechnologies) for 4 days. IFN-gamma secretion in culture supernatants can be measured by ELISA (BD biosciences or R&D systems kits). T cell proliferation can be measured by CFSE dilution using Flow cytometry.

In some embodiments, a tumor-based mixed lymphocyte reaction (MLR) assay can be used to confirm T cell activation (see, for example, McWhirter et al. (2006) *Proc. Natl. Acad. Sci. U.S.A.* 103:1041). For example, dendritic cells (DC's) can be generated by culturing monocytes isolated from PBMC's using a monocyte purification kit (Miltenyi Biotec) and cultured for 5 days with 500 U/ml IL-4, 800 U/ml GM-CSF and 100 µg/ml of IFN-gamma. Mixed lymphocyte cultures can be set up in 24-well plates using dendritic cells ($2 \times 10^5$), allogenic CD3+ T cells ($1 \times 10^6$), and irradiated tumor cells expressing HHLA2 ($2 \times 10^5$) in the presence of anti-HHLA2 mAbs or isotype controls (10 µg/ml) for 48 hrs. Supernatants are harvested and evaluated for cytokine production using a multiplex cytokine assay kit.

Figure 7:
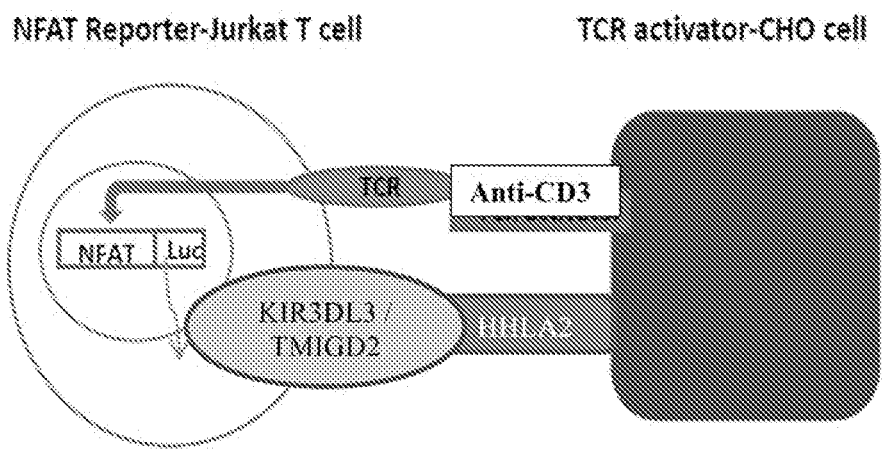
FIG. 7 shows a schematic of a Jurkat NFAT receptor gene assay.

In some embodiments, Jurkat T cell NFAT-Luc reporter gene assays can be used to confirm T cell activation (see, for example, the BPS bioscience website and Wang et al. (2017) *J. Pharm. Biomed. Anal.* 145:247). For example, Jurkat T cells transfected with the NFAT-Luciferase reporter gene cassette (BPS bioscience) and KIR3DL receptor (see assay #1 below) or TMIGD2 receptor (see assay #2 below) are stimulated with CHO cells transfected with transmembrane Anti-CD3 scFV (BPS bioscience) and HHLA2 in the presence or absence of anti-HHLA2 mAbs (FIG. 7). Exemplary Jurkat NFAT receptor gene assay configurations are listed in Table 5 below. $5 \times 10^4$ CHO cells are seeded in 96-well assay plates and cultured for 12-14 hrs. Adherent CHO cells are pre-incubated with anti-HHLA2 mAb or isotype control at 10 µg/ml for 1 hr at 37° C. $1 \times 10^5$ Jurkat cells are co-cultured with CHO cells for 6 hrs and luminescent substrate is added and luciferase units are quantitated using a luminometer.

TABLE 5

| Responder Jurkat NFAT cell | Stimulating CHO cell | Response |
|---|---|---|
| Assay #1: KIR3DL3 Assay | | |
| Jurkat NFAT/KIR3DL3 (Accession #BC143802.1) | CHO-parental cell | No Activation |
| Jurkat NFAT/KIR3DL3 (Accession #BC143802.1) | CHO-Anti-CD3 Fv (same anti-CD3 clone used for PD-1 assay) | Activation |
| Jurkat NFAT/KIR3DL3 (Accession #BC143802.1) | CHO-Anti-CD3 Fv/HHLA2 (same anti-CD3 clone used for PD-1 assay) | Inhibition |
| Jurkat NFAT/KIR3DL3 (Accession #BC143802.1) | CHO-Anti-CD3 Fv/HHLA2 + Anti-HHLA2 6F10 mAb (same anti-CD3 clone used for PD-1 assay) | Reversal of Inhibition |
| Assay #2: TMIGD2 Assay | | |
| Jurkat NFAT/TMIGD2 | CHO-parental cell | No Activation |
| Jurkat NFAT/TMIGD2 | CHO-Anti-CD3 FAT (same anti-CD3 clone used for PD-1 assay) | Activation |
| Jurkat NFAT/TMIGD2 | CHO-Anti-CD3 Fv/HHLA2 (same anti-CD3 clone used for PD-1 assay) | Enhanced Activation |
| Jurkat NFAT/TMIGD2 | CHO-Anti-CD3 Fv/HHLA2 + Anti-HHLA2 6F10 mAb (same anti-CD3 clone used for PD-1 assay) | Reversal of Enhanced Activation |

Example 6: In Vivo Confirmation of Activity of HHLA2 mAbs and Animal Model Development In addition, methods of in vivo characterization of antibodies are well-known in the art, such as described in Wang et al. (2014) *Cancer Immunol. Res.* 2:846, Brown et al. (2003) *J. Immunol.* 170:1257, Zhao et al. (2013) *Proc. Natl. Acad. Sci. U.S.A.* 110:9879, Zhu et al. (2013) *Nat. Comm.* 4:2043, and Sinclair et al. (2004) *Viral Immunol.* 17:445). The absence of HHLA2 pathway in rodents, dogs and other conventional species for tumor models requires new animal tumor or pharmacology models.

Figure 8:
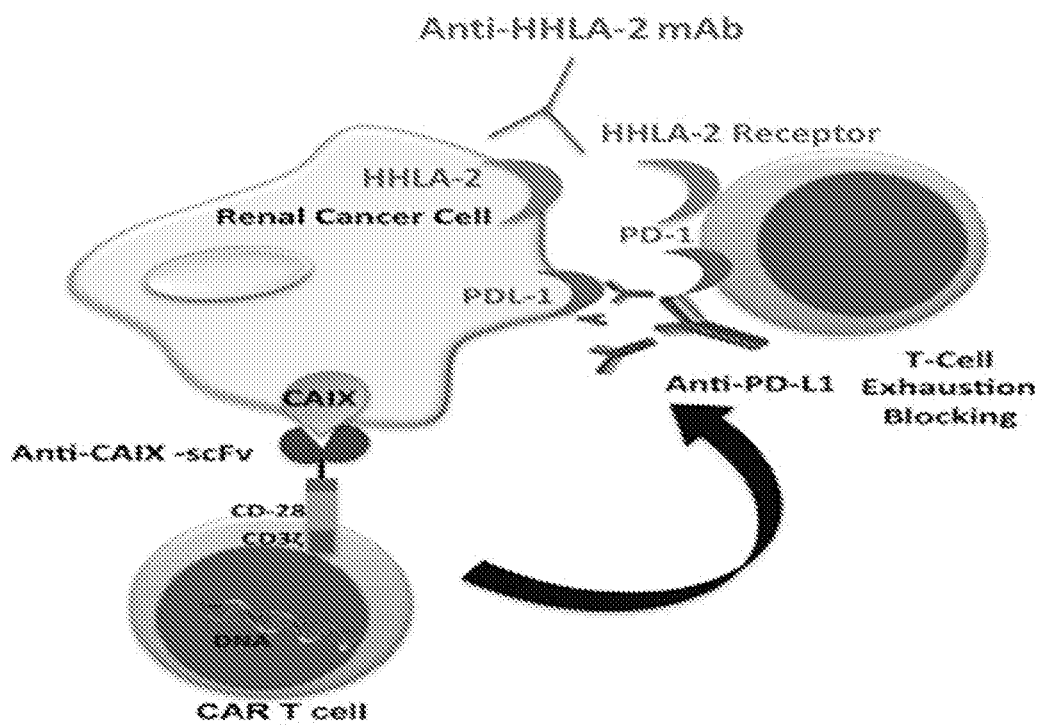
FIG. 8 shows a CAR-T cell model.
Figure 9:
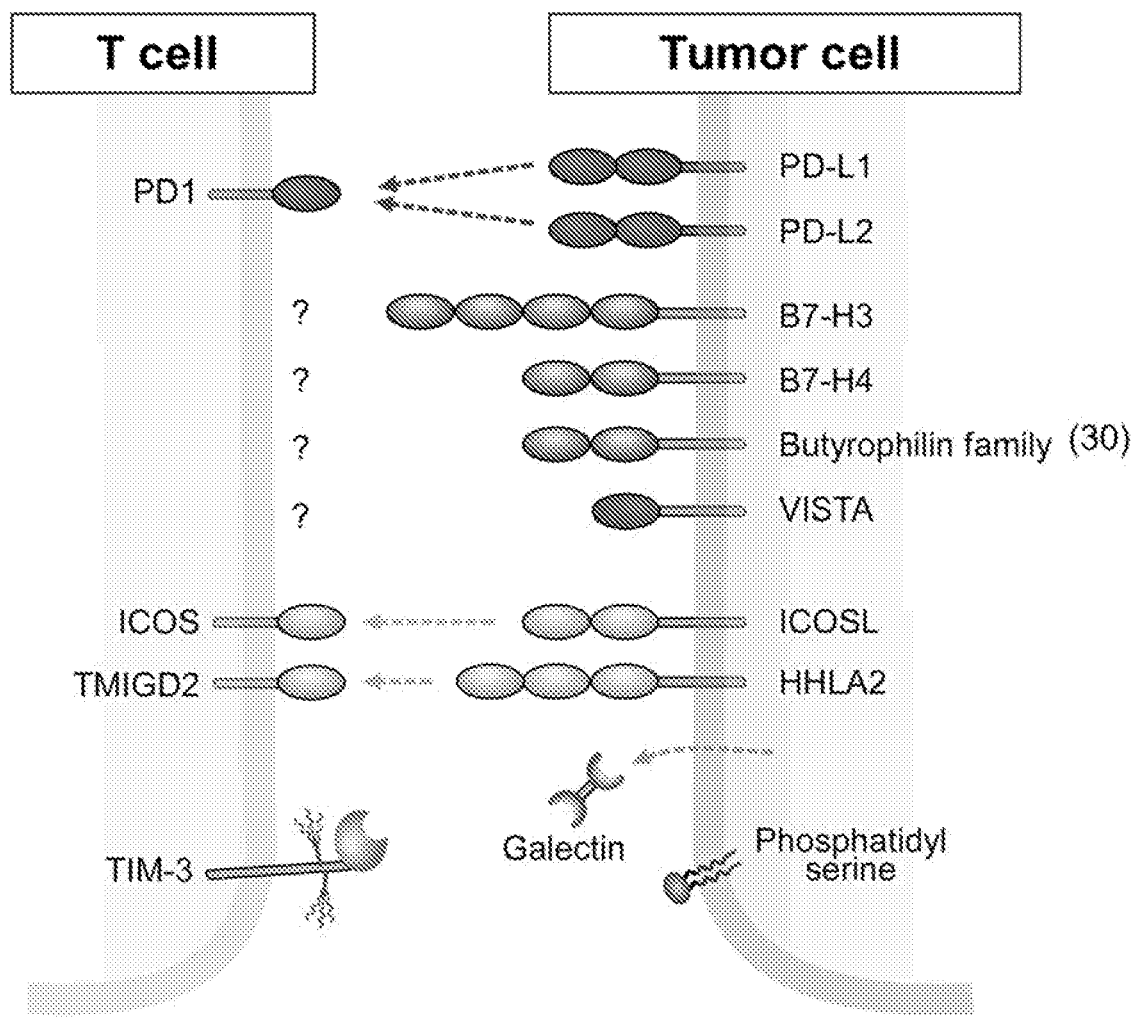
FIG. 9 shows that inhibitory B7 family members that can be expressed by tumors.
Figure 10:
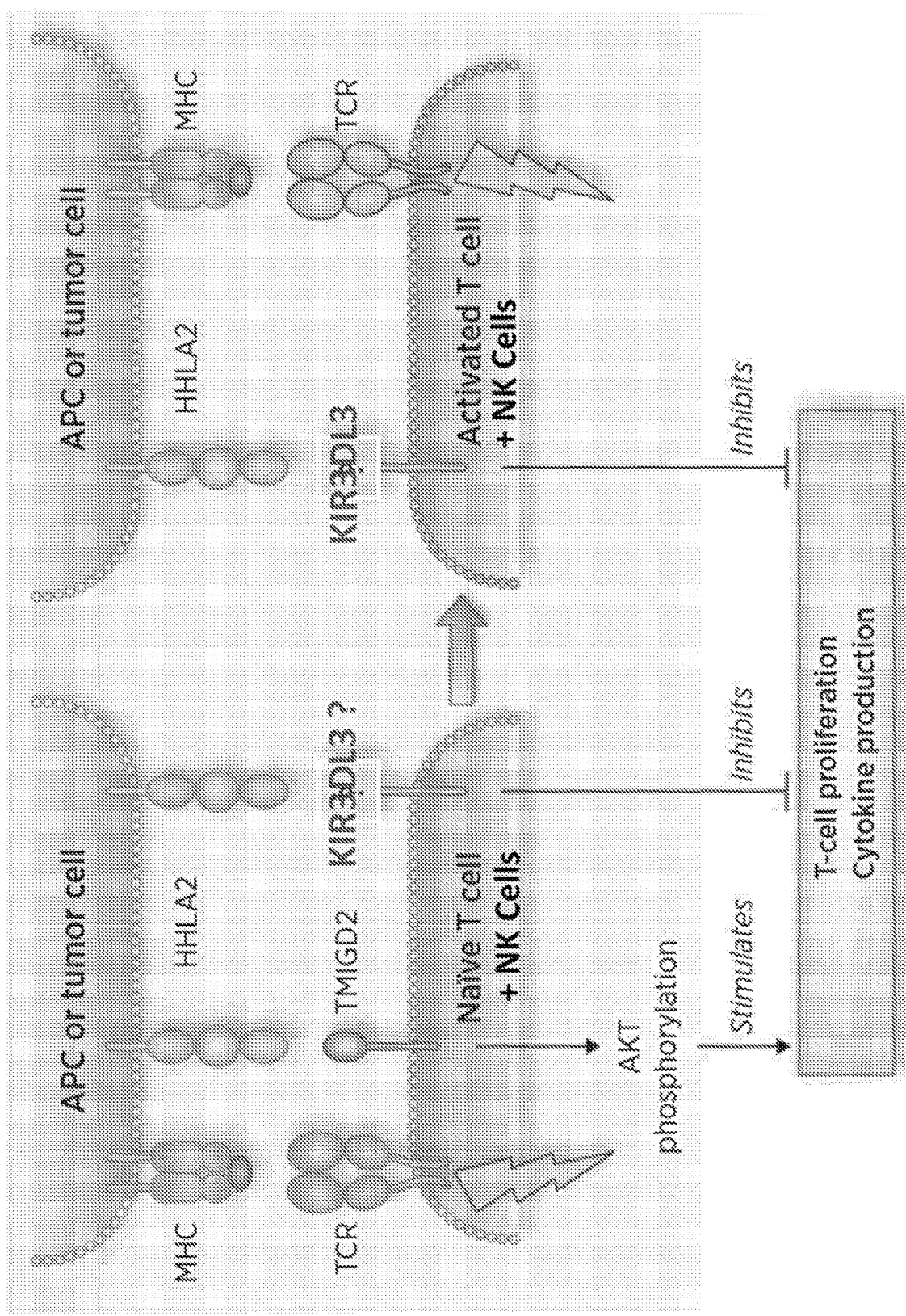
FIG. 10 shows a model for HHLA2 interaction with two receptors (stimulatory and inhibitory HHLA2 receptors) to regulate T-cell functions. Concomitant with T-cell receptor (TCR) signaling, TMIGD2 on naive T cells interacts with HHLA2 on APCs and co-stimulates T-cell proliferation and cytokine production via a pathway involving AKT phosphorylation. With repetitive T-cell activation, expression of stimulatory receptor TMIGD2 is gradually lost, allowing expression of a the inhibitory receptor KIR3DL3 to become dominant. HHLA2 on APCs or tumor cells can interact with this second receptor and exert a co-inhibitory function. This figure is adapted from Xiao and Freeman et al. (2015) *Clin. Cancer Res.* 21:2201-2203.

In some embodiments, a chimeric antigen receptor-T cell (CAR-T) model is used (FIG. 8). For example, NSG mice are implanted with human renal cancer cell line cells expressing carbonic anhydrase IX (CAIX), HHLA2, and PD-L1. Human T cells (CAR-T) expressing anti-carbonic anhydrase IX (CAIX)-targeted chimeric antigen receptor (anti-CAIX CAR T cells) and PD-1 and KIR3DL receptors are injected intravenously along with anti-HHLA2 or KIR3DL mAbs either alone or in combination with anti-PD-1/L-1 mAbs. Tumor growth is quantified by bioluminescence imaging following luciferin IP injection (for example, as described in Suarez et al. (2016) *Oncotarget* 7:34341).

In some embodiments, CAR-T cell tumor model in SCID mice are developed. SCID mice bearing HeLa-CD19-HHLA2 tumors are dosed with HHLA2 mabs and CD19/KIR3DL3 CAR-T cells, and tumor growth inhibition is evaluated. Six-week old female SCID mice (Jackson Laboratories, Bar Harbor, ME) are utilized. Each mouse is injected subcutaneously (SC) on day 0 with 100 µl of sterile PBS containing $2\times10^6$ HeLa-CD19, or HeLa-CD19+HHLA2 cells. CAR-T cells in PBS are injected intratumorally on days 19 ($5\times10^6$ cells) and 33 ($9\times10^6$ cells), and tumor growth followed daily. Antibody dosing occurs three times per week via intraperitoneal (IP) dosing. Body weight is monitored twice a week. Tumor sizes are measured daily with calipers and tumor volume (in mm$^3$) determined using the formula W2L/2, where W is tumor width and L is tumor length. The study length is approximately 45 days and 10 mice are used per arm. Mice are dosed with HHLA2 mAbs based on the PK profile of these antibodies.

At the end of the experiment, tumors are excised, terminal bleed is performed and serum is stored for ELISA and FACS analysis. Tumors are harvested, weighed and half of the tumor is freshly frozen and half is fixed in 4% paraformaldehyde, then embedded in paraffin for H&E staining and immunohistochemistry (IHC). Exemplary CD19/KIR3DL3 CAR-T cell tumor model configurations are listed in Table 12 below.

TABLE 12 evaluation of HHLA2 mAbs in CD19/KIR3DL3 CAR-T cell tumor model in vivo

| Tumor | Treatment | Expected outcome |
|---|---|---|
| HeLa/CD19/HHLA2 | No T cells | Tumor Growth |
| HeLa/CD19/HHLA2 | CAR-T/aCD19 | Inhibition of tumor growth |
| HeLa/CD19/HHLA2 | CAR-T/aCD19/KIR3DL3 + Isotype control | Tumor Growth |
| HeLa/CD19/HHLA2 | CAR-T/aCD19/KIR3DL3 + HHLA2 mAb | Inhibition of tumor growth |

Figure 24A:
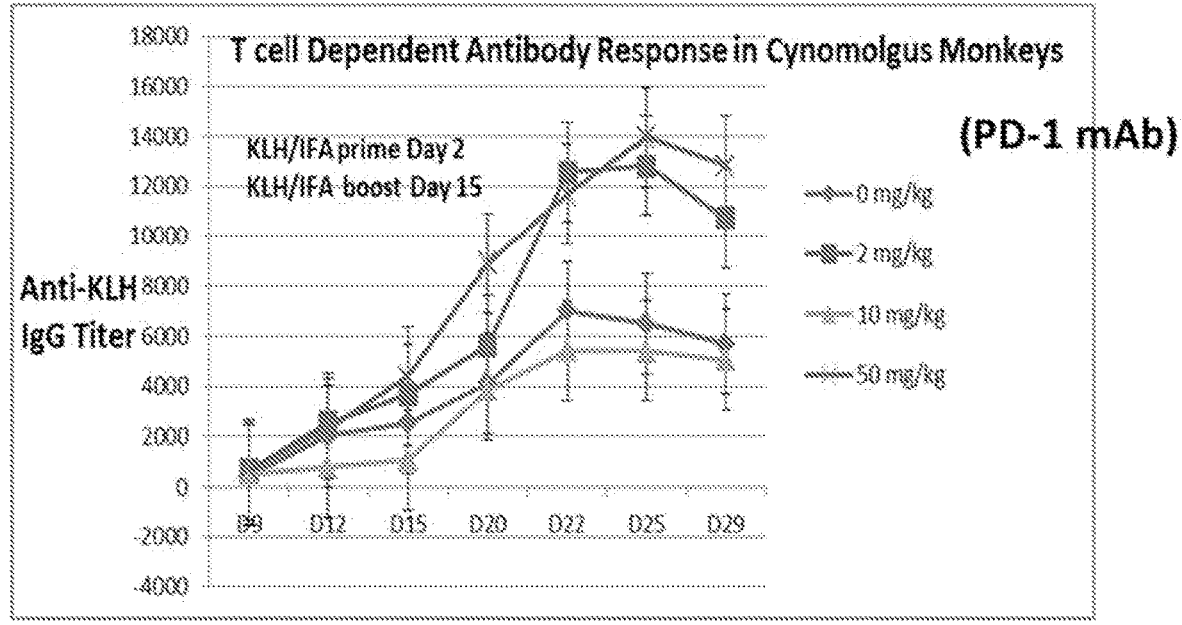
FIGS. 24A and 24B show how HHLA2 mAbs in cynomolgus monkey T cell model can be evaluated. Cynomolgus monkeys are administered HHLA2 mAbs and are immunized with KLH, and T cell-dependent antibody and cell-mediated responses are evaluated. NK cytotoxicity is evaluated ex vivo.
Figure 24B:
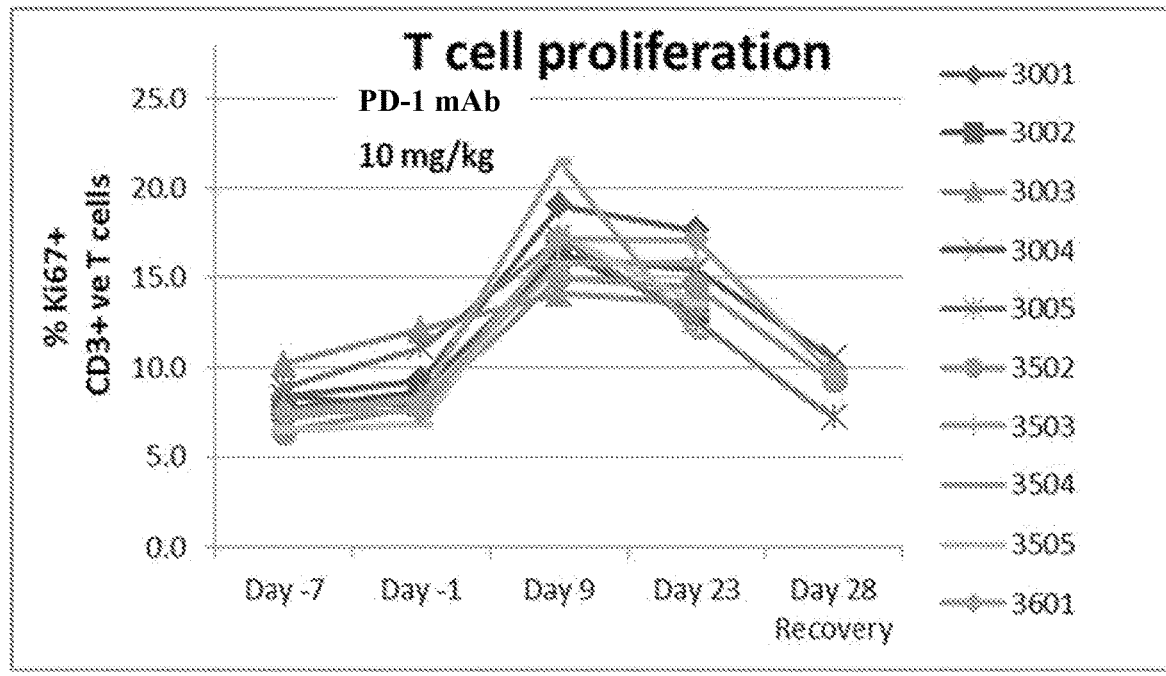

In some embodiments, HHLA2 mAbs are confirmed to have in vivo activity using an antigen prime and boost assays confirming T cell proliferation, cytokine, and/or T cell-dependent antibody responses (TDAR) in cynomolgus monkeys. In some embodiments, cynomolgus monkey KLH antigen challenge T cell model is generated and used (FIGS. 24A and 24B). For example, cynomolgus monkeys dosed intravenously with anti-HHLA2 mAb are immunized on day 2 with KLH (0.1 mg) in incomplete Freund's adjuvant and boosted 14 days later with low dose KLH in incomplete Freund's adjuvant. Pre- and post-immunization bleeds are evaluated for the enhanced production of anti-KLH IgG antibodies using an immunoassay. Cynomolgus monkeys are treated with an HHLA2 mAb on day 1 and receive weekly IV dosing of an HHLA2 mAb at 2–50 mg/kg. PBMC isolated from cynomolgus monkeys pre- and post-dose anti-HHLA2 mAb treatment are evaluated for T cell dependent anti-KLH antibody response, T and NK cell proliferation by Ki67 staining and flow cytometry, and NK cytotoxicity by CD107a FACS staining in vivo or by ex vivo cytotoxicity against K562 cells. In some embodiments, cynomolgus monkey SIV model is developed and used to evaluate HHLA2 mAbs in vivo.

Figure 23A:
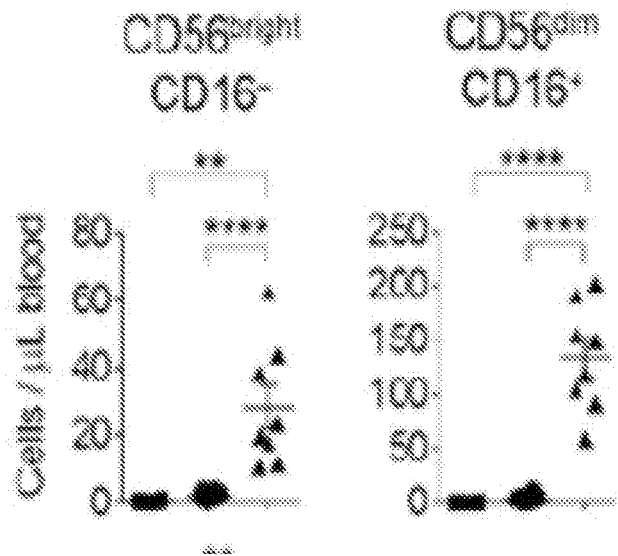
FIGS. 23A-23C show how HHLA2 mAbs in humanized SRG-15 mouse tumor model (has both T and NK cells) can be evaluated. HHLA2 mAbs are administered to humanized SRG-15 mouse bearing HHLA2-expressing tumor cells, and tumor growth inhibition is evaluated. The figures are adapted from Herndler-Brandstetter D et al. (2017) 114: E9626-E9634.
Figure 23B:
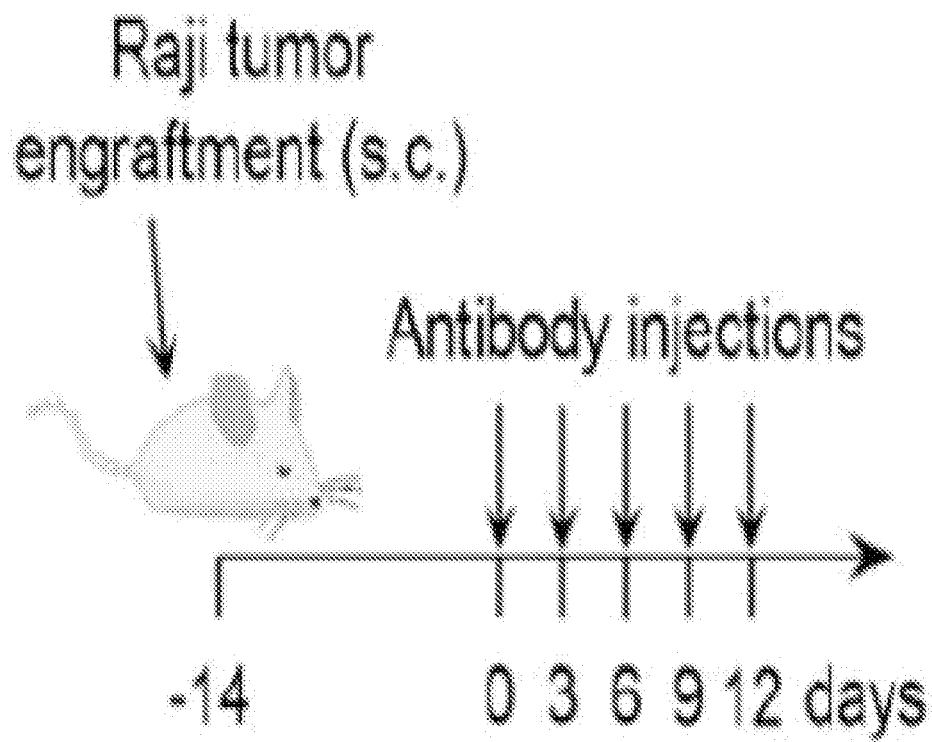
Figure 23C:
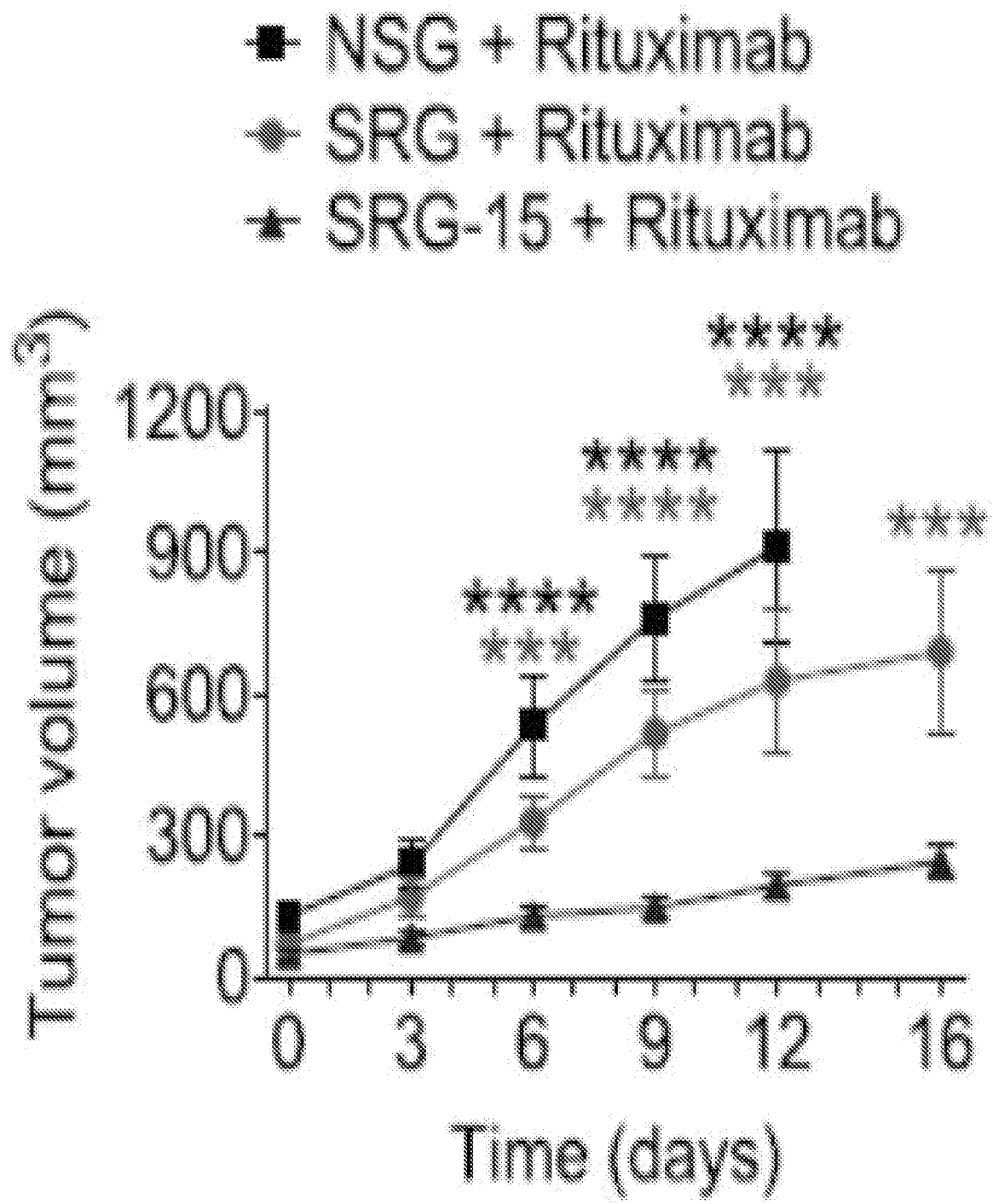

In some embodiments, the humanized SRG-15 mouse tumor model is used and the effects of HHLA2 mAbs on human tumors in humanized SRG-15 (Flavell) or NSG-15 (Greiner) mice are tested (FIGS. 23A-23C; Herndler-Brandstetter D et al. (2017) 114:E9626-E9634).

Example 7: HHLA2 mAbs Cell Binding and Receptor Blocking Characteristics

Figure 12A:
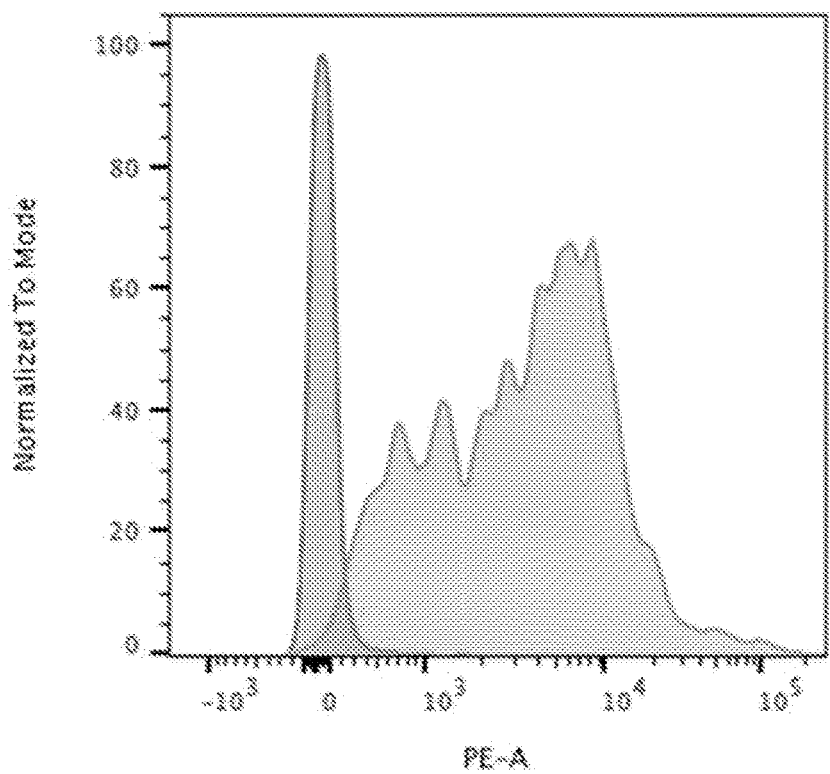
FIGS. 12A and 12B show expression of TMIGD2 (FIG. 12A) or KIR3DL3 (FIG. 12B) on transfected 293T Cells. TMIGD2 or KIR3DL3 cDNA in pEF-Puro expression vector was transiently transfected in 293T cells and stained 48-72 hours later with (1) TMIGD2 mAb (R&D systems catalog #MAB83162; clone #953743) followed by goat-anti-mouse IgG F(ab)$_2$-PE (R&D Systems Catlaog F0102B or (2) KIR3DL3-PE conjugated mAb (R&D Systems catalog #FAB8919R: clone #1 136), respectively, and detected by flow cytometry.
Figure 12B:
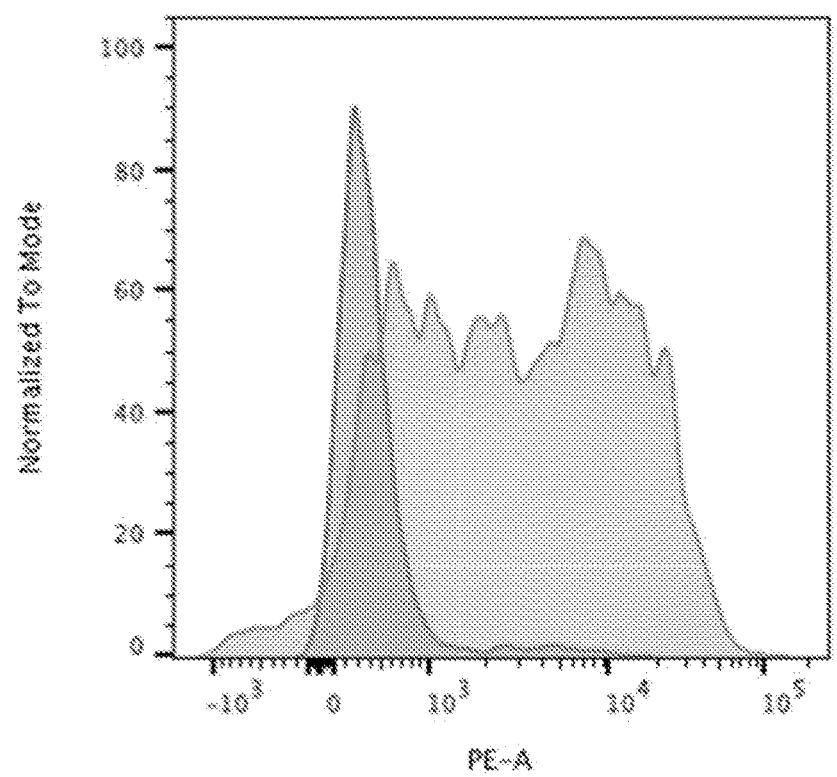
Figure 12C:
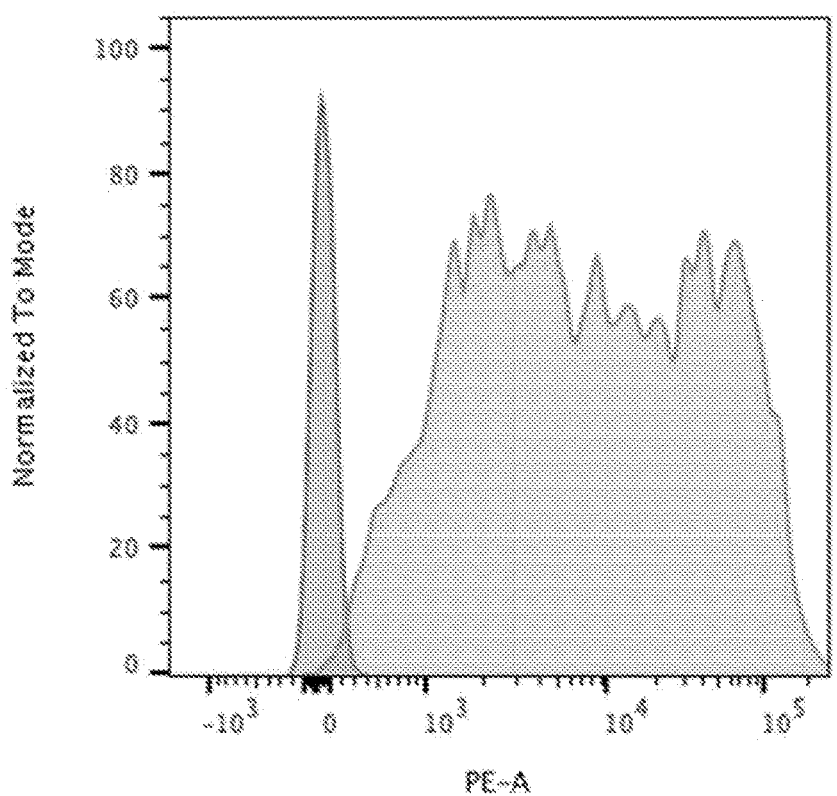
FIGS. 12C and 12D show HHLA2-Fc binding to TMIGD2 (FIG. 12C) or KIR3DL3 (FIG. 12D) transfected 293T cells. HHLA2-mIgG2a binding to 293T cells transiently transfected with TMIGD2 or KIR3DL3 was detected using a PE-labeled Fab$_2$ goat anti-mouse IgG2a antibody (absorbed for cross-reactivity with human Ig, Southern Biotech Catalog #1082-09) by flow cytometry.
Figure 12D:
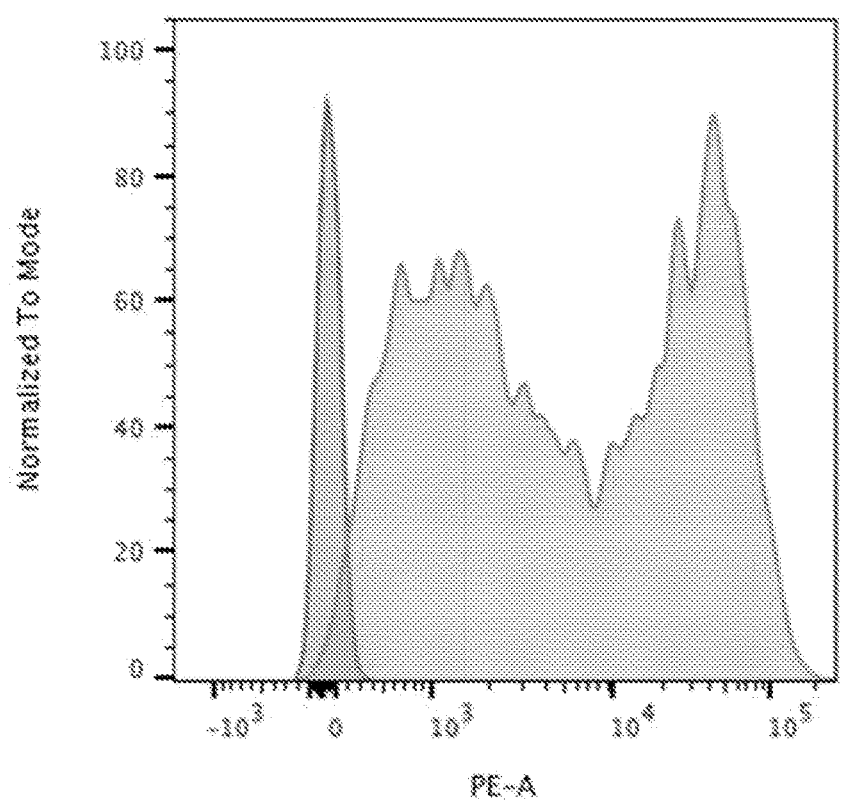

HHLA2 mAb binding and blocking characteristics were analyzed. For example, EC50's for HHLA2 mAbs binding to HHLA2, and IC50's of HHLA2 mAbs blockade of HHLA2 binding to TMIGD2 or KIR3DL3 were detected. Expression of TMIGD2 and KIR3DL3 on transfected 293T cells was detected by flow cytometry (FIGS. 12A and 12B). HHLA2-Fc binding to TMIGD2 and KIR3DL3 transfected 293T cells was shown (FIGS. 12C and 12D). Stably-transfected 300.19 pre-B cells expressing HHLA2, TMIGD2, or KIR3DL3 were also generated.

HHLA2 mAb cell binding and receptor blockade experiments were then performed. In one experiment, different concentrations of HHLA2 mAbs were incubated with HHLA2-transfected 300.19 pre-B cells for 30 minutes at 4° C. HHLA2 mAb binding to transfected 300.19 cells was detected with PE-labeled goat anti-mouse IgG (H+L). For HHLA2 mAb blocking experiments different concentration of HHLA2 mAbs were pre-incubated with 4 ug/ml of HHLA2-mIgG2a at a 1:1 ratio for 30 minutes and added to either TMIGD2 or KIR3DL3 transfected 293T cells and incubated for 30 minutes at 4° C. HHLA2-mIgG2a binding to TMIGD2 or KIR3DL3 transfected 293T cells was detected with a PE labeled Fab2 goat anti-mIgG2a antibody. EC50 and IC50 analyses were conducted using Graph Pad Prism. Data are shown in Table 6. It was shown that HHLA2 mAb clone 2C4 has desired properties of complete KIR3DL3 blockade and partial TMIGD2 blockade (Table 6).

TABLE 6

HHLA2 mAb cell binding and receptor blockade experiment #1

| HHLA2 mAb (Isotype)\ | [1]HHLA2 Binding EC50 (ug/ml) | [2]TMIGD2 Blocking IC50 (ug/ml) | | [2]KIR3DL3 Blocking IC50 (ug/ml) | |
|---|---|---|---|---|---|
| 1C8 (IgG2a) | 0.63 | + | 1.65 | + | 1.15 |
| 2C4 (IgG1) | 0.24 | +/− | 28.2 | + | 0.52 |
| 2G2 (IgG1) | 0.21 | + | 0.85 | + | 0.53 |
| 4D1 (IgG1) | 0.44 | + | 0.56 | + | 0.68 |
| 6D10 (IgG1) | 22.5 | +/− | 11.7 | +/− | 7.0 |
| 6F10 (IgG1) | 0.25 | + | 0.55 | + | 0.9 |

[1]HHLA2 mAb binding to HHLA2 transfected 300.19 mouse pre-B cell line
[2]HHLA2 mAb blockade of HHLA2-mIgG2a binding to TMIGD2 or KIR3DL3 transfected 293T cells (transients)

In another experiment, different concentrations of HHLA2 mAbs were incubated with HHLA2-transfected 300.19 pre-B cells for 30 minutes at 4° C. HHLA2 mAb binding to transfected 300.19 cells was detected with PE-labeled goat anti-mouse IgG (H+L). For HHLA2 mAb blocking experiments different concentration of HHLA2 mAbs were pre-incubated with 4 μg/ml of HHLA2-mIgG2a at a 1:1 ratio for 30 minutes and added to either TMIGD2 or KIR3DL3 transfected 300.19 pre-B cells and incubated for 30 minutes at 4° C. HHLA2-mIgG2a binding to TMIGD2 or KIR3DL3 transfected 300.19 pre-B cells was detected with a PE labeled Fab2 goat anti-mIgG2a antibody. EC50 and IC50 analyses were conducted using Graph Pad Prism. Data are shown in Table 7. It was shown that HHLA2 mAb clone 2C4 has desired properties of complete KIR3DL3 blockade and partial TMIGD2 blockade (Table 7).

TABLE 7

HHLA2 mAb cell binding and receptor blockade experiment #2

| HHLA2 mAb (Isotype)\ | [1]HHLA2 Binding EC50 (ug/ml) | [2]TMIGD2 Blocking IC50 (ug/ml) | | [2]KIR3DL3 Blocking IC50 (ug/ml) | |
|---|---|---|---|---|---|
| 2C4 (IgG1) | 0.29 | +/− | 7.3 | + | 0.97 |
| 5H4 (IgG1) | 2.03 | +/− | 9.63 | + | 1.25 |
| 6F10 (IgG1) | 0.22 | + | 0.92 | + | 0.74 |
| 6G8 (IgG1) | 2.14 | +/− | 10.85 | + | 1.18 |

Figure 13A:
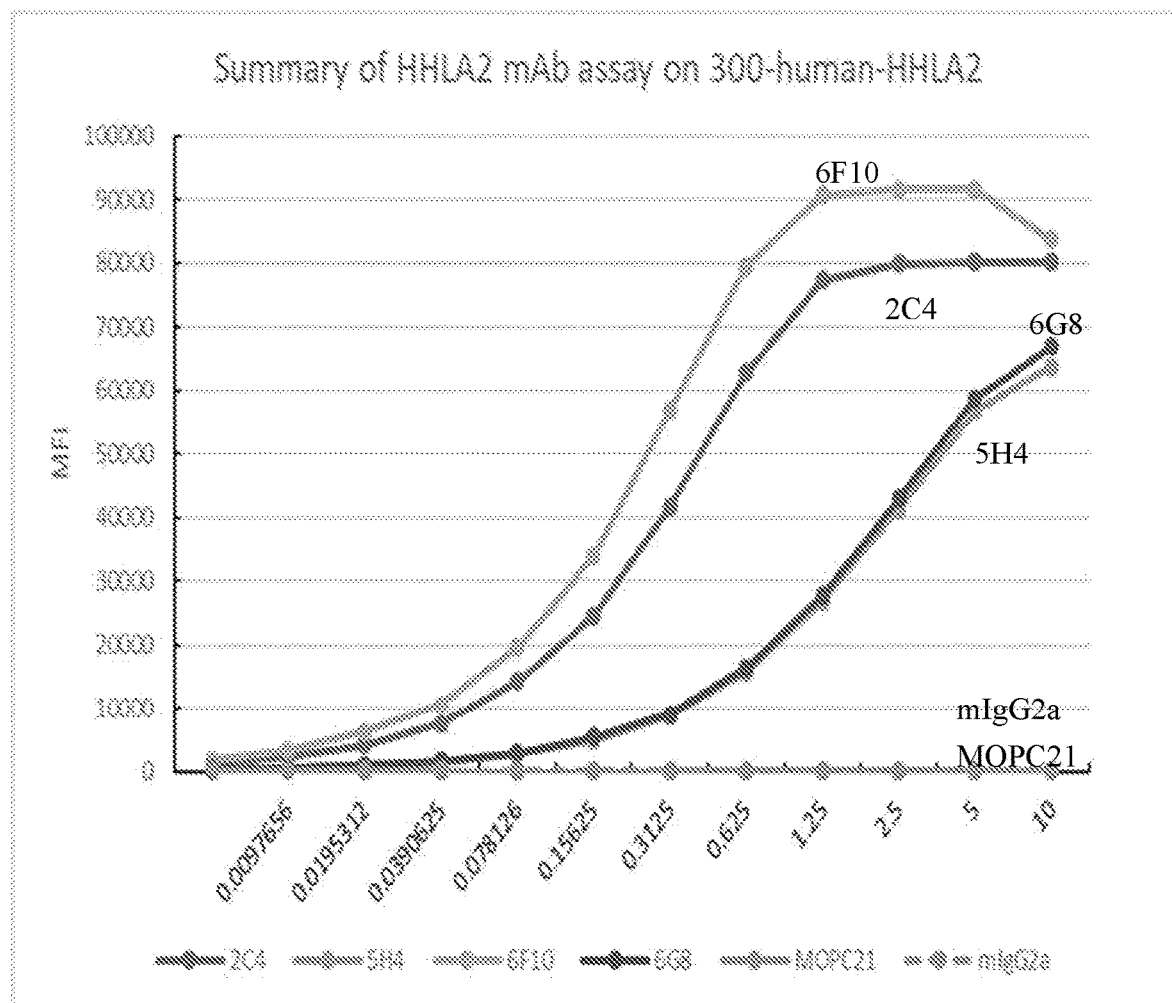
FIGS. 13A and 13B show HHLA2 mAb binding to human and cynomolgus monkey HHLA2. Different concentrations of HHLA2 mAbs were incubated with either human or cynomolgus monkey HHLA2-transfected 300.19 pre-B cells for 30 minutes at 4° C. HHLA2 mAb binding to transfected 300.19 cells was detected with a PE-labeled goat anti-mouse IgG (H+L) by flow cytometry.
Figure 13B:
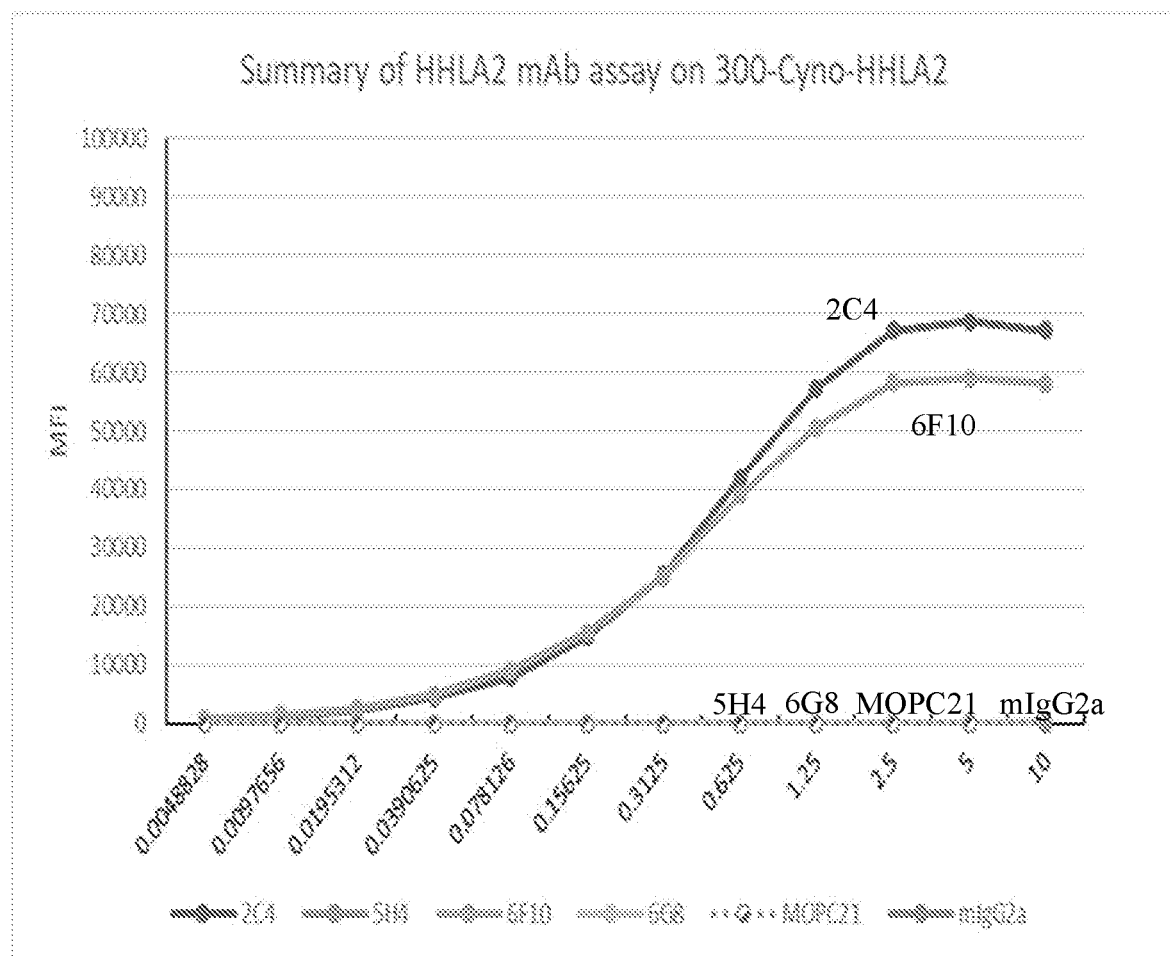

[1]HHLA2 mAb binding to HHLA2 transfected 300.19 mouse pre-B cells
[2]HHLA2 mAb blockade of HHLA2-mIgG2a binding to TMIGD2 or KIR3DL3 transfected 300.19 pre-B cells Binding of different HHLA2 mAbs to human and cynomolgus monkey HHLA2 was also tested and EC50 binding analysis was conducted (FIGS. 13A and 13B). Different concentrations of HHLA2 mAbs were incubated with either human or cynomolgus monkey HHLA2-transfected 300.19 pre-B cells for 30 minutes at 4° C. HHLA2 mAb binding to transfected 300.19 cells was detected with PE-labeled goat anti-mouse IgG (H+L). EC50 analysis was conducted using Graph Pad Prism. Data are shown in Table 8.

TABLE 8

HHLA2 mAb binding to human and cynomolgus monkey hhla2

| HHLA2 mAb (Isotype) | [1]Human HHLA2 Binding EC50 (ug/ml) | Cynomolgus Monkey HHLA2 Binding EC50 (ug/ml) |
|---|---|---|
| 2C4 (IgG1) | 0.29 | 0.47 |
| 5H4 (IgG1) | 2.03 | No binding |
| 6F10 (IgG1) | 0.22 | 0.40 |
| 6G8 (IgG1) | 2.14 | No binding |

[1]HHLA2 mAb binding to human HHLA2 transfected 300.19 mouse pre-B cells
[2]HHLA2 mAb binding to cynomolgus monkey transfected 300.19 mouse pre-B cells

Example 8: In Vitro Confirmation of Activity of HHLA2 mAbs

In some embodiments, the cytotoxicity of CAR-T cells expressing CD19 and KIRDL3 (CAR-T/CD19/KIRDL3) against HeLa-CD19 and HHLA2 expressing target tumor cells is evaluated either in the presence or absence of HHLA2 mAbs. CAR-T/CD19/KIRDL3 cells are generated. A lentiviral plasmid expressing anti-CD19 scFv and KIR3DL3 is constructed and subcloned into a second-generation CAR cassette containing a secretory signal peptide from GM-CSF, a hinge region, transmembrane domain and costimulatory domain from CD28, and the CD3(activation domain. Ten million growth-arrested HEK293FT cells are seeded into T75 flasks and cultured overnight, then transfected with the pPACKH1 Lentivector Packaging mix (System Biosciences, Palo Alto, CA) and 10 μg of each lentiviral vector containing anti-CD19 scFv and KIR3DL3 using the CalPhos™ Transfection Kit (Takara, Mountain View, CA). One day later, the medium is replaced with fresh medium, and 48 h later the lentivirus-containing medium is collected. The medium is cleared of cell debris by centrifugation at 2100 g for 30 min. The virus particles are collected by centrifugation at 112,000 g for 100 min, aliquoted and frozen at−80° C. The titers of the virus preparations are determined by quantitative RT-PCR using the Lenti-X™ qRT-PCR kit.

PBMC are isolated from human peripheral blood mononuclear cells (provided by Dana Farber Cancer Institute in accordance with its approved IRB protocol) suspended at $1\times10^6$ cells/ml in AIM V medium containing 10% FBS and 300 U/ml IL-2, mixed with an equal number (1:1 ratio) of CD3/CD28 Dynabeads (Thermo Fisher), and cultured in non-treated 24-well plates (0.5 ml per well). At 24 and 48 hours, lentivirus is added to the cultures at a multiplicity of infection (MOI) of 5, along with 1 µl of TransPlus™ transduction enhancer (AlStem). As the T cells proliferate over the next two weeks, the cells are counted every 2-3 days and fresh medium with 300 U/ml IL-2 was added to the cultures to maintain the cell density at $1-3\times10^6$ cells/ml. CAR expression is assessed by flow cytometry using anti-CD4, CD8 and CD19 antibodies. Thus, prior to transduction, T cells are activated using an anti-CD3 antibody in combination with anti-CD28 antibody costimulation. Rapid expansion of CAR-T cells in culture is generally achieved within two weeks, driven by the presence of exogenous IL-2. This CAR is hereafter called CAR-T/CD19/KIRDL3.

HHLA2 transfected HeLa-CD19 cells are generated. HeLa-CD19 expressing cells are transfected with HHLA2_pIRESneo3 by Lipofectamine® 2000 (Invitrogen). Stable clones are generated by G418 selection and limiting dilution, and evaluated for HHLA2 expression by flow cytometry.

KIR3DL3 inhibition of primary T cells in vitro in real-time cytotoxicity assay (RTCA) is performed. Adherent target cells (HeLa or HeLa-CD19) are seeded into 96-well E-plates (Acea Biosciences, San Diego, CA) at $1\times10^4$ cells per well and monitored in culture overnight with the impedance-based real-time cell analysis (RTCA) xCELLigence system (Acea Biosciences). The next day, the medium is removed and replaced with AIM V-AlbuMAX® medium containing 10% FBS±$1\times10^5$ effector cells (CAR-T/CD19/KIRDL3 cells or non-transduced T cells), in triplicate. The cells in the E-plates are monitored for another 2-3 days with the RTCA system, and impedance plotted over time. Cytolysis is calculated as (impedance of target cells without effector cells-impedance of target cells with effector cells)×100/impedance of target cells without effector cells.

Cytokine secretion is also evaluated. In some embodiments, cytokine induction assay is performed. For example, the HeLa-CD19/HHLA2 target cells are cultured with the effector CAR-T/CD19/KIRDL3 cells or non-transduced T cells at a 1:1 ratio ($1\times10^4$ cells each) in U-bottom 96-well plates with 200 ml of AIM V-AlbuMAX® medium containing 10% FBS, in triplicate. After 16 h the top 150 ml of medium is transferred to V-bottom 96-well plates and centrifuged at 300 g for 5 min to pellet any residual cells. The top 120 ml of supernatant is transferred to a new 96-well plate and analyzed by ELISA for human IFN-y and IL-2 levels using kits from Thermo Fisher according to the manufacturer's protocol.

Exemplary CAR-T cell cytotoxicity model in vitro configurations are listed in Table 11 below.

TABLE 11

Evaluation of HHLA2 mAbs in CAR-T cell cytotoxicity model in vitro

| Tumor | Treatment | Expected outcome |
|---|---|---|
| HeLa/CD19/HHLA2 | No T cells | No activation |
| HeLa/CD19/HHLA2 | CAR-T/aCD19 | T cell activation |
| HeLa/CD19/HHLA2 | CAR-T/aCD19/KIR3DL3 + Isotype control | Inhibition of T cell activation |

TABLE 11-continued

Evaluation of HHLA2 mAbs in CAR-T cell cytotoxicity model in vitro

| Tumor | Treatment | Expected outcome |
|---|---|---|
| HeLa/CD19/HHLA2 | CAR-T/aCD19/KIR3DL3 + HHLA2 mAb | Reversal of T cell activation |

In some embodiments, KIR3DL3 inhibition of NK cytotoxicity assay is performed. KIR3DL3 transfected NK92 cells are generated. For example, NK92 cells are transfected with the KIR3DL3 puroEIF2 vector and selected for puromycin resistance, and KIR3DL3 expression is detected by flow cytometry.

HHLA2 transfected K562 target cells are generated. For example, target K562 cells are transfected with HHLA2 pIRESneo3 and selected for neomycin resistance, and HHLA2 expression was detected by flow cytometry.

NK92 cells transfected with KIR3DL3 are evaluated for NK cyototoxicty against K562 cells (+ or – HHLA2) at different E/T ratios in the presence or absence of HHLA2 mAbs in a 4 hour cytotoxicity assay. Exemplary CAR-T cell cytotoxicity model in vitro configurations are listed in Table 13 below.

TABLE 13

Evaluation of HHLA2 mAbs in NK cytotoxicity model

| Effector NK cells | Target K562 cell | Expected response |
|---|---|---|
| NK92/KIRDL3 | K562 | Cytotoxicity |
| NK92/KIRDL3 | K562/HHLA2 + Isotype control | Inhibition of cytotoxicity |
| NK92/KIRDL3 | K562/HHLA2 + HHLA2 mAb | Cytotoxicity |

In some embodiments, KIR3DL3 signaling pathway in Jurkat T cells is studied.

INCORPORATION BY REFERENCE

All publications, patents, and patent applications mentioned herein are hereby incorporated by reference in their entirety as if each individual publication, patent or patent application was specifically and individually indicated to be incorporated by reference. In case of conflict, the present application, including any definitions herein, will control.

Also incorporated by reference in their entirety are any polynucleotide and polypeptide sequences which reference an accession number correlating to an entry in a public database, such as those maintained by The Institute for Genomic Research (TIGR) on the World Wide Web at tigr.org and/or the National Center for Biotechnology Information (NCBI) on the World Wide Web at ncbi.nlm.nih.gov.

EQUIVALENTS

Those skilled in the art will recognize, or be able to ascertain using no more than routine experimentation, many equivalents to the specific embodiments of the present invention described herein. Such equivalents are intended to be encompassed by the following claims.

What is claimed is:

1. An anti-HHLA2 monoclonal antibody, or antigen-binding fragment thereof, wherein the monoclonal antibody, or antigen-binding fragment thereof comprises:
   a) a VH comprising a VH CDR1 amino acid sequence of SEQ ID NO: 206, a VH CDR2 amino acid sequence of SEQ ID NO: 210, and a VH CDR3 amino acid sequence of SEQ ID NO: 214; and
   b) a VL comprising a VL CDR1 amino acid sequence of SEQ ID NO: 224, a VL CDR2 amino acid sequence of SEQ ID NO: 228, and a VL CDR3 amino acid sequence of SEQ ID NO: 232.

2. The anti-HHLA2 monoclonal antibody, or antigen-binding fragment thereof, of claim 1, wherein the monoclonal antibody, or antigen-binding fragment thereof comprises:
   a) a VH comprising an amino acid sequence of SEQ ID NO: 199; and
   b) a $V_L$ comprising an amino acid sequence of SEQ ID NO: 217.

3. The anti-HHLA2 monoclonal antibody, or antigen-binding fragment thereof, of claim 1, wherein the monoclonal antibody, or antigen-binding fragment thereof:
   i) is a chimeric antibody, humanized antibody, composite antibody, or murine antibody:
   ii) is detectably labeled:
   iii) comprises an effector domain:
   iv) is selected from the group consisting of Fv, Fav, F(ab')2, Fab', dsFv, scFv, and sc(Fv)2, and diabody fragments:
   v) inhibits a) the binding of HHLA2 to TMIGD2, b) the binding of HHLA2 to KIR3DL3, or c) the binding of HHLA2 to TMJGD2 and the binding of HHLA2 to KIR3DL3; or
   vi) specifically binds HHLA2.

4. An isolated nucleic acid molecule that encodes the anti-HHLA2 monoclonal antibody, or antigen-binding fragment thereof of claim 1.

5. A vector comprising the isolated nucleic acid of claim 4.

6. A host cell which comprises the isolated nucleic acid of claim 4.

7. A device or kit comprising at least one anti-HHLA2 monoclonal antibody, or antigen-binding fragment thereof, according to claim 1.

8. A method of producing the anti-HHLA2 monoclonal antibody, or antigen-binding fragment thereof, according to claim 1, which comprises the steps of: (i) culturing a transformed host cell comprising a nucleic acid sequence encoding at least one anti-HHLA2 monoclonal antibody according to claim 1 under conditions suitable to allow expression of said anti-HHLA2 monoclonal antibody, or antigen-binding fragment thereof; and (ii) recovering the expressed anti-HHLA2 monoclonal antibody, or antigen-binding fragment thereof.

9. A method of detecting the presence or level of an HHLA2 polypeptide comprising obtaining a sample and detecting said polypeptide in the sample by contacting the sample with the ene anti-HHLA2 monoclonal antibody, or antigen-binding fragment thereof, according to claim 1.

10. A method for monitoring the progression of a disorder associated with aberrant HHLA2 expression in a subject, the method comprising: a) detecting in a subject sample at a first point in time the level of HHLA2 comprising contacting the sample with the anti-HHLA2 monoclonal antibody, or antigen-binding fragment thereof, according to claim 1; b) repeating step a) at a subsequent point in time; and c) comparing the level of HHLA2 detected in steps a) and b.

11. A method of assessing the efficacy of a therapy for a disorder associated with aberrant HHLA2 expression in a subject, the method comprising: a) determining the level of HHLA2 in a first and second sample comprising contacting the first and second sample with the anti-HHLA2 monoclonal antibody, or antigen-binding fragment thereof, according to claim 1, wherein the first sample is obtained from the subject prior to treatment and the second sample is obtained from the subject after administration of treatment and b) comparing the level of HHLA2 detected in the first and second samples, wherein a significantly lower level of HHLA2 in the second sample, relative to the first sample, is an indication that the therapy is efficacious for inhibiting the disorder in the subject.

12. A method of assessing the efficacy of a test compound for inhibiting a disorder associated with aberrant HHLA2 expression in a subject, the method comprising: a) determining the level of HHLA2 comprising contacting the anti-HHLA2 monoclonal antibody, or antigen-binding fragment thereof, according to claim 1, with a first sample and a second sample obtained from the subject and exposed to the test compound; and b) determining the level of HHLA2 in a second sample obtained from the subject, wherein the first sample is exposed to the test compound, and wherein a significantly lower level of HHLA2 in the first sample relative to the second sample, is an indication that the test compound is efficacious for inhibiting the disorder in the subject; and/or ii) the first and second samples are portions of a single sample obtained from the subject or portions of pooled samples obtained from the subject.

13. The method of claim 10, wherein the disorder is an HHLA2 expressing cancer.

14. The method of claim 9, wherein the sample is obtained from a human subject.

15. A method of treating a subject afflicted with a HHLA2 expressing cancer comprising administering to the subject at least one anti-HHLA2 monoclonal antibody, or antigen-binding fragment thereof, according to claim 1.

16. The method of claim 15, wherein
   the anti-HHLA2 monoclonal antibody, or antigen-binding fragment thereof, is conjugated to a cytotoxic agent selected from the group consisting of a chemotherapeutic agent, a biologic agent, a toxin, and a radioactive isotope.

17. A method of modulating an immune response in a subject, comprising administering the anti-HHLA2 monoclonal antibody, or antigen-binding fragment thereof of claim 1, wherein the anti-HHLA2 monoclonal antibody, or antigen-binding fragment thereof inhibits the interaction between HHLA2 and KIRDL3.

18. A method of modulating an immune response in a subject, comprising administering the anti-HHLA2 monoclonal antibody, or antigen-binding fragment thereof of claim 1, wherein the anti-HHLA2 monoclonal antibody, or antigen-binding fragment thereof does not block or significantly inhibit the interaction between HHLA2 and its binding stimulatory receptor, TMIGD2.

19. The method of claim 15, wherein a further therapy for treating cancer is administered to the subject; wherein the therapy is selected from immunotherapy, checkpoint blockade, cancer vaccines, chimeric antigen receptors, chemotherapy, radiation, target therapy, and surgery is administered to the subject.

* * * * *

UNITED STATES PATENT AND TRADEMARK OFFICE
CERTIFICATE OF CORRECTION

| | | |
|---|---|---|
| PATENT NO. | : 12,103,972 B2 | Page 1 of 1 |
| APPLICATION NO. | : 17/044493 | |
| DATED | : October 1, 2024 | |
| INVENTOR(S) | : Gordon J. Freeman et al. | |

It is certified that error appears in the above-identified patent and that said Letters Patent is hereby corrected as shown below:

In the Claims

In Claim 3, at Column 401, Line 45, replace --TMJGD2-- with "TMIGD2".

Signed and Sealed this
Thirtieth Day of September, 2025

John A. Squires
*Director of the United States Patent and Trademark Office*